US012589168B2

(12) United States Patent
Burns et al.

(10) Patent No.: US 12,589,168 B2
(45) Date of Patent: Mar. 31, 2026

(54) COMPOSITIONS AND METHODS FOR TREATING SENSORINEURAL HEARING LOSS USING OTOFERLIN DUAL VECTOR SYSTEMS

(71) Applicants: Decibel Therapeutics, Inc., Boston, MA (US); Regeneron Pharmaceuticals, Inc., Tarrytown, NY (US)

(72) Inventors: Joseph Burns, Newton, MA (US); Kathryn Ellis, Arlington, MA (US); Tyler Gibson, Boston, MA (US); Adam Palermo, Somerville, MA (US); Martin Schwander, Auburndale, MA (US); Jonathon Whitton, Cambridge, MA (US); Leah Sabin, Goldens Bridge, NY (US); Christos Kyratsous, Irvington, NY (US); Meghan Drummond Samuelson, Katonah, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 987 days.

(21) Appl. No.: 17/733,744

(22) Filed: Apr. 29, 2022

(65) Prior Publication Data

US 2022/0265865 A1      Aug. 25, 2022

Related U.S. Application Data

(63) Continuation of application No. PCT/US2020/058265, filed on Oct. 30, 2020.

(60) Provisional application No. 63/023,058, filed on May 11, 2020, provisional application No. 62/971,504, filed on Feb. 7, 2020, provisional application No. 62/965,776, filed on Jan. 24, 2020, provisional application No. 62/928,290, filed on Oct. 30, 2019.

(51) Int. Cl.
| | |
|---|---|
| *C12N 15/86* | (2006.01) |
| *A61K 48/00* | (2006.01) |
| *A61P 27/16* | (2006.01) |
| *C07K 14/47* | (2006.01) |

(52) U.S. Cl.
CPC ...... *A61K 48/0075* (2013.01); *C07K 14/4716* (2013.01); *C12N 15/86* (2013.01); *A01K 2227/105* (2013.01); *A01K 2267/0306* (2013.01); *C12N 2750/14143* (2013.01); *C12N 2800/40* (2013.01); *C12N 2830/008* (2013.01); *C12N 2840/44* (2013.01)

(58) Field of Classification Search
CPC .. C12N 15/86; C12N 15/864; C12N 15/8645; C12N 2800/40; C12N 2830/42; C12N 2840/44; A61P 27/16; C07K 14/47; C07K 14/4716

See application file for complete search history.

(56) References Cited

U.S. PATENT DOCUMENTS

| | | | |
|---|---|---|---|
| 6,436,392 B1 | 8/2002 | Engelhardt et al. | |
| 6,544,786 B1 | 4/2003 | Xiao et al. | |
| 6,808,922 B1 | 10/2004 | Bebbington et al. | |
| 6,897,045 B2 | 5/2005 | Engelhardt et al. | |
| 7,803,622 B2 | 9/2010 | Engelhardt et al. | |
| 8,236,557 B2 | 8/2012 | Dongsheng et al. | |
| 8,298,818 B2 | 10/2012 | Boye et al. | |
| 10,214,572 B2 | 2/2019 | Boye et al. | |
| 11,325,956 B2 | 5/2022 | Boye et al. | |
| 11,525,139 B2 | 12/2022 | Simons et al. | |
| 11,660,353 B2 * | 5/2023 | Burns .................. | A61K 48/005 514/44 R |
| 11,781,145 B2 | 10/2023 | Simons et al. | |
| 11,807,867 B2 | 11/2023 | Simons et al. | |
| 12,188,041 B2 | 1/2025 | Dyka et al. | |
| 12,233,136 B2 * | 2/2025 | Burns ................ | C07K 14/4716 |
| 12,252,520 B2 * | 3/2025 | Burns ................... | C12N 15/86 |
| 2003/0219741 A1 | 11/2003 | Isogai et al. | |
| 2004/0022766 A1 * | 2/2004 | Acland ................. | C12N 15/86 424/93.2 |
| 2004/0072154 A1 | 4/2004 | Morris et al. | |
| 2007/0161031 A1 | 7/2007 | Trinklein et al. | |

(Continued)

FOREIGN PATENT DOCUMENTS

| | | |
|---|---|---|
| CA | 3034527 A1 | 3/2018 |
| WO | WO-01/25465 A1 | 4/2001 |

(Continued)

OTHER PUBLICATIONS

Kingdoms of Life, waynesword.palomar.edu/trfeb98.htm, last visited Apr. 8, 2021.*
Mammal, en.wikipedia.org/wiki/Mammal, last visited Aug. 31, 2022.*
www.calculator.net/exponent-calculator; last visited Mar. 31, 2025.*
Moreira et al, Hot spots—A review of the protein-protein interface determinant amino-acid residues, Proteins 68: 803-812, 2007.*
Ng et al, Predicting the Effects of Amino Acid Substitutions on Protein Function, Annual Review Genomics Human Genetics 7: 61-80, 2006.*
Fumoto et al, Targeted Gene Delivery: Importance of Administration Routes, Intech, Novel Gene Therapy Approaches, p. 3-31; editors Wei and Good, publisher Books on Demand, 2013.*

(Continued)

*Primary Examiner* — Kevin K Hill
(74) *Attorney, Agent, or Firm* — Clark & Elbing LLP

(57) ABSTRACT

The disclosure features compositions and methods for the treatment of sensorineural hearing loss and auditory neuropathy, particularly forms of the disease that are associated with a mutation in otoferlin (OTOF), by way of OTOF gene therapy. The disclosure provides a variety of compositions that include a first nucleic acid vector that contains a polynucleotide encoding an N-terminal portion of an OTOF isoform 5 protein and a second nucleic acid vector that contains a polynucleotide encoding a C-terminal portion of an OTOF isoform 5 protein. These vectors can be used to increase the expression of OTOF in a subject, such as a human subject suffering from sensorineural hearing loss.

4 Claims, 11 Drawing Sheets

Specification includes a Sequence Listing.

(56) References Cited

U.S. PATENT DOCUMENTS

| | | | |
|---|---|---|---|
| 2007/0161110 A1 | 7/2007 | Iida et al. | |
| 2008/0249052 A1 | 10/2008 | Duan et al. | |
| 2009/0215879 A1* | 8/2009 | Diprimio | A61K 31/7088 |
| | | | 435/320.1 |
| 2010/0003218 A1 | 1/2010 | Duan et al. | |
| 2010/0266551 A1 | 10/2010 | Richard et al. | |
| 2012/0003190 A1 | 1/2012 | Yamoah et al. | |
| 2012/0087862 A1 | 4/2012 | Hood et al. | |
| 2013/0210895 A1 | 8/2013 | Boye et al. | |
| 2014/0249208 A1 | 9/2014 | Bancel et al. | |
| 2014/0256802 A1 | 9/2014 | Boye et al. | |
| 2015/0065562 A1 | 3/2015 | Yazicioglu et al. | |
| 2015/0111955 A1* | 4/2015 | High | C12N 15/86 |
| | | | 435/456 |
| 2015/0209406 A1 | 7/2015 | Chen | |
| 2016/0022836 A1 | 1/2016 | Banfi et al. | |
| 2016/0076054 A1* | 3/2016 | Auricchio | C12N 15/86 |
| | | | 435/320.1 |
| 2018/0015172 A1 | 1/2018 | Muzyczka et al. | |
| 2018/0055908 A1* | 3/2018 | Petit | A61K 9/0019 |
| 2018/0327779 A1 | 11/2018 | Colella et al. | |
| 2019/0002916 A1 | 1/2019 | Kalatzis et al. | |
| 2019/0153050 A1 | 5/2019 | Boye et al. | |
| 2019/0185864 A1 | 6/2019 | Simons et al. | |
| 2019/0309326 A1 | 10/2019 | Maclaren et al. | |
| 2020/0155705 A1 | 5/2020 | Burns et al. | |
| 2020/0157573 A1 | 5/2020 | Boye et al. | |
| 2021/0130421 A1 | 5/2021 | Boye et al. | |
| 2021/0236654 A1 | 8/2021 | Burns et al. | |
| 2021/0388045 A1 | 12/2021 | Burns et al. | |
| 2021/0395778 A1 | 12/2021 | Dyka et al. | |
| 2021/0395781 A1 | 12/2021 | Burns et al. | |
| 2022/0064671 A1 | 3/2022 | Maranga et al. | |
| 2022/0265865 A1 | 8/2022 | Burns et al. | |
| 2023/0103708 A1* | 4/2023 | Vetter | A61K 48/0058 |
| | | | 424/93.21 |
| 2023/0149565 A1 | 5/2023 | Boye et al. | |
| 2024/0011039 A1 | 1/2024 | Simons et al. | |
| 2024/0131186 A1 | 4/2024 | Burns et al. | |
| 2024/0148905 A1 | 5/2024 | Palermo et al. | |
| 2024/0309399 A1 | 9/2024 | Hu et al. | |
| 2025/0127926 A1 | 4/2025 | Burns et al. | |

FOREIGN PATENT DOCUMENTS

| | | | |
|---|---|---|---|
| WO | WO-2001/070972 A2 | 9/2001 | |
| WO | WO-2008/088895 A2 | 7/2008 | |
| WO | WO-2009/100438 A2 | 8/2009 | |
| WO | WO-2013/075008 A1 | 5/2013 | |
| WO | WO-2013/158879 A1 | 10/2013 | |
| WO | WO-2014/140051 A1 | 9/2014 | |
| WO | WO-2014/170480 A1 | 10/2014 | |
| WO | WO-2014/193716 A2 | 12/2014 | |
| WO | WO-2016/131981 A1 | 8/2016 | |
| WO | WO-2016/139321 A1 | 9/2016 | |
| WO | WO-2017/049252 A1 | 3/2017 | |
| WO | WO-2017/100791 A1 | 6/2017 | |
| WO | WO-2017/216560 A1 | 12/2017 | |
| WO | WO 18/039375 * | 3/2018 | |
| WO | WO-2018/039375 A1 | 3/2018 | |
| WO | WO-2018/145111 A1 | 8/2018 | |
| WO | WO-2018/162748 A1 | 9/2018 | |
| WO | WO 18/204734 * | 11/2018 | |
| WO | WO-2018/204734 A1 | 11/2018 | |
| WO | WO-2019/162396 A1 | 8/2019 | |
| WO | WO-2019/165292 A1 | 8/2019 | |
| WO | WO-2019/183641 A1 | 9/2019 | |
| WO | WO 20/093018 * | 5/2020 | |
| WO | WO-2020/093018 A1 | 5/2020 | |
| WO | WO-2020/097372 A1 | 5/2020 | |
| WO | WO-2020/148458 A1 | 7/2020 | |
| WO | WO-2020/163743 A1 | 8/2020 | |
| WO | WO-2024/173835 A2 | 8/2024 | |

OTHER PUBLICATIONS

Daya et al, Gene Therapy Using Adeno-Associated Virus Vectors, Clin. Microbiol. Rev. 21(4): 583-593, 2008.*

Huang et al, Genetic Manipulation of Brown Fat via Oral Administration of an Engineered Recombinant Adeno-associated Viral Serotype Vector, Molecular Therapy 24(6): 1062-1069, 2016.*

Tian et al, Aerosol Inhalation-mediated Delivery of an Adeno-associated Virus 5-expressed Antagonistic Interleukin-4 Mutant Ameliorates Experimental Murine Asthma, Archives of Medical Research 50: 384-392, 2019.*

Ghoraba et al, Ocular Gene Therapy: A Literature Review with Special Focus on Immune and Inflammatory Responses, Clinical Opthalmology 16: 1753-1771, 2022.*

Mingozzi and High, Immune responses to AAV vectors: overcoming barriers to successful gene therapy, Blood 122(1): 23-36, 2013.*

Kattenhorn et al, Adeno-Associated Virus Gene Therapy for Liver Disease, Human Gene Therapy 27(12): 947-961, Nov. 28, 2016.*

Ferdowsian et al, Primates in Medical Research: A Matter of Convenience, not Sound Science, The Hastings Center, www.thehastingscenter.org/primates-in-medical-research-convenience-not-sound-science/; Jul. 8, 2022.*

Perrin, Make Mouse Studies Work, Nature (507): 423-425, 2014.*

Greenberg, Gene Therapy for heart failure, Trends in Cardiovascular Medicine 27: 216-222, 2017.*

Maguire et al, Viral vectors for gene delivery to the inner ear, Hearing Research 394: e107927, 13 pages, doi.org/10.1016/j.heares.2020.107927, 2020.*

Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023.*

Alemi, Progress Report: AOS Research Grant: Restoration of Hearing in the Otoferlin Knockout Mouse using Viral Gene Therapy, 145th Annual Meeting of the American Otological Society, Apr. 21-22, San Diego, California, Abstract 68, 2012.*

Wang, Aihui, Dissertation: "Molecular Cloning of an Unconventional Myosin MYO15 and the Identification of Mutations of MYO15 Responsible for Human Nonsyndromic Deafness DFNB3," Doctor of Philosophy, Graduate Program in Genetics, Michigan State University (1999) (140 pages).

Liang et al., "Characterization of the Human and Mouse Unconventional Myosin XV Genes Responsible for Hereditary Deafness DFNB3 and Shaker 2," Genomics. 61(3):243-258 (1999).

Yuhe, Liu, "Preparation of adeno-associated virus vector and its application in cochlea transgenic research," Chinese Journal of Otology. 4(4):343-347 (2006) (6 pages).

Hirsch et al., "Delivering Transgenic DNA Exceeding the Carrying Capacity of AAV Vectors," available in PMC Aug. 3, 2016, published in final edited form as: Methods Mol Biol. 13382:21-39 (2016) (20 pages).

Majewski and Ott, "GT Repeats Are Associated with Recombination on Human Chromosome 22," Genome Res. 10(8): 1108-1144 (Aug. 2000) (7 pages).

Lostal et al., "Full-Length Dystrophin Reconstitution with Adeno-Associated Viral Vectors," Human Gene Ther. 25(6): 552-562 (Jun. 2014) (11 pages).

Gao et al., "The Dystrophin Complex: structure, function and implications for therapy," available in PMC Jul. 1, 2016, published in final edited form as: Compr Physiol. 5(3): 1223-1239 (Jul. 2015) (33 pages).

Dyka et al., "Dual adeno-associated virus vectors result in efficient in vitro and in vivo expression of an oversized gene, MYO7A," Human Gene Ther Methods. 25(2): 166-77 (Apr. 2014) (12 pages).

Pryadkina et al., "A comparison of AAV strategies distinguishes overlapping vectors for efficient systemic delivery of the 6.2 kb Dysferlin coding sequence," Mol Ther Methods Clin Dev. 2: 15009 (Mar. 2015) (12 pages).

Geleoc et al., "Sound strategies for hearing restoration," available in PMC Aug. 29, 2014, published in final edited form as: Science. 344(6184):1241062 (May 2014) (20 pages).

(56)                    References Cited

OTHER PUBLICATIONS

Corns et al., "Mechanotransduction is required for establishing and maintaining mature inner hair cells and regulating efferent innervation," Nat Commun. 9(1):4015 (Oct. 2018) (15 pages).

Yoshimura et al., "Enhanced viral-mediated cochlear gene delivery in adult mice by combining canal fenestration with round window membrane inoculation," Scientific Reports. 8:2980 (with supplemental material) (Feb. 2018) (14 pages).

Pangrsic et al., "Otoferlin: a multi-$C_2$ domain protein essential for hearing," Trends in Neurosciences. 35(11): 671-680 (2012) (10 pages).

Holt et al., "Split otoferlin reunited," EMBO Molecular Medicine. 11:(1)e9995 (Jan. 2019) (3 pages).

Suzuki et al., "Cochlear gene therapy with ancestral AAV in adult mice: complete transduction of inner hair cells without cochlear dysfunction," Scientific Reports. 7(1):45524 (Apr. 2017) (11 pages).

Tertrais et al., "Viral Transfer of Mini-Otoferlins Partially Restores the Fast Component of Exocytosis and Uncovers Ultrafast Endocytosis in Auditory Hair Cells of Otoferlin Knock-Out Mice," J. Neurosci. 39(18):3394-3411 (May 2019) (18 pages).

Petrs-Silva et al., "Novel Properties of Tyrosine-mutant AAV2 Vectors in the Mouse Retina," Molecular Therapy. 19(2):293-301 (Feb. 2011) (9 pages).

American Academy of Audiology, "Children's Hospital of Philadelphia Performs First Gene Therapy Procedure to Treat Genetic Hearing Loss in United States," <https://www.audiology.org/childrens-hospital-of-philadelphia-performs-first-gene-therapy-procedure-to-treat-genetic-hearing-loss-in-united-states/>, dated Jan. 26, 2024 (2 pages).

Yoshimura et al., "Targeted Allele Suppression Prevents Progressive Hearing Loss in the Mature Murine Model of Human TMC1 Deafness," Molecular Therapy. 27(3):681-690 (with supplemental material) (Mar. 2019) (17 pages).

Akil et al., "Surgical Method for Virally Mediated Gene Delivery to the Mouse Inner Ear through the Round Window Membrane," Journal of Visualized Experiments. 97(1):e52187 (Mar. 2015) (7 pages).

Liu et al., "Specific and Efficient Transduction of *Cochlear* Inner Hair Cells with Recombinant Adeno-associated Virus Type 3 Vector," Molecular Therapy. 12(4):725-733 (Oct. 2005) (9 pages).

"Basics of sound, the Ear, and Hearing," *Hearing Loss: Determining Eligibility for Social Security Benefits*. Edited by Robert A. Dobie and Susan Van Hemel, 42-68 (2004) (61 pages).

Akil et al., "AAV-Mediated Gene Delivery to the Inner Ear," *Adeno-Associated Virus Vectors: Design and Delivery*. Methods in Molecular Biology. Edited by Michael J. Castle, 271-282 (2019) [published online on Jan. 1, 2019] (16 pages).

Langouet-Astrie et al., "Characterization of intravitreally delivered capsid mutant AAV2-Cre vector to induce tissue-specific mutations in murine retinal ganglion cells," Experimental Eye Research. 151(1):61-67 (Jul. 2016) (7 pages).

Li et al., "A novel bispecific molecule delivered by recombinant AAV2 suppresses ocular inflammation and choroidal neovascularization," J. Cell. Mol. Med. 21(8):1555-1571 (Aug. 2017) (17 pages).

Lopes-Pacheco et al., "Self-complementary and tyrosine-mutant rAAV vectors enhance transduction in cystic fibrosis bronchial epithelial cells," Experimental Cell Research. 372:99-107 (Sep. 2018) (9 pages).

Petrs-Silva et al., "High-efficiency Transduction of the Mouse Retina by Tyrosine-mutant AAV Serotype Vectors," Molecular Therapy. 17(3):463-471 (Mar. 2009) (9 pages).

Kilpatrick et al., "Adeno-associated virus-mediated gene delivery into the scala media of the normal and deafened adult mouse ear," Gene Therapy. 18(6):569-578 (Jan. 2011) (10 pages).

Tao et al., "Delivery of Adeno-Associated Virus Vectors in Adult Mammalian Inner-Ear Cell Subtypes Without Auditory Dysfunction," Human Gene Therapy. 29(4):492-506 (Nov. 2017) (15 pages).

Zhang et al., "Cochlear Gene Therapy for Sensorineural Hearing Loss: Current Status and Major Remaining Hurdles for Translational Success," Front. Mol. Neurosci. 11(221):1-15 (Jun. 2018) (15 pages).

Roux et al., "Otoferlin, Defective in a Human Deafness Form, Is Essential for Exocytosis at the Auditory Ribbon Synapse," Cell. 127(2):277-289 (Oct. 2006) (13 pages).

"Genetic Hearing Loss With No Associated Abnormalities," *Hereditary Hearing Loss and Its Syndromes, Third Edition*. Helga V. Toriello and Shelley D. Smith. 164-165 (2013) (4 pages).

Ahmed et al., "Emerging Gene Therapies for Genetic Hearing Loss," JARO. 18(5):649-670 (Aug. 2017) (22 pages).

Zhang et al., "Temperature sensitive auditory neuropathy," Hearing Research. 335(1):53-63 (Jan. 2016) (11 pages).

Hamosh et al. "Otoferlin; Otof," OMIM. (Apr. 2015) (8 pages) retrieved via The Wayback Machine on Jul. 29, 2015, URL: <https://web.archive.org/web/20150729163826/http://omim.org/entry/603681>.

Michalski et al., "Genetics of auditory mechano-electrical transduction," Pflugers Arch. 467(1):49-72 (2015).

GenBank Accession No. JN953192.1, "Mus musculus targeted KO-first, conditional ready, lacZ-tagged mutant allele Myo15:tm1a(EUCOMM)Wtsi; transgenic," retrieved from <https://www.ncbi.nlm.nih.gov/nuccore/JN953192>, dated Nov. 5, 2011 (11 pages).

Caberlotto et al., "Usher type 1G protein sans is a critical component of the tip-link complex, a structure controlling actin polymerization in stereocilia," Proc Natl Acad Sci U S A. 108(14):5825-30 (2011) (14 pages).

Schlabach et al., "Synthetic design of strong promoters," Proc Natl Acad Sci U S A. 107(6):2538-43 (2010).

International Search Report and Written Opinion for International Application No. PCT/US2019/029366, mailed Sep. 10, 2019 (17 pages).

Boëda et al., "A specific promoter of the sensory cells of the inner ear defined by transgenesis," Hum Mol Genet. 10(15):1581-1589 (2001) (10 pages).

Belyantseva et al., "Myosin XVa localizes to the tips of inner ear sensory cell stereocilia and is essential for staircase formation of the hair bundle," Proc Natl Acad Sci U S A. 100(24):13958-63 (2003).

GenBank Accession No. JN957158.1, "Mus musculus targeted non-conditional, lacZ-tagged mutant allele Myo15:tm1e(EUCOMM)Wtsi; transgenic," retrieved from <https://www.ncbi.nlm.nih.gov/nucleotide/JN957158.1>, dated Nov. 5, 2011 (12 pages).

International Search Report and Written Opinion for International Patent Application No. PCT/US2020/017292, mailed Jun. 26, 2020 (18 pages).

Akil et al., "Dual AAV gene therapy restores hearing in a mouse model for human genetic Deafness," International Symposium on Inner Ear Therapies (ISIET), Marrakech, Morocco. 21 (2017) (Abstract only).

Akil et al., "Dual AAV-mediated gene therapy restores hearing in a DFNB9 mouse model," Proc Natl Acad Sci U S A. 116(10):4496-4501 (2019).

Al-Moyed et al., "A dual AAV viral vector approach partially restores exocytosis and rescues hearing in deaf otoferlin knock-out mice," ARO Abstracts. 41:76 (2018) (Abstract only).

Al-Moyed et al., "A dual-AAV approach restores fast exocytosis and partially rescues auditory function in deaf otoferlin knock-out mice," EMBO Molecular Medicine. 11(1):e9396 (2019) (13 pages).

Alemi, "Progress Report: AOS Research Grant: Restoration of Hearing in the Otoferlin Knockout Mouse using Viral Gene Therapy," 145th Annual Meeting of the American Otological Society, Inc, Apr. 21-22, San Diego, California. 68 (2012) (Abstract only).

Choi et al., "Identities and frequencies of mutations of the otoferlin gene (OTOF) causing DFNB9 deafness in Pakistan," available in PMC Oct. 1, 2012, published in final edited form as: Clin Genet. 75(3):237-243 (2009) (10 pages).

Duan et al., "Expanding AAV Packaging Capacity with Trans-splicing or Overlapping Vectors: A Quantitative Comparison," Mol Ther. 4(4):383-91 (2001).

(56)  References Cited

OTHER PUBLICATIONS

McClements et al., "Adeno-associated Virus (AAV) Dual Vector Strategies for Gene Therapy Encoding Large Transgenes," Yale J Biol Med. 90(4):611-623 (2017).

Trapani et al., "Effective delivery of large genes to the retina by dual AAV vectors," EMBO Mol Med. 6(2):194-211 (2014).

Trapani et al., "Improved dual AAV vectors with reduced expression of truncated proteins are safe and effective in the retina of a mouse model of Stargardt disease," Hum Mol Genet. 24(23):6811-25 (2015).

Yasunaga et al., "*OTOF* Encodes Multiple Long and Short Isoforms: Genetic Evidence That the Long Ones Underlie Recessive Deafness DFNB9," Am J Hum Genet. 67(3):591-600 (2000).

Xu et al., "Trans-Splicing Adeno-Associated Viral Vector-Mediated Gene Therapy Is Limited by the Accumulation of Spliced mRNA but Not by Dual Vector Coinfection Efficiency," available in PMC Jun. 19, 2008, published in final edited form as: Hum Gene Ther. 15(9):896-905 (2004) (17 pages).

Ghosh et al., "A Hybrid Vector System Expands Adeno-associated Viral Vector Packaging Capacity in a Transgene-independent Manner," The American Society of Gene Therapy. 16(1):124-130 (2008).

Ghosh et al., "Efficient Transgene Reconstitution with Hybrid Dual AAV Vectors Carrying the Minimized Bridging Sequences," Hum Gene Ther. 22(1):77-83 (2011).

International Search Report and Written Opinion for International Application No. PCT/US2020/017257, dated Apr. 29, 2020 (22 pages).

International Search Report and Written Opinion for International Patent Application No. PCT/US2020/058265, mailed Feb. 8, 2021 (15 pages).

Skarnes et al., "A conditional knockout resource for the genome-wide study of mouse gene function," available in PMC Feb. 14, 2013, published in final edited form as: Nature. 474(7351):337-342 (2011) (18 pages).

Boye et al., "Transduction and Tropism of an Abbreviated Form of CMV-Chicken β-Actin Promoter (CBA) With AAV in Mouse Retina," ARVO Annual Meeting Abstract May 2006, published in: Investigative Opthalmology & Visual Science. 47: 852 (2006) (2 pages) (Abstract only).

Lovell, "Mouse DNA sequence from clone RP23-135F6 on chromosome 11," European Nucleotide Archive, EMBL-EBI. (2012) (15 pages).

Higashimoto et al., "The woodchuck hepatitis virus post-transcriptional regulatory element reduces readthrough transcription from retroviral vectors," Gene Ther. 14(17):1298-304 (2007).

U.S. Appl. No. 19/063,826, filed Feb. 26, 2025, Burns et al.

"Types of CFTR Mutations," Cystic Fibrosis Foundation. <https://www.cff.org/research-clinical-trials/types-cftr-mutations#:-:text=>, accessed Mar. 1, 2025 (9 pages).

Akil et al., "Restoration of Hearing in the VGLUT3 Knockout Mouse Using Virally Mediated Gene Therapy," Neuron. 75:283-293 (2012).

Al-Hussaini et al., "Mature retinal pigment epithelium cells are retained in the cell cycle and proliferate in vivo," Mol Vis. 14:1784-91 (2008).

Allocca et al., "Serotype-dependent packaging of large genes in adeno-associated viral vectors results in effective gene delivery in mice," J Clin Invest. 118(5):1955-64 (May 2008) (11 pages).

Avraham, "What's hot about otoferlin," EMBO J. 35(23):2502-4 (Nov. 7, 2016).

Barnes et al., "Remarkable Rigidity of the Single Î±-Helical Domain of Myosin-VI as Revealed by NMR Spectroscopy," J Am Chem Soc. 141(22):9004-9017 (Jun. 2019).

Calabro, Exploring MYO7A function in novel mouse models and improving AAV-Dual Vector gene therapy for Usher Syndrome 1B. Phd dissertation. University of Florida. pp. 1-138 (Dec. 2019).

Chen et al., "Molecular cloning and domain structure of human myosin-VIIa, the gene product defective in Usher syndrome 1B," Genomics 36(3):440-8 (Sep. 15, 1996).

Daya et al., "Gene therapy using adeno-associated virus vectors," Clin Microbiol Rev. 21(4):583-93 (Oct. 2008).

Dong et al., "Characterization of genome integrity for oversized recombinant AAV vector," Mol Ther. 18(1):87-92 (Jan. 2010).

Duan et al., "Circular intermediates of recombinant adeno-associated virus have defined structural characteristics responsible for long-term episomal persistence in muscle tissue," J Virol. 72(11):8568-77 (Nov. 1998).

Freni et al., "Cochlear Implant Surgery: Endomeatal Approach versus Posterior Tympanotomy," Int. J. Environ. Res. Public Health 17:4187 (Jun. 2020) (9 pages).

GenBank: U39226.1, "Human myosin VIIa (USH1B) mRNA, complete cds" (Jul. 11, 1996) (4 pages).

GenPept Accession NP_001274418.1, dated Apr. 23, 2017, (4 pages) retrieved from https://www.ncbi.nlm.nih.gov/protein/566559996?sat=46&satkey=73202094.

Hashimoto et al., "Lentiviral gene replacement therapy of retinas in a mouse model for Usher syndrome type 1B," Gene Ther. 14(7):584-94 (Apr. 2007) (21 pages).

Jacobson et al., "Usher syndromes due to MYO7A, PCDH15, USH2A or GPR98 mutations share retinal disease mechanism," Hum Mol Genet. 17(15):2405-15 (Aug. 1, 2008).

Kim et al., "Direct isolation and identification of promoters in the human genome," Genome Res. 15(6):830-9 (Jun. 2005) (11 pages).

Lai et al., "Evidence for the failure of adeno-associated virus serotype 5 to package a viral genome > or =8.2 kb," Mol Ther. 18(1):75-9 (Jan. 2010).

Laine et al., "Cell cycle regulation in the inner ear sensory epithelia: role of cyclin D1 and cyclin-dependent kinase inhibitors," Dev Biol. 337(1):134-46 (Jan. 2010).

Li et al., "High-efficiency transduction of fibroblasts and mesenchymal stem cells by tyrosine-mutant AAV2 vectors for their potential use in cellular therapy," Hum Gene Ther. 21(11):1527-43 (Nov. 2010) (17 pages).

Lopes et al., "Retinal gene therapy with a large MYO7A cDNA using adeno-associated virus," Gene Ther. 20(8):824-33 (Aug. 2013) (21 pages).

McClements et al., "A fragmented adeno-associated viral dual vector strategy for treatment of diseases caused by mutations in large genes leads to expression of hybrid transcripts," J Genet Syndr Gene Ther. 7(5):311 (Nov. 14, 2016) (16 pages).

NCBI Accession No. NP_001274418. otoferlin isoform e [ *Homo sapiens* (human) ]. Retrieved Apr. 27, 2025_https://www.ncbi.nlm. nih.gov/protein/NP_001274418 (4 pages).

NCBI Reference Sequence: NM_001632.5, "*Homo sapiens* alkaline phosphatase, placental (ALPP), mRNA" (Apr. 4, 2024) (5 pages).

NCBI Reference Sequence: NP_000251.3, "unconventional myosin-VIIa isoform 1 [*Homo sapiens*]" (Dec. 11, 2024) (5 pages).

Orthwein et al., "A mechanism for the suppression of homologous recombination in G1 cells," Nature. 528(7582):422-6 (Dec. 2015); retraction in: Nature. 638(8051):844 (Feb. 2025) (35 pages).

OTOF sequence comparison of Yasunaga SEQ ID No. 70 with present SEQ ID No. 5 (dated Apr. 12, 2024), from U.S. Appl. No. 17/290,082 Office Action, Apr. 18, 2024, 5 pages.

Regalado et al., "Some deaf children in China can hear after gene therapy treatment," MIT Technology Review. <https://www.technologyreview.com/2023/10/27/1082551/gene-treatment-deaf-children-hearing-china/>, published Oct. 27, 2023 (7 pages).

Weil et al., "Human myosin VIIA responsible for the Usher 1B syndrome: a predicted membrane-associated motor protein expressed in developing sensory epithelia," Proc Natl Acad Sci USA. 93(8):3232-7 (Apr. 16, 1996).

Wu et al., "Effect of genome size on AAV vector packaging," Mol Ther. 18(1):80-6 (Jan. 2010).

Yan et al., "Inverted terminal repeat sequences are important for intermolecular recombination and circularization of adeno-associated virus genomes," J Virol. 79(1):364-79 (Jan. 2005).

Zhang et al., "Single amino acid change alters specificity of the multi-allelic wheat stem rust resistance locus SR9," Nat Commun. 14(1):7354 (Nov. 2023) (12 pages).

* cited by examiner

V5 isoform
Dose: 7E9 vg/ear

V1 isoform
Dose: 3E9 vg/ear

FIG. 8

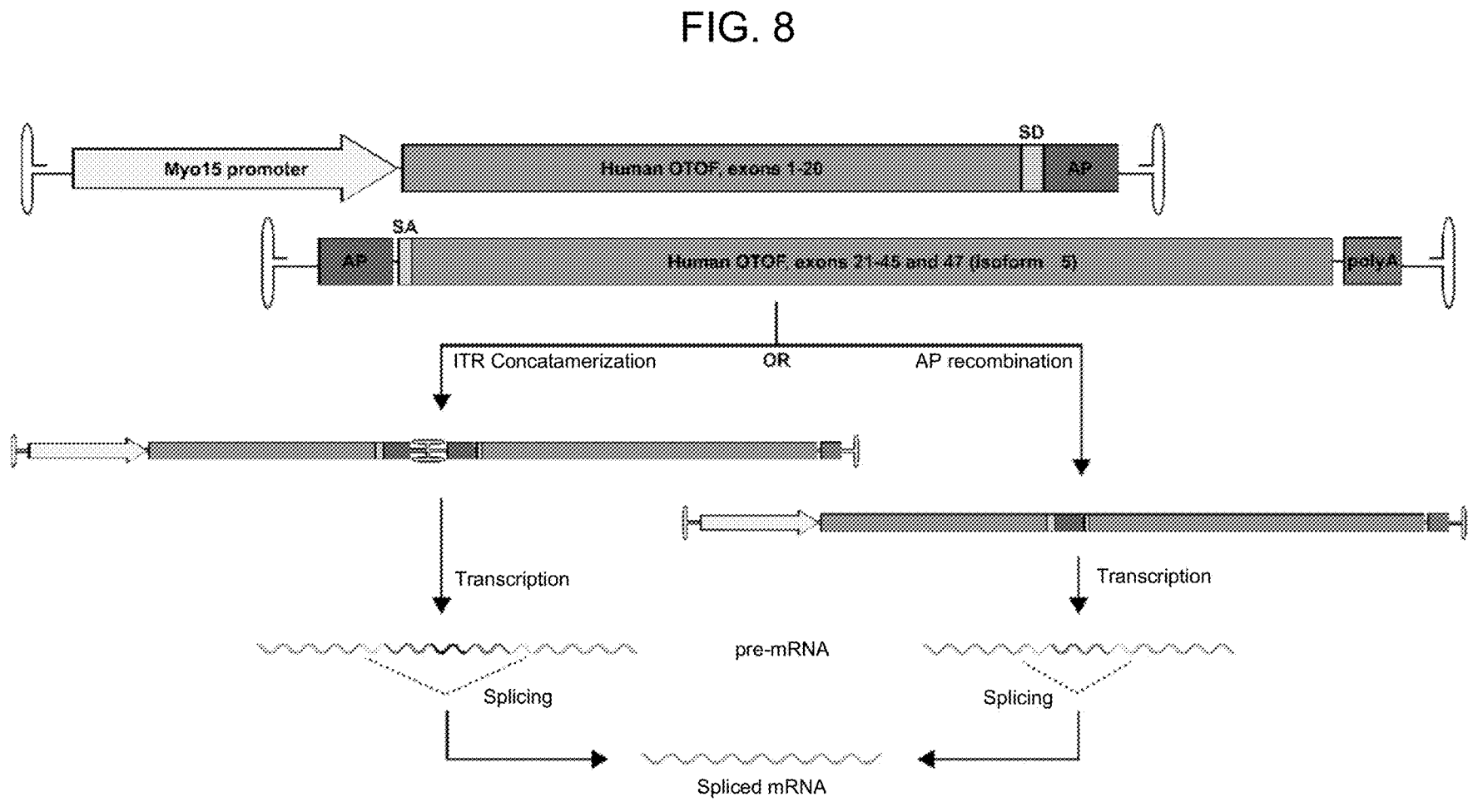

Myo15 promoter

Human OTOF exons 1-20

SD

AP

SA

AP

Human OTOF exons 21-45 and 47 (isoform 5)

PolyA

AP recombination

ITR Concatamerization

QR

Transcription

Transcription pre-mRNA

Splicing

Splicing

Spliced mRNA

COMPOSITIONS AND METHODS FOR TREATING SENSORINEURAL HEARING LOSS USING OTOFERLIN DUAL VECTOR SYSTEMS

SEQUENCE LISTING

The instant application contains a Sequence Listing which has been submitted electronically in ASCII format and is hereby incorporated by reference in its entirety. The ASCII copy, created on Apr. 25, 2022, is named 51471-004006_Sequence_Listing_4_25_22_ST25 and is 222,051 bytes in size.

FIELD OF THE INVENTION

Described herein are compositions and methods for the treatment of sensorineural hearing loss and auditory neuropathy, particularly forms of the disease that are associated with mutations in otoferlin (OTOF), by way of OTOF gene therapy. The disclosure provides dual vector systems that include a first nucleic acid vector that contains a polynucleotide encoding an N-terminal portion of an OTOF isoform 5 protein and a second nucleic acid vector that contains a polynucleotide encoding a C-terminal portion of an OTOF isoform 5 protein. These vectors can be used to increase the expression of or provide wild-type OTOF to a subject, such as a human subject suffering from sensorineural hearing loss.

BACKGROUND

Sensorineural hearing loss is a type of hearing loss caused by defects in the cells of the inner ear or the neural pathways that project from the inner ear to the brain. Although sensorineural hearing loss is often acquired, and can be caused by noise, infections, head trauma, ototoxic drugs, or aging, there are also congenital forms of sensorineural hearing loss associated with autosomal recessive mutations. One such form of autosomal recessive sensorineural hearing loss is associated with mutation of the otoferlin (OTOF) gene, which is implicated in prelingual nonsyndromic hearing loss. In recent years, efforts to treat hearing loss have increasingly focused on gene therapy as a possible solution; however, OTOF is too large to allow for treatment using standard gene therapy approaches. There is a need for new therapeutics to treat OTOF-related sensorineural hearing loss.

SUMMARY OF THE INVENTION

The present invention is based on the inventors' discovery that OTOF isoform 5 was preferentially expressed in the inner ear of non-human primates, and that human OTOF isoform 5, but not human OTOF isoform 1, was able to rescue hearing in genetically engineered, congenitally deaf mice with Otoferlin deficiency. Accordingly, the invention provides compositions and methods for treating sensorineural hearing loss or auditory neuropathy in a subject, such as a human subject. The compositions and methods of the disclosure pertain to dual vector systems for the delivery of a polynucleotide encoding an otoferlin (OTOF) isoform 5 protein to a subject having or at risk of developing sensorineural hearing loss or auditory neuropathy (e.g., a subject with a mutation in OTOF). For example, using the compositions and methods described herein, a first nucleic acid vector (e.g., a first adeno-associated virus (AAV) vector) and a second nucleic acid vector (e.g., a second AAV vector) that each encode a portion of a functional OTOF isoform 5 protein may be delivered to a subject by way of viral gene therapy. The compositions and methods described herein may also be used to increase expression of a WT OTOF protein (e.g., a full-length OTOF isoform 5 protein) in a cochlear hair cell (e.g., an inner hair cell) and/or to treat a subject having or at risk of developing sensorineural hearing loss, such as a subject having a mutation in OTOF.

In a first aspect, the invention provides a dual vector system including a first AAV vector comprising a Myo15 promoter operably linked to a first coding polynucleotide that encodes an N-terminal portion of an Otoferlin (OTOF) isoform 5 protein, a splice donor sequence positioned 3' of the first coding polynucleotide, and a first recombinogenic region positioned 3' of the splice donor sequence; and a second AAV vector comprising a second recombinogenic region, a splice acceptor sequence positioned 3' of the second recombinogenic region, a second coding polynucleotide that encodes a C-terminal portion of the OTOF isoform 5 protein positioned 3' of the splice acceptor sequence, and a poly(A) sequence positioned 3' of the second coding polynucleotide; in which the first coding polynucleotide and the second coding polynucleotide that encode the OTOF isoform 5 protein do not overlap, and in which neither the first nor the second AAV vector encodes the full-length OTOF isoform 5 protein.

In some embodiments, the first AAV vector and the second AAV vector include an AAV1 capsid.

In some embodiments, the first AAV vector and the second AAV vector include an AAV9 capsid.

In some embodiments, the Myo15 promoter comprises a first region having at least 85% sequence identity (e.g., 85%, 90%, 95%, 96%, 97%, 98%, 99%, or more, sequence identity) to SEQ ID NO: 7 or a functional portion or derivative thereof including the sequence of SEQ ID NO: 9 and/or SEQ ID NO: 10 joined (e.g., operably linked) to a second region having at least 85% sequence identity (e.g., 85%, 90%, 95%, 96%, 97%, 98%, 99%, or more, sequence identity) to SEQ ID NO: 8 or a functional portion or derivative thereof including the sequence of SEQ ID NO: 14 and/or SEQ ID NO: 15, optionally containing a linker comprising one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 7. In some embodiments, the second region comprises or consists of the sequence of SEQ ID NO: 8. In some embodiments, the Myo15 promoter comprises or consists of the sequence of SEQ ID NO: 19. In some embodiments, the Myo15 promoter comprises or consists of the sequence of SEQ ID NO: 21. In some embodiments, the Myo15 promoter comprises or consists of the sequence of SEQ ID NO: 22. In some embodiments, the Myo15 promoter comprises or consists of the sequence of SEQ ID NO: 36. In some embodiments, the Myo15 promoter comprises or consists of the sequence of SEQ ID NO: 37. In some embodiments, the Myo15 promoter comprises or consists of the sequence of SEQ ID NO: 42. In some embodiments, the Myo15 promoter comprises or consists of the sequence of SEQ ID NO: 43.

In some embodiments, the Myo15 promoter comprises a first region having at least 85% sequence identity (e.g., 85%, 90%, 95%, 96%, 97%, 98%, 99%, or more, sequence identity) to SEQ ID NO: 8 or a functional portion or derivative thereof including the sequence of SEQ ID NO: 14 and/or SEQ ID NO: 15, joined (e.g., operably linked) to a second region having at least 85% sequence identity (e.g., 85%, 90%, 95%, 96%, 97%, 98%, 99%, or more, sequence identity) to SEQ ID NO: 7 or a functional portion or derivative thereof including the sequence of SEQ ID NO: 9 and/or SEQ ID NO: 10, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 8. In some embodiments, the second region comprises or consists of the sequence of SEQ ID NO: 7. In some embodiments, the Myo15 promoter comprises or consists of the sequence of SEQ ID NO: 20. In some embodiments, the Myo15 promoter comprises or consists of the sequence of SEQ ID NO: 41.

In some embodiments, the Myo15 promoter comprises a region having at least 85% sequence identity (e.g., 85%, 90%, 95%, 96%, 97%, 98%, 99%, or more, sequence identity) to SEQ ID NO: 7 or a functional portion or derivative thereof including the sequence of SEQ ID NO: 9 and/or SEQ ID NO: 10. In some embodiments, the region comprises or consists of the sequence of SEQ ID NO: 7.

In some embodiments, the Myo15 promoter comprises a region having at least 85% sequence identity (e.g., 85%, 90%, 95%, 96%, 97%, 98%, 99%, or more, sequence identity) to SEQ ID NO: 8 or a functional portion or derivative thereof including the sequence of SEQ ID NO: 14 and/or SEQ ID NO: 15. In some embodiments, the region comprises or consists of the sequence of SEQ ID NO: 8.

In some embodiments, the functional portion of SEQ ID NO: 7 contains the sequence of SEQ ID NO: 9. In some embodiments, the functional portion of SEQ ID NO: 7 contains the sequence of SEQ ID NO: 10. In some embodiments, the functional portion of SEQ ID NO: 7 contains the sequence of SEQ ID NO: 9 and the sequence of SEQ ID NO: 10. In some embodiments, the functional portion of SEQ ID NO: 7 contains the sequence of SEQ ID NO: 11. In some embodiments, the functional portion of SEQ ID NO: 7 contains the sequence of SEQ ID NO: 12. In some embodiments, the functional portion of SEQ ID NO: 7 contains the sequence of SEQ ID NO: 13. In some embodiments, the functional portion of SEQ ID NO: 7 contains the sequence of SEQ ID NO: 33.

In some embodiments, the functional portion of SEQ ID NO: 8 contains the sequence of SEQ ID NO: 14. In some embodiments, the functional portion of SEQ ID NO: 8 contains the sequence of SEQ ID NO: 15. In some embodiments, the functional portion of SEQ ID NO: 8 contains the sequence of SEQ ID NO: 34. In some embodiments, the functional portion of SEQ ID NO: 8 contains the sequence of SEQ ID NO: 35. In some embodiments, the functional portion of SEQ ID NO: 8 contains the sequence of SEQ ID NO: 14 and the sequence of SEQ ID NO: 15. In some embodiments, the functional portion of SEQ ID NO: 8 contains the sequence of SEQ ID NO: 16. In some embodiments, the functional portion of SEQ ID NO: 8 contains the sequence of SEQ ID NO: 17. In some embodiments, the functional portion of SEQ ID NO: 8 contains the sequence of SEQ ID NO: 18. In some embodiments, the functional portion of SEQ ID NO: 8 contains the sequence of SEQ ID NO: 38.

In some embodiments, the Myo15 promoter has at least 85% sequence identity (e.g., 85%, 90%, 95%, 96%, 97%, 98%, 99%, or more, sequence identity) to the nucleic acid sequence of any one of SEQ ID NOs: 33-41. In some embodiments, the Myo15 promoter comprises or consists of the sequence of SEQ ID NO: 33. In some embodiments, the Myo15 promoter comprises or consists of the sequence of SEQ ID NO: 34. In some embodiments, the Myo15 promoter comprises or consists of the sequence of SEQ ID NO: 35. In some embodiments, the Myo15 promoter comprises or consists of the sequence of SEQ ID NO: 36. In some embodiments, the Myo15 promoter comprises or consists of the sequence of SEQ ID NO: 37. In some embodiments, the Myo15 promoter comprises or consists of the sequence of SEQ ID NO: 38. In some embodiments, the Myo15 promoter comprises or consists of the sequence of SEQ ID NO: 39. In some embodiments, the Myo15 promoter comprises or consists of the sequence of SEQ ID NO: 40. In some embodiments, the Myo15 promoter comprises or consists of the sequence of SEQ ID NO: 41.

In some embodiments, the Myo15 promoter comprises a first region having at least 85% sequence identity (e.g., 85%, 90%, 95%, 96%, 97%, 98%, 99%, or more, sequence identity) to SEQ ID NO: 23 or a functional portion or derivative thereof including the sequence of SEQ ID NO: 25 joined (e.g., operably linked) to a second region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, optionally containing a linker comprising one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region. In some embodiments, the first region comprises or consists of the sequence of SEQ ID NO: 23. In some embodiments, the second region comprises or consists of the sequence of SEQ ID NO: 24. In some embodiments, the Myo15 promoter comprises or consists of the sequence of SEQ ID NO: 31. In some embodiments, the Myo15 promoter comprises or consists of the sequence of SEQ ID NO: 32.

In some embodiments, the Myo15 promoter comprises a first region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, joined (e.g., operably linked) to a second region having at least 85% sequence identity (e.g., 85%, 90%, 95%, 96%, 97%, 98%, 99%, or more, sequence identity) to SEQ ID NO: 23 or a functional portion or derivative thereof including the sequence of SEQ ID NO: 25, optionally containing a linker including one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region. In some embodiments, the first region comprises or consists of the sequence of SEQ ID NO: 24. In some embodiments, the second region comprises or consists of the sequence of SEQ ID NO: 23.

In some embodiments, the Myo15 promoter comprises a region having at least 85% sequence identity (e.g., 85%, 90%, 95%, 96%, 97%, 98%, 99%, or more, sequence identity) to SEQ ID NO: 23 or a functional portion or derivative thereof including the sequence of SEQ ID NO: 25. In some embodiments, the region comprises or consists of the sequence of SEQ ID NO: 23.

In some embodiments, the Myo15 promoter comprises a region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27. In some embodiments, the region comprises or consists of the sequence of SEQ ID NO: 24.

In some embodiments, the functional portion of SEQ ID NO: 23 contains the sequence of SEQ ID NO: 25.

In some embodiments, the functional portion of SEQ ID NO: 24 contains the sequence of SEQ ID NO: 26. In some embodiments, the functional portion of SEQ ID NO: 24 contains the sequence of SEQ ID NO: 27. In some embodiments, the functional portion of SEQ ID NO: 24 contains the sequence of SEQ ID NO: 26 and the sequence of SEQ ID NO: 27. In some embodiments, the functional portion of SEQ ID NO: 24 contains the sequence of SEQ ID NO: 28. In some embodiments, the functional portion of SEQ ID NO: 24 contains the sequence of SEQ ID NO: 29. In some embodiments, the functional portion of SEQ ID NO: 24 contains the sequence of SEQ ID NO: 30.

In another aspect, the invention provides a dual vector system including a first AAV1 vector containing a ubiquitous promoter operably linked to a first coding polynucleotide that encodes an N-terminal portion of an OTOF isoform 5 protein, a splice donor sequence positioned 3' of the first coding polynucleotide, and a first recombinogenic region positioned 3' of the splice donor sequence; and a second AAV1 vector containing a second recombinogenic region, a splice acceptor sequence positioned 3' of the second recombinogenic region, a second coding polynucleotide that encodes a C-terminal portion of the OTOF isoform 5 protein positioned 3' of the splice acceptor sequence, and a poly(A) sequence positioned 3' of the second coding polynucleotide; in which the first coding polynucleotide and the second coding polynucleotide that encode the OTOF isoform 5 protein do not overlap, and in which neither the first nor second AAV1 vector encodes the full-length OTOF isoform 5 protein.

In some embodiments, the ubiquitous promoter is selected from the group consisting of a CAG promoter, a cytomegalovirus (CMV) promoter, and a truncated CMV-chicken β-actin promoter (smCBA). In some embodiments, the ubiquitous promoter is the smCBA promoter. In some embodiments, the smCBA promoter comprises or consists of the sequence of SEQ ID NO: 44.

In some embodiments of any of the foregoing aspects, the first and second recombinogenic regions are the same.

In some embodiments of any of the foregoing aspects, the first recombinogenic region and/or the second recombinogenic region is an AK recombinogenic region. In some embodiments, the AK recombinogenic region comprises or consists of the sequence of SEQ ID NO: 47.

In some embodiments of any of the foregoing aspects, the first recombinogenic region and/or the second recombinogenic region is an AP gene fragment. In some embodiments, the AP gene fragment comprises or consists of the sequence of any one of SEQ ID NOs: 48-53. In some embodiments, the AP gene fragment comprises or consists of the sequence of SEQ ID NO: 51.

In some embodiments of any of the foregoing aspects, each of the first and second coding polynucleotides encode about half of the OTOF isoform 5 protein sequence.

In some embodiments of any of the foregoing aspects, the first coding polynucleotide encodes amino acids 1-802 of SEQ ID NO: 1. In some embodiments of any of the foregoing aspects, the second coding polynucleotide encodes amino acids 803-1997 of SEQ ID NO: 1.

In some embodiments of any of the foregoing aspects, the first and second coding polynucleotides are divided at an OTOF exon boundary. In some embodiments, the first and second coding polynucleotides are divided at the boundary between exons 20 and 21 of OTOF.

In some embodiments of any of the foregoing aspects, the first coding polynucleotide consists of exons 1-20 of a polynucleotide encoding the OTOF isoform 5 protein and the second coding polynucleotide consists of exons 21-45 and 47 of a polynucleotide encoding the OTOF isoform 5 protein (e.g., a polynucleotide encoding a human OTOF isoform 5 protein).

In some embodiments of any of the foregoing aspects, the first and second coding polynucleotides that encode the OTOF isoform 5 protein do not comprise introns.

In some embodiments of any of the foregoing aspects, the OTOF isoform 5 protein is a human OTOF isoform 5 protein (e.g., the protein having the sequence of SEQ ID NO: 1).

In some embodiments of any of the foregoing aspects, the OTOF isoform 5 protein comprises the sequence of SEQ ID NO: 1 or a variant thereof having one or more (e.g., 1, 2, 3, 4, 5, 6, 7, 8, 9, 10, 11, 12, 13, 14, 15, 16, 17, 18, 19, 20 or more) conservative amino acid substitutions. In some embodiments, no more than 10% (10%, 9%, 8%, 7%, 6%, 5%, 4%, 3%, 2%, 1%, or fewer) of the amino acids in the OTOF isoform 5 protein variant are conservative amino acid substitutions. In some embodiments, the OTOF isoform 5 protein consists of the sequence of SEQ ID NO: 1.

In some embodiments of any of the foregoing aspects, the OTOF isoform 5 protein is encoded by the sequence of SEQ ID NO: 2.

In some embodiments of any of the foregoing aspects, the OTOF isoform 5 protein is encoded by the sequence of SEQ ID NO: 3.

In some embodiments of any of the foregoing aspects, the N-terminal portion of the OTOF isoform 5 protein consists of the sequence of SEQ ID NO: 58 or a variant thereof having one or more (e.g., 1, 2, 3, 4, 5, 6, 7, 8, 9, 10, 11, 12, 13, 14, 15, 16, 17, 18, 19, 20 or more) conservative amino acid substitutions. In some embodiments, no more than 10% (10%, 9%, 8%, 7%, 6%, 5%, 4%, 3%, 2%, 1%, or fewer) of the amino acids in the N-terminal portion of the OTOF isoform 5 protein variant are conservative amino acid substitutions. In some embodiments, the N-terminal portion of the OTOF isoform 5 protein consists of the sequence of SEQ ID NO: 58. In some embodiments, the N-terminal portion of the OTOF isoform 5 protein is encoded by the sequence of SEQ ID NO: 56.

In some embodiments of any of the foregoing aspects, the C-terminal portion of the OTOF isoform 5 protein consists of the sequence of SEQ ID NO: 59 or a variant thereof having one or more (e.g., 1, 2, 3, 4, 5, 6, 7, 8, 9, 10, 11, 12, 13, 14, 15, 16, 17, 18, 19, 20 or more) conservative amino acid substitutions. In some embodiments, no more than 10% (10%, 9%, 8%, 7%, 6%, 5%, 4%, 3%, 2%, 1%, or fewer) of the amino acids in the C-terminal portion of the OTOF isoform 5 protein variant are conservative amino acid substitutions. In some embodiments, the C-terminal portion of the OTOF isoform 5 protein consists of the sequence of SEQ ID NO: 59. In some embodiments, the C-terminal portion of the OTOF isoform 5 protein is encoded by the sequence of SEQ ID NO: 57.

In some embodiments of any of the foregoing aspects, the first vector includes a first inverted terminal repeat (ITR) sequence 5' of the promoter and a second ITR sequence 3' of the recombinogenic region, and the second vector includes a first ITR sequence 5' of the recombinogenic region and a second ITR sequence 3' of the poly(A) sequence. In some embodiments, the ITRs in the first vector and second vector are AAV2 ITRs. In some embodiments, the ITRs in the first vector and second vector have at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to AAV2 ITRs.

In some embodiments of any of the foregoing aspects, the poly(A) sequence is a bovine growth hormone (bGH) poly (A) signal sequence.

In some embodiments of any of the foregoing aspects, the splice donor sequence in the first vector comprises or consists of the sequence of SEQ ID NO: 54.

In some embodiments of any of the foregoing aspects, the splice acceptor sequence in the second vector comprises or consists of the sequence of SEQ ID NO: 55.

In some embodiments of any of the foregoing aspects, the first AAV vector comprises a Kozak sequence 3' of the promoter and 5' of the first coding polynucleotide that encodes the N-terminal portion of the OTOF isoform 5 protein.

In some embodiments of any of the foregoing aspects, the first AAV vector contains a polynucleotide sequence comprising the sequence of nucleotides 2272 to 6041 of SEQ ID NO: 60. In some embodiments of any of the foregoing aspects, the first AAV vector contains a polynucleotide sequence comprising or consisting of the sequence of nucleotides 2049 to 6264 of SEQ ID NO: 60.

In some embodiments of any of the foregoing aspects, the first AAV vector contains a polynucleotide sequence comprising the sequence of nucleotides 182 to 3949 of SEQ ID NO: 62. In some embodiments of any of the foregoing aspects, the first AAV vector contains a polynucleotide sequence comprising or consisting of the sequence of nucleotides 19 to 4115 of SEQ ID NO: 62.

In some embodiments of any of the foregoing aspects, the first AAV vector contains a polynucleotide sequence comprising the sequence of positions 2267 to 6014 of SEQ ID NO: 64. In some embodiments of any of the foregoing aspects, the first AAV vector contains a polynucleotide sequence comprising or consisting of the sequence of positions 2049 to 6237 of SEQ ID NO: 64.

In some embodiments of any of the foregoing aspects, the first AAV vector contains a polynucleotide sequence comprising the sequence of positions 177 to 3924 of SEQ ID NO: 65. In some embodiments of any of the foregoing aspects, the first AAV vector contains a polynucleotide sequence comprising or consisting of the sequence of positions 19 to 4090 of SEQ ID NO: 65.

In some embodiments of any of the foregoing aspects, the second AAV vector contains a polynucleotide sequence comprising the sequence of nucleotides 2267 to 6476 of SEQ ID NO: 61. In some embodiments of any of the foregoing aspects, the second AAV vector contains a polynucleotide sequence comprising or consisting of the sequence of nucleotides 2049 to 6693 of SEQ ID NO: 61.

In some embodiments of any of the foregoing aspects, the second AAV vector contains a polynucleotide sequence comprising the sequence of nucleotides 187 to 4396 of SEQ ID NO: 63. In some embodiments of any of the foregoing aspects, the second AAV vector contains a polynucleotide sequence comprising or consisting of the sequence of nucleotides 19 to 4589 of SEQ ID NO: 63.

In some embodiments of any of the foregoing aspects, the first AAV vector contains a polynucleotide sequence comprising the sequence of nucleotides 235 to 4004 of SEQ ID NO: 66. In some embodiments of any of the foregoing aspects, the first AAV vector contains a polynucleotide sequence comprising or consisting of the sequence of nucleotides 12 to 4227 of SEQ ID NO: 66.

In some embodiments of any of the foregoing aspects, the first AAV vector contains a polynucleotide sequence comprising the sequence of nucleotides 230 to 3977 of SEQ ID NO: 68. In some embodiments of any of the foregoing aspects, the first AAV vector contains a polynucleotide sequence comprising or consisting of the sequence of nucleotides 12 to 4200 of SEQ ID NO: 68.

In some embodiments of any of the foregoing aspects, the second AAV vector contains a polynucleotide sequence comprising the sequence of nucleotides 229 to 4438 of SEQ ID NO: 67. In some embodiments of any of the foregoing aspects, the second AAV vector contains a polynucleotide sequence comprising or consisting of the sequence of nucleotides 12 to 4655 of SEQ ID NO: 67.

In another aspect, the invention provides a pharmaceutical composition containing a dual vector system of the invention and a pharmaceutically acceptable excipient. In some embodiments, the pharmaceutical composition is formulated for administration to the inner ear.

In another aspect, the invention provides a kit containing a dual vector system or pharmaceutical composition of the invention.

In another aspect, the invention provides a method of increasing OTOF expression (e.g., wild-type OTOF expression, e.g., full-length OTOF isoform 5 expression) in a subject in need thereof by administering to the subject a therapeutically effective amount of a dual vector system of the invention.

In another aspect, the invention provides a method of treating a subject having or at risk of developing sensorineural hearing loss by administering to the subject a therapeutically effective amount of a dual vector system of the invention.

In another aspect, the invention provides a method of treating a subject having or at risk of developing auditory neuropathy by administering to the subject a therapeutically effective amount of a dual vector system of the invention.

In some embodiments of any of the foregoing aspects, the subject has a mutation in OTOF.

In some embodiments of any of the foregoing aspects, the subject has been identified as having a mutation in OTOF.

In some embodiments of any of the foregoing aspects, the method further includes identifying the subject as having a mutation in OTOF prior to administering the composition.

In some embodiments of any of the foregoing aspects, the subject has or has been identified as having Deafness, Autosomal Recessive 9 (DFNB9).

In some embodiments of any of the foregoing aspects, the method further includes the step of evaluating the hearing of the subject prior to administering the dual vector system.

In some embodiments of any of the foregoing aspects, the dual vector system is administered locally to the ear. In some embodiments, the dual vector system is administered by injection through the round window membrane, injection into a semicircular canal, canalostomy, insertion of a catheter through the round window membrane, transtympanic injection, or intratympanic injection.

In some embodiments of any of the foregoing aspects, the method increases OTOF expression in a cochlear hair cell. In some embodiments, the cochlear hair cell is an inner hair cell.

In some embodiments of any of the foregoing aspects, the subject is a mammal. In some embodiments, the subject is a human.

In some embodiments of any of the foregoing aspects, the method further comprises evaluating the hearing of the subject after administering the dual vector system.

In some embodiments of any of the foregoing aspects, the dual vector system increases OTOF expression in a cell (e.g., a cochlear hair cell), improves hearing (e.g., as assessed by standard tests, such as audiometry, auditory brainstem response (ABR), electrocochleography (ECOG), and otoacoustic emissions), prevents or reduces hearing loss, delays the development of hearing loss, slows the progression of hearing loss, improves speech discrimination, or improves hair cell function.

In some embodiments of any of the foregoing aspects, the dual vector system is administered in an amount sufficient to increase OTOF expression in a cochlear hair cell, prevent or reduce hearing loss, delay the development of hearing loss, slow the progression of hearing loss, improve hearing (e.g., as assessed by standard tests, such as audiometry, ABR, ECOG, and otoacoustic emissions), improve speech discrimination, or improve hair cell function.

In another aspect, the invention provides a method of increasing OTOF expression in a cell by introducing a dual vector system of the invention into the cell.

In some embodiments, the cell is a cochlear hair cell. In some embodiments, the cell is an inner hair cell. In some embodiments, the cell is a mammalian cell. In some embodiments, the cell is a human cell.

In some embodiments of any of the foregoing aspects, the first vector and the second vector are administered concurrently.

In some embodiments of any of the foregoing aspects, the first vector and the second vector are administered sequentially.

In some embodiments of any of the foregoing aspects, the first vector and the second vector are administered at a concentration of $1\times10^7$ vector genomes (VG)/ear to about $2\times10^{15}$ VG/ear (e.g., $1\times10^7$ VG/ear, $2\times10^7$ VG/ear, $3\times10^7$ VG/ear, $4\times10^7$ VG/ear, $5\times10^7$ VG/ear, $6\times10^7$ VG/ear, $7\times10^7$ VG/ear, $8\times10^7$VG/ear, $9\times10^7$ VG/ear, $1\times10^8$ VG/ear, $2\times10^8$ VG/ear, $3\times10^8$ VG/ear, $4\times10^8$VG/ear, $5\times10^8$ VG/ear, $6\times10^8$ VG/ear, $7\times10^8$ VG/ear, $8\times10^8$ VG/ear, $9\times10^8$ VG/ear, $1\times10^9$ VG/ear, $2\times10^9$ VG/ear, $3\times10^9$VG/ear, $4\times10^9$ VG/ear, $5\times10^9$ VG/ear, $6\times10^9$ VG/ear, $7\times10^9$ VG/ear, $8\times10^9$VG/ear, $9\times10^9$ VG/ear, $1\times10^{10}$ VG/ear, $2\times10^{10}$ VG/ear, $3\times10^{10}$ VG/ear, $4\times10^{10}$ VG/ear, $5\times10^{10}$ VG/ear, $6\times10^{10}$ VG/ear, $7\times10^{10}$ VG/ear, $8\times10^{10}$ VG/ear, $9\times10^{10}$ VG/ear, $1\times10^{11}$ VG/ear, $2\times10^{11}$ VG/ear, $3\times10^{11}$ VG/ear, $4\times10^{11}$ VG/ear, $5\times10^{11}$ VG/ear, $6\times10^{11}$ VG/ear, $7\times10^{11}$ VG/ear, $8\times10^{11}$ VG/ear, $9\times10^{11}$ VG/ear, $1\times10^{12}$ VG/ear, $2\times10^{12}$ VG/ear, $3\times10^{12}$ VG/ear, $4\times10^{12}$ VG/ear, $5\times10^{12}$ VG/ear, $6\times10^{12}$ VG/ear, $7\times10^{12}$ VG/ear, $8\times10^{12}$ VG/ear, $9\times10^{12}$ VG/ear, $1\times10^{13}$ VG/ear, $2\times10^{13}$ VG/ear, $3\times10^{13}$ VG/ear, $4\times10^{13}$ VG/ear, $5\times10^{13}$ VG/ear, $6\times10^{13}$ VG/ear, $7\times10^{13}$ VG/ear, $8\times10^{13}$ VG/ear, $9\times10^{13}$ VG/ear, $1\times10^{14}$ VG/ear, $2\times10^{14}$ VG/ear, $3\times10^{14}$ VG/ear, $4\times10^{14}$ VG/ear, $5\times10^{14}$ VG/ear, $6\times10^{14}$ VG/ear, $7\times10^{14}$VG/ear, $8\times10^{14}$VG/ear, $9\times10^{14}$ VG/ear, $1\times10^{15}$ VG/ear, or $2\times10^{15}$ VG/ear).

Definitions

As used herein, the term "about" refers to a value that is within 10% above or below the value being described.

As used herein, "administration" refers to providing or giving a subject a therapeutic agent (e.g., a composition containing a first nucleic acid vector containing a polynucleotide that encodes an N-terminal portion of an otoferlin protein and a second nucleic acid vector containing a polynucleotide that encodes a C-terminal portion of an otoferlin protein), by any effective route. Exemplary routes of administration are described herein below.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the term "cochlear hair cell" refers to group of specialized cells in the inner ear that are involved in sensing sound. There are two types of cochlear hair cells: inner hair cells and outer hair cells. Damage to cochlear hair cells and genetic mutations that disrupt cochlear hair cell function are implicated in hearing loss and deafness.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

| Representative physicochemical properties of naturally-occurring amino acids | | | | | |
| --- | --- | --- | --- | --- | --- |
| Amino Acid | 3 Letter Code | 1 Letter Code | Side-chain Polarity | Electrostatic character at physiological pH (7.4) | Steric Volume[†] |
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |

TABLE 1-continued

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in A³: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the terms "effective amount," "therapeutically effective amount," and a "sufficient amount" of a composition, vector construct, or viral vector described herein refer to a quantity sufficient to, when administered to the subject in need thereof, including a mammal, for example a human, effect beneficial or desired results, including clinical results, and, as such, an "effective amount" or synonym thereto depends upon the context in which it is being applied. For example, in the context of treating sensorineural hearing loss, it is an amount of the composition, vector construct, or viral vector sufficient to achieve a treatment response as compared to the response obtained without administration of the composition, vector construct, or viral vector. The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, or viral vector of the present disclosure is an amount which results in a beneficial or desired result in a subject as compared to a control. Note that when a combination of active ingredients is administered, the effective amount of the combination may or may not include amounts of each ingredient that would have been effective if administered individually. As defined herein, a therapeutically effective amount of a composition, vector construct, viral vector or cell of the present disclosure may be readily determined by one of ordinary skill by routine methods known in the art. Dosage regime may be adjusted to provide the optimum therapeutic response.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human cochlear hair cell).

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell, e.g., a human cochlear hair cell). Exogenous materials include those that are provided from an external source to an organism or to cultured matter extracted there from.

As used herein, the term "hair cell-specific expression" refers to production of an RNA transcript or polypeptide primarily within hair cells (e.g., cochlear hair cells) as compared to other cell types of the inner ear (e.g., spiral ganglion neurons, glia, or other inner ear cell types). Hair cell-specific expression of a transgene can be confirmed by comparing transgene expression (e.g., RNA or protein expression) between various cell types of the inner ear (e.g., hair cells vs. non-hair cells) using any standard technique (e.g., quantitative RT PCR, immunohistochemistry, Western Blot analysis, or measurement of the fluorescence of a reporter (e.g., GFP) operably linked to a promoter). A hair cell-specific promoter induces expression (e.g., RNA or protein expression) of a transgene to which it is operably linked that is at least 50% greater (e.g., 50%, 75%, 100%, 125%, 150%, 175%, 200% greater or more) in hair cells (e.g., cochlear hair cells) compared to at least 3 (e.g., 3, 4, 5, 6, 7, 8, 9, 10, or more) of the following inner ear cell types: Border cells, inner phalangeal cells, inner pillar cells, outer pillar cells, first row Deiter cells, second row Deiter cells, third row Deiter cells, Hensen's cells, Claudius cells, inner sulcus cells, outer sulcus cells, spiral prominence cells, root cells, interdental cells, basal cells of the stria vascularis, intermediate cells of the stria vascularis, marginal cells of the stria vascularis, spiral ganglion neurons, Schwann cells.

As used herein, the terms "increasing" and "decreasing" refer to modulating resulting in, respectively, greater or lesser amounts, of function, expression, or activity of a metric relative to a reference. For example, subsequent to administration of a composition in a method described herein, the amount of a marker of a metric (e.g., OTOF expression) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "intron" refers to a region within the coding region of a gene, the nucleotide sequence of which is not translated into the amino acid sequence of the corresponding protein. The term intron also refers to the corresponding region of the RNA transcribed from a gene. Introns are transcribed into pre-mRNA, but are removed during processing, and are not included in the mature mRNA.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, administration to the inner ear, and administration to a mucous membrane of the subject, wherein the administration is intended to have a local and not a systemic effect.

As used herein, the term "operably linked" refers to a first molecule that can be joined to a second molecule, wherein the molecules are so arranged that the first molecule affects the function of the second molecule. The term "operably linked" includes the juxtaposition of two or more components (e.g., a promoter and another sequence element) such that both components function normally and allow for the possibility that at least one of the components can mediate a function that is exerted upon at least one of the other components. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the terms "otoferlin isoform 5" and "OTOF isoform 5" refer to an isoform of the gene associated with nonsyndromic recessive deafness DFNB9. The human isoform of the gene is associated with reference sequence NM_001287489, and the transcript includes exons 1-45 and 47 of human otoferlin, but lacks exon 46 of the OTOF gene. The human OTOF isoform 5 protein is also known as Otoferlin isoform e. The terms "otoferlin isoform 5" and "OTOF isoform 5" also refer to variants of the wild-type OTOF isoform 5 protein and polynucleotides encoding the same, such as variant proteins having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the amino acid sequence of a wild-type OTOF isoform 5 protein (e.g., SEQ ID NO: 1) or polynucleotides having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the polynucleotide sequence of a wild-type OTOF isoform 5 gene, provided that the OTOF isoform 5 analog encoded retains the therapeutic function of wild-type OTOF isoform 5. OTOF isoform 5 protein variants can have one or more (e.g., 1, 2, 3, 4, 5, 6, 7, 8, 9, 10, 11, 12, 13, 14, 15, 16, 17, 18, 19, 20, or more) conservative amino acid substitutions relative to a wild-type OTOF isoform 5 (e.g., SEQ ID NO: 1), provided that the that the OTOF isoform 5 variant retains the therapeutic function of wild-type OTOF isoform 5 and has no more than 10% amino acid substitutions in an N-terminal portion of the amino acid sequence and no more than 10% amino acid substitutions in a C-terminal portion of the amino acid sequence. As used herein, OTOF isoform 5 may refer to the protein localized to inner hair cells or to the gene encoding this protein, depending upon the context, as will be appreciated by one of skill in the art. OTOF isoform 5 may refer to human OTOF isoform 5 or to a homolog from another mammalian species. Murine otoferlin contains one additional exon relative to human otoferlin (48 exons in murine otoferlin), and the exons of murine otoferlin that correspond to those that encode human OTOF isoform 5 are 1-5, 7-46, and 48. The exon numbering convention used herein is based on the exons currently understood to be present in the consensus transcripts of human OTOF.

As used herein, the term "plasmid" refers to a to an extrachromosomal circular double stranded DNA molecule into which additional DNA segments may be ligated. A plasmid is a type of vector, a nucleic acid molecule capable of transporting another nucleic acid to which it has been linked. Certain plasmids are capable of autonomous replication in a host cell into which they are introduced (e.g., bacterial plasmids having a bacterial origin of replication and episomal mammalian plasmids). Other vectors (e.g., non-episomal mammalian vectors) can be integrated into the genome of a host cell upon introduction into the host cell, and thereby are replicated along with the host genome. Certain plasmids are capable of directing the expression of genes to which they are operably linked.

As used herein, the terms "nucleic acid" and "polynucleotide," used interchangeably herein, refer to a polymeric form of nucleosides in any length. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules containing nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

As used herein, the terms "complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C), although other known Tm computations take into account nucleic acid structural characteristics.

As used herein, the term "promoter" refers to a recognition site on DNA that is bound by an RNA polymerase. The polymerase drives transcription of the transgene. Exemplary promoters suitable for use with the compositions and methods described herein include ubiquitous promoters (e.g., the CAG promoter, cytomegalovirus (CMV) promoter, and smCBA promoter) and cochlear hair cell-specific promoters (e.g., the Myosin 15 (Myo15) promoter).

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full-length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

$$100 \text{ multiplied by (the fraction X/Y)}$$

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "derivative" as used herein refers to a nucleic acid, peptide, or protein or a variant or analog thereof comprising one or more mutations and/or chemical modifications as compared to a corresponding full-length wild-type nucleic acid, peptide, or protein. Non-limiting examples of chemical modifications involving nucleic acids include, for example, modifications to the base moiety, sugar moiety, phosphate moiety, phosphate-sugar backbone, or a combination thereof.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio. Preferably, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "recombinogenic region" refers to a region of homology that mediates recombination between two different sequences.

As used herein, the term "regulatory sequence" includes promoters, enhancers and other expression control elements (e.g., polyadenylation signals) that control the transcription or translation of the polynucleotides that encode OTOF. Such regulatory sequences are described, for example, in Goeddel, Gene Expression Technology: Methods in Enzymology 185 (Academic Press, San Diego, CA, 1990); incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection, Nucleofection, squeeze-poration, sonoporation, optical transfection, Magnetofection, impalefection and the like.

As used herein, the terms "subject" and "patient" refer to an animal (e.g., a mammal, such as a human), veterinary animals (e.g., cats, dogs, cows, horses, sheep, pigs, etc.) and experimental animal models of diseases (e.g., mice, rats). A subject to be treated according to the methods described herein may be one who has been diagnosed with hearing loss (e.g., hearing loss associated with a mutation in OTOF), or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the terms "transduction" and "transduce" refer to a method of introducing a vector construct or a part thereof into a cell. Wherein the vector construct is contained in a viral vector such as for example an AAV vector, transduction refers to viral infection of the cell and subsequent transfer and integration of the vector construct or part thereof into the cell genome.

As used herein, "treatment" and "treating" of a state, disorder or condition can include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO94/11026; incorporated herein by reference as it pertains to vectors suitable for the expression of a gene of interest. Expression vectors suitable for use with the compositions and methods described herein contain a polynucleotide sequence as well as, e.g., additional sequence elements used for the expression of proteins and/or the integration of these polynucleotide sequences into the genome of a mammalian cell. Certain vectors that can be used for the expression of OTOF as described herein include vectors that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "wild-type" refers to a genotype with the highest frequency for a particular gene in a given organism.

In another set of experiments, Homozygous OTOF-Q828X mice were treated with an AAV1-truncated chimeric CMV-chicken β-actin (smCBA; SEQ ID NO: 44)-hOTOF (isoform 5, SEQ ID NO: 1) dual hybrid vector system by injection through the round window membrane and ABR thresholds were used to assess hearing function as described above (FIG. 3B). Untreated animals showed no detectable recovery in hearing function, while treated animals exhibited a robust recovery at four weeks post-treatment (Otof HOM at 4 weeks after treatment). When the same mice were evaluated at eight weeks post-treatment (Otof HOM at 8 weeks after treatment), ABR thresholds increased, suggesting less durable recovery with the smCBA promoter. ABR thresholds from heterozygous mice were also tested.

Figure 3A:
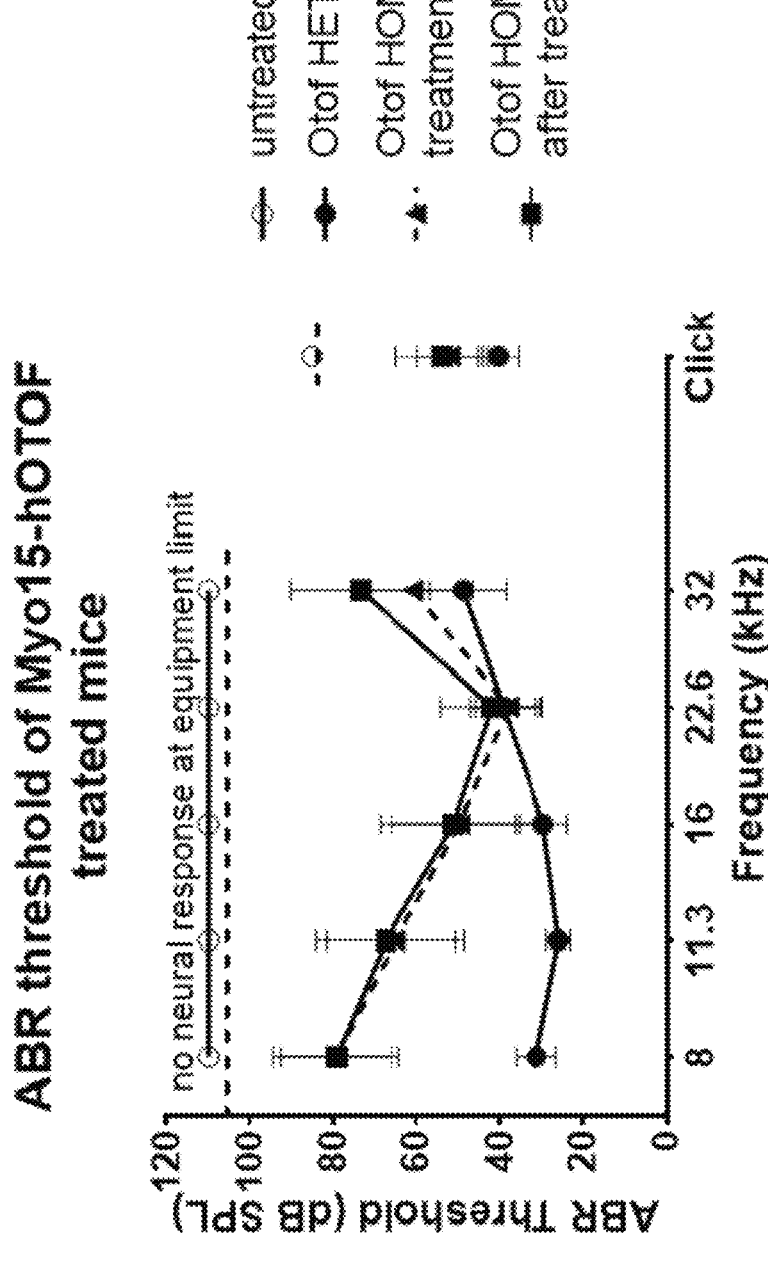
FIGS. 3A-3C are a series of graphs showing electrophysiological signatures of hearing function in mice treated with viral vectors expressing OTOF via dual hybrid vector systems. Homozygous OTOF-Q828X mice were treated with an AAV1-Myo15 (SEQ ID NO: 21)-hOTOF (isoform 5, SEQ ID NO: 1) dual hybrid vector system by injection through the round window membrane and auditory brainstem response (ABR) thresholds were used to assess hearing function (FIG. 3A). Untreated animals (untreated Otof HOM) showed no detectable recovery in hearing function, whereas treated animals exhibited robust recovery, which was consistent from four weeks post-treatment (Otof HOM at 4 weeks after treatment) to eight weeks post-treatment (Otof HOM at 8-11 weeks after treatment). ABR thresholds from heterozygous mice (Otof HET) were also tested.
Figure 3B:
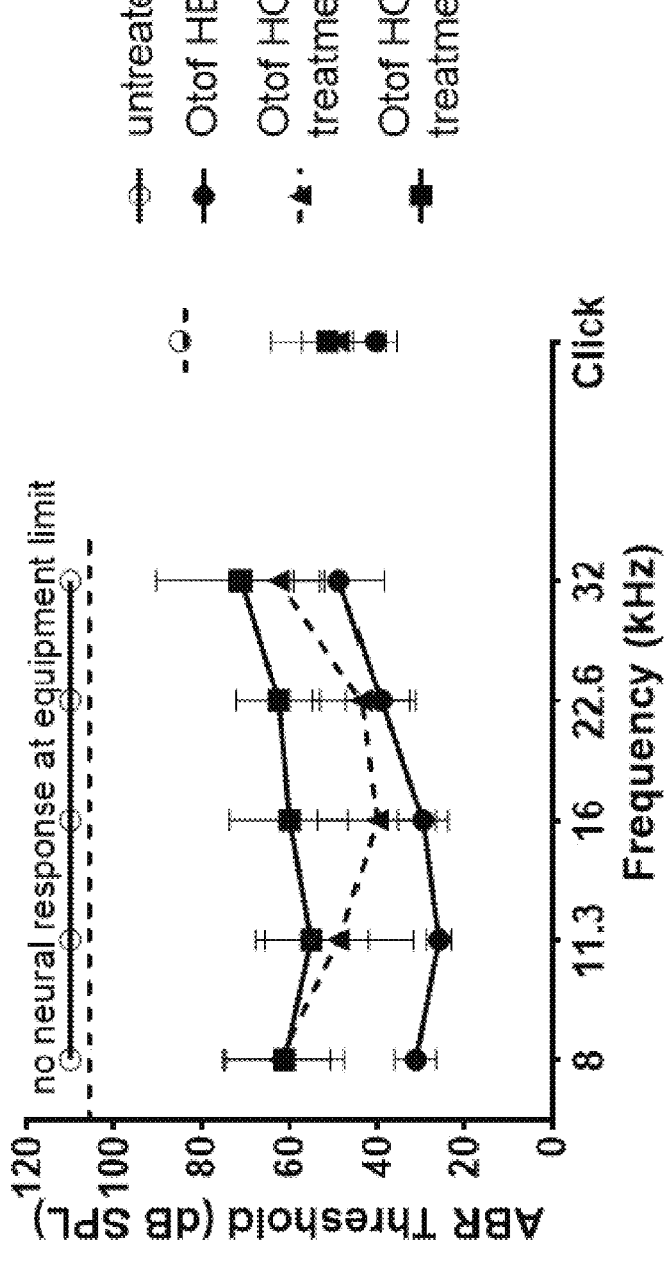
Figure 3C:
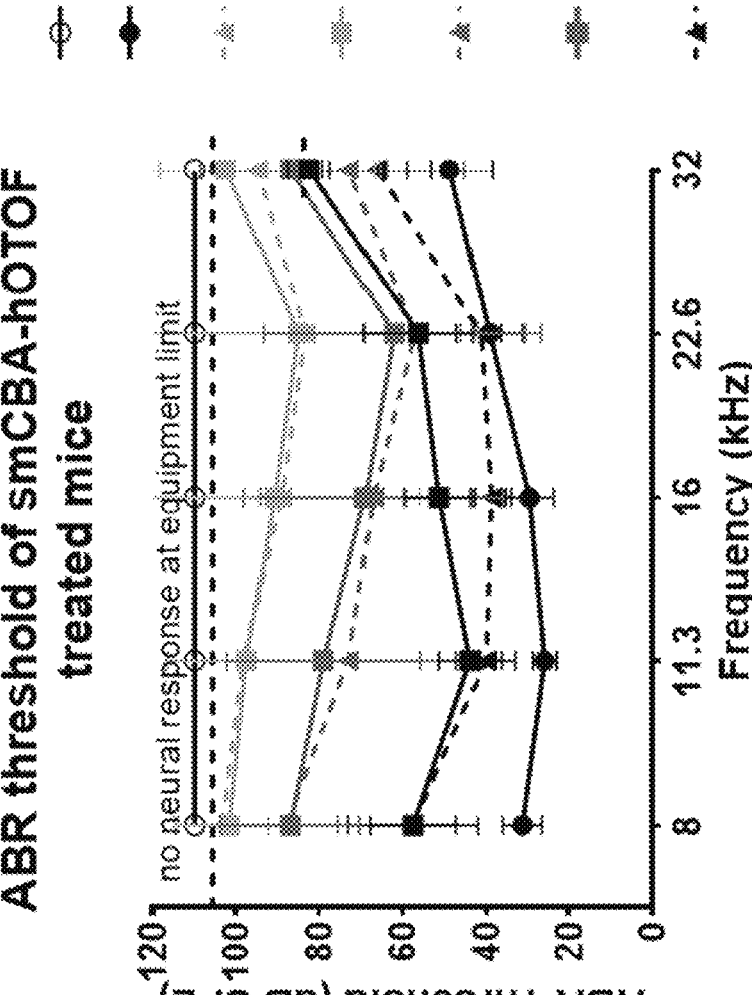

In yet another set of experiments, homozygous OTOF-Q828X mice were treated with an AAV1-smCBA (SEQ ID NO: 44)-hOTOF (isoform 5, SEQ ID NO: 1) dual hybrid vector system by injection through the round window membrane at low, medium (mid), and high doses and ABR thresholds were used to assess hearing function at four weeks and eight weeks post-treatment (FIG. 3C). A dose-dependent recovery in ABR thresholds was observed at both timepoints. When comparing the eight weeks versus the four weeks timepoints, recovery was steady for the low and mid doses, but decreased for the high dose animals. ABR thresholds for HET animals were also tested.

Figure 4:
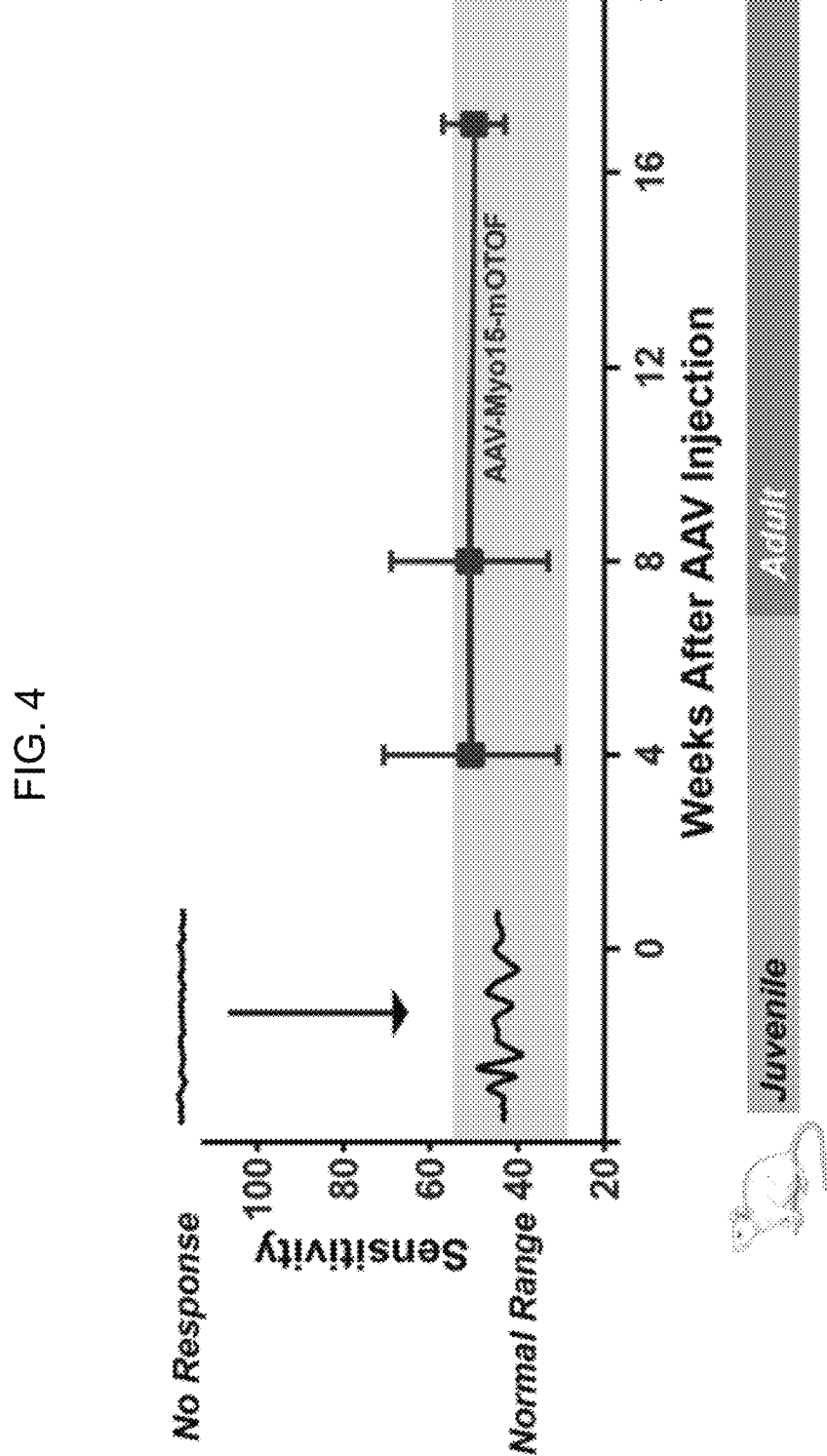

FIG. 4 is a graph showing the durability of hearing recovery in mice treated with viral vectors expressing OTOF via dual hybrid vector systems. Homozygous OTOF-Q828X mice were treated with AAV2quad(Y-F)-Myo15 (SEQ ID NO: 21)-murine OTOF (mOTOF, transcript variant 1, RefSeq NM_001100395) and AAV2quad(Y-F)-Myo15 (SEQ ID NO: 31)-mOTOF (transcript variant 1, RefSeq NM_001100395) dual hybrid vector systems by injection through the round window membrane and ABR thresholds were used to assess hearing function. Untreated animals showed no detectable recovery in hearing function, whereas treated animals exhibited robust recovery, which was consistent from four weeks post-treatment to seventeen weeks post-treatment (FIG. 4). The graph depicts mean hearing thresholds at 22.6 kHz+/−standard deviation.

Figures 5A, 5B, 5C:
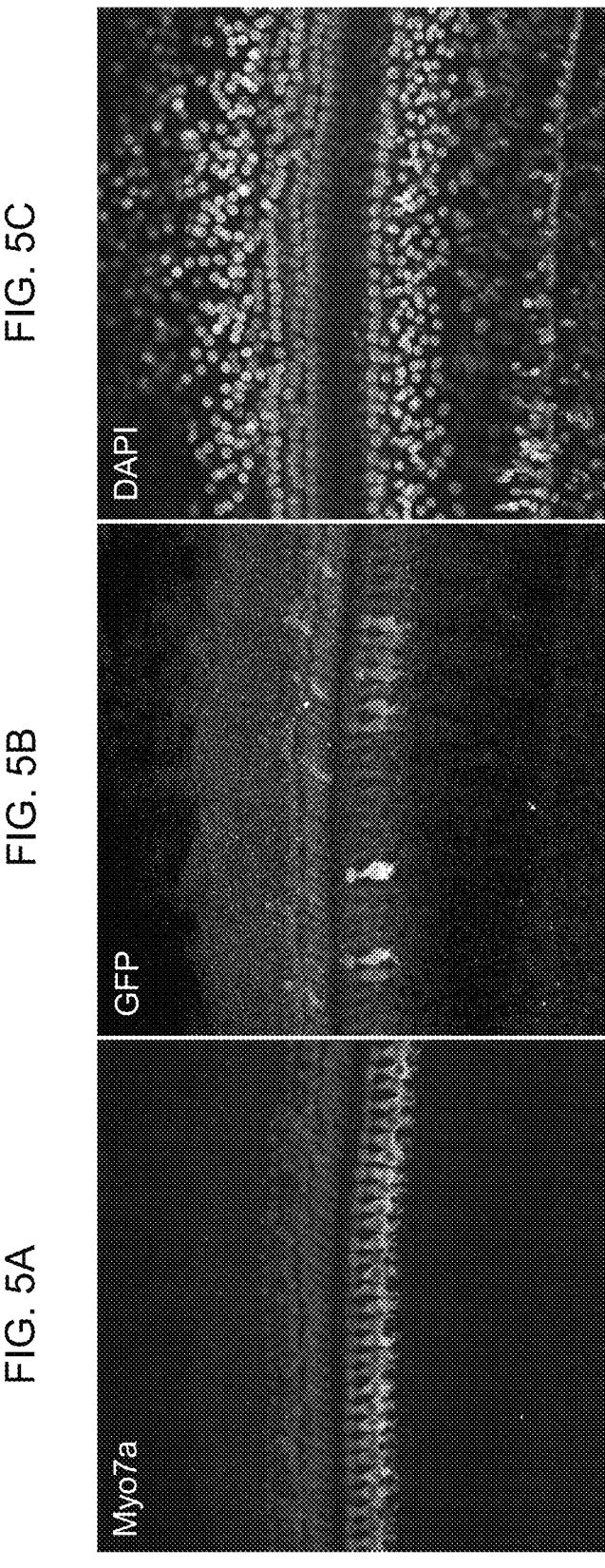

FIGS. 5A-5C are a series of fluorescent images of non-human primate cochlea showing that dual hybrid vectors can be used to express full length, functional GFP in hair cells. A non-human primate (NHP) received a local injection to the round window of the inner ear at a flow rate of 6 μL/min with an AAV1-Myo15 (SEQ ID NO: 21)-GFP (viral titer of 3.18E13 vg/mL for the 5' vector and 3.42E13 vg/mL for the 3' vector) dual hybrid vector system. Four weeks post-injection, inner ears were removed, and a surface preparation of the basilar membranes was made. Dual hybrid vectors resulted in GFP expression in hair cells across the entire baso-apical axis of the cochlea. High magnification images at 4 kHz showed GFP expression was observed within inner hair cells (IHCs) (FIG. 5B). Immunohistochemistry for Myo7A was used to visualize hair cells (FIG. 5A) and nuclei were stained with DAPI (FIG. 5C).

Figure 6:
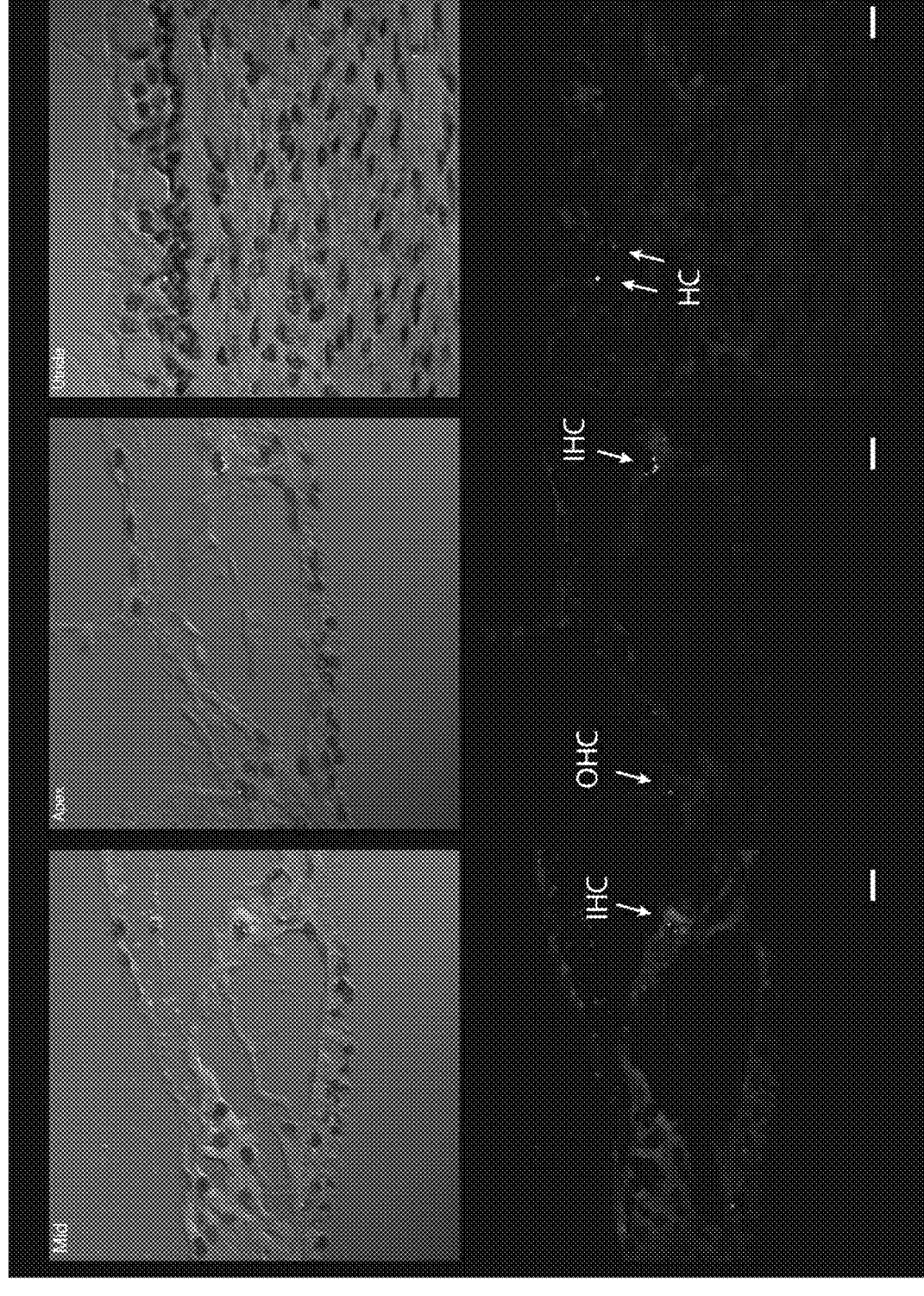

FIG. 6 is a series of images of sections with differential interference contrast images (top three panels) and corresponding BaseScope™ fluorescent staining specific for the exon 20/exon 21 junction of human OTOF (bottom three panels) from various areas of NHP ears four weeks after being treated with a dual hybrid viral vector system described in Example 6 herein to express full length OTOF. The fluorescent staining is specific for full length human OTOF transcript generated from the dual vectors. "IHC" refers to inner hair cells. "OHC" refers to outer hair cells. "HC" refers to hair cells. The scale bars seen in the lower panels represent a scale of 10 μm.

Figure 7A:
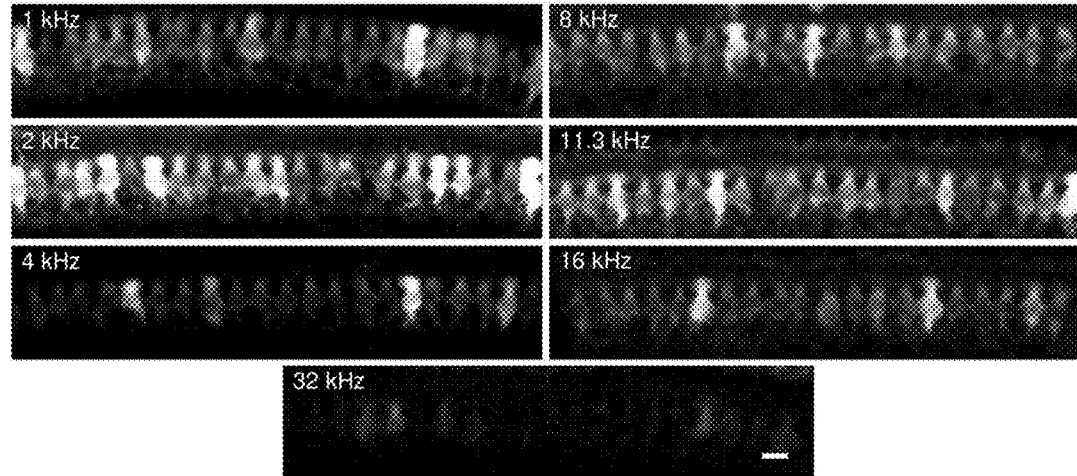
Figure 7B:
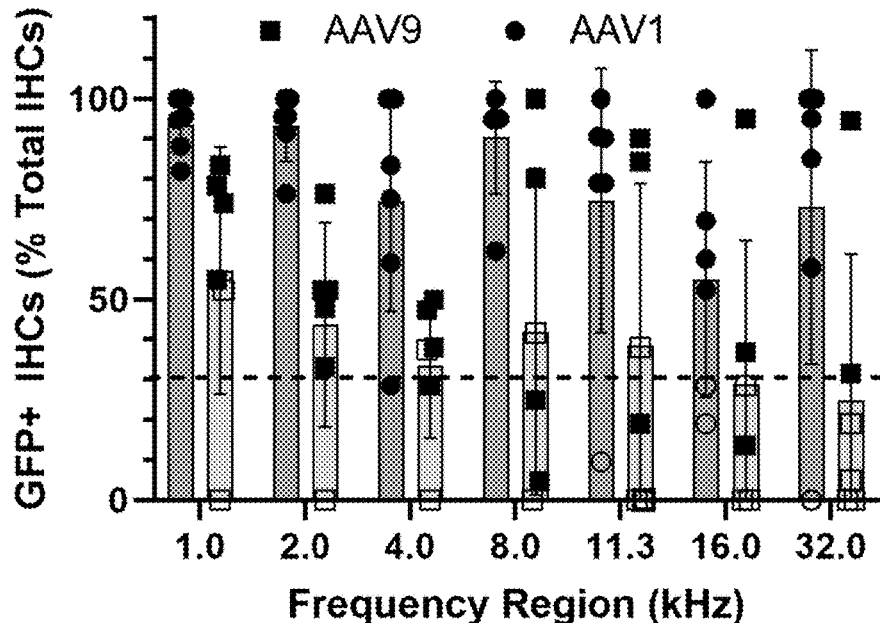

FIGS. 7A-7B represent the expression of GFP in inner hair cells at various locations in the organ of Corti in NHP treated with a dual vector system expressing eGFP under the control of a Myo15 promoter in either an AAV1 or AAV9 vector as described in Example 6. FIG. 7A shows a series of confocal images of inner hair cells at different frequency locations across the organ of Corti and the corresponding eGFP-signal after AAV1 dual hybrid GFP transduction. FIG. 7B is a graph showing a quantification of the number of inner hair cells expressing eGFP in various regions of the organ of Corti.

FIG. 8 is a schematic depicting an exemplary dual vector system of the invention. The 5' vector contains, from 5' to 3' a Myo15 promoter, the first 20 exons of the 5' half of the human otoferlin isoform 5 coding sequence, a splice donor site (SD), and an alkaline phosphatase (AP)-derived homology region. The 3' vector contains, from 5' to 3', a copy of the AP homology region, a complementary splice acceptor site (SA), the remaining 3' portion of the human otoferlin isoform 5 coding sequence (exons 21-45 and 47), and a polyadenylation (polyA) signal. Both the 5' and 3' vectors contain flanking inverted terminal repeats (ITRs). These vectors are designed to reconstitute a functional human OTOF isoform 5 gene cassette when co-transduced into the same target cell and vector recombination can occur through two recombinogenic mechanisms in vivo. The ITRs naturally associate during second strand DNA synthesis and extension and the identical AP sequences in each vector can undergo homologous recombination, forming a functional human OTOF isoform 5 cassette in either case. The resultant double-stranded DNA can express RNA from the Myo15 promoter, and the SD/SA sites facilitate the removal by splicing of the AP region and ITR sequences to generate a mature mRNA encoding the full-length human OTOF isoform 5 coding sequence.

DETAILED DESCRIPTION

Described herein are compositions and methods for the treatment of sensorineural hearing loss or auditory neuropathy in a subject (such as a mammalian subject, for instance, a human) by administering a first nucleic acid vector (e.g., an AAV vector) containing a promoter and a polynucleotide encoding an N-terminal portion of an otoferlin (OTOF) isoform 5 protein (e.g., a wild-type (WT) human OTOF isoform 5 protein) and a second nucleic acid vector (e.g., an AAV vector) containing a polynucleotide encoding a C-terminal portion of an OTOF isoform 5 protein and a polyadenylation (poly(A)) sequence. When introduced into a mammalian cell, such as a cochlear hair cell, the polynucleotides encoded by the two nucleic acid vectors can combine to form a nucleic acid molecule that encodes the full-length OTOF isoform 5 protein. The compositions and methods described herein can, therefore, be used to induce or increase expression of WT OTOF isoform 5 in cochlear hair cells of a subject who has an OTOF deficiency (e.g., low OTOF expression or an OTOF mutation that impairs OTOF expression or function).

Otoferlin

OTOF is a 230 kDa membrane protein that contains at least six C2 domains implicated in calcium, phospholipid, and protein binding. Human OTOF is encoded by a gene that contains 47 exons, and the full-length protein is made up of 1,997 amino acids. OTOF is located at ribbon synapses in inner hair cells, where it is believed to function as a calcium sensor in synaptic vesicle fusion, triggering the fusion of neurotransmitter-containing vesicles with the plasma membrane. It has also been implicated in vesicle replenishment and clathrin-mediated endocytosis, and has been shown to interact with Myosin VI, Rab8b, SNARE proteins, calcium channel Cav1.3, Ergic2, and AP-2. The mechanism by which OTOF mediates exocytosis and the physiological significance of its interactions with its binding partners remain to be determined.

There are multiple long and short isoforms of the Otoferlin gene. Studies of human genetic deafness have suggested that long isoforms are important for inner ear function. However, the role of these individual long isoforms and other protein variants in inner ear function is not understood. To develop effective gene transfer therapies for patients who experience deafness secondary to genetically driven Otoferlin deficiency, a cDNA sequence that encodes functional OTOF isoforms in the ear must be identified.

The present invention is based, in part, on the discovery that OTOF isoform 5 was preferentially expressed in the inner ear of non-human primates, and that human OTOF isoform 5, but not human OTOF isoform 1, was able to rescue hearing in genetically engineered, congenitally deaf mice with Otoferlin deficiency. Accordingly, the dual vector systems described herein (e.g., dual vector systems for the expression of OTOF isoform 5) may be used to treat sensorineural hearing loss or auditory neuropathy in human subjects having a deficiency (e.g., mutation) in the OTOF gene.

Otoferlin-Associated Hearing Loss

OTOF was first identified by a study investigating the genetics of a non-syndromic form of deafness, autosomal recessive deafness-9 (DFNB9). Mutations in OTOF have since been found to cause sensorineural hearing loss in patients throughout the world, with many patients carrying OTOF mutations having auditory neuropathy, a disorder in which the inner ear detects sound, but is unable to properly transmit sound from the ear to the brain. These patients have an abnormal auditory brainstem response (ABR) and impaired speech discrimination with initially normal otoacoustic emissions. Patients carrying homozygous or compound heterozygous mutations often develop hearing loss in early childhood, and the severity of hearing impairment has been found to vary with the location and type of mutation in OTOF.

The compositions and methods described herein can be used to treat sensorineural hearing loss or auditory neuropathy by administering a first nucleic acid vector containing a polynucleotide encoding an N-terminal portion of an OTOF isoform 5 protein and a second nucleic acid vector containing a polynucleotide encoding a C-terminal portion of an OTOF isoform 5 protein. The full-length OTOF isoform 5 coding sequence is too large to include in the type of vector that is commonly used for gene therapy (e.g., an adeno-associated virus (AAV) vector, which is thought to have a packaging limit of 5 kb). The compositions and methods described herein overcome this problem by dividing the OTOF isoform 5 coding sequence between two different nucleic acid vectors (e.g., AAV vectors) that can combine in a cell to reconstitute the full-length OTOF isoform 5 sequence. These compositions and methods can be used to treat subjects having one or more mutations in the OTOF gene, e.g., an OTOF mutation that reduces OTOF expression, reduces OTOF function, or is associated with hearing loss (e.g., a frameshift mutation, a nonsense mutation, a deletion, or a missense substitution). When the first and second nucleic acid vectors are administered in a composition, the polynucleotides encoding the N-terminal and C-terminal portions of OTOF isoform 5 can combine within a cell (e.g., a human cell, e.g., a cochlear hair cell) to form a single nucleic acid molecule that contains the full-length OTOF isoform 5 coding sequence (e.g., through homologous recombination and/or splicing).

The nucleic acid vectors (e.g., AAV vectors) used in the compositions and methods described herein include polynucleotide sequences that encode wild-type OTOF isoform 5, or a variant thereof, such as a polynucleotide sequences that, when combined, encode a protein having at least 85% sequence identity (e.g., 85%, 90%, 95%, 96%, 97%, 98%, 99%, or more, sequence identity) to the amino acid sequence of wild-type mammalian (e.g., human or mouse) OTOF isoform 5. The polynucleotides used in the nucleic acid vectors described herein can encode an N-terminal portion and a C-terminal portion of an OTOF isoform 5 amino acid sequence in Table 2 below (e.g., two portions that, when combined, encode a full-length OTOF isoform 5 amino acid sequence listed in Table 2, e.g., SEQ ID NO: 1).

According to the methods described herein, a subject can be administered a composition containing a first nucleic acid vector and a second nucleic acid vector that contain an N-terminal and C-terminal portion, respectively, of a polynucleotide sequence encoding the amino acid sequence of SEQ ID NO: 1, or a polynucleotide sequence encoding an amino acid sequence having at least 85% sequence identity (e.g., 85%, 90%, 95%, 96%, 97%, 98%, 99%, or more, sequence identity) to the amino acid sequence of SEQ ID NO: 1, or a polynucleotide sequence encoding an amino acid sequence that contains one or more conservative amino acid substitutions relative to SEQ ID NO: 1 (e.g., 1, 2, 3, 4, 5, 6, 7, 8, 9, 10, 11, 12, 13, 14, 15, 16, 17, 18, 19, 20 or more conservative amino acid substitutions), provided that the OTOF analog encoded retains the therapeutic function of wild-type OTOF isoform 5 (e.g., the ability to regulate exocytosis at ribbon synapses or rescue or improve ABR response in an animal model of hearing loss related to Otoferlin gene deficiency (e.g., OTOF mutation)). No more than 10% of the amino acids in the N-terminal portion of the human OTOF isoform 5 protein and no more than 10% of the amino acids in the C-terminal portion of the human OTOF isoform 5 protein may be replaced with conservative amino acid substitutions. The OTOF isoform 5 protein may be encoded by a polynucleotide having the sequence of SEQ ID NO: 2 or SEQ ID NO: 3. The OTOF isoform 5 protein may also be encoded by a polynucleotide having single nucleotide variants (SNVs) that have been found to be non-pathogenic in human subjects. The OTOF isoform 5 protein may be a human OTOF isoform 5 protein or may be a homolog of the human isoform 5 protein from another mammalian species (e.g., mouse, rat, cow, horse, goat, sheep, donkey, cat, dog, rabbit, guinea pig, or other mammal).

TABLE 2

OTOF Sequences

| SEQ ID NO. | Sequence Name | Sequence |
|---|---|---|
| 1 | Human OTOF isoform 5 protein (NP_001274418.1), also called human otoferlin isoform e, 1997 aa | MALLIHLKTVSELRGRGDRIAKVTFRGQSFYSRVLENCEDVADFDE TFRWPVASSIDRNEMLEIQVFNYSKVFSNKLIGTFRMVLQKVVEES HVEVTDTLIDDNNAIIKTSLCVEVRYQATDGTVGSWDDGDFLGDES LQEEEKDSQETDGLLPGSRPSSRPPGEKSFRRAGRSVFSAMKLGK NRSHKEEPQRPDEPAVLEMEDLDHLAIRLGDGLDPDSVSLASVTAL TTNVSNKRSKPDIKMEPSAGRPMDYQVSITVIEARQLVGLNMDPVV CVEVGDDKKYTSMKESTNCPYYNEYFVFDFHVSPDVMFDKIIKISVI HSKNLLRSGTLVGSFKMDVGTVYSQPEHQFHHKWAILSDPDDISS |

TABLE 2-continued

| OTOF Sequences | | |
| --- | --- | --- |

| SEQ ID NO. | Sequence Name | Sequence |
| --- | --- | --- |
| | | GLKGYVKCDVAVVGKGDNIKTPHKANETDEDDIEGNLLLPEGVPPE |
| | | RQWARFYVKIYRAEGLPRMNTSLMANVKKAFIGENKDLVDPYVQV |
| | | FFAGQKGKTSVQKSSYEPLWNEQVVFTDLFPPLCKRMKVQIRDSD |
| | | KVNDVAIGTHFIDLRKISNDGDKGFLPTLGPAWVNMYGSTRNYTLL |
| | | DEHQDLNEGLGEGVSFRARLLLGLAVEIVDTSNPELTSSTEVQVEQ |
| | | ATPISESCAGKMEEFFLFGAFLEASMIDRRNGDKPITFEVTIGNYGN |
| | | EVDGLSRPQRPRPRKEPGDEEEVDLIQNASDDEAGDAGDLASVSS |
| | | TPPMRPQVTDRNYFHLPYLERKPCIYIKSWWPDQRRRLYNANIMD |
| | | HIADKLEEGLNDIQEMIKTEKSYPERRLRGVLEELSCGCCRFLSLAD |
| | | KDQGHSSRTRLDRERLKSCMRELENMGQQARMLRAQVKRHTVRD |
| | | KLRLCQNFLQKLRFLADEPQHSIPDIFIWMMSNNKRVAYARVPSKD |
| | | LLFSIVEEETGKDCAKVKTLFLKLPGKRGFGSAGWTVQAKVELYLW |
| | | LGLSKQRKEFLCGLPCGFQEVKAAQGLGLHAFPPVSLVYTKKQAF |
| | | QLRAHMYQARSLFAADSSGLSDPFARVFFINQSQCTEVLNETLCPT |
| | | WDQMLVFDNLELYGEAHELRDDPPIIVIEIYDQDSMGKADFMGRTF |
| | | AKPLVKMADEAYCPPRFPPQLEYYQIYRGNATAGDLLAAFELLQIG |
| | | PAGKADLPPINGPVDVDRGPIMPVPMGIRPVLSKYRVEVLFWGLRD |
| | | LKRVNLAQVDRPRVDIECAGKGVQSSLIHNYKKNPNFNTLVKWFEV |
| | | DLPENELLHPPLNIRVVDCRAFGRYTLVGSHAVSSLRRFIYRPPDRS |
| | | APSWNTTVRLLRRCRVLCNGGSSSHSTGEVVVTMEPEVPIKKLET |
| | | MVKLDATSEAVVKVDVAEEEKEKKKKKKGTAEEPEEEEPDESMLD |
| | | WWSKYFASIDTMKEQLRQQEPSGIDLEEKEEVDNTEGLKGSMKGK |
| | | EKARAAKEEKKKKTQSSGSGQGSEAPEKKKPKIDELKVYPKELESE |
| | | FDNFEDWLHTFNLLRGKTGDDEDGSTEEERIVGRFKGSLCVYKVPL |
| | | PEDVSREAGYDSTYGMFQGIPSNDPINVLVRVYVVRATDLHPADIN |
| | | GKADPYIAIRLGKTDIRDKENYISKQLNPVFGKSFDIEASFPMESMLT |
| | | VAVYDWDLVGTDDLIGETKIDLENRFYSKHRATCGIAQTYSTHGYNI |
| | | WRDPMKPSQILTRLCKDGKVDGPHFGPPGRVKVANRVFTGPSEIE |
| | | DENGQRKPTDEHVALLALRHWEDIPRAGCRLVPEHVETRPLLNPD |
| | | KPGIEQGRLELWVDMFPMDMPAPGTPLDISPRKPKKYELRVIIWNT |
| | | DEVVLEDDDFFTGEKSSDIFVRGWLKGQQEDKQDTDVHYHSLTGE |
| | | GNFNWRYLFPPFDYLAAEEKIVISKKESMFSWDETEYKIPARLTLQIW |
| | | DADHFSADDFLGAIELDLNRFPRGAKTAKQCTMEMATGEVDVPLV |
| | | SIFKQKRVKGWWPLLARNENDEFELTGKVEAELHLLTAEEAEKNPV |
| | | GLARNEPDPLEKPNRPDTAFVWFLNPLKSIKYLICTRYKWLIIKIVLAL |
| | | LGLLMLGLFLYSLPGYMVKKLLGA |
| 2 | DNA sequence encoding the human otoferlin isoform 5 protein (SEQ ID NO: 1), 5994 bp, corresponds to the coding sequence documented in NM_001287489 | ATGGCCTTGCTCATCCACCTCAAGACAGTCTCGGAGCTGCGGG |
| | | GCAGGGGCGACCGGATCGCCAAAGTGACTTTCCGAGGGCAATC |
| | | CTTCTACTCTCGGGTCCTGGAGAACTGTGAGGATGTGGCTGACT |
| | | TTGATGAGACATTTCGGTGGCCGGTGGCCAGCAGCATCGACAG |
| | | AAATGAGATGCTGGAGATTCAGGTTTTCAACTACAGCAAAGTCTT |
| | | CAGCAACAAGCTCATCGGGACCTTCCGCATGGTGCTGCAGAAG |
| | | GTGGTAGAGGAGAGCCATGTGGAGGTGACTGACACGCTGATTG |
| | | ATGACAACAATGCTATCATCAAGACCAGCCTGTGCGTGGAGGTC |
| | | CGGTATCAGGCCACTGACGGCACAGTGGGCTCCTGGGACGATG |
| | | GGGACTTCCTGGGAGATGAGTCTCTTCAAGAGGAAGAGAAGGA |
| | | CAGCCAAGAGACGGATGGACTGCTCCCAGGCTCCCGGCCCAGC |
| | | TCCCGGCCCCCAGGAGAGAAGAGCTTCCGGAGAGCCGGGAGG |
| | | AGCGTGTTCTCCGCCATGAAGCTCGGCAAAAACCGGTCTCACAA |
| | | GGAGGAGCCCCAAAGACCAGATGAACCGGCGGTGCTGGAGAT |
| | | GGAAGACCTTGACCATCTGGCCATTCGGCTAGGAGATGGGACTG |
| | | GATCCCGACTCGGTGTCTCTAGCCTCAGTCACAGCTCTCACCAC |
| | | TAATGTCTCCAACAAGCGATCTAAGCCAGACATTAAGATGGAGC |
| | | CAAGTGCTGGGCGGCCCATGGATTACCAGGTCAGCATCACGGT |
| | | GATCGAGGCCCGGCAGCTGGTGGGCTTGAACATGGACCCTGTG |
| | | GTGTGCGTGGAGGTGGGTGACGACAAGAAGTACACATCCATGA |
| | | AGGAGTCCACTAACTGCCCCTATTACAACGAGTACTTCGTCTTC |
| | | GACTTCCATGTCTCTCCGGATGTCATGTTTGACAAGATCATCAAG |
| | | ATTTCGGTGATTCACTCCAAGAACCTGCTGCGCAGTGGCACCCT |
| | | GGTGGGCTCCTTCAAAATGGACGTGGGAACCGTGTACTCGCAG |
| | | CCAGAGCACCAGTTCCATCACAAGTGGGCCATCCTGTCTGACCC |
| | | CGATGACATCTCCTCGGGGCTGAAGGGCTACGTGAAGTGTGAC |
| | | GTTGCCGTGGTGGGCAAAGGGGACAACATCAAGACGCCCCACA |
| | | AGGCCAATGAGACCGACGAAGATGACATTGAGGGGAACTTGCT |
| | | GCTCCCCGAGGGGGTGCCCCCCGAACGCCAGTGGGCCCGGTT |
| | | CTATGTGAAAATTTACCGAGCAGAGGGGCTGCCCCGTATGAACA |
| | | CAAGCCTCATGGCCAATGTAAAGAAGGCTTTCATCGGTGAAAC |
| | | AAGGACCTCGTGGACCCCTACGTGCAAGTCTTCTTTGCTGGCCA |
| | | GAAGGGCAAGACTTCAGTGCAGAAGAGCAGCTATGAGCCCCTG |
| | | TGGAATGAGCAGGTCGTCTTTACAGACCTCTTCCCCCCCACTCTG |
| | | CAAACGCATGAAGGTGCAGATCCGAGACTCGGACAAGGTCAAC |
| | | GACGTGGCCATCGGCACCCACTTCATTGACCTGCGCAAGATTTC |
| | | TAATGACGGAGACAAAGGCTTCCTGCCCCACACTGGGCCCAGCC |
| | | TGGGTGAACATGTACGGCTCCACACGTAACTACACGCTGCTGGA |

TABLE 2-continued

OTOF Sequences

| SEQ ID NO. | Sequence Name | Sequence |
|---|---|---|
| | | TGAGCATCAGGACCTGAACGAGGGCCTGGGGGAGGGTGTGTC |
| | | CTTCCGGGCCCGGCTCCTGCTGGGCCTGGCTGTGGAGATCGTA |
| | | GACACCTCCAACCCTGAGCTCACCAGCTCCACAGAGGTGCAGG |
| | | TGGAGCAGGCCACGCCCATCTCGGAGAGCTGTGCAGGTAAAAT |
| | | GGAAGAATTCTTTCTCTTTGGAGCCTTCCTGGAGGCCTCAATGA |
| | | TCGACCGGAGAAACGGAGACAAGCCCATCACCTTTGAGGTCAC |
| | | CATAGGCAACTATGGGAACGAAGTTGATGGCCTGTCCCGGCCC |
| | | CAGCGGCCTCGGCCCCGGAAGGAGCCGGGGGATGAGGAAGAA |
| | | GTAGACCTGATTCAGAACGCAAGTGATGACGAGGCCGGTGATG |
| | | CCGGGGACCTGGCCTCAGTCTCCTCCACTCCACCAATGCGGCC |
| | | CCAGGTCACCGACAGGAACTACTTCCATCTGCCCTACCTGGAGC |
| | | GAAAGCCCTGCATCTACATCAAGAGCTGGTGGCCGGACCAGCG |
| | | CCGCCGCCTCTACAATGCCAACATCATGGACCACATTGCCGACA |
| | | AGCTGGAAGAAGGCCTGAACGACATACAGGAGATGATCAAAAC |
| | | GGAGAAGTCCTACCCTGAGCGTCGCCTGCGGGGCGTCCTGGA |
| | | GGAGCTGAGCTGTGGCTGCTGCCGCTTCCTCTCCCTCGCTGAC |
| | | AAGGACCAGGGCCACTCATCCCGCACCAGGCTTGACCGGGGAGC |
| | | GCCTCAAGTCCTGCATGAGGGAGCTGGAAAACATGGGGCAGCA |
| | | GGCCAGGATGCTGCGGGCCCAGGTGAAGCGGCACACGGTGCG |
| | | GGACAAGCTGAGGCTGTGCCAGAACTTCCTGCAGAAGCTGCGC |
| | | TTCCTGGCGGACGAGCCCCAGCACAGCATTCCCGACATCTTCAT |
| | | CTGGATGATGAGCAACAACAAGCGTGTCGCCTATGCCCGTGTG |
| | | CCCTCCAAGGACCTGCTCTTCTCCATCGTGGAGGAGGAGACTG |
| | | GCAAGGACTGCGCCAAGGTCAAGACGCTCTTCCTTAAGCTGCC |
| | | AGGGAAGCGGGGCTTCGGCTCGGCAGGCTGGACAGTGCAGGC |
| | | CAAGGTGGAGCTGTACCTGTGGCTGGGCCTCAGCAAACAGCGC |
| | | AAGGAGTTCCTGTGCGGCCTGCCCCTGTGGCTTCCAGGAGGTCA |
| | | AGGCAGCCCAGGGCCTGGGCCTGCATGCCTTCCCACCCGTCAG |
| | | CCTGGTCTACACCAAGAAGCAGGCGTTCCAGCTCCGAGCGCAC |
| | | ATGTACCAGGCCCGCAGCCTCTTTGCCGCCGACAGCAGCGGAC |
| | | TCTCAGACCCCTTTGCCCGCGTCTTCTTCATCAATCAGAGTCAG |
| | | TGCACAGAGGTGCTGAATGAGACCCTGTGTCCCACCTGGGACC |
| | | AGATGCTGGTGTTCGACAACCTGGAGCTCTATGGTGAAGCTCAT |
| | | GAGCTGAGGGACGATCCGCCCATCATTGTCATTGAAATCTATGA |
| | | CCAGGATTCCATGGGCAAAGCTGACTTCATGGGCCGGACCTTC |
| | | GCCAAACCCCTGGTGAAGATGGCAGACGAGGCGTACTGCCCAC |
| | | CCCGCTTCCCACCTCAGCTCGAGTACTACCAGATCTACCGTGGC |
| | | AACGCCACAGCTGGAGACCTGCTGGCGGCCTTCGAGCTGCTGC |
| | | AGATTGGACCAGCAGGGAAGGCTGACCTGCCCCCCATCAATGG |
| | | CCCGGTGGACGTGGACCGAGGTCCCATCATGCCCGTGCCCATG |
| | | GGCATCCGGCCCGTGCTCAGCAAGTACCGAGTGGAGGTGCTGT |
| | | TCTGGGGCCTACGGGACCTAAAGCGGGTGAACCTGGCCCAGGT |
| | | GGACCGGCCACGGGTGGACATCGAGTGTGCAGGGAAGGGGGT |
| | | GCAGTCGTCCCTGATCCACAATTATAAGAAGAACCCCAACTTCA |
| | | ACACCCTCGTCAAGTGGTTTGAAGTGGACCTCCCAGAGAACGA |
| | | GCTGCTGCACCCGCCCTTGAACATCCGTGTGGTGGACTGCCGG |
| | | GCCTTCGGTCGCTACACACTGGTGGGCTCCCATGCCGTCAGCT |
| | | CCCTGCGACGCTTCATCTACCGGCCCCCAGACCGCTCGGCCCC |
| | | CAGCTGGAACACCACGGTCAGGCTTCTCCGGCGCTGCCGTGTG |
| | | CTGTGCAATGGGGGCTCCTCCTCTCACTCCACAGGGGAGGTTG |
| | | TGGTGACTATGGAGCCAGAGGTACCCATCAAGAAACTGGAGAC |
| | | CATGGTGAAGCTGGACGCGACTTCTGAAGCTGTTGTCAAGGTG |
| | | GATGTGGCTGAGGAGGAGAAGGAGAAGAAGAAGAAGAAGAAGG |
| | | GCACTGCGGAGGAGCCAGAGGAGGAGGAGGAGCCAGACGAGAGCA |
| | | TGCTGGACTGGTGGTCCAAGTACTTTGCCTCCATTGACACCATG |
| | | AAGGAGCAACTTCGACAACAAGAGCCCTCTGGAATTGACTTGGA |
| | | GGAGAAGGAGGAAGTGGACAATACCGAGGGCCTGAAGGGGTC |
| | | AATGAAGGGCAAGGAGAAGGCAAGGGCTGCCAAAGAGGAGAAG |
| | | AAGAAGAAAACTCAGAGCTCTGGCTCTGGCCAGGGGTCCGAGG |
| | | CCCCCGAGAAGAAGAAACCCAAGATTGATGAGCTTAAGGTATAC |
| | | CCCAAAGAGCTGGAGTCCGAGTTTGATAACTTTGAGGACTGGCT |
| | | GCACACTTTCAACTTGCTTCGGGGCAAGACCGGGGATGATGAG |
| | | GATGGCTCCACCGAGGAGGAGCGCATTGTGGGACGCTTCAAGG |
| | | GCTCCCTCTGCGTGTACAAAGTGCCACTCCCAGAGGACGTGTC |
| | | CCGGGAAGCCGGCTACGACTCCACCTACGGCATGTTCCAGGGC |
| | | ATCCCGAGCAATGACCCCATCAATGTGCTGGTCCGAGTCTATGT |
| | | GGTCCGGGCCACGGACCTGCACCCTGCTGACATCAACGGCAAA |
| | | GCTGACCCCTACATCGCCATCCGGCTAGGCAAGACTGACATCC |
| | | GCGACAAGGAGAACTACATCTCCAAGCAGCTCAACCCTGTCTTT |
| | | GGGAAGTCCTTTGACATCGAGGCCTCCTTCCCCATGGAATCCAT |
| | | GCTGACGGTGGCTGTGTATGACTGGGACCTGGTGGGCACTGAT |
| | | GACCTCATTGGGGAAACCAAGATCGACCTGGAGAACCGCTTCTA |
| | | CAGCAAGCACCGCGCCACCTGCGGCATCGCCCAGACCTACTCC |
| | | ACACATGGCTACAATATCTGGCGGGACCCCATGAAGCCCAGCC |
| | | AGATCCTGACCCGCCTCTGCAAAGACGGCAAAGTGGACGGCCC |

TABLE 2-continued

OTOF Sequences

| SEQ ID NO. | Sequence Name | Sequence |
|---|---|---|
| | | CCACTTTGGGCCCCCTGGGAGAGTGAAGGTGGCCAACCGCGTC |
| | | TTCACTGGGCCCTCTGAGATTGAGGACGAGAACGGTCAGAGGA |
| | | AGCCCACAGACGAGCATGTGGCGCTGTTGGCCCTGAGGCACTG |
| | | GGAGGACATCCCCCGCGCAGGCTGCCGCCTGGTGCCAGAGCA |
| | | TGTGGAGACGAGGCCGCTGCTCAACCCCGACAAGCCGGGCATC |
| | | GAGCAGGGCCGCCTGGAGCTGTGGGTGGACATGTTCCCCATGG |
| | | ACATGCCAGCCCCTGGGACGCCTCTGGACATCTCACCTCGGAA |
| | | GCCCAAGAAGTACGAGCTGCGGGTCATCATCTGGAACACAGAT |
| | | GAGGTGGTCTTGGAGGACGACGACTTCTTCACAGGGGAGAAGT |
| | | CCAGTGACATCTTCGTGAGGGGGTGGCTGAAGGGCCAGCAGGA |
| | | GGACAAGCAGGACACAGACGTCCACTACCACTCCCTCACTGGC |
| | | GAGGGCAACTTCAACTGGCGCTACCTGTTCCCCTTCGACTACCT |
| | | GGCGGCGGAGGAGAAGATCGTCATCTCCAAGAAGGAGTCCATG |
| | | TTCTCCTGGGACGAGACCGAGTACAAGATCCCCGCGCGGCTCA |
| | | CCCTGCAGATCTGGGATGCGGACCACTTCTCCGCTGACGACTT |
| | | CCTGGGGGCCATCGAGCTGGACCTGAACCGGTTCCCGCGGGG |
| | | CGCAAAGACAGCCAAGCAGTGCACCATGGAGATGGCCACCGGG |
| | | GAGGTGGACGTGCCCCTCGTGTCCATCTTCAAGCAAAAGCGCG |
| | | TCAAAGGCTGGTGGCCCCTCCTGGCCCGCAATGAGAACGATGA |
| | | GTTTGAGCTCACGGGCAAGGTGGAGGCTGAGCTGCATTTACTG |
| | | ACAGCAGAGGAGGCAGAGAAGAACCCAGTGGGCCTGGCCCGC |
| | | AATGAACCTGACCCCCTAGAGAAACCCAACCGGCCCGACACGG |
| | | CCTTCGTCTGGTTCCTCAACCCTCTCAAGTCCATCAAGTACCTCA |
| | | TCTGCACCCGGTACAAGTGGCTCATCATCAAGATCGTGCTGGCG |
| | | CTGTTGGGGCTGCTCATGTTGGGGCTCTTCCTCTACAGCCTCCC |
| | | TGGCTACATGGTCAAAAAGCTCCTTGGGGCATGA |
| 3 | Codon-optimized (CO) DNA sequence encoding the human otoferlin isoform 5 protein (SEQ ID NO: 1), 5994 bp | ATGGCACTGCTGATCCACCTGAAAACCGTCTCCGAACTGAGAGG |
| | | CAGAGGGGACAGAATCGCTAAAGTCACCTTCCGGGGACAGAGC |
| | | TTTTACAGCAGGGTGCTGGAGAACTGCGAGGACGTGGCCGACT |
| | | TTGACGAGACATTCAGGTGGCCCGTGGCCAGCTCCATCGATCG |
| | | CAATGAGATGCTGGAGATCCAGGTGTTTAACTATAGCAAGGTGT |
| | | CTCCAATAAGCTGATCGGCACCTTCCGGATGGTGCTGCAGAAG |
| | | GTGGTGGAGGAGTCCCACGTGGAGGTGACCGACACACTGATCG |
| | | ACGATAACAATGCCATCATCAAGACATCCCTGTGCGTGGAGGTG |
| | | CGCTACCAGGCCACCGATGGCACAGTGGGCTCTTGGGACGATG |
| | | GCGACTTCCTGGGCGATGAGTCCCTGCAGGAGGAGGAGAAGGA |
| | | CTCTCAGGAGACAGATGGCCTGCTGCCTGGCTCCCGGCCATCT |
| | | AGCCGCCCCCCTGGCGAGAAGTCTTTTAGGAGAGCCGGCAGGT |
| | | CCGTGTTCTCTGCCATGAAGCTGGGCAAGAACAGGAGCCACAA |
| | | GGAGGAGCCTCAGAGGCCCGACGAGCCAGCCGTGCTGGAGAT |
| | | GGAGGACCTGGATCACCTGGCCATCAGACTGGGCGATGGCCTG |
| | | GACCCTGATAGCGTGTCCCTGGCCTCCGTGACCGCCCTGACCA |
| | | CAAACGTGTCTAATAAGCGGAGCAAGCCAGACATCAAGATGGAG |
| | | CCATCTGCCGGCAGGCCCATGGATTACCAGGTGAGCATCACAG |
| | | TGATCGAGGCCAGACAGCTGGTGGGCCTGAACATGGACCCCGT |
| | | GGTGTGCGTGGAAGTGGGCGACGATAAGAAGTACACCTCCATG |
| | | AAGGAGTCTACAAACTGTCCATACTACAACGAGTACTTCGTGTTT |
| | | GATTTCCACGTGAGCCCCGACGTGATGTTCGATAAGATCATCAA |
| | | GATCAGCGTGATCCACTCCAAGAATCTGCTGCGGGTCTGGCACC |
| | | CTGGTGGGAAGCTTTAAGATGGACGTGGGCACAGTGTACTCTCA |
| | | GCCTGAGCACCAGTTCCACCACAAGTGGGCCATCCTGAGCGAT |
| | | CCAGACGATATCTCCTCTGGCCTGAAGGGCTATGTGAAGTGCGA |
| | | CGTGGCAGTGGTGGGCAAGGGCGATAACATCAAGACCCCACAC |
| | | AAGGCCAATGAGACAGACGAGGACGATATCGAGGGAAACCTGC |
| | | TGCTGCCAGAGGGAGTGCCACCCGAGAGGCAGTGGGCCAGGT |
| | | TCTACGTGAAGATCTATAGGGCAGAGGGCCTGCCTAGGATGAA |
| | | CACCAGCCTGATGGCCAATGTGAAGAAGGCCTTCATCGGCGAG |
| | | AACAAGGACCTGGTGGATCCCTACGTGCAGGTGTTCTTTGCCG |
| | | GCCAGAAGGGCAAGACCTCCGTGCAGAAGAGCTCCTATGAGCC |
| | | TCTGTGGAATGAGCAGGTGGTGTTTACAGACCTGTTCCCTCCAC |
| | | TGTGCAAGAGGATGAAGGTGCAGATCAGAGACTCTGATAAGGT |
| | | GAACGACGTGGCCATCGGCACCCACTTTATCGATCTGAGGAAG |
| | | ATCAGCAATGACGGCGATAAGGGCTTCCTGCCCACCCTGGGCC |
| | | CCGCCTGGGTGAACATGTACGGCAGCACCAGAAATTATACACTG |
| | | CTGGACGAGCACCAGGATCTGAACGAGGGCCTGGGCGAGGGC |
| | | GTGAGCTTTAGAGCCAGGCTGCTGCTGGGCCTGGCCGTGGAGA |
| | | TCGTGGACACCTCCAATCCCGAGCTGACCCTCTAGCACAGAGGT |
| | | GCAGGTGGAGCAGGCCACACCTATCTCTGAGAGCTGTGCCGGC |
| | | AAGATGGAGGAGTTCTTTCTGTTTGGCGCCTTCCTTGGAGGCCTC |
| | | CATGATCGACCGGCGCAACGGCGATAAGCCTATCACCTTCGAG |
| | | GTGACAATCGGCAACTACGGCAATGAGGTGGACGGCCTGTCTC |
| | | GGCCCCAGCGCCCAAGGCCCAGAAAGGAGCCTGGCGACGAGG |
| | | AGGAGGTGGATCTGATCCAGAACGCCAGCGACGATGAGGCAGG |
| | | CGACGCAGGCGATCTGGCCTCCGTGTCCTCTACCCCCCCCTATG |

TABLE 2-continued

OTOF Sequences

| SEQ ID NO. | Sequence Name | Sequence |
|---|---|---|
| | | CGGCCACAGGTGACAGACCGCAATTACTTTCACCTGCCTTATCT |
| | | GGAGCGCAAGCCATGCATCTACATCAAGTCTTGGTGGCCCGAT |
| | | CAGAGGAGACGGCTGTATAACGCCAATATCATGGACCACATCGC |
| | | CGATAAGCTGGAGGAGGGCCTGAATGACATCCAGGAGATGATC |
| | | AAGACCGAGAAGTCCTATCCAGAGCGCAGGCTGAGGGGCGTGC |
| | | TGGAGGAGCTGAGCTGTGGCTGCTGTAGATTCCTGTCCCTGGC |
| | | CGACAAGGATCAGGGGCACTCATCACGGACACGGCTGGACCGG |
| | | GAGCGGCTGAAATCATGTATGCGGGAGCTGGAAAATATGGGAC |
| | | AGCAGGCAAGGATGCTGCGCGCCCAGGTGAAGAGGCACACCG |
| | | TGAGAGACAAGCTGCGGCTGTGCCAGAACTTCCTGCAGAAGCT |
| | | GCGCTTTCTGGCCGATGAGCCACAGCACAGCATCCCCGACATC |
| | | TTCATCTGGATGATGTCCAACAATAAGAGAGTGGCCTACGCCCG |
| | | GGTGCCCTCTAAGGATCTGCTGTTTAGCATCGTGGAGGAGGAG |
| | | ACAGGCAAGGACTGTGCCAAGGTGAAGACCCTGTTCCTGAAGC |
| | | TGCCTGGCAAGAGAGGCTTTGGCAGCGCCGGATGGACCGTGCA |
| | | GGCAAAGGTGGAGCTGTATCTGTGGCTGGGCCTGTCTAAGCAG |
| | | CGGAAGGAGTTCCTGTGCGGCCTGCCCTGTGGCTTTCAGGAGG |
| | | TGAAGGCAGCACAGGGACTGGGACTGCACGCCTTCCCCCCCGT |
| | | GAGCCTGGTGTACACCAAGAAGCAGGCCTTTCAGCTGAGGGCC |
| | | CATATGTACCAGGCCAGGTCTCTGTTCGCCGCCGATAGCTCCG |
| | | GACTGAGCGACCCTTTTGCCAGGGTGTTCTTTATCAATCAGAGC |
| | | CAGTGCACAGAGGTGCTGAACGAGACCCTGTGCCCAACATGGG |
| | | ATCAGATGCTGGTGTTCGACAACCTGGAGCTGTACGGAGAGGC |
| | | ACACGAGCTGAGGGACGATCCACCCATCATCGTGATCGAGATCT |
| | | ATGATCAGGACTCCATGGGCAAGGCCGATTTCATGGGCAGGAC |
| | | CTTTGCCAAGCCCCTGGTGAAGATGGCCGACGAGGCCTACTGC |
| | | CCTCCAAGATTCCCCCCTCAGCTCGAGTACTATCAGATCTATAG |
| | | GGGAAATGCAACCGCCGGAGACCTGCTGGCCGCCTTTGAGCTG |
| | | CTGCAGATCGGCCCCGCCGGAAAGGCAGACCTGCCACCCATCA |
| | | ACGGCCCAGTGGATGTGGACAGAGGCCCCATCATGCCTGTGCC |
| | | AATGGGCATCAGACCAGTGCTGTCCAAGTACAGGGTGGAGGTG |
| | | CTGTTCTGGGGACTGCGCGACCTGAAGAGGGTGAATCTGGCCC |
| | | AGGTGGATAGGCCCAGAGTGGACATCGAGTGCGCCGGAAAGG |
| | | GCGTGCAGTCTAGCCTGATCCACAACTATAAGAAGAACCCAAAT |
| | | TTCAACACCCTGGTGAAGTGGTTTGAGGTGGATCTGCCCGAGAA |
| | | TGAGCTGCTGCACCCTCCACTGAACATCCGGGTGGTGGACTGT |
| | | AGAGCCTTCGGCAGGTACACCCTGGTGGGCAGCCACGCCGTGA |
| | | GCAGCCTGAGGGAGGTTCATCTACAGGCCCCCTGACAGGTCCGC |
| | | CCCTTCTTGGAATACCACAGTGAGACTGCTGCGGCGCTGCAGG |
| | | GTGCTGTGCAACGGAGGCAGCTCCTCTCACTCTACCGGCGAGG |
| | | TGGTGGTGACAATGGAGCCTGAGGTACCCATCAAGAAGCTGGA |
| | | GACCATGGTGAAGCTGGATGCCACAAGCGAGGCAGTGGTGAAG |
| | | GTGGACGTGGCAGAGGAGGAGAAGGAGAAGAAGAAGAAGAAG |
| | | AAGGGAACCGCCGAGGAGCCTGAGGAAGAGGAGCCAGATGAG |
| | | AGCATGCTGGACTGGTGGTCCAAGTACTTCGCCTCTATCGACAC |
| | | AATGAAGGAGCAGCTGAGACAGCAGGAGCCTAGCGGCATCGAT |
| | | CTGGAGGAGAAGGAGGAGGTGGACAATACCGAGGGCCTGAAG |
| | | GGCTCCATGAAGGGCAAGGAGAAGGCAAGGGCAGCAAAGGAA |
| | | GAGAAGAAGAAGAAGACCCAGAGCAGCGGCTCTGGACAGGGCA |
| | | GCGAGGCACCAGAGAAGAAGAAGCCTAAGATCGATGAGCTGAA |
| | | GGTGTACCCAAAGGAGCTGGAGTCCGAGTTCGATAATTTTGAGG |
| | | ACTGGCTGCACACCTTCAACCTGCTGCGCGGCAAGACAGGCGA |
| | | CGATGAGGACGGCAGCACCGAGGAGGAGAGAATCGTGGGCCG |
| | | GTTTAAGGGCTCCCTGTGCGTGTACAAGGTGCCACTGCCTGAG |
| | | GACGTGAGCAGGGAGGCCGGATACGACTCTACCTATGGCATGT |
| | | TCCAGGGCATCCCCTCTAATGATCCTATCAACGTGCTGGTGCGC |
| | | GTGTATGTGGTGAGGGCCACAGATCTGCACCCCGCCGACATCA |
| | | ACGGCAAGGCCGACCCTTACATCGCCATCCGCCTGGGCAAGAC |
| | | CGATATCAGGGACAAGGAGAATTATATCTCCAAGCAGCTGAACC |
| | | CCGTGTTCGGCAAGTCTTTTGACATCGAGGCCAGCTTCCCTATG |
| | | GAGTCCATGCTGACCGTGGCCGTGTACGATTGGGACCTGGTGG |
| | | GCACCGACGATCTGATCGGCGAGACAAAGATCGATCTGGAGAA |
| | | TCGCTTTTATTCTAAGCACAGGGCAACCTGCGGAATCGCACAGA |
| | | CCTACAGCACACACGGCTATAACATCTGGCGCGACCCCATGAA |
| | | GCCTAGCCAGATCCTGACAAGGCTGTGCAAGGATGGCAAGGTG |
| | | GACGGACCACACTTCGGACCACCCGGCAGAGTGAAGGTGGCCA |
| | | ATCGGGTGTTTACAGGCCCTTCCGAGATCGAGGATGAGAACGG |
| | | CCAGCGCAAGCCAACCGACGAGCACGTGGCCCTGCTGGCCCT |
| | | GAGGCACTGGGAGGATATCCCAAGGGCCGGATGTAGGCTGGTG |
| | | CCTGAGCACGTGGAGACCAGACCACTGCTGAATCCAGACAAGC |
| | | CAGGAATCGAGCAGGGCAGGCTGGAGCTGTGGGTGGATATGTT |
| | | CCCAATGGACATGCCAGCCCCAGGAACACCCCTGGATATCTCC |
| | | CCTAGAAAGCCAAAGAAGTACGAGCTGAGAGTGATCATCTGGAA |
| | | CACAGACGAGGTGGTGCTGGAGGACGATGACTTCTTTACCGGC |
| | | GAGAAGTCTAGCGATATCTTTGTGCGCGGATGGCTGAAGGGAC |

TABLE 2-continued

OTOF Sequences

| SEQ ID NO. | Sequence Name | Sequence |
|---|---|---|
|  |  | AGCAGGAGGACAAGCAGGATACAGACGTGCACTACCACTCCCT |
|  |  | GACCGGCGAGGGCAATTTCAACTGGAGATACCTGTTCCCTTTTG |
|  |  | ATTATCTGGCCGCCGAGGAGAAGATCGTGATCTCTAAGAAGGAG |
|  |  | AGCATGTTTTCCTGGGACGAGACAGAGTATAAGATCCCAGCCAG |
|  |  | ACTGACCCTGCAGATCTGGGATGCCGACCACTTCAGCGCCGAT |
|  |  | GACTTTCTGGGCGCCATCGAGCTGGACCTGAACCGGTTCCCAA |
|  |  | GAGGCGCCAAGACCGCCAAGCAGTGCACAATGGAGATGGCAAC |
|  |  | CGGAGAGGTGGACGTGCCTCTGGTGTCTATCTTCAAGCAGAAG |
|  |  | CGGGTGAAGGGATGGTGGCCACTGCTGGCCAGGAACGAGAAT |
|  |  | GATGAGTTTGAGCTGACAGGCAAGGTGGAGGCAGAGCTGCACC |
|  |  | TGCTGACCGCCGAGGAGGCAGAGAAGAACCCAGTGGGCCTGG |
|  |  | CCAGGAATGAGCCCGACCCTCTGGAGAAGCCAAACAGGCCCGA |
|  |  | TACAGCCTTCGTGTGGTTTCTGAATCCTCTGAAGAGCATCAAGT |
|  |  | ACCTGATCTGTACCAGGTATAAGTGGCTGATCATCAAGATCGTG |
|  |  | CTGGCCCTGCTGGGACTGCTGATGCTGGGCCTGTTTCTGTACTC |
|  |  | CCTGCCCGGCTATATGGTGAAGAAGCTGCTGGGCGCCTGA |
| 4 | Human OTOF isoform 1 protein (NP_919224.1), also called human otoferlin isoform a, 1997 aa | MALLIHLKTVSELRGRGDRIAKVTFRGQSFYSRVLENCEDVADFDE TFRWPVASSIDRNEMLEIQVFNYSKVFSNKLIGTFRMVLQKVVEES HVEVTDTLIDDNNAIIKTSLCVEVRYQATDGTVGSWDDGDFLGDES LQEEEKDSQETDGLLPGSRPSSRPPGEKSFRRAGRSVFSAMKLGK NRSHKEEPQRPDEPAVLEMEDLDHLAIRLGDGLDPDSVSLASVTAL TTNVSNKRSKPDIKMEPSAGRPMDYQVSITVIEARQLVGLNMDPVV CVEVGDDKKYTSMKESTNCPYYNEYFVFDFHVSPDVMFDKIIKISVI HSKNLLRSGTLVGSFKMDVGTVYSQPEHQFHHKWAILSDPDDISS GLKGYVKCDVAVVGKGDNIKTPHKANETDEDDIEGNLLLPEGVPPE RQWARFYVKIYRAEGLPRMNTSLMANVKKAFIGENKDLVDPYVQV FFAGQKGKTSVQKSSYEPLWNEQVVFTDLFPPLCKRMKVQIRDSD KVNDVAIGTHFIDLRKISNDGDKGFLPTLGPAWVNMYGSTRNYTLL DEHQDLNEGLGEGVSFRARLLLGLAVEIVDTSNPELTSSTEVQVEQ ATPISESCAGKMEEFFLFGAFLEASMIDRRNGDKPITFEVTIGNYGN EVDGLSRPQRPRPRKEPGDEEEVDLIQNASDDEAGDAGDLASVSS TPPMRPQVTDRNYFHLPYLERKPCIYIKSWWPDQRRRLYNANIMD HIADKLEEGLNDIQEMIKTEKSYPERRLRGVLEELSCGCCRFLSLAD KDQGHSSRTRLDRERLKSCMRELENMGQQARMLRAQVKRHTVRD KLRLCQNFLQKLRFLADEPQHSIPDIFIWMMSNNKRVAYARVPSKD LLFSIVEEETGKDCAKVKTLFLKLPGKRGFGSAGWTVQAKVELYLW LGLSKQRKEFLCGLPCGFQEVKAAQGLGLHAFPPVSLVYTKKQAF QLRAHMYQARSLFAADSSGLSDPFARVFFINQSQCTEVLNETLCPT WDQMLVFDNLELYGEAHELRDDPPIIVIEIYDQDSMGKADFMGRTF AKPLVKMADEAYCPPRFPPQLEYYQIYRGNATAGDLLAAFELLQIG PAGKADLPPINGPVDVDRGPIMPVPMGIRPVLSKYRVEVLFWGLRD LKRVNLAQVDRPRVDIECAGKGVQSSLIHNYKKNPNFNTLVKWFEV DLPENELLHPPLNIRVVDCRAFGRYTLVGSHAVSSLRRFIYRPPDRS APSWNTTVRLLRRCRVLCNGGSSSHSTGEVVVTMEPEVPIKKLET MVKLDATSEAVVKVDVAEEEKEKKKKKKGTAEEPEEEEPDESMLD WWSKYFASIDTMKEQLRQQEPSGIDLEEKEEVDNTEGLKGSMKGK EKARAAKEEKKKKTQSSGSGQGSEAPEKKKPKIDELKVYPKELESE FDNFEDWLHTFNLLRGKTGDDEDGSTEEERIVGRFKGSLCVYKVPL PEDVSREAGYDSTYGMFQGIPSNDPINVLVRVYVVRATDLHPADIN GKADPYIAIRLGKTDIRDKENYISKQLNPVFGKSFDIEASFPMESMLT VAVYDWDLVGTDDLIGETKIDLENRFYSKHRATCGIAQTYSTHGYNI WRDPMKPSQILTRLCKDGKVDGPHFGPPGRVKVANRVFTGPSEIE DENGQRKPTDEHVALLALRHWEDIPRAGCRLVPEHVETRPLLNPD KPGIEQGRLELWVDMFPMDMPAPGTPLDISPRKPKKYELRVIIWNT DEVVLEDDDFFTGEKSSDIFVRGWLKGQQEDKQDTDVHYHSLTGE GNFNWRYLFPPFDYLAAEEKIVISKKESMFSWDETEYKIPARLTLQIW DADHFSADDFLGAIELDLNRFPRGAKTAKQCTMEMATGEVDVPLV SIFKQKRVKGWWPLLARNENDEFELTGKVEAELHLLTAEEAEKNPV GLARNEPDPLEKPNRPDTSFIWFLNPLKSARYFLWHTYRWLLLKLL LLLLLLLLLALFLYSVPGYLVKKILGA |
| 5 | DNA sequence encoding the human otoferlin isoform 1 protein (SEQ ID NO: 4), 5979 bp, corresponds to the coding sequence documented in NM_001100395 | ATGGCCCTGATTGTTCACCTCAAGACTGTCTCAGAGCTCCGAGG CAAAGGTGACCGGATTGCCAAAGTCACTTTCCGAGGGCAGTCTT TCTACTCCCGGGTCCTGGAGAACTGCGAGGGTGTGGCTGACTT TGATGAGACGTTCCGGTGGCCAGTGGCCAGCATCGACCGG AATGAAGTGTTGGAGATTCAGATTTTCAACTACAGCAAAGTCTTC AGCAACAAGCTGATAGGGACCTTCTGCATGGTGCTGCAGAAAGT GGTGGAGGAGAATCGGGTAGAGGTGACCGACACGCTGATGGAT GACAGCAATGCTATCATCAAGACCAGCCTGAGCATGGAGGTCC GGTATCAGGCCACAGATGGCACTGTGGGCCCCTGGGATGATGG AGACTTCCTGGGAGATGAATCCCTCCAGGAGGAGAAGGACAGC CAGGAGACAGATGGGCTGCTACCTGGTTCCCGACCCAGCACCC GGATATCTGGCGAGAAGAGCTTTCGCAGCAAAGGCAGAGAGAA GACCAAGGGAGGCAGAGATGGCGAGCACAAAGCGGGAAGGAG |

TABLE 2-continued

OTOF Sequences

| SEQ ID NO. | Sequence Name | Sequence |
|---|---|---|
| | | TGTGTTCTCGGCCATGAAACTCGGCAAAACTCGGTCCCACAAAG<br>AGGAGCCCCAAAGACAAGATGAGCCAGCAGTGCTGGAGATGGA<br>GGACCTGGACCACCTAGCCATTCAGCTGGGGGATGGGCTGGAT<br>CCTGACTCCGTGTCTCTAGCCTCGGTCACCGCTCTCACCAGCAA<br>TGTCTCCAACAAACGGTCTAAGCCAGATATTAAGATGGAGCCCA<br>GTGCTGGAAGGCCCATGGATTACCAGGTCAGCATCACAGTGATT<br>GAGGCTCGGCAGCTGGTGGGCTTGAACATGGACCCTGTGGTGT<br>GTGTGGAGGTGGGTGATGACAAGAAATACACGTCAATGAAGGA<br>GTCCACAAACTGCCCTTACTACAACGAGTACTTTGTCTTCGACTT<br>CCATGTCTCTCCTGATGTCATGTTTGACAAGATCATCAAGATCTC<br>GGTTATCCATTCTAAGAACCTGCTTCGGAGCGGCACCCTGGTGG<br>GTTCCTTCAAAATGGATGTGGGGACTGTGTATTCCCAGCCTGAA<br>CACCAGTTCCATCACAAATGGGCCATCCTGTCAGACCCCGATGA<br>CATCTCTGCTGGGTTGAAGGGTTATGTAAAGTGTGATGTCGCTG<br>TGGTGGGCAAGGGAGACAACATCAAGACACCCCACAAGGCCAA<br>CGAGACGGATGAGGACGACATTGAAGGGAACTTGCTGCTCCCC<br>GAGGGCGTGCCCCCCGAACGGCAGTGGGCACGGTTCTATGTGA<br>AAATTTACCGAGCAGAGGGACTGCCCCGGATGAACACAAGCCT<br>CATGGCCAACGTGAAGAAGGCGTTCATCGGTGAGAACAAGGAC<br>CTCGTCGACCCCTATGTGCAAGTCTTCTTTGCTGGACAAAAGGG<br>CAAAACATCAGTGCAGAAGAGCAGCTATGAGCCGCTATGGAATG<br>AGCAGGTCGTCTTCACAGACTTGTTCCCCCCACTCTGCAAACGC<br>ATGAAGGTGCAGATCCGGGACTCTGACAAGGTCAATGATGTGG<br>CCATCGGCACCCACTTCATCGACCTGCGCAAGATTTCCAACGAT<br>GGAGACAAAGGCTTCCTGCCTACCCTCGGTCCAGCCTGGGTGA<br>ACATGTACGGCTCCACGCGCAACTACACACTGCTGGACGAGCA<br>CCAGGACTTGAATGAAGGCCTGGGGGAGGGTGTGTCCTTCCGG<br>GCCCGCCTCATGTTGGGACTAGCTGTGGAGATCCTGGACACCT<br>CCAACCCAGAGCTCACCAGCTCCACGGAGGTGCAGGTGGAGCA<br>GGCCACGCCTGTCTCGGAGAGCTGCACAGGGAGAATGGAAGAA<br>TTTTTTCTATTTGGAGCCTTCTTGGAAGCCTCAATGATTGACCGG<br>AAAAATGGGGACAAGCCAATTACCTTTGAGGTGACCATAGGAAA<br>CTACGGCAATGAAGTCGATGGTATGTCCCGGCCCCTGAGGCCT<br>CGGCCCCGGAAAGAGCCTGGGGATGAAGAAGAGGTAGACCTGA<br>TTCAGAACTCCAGTGACGATGAAGGTGACGAAGCCGGGGACCT<br>GGCCTCGGTGTCCTCCACCCCACCTATGCGGCCCCAGATCACG<br>GACAGGAACTATTTCCACCTGCCCTACCTGGAGCGCAAGCCCT<br>GCATCTATATCAAGAGCTGGTGGCCTGACCAGAGGCGGCGCCT<br>CTACAATGCCAACATCATGGATCACATTGCTGACAAGCTGGAAG<br>AAGGCCTGAATGATGTACAGGAGATGATCAAAACGGAGAAGTCC<br>TACCCGGAGCGCCGCCTGCGGGGTGTGCTAGAGGAACTCAGCT<br>GTGGCTGCCACCGCTTCCTCTCCCTCTCGGACAAGGACCAGGG<br>CCGCTCGTCCCGCACCAGGCTGGATCGAGAGCGTCTTAAGTCC<br>TGTATGAGGGAGTTGGAGAGCATGGGACAGCAGGCCAAGAGCC<br>TGAGGGCTCAGGTGAAGCGGCACACTGTTCGGGACAAGCTGAG<br>GTCATGCCAGAACTTTCTGCAGAAGCTACGCTTCCTGGCGGATG<br>AGCCCCAGCACAGCATTCCTGATGTGTTCATTTGGATGATGAGC<br>AACAACAAACGTATCGCCTATGCCCGCGTGCCTTCCAAAGACCT<br>GCTCTTCTCCATCGTGGAGGAGGAACTGGGCAAGGACTGCGCC<br>AAAGTCAAGACCCTCTTCCTGAAGCTGCCAGGGAAGAGGGGCT<br>TCGGCTCGGCAGGCTGGACAGTACAGGCCAAGCTGGAGCTCTA<br>CCTGTGGCTGGGCCTCAGCAAGCAGCGAAAGGACTTCCTGTGT<br>GGTCTGCCCTGTGGCTTCGAGGAGGTCAAGGCAGCCCAAGGCC<br>TGGGCCTGCATTCCTTTCCGCCCATCAGCCTAGTCTACACCAAG<br>AAGCAAGCCTTCCAGCTCCGAGCACACATGTATCAGGCCCGAA<br>GCCTCTTTGCTGCTGACAGCAGTGGGCTCTCTGATCCCTTTGCC<br>CGTGTCTTCTTCATCAACCAGAGCCAATGCACTGAGGTTCTAAA<br>CGAGACACTGTGTCCCACCTGGGACCAGATGCTGGTATTTGACA<br>ACCTGGAGCTGTACGGTGAAGCTCACGAGTTACGAGATGATCC<br>CCCCATCATTGTCATTGAAATCTACGACCAGGACAGCATGGGCA<br>AAGCCGACTTCATGGGCCGGACCTTCGCCAAGCCCCTGGTGAA<br>GATGGCAGATGAAGCATACTGCCCACCTCGCTTCCCGCCGCAG<br>CTTGAGTACTACCAGATCTACCGAGGCAGTGCCACTGCCGGAG<br>ACCTACTGGCTGCCTTCGAGCTGCTGCAGATTGGGCCATCAGG<br>GAAGGCTGACCTGCCACCCATCAATGGCCCAGTGGACATGGAC<br>AGAGGGCCCATCATGCCTGTGCCCGTGGGAATCCGGCCAGTGC<br>TCAGCAAGTACCGAGTGGAGGTGCTGTTCTGGGGCCTGAGGGA<br>CCTAAAGAGGGTGAACCTGGCCCAGGTGGACCGACCACGGGTG<br>GACATCGAGTGTGCAGGAAAGGGGGTACAATCCTCCCTGATTCA<br>CAATTATAAGAAGAACCCCAACTTCAACACGCTGGTCAAGTGGT<br>TTGAAGTGGACCTCCCGGAGAATGAGCTCCTGCACCCACCCTT<br>GAACATCCGAGTGGTAGATTGCCGGGCCTTTGGACGATACACC<br>CTGGTGGGTTCCCACGCAGTCAGCTCACTGAGGCGCTTCATCTA<br>CCGACCTCCAGACCGCTCAGCCCCCAACTGGAACACCACAGGG<br>GAGGTTGTAGTAAGCATGGAGCCTGAGGAGCCAGTTAAGAAGC |

TABLE 2-continued

OTOF Sequences

| SEQ ID NO. | Sequence Name | Sequence |
|---|---|---|
| | | TGGAGACCATGGTGAAACTGGATGCGACTTCTGATGCTGTGGTC AAGGTGGATGTGGCTGAAGATGAGAAGGAAAGGAAGAAGAAGA AAAAGAAAGGCCCGTCAGAGGAGCCAGAGGAGGAAGAGCCCG ATGAGAGCATGCTGGATTGGTGGTCCAAGTACTTCGCCTCCATC GACACAATGAAGGAGCAACTTCGACAACATGAGACCTCTGGAAC TGACTTGGAAGAGAAGGAAGAGATGGAAAGCGCTGAGGGCCTG AAGGGACCAATGAAGAGCAAGGAGAAGTCCAGAGCTGCAAAGG AGGAGAAAAAGAAGAAAAACCAGAGCCCTGGCCCTGGCCAGGG ATCGGAGGCTCCTGAGAAGAAGAAAGCCAAGATCGATGAGCTTA AGGTGTACCCCAAGGAGCTGGAATCGGAGTTTGACAGCTTTGA GGACTGGCTGCACACCTTCAACCTGTTGAGGGGCAAGACGGGA GATGATGAGGATGGCTCCACAGAGGAGGAGCGCATAGTAGGCC GATTCAAGGGCTCCCTCTGTGTGTACAAAGTGCCACTCCCAGAA GATGTATCTCGAGAAGCTGGCTATGATCCCACCTATGGAATGTT CCAGGGCATCCCAAGCAATGACCCCATCAATGTGCTGGTCCGA ATCTATGTGGTCCGGGCCACAGACCTGCACCCGGCCGACATCA ATGGCAAAGCTGACCCCTATATTGCCATCAAGTTAGGCAAGACC GACATCCGAGACAAGGAGAACTACATCTCCAAGCAGCTCAACCC TGTGTTTGGGAAGTCCTTTGACATTGAGGCCTCCTTCCCCATGG AGTCCATGTTGACAGTGGCCGTGTACGACTGGGATCTGGTGGG CACTGATGACCTCATCGGAGAAACCAAGATTGACCTGGAAAACC GCTTCTACAGCAAGCATCGCGCCACCTGCGGCATCGCACAGAC CTATTCCATACATGGCTACAATATCTGGAGGGACCCCATGAAGC CCAGCCAGATCCTGACACGCCTCTGTAAAGAGGGCAAAGTGGA CGGCCCCCACTTTGGTCCCCATGGGAGAGTGAGGGTTGCCAAC CGTGTCTTCACGGGGCCTTCAGAAATAGAGGATGAGAATGGTCA GAGGAAGCCCACAGATGAGCACGTGGCACTGTCTGCTCTGAGA CACTGGGAGGACATCCCCCGGGTGGGCTGCCGCCTTGTGCCG GAACACGTGGAGACCAGGCCGCTGCTCAACCCTGACAAGCCAG GCATTGAGCAGGGCCGCCTGGAGCTGTGGGTGGACATGTTCCC CATGGACATGCCAGCCCCTGGGACACCTCTGGATATATCCCCCA GGAAACCCAAGAAGTACGAGCTGCGGGTCATCGTGTGGAACAC AGACGAGGTGGTCCTGGAAGACGATGATTTCTTCACGGGGAGAG AAGTCCAGTGACATTTTTGTGAGGGGGTGGCTGAAGGGCCAGC AGGAGGACAAACAGGACACAGATGTCCACTATCACTCCCTCACG GGGGAGGGCAACTTCAACTGGAGATACCTCTTCCCCTTCGACTA CCTAGCGGCCGAAGAGAAGATCGTTTATGTCCAAAAAGGAGTCTA TGTTCTCCTGGGATGAGACGGAGTACAAGATCCCTGCGCGGCT CACCCTGCAGATCTGGGACGCTGACCACTTCTCGGCTGACGAC TTCCTGGGGGCTATCGAGCTGGACCTGAACCGGTTCCCGAGGG GCGCTAAGACAGCCAAGCAGTGCACCATGGAGATGGCCACCGG GGAGGTGGACGTACCCCTGGTTTCCATCTTTAAACAGAAACGTG TCAAAGGCTGGTGGCCCCTCCTGGCCCGCAATGAGAATGATGA GTTTGAGCTCACAGGCAAAGTGGAGGCGGAGCTACACCTACTC ACGGCAGAGGAGGCAGAGAAGAACCCTGTGGGCCTGGCTCGC AATGAACCTGATCCCCTAGAAAAAACCCAACCGGCCTGACACGGC ATTCGTCTGGTTCCTGAACCCACTCAAATCTATCAAGTACCTCAT CTGCACCCGGTACAAGTGGCTGATCATCAAGATCGTGCTGGCG CTGCTGGGGCTGCTCATGCTGGCCCTCTTCCTTTACAGCCTCCC AGGCTACATGGTCAAGAAGCTCCTAGGGGCCTGA |
| 6 | Codon-optimized (CO) DNA sequence encoding the human otoferlin isoform 1 protein (SEQ ID NO: 4), 5994 bp | ATGGCACTGCTGATCCACCTGAAAACCGTCTCCGAACTGAGAGG CAGAGGGGACAGAATCGCTAAAGTCACCTTCCGGGGACAGAGC TTTTACAGCAGGGTGCTGGAGAACTGCGAGGACGTGGCCGACT TTGACGAGACATTCAGGTGGCCCGTGGCCAGCTCCATCGATCG CAATGAGATGCTGGAGATCCAGGTGTTTAACTATAGCAAGGTGT TCTCCAATAAGCTGATCGGCACCTTCCGGATGGTGCTGCAGAAG GTGGTGGAGGAGTCCCACGTGGAGGTGACCGACACCACTGATCG ACGATAACAATGCCATCATCAAGACATCCCTGTGCGTGGAGGTG CGCTACCAGGCCACCGATGGCACAGTGGGCTCTTGGGACGATG GCGACTTCCTGGGCGATGAGTCCCTGCAGGAGGAGGAGAAGGA CTCTCAGGAGACAGATGGCCTGCTGCCTGGCTCCCGGCCATCT AGCCGCCCCCCTGGCGAGAAGTCTTTTAGGAGAGCCGGCAGGT CCGTGTTCTCTGCCATGAAGCTGGGCAAGAACAGGAGCCACAA GGAGGAGCCTCAGAGGCCCGACGAGCCAGCCGTGCTGGAGAT GGAGGACCTGGATCACCTGGCCATCGAGACTGGGCGATGGCCTG GACCCTGATAGCGTGTCCCTGGCCTCCGTGACCGCCCTGACCA CAAACGTGTCTAATAAGCGGAGCAAGCCAGACATCAAGATGGAG CCATCTGCCGGCAGGCCCATGGATTACCAGGTGAGCATCACAG TGATCGAGGCCAGACAGCTGGTGGGCCTGAACATGGGACCCCGT GGTGTGCGTGGAAGTGGGCGACGATAAGAAGTACACCTCCATG AAGGAGTCTACAAACTGTCCATACTACAACGAGTACTTCGTGTTT GATTTCCACGTGAGCCCCGACGTGATGTTCGATAAGATCATCAA GATCAGCGTGATCCACTCCAAGAATCTGCTGCGGGTCTGGCACC CTGGTGGGAAGCTTTAAGATGGACGTGGGCACAGTGTACTCTCA |

TABLE 2-continued

OTOF Sequences

| SEQ ID NO. | Sequence Name | Sequence |
|---|---|---|
| | | GCCTGAGCACCAGTTCCACCACAAGTGGGCCATCCTGAGCGAT |
| | | CCAGACGATATCTCCTCTGGCCTGAAGGGCTATGTGAAGTGCGA |
| | | CGTGGCAGTGGTGGGCAAGGGCGATAACATCAAGACCCCACAC |
| | | AAGGCCAATGAGACAGACGAGGACGATATCGAGGGAAACCTGC |
| | | TGCTGCCAGAGGGAGTGCCACCCGAGAGGCAGTGGGCCAGGT |
| | | TCTACGTGAAGATCTATAGGGCAGAGGGCCTGCCTAGGATGAA |
| | | CACCAGCCTGATGGCCAATGTGAAGAAGGCCTTCATCGGCGAG |
| | | AACAAGGACCTGGTGGATCCCTACGTGCAGGTGTTCTTTGCCG |
| | | GCCAGAAGGGCAAGACCTCCGTGCAGAAGAGCTCCTATGAGCC |
| | | TCTGTGGAATGAGCAGGTGGTGTTTACAGACCTGTTCCCTCCAC |
| | | TGTGCAAGAGGATGAAGGTGCAGATCAGAGACTCTGATAAGGT |
| | | GAACGACGTGGCCATCGGCACCCACTTTATCGATCTGAGGAAG |
| | | ATCAGCAATGACGGCGATAAGGGCTTCCTGCCCACCCTGGGCC |
| | | CCGCCTGGGTGAACATGTACGGCAGCACCAGAAATTATACACTG |
| | | CTGGACGAGCACCAGGATCTGAACGAGGGCCTGGGCGAGGGC |
| | | GTGAGCTTTAGAGCCAGGCTGCTGCTGGGCCTGGCCGTGGAGA |
| | | TCGTGGACACCTCCAATCCCGAGCTGACCTCTAGCACAGAGGT |
| | | GCAGGTGGAGCAGGCCACACCTATCTCTGAGAGCTGTGCCGGC |
| | | AAGATGGAGGAGTTCTTTCTGTTTGGCGCCTTCCTGGAGGCCTC |
| | | CATGATCGACCGGCGCAACGGCGATAAGCCTATCACCTTCGAG |
| | | GTGACAATCGGCAACTACGGCAATGAGGTGGACGGCCTGTCTC |
| | | GGCCCCAGCGCCCAAGGCCCAGAAAGGAGCCTGGCGACGAGG |
| | | AGGAGGTGGATCTGATCCAGAACGCCAGCGACGATGAGGCAGG |
| | | CGACGCAGGCGATCTGGCCTCCGTGTCCTCTACCCCCCCTATG |
| | | CGGCCACAGGTGACAGACCGCAATTACTTTCACCTGCCTTATCT |
| | | GGAGCGCAAGCCATGCATCTACATCAAGTCTTGGTGGCCCGAT |
| | | CAGAGGAGACGGCTGTATAACGCCAATATCATGGACCACATCGC |
| | | CGATAAGCTGGAGGAGGGCCTGAATGACATCCAGGAGATGATC |
| | | AAGACCGAGAAGTCCTATCCAGAGCGCAGGCTGAGGGGCGTGC |
| | | TGGAGGAGCTGAGCTGTGGCTGCTGTAGATTCCTGTCCCTGGC |
| | | CGACAAGGATCAGGGGCACTCATCACGGACACGGCTGGACCGG |
| | | GAGCGGCTGAAATCATGTATGCGGGAGCTGGAAAATATGGGAC |
| | | AGCAGGCAAGGATGCTGCGCGCCCAGGTGAAGAGGCACACCG |
| | | TGAGAGACAAGCTGCGGCTGTGCCAGAACTTCCTGCAGAAGCT |
| | | GCGCTTTCTGGCCGATGAGCCACAGCACAGCATCCCCGACATC |
| | | TTCATCTGGATGATGTCCAACAATAAGAGAGTGGCCTACGCCCG |
| | | GGTGCCCTCTAAGGATCTGCTGTTTAGCATCGTGGAGGAGGAG |
| | | ACAGGCAAGGACTGTGCCAAGGTGAAGACCCTGTTCCTGAAGC |
| | | TGCCTGGCAAGAGAGGCTTTGGCAGCGCCGGATGGACCGTGCA |
| | | GGCAAAGGTGGAGCTGTATCTGTGGCTGGGCCTGTCTAAGCAG |
| | | CGGAAGGAGTTCCTGTGCGCGCCTGCCCTGTGGCTTTCAGGAGG |
| | | TGAAGGCAGCACAGGGACTGGGACTGCACGCCTTCCCCCCCGT |
| | | GAGCCTGGTGTACACCAAGAAGCAGGCCTTTCAGCTGAGGGCC |
| | | CATATGTACCAGGCCAGGTCTCTGTTCGCCGCCGATAGCTCCG |
| | | GACTGAGCGACCCTTTTGCCAGGGTGTTCTTTATCAATCAGAGC |
| | | CAGTGCACAGAGGTGCTGAACGAGACCCTGTGCCCAACATGGG |
| | | ATCAGATGCTGGTGTTCGACAACCTGGAGCTGTACGGAGAGGC |
| | | ACACGAGCTGAGGGACGATCCACCCATCATCGTGATCGAGATCT |
| | | ATGATCAGGACTCCATGGGCAAGGCCGATTTCATGGGCAGGAC |
| | | CTTTGCCAAGCCCCTGGTGAAGATGGCCGACGAGGCCTACTGC |
| | | CCTCCAAGATTCCCCCCTCAGCTCGAGTACTATCAGATCTATAG |
| | | GGGAAATGCAACCGCCGGAGACCTGCTGGCCGCCTTTGAGCTG |
| | | CTGCAGATCGGCCCCGCCGGAAAGGCAGACCTGCCACCCATCA |
| | | ACGGCCCAGTGGATGTGGACAGAGGCCCCATCATGCCTGTGCC |
| | | AATGGGCATCAGACCAGTGCTGTCCAAGTACAGGGTGGAGGTG |
| | | CTGTTCTGGGGACTGCGCGACCTGAAGAGGGTGAATCTGGCCC |
| | | AGGTGGATAGGCCCAGAGTGGACATCGAGTGCGCCGGAAAGG |
| | | GCGTGCAGTCTAGCCTGATCCACAACTATAAGAAGAACCCAAAT |
| | | TTCAACACCCTGGTGAAGTGGTTTGAGGTGGATCTGCCCGAGAA |
| | | TGAGCTGCTGCACCCTCCACTGAACATCCGGGTGGTGGACTGT |
| | | AGAGCCTTCGGCAGGTACACCCTGGTGGGCAGCCACGCCGTGA |
| | | GCAGCCTGAGGAGGTTCATCTACAGGCCCCCTGACAGGTCCGC |
| | | CCCTTCTTGGAATACCACAGTGAGACTGCTGCGGCGCTGCAGG |
| | | GTGCTGTGCAACGGAGGCAGCTCCTCTCACTCTACCGGCGAGG |
| | | TGGTGGTGACAATGGAGCCTGAGGTACCCATCAAGAAGCTGGA |
| | | GACCATGGTGAAGCTGGATGCCACAAGCGAGGCAGTGGTGAAG |
| | | GTGGACGTGGCAGAGGAGGAGAAGGAGAAGAAGAAGAAGAAG |
| | | AAGGGAACCGCCGAGGAGCCTGAGGAAGAGGAGCCAGATGAG |
| | | AGCATGCTGGACTGGTGGTCCAAGTACTTCGCCTCTATCGACAC |
| | | AATGAAGGAGCAGCTGAGACAGCAGGAGCCTAGCGGCATCGAT |
| | | CTGGAGGAGAAGGAGGAGGTGGACAATACCGAGGGCCTGAAG |
| | | GGCTCCATGAAGGGCAAGGAGAAGGCAAGGGCAGCAAAGGAA |
| | | GAGAAGAAGAAGAAGACCCAGAGCAGCGGCTCTGGACAGGGCA |
| | | GCGAGGCACCAGAGAAGAAGAAGCCTAAGATCGATGAGCTGAA |
| | | GGTGTACCCAAAGGAGCTGGAGTCCGAGTTCGATAATTTTGAGG |

TABLE 2-continued

OTOF Sequences

| SEQ ID NO. | Sequence Name | Sequence |
|---|---|---|

```
ACTGGCTGCACACCTTCAACCTGCTGCGCGGCAAGACAGGCGA
CGATGAGGACGGCAGCACCGAGGAGGAGAGAATCGTGGGCCG
GTTTAAGGGCTCCCTGTGCGTGTACAAGGTGCCACTGCCTGAG
GACGTGAGCAGGGAGGCCGGATACGACTCTACCTATGGCATGT
TCCAGGGCATCCCCTCTAATGATCCTATCAACGTGCTGGTGCGC
GTGTATGTGGTGAGGGCCACAGATCTGCACCCCGCCGACATCA
ACGGCAAGGCCGACCCTTACATCGCCATCCGCCTGGGCAAGAC
CGATATCAGGGACAAGGAGAATTATATCTCCAAGCAGCTGAACC
CCGTGTTCGGCAAGTCTTTTGACATCGAGGCCAGCTTCCCTATG
GAGTCCATGCTGACCGTGGCCGTGTACGATTGGGACCTGGTGG
GCACCGACGATCTGATCGGCGAGACAAAGATCGATCTGGAGAA
TCGCTTTTATTCTAAGCACAGGGCAACCTGCGGAATCGCACAGA
CCTACAGCACACACGGCTATAACATCTGGCGCGACCCCATGAA
GCCTAGCCAGATCCTGACAAGGCTGTGCAAGGATGGCAAGGTG
GACGGACCACACTTCGGACCACCCGGCAGAGTGAAGGTGGCCA
ATCGGGTGTTTACAGGCCCTTCCGAGATCGAGGATGAGAACGG
CCAGCGCAAGCCAACCGACGAGCACGTGGCCCTGCTGGCCCT
GAGGCACTGGGAGGATATCCCAAGGGCCGGATGTAGGCTGGTG
CCTGAGCACGTGGAGACCAGACCACTGCTGAATCCAGACAAGC
CAGGAATCGAGCAGGGCAGGCTGGAGCTGTGGGTGGATATGTT
CCCAATGGACATGCCAGCCCCAGGAACACCCCTGGATATCTCC
CCTAGAAAGCCAAAGAAGTACGAGCTGAGAGTGATCATCTGGAA
CACAGACGAGGTGGTGCTGGAGGACGATGACTTCTTTACCGGC
GAGAAGTCTAGCGATATCTTTGTGCGCGGATGGCTGAAGGGAC
AGCAGGAGGACAAGCAGGATACAGACGTGCACTACCACTCCCT
GACCGGCGAGGGCAATTTCAACTGGAGATACCTGTTCCCTTTTG
ATTATCTGGCCGCCGAGGAGAAGATCGTGATCTCTAAGAAGGAG
AGCATGTTTTCCTGGGACGAGACAGAGTATAAGATCCCAGCCAG
ACTGACCCTGCAGATCTGGGATGCCGACCACTTCAGCGCCGAT
GACTTTCTGGGCGCCATCGAGCTGGACCTGAACCGGTTCCCAA
GAGGCGCCAAGACCGCCAAGCAGTGCACAATGGAGATGGCAAC
CGGAGAGGTGGACGTGCCTCTGGTGTCTATCTTCAAGCAGAAG
AGGGTGAAGGGCTGGTGGCCACTGCTGGCCAGAAACGAGAATG
ATGAGTTTGAGCTGACAGGCAAGGTGGAGGCAGAGCTGCACCT
GCTGACCGCCGAGGAGGCAGAGAAGAACCCAGTGGGCCTGGC
CAGGAATGAGCCCGACCCTCTGGAGAAGCCAAACAGGCCCGAC
ACCAGCTTCATCTGGTTTCTGAATCCTCTGAAGTCCGCCCGGTA
CTTCCTGTGGCACACCTATCGCTGGCTGCTGCTGAAGCTGTTAT
TACTGTTATTACTGCTGCTGCTGCTGGCCCTGTTTCTGTACAGC
GTGCCCGGCTATCTGGTGAAGAAGATCCTGGGCGCCTGA
```

40

Expression of OTOF in Mammalian Cells

Mutations in OTOF have been linked to sensorineural hearing loss and auditory neuropathy. The compositions and methods described herein increase the expression of WT OTOF isoform 5 protein by administering a first nucleic acid vector that contains a polynucleotide encoding an N-terminal portion of an OTOF isoform 5 protein and a second nucleic acid vector that contains a polynucleotide encoding a C-terminal portion of an OTOF isoform 5 protein. In order to utilize nucleic acid vectors for therapeutic application in the treatment of sensorineural hearing loss and auditory neuropathy, they can be directed to the interior of the cell, and, in particular, to specific cell types. A wide array of methods has been established for the delivery of proteins to mammalian cells and for the stable expression of genes encoding proteins in mammalian cells.

Polynucleotides Encoding OTOF

One platform that can be used to achieve therapeutically effective intracellular concentrations of OTOF isoform 5 in mammalian cells is via the stable expression of the gene encoding OTOF isoform 5 (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

OTOF isoform 5 can also be introduced into a mammalian cell by targeting vectors containing portions of a gene encoding an OTOF isoform 5 protein to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding an OTOF isoform 5 protein by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode an OTOF protein downstream of a mammalian promoter (e.g., a polynucleotide that encodes an N-terminal portion of an OTOF isoform 5 protein downstream of a mammalian promoter). Promoters that are useful for the expression of an OTOF protein in mammalian cells include ubiquitous promoters and cochlear hair cell-specific promoters. Ubiquitous promoters include the CAG promoter, the cytomegalovirus (CMV) promoter, and a truncated form of the chimeric CMV-chicken β-actin promoter (CBA), in which the hybrid chicken β-actin/rabbit β-globin intron is greatly shortened to produce a smaller version of the promoter called smCBA. Cochlear hair cell-specific promoters include the Myosin 15 (Myo15) promoter. Myo15 promoter sequences for use in the methods and compositions described herein are described below and in Table 3. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of Moloney virus, Epstein barr virus (EBV) promoter, and the Rous sarcoma virus (RSV) promoter.

Murine Myosin 15 Promoters

In some embodiments, the Myo15 promoter for use in the compositions and methods described herein includes polynucleotide sequences from regions of the murine Myo15 locus that are capable of expressing a transgene specifically in hair cells, or variants thereof, such as a polynucleotide sequences that have at least 85% sequence identity (e.g., 85%, 90%, 95%, 96%, 97%, 98%, 99%, or more, sequence identity) to regions of the murine Myo15 locus that are capable of expressing a transgene specifically in hair cells. These regions include polynucleotide sequences immediately preceding the murine Myo15 translation start site and an upstream regulatory element that is located over 5 kb from the murine Myo15 translation start site. The murine Myo15 promoter for use in the compositions and methods described herein can optionally include a linker operably linking the regions of the murine Myo15 locus that are capable of expressing a transgene specifically in hair cells, or the regions of the murine Myo15 locus can be joined directly without an intervening linker.

In some embodiments, the murine Myo15 promoter for use in the compositions and methods described herein contains a first region (an upstream regulatory element) having at least 85% sequence identity (e.g., 85%, 90%, 95%, 96%, 97%, 98%, 99%, or more, sequence identity) to a region containing the first non-coding exon of the murine Myo15 gene (nucleic acids from −6755 to −7209 with respect to the murine Myo15 translation start site, the sequence of which is set forth in SEQ ID NO: 7) or a functional portion or derivative thereof joined (e.g., operably linked) to a second region having at least 85% sequence identity (e.g., 85%, 90%, 95%, 96%, 97%, 98%, 99%, or more, sequence identity) to the polynucleotide sequence immediately preceding the murine Myo15 translation start site (nucleic acids from −1 to −1157 with respect to the murine Myo15 translation start site, the sequence of which is set forth in SEQ ID NO: 8) or a functional portion or derivative thereof. The functional portion of SEQ ID NO: 7 may have the sequence of nucleic acids from −7166 to −7091 with respect to the murine Myo15 translation start site (set forth in SEQ ID NO: 9) and/or the sequence of nucleic acids from −7077 to −6983 with respect to the murine Myo15 translation start site (set forth in SEQ ID NO: 10). The first region may contain the polynucleotide sequence of SEQ ID NO: 9 fused to the polynucleotide sequence of SEQ ID NO: 10 with no intervening nucleic acids, as set forth in SEQ ID NO: 11, or the first region may contain the polynucleotide sequence of SEQ ID NO: 10 fused to the polynucleotide sequence of SEQ ID NO: 9 with no intervening nucleic acids, as set forth in SEQ ID NO: 12. Alternatively, the first region may contain the sequences of SEQ ID NO: 9 and SEQ ID NO: 10 joined by the endogenous intervening polynucleotide sequence (e.g., the first region may have or include the sequence of nucleic acids from −7166 to −6983 with respect to the murine Myo15 translation start site, as set forth in SEQ ID NO: 13 and SEQ ID NO: 33) or a nucleic acid linker. In a murine Myo15 promoter in which the first region contains both SEQ ID NO: 9 and SEQ ID NO: 10, the two sequences can be included in any order (e.g., SEQ ID NO: 9 may be joined to (e.g., precede) SEQ ID NO: 10, or SEQ ID NO: 10 may be joined to (e.g., precede) SEQ ID NO: 9). The functional portion of SEQ ID NO: 8 may have the sequence of nucleic acids from −590 to −509 with respect to the murine Myo15 translation start site (set forth in SEQ ID NO: 14) and/or the sequence of nucleic acids from −266 to −161 with respect to the murine Myo15 translation start site (set forth in SEQ ID NO: 15). In some embodiments, the sequence containing SEQ ID NO: 14 has the sequence of SEQ ID NO: 34. In some embodiments, the sequence containing SEQ ID NO: 15 has the sequence of SEQ ID NO: 35. The second region may contain the polynucleotide sequence of SEQ ID NO: 14 fused to the polynucleotide sequence of SEQ ID NO: 15 with no intervening nucleic acids, as set forth in SEQ ID NO: 16, or the second region may contain the polynucleotide sequence of SEQ ID NO: 15 fused to the polynucleotide sequence of SEQ ID NO: 14 with no intervening nucleic acids, as set forth in SEQ ID NO: 17. The second region may contain the nucleic acid sequence of SEQ ID NO: 34 fused to the nucleic acid sequence of SEQ ID NO: 35 with no intervening nucleic acids, as set forth in SEQ ID NO: 38, or the second region may contain the nucleic acid sequence of SEQ ID NO: 35 fused to the nucleic acid sequence of SEQ ID NO: 34 with no intervening nucleic acids. Alternatively, the second region may contain the sequences of SEQ ID NO: 14 and SEQ ID NO: 15 joined by the endogenous intervening polynucleotide sequence (e.g., the second region may have the sequence of nucleic acids from −590 to −161 with respect to the murine Myo15 translation start site, as set forth in SEQ ID NO: 18) or a nucleic acid linker. In a murine Myo15 promoter in which the second region contains both SEQ ID NO: 14 and SEQ ID NO: 15, the two sequences can be included in any order (e.g., SEQ ID NO: 14 may be joined to (e.g., precede) SEQ ID NO: 15, or SEQ ID NO: 15 may be joined to (e.g., precede) SEQ ID NO: 14).

The first region and the second region of the murine Myo15 promoter can be joined directly or can be joined by a nucleic acid linker. For example, the murine Myo15 promoter can contain the sequence of SEQ ID NO: 7 or a functional portion or derivative thereof (e.g., any one or more of SEQ ID NOs: 9-13 and 33, e.g., SEQ ID NOs 9 and 10) fused to the sequence of SEQ ID NO: 8 or a functional portion or derivative thereof (e.g., any one or more of SEQ ID NOs: 14-18, 34, 35, and 38, e.g., SEQ ID NOs 14 and 15) with no intervening nucleic acids. For example, the polynucleotide sequence of the murine Myo15 promoter that results from direct fusion of SEQ ID NO: 7 to SEQ ID NO: 8 is set forth in SEQ ID NO: 19. Alternatively, a linker can be used to join the sequence of SEQ ID NO: 7 or a functional portion or derivative thereof (e.g., any one or more of SEQ ID NOs: 9-13 and 33, e.g., SEQ ID NOs 9 and 10) to the sequence of SEQ ID NO: 8 or a functional portion or derivative thereof (e.g., any one or more of SEQ ID NOs: 14-18, 34, 35, and 38, e.g., SEQ ID NOs 14 and 15). Exemplary Myo15 promoters containing functional portions of both SEQ ID NO: 7 and SEQ ID NO: 8 are provided in SEQ ID NOs: 21, 22, 36, 37, 42, and 43.

The length of a nucleic acid linker for use in a murine Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the murine Myo15 promoter described herein do not disrupt the ability of the murine Myo15 promoter of the invention to induce transgene expression in hair cells.

In some embodiments, the sequence of SEQ ID NO: 7 or a functional portion or derivative thereof (e.g., any one or more of SEQ ID NOs: 9-13 and 33, e.g., SEQ ID NOs 9 and 10) is joined (e.g., operably linked) to the sequence of SEQ ID NO: 8 or a functional portion or derivative thereof (e.g., any one or more of SEQ ID NOs: 14-18, 34, 35, and 38, e.g., SEQ ID NOs 14 and 15), and, in some embodiments, the order of the regions is reversed (e.g., the sequence of SEQ ID NO: 8 or a functional portion or derivative thereof (e.g., any one or more of SEQ ID NOs: 14-18, 34, 35, and 38, e.g., SEQ ID NOs 14 and 15) is joined (e.g., operably linked) to the sequence of SEQ ID NO: 7 or a functional portion or derivative thereof (e.g., any one or more of SEQ ID NOs: 9-13 and 33, e.g., SEQ ID NOs 9 and 10)). For example, the polynucleotide sequence of a murine Myo15 promoter that results from direct fusion of SEQ ID NO: 8 to SEQ ID NO: 7 is set forth in SEQ ID NO: 20. An example of a murine Myo15 promoter in which a functional portion or derivative of SEQ ID NO: 8 precedes a functional portion or derivative of SEQ ID NO: 7 is provided in SEQ ID NO: 41. Regardless of order, the sequence of SEQ ID NO: 7 or a functional portion or derivative thereof and the sequence of SEQ ID NO: 8 or a functional portion or derivative thereof can be joined by direct fusion or a nucleic acid linker, as described above.

In some embodiments, the murine Myo15 promoter for use in the compositions and methods described herein contains a region having at least 85% sequence identity (e.g., 85%, 90%, 95%, 96%, 97%, 98%, 99%, or more, sequence identity) to a region containing the first non-coding exon of the murine Myo15 gene (nucleic acids from −6755 to −7209 with respect to the murine Myo15 translation start site, the sequence of which is set forth in SEQ ID NO: 7) or a functional portion or derivative thereof. The functional portion of SEQ ID NO: 7 may have the sequence of nucleic acids from −7166 to −7091 with respect to the murine Myo15 translation start site (set forth in SEQ ID NO: 9) and/or the sequence of nucleic acids from −7077 to −6983 with respect to the murine Myo15 translation start site (set forth in SEQ ID NO: 10). The murine Myo15 promoter may contain the polynucleotide sequence of SEQ ID NO: 9 fused to the polynucleotide sequence of SEQ ID NO: 10 with no intervening nucleic acids, as set forth in SEQ ID NO: 11, or the murine Myo15 promoter may contain the polynucleotide sequence of SEQ ID NO: 10 fused to the polynucleotide sequence of SEQ ID NO: 9 with no intervening nucleic acids, as set forth in SEQ ID NO: 12. Alternatively, the murine Myo15 promoter may contain the sequences of SEQ ID NO: 9 and SEQ ID NO: 10 joined by the endogenous intervening polynucleotide sequence (e.g., the first region may have or include the sequence of nucleic acids from −7166 to −6983 with respect to the murine Myo15 translation start site, as set forth in SEQ ID NO: 13 and SEQ ID NO: 33) or a polynucleotide linker. In a murine Myo15 promoter that contains both SEQ ID NO: 9 and SEQ ID NO: 10, the two sequences can be included in any order (e.g., SEQ ID NO: 9 may be joined to (e.g., precede) SEQ ID NO: 10, or SEQ ID NO: 10 may be joined to (e.g., precede) SEQ ID NO: 9).

In some embodiments, the murine Myo15 promoter for use in the compositions and methods described herein contains a region having at least 85% sequence identity (e.g., 85%, 90%, 95%, 96%, 97%, 98%, 99%, or more, sequence identity) to the polynucleotide sequence immediately upstream of the murine Myo15 translation start site (nucleic acids from −1 to −1157 with respect to the murine Myo15 translation start site, the sequence of which is set forth in SEQ ID NO: 8) or a functional portion or derivative thereof. The functional portion of SEQ ID NO: 8 may have the sequence of nucleic acids from −590 to −509 with respect to the murine Myo15 translation start site (set forth in SEQ ID NO: 14) and/or the sequence of nucleic acids from −266 to −161 with respect to the murine Myo15 translation start site (set forth in SEQ ID NO: 15). In some embodiments, the sequence containing SEQ ID NO: 14 has the sequence of SEQ ID NO: 34. In some embodiments, the sequence containing SEQ ID NO: 15 has the sequence of SEQ ID NO: 35. The murine Myo15 promoter may contain the polynucleotide sequence of SEQ ID NO: 14 fused to the polynucleotide sequence of SEQ ID NO: 15 with no intervening nucleic acids, as set forth in SEQ ID NO: 16, or the murine Myo15 promoter may contain the polynucleotide sequence of SEQ ID NO: 15 fused to the polynucleotide sequence of SEQ ID NO: 14 with no intervening nucleic acids, as set forth in SEQ ID NO: 17. The murine Myo15 promoter may contain the nucleic acid sequence of SEQ ID NO: 34 fused to the nucleic acid sequence of SEQ ID NO: 35 with no intervening nucleic acids, as set forth in SEQ ID NO: 38, or the murine Myo15 promoter may contain the nucleic acid sequence of SEQ ID NO: 35 fused to the nucleic acid sequence of SEQ ID NO: 41 with no intervening nucleic acids. Alternatively, the murine Myo15 promoter may contain the sequences of SEQ ID NO: 14 and SEQ ID NO: 15 joined by the endogenous intervening polynucleotide sequence (e.g., the second region may have the sequence of nucleic acids from −590 to −161 with respect to the murine Myo15 translation start site, as set forth in SEQ ID NO: 18) or a nucleic acid linker. In a murine Myo15 promoter that contains both SEQ ID NO: 14 and SEQ ID NO: 15, the two sequences can be included in any order (e.g., SEQ ID NO: 14 may be joined to (e.g., precede) SEQ ID NO: 15, or SEQ ID NO: 15 may be joined to (e.g., precede) SEQ ID NO: 14).

In some embodiments, the murine Myo15 promoter for use in the compositions and methods described herein contains a functional portion or derivative of a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the murine Myo15 translation start site, the sequence of which is set forth in SEQ ID NO: 7) flanked on either side by a functional portion or derivative of a region having at least 85% sequence identity (e.g., 85%, 90%, 95%, 96%, 97%, 98%, 99%, or more, sequence identity) to the nucleic acid sequence immediately upstream of the murine Myo15 translation start site (nucleic acids from −1 to −1157 with respect to the murine Myo15 translation start site, the sequence of which is set forth in SEQ ID NO: 8). For example, a functional portion or derivative of SEQ ID NO: 8, such as SEQ ID NO: 14 or 34 may be directly fused or joined by a nucleic acid linker to a portion of SEQ ID NO: 7, such as any one of SEQ ID NOs: 9-13 and 33, which is directly fused or joined by a nucleic acid linker to a different functional portion of SEQ ID NO: 8, such as SEQ ID NO: 15 or 35. In other embodiments, a functional portion or derivative of SEQ ID NO: 8, such as SEQ ID NO: 15 or 35 may be directly fused or joined by a nucleic acid linker to a portion of SEQ ID NO: 7, such as any one of SEQ ID NOs: 9-13 and 33, which is directly fused or joined by a nucleic acid linker to a different functional portion of SEQ ID NO: 8, such as SEQ ID NO: 14 or 34. For example, polynucleotides having at least 85% sequence identity (e.g., 85%, 90%, 95%, 96%, 97%, 98%, 99%, or more, sequence identity) to the nucleic acid sequence of SEQ ID NOs: 34, 33, and 35 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 39. In some embodiments, polynucleotides having at least 85% sequence identity (e.g., 85%, 90%, 95%, 96%, 97%, 98%, 99%, or more, sequence identity) to the nucleic acid sequence of SEQ ID NOs: 35, 33, and 34 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 40.

Human Myosin 15 Promoters

The polynucleotides of the compositions and methods described herein may also include nucleic acid sequences from regions of the human Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the human Myo15 locus that are capable of expressing a transgene specifically in hair cells. The polynucleotides of the compositions and methods described herein can optionally include a linker operably linking the regions of the human Myo15 locus that are capable of expressing a transgene specifically in hair cells, or the regions of the human Myo15 locus can be joined directly without an intervening linker.

In some embodiments, the human Myo15 promoter for use in the compositions and methods described herein contains a first region having at least 85% sequence identity (e.g., 85%, 90%, 95%, 96%, 97%, 98%, 99%, or more, sequence identity) to the sequence set forth in SEQ ID NO: 23 or a functional portion or derivative thereof joined (e.g., operably linked) to a second region having at least 85% sequence identity (e.g., 85%, 90%, 95%, 96%, 97%, 98%, 99%, or more, sequence identity) to the sequence set forth in SEQ ID NO: 24 or a functional portion or derivative thereof. The functional portion of SEQ ID NO: 23 may have the sequence set forth in SEQ ID NO: 25. The functional portion of SEQ ID NO: 24 may have the sequence set forth in SEQ ID NO: 26 and/or the sequence set forth in SEQ ID NO: 27.

The second region may contain the nucleic acid sequence of SEQ ID NO: 26 fused to the nucleic acid sequence of SEQ ID NO: 27 with no intervening nucleic acids, as set forth in SEQ ID NO: 28, or the second region may contain the nucleic acid sequence of SEQ ID NO: 27 fused to the nucleic acid sequence of SEQ ID NO: 26 with no intervening nucleic acids, as set forth in SEQ ID NO: 29. Alternatively, the second region may contain the sequences of SEQ ID NO: 26 and SEQ ID NO: 27 joined by the endogenous intervening nucleic acid sequence (as set forth in SEQ ID NO: 30) or a nucleic acid linker. In a human Myo15 promoter in which the second region contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26).

The first region and the second region of the human Myo15 promoter can be joined directly or can be joined by a nucleic acid linker. For example, the human Myo15 promoter can contain the sequence of SEQ ID NO: 23 or a functional portion or derivative thereof (e.g., SEQ ID NO: 25) fused to the sequence of SEQ ID NO: 24 or a functional portion or derivative thereof (e.g., any one or more of SEQ ID NOs: 26-30, e.g., SEQ ID NOs: 26 and/or 27) with no intervening nucleic acids. Alternatively, a linker can be used to join the sequence of SEQ ID NO: 23 or a functional portion or derivative thereof (e.g., SEQ ID NO: 25) to the sequence of SEQ ID NO: 24 or a functional portion or derivative thereof (e.g., any one or more of SEQ ID NOs: 26-30, e.g., SEQ ID NOs: 26 and/or 27). Exemplary human Myo15 promoters containing functional portions of both SEQ ID NO: 23 and SEQ ID NO: 24 are provided in SEQ ID NOs: 31 and 32.

In some embodiments, the sequence of SEQ ID NO: 23 or a functional portion or derivative thereof (e.g., SEQ ID NO: 25) is joined (e.g., operably linked) to the sequence of SEQ ID NO: 24 or a functional portion or derivative thereof (e.g., any one or more of SEQ ID NOs: 26-30, e.g., SEQ ID NOs: 26 and 27), and, in some embodiments, the order of the regions is reversed (e.g., the sequence of SEQ ID NO: 24 or a functional portion or derivative thereof (e.g., any one or more of SEQ ID NOs: 26-30, e.g., SEQ ID NOs: 26 and/or 27) is joined (e.g., operably linked) to the sequence of SEQ ID NO: 23 or a functional portion or derivative thereof (e.g., SEQ ID NO: 25)). Regardless of order, the sequence of SEQ ID NO: 23 or a functional portion or derivative thereof and the sequence of SEQ ID NO: 24 or a functional portion or derivative thereof can be joined by direct fusion or a nucleic acid linker, as described above.

In some embodiments, the human Myo15 promoter for use in the compositions and methods described herein contain a region having at least 85% sequence identity (e.g., 85%, 90%, 95%, 96%, 97%, 98%, 99%, or more, sequence identity) to a region containing the sequence set forth in SEQ ID NO: 23 or a functional portion or derivative thereof. The functional portion of SEQ ID NO: 23 may have the sequence of nucleic acids set forth in SEQ ID NO: 25.

In some embodiments, the human Myo15 promoter for use in the compositions and methods described herein contains a region having at least 85% sequence identity (e.g., 85%, 90%, 95%, 96%, 97%, 98%, 99%, or more, sequence identity) to the sequence set forth in SEQ ID NO: 18 or a functional portion or derivative thereof. The functional portion of SEQ ID NO: 24 may have the sequence set forth in SEQ ID NO: 26 and/or the sequence set forth in SEQ ID NO: 27. The human Myo15 promoter may contain the nucleic acid sequence of SEQ ID NO: 26 fused to the nucleic acid sequence of SEQ ID NO: 27 with no intervening nucleic acids, as set forth in SEQ ID NO: 28, or the human Myo15 promoter may contain the nucleic acid sequence of SEQ ID NO: 27 fused to the nucleic acid sequence of SEQ ID NO: 26 with no intervening nucleic acids, as set forth in SEQ ID NO: 29. Alternatively, the human Myo15 promoter may contain the sequences of SEQ ID NO: 26 and SEQ ID NO: 27 joined by the endogenous intervening nucleic acid sequence (e.g., as set forth in SEQ ID NO: 30) or a nucleic acid linker. In a human Myo15 promoter that contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26).

The length of a nucleic acid linker for use in a human Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the human Myo15 promoters described herein do not disrupt the ability of the Myo15 promoter of the invention to induce transgene expression in hair cells.

The foregoing Myo15 promoter sequences are summarized in Table 3, below.

TABLE 3

| | | |
|---|---|---|
| | Exemplary nucleotide sequences for use in the Myo15 promoter described herein | |
| SEQ ID NO. | Description of polynucleotide sequence | Polynucleotide Sequence |
| 7 | Region containing non-coding exon 1 of murine Myo15 (−6755 to −7209) | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTAT |
| 8 | Region immediately preceding the translation start site of murine Myo15 (−1 to −1157) | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT GCTAACCCTGACCAAGCTACCTATTACTTACCCTCCTCTTTCT CCTCCTCCTCTTTCTCCTTCTCCTGCTTCCCCTCTTCCTTCTC CCTCCCTTCCTCTCCCTCCTCCCCCTCCTTGGCTGTGATCAG ATCCAGAGCCTGAATGAGCCTCCTGACCCCACACCCCCACTA GCATGGGCCTGCAAGTGCCCAGAAGTCCCTCCTGCCTCCTA AACTGCCCAGCCGATCCATTAGCTCTTCCTTCTTCCCAGTGA AAGAAGCAGGCACAGCCTGTCCCTCCCGTTCTACAGAAAGG AAGCTACAGCACAGGGAGGGCCAAAGGCCTTCCTGGGACTA GACAGTTGATCAACAGCAGGACTGGAGAGCTGGGCTCCATTT TTGTTCCTTGGTGCCCTGCCCCTCCCCATGACCTGCAGAGAC ATTCAGCCTGCCAGGCTTTATGAGGTGGGAGCTGGGCTCTC CCTGATGTATTATTCAGCTCCCTGGAGTTGGCCAGCTCCTGT TACACTGGCCACAGCCCTGGGCATCCGCTTCTCACTTCTAGT TTCCCCTCCAAGGTAATGTGGTGGGTCATGATCATTCTATCCT GGCTTCAGGGACCTGACTCCACTTTGGGGCCATTCGAGGGG TCTAGGGTAGATGATGTCCCCCTGTGGGGATTAATGTCCTGC TCTGTAAAACTGAGCTAGCTGAGATCCAGGAGGGCTTGGCCA GAGACAGCAAGTTGTTGCCATGGTGACTTTAAAGCCAGGTTG CTGCCCCAGCACAGGCCTCCCAGTCTACCCTCACTAGAAAAC AACACCCAGGCACTTTCCACCACCTCTCAAAGGTGAAACCCA AGGCTGGTCTAGAGAATGAATTATGGATCCTCGCTGTCCGTG CCACCCAGCTAGTCCCAGCGGCTCAGACACTGAGGAGAGAC TGTAGGTTCAGCTACAAGCAAAAAGACCTAGCTGGTCTCCAA GCAGTGTCTCCAAGTCCCTGAACCTGTGACACCTGCCCCAG GCATCATCAGGCACAGAGGGCCACC |
| 9 | Portion of SEQ ID NO: 7 (−7166 to −7091) | CCCATGTCAGCTGCTTGTGCTTTCCAGAGACAAAACAGGAAT AATAGATGTCATTAAATATACATTGGGCCCCAGG |
| 10 | Portion of SEQ ID NO: 7 (−7077 to −6983) | AGCCTGAGCCTCCTTTCCATCTCTGTGGAGGCAGACATAGGA CCCCCAACAAACAGCATGCAGGTTGGGAGCCAGCCACAGGA CCCAGGTAAGGG |
| 11 | Portion of SEQ ID NO: 7 (SEQ ID NO: 9 fused to SEQ ID NO: 10) | CCCATGTCAGCTGCTTGTGCTTTCCAGAGACAAAACAGGAAT AATAGATGTCATTAAATATACATTGGGCCCCAGGAGCCTGAG CCTCCTTTCCATCTCTGTGGAGGCAGACATAGGACCCCCAAC AAACAGCATGCAGGTTGGGAGCCAGCCACAGGACCCAGGTA AGGG |

TABLE 3-continued

| SEQ ID NO. | Description of polynucleotide sequence | Polynucleotide Sequence |
|---|---|---|
| | Exemplary nucleotide sequences for use in the Myo15 promoter described herein | |
| 12 | Portion of SEQ ID NO: 7 (SEQ ID NO: 10 fused to SEQ ID NO: 9) | AGCCTGAGCCTCCTTTCCATCTCTGTGGAGGCAGACATAGGA CCCCCAACAAACAGCATGCAGGTTGGGAGCCAGCCACAGGA CCCAGGTAAGGGCCCATGTCAGCTGCTTGTGCTTTCCAGAGA CAAAACAGGAATAATAGATGTCATTAAATATACATTGGGCCCC AGG |
| 13 | Portion of SEQ ID NO: 7 (-7166 to -6983) | CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGG |
| 14 | Portion of SEQ ID NO: 8 (-590 to -509) | TGAGGTGGGAGCTGGGCTCTCCCTGATGTATTATTCAGCTCC CTGGAGTTGGCCAGCTCCTGTTACACTGGCCACAGCCCTG |
| 15 | Portion of SEQ ID NO: 8 (-266 to -161) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 16 | Portion of SEQ ID NO: 8 (SEQ ID NO: 14 fused to SEQ ID NO: 15) | TGAGGTGGGAGCTGGGCTCTCCCTGATGTATTATTCAGCTCC CTGGAGTTGGCCAGCTCCTGTTACACTGGCCACAGCCCTG CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 17 | Portion of SEQ ID NO: 8 (SEQ ID NO: 15 fused to SEQ ID NO: 14) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCTTGAGGTGGGAGCTGGGCTCT CCCTGATGTATTATTCAGCTCCCTGGAGTTGGCCAGCTCCTG TTACACTGGCCACAGCCCTG |
| 18 | Portion of SEQ ID NO: 8 (-590 to -161) | TGAGGTGGGAGCTGGGCTCTCCCTGATGTATTATTCAGCTCC CTGGAGTTGGCCAGCTCCTGTTACACTGGCCACAGCCCTGG GCATCCGCTTCTCACTTCTAGTTTCCCCTCCAAGGTAATGTG GTGGGTCATGATCATTCTATCCTGGCTTCAGGGACCTGACTC CACTTTGGGGCCATTCGAGGGGTCTAGGGTAGATGATGTCC CCCTGTGGGGATTAATGTCCTGCTCTGTAAAACTGAGCTAGC TGAGATCCAGGAGGGCTTGGCCAGAGACAGCAAGTTGTTGC CATGGTGACTTTAAAGCCAGGTTGCTGCCCCAGCACAGGCCT CCCAGTCTACCCTCACTAGAAAACAACACCCAGGCACTTTCC ACCACCTCTCAAAGGTGAAACCCAAGGCTGGTCTAGAGAATG AATTATGGATCCT |
| 19 | SEQ ID NO: 7 fused to SEQ ID NO: 8 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTATGGTC TCACCCAGCATTTTCACTTCTAATAAGTTCAAATGTGATACGG CACCTTTCTAAAAATTAGTTTTCAGGGAAATAGGGTTCAAAAC TGGTAGTGGTAGGGTCCATTCTCACGACCCCCAGGCCTGCT AACCCTGACCAAGCTACCTATTACTTACCCTCCTCTTTCTCCT CCTCCTCTTTCTCCTTCTCCTGCTTCCCCTCTTCCTTCTCCCT CCCTTCCTCTCCCTCCTCCCCCTCCTTGGCTGTGATCAGATC CAGAGCCTGAATGAGCCTCCTGACCCCACACCCCCACTAGC ATGGGCCTGCAAGTGCCCAGAAGTCCCTCCTGCCTCCTAAAC TGCCCAGCCGATCCATTAGCTCTTCCTTCTTCCCAGTGAAAG AAGCAGGCACAGCCTGTCCCTCCCGTTCTACAGAAAGGAAG CTACAGCACAGGGAGGGCCAAAGGCCTTCCTGGGACTAGAC AGTTGATCAACAGCAGGACTGGAGAGCTGGGCTCCATTTTTG TTCCTTGGTGCCCTGCCCCTCCCCATGACCTGCAGAGACATT CAGCCTGCCAGGCTTTATGAGGTGGGAGCTGGGCTCTCCCT GATGTATTATTCAGCTCCCTGGAGTTGGCCAGCTCCTGTTAC ACTGGCCACAGCCCTGGGCATCCGCTTCTCACTTCTAGTTTC CCCTCCAAGGTAATGTGGTGGGTCATGATCATTCTATCCTGG CTTCAGGGACCTGACTCCACTTTGGGGCCATTCGAGGGGTC TAGGGTAGATGATGTCCCCCTGTGGGGATTAATGTCCTGCTC |

TABLE 3-continued

Exemplary nucleotide sequences for use
in the Myo15 promoter described herein

| SEQ ID NO. | Description of polynucleotide sequence | Polynucleotide Sequence |
|---|---|---|
| | | TGTAAAACTGAGCTAGCTGAGATCCAGGAGGGCTTGGCCAG AGACAGCAAGTTGTTGCCATGGTGACTTTAAAGCCAGGTTGC TGCCCCAGCACAGGCCTCCCAGTCTACCCTCACTAGAAAACA ACACCCAGGCACTTTCCACCACCTCTCAAAGGTGAAACCCAA GGCTGGTCTAGAGAATGAATTATGGATCCTCGCTGTCCGTGC CACCCAGCTAGTCCCAGCGGCTCAGACACTGAGGAGAGACT GTAGGTTCAGCTACAAGCAAAAAGACCTAGCTGGTCTCCAAG CAGTGTCTCCAAGTCCCTGAACCTGTGACACCTGCCCCAGG CATCATCAGGCACAGAGGGCCACC |
| 20 | SEQ ID NO: 8 fused to SEQ ID NO: 7 | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT GCTAACCCTGACCAAGCTACCTATTACTTACCCTCCTCTTTCT CCTCCTCCTCTTTCTCCTTCTCCTGCTTCCCCTCTTCCTTCTC CCTCCCTTCCTCTCCCTCCTCCCCCTCCTTGGCTGTGATCAG ATCCAGAGCCTGAATGAGCCTCCTGACCCCACACCCCCACTA GCATGGGCCTGCAAGTGCCCAGAAGTCCCTCCTGCCTCCTA AACTGCCCAGCCGATCCATTAGCTCTTCCTTCTTCCCAGTGA AAGAAGCAGGCACAGCCTGTCCCTCCCGTTCTACAGAAAGG AAGCTACAGCACAGGGAGGGCAAAGGCCTTCCTGGGACTA GACAGTTGATCAACAGCAGGACTGGAGAGCTGGGCTCCATTT TTGTTCCTTGGTGCCCTGCCCCTCCCCATGACCTGCAGAGAC ATTCAGCCTGCCAGGCTTTATGAGGTGGGAGCTGGGCTCTC TACACTGGCCACAGCCCTGGGCATCCGCTTCTCACTTCTAGT TTCCCCTCCAAGGTAATGTGGTGGGTCATGATCATTCTATCCT GGCTTCAGGGACCTGACTCCACTTTGGGGCCATTCGAGGGG TCTAGGGTAGATGATGTCCCCCTGTGGGGATTAATGTCCTGC TCTGTAAAACTGAGCTAGCTGAGATCCAGGAGGGCTTGGCCA GAGACAGCAAGTTGTTGCCATGGTGACTTTAAAGCCAGGTTG CTGCCCCAGCACAGGCCTCCCAGTCTACCCTCACTAGAAAAC AACACCCAGGCACTTTCCACCACCTCTCAAAGGTGAAACCCA AGGCTGGTCTAGAGAATGAATTATGGATCCTCGCTGTCCGTG CCACCCAGCTAGTCCCAGCGGCTCAGACACTGAGGAGAGAC TGTAGGTTCAGCTACAAGCAAAAAGACCTAGCTGGTCTCCAA GCAGTGTCTCCAAGTCCCTGAACCTGTGACACCTGCCCCAG GCATCATCAGGCACAGAGGGCCACCCTGCAGCTCAGCCTAC TACTTGCTTTCCAGGCTGTTCCTAGTTCCCATGTCAGCTGCTT GTGCTTTCCAGAGACAAAACAGGAATAATAGATGTCATTAAAT ATACATTGGGCCCCAGGCGGTCAATGTGGCAGCCTGAGCCT CCTTTCCATCTCTGTGGAGGCAGACATAGGACCCCCAACAAA CAGCATGCAGGTTGGGAGCCAGCCACAGGACCCAGGTAAGG GGCCCTGGGTCCTTAAGCTTCTGCCACTGGCTCCGGCATTG CAGAGAGAAGAGAAGGGGCGGCAGAGCTGAACCTTAGCCTT GCCTTCCTGGGTACCCTTCTGAGCCTCACTGTCTTCTGTGAG ATGGGCAAAGTGCGGGTGTGACTCCTTGGCAACGGTGTTAC ACCAGGGCAGGTAAAGTTGTAGTTATTTGTGGGGTACACCAG GACTGTTAAAGGTGTAACTAT |
| 21 | Portion of SEQ ID NO: 7 that contains SEQ ID NO: 9 and SEQ ID NO: 10 fused to portion of SEQ ID NO: 8 that contains SEQ ID NO: 14 and SEQ ID NO: 15 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GACTGGAGAGCTGGGCTCCATTTTTGTTCCTTGGTGCCCTGC CCCTCCCCATGACCTGCAGAGACATTCAGCCTGCCAGGCTTT ATGAGGTGGGAGCTGGGCTCTCCCTGATGTATTATTCAGCTC CCTGGAGTTGGCCAGCTCCTGTTACACTGGCCACAGCCCTG GGCATCCGCTTCTCACTTCTAGTTTCCCCTCCAAGGTAATGT GGTGGGTCATGATCATTCTATCCTGGCTTCAGGGACCTGACT CCACTTTGGGGCCATTCGAGGGGTCTAGGGTAGATGATGTC CCCCTGTGGGGATTAATGTCCTGCTCTGTAAAACTGAGCTAG CTGAGATCCAGGAGGGCTTGGCCAGAGACAGCAAGTTGTTG CCATGGTGACTTTAAAGCCAGGTTGCTGCCCCAGCACAGGC CTCCCAGTCTACCCTCACTAGAAAACAACACCCAGGCACTTT CCACCACCTCTCAAAGGTGAAACCCAAGGCTGGTCTAGAGAA TGAATTATGGATCCTCGCTGTCCGTGCCACCCAGCTAGTCCC AGCGGCTCAGACACTGAGGAGAGACTGTAGGTTCAGCTACA AGCAAAAAGACCTAGCTGGTCTCCAAGCAGTGTCTCCAAGTC CCTGAACCTGTGACACCTGCCCCAGGCATCATCAGGCACAG AGGGCCACC |

TABLE 3-continued

Exemplary nucleotide sequences for use
in the Myo15 promoter described herein

| SEQ ID NO. | Description of polynucleotide sequence | Polynucleotide Sequence |
|---|---|---|
| 22 | Portion of SEQ ID NO: 7 that contains SEQ ID NO: 9 and SEQ ID NO: 10 fused to portion of SEQ ID NO: 8 that contains SEQ ID NO: 14 and SEQ ID NO: 15 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTTTTATGAGGT GGGAGCTGGGCTCTCCCTGATGTATTATTCAGCTCCCTGGAG TTGGCCAGCTCCTGTTACACTGGCCACAGCCCTGGGCATCC GCTGCCATGGTGACTTTAAAGCCAGGTTGCTGCCCCAGCACA GGCCTCCCAGTCTACCCTCACTAGAAAACAACACCCAGGCAC TTTCCACCACCTCTCAAAGGTGAAACCCAAGGCTGGTCTAGA GAATGAATTATGGATCCTCGCTGTCCGTGCCACCCAGCTAGT CCCAGCGGCTCAGACACTG |
| 23 | Region 1 of the human Myo15 promoter | GTATGCCTTTTGAGATGGATGCAGCAGGTTCTGTGAGGCTGC CAGGAGGGGTAGAGTTCCCGGGGGCCTCGGGCCCCGCTGG AGTGTGGAGCAGGCCCATGCTCAGCTCTCCAGGCTGTTCGT GGCTCCCCTGTCAGCTGCTCACTCCTTTCCAGAGACAAAACA GGAATAATAGACATCATTAAATATACATAGGGCCCCAGGCGG TCGGCGTGGTGGGCTGGGCCTCCCTTCC |
| 24 | Region 2 of human Myo15 promoter | TGCCCTGCCTTCTGAGCCGGCAGCCTGGCTCCCCACCCCAT GTATTATTCAGCTCCTGAGAGCCAGCCAGCTCCTGTTACACT GACCGCAGCCCAGCACCTGCTCTGCCCATTCCCCTCCTCCC TTGCCTAGGACCTAGAGGGTTCAAAGTTCTCCTCCAAGATGA CTTGGTGGGCTTTGGCCATCCCACCCTAGGCCCCACTTCTG GCCCAGTGCAGGTGTGCTGGTGATTTAGGGCAGGTGGCATT CCATCTCTGTGGCTCAATGTCTTCCTCTGTGAAGCCGAAGTG ACCCAAGGGCTCCCTTCATGGGGTTGAGCCAGCTGTGGCCC AGGGAGGGCCTAACCAGGATGAGCACTGATGTTGCCATGAC GACTCCGAGGCCAGAATGTCTCCCCCAGCACAGGCCTCATA GGCAGGCTTCCCCATCCTGGTAAACAACACCCACACACTTTC TACTACTGCTCTAGGGTGAAACCCAAGGCGCTCTAGAGGAGA TGAATTATGGATCCGCCCTCCCGGAATCCTGGCTCGGCCCTC CCCACGCCACCCAGGGCCAGTCGGGTCTGCTCACAGCCCGA GGAGGCCGCGTGTCCAGCCGCGGGCAAGAGACAGAGCAGG TCCCTGTGTCTCCAAGTCCCTGAGCCCGTGACACCGGCCCC AGGCCCTGTAGAGAGCAGGCAGCCACC |
| 25 | Portion of SEQ ID NO: 23 | CCCCTGTCAGCTGCTCACTCCTTTCCAGAGACAAAACAGGAA TAATAGACATCATTAAATATACATAGGGCCCCAGG |
| 26 | Portion of SEQ ID NO: 24 | TGAGCCGGCAGCCTGGCTCCCCACCCCATGTATTATTCAGCT CCTGAGAGCCAGCCAGCTCCTGTTACACTGACCGCAGCCC |
| 27 | Portion of SEQ ID NO: 24 | CACAGGCCTCATAGGCAGGCTTCCCCATCCTGGTAAACAACA CCCACACACTTTCTACTACTGCTCTAGGGTGAAACCCAAGGC GCTCTAGAGGAGATGAATTATGGATCC |
| 28 | Portion of SEQ ID NO: 24 (SEQ ID NO: 26 fused to SEQ ID NO: 27) | TGAGCCGGCAGCCTGGCTCCCCACCCCATGTATTATTCAGCT CCTGAGAGCCAGCCAGCTCCTGTTACACTGACCGCAGCCCC ACAGGCCTCATAGGCAGGCTTCCCCATCCTGGTAAACAACAC CCACACACTTTCTACTACTGCTCTAGGGTGAAACCCAAGGCG CTCTAGAGGAGATGAATTATGGATCC |
| 29 | Portion of SEQ ID NO: 24 (SEQ ID NO: 27 fused to SEQ ID NO: 26) | CACAGGCCTCATAGGCAGGCTTCCCCATCCTGGTAAACAACA CCCACACACTTTCTACTACTGCTCTAGGGTGAAACCCAAGGC GCTCTAGAGGAGATGAATTATGGATCCTGAGCCGGCAGCCT GGCTCCCCACCCCATGTATTATTCAGCTCCTGAGAGCCAGCC AGCTCCTGTTACACTGACCGCAGCCC |
| 30 | Portion of SEQ ID NO: 24 (contiguous sequence including SEQ ID NO: 26 and SEQ ID NO: 27) | TGAGCCGGCAGCCTGGCTCCCCACCCCATGTATTATTCAGCT CCTGAGAGCCAGCCAGCTCCTGTTACACTGACCGCAGCCCA GCACCTGCTCTGCCCATTCCCCTCCTCCCTTGCCTAGGACCT AGAGGGTTCAAAGTTCTCCTCCAAGATGACTTGGTGGGCTTT GGCCATCCCACCCTAGGCCCCACTTCTGGCCCAGTGCAGGT GTGCTGGTGATTTAGGGCAGGTGGCATTCCATCTCTGTGGCT CAATGTCTTCCTCTGTGAAGCCGAAGTGACCCAAGGGCTCCC TTCATGGGGTTGAGCCAGCTGTGGCCCAGGGAGGGCCTAAC CAGGATGAGCACTGATGTTGCCATGACGACTCCGAGGCCAG |

TABLE 3-continued

Exemplary nucleotide sequences for use
in the Myo15 promoter described herein

| SEQ ID NO. | Description of polynucleotide sequence | Polynucleotide Sequence |
|---|---|---|
| | | AATGTCTCCCCCAGCACAGGCCTCATAGGCAGGCTTCCCCAT<br>CCTGGTAAACAACACCCACACACTTTCTACTACTGCTCTAGG<br>GTGAAACCCAAGGCGCTCTAGAGGAGATGAATTATGGATCC |
| 31 | Polynucleotide containing SEQ ID NO: 23 and SEQ ID NO: 24 | GTATGCCTTTTGAGATGGATGCAGCAGGTTCTGTGAGGCTGC<br>CAGGAGGGGTAGAGTTCCCGGGGGCCTCGGGCCCCGCTGG<br>AGTGTGGAGCAGGCCCATGCTCAGCTCTCCAGGCTGTTCGT<br>GGCTCCCCTGTCAGCTGCTCACTCCTTTCCAGAGACAAAACA<br>GGAATAATAGACATCATTAAATATACATAGGGCCCCAGGCGG<br>TCGGCGTGGTGGGCTGGGCCTCCCTTCCCCATAACACTGAG<br>CTGCTCTGCTGGGCCAACCGTGCTCCTGGGCCAGCCAGAGG<br>ACCCCCATGAGGCGGCATGCAGGCGGGGAGCAGGCCACAG<br>AACGCAGGTAAGGAGACCTTAGCCTAGAGTCCTTGGGGTCT<br>GTCACTGGCCACCCTCGCATCCCAGGCTGCAGGAAACTGAG<br>GCCCAGAGAGGACAAGGACTTTCCTGGACCCACACAGCCAG<br>TCAGTGACAGAGCCTAGGGTCTGAGCCAGGCCTGACCCAAC<br>CTCCATTTCTGCCTCTCTACCCCTGCCCCCGCCCCAACACAC<br>ACACACACAAGTGGAGTTCCACTGAAACGCCCCTCCTTGC<br>CCTGCCTTCTGAGCCGGCAGCCTGGCTCCCCACCCCATGTA<br>TTATTCAGCTCCTGAGAGCCAGCCAGCTCCTGTTACACTGAC<br>CGCAGCCCAGCACCTGCTCTGCCCATTCCCCTCCTCCCTTGC<br>CTAGGACCTAGAGGGTTCAAAGTTCTCCTCCAAGATGACTTG<br>GTGGGCTTTGGCCATCCCACCCTAGGCCCCACTTCTGGCCC<br>AGTGCAGGTGTGCTGGTGATTTAGGGCAGGTGGCATTCCAT<br>CTCTGTGGCTCAATGTCTTCCTCTGTGAAGCCGAAGTGACCC<br>AAGGGCTCCCTTCATGGGGTTGAGCCAGCTGTGGCCCAGGG<br>AGGGCCTAACCAGGATGAGCACTGATGTTGCCATGACGACT<br>CCGAGGCCAGAATGTCTCCCCCAGCACAGGCCTCATAGGCA<br>GGCTTCCCCATCCTGGTAAACAACACCCACACACTTTCTACT<br>ACTGCTCTAGGGTGAAACCCAAGGCGCTCTAGAGGAGATGA<br>ATTATGGATCCGCCCTCCCGGAATCCTGGCTCGGCCCTCCC<br>CACGCCACCCAGGGCCAGTCGGGTCTGCTCACAGCCCGAG<br>GAGGCCGCGTGTCCAGCCGCGGGCAAGAGACAGAGCAGGT<br>CCCTGTGTCTCCAAGTCCCTGAGCCCGTGACACCGGCCCCA<br>GGCCCTGTAGAGAGCAGGCAGCCACC |
| 32 | Polynucleotide containing SEQ ID NO: 25, SEQ ID NO: 26, and SEQ ID NO: 27 | GCAGGCCCATGCTCAGCTCTCCAGGCTGTTCGTGGCTCCCC<br>TGTCAGCTGCTCACTCCTTTCCAGAGACAAAACAGGAATAAT<br>AGACATCATTAAATATACATAGGGCCCCAGGCGGTCGGCGTG<br>GTGGGCTGGGCCTCCCTTCCCCATAACACTGAGCTGCTCTG<br>CTGGGCCAACCGTGCTCCTGGGCCAGCCAGAGGACCCCCAT<br>GAGGCGGCATGCAGGCGGGGAGCAGGCCACAGAACGCAGG<br>TAAGGAGACCTTGCCTTCTGAGCCGGCAGCCTGGCTCCCCA<br>CCCCATGTATTATTCAGCTCCTGAGAGCCAGCCAGCTCCTGT<br>TACACTGACCGCAGCCCAGCACCTGCTCTGCCCATTCCCCTC<br>CTCCCTTGCCTAGGACCTAGAGGGTTCAAAGTTCTCCTCCAA<br>GATGACTTGGTGGGCTTTGGCCATCGGGCCTAACCAGGATG<br>AGCACTGATGTTGCCATGACGACTCCGAGGCCAGAATGTCTC<br>CCCCAGCACAGGCCTCATAGGCAGGCTTCCCCATCCTGGTA<br>AACAACACCCACACACTTTCTACTACTGCTCTAGGGTGAAAC<br>CCAAGGCGCTCTAGAGGAGATGAATTATGGATCCGCCCTCC<br>CGGAATCCTGGCTCGGCCCTCCCCACGC |
| 33 | Portion of SEQ ID NO: 7 that contains SEQ ID NO: 9 and SEQ ID NO: 10 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTT |
| 34 | Portion of SEQ ID NO: 8 that contains SEQ ID NO: 14 | TTTATGAGGTGGGAGCTGGGCTCTCCCTGATGTATTATTCAG<br>CTCCCTGGAGTTGGCCAGCTCCTGTTACACTGGCCACAGCC<br>CTGGGCATCCGC |
| 35 | Portion of SEQ ID NO: 8 that contains SEQ ID NO: 15 | TGCCATGGTGACTTTAAAGCCAGGTTGCTGCCCCAGCACAG<br>GCCTCCCAGTCTACCCTCACTAGAAAACAACACCCAGGCACT<br>TTCCACCACCTCTCAAAGGTGAAACCCAAGGCTGGTCTAGAG<br>AATGAATTATGGATCCTCGCTGTCCGTGCCACCCAGCTAGTC<br>CCAGCGGCTCAGACACTG |

TABLE 3-continued

Exemplary nucleotide sequences for use
in the Myo15 promoter described herein

| SEQ ID NO. | Description of polynucleotide sequence | Polynucleotide Sequence |
|---|---|---|
| 36 | SEQ ID NO: 33 fused to SEQ ID NO: 34 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTTTTTATGAGGT<br>GGGAGCTGGGCTCTCCCTGATGTATTATTCAGCTCCCTGGAG<br>TTGGCCAGCTCCTGTTACACTGGCCACAGCCCTGGGCATCC<br>GC |
| 37 | SEQ ID NO: 33 fused to SEQ ID NO: 35 | CTGCAGCTCAGCCTACTACTTGCTTTCCAGGCTGTTCCTAGT<br>TCCCATGTCAGCTGCTTGTGCTTTCCAGAGACAAAACAGGAA<br>TAATAGATGTCATTAAATATACATTGGGCCCCAGGCGGTCAAT<br>GTGGCAGCCTGAGCCTCCTTTCCATCTCTGTGGAGGCAGAC<br>ATAGGACCCCCAACAAACAGCATGCAGGTTGGGAGCCAGCC<br>ACAGGACCCAGGTAAGGGGCCCTGGGTCCTTTGCCATGGTG<br>ACTTTAAAGCCAGGTTGCTGCCCCAGCACAGGCCTCCCAGTC<br>TACCCTCACTAGAAAACAACACCCAGGCACTTTCCACCACCT<br>CTCAAAGGTGAAACCCAAGGCTGGTCTAGAGAATGAATTATG<br>GATCCTCGCTGTCCGTGCCACCCAGCTAGTCCCAGCGGCTC<br>AGACACTG |
| 38 | SEQ ID NO: 34 fused to SEQ ID NO: 35 | TTTATGAGGTGGGAGCTGGGCTCTCCCTGATGTATTATTCAG<br>CTCCCTGGAGTTGGCCAGCTCCTGTTACACTGGCCACAGCC<br>CTGGGCATCCGCTGCCATGGTGACTTTAAAGCCAGGTTGCTG<br>CCCCAGCACAGGCCTCCCAGTCTACCCTCACTAGAAAACAAC<br>ACCCAGGCACTTTCCACCACCTCTCAAAGGTGAAACCCAAGG<br>CTGGTCTAGAGAATGAATTATGGATCCTCGCTGTCCGTGCCA<br>CCCAGCTAGTCCCAGCGGCTCAGACACTG |
| 39 | SEQ ID NO: 34 fused to SEQ ID NO: 33, which is fused to SEQ ID NO: 35 | TTTATGAGGTGGGAGCTGGGCTCTCCCTGATGTATTATTCAG<br>CTCCCTGGAGTTGGCCAGCTCCTGTTACACTGGCCACAGCC<br>CTGGGCATCCGCCTGCAGCTCAGCCTACTACTTGCTTTCCAG<br>GCTGTTCCTAGTTCCCATGTCAGCTGCTTGTGCTTTCCAGAG<br>ACAAAACAGGAATAATAGATGTCATTAAATATACATTGGGCCC<br>CAGGCGGTCAATGTGGCAGCCTGAGCCTCCTTTCCATCTCTG<br>TGGAGGCAGACATAGGACCCCCAACAAACAGCATGCAGGTT<br>GGGAGCCAGCCACAGGACCCAGGTAAGGGGCCCTGGGTCC<br>TTTGCCATGGTGACTTTAAAGCCAGGTTGCTGCCCCAGCACA<br>GGCCTCCCAGTCTACCCTCACTAGAAAACAACACCCAGGCAC<br>TTTCCACCACCTCTCAAAGGTGAAACCCAAGGCTGGTCTAGA<br>GAATGAATTATGGATCCTCGCTGTCCGTGCCACCCAGCTAGT<br>CCCAGCGGCTCAGACACTG |
| 40 | SEQ ID NO: 35 fused to SEQ ID NO: 33, which is fused to SEQ ID NO: 34 | TGCCATGGTGACTTTAAAGCCAGGTTGCTGCCCCAGCACAG<br>GCCTCCCAGTCTACCCTCACTAGAAAACAACACCCAGGCACT<br>TTCCACCACCTCTCAAAGGTGAAACCCAAGGCTGGTCTAGAG<br>AATGAATTATGGATCCTCGCTGTCCGTGCCACCCAGCTAGTC<br>CCAGCGGCTCAGACACTGCTGCAGCTCAGCCTACTACTTGCT<br>TTCCAGGCTGTTCCTAGTTCCCATGTCAGCTGCTTGTGCTTTC<br>CAGAGACAAAACAGGAATAATAGATGTCATTAAATATACATTG<br>GGCCCCAGGCGGTCAATGTGGCAGCCTGAGCCTCCTTTCCA<br>TCTCTGTGGAGGCAGACATAGGACCCCCAACAAACAGCATG<br>CAGGTTGGGAGCCAGCCACAGGACCCAGGTAAGGGGCCCT<br>GGGTCCTTTTTATGAGGTGGGAGCTGGGCTCTCCCTGATGTA<br>TTATTCAGCTCCCTGGAGTTGGCCAGCTCCTGTTACACTGGC<br>CACAGCCCTGGGCATCCGC |
| 41 | SEQ ID NO: 34 fused to SEQ ID NO: 35, which is fused to SEQ ID NO: 33 | TTTATGAGGTGGGAGCTGGGCTCTCCCTGATGTATTATTCAG<br>CTCCCTGGAGTTGGCCAGCTCCTGTTACACTGGCCACAGCC<br>CTGGGCATCCGCTGCCATGGTGACTTTAAAGCCAGGTTGCTG<br>CCCCAGCACAGGCCTCCCAGTCTACCCTCACTAGAAAACAAC<br>ACCCAGGCACTTTCCACCACCTCTCAAAGGTGAAACCCAAGG<br>CTGGTCTAGAGAATGAATTATGGATCCTCGCTGTCCGTGCCA<br>CCCAGCTAGTCCCAGCGGCTCAGACACTGCTGCAGCTCAGC<br>CTACTACTTGCTTTCCAGGCTGTTCCTAGTTCCCATGTCAGCT<br>GCTTGTGCTTTCCAGAGACAAAACAGGAATAATAGATGTCATT<br>AAATATACATTGGGCCCCAGGCGGTCAATGTGGCAGCCTGA<br>GCCTCCTTTCCATCTCTGTGGAGGCAGACATAGGACCCCCAA<br>CAAACAGCATGCAGGTTGGGAGCCAGCCACAGGACCCAGGT<br>AAGGGGCCCTGGGTCCTTT |

TABLE 3-continued

Exemplary nucleotide sequences for use
in the Myo15 promoter described herein

| SEQ ID NO. | Description of polynucleotide sequence | Polynucleotide Sequence |
|---|---|---|
| 42 | Portion of SEQ ID NO: 7 that contains SEQ ID NO: 9 and SEQ ID NO: 10 fused to portion of SEQ ID NO: 8 that contains SEQ ID NO: 14 and SEQ ID NO: 15 | TGCAGCTCAGCCTACTACTTGCTTTCCAGGCTGTTCCTAGTT CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GACTGGAGAGCTGGGCTCCATTTTTGTTCCTTGGTGCCCTGC CCCTCCCCATGACCTGCAGAGACATTCAGCCTGCCAGGCTTT ATGAGGTGGGAGCTGGGCTCTCCCTGATGTATTATTCAGCTC CCTGGAGTTGGCCAGCTCCTGTTACACTGGCCACAGCCCTG GGCATCCGCTTCTCACTTCTAGTTTCCCCTCCAAGGTAATGT GGTGGGTCATGATCATTCTATCCTGGCTTCAGGGACCTGACT CCACTTTGGGGCCATTCGAGGGGTCTAGGGTAGATGATGTC CCCCTGTGGGGATTAATGTCCTGCTCTGTAAAACTGAGCTAG CTGAGATCCAGGAGGGCTTGGCCAGAGACAGCAAGTTGTTG CCATGGTGACTTTAAAGCCAGGTTGCTGCCCCAGCACAGGC CTCCCAGTCTACCCTCACTAGAAAACAACACCCAGGCACTTT CCACCACCTCTCAAAGGTGAAACCCAAGGCTGGTCTAGAGAA TGAATTATGGATCCTCGCTGTCCGTGCCACCCAGCTAGTCCC AGCGGCTCAGACACTGAGGAGAGACTGTAGGTTCAGCTACA AGCAAAAAGACCTAGCTGGTCTCCAAGCAGTGTCTCCAAGTC CCTGAACCTGTGACACCTGCCCCAGGCATCATCAGGCACAG AGGGCCACC |
| 43 | Portion of SEQ ID NO: 7 that contains SEQ ID NO: 9 and SEQ ID NO: 10 fused to portion of SEQ ID NO: 8 that contains SEQ ID NO: 14 and SEQ ID NO: 15 | TGCAGCTCAGCCTACTACTTGCTTTCCAGGCTGTTCCTAGTT CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTTTTATGAGGT GGGAGCTGGGCTCTCCCTGATGTATTATTCAGCTCCCTGGAG TTGGCCAGCTCCTGTTACACTGGCCACAGCCCTGGGCATCC GCTGCCATGGTGACTTTAAAGCCAGGTTGCTGCCCCAGCACA GGCCTCCCAGTCTACCCTCACTAGAAAACAACACCCAGGCAC TTTCCACCACCTCTCAAAGGTGAAACCCAAGGCTGGTCTAGA GAATGAATTATGGATCCTCGCTGTCCGTGCCACCCAGCTAGT CCCAGCGGCTCAGACACTG |

40

Additional Myo15 promoters useful in conjunction with the compositions and methods described herein include nucleic acid molecules that have at least 85% sequence identity (e.g., 85%, 90%, 95%, 96%, 97%, 98%, 99%, or more, sequence identity) to the polynucleotide sequences set forth in Table 3, as well as functional portions or derivatives of the polynucleotide sequences set forth in Table 3. The Myo15 promoters listed in Table 3 are characterized in International Application Publication Nos. WO2019210181A1 and WO2020163761A1, which are incorporated herein by reference.

In embodiments in which an smCBA promoter is included in a dual vector system described herein (e.g., in the first vector in a dual vector system), the smCBA promoter may have the sequence of the smCBA promoter described in U.S. Pat. No. 8,298,818, which is incorporated herein by reference. In some embodiments, the smCBA promoter has the sequence of:

(SEQ ID NO: 44)
GGTACCTAGTTATTAATAGTAATCAATTACGGGGTCATTAGTTCATAG

CCCATATATGGAGTTCCGCGTTACATAACTTACGGTAAATGGCCCGCC

TGGCTGACCGCCCAACGACCCCCGCCCATTGACGTCAATAATGACGTA

-continued
TGTTCCCATAGTAACGCCAATAGGGACTTTCCATTGACGTCAATGGGT

GGAGTATTTACGGTAAACTGCCCACTTGGCAGTACATCAAGTGTATCA

TATGCCAAGTACGCCCCCTATTGACGTCAATGACGGTAAATGGCCCGC

CTGGCATTATGCCCAGTACATGACCTTATGGGACTTTCCTACTTGGCA

GTACATCTACGTATTAGTCATCGCTATTACCATGGTCGAGGTGAGCCC

CACGTTCTGCTTCACTCTCCCCATCTCCCCCCCCTCCCCACCCCCAAT

TTTGTATTTATTTATTTTTTAATTATTTTGTGCAGCGATGGGGGCGGG

GGGGGGGGGGGGGCGCGCGCCAGGCGGGGCGGGGCGGGGCGAGGGGCG

GGGCGGGGCGAGGCGGAGAGGTGCGGCGGCAGCCAATCAGAGCGGCGC

GCTCCGAAAGTTTCCTTTTATGGCGAGGCGGCGGCGGCGGCGGCCCTA

TAAAAAGCGAAGCGCGCGGCGGGCGGGAGTCGCTGCGCGCTGCCTTCG

CCCCGTGCCCCGCTCCGCCGCCGCCTCGCGCCGCCCGCCCCGGCTCTG

ACTGACCGCGTTACTCCCACAGGTGAGCGGGCGGGACGGCCCTTCTCC

TCCGGGCTGTAATTAGCGCTTGGTTTAATGACGGCTTGTTTCTTTTCT

GTGGCTGCGTGAAAGCCTTGAGGGGCTCCGGGAGCTAGAGCCTCTGCT

-continued

```
AACCATGTTCATGCCTTCTTCTTTTTCCTACAGCTCCTGGGCAACGTG

CTGGTTATTGTGCTGTCTCATCATTTTGGCA.
```

Once a polynucleotide encoding OTOF has been incorporated into the nuclear DNA of a mammalian cell or stabilized in an episomal monomer or concatemer, the transcription of this polynucleotide can be induced by methods known in the art. For example, expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, CA) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode an OTOF protein and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding an OTOF protein, for example, at a position 5' or 3' to this gene. In a preferred orientation, the enhancer is positioned at the 5' side of the promoter, which in turn is located 5' relative to the polynucleotide encoding an OTOF protein.

The nucleic acid vectors described herein may include a Woodchuck Posttranscriptional Regulatory Element (WPRE). The WPRE acts at the mRNA level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo. The WPRE can be located in the second nucleic acid vector between the polynucleotide encoding a C-terminal portion of an OTOF protein and the poly(A) sequence. In some embodiments of the compositions and methods described herein, the WPRE has the sequence:

```
                                    (SEQ ID NO: 45)
GATCCAATCAACCTCTGGATTACAAAATTTGTGAAAGATTGACTGGTATT

CTTAACTATGTTGCTCCTTTTACGCTATGTGGATACGCTGCTTTAATGCC

TTTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAGG

CAACGTGGCGTGGTGTGCACTGTGTTTGCTGACGCAACCCCCACTGGTTG

GGGCATTGCCACCACCTGTCAGCTCCTTTCCGGGACTTTCGCTTTCCCCC

TCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAA

ATCATCGTCCTTTCCTTGGCTGCTCGCCTGTGTTGCCACCTGGATTCTGC

GCGGGACGTCCTTCTGCTACGTCCCTTCGGCCCTCAATCCAGCGGACCTT

CCTTCCCGCGGCCTGCTGCCGGCTCTGCGGCCTCTTCCGCGTCTTCGA.
```

In other embodiments, the WPRE has the sequence:

```
                                    (SEQ ID NO: 46)
AATCAACCTCTGGATTACAAAATTTGTGAAAGATTGACTGGTATTCTTAA

CTATGTTGCTCCTTTTACGCTATGTGGATACGCTGCTTTAATGCCTTTGT

ATCATGCTATTGCTTCCCGTATGGCTTTCATTTTCTCCTCCTTGTATAAA

TCCTGGTTAGTTCTTGCCACGGCGGAACTCATCGCCGCCTGCCTTGCCCG

CTGCTGGACAGGGGCTCGGCTGTTGGGCACTGACAATTCCGTGGTGTTTA

TTTGTGAAATTTGTGATGCTATTGCTTTATTTGTAACCATCTAGCTTTAT

TTGTGAAATTTGTGATGCTATTGCTTTATTTGTAACCATTATAAGCTGCA

ATAAACAAGTTAACAACAACAATTGCATTCATTTTATGTTTCAGGTTCAG

GGGGAGATGTGGGAGGTTTTTTAAA
```

In some embodiments, the nucleic acid vectors for use in the compositions and methods described herein include a reporter sequence, which can be useful in verifying OTOF gene expression, for example, in specific cells and tissues (e.g., in cochlear hair cells). Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Dual Hybrid Vectors for Expressing OTOF

An OTOF isoform 5 protein (e.g., an OTOF isoform 5 protein having the sequence of SEQ ID NO: 1) can be expressed in mammalian cells using a dual hybrid vector system. This approach uses two nucleic acid vectors (e.g., two adeno-associated virus vectors) to express a single, large protein. Each of the two nucleic acid vectors (e.g., two adeno-associated virus vectors) contains a portion of a polynucleotide that encodes the protein (e.g., one vector contains a polynucleotide encoding an N-terminal portion of the protein and the other vector contains a polynucleotide encoding a C-terminal portion of the protein, and the polynucleotide encoding the N-terminal portion of the protein and the polynucleotide encoding the C-terminal portion of the protein do not overlap). The dual hybrid vectors also feature an overlapping region at which homologous recombination can occur (e.g., a recombinogenic region that is contained within each vector) and splice donor and splice acceptor sequences (e.g., the first vector contains a splice donor sequence and the second vector contains a splice acceptor sequence). The recombinogenic region is 3' of the splice donor sequence in the first nucleic acid vector and 5' of the splice acceptor sequence in the second nucleic acid vector. The first and second polynucleotide sequences can then join to form a single sequence based on one of two mechanisms: 1) recombination at the overlapping region, or 2) concatemerization of the ITRs. The remaining recombinogenic region(s) and/or the concatemerized ITRs can be removed by splicing, leading to the formation of a contiguous polynucleotide sequence that encodes the full-length protein of interest.

Recombinogenic regions that can be used in the compositions and methods described herein include the F1 phage AK gene having a sequence of: GGGATTTTGCCGATTTCGGCCTATTGGTTAA AAAATGAGCTGATTTAACAAAAATTTAACGCGAATTTTAACAAAAT (SEQ ID NO: 47) and alkaline phosphatase (AP) gene fragments as described in U.S. Pat. No. 8,236,557, which are incorporated herein by reference. In some embodiments, the AP gene fragment has the sequence of:

```
                                       (SEQ ID NO: 48)
CCCCGGGTGCGCGGCGTCGGTGGTGCCGGCGGGGGGCGCCAGGTCGCAGG

CGGTGTAGGGCTCCAGGCAGGCGGCGAAGGCCATGACGTGCGCTATGAAG

GTCTGCTCCTGCACGCCGTGAACCAGGTGCGCCTGCGGGCCGCGCGCGAA

CACCGCCACGTCCTCGCCTGCGTGGGTCTCTTCGTCCAGGGGCACTGCTG

ACTGCTGCCGATACTCGGGGCTCCCGCTCTCGCTCTCGGTAACATCCGGC

CGGGCGCCGTCCTTGAGCACATAGCCTGGACCGTTTCCGTATAGGAGGAC

CGTGTAGGCCTTCCTGTCCCGGGCCTTGCCAGCGGCCAGCCCGATGAAGG

AGCTCCCTCGCAGGGGGTAGCCTCCGAAGGAGAAGACGTGGGAGTGGTCG

GCAGTGACGAGGCTCAGCGTGTCCTCCTCGCTGGTGAGCTGGCCCGCCCT

CTCAATGGCGTCGTCGAACATGATCGTCTCAGTCAGTGCCCGGTAAGCCC

TGCTTTCATGATGACCATGGTCGATGCGACCACCCTCCACGAAGAGGAAG

AAGCCGCGGGGGTGTCTGCTCAGCAGGCGCAGGGCAGCCTCTGTCATCTC

CATCAGGGAGGGGTCCAGTGTGGAGTCTCGGTGGATCTCGTATTTCATGT

CTCCAGGCTCAAAGAGACCCATGAGATGGGTCACAGACGGGTCCAGGGAA

GCCTGCATGAGCTCAGTGCGGTTCCACACGTACCGGGCACCCTGGCGTTC
```

-continued

```
GCCGAGCCATTCCTGCACCAGATTCTTCCCGTCCAGCCTGGTCCCACCTT

GGCTGTAGTCATCTGGGTACTCAGGGTCTGGGGTTCCCATGCGAAACATG

TACTTTCGGCCTCCA.
```

In some embodiments, the AP gene fragment has the sequence of:

```
                                       (SEQ ID NO: 49)
CCCCGGGTGCGCGGCGTCGGTGGTGCCGGCGGGGGGCGCCAGGTCGCAGG

CGGTGTAGGGCTCCAGGCAGGCGGCGAAGGCCATGACGTGCGCTATGAAG

GTCTGCTCCTGCACGCCGTGAACCAGGTGCGCCTGCGGGCCGCGCGCGAA

CACCGCCACGTCCTCGCCTGCGTGGGTCTCTTCGTCCAGGGGCACTGCTG

ACTGCTGCCGATACTCGGGGCTCCCGCTCTCGCTCTCGGTAACATCCGGC

CGGGCGCCGTCCTTGAGCACATAGCCTGGACCGTTTCCGTATAGGAGGAC

CGTGTAGGCCTTCCTGTCCCGGGCCTTGCCAGCGGCCAGCCCGATGAAGG

AGCTCCCTCGCAGGGGGTAGCCTCCGAAGGAGAAGACGTGGGAGTGGTCG

GCAGTGACGAGGCTCAGCGTGTCCTCCTCG CTGGTGA.
```

In some embodiments, the AP gene fragment has the sequence of:

```
                                       (SEQ ID NO: 50)
GCTGGCCCGCCCTCTCAATGGCGTCGTCGAACATGATCGTCTCAGTCAGT

GCCCGGTAAGCCCTGCTTTCATGATGACCATGGTCGATGCGACCACCCTC

CACGAAGAGGAAGAAGCCGCGGGGGTGTCTGCTCAGCAGGCGCAGGGCAG

CCTCTGTCATCTCCATCAGGGAGGGGTCCAGTGTGGAGTCTCGGTGGATC

TCGTATTTCATGTCTCCAGGCTCAAAGAGACCCATGAGATGGGTCACAGA

CGGGTCCAGGGAAGCCTGCATGAGCTCAGTGCGGTTCCACACGTACCGGG

CACCCTGGCGTTCGCCGAGCCATTCCTGCACCAGATTCTTCCCGTCCAGC

CTGGTCCCACCTTGGCTGTAGTCATCTGGGTACTCAGGGTCTGGGGTTCC

CATGCGAAACATGTACTTTCGGCCTCCA.
```

In some embodiments, the AP gene fragment has the sequence of:

```
                                       (SEQ ID NO: 51)
CCCCGGGTGCGCGGCGTCGGTGGTGCCGGCGGGGGGCGCCAGGTCGCAGG

CGGTGTAGGGCTCCAGGCAGGCGGCGAAGGCCATGACGTGCGCTATGAAG

GTCTGCTCCTGCACGCCGTGAACCAGGTGCGCCTGCGGGCCGCGCGCGAA

CACCGCCACGTCCTCGCCTGCGTGGGTCTCTTCGTCCAGGGGCACTGCTG

ACTGCTGCCGATACTCGGGGCTCCCGCTCTCGCTCTCGGTAACATCCGGC

CGGGCGCCGTCCTTGAGCACATAGCCTGGACCGTTTC
```

In some embodiments, the AP gene fragment has the sequence of:

```
                                       (SEQ ID NO: 52)
CGTATAGGAGGACCGTGTAGGCCTTCCTGTCCCGGGCCTTGCCAGCGGCC

AGCCCGATGAAGGAGCTCCCTCGCAGGGGGTAGCCTCCGAAGGAGAAGAC
```

-continued

GTGGGAGTGGTCGGCAGTGACGAGGCTCAGCGTGTCCTCCTCGCTGGTGA

GCTGGCCCGCCCTCTCAATGGCGTCGTCGAACATGATCGTCTCAGTCAGT

GCCCGGTAAGCCCTGCTTTCATGATGACCATGGTCGATGCGACCACCCTC

CACGAAGAGGAAGAAGCCGCGGGGGTGTCTGCTCAGCAGG.

In some embodiments, the AP gene fragment has the sequence of:

(SEQ ID NO: 53)
CGCAGGGCAGCCTCTGTCATCTCCATCAGGGAGGGGTCCAGTGTGGAGTC

TCGGTGGATCTCGTATTTCATGTCTCCAGGCTCAAAGAGACCCATGAGAT

GGGTCACAGACGGGTCCAGGGAAGCCTGCATGAGCTCAGTGCGGTTCCAC

ACGTACCGGGCACCCTGGCGTTCGCCGAGCCATTCCTGCACCAGATTCTT

CCCGTCCAGCCTGGTCCCACCTTGGCTGTAGTCATCTGGGTACTCAGGGT

CTGGGGTTCCCATGCGAAACATGTACTTTCGGCCTCCA.

An exemplary splice donor sequence for use in the methods and compositions described herein can include the sequence:

(SEQ ID NO: 54)
GTAAGTATCAAGGTTACAAGACAGGTTTAAGGAGACCAATAGAAACTGGG

CTTGTCGAGACAGAGAAGACTCTTGCGTTTCTGA.

An exemplary splice acceptor sequence for use in the methods and compositions described herein can include the sequence:

(SEQ ID NO: 55)
TAGGCACCTATTGGTCTTACTGACATCCACTTTGCCTTTCTCTCCACAG.

Additional examples of splice donor and splice acceptor sequences are known in the art.

Dual hybrid vectors for use in the methods and compositions described herein are designed such that approximately half of the OTOF gene is contained within each vector (e.g., each vector contains a polynucleotide that encodes approximately half of the OTOF isoform 5 protein). The determination of how to split the polynucleotide sequence between the two nucleic acid vectors can be made based on the size of the promoter and the locations of the portions of the polynucleotide that encode the OTOF C2 domains. When a short promoter is used in the dual hybrid vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as CAG, CMV, smCBA, or a Myo15 promoter having a sequence that is 1 kb or shorter (e.g., a Myo15 promoter described hereinabove, e.g., a Myo15 promoter having the sequence of SEQ ID NO: 21 or SEQ ID NO: 42), the OTOF polynucleotide sequence can be divided between the two nucleic acid vectors at an exon boundary that occurs after the portion of the polynucleotide that encodes the C2D domain and before the portion of the polynucleotide that encodes C2E domain, for example, the exon 26/27 boundary. The nucleic acid vectors containing promoters of this size can optionally contain OTOF UTRs (e.g., full-length 5' and 3' UTRs). When a long promoter is used in the dual hybrid vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 19), the OTOF polynucleotide sequence can be divided between the two nucleic acid vectors at an exon boundary that occurs after the portion of the polynucleotide that encodes the C2C domain, and either before the portion of the polynucleotide that encodes the C2D domain, such as the exon 19/20 boundary or the exon 20/21 boundary, or within the portion of the polynucleotide that encodes the C2D domain, such as the exon 25/26 boundary. A short promoter (e.g., a CMV promoter, CAG promoter, smCBA promoter, or a Myo15 promoter having a sequence that is 1 kb or shorter, e.g., a Myo15 promoter having the sequence of SEQ ID NO: 21 or SEQ ID NO: 42) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary dual hybrid vector system that uses a short promoter includes a first nucleic acid vector containing a CAG promoter operably linked to exons 1-26 of a polynucleotide encoding an OTOF isoform 5 protein (e.g., human OTOF isoform 5, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 27-45 and 47 of a polynucleotide encoding an OTOF isoform 5 protein (e.g., human OTOF isoform 5, e.g., SEQ ID NO: 1), and a poly(A) sequence (e.g., a bGH poly(A) signal sequence). The first and second nucleic acid vectors can also contain full-length 5' and 3' OTOF UTRs, respectively (e.g., the 127 bp human OTOF 5' UTR can be included in the first nucleic acid vector, and the 1035 bp human OTOF 3' UTR can be included in the second nucleic acid vector). Another exemplary dual hybrid vector system that uses a short promoter includes a first nucleic acid vector containing a smCBA promoter or a Myo15 promoter that is 1 kb or shorter (e.g., a Myo15 promoter having the sequence of SEQ ID NO: 21 or SEQ ID NO: 42) operably linked to exons 1-20 of a polynucleotide encoding an OTOF isoform 5 protein (e.g., human OTOF isoform 5, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 21-45 and 47 of a polynucleotide encoding an OTOF isoform 5 protein (e.g., human OTOF, e.g., SEQ ID NO: 1), and a poly(A) sequence (e.g., a bGH poly(A) signal sequence). The first nucleic acid vector can also contain the full-length 5' OTOF UTRs (e.g., the 127 bp human OTOF 5' UTR can be included in the first nucleic acid vector). The CMV promoter can be used in place of the CAG, smCBA, or Myo15 promoter in either of the foregoing dual vector systems.

An exemplary dual hybrid vector system that uses a long promoter includes a first nucleic acid vector containing a Myo15 promoter that is longer than 1 kb (e.g., SEQ ID NO: 19) operably linked to exons 1-19 or exons 1-20 of a polynucleotide encoding an OTOF isoform 5 protein (e.g., human OTOF isoform 5, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 20-45 and 47 (when the first nucleic acid vector contains exons 1-19 of the polynucleotide) or exons 21-45 and 47 (when the first nucleic acid vector contains exons 1-20 of the polynucleotide) of a polynucleotide encoding an OTOF isoform 5 protein (e.g., human OTOF isoform 5, e.g., SEQ ID NO: 1), and a poly(A) sequence (e.g., a bGH poly(A) signal sequence). Neither the first nor the second nucleic acid vector in the foregoing Myo15 promoter dual hybrid vector system contains an OTOF UTR. A short promoter (e.g., a CMV promoter, CAG promoter, smCBA promoter, or a Myo15 promoter having a sequence that is 1 kb or shorter, e.g., a Myo15 promoter having the sequence of SEQ ID NO: 21 or SEQ ID NO: 42) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a dual hybrid vector system in which the first nucleic acid vector contains a Myo15 promoter that is longer than 1 kb (e.g., SEQ ID NO: 19) operably linked to exons 1-25 of a polynucleotide encoding an OTOF isoform 5 protein (e.g., human OTOF isoform 5, e.g., SEQ ID NO: 1), a splice donor sequence 3' of the polynucleotide sequence, and a recombinogenic region 3' of the splice donor sequence; and in which the second nucleic acid vector contains a recombinogenic region, a splice acceptor sequence 3' of the recombinogenic region, a polynucleotide 3' of the splice acceptor sequence that contains exons 26-45 and 47 of a polynucleotide encoding an OTOF protein (e.g., human OTOF isoform 5, e.g., SEQ ID NO: 1), and a poly(A) sequence (e.g., a bGH poly(A) signal sequence), the second nucleic acid can also contain a full-length OTOF 3' UTR (e.g., the 1035 bp human OTOF UTR). A short promoter (e.g., a CMV promoter, CAG promoter, smCBA promoter, or a Myo15 promoter having a sequence that is 1 kb or shorter, e.g., a Myo15 promoter having the sequence of SEQ ID NO: 21 or SEQ ID NO: 42) can also be used in the foregoing dual vector system designed for large promoters. If these dual vector systems contain a short promoter, they may also include a 5' OTOF UTR in the first vector.

The polynucleotide sequence encoding an OTOF isoform 5 protein can be a cDNA sequence (e.g., a sequence that does not include introns). In some embodiments, the first and/or the second nucleic acid vector in the dual vector system can include intronic sequence. The intronic sequence may be included between one or more exons in the OTOF coding sequence, or the intronic sequence can be included between an exon of the coding sequence and another component of the nucleic acid vector (e.g., between an exon of the OTOF coding sequence and the splice donor sequence in the first nucleic acid vector or between an exon of the OTOF coding sequence and the splice acceptor sequence in the second nucleic acid vector).

In some embodiments, the polynucleotide encoding OTOF isoform 5 is divided between the first and second nucleic acid vectors (e.g., AAV vectors) in the dual vector system at the exon 20/21 boundary. When the polynucleotide encoding OTOF isoform 5 is divided between the first and second nucleic acid vectors (e.g., AAV vectors) at the exon 20/21 boundary, the polynucleotide sequence encoding the N-terminal portion of OTOF has the sequence of:

(SEQ ID NO: 56)

```
ATGGCCTTGCTCATCCACCTCAAGACAGTCTCGGAGCTGCGGGGCAGGGGCGACC

GGATCGCCAAAGTGACTTTCCGAGGGCAATCCTTCTACTCTCGGGTCCTGGAGAAC

TGTGAGGATGTGGCTGACTTTGATGAGACATTTCGGTGGCCGGTGGCCAGCAGCAT

CGACAGAAATGAGATGCTGGAGATTCAGGTTTTCAACTACAGCAAAGTCTTCAGCAA

CAAGCTCATCGGGACCTTCCGCATGGTGCTGCAGAAGGTGGTAGAGGAGAGCCAT

GTGGAGGTGACTGACACGCTGATTGATGACAACAATGCTATCATCAAGACCAGCCT

GTGCGTGGAGGTCCGGTATCAGGCCACTGACGGCACAGTGGGCTCCTGGGACGAT

GGGGACTTCCTGGGAGATGAGTCTCTTCAAGAGGAAGAGAAGGACAGCCAAGAGA

CGGATGGACTGCTCCCAGGCTCCCGGCCCAGCTCCCGGCCCCCAGGAGAGAAGA

GCTTCCGGAGAGCCGGGAGGAGCGTGTTCTCCGCCATGAAGCTCGGCAAAAACCG

GTCTCACAAGGAGGAGCCCAAAGACCAGATGAACCGGCGGTGCTGGAGATGGAA

GACCTTGACCATCTGGCCATTCGGCTAGGAGATGGACTGGATCCCGACTCGGTGTC

TCTAGCCTCAGTCACAGCTCTCACCACTAATGTCTCCAACAAGCGATCTAAGCCAGA

CATTAAGATGGAGCCAAGTGCTGGGCGGCCCATGGATTACCAGGTCAGCATCACGG

TGATCGAGGCCCGGCAGCTGGTGGGCTTGAACATGGACCCTGTGGTGTGCGTGGA

GGTGGGTGACGACAAGAAGTACACATCCATGAAGGAGTCCACTAACTGCCCCTATT

ACAACGAGTACTTCGTCTTCGACTTCCATGTCTCTCCGGATGTCATGTTTGACAAGA

TCATCAAGATTTCGGTGATTCACTCCAAGAACCTGCTGCGCAGTGGCACCCTGGTG

GGCTCCTTCAAAATGGACGTGGGAACCGTGTACTCGCAGCCAGAGCACCAGTTCCA
```

-continued

TCACAAGTGGGCCATCCTGTCTGACCCCGATGACATCTCCTCGGGGCTGAAGGGCT

ACGTGAAGTGTGACGTTGCCGTGGTGGGCAAAGGGGACAACATCAAGACGCCCCA

CAAGGCCAATGAGACCGACGAAGATGACATTGAGGGGAACTTGCTGCTCCCCGAG

GGGGTGCCCCCCGAACGCCAGTGGGCCCGGTTCTATGTGAAAATTTACCGAGCAG

AGGGGCTGCCCCGTATGAACACAAGCCTCATGGCCAATGTAAAGAAGGCTTTCATC

GGTGAAAACAAGGACCTCGTGGACCCCTACGTGCAAGTCTTCTTTGCTGGCCAGAA

GGGCAAGACTTCAGTGCAGAAGAGCAGCTATGAGCCCCTGTGGAATGAGCAGGTC

GTCTTTACAGACCTCTTCCCCCCACTCTGCAAACGCATGAAGGTGCAGATCCGAGA

CTCGGACAAGGTCAACGACGTGGCCATCGGCACCCACTTCATTGACCTGCGCAAGA

TTTCTAATGACGGAGACAAAGGCTTCCTGCCCACACTGGGCCCAGCCTGGGTGAAC

ATGTACGGCTCCACACGTAACTACACGCTGCTGGATGAGCATCAGGACCTGAACGA

GGGCCTGGGGGAGGGTGTGTCCTTCCGGGCCCGGCTCCTGCTGGGCCTGGCTGT

GGAGATCGTAGACACCTCCAACCCTGAGCTCACCAGCTCCACAGAGGTGCAGGTG

GAGCAGGCCACGCCCATCTCGGAGAGCTGTGCAGGTAAAATGGAAGAATTCTTTCT

CTTTGGAGCCTTCCTGGAGGCCTCAATGATCGACCGGAGAAACGGAGACAAGCCCA

TCACCTTTGAGGTCACCATAGGCAACTATGGGAACGAAGTTGATGGCCTGTCCCGG

CCCCAGCGGCCTCGGCCCCGGAAGGAGCCGGGGGATGAGGAAGAAGTAGACCTG

ATTCAGAACGCAAGTGATGACGAGGCCGGTGATGCCGGGGACCTGGCCTCAGTCT

CCTCCACTCCACCAATGCGGCCCCAGGTCACCGACAGGAACTACTTCCATCTGCCC

TACCTGGAGCGAAAGCCCTGCATCTACATCAAGAGCTGGTGGCCGGACCAGCGCC

GCCGCCTCTACAATGCCAACATCATGGACCACATTGCCGACAAGCTGGAAGAAGGC

CTGAACGACATACAGGAGATGATCAAAACGGAGAAGTCCTACCCTGAGCGTCGCCT

GCGGGGCGTCCTGGAGGAGCTGAGCTGTGGCTGCTGCCGCTTCCTCTCCCTCGCT

GACAAGGACCAGGGCCACTCATCCCGCACCAGGCTTGACCGGGAGCGCCTCAAGT

CCTGCATGAGGGAGCTG.

When the polynucleotide encoding OTOF isoform 5 is divided between the first and second nucleic acid vectors (e.g., AAV vectors) at the exon 20/21 boundary, the polynucleotide sequence encoding the C-terminal portion of OTOF has the sequence of:

(SEQ ID NO: 57)

GAAAACATGGGCAGCAGGCCAGGATGCTGCGGGCCCAGGTGAAGCGGCACACG

GTGCGGGACAAGCTGAGGCTGTGCCAGAACTTCCTGCAGAAGCTGCGCTTCCTGG

CGGACGAGCCCCAGCACAGCATTCCCGACATCTTCATCTGGATGATGAGCAACAAC

AAGCGTGTCGCCTATGCCCGTGTGCCCTCCAAGGACCTGCTCTTCTCCATCGTGGA

GGAGGAGACTGGCAAGGACTGCGCCAAGGTCAAGACGCTCTTCCTTAAGCTGCCA

GGGAAGCGGGGCTTCGGCTCGGCAGGCTGGACAGTGCAGGCCAAGGTGGAGCTG

TACCTGTGGCTGGGCCTCAGCAAACAGCGCAAGGAGTTCCTGTGCGGCCTGCCCT

GTGGCTTCCAGGAGGTCAAGGCAGCCCAGGGCCTGGGCCTGCATGCCTTCCCACC

CGTCAGCCTGGTCTACACCAAGAAGCAGGCGTTCCAGCTCCGAGCGCACATGTACC

AGGCCCGCAGCCTCTTTGCCGCCGACAGCAGCGGACTCTCAGACCCCTTTGCCCG

CGTCTTCTTCATCAATCAGAGTCAGTGCACAGAGGTGCTGAATGAGACCCTGTGTCC

-continued

```
CACCTGGGACCAGATGCTGGTGTTCGACAACCTGGAGCTCTATGGTGAAGCTCATG

AGCTGAGGGACGATCCGCCCATCATTGTCATTGAAATCTATGACCAGGATTCCATGG

GCAAAGCTGACTTCATGGGCCGGACCTTCGCCAAACCCCTGGTGAAGATGGCAGAC

GAGGCGTACTGCCCACCCCGCTTCCCACCTCAGCTCGAGTACTACCAGATCTACCG

TGGCAACGCCACAGCTGGAGACCTGCTGGCGGCCTTCGAGCTGCTGCAGATTGGA

CCAGCAGGGAAGGCTGACCTGCCCCCCATCAATGGCCCGGTGGACGTGGACCGAG

GTCCCATCATGCCCGTGCCCATGGGCATCCGGCCCGTGCTCAGCAAGTACCGAGT

GGAGGTGCTGTTCTGGGGCCTACGGGACCTAAAGCGGGTGAACCTGGCCCAGGTG

GACCGGCCACGGGTGGACATCGAGTGTGCAGGGAAGGGGGTGCAGTCGTCCCTG

ATCCACAATTATAAGAAGAACCCCAACTTCAACACCCTCGTCAAGTGGTTTGAAGTG

GACCTCCCAGAGAACGAGCTGCTGCACCCGCCCTTGAACATCCGTGTGGTGGACT

GCCGGGCCTTCGGTCGCTACACACTGGTGGGCTCCCATGCCGTCAGCTCCCTGCG

ACGCTTCATCTACCGGCCCCCAGACCGCTCGGCCCCCAGCTGGAACACCACGGTC

AGGCTTCTCCGGCGCTGCCGTGTGCTGTGCAATGGGGGCTCCTCCTCTCACTCCAC

AGGGGAGGTTGTGGTGACTATGGAGCCAGAGGTACCCATCAAGAAACTGGAGACC

ATGGTGAAGCTGGACGCGACTTCTGAAGCTGTTGTCAAGGTGGATGTGGCTGAGGA

GGAGAAGGAGAAGAAGAAGAAGAAGGGCACTGCGGAGGAGCCAGAGGAGGA

GGAGCCAGACGAGAGCATGCTGGACTGGTGGTCCAAGTACTTTGCCTCCATTGACA

CCATGAAGGAGCAACTTCGACAACAAGAGCCCTCTGGAATTGACTTGGAGGAGAAG

GAGGAAGTGGACAATACCGAGGGCCTGAAGGGGTCAATGAAGGGCAAGGAGAAGG

CAAGGGCTGCCAAAGAGGAGAAGAAGAAGAAAACTCAGAGCTCTGGCTCTGGCCA

GGGGTCCGAGGCCCCCGAGAAGAAGAAACCCAAGATTGATGAGCTTAAGGTATACC

CCAAAGAGCTGGAGTCCGAGTTTGATAACTTTGAGGACTGGCTGCACACTTTCAACT

TGCTTCGGGGCAAGACCGGGGATGATGAGGATGGCTCCACCGAGGAGGAGCGCAT

TGTGGGACGCTTCAAGGGCTCCCTCTGCGTGTACAAAGTGCCACTCCCAGAGGACG

TGTCCCGGGAAGCCGGCTACGACTCCACCTACGGCATGTTCCAGGGCATCCCGAG

CAATGACCCCATCAATGTGCTGGTCCGAGTCTATGTGGTCCGGGCCACGGACCTGC

ACCCTGCTGACATCAACGGCAAAGCTGACCCCTACATCGCCATCCGGCTAGGCAAG

ACTGACATCCGCGACAAGGAGAACTACATCTCCAAGCAGCTCAACCCTGTCTTTGG

GAAGTCCTTTGACATCGAGGCCTCCTTCCCCATGGAATCCATGCTGACGGTGGCTG

TGTATGACTGGGACCTGGTGGGCACTGATGACCTCATTGGGGAAACCAAGATCGAC

CTGGAGAACCGCTTCTACAGCAAGCACCGCGCCACCTGCGGCATCGCCCAGACCT

ACTCCACACATGGCTACAATATCTGGCGGGACCCCATGAAGCCCAGCCAGATCCTG

ACCCGCCTCTGCAAAGACGGCAAAGTGGACGGCCCCCACTTTGGGCCCCCTGGGA

GAGTGAAGGTGGCCAACCGCGTCTTCACTGGGCCCTCTGAGATTGAGGACGAGAA

CGGTCAGAGGAAGCCCACAGACGAGCATGTGGCGCTGTTGGCCCTGAGGCACTGG

GAGGACATCCCCCGCGCAGGCTGCCGCCTGGTGCCAGAGCATGTGGAGACGAGG

CCGCTGCTCAACCCCGACAAGCCGGGCATCGAGCAGGGCCGCCTGGAGCTGTGG

GTGGACATGTTCCCCATGGACATGCCAGCCCCTGGGACGCCTCTGGACATCTCACC

TCGGAAGCCCAAGAAGTACGAGCTGCGGGTCATCATCTGGAACACAGATGAGGTG
```

-continued

```
GTCTTGGAGGACGACGACTTCTTCACAGGGGAGAAGTCCAGTGACATCTTCGTGAG

GGGGTGGCTGAAGGGCCAGCAGGAGGACAAGCAGGACACAGACGTCCACTACCAC

TCCCTCACTGGCGAGGGCAACTTCAACTGGCGCTACCTGTTCCCCTTCGACTACCT

GGCGGCGGAGGAGAAGATCGTCATCTCCAAGAAGGAGTCCATGTTCTCCTGGGAC

GAGACCGAGTACAAGATCCCCGCGCGGCTCACCCTGCAGATCTGGGATGCGGACC

ACTTCTCCGCTGACGACTTCCTGGGGGGCCATCGAGCTGGACCTGAACCGGTTCCCG

CGGGGCGCAAAGACAGCCAAGCAGTGCACCATGGAGATGGCCACCGGGGAGGTG

GACGTGCCCCTCGTGTCCATCTTCAAGCAAAAGCGCGTCAAAGGCTGGTGGCCCCT

CCTGGCCCGCAATGAGAACGATGAGTTTGAGCTCACGGGCAAGGTGGAGGCTGAG

CTGCATTTACTGACAGCAGAGGAGGCAGAGAAGAACCCAGTGGGCCTGGCCCGCA

ATGAACCTGACCCCCTAGAGAAACCCAACCGGCCCGACACGGCCTTCGTCTGGTTC

CTCAACCCTCTCAAGTCCATCAAGTACCTCATCTGCACCCGGTACAAGTGGCTCATC

ATCAAGATCGTGCTGGCGCTGTTGGGGCTGCTCATGTTGGGGCTCTTCCTCTACAG

CCTCCCTGGCTACATGGTCAAAAAGCTCCTTGGGGCATGA.
```

In embodiments in which the polynucleotide encoding OTOF isoform 5 is divided between the first and second nucleic acid vectors (e.g., AAV vectors) at the exon 20/21 boundary, the N-terminal portion of the OTOF polypeptide has the sequence of:

(SEQ ID NO: 58)

```
MALLIHLKTVSELRGRGDRIAKVTFRGQSFYSRVLENCEDVADFDETFRW

PVASSIDRNEMLEIQVFNYSKVFSNKLIGTFRMVLQKVVEESHVEVTDTL

IDDNNAIIKTSLCVEVRYQATDGTVGSWDDGDFLGDESLQEEEKDSQETD

GLLPGSRPSSRPPGEKSFRRAGRSVFSAMKLGKNRSHKEEPQRPDEPAVL

EMEDLDHLAIRLGDGLDPDSVSLASVTALTTNVSNKRSKPDIKMEPSAGR

PMDYQVSITVIEARQLVGLNMDPVVCVEVGDDKKYTSMKESTNCPYYNEY

FVFDPHVSPDVMFDKIIKISVIHSKNLLRSGTLVGSFKMDVGTVYSQPEH

QFHHKWAILSDPDDISSGLKGYVKCDVAVVGKGDNIKTPHKANETDEDDI

EGNLLLPEGVPPERQWARFYVKIYRAEGLPRMNTSLMANVKKAFIGENKD

LVDPYVQVFFAGQKGKTSVQKSSYEPLWNEQVVFTDLFPPLCKRMKVQIR

DSDKVNDVAIGTHFIDLRKISNDGDKGFLPTLGPAWVNMYGSTRNYTLLD

EHQDLNEGLGEGVSFRARLLLGLAVEIVDTSNPELTSSTEVQVEQATPIS

ESCAGKMEEFFLFGAFLEASMIDRRNGDKPITFEVTIGNYGNEVDGLSRP

QRPRPRKEPGDEEEVDLIQNASDDEAGDAGDLASVSSTPPMRPQVTDRNY

FHLPYLERKPCIYIKSWWPDQRRRLYNANIMDHIADKLEEGLNDIQEMIK

TEKSYPERRLRGVLEELSCGCCRFLSLADKDQGHSSRTRLDRERLKSCMR

EL.
```

In embodiments in which the polynucleotide encoding OTOF isoform 5 is divided between the first and second nucleic acid vectors (e.g., AAV vectors) at the exon 20/21 boundary, the C-terminal portion of the OTOF polypeptide has the sequence of:

(SEQ ID NO: 59)

```
ENMGQQARMLRAQVKRHTVRDKLRLCQNFLQKLRFLADEPQHSIPDIFIW

MMSNNKRVAYARVPSKDLLFSIVEEETGKDCAKVKTLFLKLPGKRGFGSA

GWTVQAKVELYLWLGLSKQRKEFLCGLPCGFQEVKAAQGLGLHAFPPVSL

VYTKKQAFQLRAHMYQARSLFAADSSGLSDPFARVFFINQSQCTEVLNET

LCPTWDQMLVFDNLELYGEAHELRDDPPIIVIEIYDQDSMGKADFMGRTF

AKPLVKMADEAYCPPRFPPQLEYYQIYRGNATAGDLLAAFELLQIGPAGK

ADLPPINGPVDVDRGPIMPVPMGIRPVLSKYRVEVLFWGLRDLKRVNLAQ

VDRPRVDIECAGKGVQSSLIHNYKKNPNFNTLVKWFEVDLPENELLHPPL

NIRVVDCRAFGRYTLVGSHAVSSLRRFIYRPPDRSAPSWNTTVRLLRRCR

VLCNGGSSSHSTGEVVVTMEPEVPIKKLETMVKLDATSEAVVKVDVAEEE

KEKKKKKKGTAEEPEEEEPDESMLDWWSKYFASIDTMKEQLRQQEPSGID

LEEKEEVDNTEGLKGSMKGKEKARAAKEEKKKKTQSSGSGQGSEAPEKKK

PKIDELKVYPKELESEFDNFEDWLHTFNLLRGKTGDDEDGSTEEERIVGR

FKGSLCVYKVPLPEDVSREAGYDSTYGMFQGIPSNDPINVLVRVYVVRAT

DLHPADINGKADPYIAIRLGKTDIRDKENYISKQLNPVFGKSFDIEASFP

MESMLTVAVYDWDLVGTDDLIGETKIDLENRFYSKHRATCGIAQTYSTHG

YNIWRDPMKPSQILTRLCKDGKVDGPHFGPPGRVKVANRVFTGPSEIEDE

NGQRKPTDEHVALLALRHWEDIPRAGCRLVPEHVETRPLLNPDKPGIEQG

RLELWVDMFPMDMPAPGTPLDISPRKPKKYELRVIIWNTDEVVLEDDDFF

TGEKSSDIFVRGWLKGQQEDKQDTDVHYHSLTGEGNFNWRYLFPFDYLAA

EEKIVISKKESMFSWDETEYKIPARLTLQIWDADHFSADDFLGAIELDLN

RFPRGAKTAKQCTMEMATGEVDVPLVSIFKQKRVKGWWPLLARNENDEFE

LTGKVEAELHLLTAEEAEKNPVGLARNEPDPLEKPNRPDTAFVWFLNPLK

SIKYLICTRYKWLIIKIVLALLGLLMLGLFLYSLPGYMVKKLLGA.
```

Transfer plasmids that may be used to produce the nucleic acid vectors for use in the compositions and methods described herein are provided in Table 4. A transfer plasmid (e.g., a plasmid containing a DNA sequence to be delivered by a nucleic acid vector, e.g., to be delivered by an AAV) may be co-delivered into producer cells with a helper plasmid (e.g., a plasmid providing proteins necessary for AAV manufacture) and a rep/cap plasmid (e.g., a plasmid that provides AAV capsid proteins and proteins that insert the transfer plasmid DNA sequence into the capsid shell) to produce a nucleic acid vector (e.g., an AAV vector) for administration. Nucleic acid vectors (e.g., a nucleic acid vector (e.g., an AAV vector) containing a polynucleotide encoding an N-terminal portion of OTOF isoform 5 and a nucleic acid vector (e.g., an AAV vector) containing a polynucleotide encoding a C-terminal portion of OTOF isoform 5) can be combined (e.g., in a single formulation) prior to administration. The following transfer plasmids are designed to produce nucleic acid vectors (e.g., AAV vectors) for co-formulation or co-administration (e.g., administration simultaneously or sequentially) in a dual hybrid vector system: SEQ ID NO: 60 and SEQ ID NO: 61; SEQ ID NO: 62 and SEQ ID NO: 63; SEQ ID NO: 64 and SEQ ID NO: 61; SEQ ID NO: 65 and SEQ ID NO: 63; SEQ ID NO: 66 and SEQ ID NO: 67; and SEQ ID NO: 68 and SEQ ID NO: 67.

TABLE 4

| Transfer plasmids for the production of dual hybrid vector systems | | |
|---|---|---|
| SEQ ID NO. | Description | Plasmid Sequence |
| 60 | 5' transgene plasmid containing the following features: Lambda (Biologically inert and inactivated DNA derived from bacteriophage lambda to reduce off-target DNA encapsidation) at positions 53-2027 ITR at positions 2049-2178 Myo15 promoter at positions 2272-3236 Kozak sequence (Site to initiate protein translation) at positions 3253-3262 N-terminal portion of human OTOF isoform 5 at positions 3259-5664 Splice donor (APSD) sequence at positions 5665-5748 AP head sequence (recombinogenic region) at positions 5755-6041 ITR at positions 6135-6264 Lambda at positions 6275-8287 Ori (origin of replication) at positions 8344-8932 Kan R (antibiotic resistance gene) at positions 9110-9919 Transgene to be transferred into vector in dual vector system at positions 2049-6264 | TCGCGCGTTTCGGTGATGACGGTGAAAACCTCTGACA CATGCAGCTCCCGGATAGAGGTCATCCTTCCTGACCA TTTCCATCATTCCAGTCGAACTCACACACAACACCAAA TGCATTTAAGTCGCTTGAAATTGCTATAAGCAGAGCAT GTTGCGCCAGCATGATTAATACAGCATTTAATACAGAG CCGTGTTTATTGAGTCGGTATTCAGAGTCTGACCAGAA ATTATTAATCTGGTGAAGTTATTCCTCTGTCATTACGTC ATGGTCGATTTCAATTTCTATTGATGCTTTCCAGTCGTA ATCAATGATGTATTTTTTGATGTTTGACCTCTGTTCATA TCCTCACAGATAAAAAATCGCCCTCACACTGGAGGGC AAAGAAGATTTCCAATAATCAGAACAAGTCGGCTCCTG TTTAGTTACGAGCGACATTGCTCCGTGTATTCACTCGT TGGAATGAATACACAGTGCAGTGTTTATTCTGTTATTTA TGCCAAAAATTAAGGCCACTATCAGGCAGCTTGTTGT TCTGTTTACCAAGTTCTCTGGCAATCATTGCCGTCGTT CGTATTGCCCATTTATCGACATATTTCCCATCTTCCTAT ACAGGAAACATTTCTTCAGGCTTAACCATGCATTCCGA TTGCAGCTTGCATCCATTGCATCGCTTGAATTGTCCAC ACCATTGATTTTTATCAATAGTCGTAGTTTAACGGATAG TCCTGGTATTGTTCCATCACATCCTGAGGATGCCCTTC GAACTCTTCAAATTCTTCTTCCTAATATCACCTTAAATA GTGGATTGCGGTAGTAAAGATTGTGCCTGTCTTTTAAC CACATCAGGCTCGGTGGTTCTCGTGTACCCCTACAGC GAGAAATCGGATAAACTATTACAACCCCTACAGTTTGT AGAGTATAGAAAATGATCCACTCGTTATTCTCGGACGA GTGTTCAGTAATGAACCTCTGGAGAGAACCATCTATAT GATCGTTATCTGGGTTTGACTTCTGCTTTTAAGCCCAG ATAACTTGCCTGAATATGTTAATGAGAGAATCGGTATT CCTCATGTGTGGCATGTTTTCGTCTTTGCTCTTGCATTT TCACTAGCAATTAATGTGCATCGATTATCAGCTATTGC CAGCGCCAGATATAAGCGATTTAAGCTAAGAAAACGCA TTAAGGTGCAAAACGATAAAGTGCGATCAGTAATTCAA AACCTTACAGGAGAGCAATCTATGGTTTTGTGCTCAGC CCTTAATGAAGGCAGGTAGTATGTGGTTACATCAAAAC AATTCCCATACATTAGTGAGTTGATTGAGCTTGGTGTG TTGAACAAAACTTTTTCCCGATGGAATGGAAAGCATAT ATTATTCCCTATTGAGGATATTTACTGGACTGAATTAGT TGCCAGCTATGATCCATATAATATTGAGATAAAGCCAA GGCCAATATCTAAGTAACTAGATAAGAGGAATCGATTT TCCCTTAATTTTCTGGCGTCCACTGCATGTTATGCCGC GTTCGCCAGGCTTGCTGTACCATGTGCGCTGATTCTT GCGCTCAATACGTTGCAGGTTGCTTTCAATCTGTTTGT GGTATTCAGCCAGCACTGTAAGGTCTATCGGATTTAGT GCGCTTTCTACTCGTGATTTCGGTTTGCGATTCAGCGA GAGAATAGGGCGGTTAACTGGTTTTGCGCTTACCCCA ACCAACAGGGGATTTGCTGCTTTCCATTGAGCCTGTTA CTCTGCGCGACGTTCGCGGCGGCGTGTTTGTGCATCC ATCTGGATTCTCCTGTCAGTTAGCTTTGGTGGTGTGTG GCAGTTGTAGTCCTGAACGAAAACCCCCCGCGATTGG CACGTTGGCAGCTAATCCGGAATCGCACTTACGGCCA ATGCTTCGTTTCGTATCACACACCCCAAAGCCTTCTGC TTTGAATGCTGCCCTTCTTCAGGGCTTAATTTTTAAGA GCGTCACCTTCATGGTGGTCAGTGCGTCCTGCTGATG TGCTCAGGCACGATTTAATTAAGGCCTTAATTAGGCTG CGCGCTCGCTCGCTCACTGAGGCCGCCCGGGCAAAG CCCGGGCGTCGGGCGACCTTTGGTCGCCCGGCCTCA GTGAGCGAGCGAGCGCGCAGAGAGGGAGTGGCCAAC TCCATCACTAGGGGTTCCTTGTAGTTAATGATTAACCC |

TABLE 4-continued

Transfer plasmids for the production of dual hybrid vector systems

SEQ
ID
NO. Description                          Plasmid Sequence

GCCATGCTACTTATCTACGTAGCCATGCTCTAGGAAGA
TCGGAATTCGCCCTTAAGCTAGCGGCGCGCCCAATTC
TGCAGCTCAGCCTACTACTTGCTTTCCAGGCTGTTCCT
AGTTCCCATGTCAGCTGCTTGTGCTTTCCAGAGACAAA
ACAGGAATAATAGATGTCATTAAATATACATTGGGCCC
CAGGCGGTCAATGTGGCAGCCTGAGCCTCCTTTCCAT
CTCTGTGGAGGCAGACATAGGACCCCCAACAAACAGC
ATGCAGGTTGGGAGCCAGCCACAGGACCCAGGTAAG
GGGCCCTGGGTCCTTAAGCTTCTGCCACTGGCTCCGG
CATTGCAGAGAGAAGAGAAGGGGCGGCAGACTGGAG
AGCTGGGCTCCATTTTTGTTCCTTGGTGCCCTGCCCCT
CCCCATGACCTGCAGAGACATTCAGCCTGCCAGGCTT
TATGAGGTGGGAGCTGGGCTCTCCCTGATGTATTATTC
AGCTCCCTGGAGTTGGCCAGCTCCTGTTACACTGGCC
ACAGCCCTGGGCATCCGCTTCTCACTTCTAGTTTCCCC
TCCAAGGTAATGTGGTGGGTCATGATCATTCTATCCTG
GCTTCAGGGACCTGACTCCACTTTGGGGCCATTCGAG
GGGTCTAGGGTAGATGATGTCCCCCTGTGGGGATTAA
TGTCCTGCTCTGTAAAACTGAGCTAGCTGAGATCCAG
GAGGGCTTGGCCAGAGACAGCAAGTTGTTGCCATGGT
GACTTTAAAGCCAGGTTGCTGCCCCAGCACAGGCCTC
CCAGTCTACCCTCACTAGAAAACAACACCCAGGCACTT
TCCACCACCTCTCAAAGGTGAAACCCAAGGCTGGTCT
AGAGAATGAATTATGGATCCTCGCTGTCCGTGCCACC
CAGCTAGTCCCAGCGGCTCAGACACTGAGGAGAGACT
GTAGGTTCAGCTACAAGCAAAAAGACCTAGCTGGTCT
CCAAGCAGTGTCTCCAAGTCCCTGAACCTGTGACACC
TGCCCCAGGCATCATCAGGCACAGAGGGCCACCAAGA
ATTCTAGCGGCCGCCACCATGGCCTTGCTCATCCACC
TCAAGACAGTCTCGGAGCTGCGGGGCAGGGGCGACC
GGATCGCCAAAGTGACTTTCCGAGGGCAATCCTTCTA
CTCTCGGGTCCTGGAGAACTGTGAGGATGTGGCTGAC
TTTGATGAGACATTTCGGTGGCCGGTGGCCAGCAGCA
TCGACAGAAATGAGATGCTGGAGATTCAGGTTTTCAAC
TACAGCAAAGTCTTCAGCAACAAGCTCATCGGGACCTT
CCGCATGGTGCTGCAGAAGGTGGTAGAGGAGAGCCA
TGTGGAGGTGACTGACACGCTGATTGATGACAACAAT
GCTATCATCAAGACCAGCCTGTGCGTGGAGGTCCGGT
ATCAGGCCACTGACGGCACAGTGGGCTCCTGGGACG
ATGGGGACTTCCTGGGAGATGAGTCTCTTCAAGAGGA
AGAGAAGGACAGCCAAGAGACGGATGGACTGCTCCCA
GGCTCCCGGCCCAGCTCCCGGCCCCCAGGAGAGAAG
AGCTTCCGGAGAGCCGGGAGGAGCGTGTTCTCCGCC
ATGAAGCTCGGCAAAAACCGGTCTCACAAGGAGGAGC
CCCAAAGACCAGATGAACCGGCGGTGCTGGAGATGG
AAGACCTTGACCATCTGGCCATTCGGCTAGGAGATGG
ACTGGATCCCGACTCGGTGTCTCTAGCCTCAGTCACA
GCTCTCACCACTAATGTCTCCAACAAGCGATCTAAGCC
AGACATTAAGATGGAGCCAAGTGCTGGGCGGCCCATG
GATTACCAGGTCAGCATCACGGTGATCGAGGCCCGGC
AGCTGGTGGGCTTGAACATGGACCCTGTGGTGTGCGT
GGAGGTGGGTGACGACAAGAAGTACACATCCATGAAG
GAGTCCACTAACTGCCCCTATTACAACGAGTACTTCGT
CTTCGACTTCCATGTCTCTCCGGATGTCATGTTTGACA
AGATCATCAAGATTTCGGTGATTCACTCCAAGAACCTG
CTGCGCAGTGGCACCCTGGTGGGCTCCTTCAAAATGG
ACGTGGGAACCGTGTACTCGCAGCCAGAGCACCAGTT
CCATCACAAGTGGGCCATCCTGTCTGACCCCGATGAC
ATCTCCTCGGGGCTGAAGGGCTACGTGAAGTGTGACG
TTGCCGTGGTGGGCAAAGGGGACAACATCAAGACGCC
CCACAAGGCCAATGAGACCGACGAAGATGACATTGAG
GGGAACTTGCTGCTCCCCGAGGGGGTGCCCCCCGAA
CGCCAGTGGGCCCGGTTCTATGTGAAAATTTACCGAG
CAGAGGGGCTGCCCCGTATGAACACAAGCCTCATGGC
CAATGTAAAGAAGGCTTTCATCGGTGAAAACAAGGACC
TCGTGGACCCCTACGTGCAAGTCTTCTTTGCTGGCCA
GAAGGGCAAGACTTCAGTGCAGAAGAGCAGCTATGAG
CCCCTGTGGAATGAGCAGGTCGTCTTTACAGACCTCTT
CCCCCCACTCTGCAAACGCATGAAGGTGCAGATCCGA
GACTCGGACAAGGTCAACGACGTGGCCATCGGCACC
CACTTCATTGACCTGCGCAAGATTTCTAATGACGGAGA
CAAAGGCTTCCTGCCCACACTGGGCCCAGCCTGGGTG
AACATGTACGGCTCCACACGTAACTACACGCTGCTGG
ATGAGCATCAGGACCTGAACGAGGGCCTGGGGGAGG

TABLE 4-continued

Transfer plasmids for the production of dual hybrid vector systems

SEQ
ID
NO. Description                    Plasmid Sequence

```
GTGTGTCCTTCCGGGCCCGGCTCCTGCTGGGCCTGG
CTGTGGAGATCGTAGACACCTCCAACCCTGAGCTCAC
CAGCTCCACAGAGGTGCAGGTGGAGCAGGCCACGCC
CATCTCGGAGAGCTGTGCAGGTAAAATGGAAGAATTC
TTTCTCTTTGGAGCCTTCCTGGAGGCCTCAATGATCGA
CCGGAGAAACGGAGACAAGCCCATCACCTTTGAGGTC
ACCATAGGCAACTATGGGAACGAAGTTGATGGCCTGT
CCCGGCCCCAGCGGCCTCGGCCCCGGAAGGAGCCG
GGGGATGAGGAAGAAGTAGACCTGATTCAGAACGCAA
GTGATGACGAGGCCGGTGATGCCGGGGACCTGGCCT
CAGTCTCCTCCACTCCACCAATGCGGCCCCAGGTCAC
CGACAGGAACTACTTCCATCTGCCCTACCTGGAGCGA
AAGCCCTGCATCTACATCAAGAGCTGGTGGCCGGACC
AGCGCCGCCGCCTCTACAATGCCAACATCATGGACCA
CATTGCCGACAAGCTGGAAGAAGGCCTGAACGACATA
CAGGAGATGATCAAAACGGAGAAGTCCTACCCTGAGC
GTCGCCTGCGGGGCGTCCTGGAGGAGCTGAGCTGTG
GCTGCTGCCGCTTCCTCTCCCTCGCTGACAAGGACCA
GGGCCACTCATCCCGCACCAGGCTTGACCGGGAGCG
CCTCAAGTCCTGCATGAGGGAGCTGGTAAGTATCAAG
GTTACAAGACAGGTTTAAGGAGACCAATAGAAACTGG
GCTTGTCGAGACAGAGAAGACTCTTGCGTTTCTGAGC
TAGCCCCCGGGTGCGCGGCGTCGGTGGTGCCGGCG
GGGGGCGCCAGGTCGCAGGCGGTGTAGGGCTCCAG
GCAGGCGGCGAAGGCCATGACGTGCGCTATGAAGGT
CTGCTCCTGCACGCCGTGAACCAGGTGCGCCTGCGG
GCCGCGCGCGAACACCGCCACGTCCTCGCCTGCGTG
GGTCTCTTCGTCCAGGGGCACTGCTGACTGCTGCCGA
TACTCGGGGCTCCCGCTCTCGCTCTCGGTAACATCCG
GCCGGGCGCCGTCCTTGAGCACATAGCCTGGACCGTT
TCGTCGACCTCGAGTTAAGGGCGAATTCCCGATAAGG
ATCTTCCTAGAGCATGGCTACGTAGATAAGTAGCATGG
CGGGTTAATCATTAACTACAAGGAACCCCTAGTGATGG
AGTTGGCCACTCCCTCTCTGCGCGCTCGCTCGCTCAC
TGAGGCCGGGCGACCAAAGGTCGCCCGACGCCCGGG
CTTTGCCCGGGCGGCCTCAGTGAGCGAGCGAGCGCG
CAGCCTTAATTAAATCCACATCTGTATGTTTTTTATATT
AATTTATTTTTTGCAGGGGGGGCATTGTTTGGTAGGTGA
GAGTTCTGAATTGCTATGTTTAGTGAGTTGTATCTATTT
ATTTTTCAATAAATACAATTAGTTATGTGTTTTGGGGGC
GATCGTGAGGCAAAGAAAACCCGGCGCTGAGGCCGG
GTTATTCTTGTTCTCTGGTCAAATTATATAGTTGGAAAA
CAAGGATGCATATATGAATGAACGATGCAGAGGCAAT
GCCGATGGCGATAGTGGGTATCAGGTAGCCGCTTATG
CTGGAAAGAAGCAATAACCCGCAGAAAAACAAAGCTC
CAAGCTCAACAAAACTAAGGGCATAGACAATAACTACC
TATGTCATATACCCATACTCTCTAATCTTGGCCAGTCG
GCGCGTTCTGCTTCCGATTAGAAACGTCAAGGCAGCA
ATCAGGATTGCAATCTTGGTTCCTGCATAGGATGACAA
TGTCGCCCCAAGACCATCTCTATGAGCTGAAAAAGAAA
CACAAGGAATGTAGTGGCGGAAAAGGAGATAGCAAAT
GCTTACGATAACGTAAGGAATTATTACTATGTAAACAC
CAGGCAAGATTCTGTTCCGTATAATTACTCCTGATAATT
AATCCTTAACTTTGCCCACCTGCCTTTTAAAACATTCCA
GTATATCACTTTTCATTCTTGCGTAGCAATATGCCCTCT
CTTCAGCTATCTCAGCATTGGTGACCTTGTTCAGAGGC
GCTGAGAGATGGCCTTTTTCTGATAGATAATGTTCTGT
TAAAATATCTCCGGCCTCATCTTTTGCCCGCAGGCTAA
TGTCTGAAAATTGAGGTGACGGGTTAAAAATAATATCC
TTGGCAACCTTTTTTATATCCCTTTTAAATTTTGGCTTA
ATGACTATATCCAATGAGTCAAAAAGCTCCCCTTCAAT
ATCTGTTGCCCCTAAGACCTTTAATATATCGCCAAATA
CAGGTAGCTTGGCTTCTACCTTCACCGTTGTTCTGCCG
ATGAAATGCTAATGCATAACATCGTCTTTGGTGGTTCC
CCTCATCAGTGGCTCTATCTGAACGCGCTCTCCACTG
CTTAATGACATTCCTTTCCCGATTAAAAAATCTGTCAGA
TCGGATGTGGTCGGCCCGAAAACAGTTCTGGCAAAAC
CAATGGTGTCGCCTTCAACAAACAAAAAAGATGGGAAT
CCCAATGATTCGTCATCTGCGAGGCTGTTCTTAATATC
TTCAACTGTAGCTTTAGAGCGATTTATCTTCTGAACCA
GACTCTTGTCATTTGTTTTGGTAAAGAGAAAAGTTTTTC
CATCGATTTTATGAATATACAAATAATTGGAGCCAACCT
TCAGGTGATGATTATCAGCCAGCAGAGAATTAAGGAAA
ACAGACAGGTTTATTGAGCACTTATCTTTCCCTTTATTT
```

TABLE 4-continued

Transfer plasmids for the production of dual hybrid vector systems

| SEQ ID NO. | Description | Plasmid Sequence |
|---|---|---|
| | | TTGCTGCGGTAAGTCGCATAAAAACCATTCTTCACAAT |
| | | TCAATCCATTTACTATGTTATGTTCTGAGGGGAGTGAA |
| | | AATTCCCCTAATTCGATGAAGATTCTTGCTAAATTGTTA |
| | | TCAGCTATGCGCCGACCAGAACACCTTGCCGATCAGC |
| | | CAAACGTCTAATCAGGCCACTGACTAGCGATAACTTTC |
| | | CCCACAACGGAACAACTCTCATTGCATGGGATAATTGG |
| | | GTACTGTGGGTTTAGTGGTTGTAAAAACACCTGACCGC |
| | | TATCCCTGATCAGTTTCTTGAAGGTAAACTCATCACCC |
| | | CCAAGTCTGGCTATACAGAAATCACCTGGCTCAACAG |
| | | CCTGCTCAGGGTCAACGAGAATTTACATTCCGTCAGG |
| | | ATAGCTTGGCTTGGAGCCTGTTGGTGCGGTCACGGAA |
| | | TTACCTTCAACCTCAAGCCAGAATGCAGAATCACTGGC |
| | | TTTTTTGGTTGTGCTTACCCATCTCTCCGCATCACCTTT |
| | | GGTAAAGGTTCTAAGCTAAGGTGAGAACATCCCTGCC |
| | | TGAACATGAGAAAAAACAGGGTACTCATACTCACTTAT |
| | | TAGTGACGGCTATGAGCAAAAGGCCAGCAAAAGGCCA |
| | | GGAACCGTAAAAAGGCCGCGTTGCTGGCGTTTTTCCA |
| | | TAGGCTCCGCCCCCCTGACGAGCATCACAAAAATCGA |
| | | CGCTCAAGTCAGAGGTGGCGAAACCCGACAGGACTAT |
| | | AAAGATACCAGGCGTTTCCCCCTGGAAGCTCCCTCGT |
| | | GCGCTCTCCTGTTCCGACCCTGCCGCTTACCGGATAC |
| | | CTGTCCGCCTTTCTCCCTTCGGGAAGCGTGGCGCTTT |
| | | CTCATAGCTCACGCTGTAGGTATCTCAGTTCGGTGTAG |
| | | GTCGTTCGCTCCAAGCTGGGCTGTGTGCACGAACCCC |
| | | CCGTTCAGCCCGACCGCTGCGCCTTATCCGGTAACTA |
| | | TCGTCTTGAGTCCAACCCGGTAAGACACGACTTATCG |
| | | CCACTGGCAGCAGCCACTGGTAACAGGATTAGCAGAG |
| | | CGAGGTATGTAGGCGGTGCTACAGAGTTCTTGAAGTG |
| | | GTGGCCTAACTACGGCTACACTAGAAGAACAGTATTTG |
| | | GTATCTGCGCTCTGCTGAAGCCAGTTACCTTCGGAAAA |
| | | AGAGTTGGTAGCTCTTGATCCGGCAAACAAACCACCG |
| | | CTGGTAGCGGTGGTTTTTTTGTTTGCAAGCAGCAGATT |
| | | ACGCGCAGAAAAAAAGGATCTCAAGAAGATCCTTTGAT |
| | | CTTTTCTACGGGGTCTGACGCTCAGTGGAACGAAAAC |
| | | TCACGTTAAGGGATTTTGGTCATGAGATTATCAAAAAG |
| | | GATCTTCACCTAGATCCTTTTAAATTAAAAATGAAGTTT |
| | | TAAATCAAGCCCAATCTGAATAATGTTACAACCAATTAA |
| | | CCAATTCTGATTAGAAAAACTCATCGAGCATCAAATGA |
| | | AACTGCAATTTATTCATATCAGGATTATCAATACCATAT |
| | | TTTTGAAAAAGCCGTTTCTGTAATGAAGGAGAAAACTC |
| | | ACCGAGGCAGTTCCATAGGATGGCAAGATCCTGGTAT |
| | | CGGTCTGCGATTCCGACTCGTCCAACATCAATACAACC |
| | | TATTAATTTCCCCTCGTCAAAAATAAGGTTATCAAGTGA |
| | | GAAATCACCATGAGTGACGACTGAATCCGGTGAGAAT |
| | | GGCAAAAGTTTATGCATTTCTTTCCAGACTTGTTCAACA |
| | | GGCCAGCCATTACGCTCGTCATCAAAATCACTCGCATC |
| | | AACCAAACCGTTATTCATTCGTGATTGCGCCTGAGCAA |
| | | GACGAAATACGCGATCGCTGTTAAAAGGACAATTACAA |
| | | ACAGGAATCGAATGCAACCGGCGCAGGAACACTGCCA |
| | | GCGCATCAACAATATTTTCACCTGAATCAGGATATTCTT |
| | | CTAATACCTGGAATGCTGTTTTTTCCGGGGATCGCAGTG |
| | | GTGAGTAACCATGCATCATCAGGAGTACGGATAAAATG |
| | | CTTGATGGTCGGAAGAGGCATAAAATTCCGTCAGCCAG |
| | | TTTAGTCTGACCATCTCATCTGTAACATCATTGGCAAC |
| | | GCTACCTTTGCCATGTTTCAGAAACAACTCTGGCGCAT |
| | | CGGGCTTCCCATACAAGCGATAGATTGTCGCACCTGA |
| | | TTGCCCGACATTATCGCGAGCCCATTTATACCCATATA |
| | | AATCAGCATCCATGTTGGAATTTAATCGCGGCCTCGAC |
| | | GTTTCCCGTTGAATATGGCTCATAACACCCCTTGTATT |
| | | ACTGTTTATGTAAGCAGACAGTTTTATTGTTCATGATGA |
| | | TATATTTTTATCTTGTGCAATGTAACATCAGAGATTTTG |
| | | AGACACGGGCCAGAGCTGCA |
| 61 | 3' transgene plasmid containing the following features: Lambda at positions 53-2027 ITR at positions 2049-2178 AP head sequence at positions 2267-2553 Splice acceptor sequence at positions 2576-2624 C-terminal portion of human OTOF isoform 5 at positions 2625-6212 | TCGCGCGTTTCGGTGATGACGGTGAAAACCTCTGACA CATGCAGCTCCCGGATAGAGGGTCATCCTTCCTGACCA TTTCCATCATTCCAGTCGAACTCACACACAACACCAAA TGCATTTAAGTCGCTTGAAATTGCTATAAGCAGAGCAT GTTGCGCCAGCATGATTAATACAGCATTTAATACAGAG CCGTGTTTATTGAGTCGGTATTCAGAGTCTGACCAGAA ATTATTAATCTGGTGAAGTTATTCCTCTGTCATTACGTC ATGGTCGATTTCAATTTCTATTGATGCTTTCCAGTCGTA ATCAATGATGTATTTTTTGATGTTTGACCTCTGTTCATA TCCTCACAGATAAAAAATCGCCCTCACACTGGAGGGC AAAGAAGATTTCCAATAATCAGAACAAGTCGGCTCCTG |

TABLE 4-continued

Transfer plasmids for the production of dual hybrid vector systems

| SEQ ID NO. Description | Plasmid Sequence |
|---|---|
| bGH poly(A) sequence at positions 6255-6476 ITR at positions 6564-6693 Lambda at positions 6704-8716 Ori at positions 8773-9361 KanR at positions 9539-10,348 Transgene to be transferred into vector in dual vector system at positions 2049-6693 | TTTAGTTACGAGCGACATTGCTCCGTGTATTCACTCGT TGGAATGAATACACAGTGCAGTGTTTATTCTGTTATTTA TGCCAAAAATTAAGGCCACTATCAGGCAGCTTTGTTGT TCTGTTTACCAAGTTCTCTGGCAATCATTGCCGTCGTT CGTATTGCCCATTTATCGACATATTTCCCATCTTCCTAT ACAGGAAACATTTCTTCAGGCTTAACCATGCATTCCGA TTGCAGCTTGCATCCATTGCATCGCTTGAATTGTCCAC ACCATTGATTTTTATCAATAGTCGTAGTTTAACGGATAG TCCTGGTATTGTTCCATCACATCCTGAGGATGCCCTTC GAACTCTTCAAATTCTTCTTCCTAATATCACCTTAAATA GTGGATTGCGGTAGTAAAGATTGTGCCTGTCTTTTAAC CACATCAGGCTCGGTGGTTCTCGTGTACCCCTACAGC GAGAAATCGGATAAACTATTACAACCCCTACAGTTTGT AGAGTATAGAAAATGATCCACTCGTTATTCTCGGACGA GTGTTCAGTAATGAACCTCTGGAGAGAACCATCTATAT GATCGTTATCTGGGTTTGACTTCTGCTTTTAAGCCCAG ATAACTTGCCTGAATATGTTAATGAGAGAATCGGTATT CCTCATGTGTGGCATGTTTTCGTCTTTGCTCTTGCATTT TCACTAGCAATTAATGTGCATCGATTATCAGCTATTGC CAGCGCCAGATATAAGCGATTTAAGCTAAGAAAACGCA TTAAGGTGCAAAACGATAAAGTGCGATCAGTAATTCAA AACCTTACAGGAGAGCAATCTATGGTTTTGTGCTCAGC CCTTAATGAAGGCAGGTAGTATGTGGTTACATCAAAAC AATTCCCATACATTAGTGAGTTGATTGAGCTTGGTGTG TTGAACAAAACTTTTTCCCGATGGAATGGAAAGCATAT ATTATTCCCTATTGAGGATATTTACTGGACTGAATTAGT TGCCAGCTATGATCCATATAATATTGAGATAAAGCCAA GGCCAATATCTAAGTAACTAGATAAGAGGAATCGATTT TCCCTTAATTTTCTGGCGTCCACTGCATGTTATGCCGC GTTCGCCAGGCTTGCTGTACCATGTGCGCTGATTCTT GCGCTCAATACGTTGCAGGTTGCTTTCAATCTGTTTGT GGTATTCAGCCAGCACTGTAAGGTCTATCGGATTTAGT GCGCTTTCTACTCGTGATTTCGGTTTGCGATTCAGCGA GAGAATAGGGCGGTTAACTGGTTTTGCGCTTACCCCA ACCAACAGGGGATTTGCTGCTTTCCATTGAGCCTGTTA CTCTGCGCGACGTTCGCGGCGGCGTGTTTGTGCATCC ATCTGGATTCTCCTGTCAGTTAGCTTTGGTGGTGTGTG GCAGTTGTAGTCCTGAACGAAAACCCCCCGCGATTGG CACGTTGGCAGCTAATCCGGAATCGCACTTACGGCCA ATGCTTCGTTTCGTATCACACACCCCAAAGCCTTCTGC TTTGAATGCTGCCCTTCTTCAGGGCTTAATTTTTAAGA GCGTCACCTTCATGGTGGTCAGTGCGTCCTGCTGATG TGCTCAGGCACGATTTAATTAAGGCCTTAATTAGGCTG CGCGCTCGCTCGCTCACTGAGGCCGCCCGGGCAAAG CCCGGGCGTCGGGCGACCTTTGGTCGCCCGGCCTCA GTGAGCGAGCGAGCGCGCAGAGAGGGAGTGGCCAAC TCCATCACTAGGGGTTCCTTGTAGTTAATGATTAACCC GCCATGCTACTTATCTACGTAGCCATGCTCTAGGAAGA TCGGAATTCGCCCTTAAGCTAGCGGCGCGCCCCCCG GGTGCGCGGCGTCGGTGGTGCCGGCGGGGGGCGCC AGGTCGCAGGCGGTGTAGGGCTCCAGGCAGGCGGCG AAGGCCATGACGTGCGCTATGAAGGTCTGCTCCTGCA CGCCGTGAACCAGGTGCGCCTGCGGGCCGCGCGCGA ACACCGCCACGTCCTCGCCTGCGTGGGTCTCTTCGTC CAGGGGCACTGCTGACTGCTGCCGATACTCGGGGCT CCCGCTCTCGCTCTCGGTAACATCCGGCCGGGCGCC GTCCTTGAGCACATAGCCTGGACCGTTTCCTTAAGCG ACGCATGCTCGCGATAGGCACCTATTGGTCTTACTGA CATCCACTTTGCCTTTCTCTCCACAGGAAAACATGGGG CAGCAGGCCAGGATGCTGCGGGCCCAGGTGAAGCGG CACACGGTGCGGGACAAGCTGAGGCTGTGCCAGAAC TTCCTGCAGAAGCTGCGCTTCCTGGCGGACGAGCCCC AGCACAGCATTCCCGACATCTTCATCTGGATGATGAGC AACAACAAGCGTGTCGCCTATGCCCGTGTGCCCTCCA AGGACCTGCTCTTCTCCATCGTGGGAGGAGGAGACTGG CAAGGACTGCGCCAAGGTCAAGACGCTCTTCCTTAAG CTGCCCAGGGAAGCGGGGCTTCGGCTCGGCAGGCTGG ACAGTGCAGGCCAAGGTGGAGCTGTACCTGTGGCTG GGCCTCAGCAAACAGCGCAAGGAGTTCCTGTGCGGC CTGCCCTGTGGCTTCCAGGAGGTCAAGGCAGCCCAG GGCCTGGGCCTGCATGCCTTCCCACCCGTCAGCCTG GTCTACACCAAGAAGCAGGCGTTCCAGCTCCGAGCGC ACATGTACCAGGCCCGCAGCCTCTTTGCCGCCGACAG CAGCGGACTCTCAGACCCCTTTGCCCGCGTCTTCTTC |

TABLE 4-continued

Transfer plasmids for the production of dual hybrid vector systems

| SEQ ID NO. | Description | Plasmid Sequence |
|---|---|---|
| | | ATCAATCAGAGTCAGTGCACAGAGGTGCTGAATGAGA |
| | | CCCTGTGTCCCACCTGGGACCAGATGCTGGTGTTCGA |
| | | CAACCTGGAGCTCTATGGTGAAGCTCATGAGCTGAGG |
| | | GACGATCCGCCCATCATTGTCATTGAAATCTATGACCA |
| | | GGATTCCATGGGCAAAGCTGACTTCATGGGCCGGACC |
| | | TTCGCCAAACCCCTGGTGAAGATGGCAGACGAGGCGT |
| | | ACTGCCCACCCCGCTTCCCACCTCAGCTCGAGTACTA |
| | | CCAGATCTACCGTGGCAACGCCACAGCTGGAGACCTG |
| | | CTGGCGGCCTTCGAGCTGCTGCAGATTGGACCAGCAG |
| | | GGAAGGCTGACCTGCCCCCCATCAATGGCCCGGTGG |
| | | ACGTGGACCGAGGTCCCATCATGCCCGTGCCCATGG |
| | | GCATCCGGCCCGTGCTCAGCAAGTACCGAGTGGAGG |
| | | TGCTGTTCTGGGGCCTACGGGACCTAAAGCGGGTGAA |
| | | CCTGGCCCAGGTGGACCGGCCACGGGTGGACATCGA |
| | | GTGTGCAGGGAAGGGGGTGCAGTCGTCCCTGATCCA |
| | | CAATTATAAGAAGAACCCCAACTTCAACACCCTCGTCA |
| | | AGTGGTTTGAAGTGGACCTCCCAGAGAACGAGCTGCT |
| | | GCACCCGCCCTTGAACATCCGTGTGGTGGACTGCCGG |
| | | GCCTTCGGTCGCTACACACTGGTGGGCTCCCATGCCG |
| | | TCAGCTCCCTGCGACGCTTCATCTACCGGCCCCCAGA |
| | | CCGCTCGGCCCCCAGCTGGAACACCACGGTCAGGCT |
| | | TCTCCGGCGCTGCCGTGTGCTGTGCAATGGGGGCTC |
| | | CTCCTCTCACTCCACAGGGGAGGTTGTGGTGACTATG |
| | | GAGCCAGAGGTACCCATCAAGAAACTGGAGACCATGG |
| | | TGAAGCTGGACGCGACTTCTGAAGCTGTTGTCAAGGT |
| | | GGATGTGGCTGAGGAGGAGAAGGAGAAGAAGAAGAA |
| | | GAAGAAGGGCACTGCGGAGGAGCCAGAGGAGGAGGA |
| | | GCCAGACGAGAGCATGCTGGACTGGTGGTCCAAGTAC |
| | | TTTGCCTCCATTGACACCATGAAGGAGCAACTTCGACA |
| | | ACAAGAGCCCTCTGGAATTGACTTGGAGGAGAAGGAG |
| | | GAAGTGGACAATACCGAGGGCCTGAAGGGGTCAATGA |
| | | AGGGCAAGGAGAAGGCAAGGGCTGCCAAAGAGGAGA |
| | | AGAAGAAGAAAACTCAGAGCTCTGGCTCTGGCCAGGG |
| | | GTCCGAGGCCCCCGAGAAGAAGAAACCCAAGATTGAT |
| | | GAGCTTAAGGTATACCCCAAAGAGCTGGAGTCCGAGT |
| | | TTGATAACTTTGAGGACTGGCTGCACACTTTCAACTTG |
| | | CTTCGGGGCAAGACCGGGGATGATGAGGATGGCTCC |
| | | ACCGAGGAGGAGCGCATTGTGGGACGCTTCAAGGGC |
| | | TCCCTCTGCGTGTACAAAGTGCCACTCCCAGAGGACG |
| | | TGTCCCGGGAAGCCGGCTACGACTCCACCTACGGCAT |
| | | GTTCCAGGGCATCCCGAGCAATGACCCCATCAATGTG |
| | | CTGGTCCGAGTCTATGTGGTCCGGGCCACGGACCTGC |
| | | ACCCTGCTGACATCAACGGCAAAGCTGACCCCTACAT |
| | | CGCCATCCGGCTAGGCAAGACTGACATCCGCGACAAG |
| | | GAGAACTACATCTCCAAGCAGCTCAACCCTGTCTTTGG |
| | | GAAGTCCTTTGACATCGAGGCCTCCTTCCCCATGGAAT |
| | | CCATGCTGACGGTGGCTGTGTATGACTGGGACCTGGT |
| | | GGGCACTGATGACCTCATTGGGGAAACCAAGATCGAC |
| | | CTGGAGAACCGCTTCTACAGCAAGCACCGCGCCACCT |
| | | GCGGCATCGCCCAGACCTACTCCACACATGGCTACAA |
| | | TATCTGGCGGGACCCCATGAAGCCCAGCCAGATCCTG |
| | | ACCCGCCTCTGCAAAGACGGCAAAGTGGACGGCCCC |
| | | CACTTTGGGCCCCCTGGGAGAGTGAAGGTGGCCAAC |
| | | CGCGTCTTCACTGGGCCCTCTGAGATTGAGGACGAGA |
| | | ACGGTCAGAGGAAGCCCACAGACGAGCATGTGGCGC |
| | | TGTTGGCCCTGAGGCACTGGGAGGACATCCCCCGCG |
| | | CAGGCTGCCGCCTGGTGCCAGAGCATGTGGAGACGA |
| | | GGCCGCTGCTCAACCCCGACAAGCCGGGCATCGAGC |
| | | AGGGCCGCCTGGAGCTGTGGGTGGACATGTTCCCCAT |
| | | GGACATGCCAGCCCCTGGGACGCCTCTGGACATCTCA |
| | | CCTCGGAAGCCCAAGAAGTACGAGCTGCGGGTCATCA |
| | | TCTGGAACACAGATGAGGTGGTCTTGGAGGACGACGA |
| | | CTTCTTCACAGGGGAGAAGTCCAGTGACATCTTCGTG |
| | | AGGGGGTGGCTGAAGGGCCAGCAGGAGGACAAGCAG |
| | | GACACAGACGTCCACTACCACTCCCTCACTGGCGAGG |
| | | GCAACTTCAACTGGCGCTACCTGTTCCCCTTCGACTAC |
| | | CTGGCGGCGGAGGAGAAGATCGTCATCTCCAAGAAG |
| | | GAGTCCATGTTCTCCTGGGACGAGACCGAGTACAAGA |
| | | TCCCCGCGCGGCTCACCCTGCAGATCTGGGATGCGG |
| | | ACCACTTCTCCGCTGACGACTTCCTGGGGGCCATCGA |
| | | GCTGGACCTGAACCGGTTCCCGCGGGGCGCAAAGAC |
| | | AGCCAAGCAGTGCACCATGGAGATGGCCACCGGGGA |
| | | GGTGGACGTGCCCCTCGTGTCCATCTTCAAGCAAAAG |
| | | CGCGTCAAAGGCTGGTGGCCCCTCCTGGCCCGCAAT |

TABLE 4-continued

Transfer plasmids for the production of dual hybrid vector systems

SEQ
ID
NO. Description                    Plasmid Sequence

GAGAACGATGAGTTTGAGCTCACGGGCAAGGTGGAG
GCTGAGCTGCATTTACTGACAGCAGAGGAGGCAGAGA
AGAACCCAGTGGGCCTGGCCCGCAATGAACCTGACCC
CCTAGAGAAACCCAACCGGCCCGACACGGCCTTCGTC
TGGTTCCTCAACCCTCTCAAGTCCATCAAGTACCTCAT
CTGCACCCGGTACAAGTGGCTCATCATCAAGATCGTG
CTGGCGCTGTTGGGGCTGCTCATGTTGGGGCTCTTCC
TCTACAGCCTCCCTGGCTACATGGTCAAAAAGCTCCTT
GGGGCATGAACGGCCGCTATGCTAGCTTGGTACCAAG
GGCGGATCCTGCATAGAGCTCGCTGATCAGCCTCGAC
TGTGCCTTCTAGTTGCCAGCCATCTGTTGTTTGCCCCT
CCCCCGTGCCTTCCTTGACCCTGGAAGGTGCCACTCC
CACTGTCCTTTCCTAATAAAATGAGGAAATTGCATCGC
ATTGTCTGAGTAGGTGTCATTCTATTCTGGGGGGTGG
GGTGGGGCAGGACAGCAAGGGGGAGGATTGGGAAGA
CAATAGCAGGCATCTCGAGTTAAGGGCGAATTCCCGA
TAAGGATCTTCCTAGAGCATGGCTACGTAGATAAGTAG
CATGGCGGGTTAATCATTAACTACAAGGAACCCCTAGT
GATGGAGTTGGCCACTCCCTCTCTGCGCGCTCGCTCG
CTCACTGAGGCCGGGCGACCAAAGGTCGCCCGACGC
CCGGGCTTTGCCCGGGCGGCCTCAGTGAGCGAGCGA
GCGCGCAGCCTTAATTAAATCCACATCTGTATGTTTTTT
ATATTAATTTATTTTTTGCAGGGGGGCATTGTTTGGTAG
GTGAGAGTTCTGAATTGCTATGTTTAGTGAGTTGTATC
TATTTATTTTTCAATAAATACAATTAGTTATGTGTTTTGG
GGGCGATCGTGAGGCAAAGAAAACCCGGCGCTGAGG
CCGGGTTATTCTTGTTCTCTGGTCAAATTATATAGTTG
GAAAACAAGGATGCATATATGAATGAACGATGCAGAG
GCAATGCCGATGGCGATAGTGGGTATCAGGTAGCCGC
TTATGCTGGAAAGAAGCAATAACCCGCAGAAAAACAAA
GCTCCAAGCTCAACAAAACTAAGGGCATAGACAATAAC
TACCTATGTCATATACCCATACTCTCTAATCTTGGCCA
GTCGGCGCGTTCTGCTTCCGATTAGAAACGTCAAGGC
AGCAATCAGGATTGCAATCTTGGTTCCTGCATAGGATG
ACAATGTCGCCCCAAGACCATCTCTATGAGCTGAAAAA
GAAACACAAGGAATGTAGTGGCGGAAAAGGAGATAGC
AAATGCTTACGATAACGTAAGGAATTATTACTATGTAAA
CACCAGGCAAGATTCTGTTCCGTATAATTACTCCTGAT
AATTAATCCTTAACTTTGCCCACCTGCCTTTTAAAACAT
TCCAGTATATCACTTTTCATTCTTGCGTAGCAATATGCC
CTCTCTTCAGCTATCTCAGCATTGGTGACCTTGTTCAG
AGGCGCTGAGAGATGGCCTTTTTCTGATAGATAATGTT
CTGTTAAAATATCTCCGGCCTCATCTTTTGCCCGCAGG
CTAATGTCTGAAAATTGAGGTGACGGGTTAAAAATAAT
ATCCTTGGCAACCTTTTTTATATCCCTTTTAAATTTTGG
CTTAATGACTATATCCAATGAGTCAAAAAGCTCCCCTT
CAATATCTGTTGCCCCTAAGACCTTTAATATATCGCCA
AATACAGGTAGCTTGGCTTCTACCTTCACCGTTGTTCT
GCCGATGAAATGCTAATGCATAACATCGTCTTTGGTGG
TTCCCCTCATCAGTGGCTCTATCTGAACGCGCTCTCCA
CTGCTTAATGACATTCCTTTCCCGATTAAAAAATCTGTC
AGATCGGATGTGGTCGGCCCGAAAACAGTTCTGGCAA
AACCAATGGTGTCGCCTTCAACAAACAAAAAAGATGGG
AATCCCAATGATTCGTCATCTGCGAGGCTGTTCTTAAT
ATCTTCAACTGTAGCTTTAGAGCGATTTATCTTCTGAAC
CAGACTCTTGTCATTTGTTTTGGTAAAGAGAAAAGTTTT
TCCATCGATTTTATGAATATACAAATAATTGGAGCCAAC
CTTCAGGTGATGATTATCAGCCAGCAGAGAATTAAGGA
AAACAGACAGGTTTATTGAGCACTTATCTTTCCCTTTAT
TTTTGCTGCGGTAAGTCGCATAAAAACCATTCTTCACA
ATTCAATCCATTTACTATGTTATGTTCTGAGGGGAGTG
AAAATTCCCCTAATTCGATGAAGATTCTTGCTAAATTGT
TATCAGCTATGCGCCGACCAGAACACCTTGCCGATCA
GCCAAACGTCTAATCAGGCCACTGACTAGCGATAACTT
TCCCCACAACGGAACAACTCTCATTGCATGGGATAATT
GGGTACTGTGGGTTTAGTGGTTGTAAAAACACCTGAC
CGCTATCCCTGATCAGTTTCTTGAAGGTAAACTCATCA
CCCCCAAGTCTGGCTATACAGAAATCACCTGGCTCAA
CAGCCTGCTCAGGGTCAACGAGAATTTACATTCCGTCA
GGATAGCTTGGCTTGGAGCCTGTTGGTGCGGTCACGG
AATTACCTTCAACCTCAAGCCAGAATGCAGAATCACTG
GCTTTTTTGGTTGTGCTTACCCATCTCTCCGCATCACC
TTTGGTAAAGGTTCTAAGCTAAGGTGAGAACATCCCTG
CCTGAACATGAGAAAAAACAGGGTACTCATACTCACTT

TABLE 4-continued

Transfer plasmids for the production of dual hybrid vector systems

| SEQ ID NO. | Description | Plasmid Sequence |
|---|---|---|

| | | ATTAGTGACGGCTATGAGCAAAAGGCCAGCAAAAGGC |
| | | CAGGAACCGTAAAAAGGCCGCGTTGCTGGCGTTTTTC |
| | | CATAGGCTCCGCCCCCCTGACGAGCATCACAAAAATC |
| | | GACGCTCAAGTCAGAGGTGGCGAAACCCGACAGGACT |
| | | ATAAAGATACCAGGCGTTTCCCCCTGGAAGCTCCCTC |
| | | GTGCGCTCTCCTGTTCCGACCCTGCCGCTTACCGGAT |
| | | ACCTGTCCGCCTTTCTCCCTTCGGGAAGCGTGGCGCT |
| | | TTCTCATAGCTCACGCTGTAGGTATCTCAGTTCGGTGT |
| | | AGGTCGTTCGCTCCAAGCTGGGCTGTGTGCACGAACC |
| | | CCCCGTTCAGCCCGACCGCTGCGCCTTATCCGGTAAC |
| | | TATCGTCTTGAGTCCAACCCGGTAAGACACGACTTATC |
| | | GCCACTGGCAGCAGCCACTGGTAACAGGATTAGCAGA |
| | | GCGAGGTATGTAGGCGGTGCTACAGAGTTCTTGAAGT |
| | | GGTGGCCTAACTACGGCTACACTAGAAGAACAGTATTT |
| | | GGTATCTGCGCTCTGCTGAAGCCAGTTACCTTCGGAA |
| | | AAAGAGTTGGTAGCTCTTGATCCGGCAAACAAACCAC |
| | | CGCTGGTAGCGGTGGTTTTTTTGTTTGCAAGCAGCAG |
| | | ATTACGCGCAGAAAAAAAGGATCTCAAGAAGATCCTTT |
| | | GATCTTTTCTACGGGGTCTGACGCTCAGTGGAACGAA |
| | | AACTCACGTTAAGGGATTTTGGTCATGAGATTATCAAA |
| | | AAGGATCTTCACCTAGATCCTTTTAAATTAAAAATGAAG |
| | | TTTTAAATCAAGCCCAATCTGAATAATGTTACAACCAAT |
| | | TAACCAATTCTGATTAGAAAAACTCATCGAGCATCAAAT |
| | | GAAACTGCAATTTATTCATATCAGGATTATCAATACCAT |
| | | ATTTTTGAAAAAGCCGTTTCTGTAATGAAGGAGAAAAC |
| | | TCACCGAGGCAGTTCCATAGGATGGCAAGATCCTGGT |
| | | ATCGGTCTGCGATTCCGACTCGTCCAACATCAATACAA |
| | | CCTATTAATTTCCCCTCGTCAAAAATAAGGTTATCAAGT |
| | | GAGAAATCACCATGAGTGACGACTGAATCCGGTGAGA |
| | | ATGGCAAAAGTTTATGCATTTCTTTCCAGACTTGTTCAA |
| | | CAGGCCAGCCATTACGCTCGTCATCAAAATCACTCGC |
| | | ATCAACCAAACCGTTATTCATTCGTGATTGCGCCTGAG |
| | | CAAGACGAAATACGCGATCGCTGTTAAAAGGACAATTA |
| | | CAAACAGGAATCGAATGCAACCGGCGCAGGAACACTG |
| | | CCAGCGCATCAACAATATTTTCACCTGAATCAGGATAT |
| | | TCTTCTAATACCTGGAATGCTGTTTTTCCGGGGATCGC |
| | | AGTGGTGAGTAACCATGCATCATCAGGAGTACGGATA |
| | | AAATGCTTGATGGTCGGAAGAGGCATAAATTCCGTCA |
| | | GCCAGTTTAGTCTGACCATCTCATCTGTAACATCATTG |
| | | GCAACGCTACCTTTGCCATGTTTCAGAAACAACTCTGG |
| | | CGCATCGGGCTTCCCATACAAGCGATAGATTGTCGCA |
| | | CCTGATTGCCCGACATTATCGCGAGCCCATTTATACCC |
| | | ATATAAATCAGCATCCATGTTGGAATTTAATCGCGGCC |
| | | TCGACGTTTCCCGTTGAATATGGCTCATAACACCCCTT |
| | | GTATTACTGTTTATGTAAGCAGACAGTTTTATTGTTCAT |
| | | GATGATATATTTTTATCTTGTGCAATGTAACATCAGAGA |
| | | TTTTGAGACACGGGCCAGAGCTGCA |

| 62 | 5' transgene plasmid containing the following features: ITR at positions 19-161 Myo15 promoter at positions 182-1146 N-terminal portion of human OTOF isoform 5 at positions 1167-3572 Splice donor sequence at positions 3573-3656 AP head sequence at positions 3663-3949 ITR at positions 3973-4115 Kan R at positions 4641-5435 pUC ori at positions 5821-6491 Transgene to be transferred into vector in dual vector system at positions 19-4115 | GGGGGGGGGGGGGGGGGGGTTGGCCACTCCCTCTCT GCGCGCTCGCTCGCTCACTGAGGCCGGGCGACCAAA GGTCGCCCGACGCCCGGGCTTTGCCCGGGCGGCCTC AGTGAGCGAGCGAGCGCGCAGAGAGGGAGTGGCCAA CTCCATCACTAGGGGTTCCTCAGATCTGAATTCGGTAC CTGCAGCTCAGCCTACTACTTGCTTTCCAGGCTGTTCC TAGTTCCCATGTCAGCTGCTTGTGCTTTCCAGAGACAA AACAGGAATAATAGATGTCATTAAATATACATTGGGCC CCAGGCGGTCAATGTGGCAGCCTGAGCCTCCTTTCCA TCTCTGTGGAGGCAGACATAGGACCCCCAACAAACAG CATGCAGGTTGGGAGCCAGCCACAGGACCCAGGTAA GGGGCCCTGGGTCCTTAAGCTTCTGCCACTGGCTCCG GCATTGCAGAGAGAAGAGAAGGGGCGGCAGACTGGA GAGCTGGGCTCCATTTTTGTTCCTTGGTGCCCTGCCC CTCCCCATGACCTGCAGAGACATTCAGCCTGCCAGGC TTTATGAGGTGGGAGCTGGGCTCTCCCTGATGTATTAT TCAGCTCCCTGGAGTTGGCCAGCTCCTGTTACACTGG CCACAGCCCTGGGCATCCGCTTCTCACTTCTAGTTTCC CCTCCAAGGTAATGTGGTGGGTCATGATCATTCTATCC TGGCTTCAGGGACCTGACTCCACTTTGGGGCCATTCG AGGGGTCTAGGGTAGATGATGTCCCCCTGTGGGGATT AATGTCCTGCTCTGTAAAACTGAGCTAGCTGAGATCCA GGAGGGCTTGGCCAGAGACAGCAAGTTGTTGCCATGG TGACTTTAAAGCCAGGTTGCTGCCCCAGCACAGGCCT CCCAGTCTACCCTCACTAGAAAACAACACCCAGGCAC TTTCCACCACCTCTCAAAGGTGAAACCCAAGGCTGGT |

TABLE 4-continued

Transfer plasmids for the production of dual hybrid vector systems

| SEQ ID NO. Description | Plasmid Sequence |
|---|---|
| | CTAGAGAATGAATTATGGATCCTCGCTGTCCGTGCCAC |
| | CCAGCTAGTCCCAGCGGCTCAGACACTGAGGAGAGAC |
| | TGTAGGTTCAGCTACAAGCAAAAAGACCTAGCTGGTCT |
| | CCAAGCAGTGTCTCCAAGTCCCTGAACCTGTGACACC |
| | TGCCCCAGGCATCATCAGGCACAGAGGGCCACCGAAT |
| | TCTAGCGGCCGCCACCATGGCCTTGCTCATCCACCTC |
| | AAGACAGTCTCGGAGCTGCGGGGCAGGGGCGACCGG |
| | ATCGCCAAAGTGACTTTCCGAGGGCAATCCTTCTACTC |
| | TCGGGTCCTGGAGAACTGTGAGGATGTGGCTGACTTT |
| | GATGAGACATTTCGGTGGCCGGTGGCCAGCAGCATCG |
| | ACAGAAATGAGATGCTGGAGATTCAGGTTTTCAACTAC |
| | AGCAAAGTCTTCAGCAACAAGCTCATCGGGACCTTCC |
| | GCATGGTGCTGCAGAAGGTGGTAGAGGAGAGCCATGT |
| | GGAGGTGACTGACACGCTGATTGATGACAACAATGCT |
| | ATCATCAAGACCAGCCTGTGCGTGGAGGTCCGGTATC |
| | AGGCCACTGACGGCACAGTGGGCTCCTGGGACGATG |
| | GGGACTTCCTGGGAGATGAGTCTCTTCAAGAGGAAGA |
| | GAAGGACAGCCAAGAGACGGATGGACTGCTCCCAGG |
| | CTCCCGGCCCAGCTCCCGGCCCCCAGGAGAGAAGAG |
| | CTTCCGGAGAGCCGGGAGGAGCGTGTTCTCCGCCAT |
| | GAAGCTCGGCAAAAACCGGTCTCACAAGGAGGAGCCC |
| | CAAAGACCAGATGAACCGGCGGTGCTGGAGATGGAA |
| | GACCTTGACCATCTGGCCATTCGGCTAGGAGATGGAC |
| | TGGATCCCGACTCGGTGTCTCTAGCCTCAGTCACAGC |
| | TCTCACCACTAATGTCTCCAACAAGCGATCTAAGCCAG |
| | ACATTAAGATGGAGCCAAGTGCTGGGCGGCCCATGGA |
| | TTACCAGGTCAGCATCACGGTGATCGAGGCCCGGCAG |
| | CTGGTGGGCTTGAACATGGACCCTGTGGTGTGCGTGG |
| | AGGTGGGTGACGACAAGAAGTACACATCCATGAAGGA |
| | GTCCACTAACTGCCCCTATTACAACGAGTACTTCGTCT |
| | TCGACTTCCATGTCTCTCCGGATGTCATGTTTGACAAG |
| | ATCATCAAGATTTCGGTGATTCACTCCAAGAACCTGCT |
| | GCGCAGTGGCACCCTGGTGGGCTCCTTCAAAATGGAC |
| | GTGGGAACCGTGTACTCGCAGCCAGAGCACCAGTTCC |
| | ATCACAAGTGGGCCATCCTGTCTGACCCCGATGACAT |
| | CTCCTCGGGGCTGAAGGGCTACGTGAAGTGTGACGTT |
| | GCCGTGGTGGGCAAAGGGGACAACATCAAGACGCCC |
| | CACAAGGCCAATGAGACCGACGAAGATGACATTGAGG |
| | GGAACTTGCTGCTCCCCGAGGGGGTGCCCCCCGAAC |
| | GCCAGTGGGCCCGGTTCTATGTGAAAATTTACCGAGC |
| | AGAGGGGCTGCCCCGTATGAACACAAGCCTCATGGCC |
| | AATGTAAAGAAGGCTTTCATCGGTGAAAACAAGGACCT |
| | CGTGGACCCCTACGTGCAAGTCTTCTTTGCTGGCCAG |
| | AAGGGCAAGACTTCAGTGCAGAAGAGCAGCTATGAGC |
| | CCCTGTGGAATGAGCAGGTCGTCTTTACAGACCTCTTC |
| | CCCCCACTCTGCAAACGCATGAAGGTGCAGATCCGAG |
| | ACTCGGACAAGGTCAACGACGTGGCCATCGGCACCCA |
| | CTTCATTGACCTGCGCAAGATTTCTAATGACGGAGACA |
| | AAGGCTTCCTGCCCACACTGGGCCCAGCCTGGGTGAA |
| | CATGTACGGCTCCACACGTAACTACACGCTGCTGGAT |
| | GAGCATCAGGACCTGAACGAGGGCCTGGGGGAGGGT |
| | GTGTCCTTCCGGGCCCGGCTCCTGCTGGGCCTGGCT |
| | GTGGAGATCGTAGACACCTCCAACCCTGAGCTCACCA |
| | GCTCCACAGAGGTGCAGGTGGAGCAGGCCACGCCCA |
| | TCTCGGAGAGCTGTGCAGGTAAAATGGAAGAATTCTTT |
| | CTCTTTGGAGCCTTCCTGGAGGCCTCAATGATCGACC |
| | GGAGAAACGGAGACAAGCCCATCACCTTTGAGGTCAC |
| | CATAGGCAACTATGGGAACGAAGTTGATGGCCTGTCC |
| | CGGCCCCAGCGGCCTCGGCCCCGGAAGGAGCCGGG |
| | GGATGAGGAAGAAGTAGACCTGATTCAGAACGCAAGT |
| | GATGACGAGGCCGGTGATGCCGGGGACCTGGCCTCA |
| | GTCTCCTCCACTCCACCAATGCGGCCCCAGGTCACCG |
| | ACAGGAACTACTTCCATCTGCCCTACCTGGAGCGAAA |
| | GCCCTGCATCTACATCAAGAGCTGGTGGCCGGACCAG |
| | CGCCGCCGCCTCTACAATGCCAACATCATGGACCACA |
| | TTGCCGACAAGCTGGAAGAAGGCCTGAACGACATACA |
| | GGAGATGATCAAAACGGAGAAGTCCTACCCTGAGCGT |
| | CGCCTGCGGGGCGTCCTGGAGGAGCTGAGCTGTGGC |
| | TGCTGCCGCTTCCTCTCCCTCGCTGACAAGGACCAGG |
| | GCCACTCATCCCGCACCAGGCTTGACCGGGAGCGCC |
| | TCAAGTCCTGCATGAGGGAGCTGGTAAGTATCAAGGT |
| | TACAAGACAGGTTTAAGGAGACCAATAGAAACTGGGC |
| | TTGTCGAGACAGAGAAGACTCTTGCGTTTCTGAGCTAG |
| | CCCCCGGGTGCGCGGCGTCGGTGGTGCCGGCGGGG |

TABLE 4-continued

Transfer plasmids for the production of dual hybrid vector systems

| SEQ ID NO. Description | Plasmid Sequence |
|---|---|
| | GGCGCCAGGTCGCAGGCGGTGTAGGGCTCCAGGCAG |
| | GCGGCGAAGGCCATGACGTGCGCTATGAAGGTCTGCT |
| | CCTGCACGCCGTGAACCAGGTGCGCCTGCGGGCCGC |
| | GCGCGAACACCGCCACGTCCTCGCCTGCGTGGGTCT |
| | CTTCGTCCAGGGGCACTGCTGACTGCTGCCGATACTC |
| | GGGGCTCCCGCTCTCGCTCTCGGTAACATCCGGCCG |
| | GGCGCCGTCCTTGAGCACATAGCCTGGACCGTTTCGT |
| | CGACTGGGGAGAGATCTGAGGAACCCCTAGTGATGGA |
| | GTTGGCCACTCCCTCTCTGCGCGCTCGCTCGCTCACT |
| | GAGGCCGCCCGGGCAAAGCCCGGGCGTCGGGCGAC |
| | CTTTGGTCGCCCGGCCTCAGTGAGCGAGCGAGCGCG |
| | CAGAGAGGGAGTGGCCAACCCCCCCCCCCCCCCCCC |
| | TGCAGCCTGGCGTAATAGCGAAGAGGCCCGCACCGAT |
| | CGCCCTTCCCAACAGTTGCGTAGCCTGAATGGCGAAT |
| | GGCGCGACGCGCCCTGTAGCGGCGCATTAAGCGCGG |
| | CGGGTGTGGTGGTTACGCGCAGCGTGACCGCTACACT |
| | TGCCAGCGCCCTAGCGCCCGCTCCTTTCGCTTTCTTC |
| | CCTTCCTTTCTCGCCACGTTCGCCGGCTTTCCCCGTCA |
| | AGCTCTAAATCGGGGGCTCCCTTTAGGGTTCCGATTTA |
| | GTGCTTTACGGCACCTCGACCCCAAAAAACTTGATTAG |
| | GGTGATGGTTCACGTAGTGGGCCATCGCCCTGATAGA |
| | CGGTTTTTCGCCCTTTGACGTTGGAGTCCACGTTCTTT |
| | AATAGTGGACTCTTGTTCCAAACTGGAACAACACTCAA |
| | CCCTATCGCGGTCTATTCTTTTGATTTATAAGGGATGTT |
| | GCCGATTTCGGCCTATTGGTTAAAAAATGAGCTGATTT |
| | AACAAAAATTTTAACAAAATTCAGAAGAACTCGTCAAGA |
| | AGGCGATAGAAGGCGATGCGCTGCGAATCGGGAGCG |
| | GCGATACCGTAAAGCACGAGGAAGCGGTCAGCCCATT |
| | CGCCGCCAAGCTCTTCAGCAATATCACGGGTAGCCAA |
| | CGCTATGTCCTGATAGCGGTCCGCCACACCCAGCCGG |
| | CCACAGTCGATGAATCCAGAAAAGCGGCCATTTTCCA |
| | CCATGATATTCGGCAAGCAGGCATCGCCATGGGTCAC |
| | GACGAGATCCTCGCCGTCGGGCATGCTCGCCTTGAGC |
| | CTGGCGAACAGTTCGGCTGGCGCGAGCCCCTGATGC |
| | TCTTCGTCCAGATCATCCTGATCGACAAGACCGGCTTC |
| | CATCCGAGTACGTGCTCGCTCGATGCGATGTTTCGCT |
| | TGGTGGTCGAATGGGCAGGTAGCCGGATCAAGCGTAT |
| | GCAGCCGCCGCATTGCATCAGCCATGATGGATACTTT |
| | CTCGGCAGGAGCAAGGTGAGATGACAGGAGATCCTG |
| | CCCCGGCACTTCGCCCAATAGCAGCCAGTCCCTTCCC |
| | GCTTCAGTGACAACGTCGAGCACAGCTGCGCAAGGAA |
| | CGCCCGTCGTGGCCAGCCACGATAGCCGCGCTGCCT |
| | CGTCTTGCAGTTCATTCAGGGCACCGGACAGGTCGGT |
| | CTTGACAAAAAGAACCGGGCGCCCCTGCGCTGACAGC |
| | CGGAACACGGCGGCATCAGAGCAGCCGATTGTCTGTT |
| | GTGCCCAGTCATAGCCGAATAGCCTCTCCACCCAAGC |
| | GGCCGGAGAACCTGCGTGCAATCCATCTTGTTCAATC |
| | ATGCGAAACGATCCTCATCCTGTCTCTTGATCAGATCT |
| | TGATCCCCTGCGCCATCAGATCCTTGGCGGCGAGAAA |
| | GCCATCCAGTTTACTTTGCAGGGCTTCCCAACCTTACC |
| | AGAGGGCGCCCCAGCTGGCAATTCCGGTTCGCTTGCT |
| | GTCCATAAAACCGCCCAGTCTAGCTATCGCCATGTAAG |
| | CCCACTGCAAGCTACCTGCTTTCTCTTTGCGCTTGCGT |
| | TTTCCCTTGTCCAGATAGCCCAGTAGCTGACATTCATC |
| | CGGGGTCAGCACCGTTTCTGCGGACTGGCTTTCTACG |
| | TGAAAAGGATCTAGGTGAAGATCCTTTTTGATAATCTC |
| | ATGACCAAAATCCCTTAACGTGAGTTTTCGTTCCACTG |
| | AGCGTCAGACCCCGTAGAAAAGATCAAAGGATCTTCTT |
| | GAGATCCTTTTTTTCTGCGCGTAATCTGCTGCTTGCAA |
| | ACAAAAAAACCACCGCTACCAGCGGTGGTTTGTTTGC |
| | CGGATCAAGAGCTACCAACTCTTTTTTCCGAAGGTAACT |
| | GGCTTCAGCAGAGCGCAGATACCAAATACTGTCCTTCT |
| | AGTGTAGCCGTAGTTAGGCCACCACTTCAAGAACTCT |
| | GTAGCACCGCCTACATACCTCGCTCTGCTAATCCTGTT |
| | ACCAGTGGCTGCTGCCAGTGGCGATAAGTCGTGTCTT |
| | ACCGGGTTGGACTCAAGACGATAGTTACCGGATAAGG |
| | CGCAGCGGTCGGGCTGAACGGGGGGTTCGTGCACAC |
| | AGCCCAGCTTGGAGCGAACGACCTACACCGAACTGAG |
| | ATACCTACAGCGTGAGCTATGAGAAAGCGCCACGCTT |
| | CCCGAAGGGAGAAAGGCGGACAGGTATCCGGTAAGC |
| | GGCAGGGTCGGAACAGGAGAGCGCACGAGGGAGCTT |
| | CCAGGGGGAAACGCCTGGTATCTTTATAGTCCTGTCG |
| | GGTTTCGCCACCTCTGACTTGAGCGTCGATTTTTGTGA |
| | TGCTCGTCAGGGGGGCGGAGCCTATGGAAAAACGCC |

TABLE 4-continued

Transfer plasmids for the production of dual hybrid vector systems

| SEQ ID NO. | Description | Plasmid Sequence |
|---|---|---|
| | | AGCAACGCGGCCTTTTTACGGTTCCTGGGCTTTTGCT GGCCTTTTGCTCACATGTTCTTTCCTGCGTTATCCCCT GATTCTGTGGATAACCGTATTACCGCCTTTGAGTGAGC TGATACCGCTCGCCGCAGCCGAACGACCGAGCGCAG CGAGTCAGTGAGCGAGGAAGCGGAAGAGCGCCCAAT ACGCAAACCGCCTCTCCCCGCGCGTTGGCCGATTCAT TAATGCAGGGCTGCA |
| 63 | 3' transgene plasmid containing the following features: ITR at positions 19-161 AP head sequence at positions 187-473 Splice acceptor sequence at positions 496-544 C-terminal portion of human OTOF isoform 5 at positions 545-4132 bGH poly(A) sequence at positions 4175-4396 ITR at positions 4447-4589 KanR at positions 5115-5909 pUC ori at positions 6295-6965 Transgene to be transferred into vector in dual vector system at positions 19-4589 | GGGGGGGGGGGGGGGGGGGTTGGCCACTCCCTCTCT GCGCGCTCGCTCGCTCACTGAGGCCGGGCGACCAAA GGTCGCCCGACGCCCGGGCTTTGCCCGGGCGGCCTC AGTGAGCGAGCGAGCGCGCAGAGAGGGAGTGGCCAA CTCCATCACTAGGGGTTCCTCAGATCTGAATTCTAGCG GCCGCCCCGGGTGCGCGGCGTCGGTGGTGCCGGC GGGGGGCGCCAGGTCGCAGGCGGTGTAGGGCTCCA GGCAGGCGGCGAAGGCCATGACGTGCGCTATGAAGG TCTGCTCCTGCACGCCGTGAACCAGGTGCGCCTGCG GGCCGCGCGCGAACACCGCCACGTCCTCGCCTGCGT GGGTCTCTTCGTCCAGGGGCCACTGCTGACTGCTGCCG ATACTCGGGGCTCCCGCTCTCGCTCTCGGTAACATCC GGCCGGGCGCCGTCCTTGAGCACATAGCCTGGACCG TTTCCTTAAGCGACGCATGCTCGCGATAGGCACCTATT GGTCTTACTGACATCCACTTTGCCTTTCTCTCCACAGG AAAACATGGGGCAGCAGGCCAGGATGCTGCGGGCCC AGGTGAAGCGGCACACGGTGCGGGACAAGCTGAGGC TGTGCCAGAACTTCCTGCAGAAGCTGCGCTTCCTGGC GGACGAGCCCCAGCACAGCATTCCCGACATCTTCATC TGGATGATGAGCAACAACAAGCGTGTCGCCTATGCCC GTGTGCCCTCCAAGGACCTGCTCTTCTCCATCGTGGA GGAGGAGACTGGCAAGGACTGCGCCAAGGTCAAGAC GCTCTTCCTTAAGCTGCCAGGGAAGCGGGGCTTCGGC TCGGCAGGCTGGACAGTGCAGGCCAAGGTGGAGCTG TACCTGTGGCTGGGCCTCAGCAAACAGCGCAAGGAGT TCCTGTGCGGCCTGCCCTGTGGCTTCCAGGAGGTCAA GGCAGCCCAGGGCCTGGGCCTGCATGCCTTCCCACC CGTCAGCCTGGTCTACACCAAGAAGCAGGCGTTCCAG CTCCGAGCGCACATGTACCAGGCCCGCAGCCTCTTTG CCGCCGACAGCAGCGGACTCTCAGACCCCTTTGCCCG CGTCTTCTTCATCAATCAGAGTCAGTGCACAGAGGTGC TGAATGAGACCCTGTGTCCCACCTGGGACCAGATGCT GGTGTTCGACAACCTGGAGCTCTATGGTGAAGCTCAT GAGCTGAGGGACGATCCGCCCATCATTGTCATTGAAA TCTATGACCAGGATTCCATGGGCAAAGCTGACTTCATG GGCCGGACCTTCGCCAAACCCCTGGTGAAGATGGCA GACGAGGCGTACTGCCCACCCCGCTTCCCACCTCAGC TCGAGTACTACCAGATCTACCGTGGCAACGCCACAGC TGGAGACCTGCTGGCGGCCTTCGAGCTGCTGCAGATT GGACCAGCAGGGAAGGCTGACCTGCCCCCCATCAAT GGCCCGGTGGACGTGGACCGAGGTCCCATCATGCCC GTGCCCATGGGCATCCGGCCCGTGCTCAGCAAGTACC GAGTGGAGGTGCTGTTCTGGGGCCTACGGGACCTAAA GCGGGTGAACCTGGCCCAGGTGGACCGGCCACGGGT GGACATCGAGTGTGCAGGGAAGGGGGTGCAGTCGTC CCTGATCCACAATTATAAGAAGAACCCCAACTTCAACA CCCTCGTCAAGTGGTTTGAAGTGGACCTCCCAGAGAA CGAGCTGCTGCACCCGCCCTTGAACATCCGTGTGGTG GACTGCCGGGCCTTCGGTCGCTACACACTGGTGGGCT CCCATGCCGTCAGCTCCCTGCGACGCTTCATCTACCG GCCCCCAGACCGCTCGGCCCCCAGCTGGAACACCAC GGTCAGGCTTCTCCGGCGCTGCCGTGTGCTGTGCAAT GGGGGCTCCTCCTCTCACTCCACAGGGGAGGTTGTG GTGACTATGGAGCCAGAGGTACCCATCAAGAAACTGG AGACCATGGTGAAGCTGGACGCGACTTCTGAAGCTGT TGTCAAGGTGGATGTGGCTGAGGAGGAGAAGGAGAA GAAGAAGAAGAAGAAGGGCACTGCGGAGGAGCCAGA GGAGGAGGAGCCAGACGAGAGCATGCTGGACTGGTG GTCCAAGTACTTTGCCTCCATTGACACCATGAAGGAGC AACTTCGACAACAAGAGCCCTCTGGAATTGACTTGGA GGAGAAGGAGGAAGTGGACAATACCGAGGGCCTGAA GGGGTCAATGAAGGGCAAGGAGAAGGCAAGGGCTGC CAAAGAGGAGAAGAAGAAGAAAACTCAGAGCTCTGGC TCTGGCCAGGGGTCCGAGGCCCCCGAGAAGAAGAAA CCCAAGATTGATGAGCTTAAGGTATACCCCAAAGAGCT GGAGTCCGAGTTTGATAACTTTGAGGACTGGCTGCAC |

TABLE 4-continued

Transfer plasmids for the production of dual hybrid vector systems

SEQ
ID
NO. Description                    Plasmid Sequence

ACTTTCAACTTGCTTCGGGGCAAGACCGGGGATGATG
                                   AGGATGGCTCCACCGAGGAGGAGCGCATTGTGGGAC
                                   GCTTCAAGGGCTCCCTCTGCGTGTACAAAGTGCCACT
                                   CCCAGAGGACGTGTCCCGGGAAGCCGGCTACGACTC
                                   CACCTACGGCATGTTCCAGGGCATCCCGAGCAATGAC
                                   CCCATCAATGTGCTGGTCCGAGTCTATGTGGTCCGGG
                                   CCACGGACCTGCACCCTGCTGACATCAACGGCAAAGC
                                   TGACCCCTACATCGCCATCCGGCTAGGCAAGACTGAC
                                   ATCCGCGACAAGGAGAACTACATCTCCAAGCAGCTCA
                                   ACCCTGTCTTTGGGAAGTCCTTTGACATCGAGGCCTC
                                   CTTCCCCATGGAATCCATGCTGACGGTGGCTGTGTAT
                                   GACTGGGACCTGGTGGGCACTGATGACCTCATTGGGG
                                   AAACCAAGATCGACCTGGAGAACCGCTTCTACAGCAA
                                   GCACCGCGCCACCTGCGGCATCGCCCAGACCTACTC
                                   CACACATGGCTACAATATCTGGCGGGACCCCATGAAG
                                   CCCAGCCAGATCCTGACCCGCCTCTGCAAAGACGGCA
                                   AAGTGGACGGCCCCCACTTTGGGCCCCCTGGGAGAG
                                   TGAAGGTGGCCAACCGCGTCTTCACTGGGCCCTCTGA
                                   GATTGAGGACGAGAACGGTCAGAGGAAGCCCACAGA
                                   CGAGCATGTGGCGCTGTTGGCCCTGAGGCACTGGGA
                                   GGACATCCCCCGCGCAGGCTGCCGCCTGGTGCCAGA
                                   GCATGTGGAGACGAGGCCGCTGCTCAACCCCGACAA
                                   GCCGGGCATCGAGCAGGGCCGCCTGGAGCTGTGGGT
                                   GGACATGTTCCCCATGGACATGCCAGCCCCTGGGACG
                                   CCTCTGGACATCTCACCTCGGAAGCCCAAGAAGTACG
                                   AGCTGCGGGTCATCATCTGGAACACAGATGAGGTGGT
                                   CTTGGAGGACGACGACTTCTTCACAGGGGAGAAGTCC
                                   AGTGACATCTTCGTGAGGGGGTGGCTGAAGGGCCAG
                                   CAGGAGGACAAGCAGGACACAGACGTCCACTACCACT
                                   CCCTCACTGGCGAGGGCAACTTCAACTGGCGCTACCT
                                   GTTCCCCTTCGACTACCTGGCGGCGGAGGAGAAGATC
                                   GTCATCTCCAAGAAGGAGTCCATGTTCTCCTGGGACG
                                   AGACCGAGTACAAGATCCCCGCGCGGCTCACCCTGCA
                                   GATCTGGGATGCGGACCACTTCTCCGCTGACGACTTC
                                   CTGGGGGCCATCGAGCTGGACCTGAACCGGTTCCCG
                                   CGGGGCGCAAAGACAGCCAAGCAGTGCACCATGGAG
                                   ATGGCCACCGGGGAGGTGGACGTGCCCCTCGTGTCC
                                   ATCTTCAAGCAAAAGCGCGTCAAAGGCTGGTGGCCCC
                                   TCCTGGCCCGCAATGAGAACGATGAGTTTGAGCTCAC
                                   GGGCAAGGTGGAGGCTGAGCTGCATTTACTGACAGCA
                                   GAGGAGGCAGAGAAGAACCCAGTGGGCCTGGCCCGC
                                   AATGAACCTGACCCCCTAGAGAAACCCAACCGGCCCG
                                   ACACGGCCTTCGTCTGGTTCCTCAACCCTCTCAAGTCC
                                   ATCAAGTACCTCATCTGCACCCGGTACAAGTGGCTCAT
                                   CATCAAGATCGTGCTGGCGCTGTTGGGGCTGCTCATG
                                   TTGGGGCTCTTCCTCTACAGCCTCCCTGGCTACATGG
                                   TCAAAAAGCTCCTTGGGGCATGAACGGCCGCTATGCT
                                   AGCTTGGTACCAAGGGCGGATCCTGCATAGAGCTCGC
                                   TGATCAGCCTCGACTGTGCCTTCTAGTTGCCAGCCATC
                                   TGTTGTTTGCCCCTCCCCCGTGCCTTCCTTGACCCTG
                                   GAAGGTGCCACTCCCACTGTCCTTTCCTAATAAAATGA
                                   GGAAATTGCATCGCATTGTCTGAGTAGGTGTCATTCTA
                                   TTCTGGGGGGTGGGGTGGGGCAGGACAGCAAGGGG
                                   GAGGATTGGGAAGACAATAGCAGGCATGCTGGGGAG
                                   AGATCTGAGGACTAGTCCGTCGACTGGGGAGAGATCT
                                   GAGGAACCCCTAGTGATGGAGTTGGCCACTCCCTCTC
                                   TGCGCGCTCGCTCGCTCACTGAGGCCGCCCGGGCAA
                                   AGCCCGGGCGTCGGGCGACCTTTGGTCGCCCGGCCT
                                   CAGTGAGCGAGCGAGCGCGCAGAGAGGGAGTGGCCA
                                   ACCCCCCCCCCCCCCCCCCTGCAGCCTGGCGTAATAG
                                   CGAAGAGGCCCGCACCGATCGCCCTTCCCAACAGTTG
                                   CGTAGCCTGAATGGCGAATGGCGCGACGCGCCCTGT
                                   AGCGGCGCATTAAGCGCGGCGGGTGTGGTGGTTACG
                                   CGCAGCGTGACCGCTACACTTGCCAGCGCCCTAGCG
                                   CCCGCTCCTTTCGCTTTCTTCCCTTCCTTTCTCGCCAC
                                   GTTCGCCGGCTTTCCCCGTCAAGCTCTAAATCGGGGG
                                   CTCCCTTTAGGGTTCCGATTTAGTGCTTTACGGCACCT
                                   CGACCCCAAAAAACTTGATTAGGGTGATGGTTCACGTA
                                   GTGGGCCATCGCCCTGATAGACGGTTTTTCGCCCTTT
                                   GACGTTGGAGTCCACGTTCTTTAATAGTGGACTCTTGT
                                   TCCAAACTGGAACAACACTCAACCCTATCGCGGTCTAT
                                   TCTTTTGATTTATAAGGGATGTTGCCGATTTCGGCCTA
                                   TTGGTTAAAAAATGAGCTGATTTAACAAAAATTTTAACA
                                   AAATTCAGAAGAACTCGTCAAGAAGGCGATAGAAGGC

TABLE 4-continued

Transfer plasmids for the production of dual hybrid vector systems

| SEQ ID NO. | Description | Plasmid Sequence |
|---|---|---|
| | | GATGCGCTGCGAATCGGGAGCGGCGATACCGTAAAG |
| | | CACGAGGAAGCGGTCAGCCCATTCGCCGCCAAGCTCT |
| | | TCAGCAATATCACGGGTAGCCAACGCTATGTCCTGATA |
| | | GCGGTCCGCCACACCCAGCCGGCCACAGTCGATGAA |
| | | TCCAGAAAAGCGGCCATTTTCCACCATGATATTCGGCA |
| | | AGCAGGCATCGCCATGGGTCACGACGAGATCCTCGCC |
| | | GTCGGGCATGCTCGCCTTGAGCCTGGCGAACAGTTCG |
| | | GCTGGCGCGAGCCCCTGATGCTCTTCGTCCAGATCAT |
| | | CCTGATCGACAAGACCGGCTTCCATCCGAGTACGTGC |
| | | TCGCTCGATGCGATGTTTCGCTTGGTGGTCGAATGGG |
| | | CAGGTAGCCGGATCAAGCGTATGCAGCCGCCGCATTG |
| | | CATCAGCCATGATGGATACTTTCTCGGCAGGAGCAAG |
| | | GTGAGATGACAGGAGATCCTGCCCCGGCACTTCGCCC |
| | | AATAGCAGCCAGTCCCTTCCCGCTTCAGTGACAACGT |
| | | CGAGCACAGCTGCGCAAGGAACGCCCGTCGTGGCCA |
| | | GCCACGATAGCCGCGCTGCCTCGTCTTGCAGTTCATT |
| | | CAGGGCACCGGACAGGTCGGTCTTGACAAAAAGAACC |
| | | GGGCGCCCCTGCGCTGACAGCCGGAACACGGCGGCA |
| | | TCAGAGCAGCCGATTGTCTGTTGTGCCCAGTCATAGC |
| | | CGAATAGCCTCTCCACCCAAGCGGCCGGAGAACCTGC |
| | | GTGCAATCCATCTTGTTCAATCATGCGAAACGATCCTC |
| | | ATCCTGTCTCTTGATCAGATCTTGATCCCCTGCGCCAT |
| | | CAGATCCTTGGCGGCGAGAAAGCCATCCAGTTTACTTT |
| | | GCAGGGCTTCCCAACCTTACCAGAGGGCGCCCCAGCT |
| | | GGCAATTCCGGTTCGCTTGCTGTCCATAAAACCGCCC |
| | | AGTCTAGCTATCGCCATGTAAGCCCACTGCAAGCTAC |
| | | CTGCTTTCTCTTTGCGCTTGCGTTTTCCCTTGTCCAGA |
| | | TAGCCCAGTAGCTGACATTCATCCGGGGTCAGCACCG |
| | | TTTCTGCGGACTGGCTTTCTACGTGAAAAGGATCTAGG |
| | | TGAAGATCCTTTTTGATAATCTCATGACCAAAATCCCTT |
| | | AACGTGAGTTTTCGTTCCACTGAGCGTCAGACCCCGT |
| | | AGAAAAGATCAAAGGATCTTCTTGAGATCCTTTTTTTCT |
| | | GCGCGTAATCTGCTGCTTGCAAACAAAAAAACCACCG |
| | | CTACCAGCGGTGGTTTGTTTGCCGGATCAAGAGCTAC |
| | | CAACTCTTTTTCCGAAGGTAACTGGCTTCAGCAGAGCG |
| | | CAGATACCAAATACTGTCCTTCTAGTGTAGCCGTAGTT |
| | | AGGCCACCACTTCAAGAACTCTGTAGCACCGCCTACA |
| | | TACCTCGCTCTGCTAATCCTGTTACCAGTGGCTGCTGC |
| | | CAGTGGCGATAAGTCGTGTCTTACCGGGTTGGACTCA |
| | | AGACGATAGTTACCGGATAAGGCGCAGCGGTCGGGCT |
| | | GAACGGGGGGTTCGTGCACACAGCCCAGCTTGGAGC |
| | | GAACGACCTACACCGAACTGAGATACCTACAGCGTGA |
| | | GCTATGAGAAAGCGCCACGCTTCCCGAAGGGAGAAAG |
| | | GCGGACAGGTATCCGGTAAGCGGCAGGGTCGGAACA |
| | | GGAGAGCGCACGAGGGAGCTTCCAGGGGGAAACGCC |
| | | TGGTATCTTTATAGTCCTGTCGGGTTTCGCCACCTCTG |
| | | ACTTGAGCGTCGATTTTTGTGATGCTCGTCAGGGGGG |
| | | CGGAGCCTATGGAAAAACGCCAGCAACGCGGCCTTTT |
| | | TACGGTTCCTGGGCTTTTGCTGGCCTTTTGCTCACATG |
| | | TTCTTTCCTGCGTTATCCCCTGATTCTGTGGATAACCG |
| | | TATTACCGCCTTTGAGTGAGCTGATACCGCTCGCCGC |
| | | AGCCGAACGACCGAGCGCAGCGAGTCAGTGAGCGAG |
| | | GAAGCGGAAGAGCGCCCAATACGCAAACCGCCTCTCC |
| | | CCGCGCGTTGGCCGATTCATTAATGCAGGGCTGCA |
| 64 | 5' transgene plasmid containing the following features: Lambda at positions 53-2027 ITR at positions 2049-2178 CMV i.e enhancer at positions 2267-2636 (part of smCBA promoter) Chicken β-actin promoter at positions 2633-2915 (part of smCBA promoter) Exon1 at positions 2916-3008 (part of smCBA promoter) Chimeric intron at positions 3008-3209 (part of smCBA promoter) Kozak sequence at positions 3226-3235 N-terminal portion of human OTOF isoform 5 at positions | TCGCGCGTTTCGGTGATGACGGTGAAAACCTCTGACA CATGCAGCTCCCGGATAGAGGTCATCCTTCCTGACCA TTTCCATCATTCCAGTCGAACTCACACACAACACCAAA TGCATTTAAGTCGCTTGAAATTGCTATAAGCAGAGCAT GTTGCGCCAGCATGATTAATACAGCATTTAATACAGAG CCGTGTTTATTGAGTCGGTATTCAGAGTCTGACCAGAA ATTATTAATCTGGTGAAGTTATTCCTCTGTCATTACGTC ATGGTCGATTTCAATTTCTATTGATGCTTTCCAGTCGTA ATCAATGATGTATTTTTTGATGTTTGACCTCTGTTCATA TCCTCACAGATAAAAAATCGCCCTCACACTGGAGGGC AAAGAAGATTTCCAATAATCAGAACAAGTCGGCTCCTG TTTAGTTACGAGCGACATTGCTCCGTGTATTCACTCGT TGGAATGAATACACAGTGCAGTGTTTATTCTGTTATTTA TGCCAAAAATTAAGGCCACTATCAGGCAGCTTTGTTGT TCTGTTTACCAAGTTCTCTGGCAATCATTGCCGTCGTT CGTATTGCCCATTTATCGACATATTTCCCATCTTCCTAT ACAGGAAACATTTCTTCAGGCTTAACCATGCATTCCGA TTGCAGCTTGCATCCATTGCATCGCTTGAATTGTCCAC ACCATTGATTTTTATCAATAGTCGTAGTTTAACGGATAG |

TABLE 4-continued

Transfer plasmids for the production of dual hybrid vector systems

| SEQ ID NO. | Description | Plasmid Sequence |
|---|---|---|
| | 3232-5637<br>Splice donor sequence at<br>positions 5638-5721<br>AP head sequence at positions<br>5728-6014<br>ITR at positions 6108-6237<br>Lambda at positions 6248-8260<br>Ori at positions 8317-8905<br>KanR at positions 9083-9892<br>Transgene to be transferred<br>into vector in dual vector<br>system at positions 2049-6237 | TCCTGGTATTGTTCCATCACATCCTGAGGATGCCCTTC<br>GAACTCTTCAAATTCTTCTTCCTAATATCACCTTAAATA<br>GTGGATTGCGGTAGTAAAGATTGTGCCTGTCTTTTAAC<br>CACATCAGGCTCGGTGGTTCTCGTGTACCCCTACAGC<br>GAGAAATCGGATAAACTATTACAACCCCTACAGTTTGT<br>AGAGTATAGAAAATGATCCACTCGTTATTCTCGGACGA<br>GTGTTCAGTAATGAACCTCTGGAGAGAACCATCTATAT<br>GATCGTTATCTGGGTTTGACTTCTGCTTTTAAGCCCAG<br>ATAACTTGCCTGAATATGTTAATGAGAGAATCGGTATT<br>CCTCATGTGTGGCATGTTTTCGTCTTTGCTCTTGCATTT<br>TCACTAGCAATTAATGTGCATCGATTATCAGCTATTGC<br>CAGCGCCAGATATAAGCGATTTAAGCTAAGAAAACGCA<br>TTAAGGTGCAAAACGATAAAGTGCGATCAGTAATTCAA<br>AACCTTACAGGAGAGCAATCTATGGTTTTGTGCTCAGC<br>CCTTAATGAAGGCAGGTAGTATGTGGTTACATCAAAAC<br>AATTCCCATACATTAGTGAGTTGATTGAGCTTGGTGTG<br>TTGAACAAAACTTTTTCCCGATGGAATGGAAAGCATAT<br>ATTATTCCCTATTGAGGATATTTACTGGACTGAATTAGT<br>TGCCAGCTATGATCCATATAATATTGAGATAAAGCCAA<br>GGCCAATATCTAAGTAACTAGATAAGAGGAATCGATTT<br>TCCCTTAATTTTCTGGCGTCCACTGCATGTTATGCCGC<br>GTTCGCCAGGCTTGCTGTACCATGTGCGCTGATTCTT<br>GCGCTCAATACGTTGCAGGTTGCTTTCAATCTGTTTGT<br>GGTATTCAGCCAGCACTGTAAGGTCTATCGGATTTAGT<br>GCGCTTTCTACTCGTGATTTCGGTTTGCGATTCAGCGA<br>GAGAATAGGGCGGTTAACTGGTTTTGCGCTTACCCCA<br>ACCAACAGGGGATTTGCTGCTTTCCATTGAGCCTGTTA<br>CTCTGCGCGACGTTCGCGGCGGCGTGTTTGTGCATCC<br>ATCTGGATTCTCCTGTCAGTTAGCTTTGGTGGTGTGTG<br>GCAGTTGTAGTCCTGAACGAAAACCCCCCGCGATTGG<br>CACGTTGGCAGCTAATCCGGAATCGCACTTACGGCCA<br>ATGCTTCGTTTCGTATCACACACCCCAAAGCCTTCTGC<br>TTTGAATGCTGCCCTTCTTCAGGGCTTAATTTTTAAGA<br>GCGTCACCTTCATGGTGGTCAGTGCGTCCTGCTGATG<br>TGCTCAGGCACGATTTAATTAAGGCCTTAATTAGGCTG<br>CGCGCTCGCTCGCTCACTGAGGCCGCCCGGGCAAAG<br>CCCGGGCGTCGGGCGACCTTTGGTCGCCCGGCCTCA<br>GTGAGCGAGCGAGCGCGCAGAGAGGGAGTGGCCAAC<br>TCCATCACTAGGGGTTCCTTGTAGTTAATGATTAACCC<br>GCCATGCTACTTATCTACGTAGCCATGCTCTAGGAAGA<br>TCGGAATTCGCCCTTAAGCTAGCGGCGCGCCGGTACC<br>TAGTTATTAATAGTAATCAATTACGGGGTCATTAGTTCA<br>TAGCCCATATATGGAGTTCCGCGTTACATAACTTACGG<br>TAAATGGCCCGCCTGGCTGACCGCCCAACGACCCCC<br>GCCCATTGACGTCAATAATGACGTATGTTCCCATAGTA<br>ACGCCAATAGGGACTTTCCATTGACGTCAATGGGTGG<br>AGTATTTACGGTAAACTGCCCACTTGGCAGTACATCAA<br>GTGTATCATATGCCAAGTACGCCCCCTATTGACGTCAA<br>TGACGGTAAATGGCCCGCCTGGCATTATGCCCAGTAC<br>ATGACCTTATGGGACTTTCCTACTTGGCAGTACATCTA<br>CGTATTAGTCATCGCTATTACCATGGTCGAGGTGAGCC<br>CCACGTTCTGCTTCACTCTCCCCATCTCCCCCCCCTCC<br>CCACCCCCAATTTTGTATTTATTTATTTTTTAATTATTTT<br>GTGCAGCGATGGGGGCGGGGGGGGGGGGGGGGGCG<br>CGCGCCAGGCGGGGCGGGGCGGGGCGAGGGGCGG<br>GGCGGGGCGAGGCGGAGAGGTGCGGCGGCAGCCAA<br>TCAGAGCGGCGCGCTCCGAAAGTTTCCTTTTATGGCG<br>AGGCGGCGGCGGCGGCGGCCCTATAAAAAGCGAAGC<br>GCGCGGCGGGCGGGAGTCGCTGCGCGCTGCCTTCGC<br>CCCGTGCCCCGCTCCGCCGCCGCCTCGCGCCGCCCG<br>CCCCGGCTCTGACTGACCGCGTTACTCCCACAGGTGA<br>GCGGGCGGGACGGCCCTTCTCCTCCGGGCTGTAATTA<br>GCGCTTGGTTTAATGACGGCTTGTTTCTTTTCTGTGGC<br>TGCGTGAAAGCCTTGAGGGGCTCCGGGAGCTAGAGC<br>CTCTGCTAACCATGTTCATGCCTTCTTCTTTTTCCTACA<br>GCTCCTGGGCAACGTGCTGGTTATTGTGCTGTCTCAT<br>CATTTTGGCAAAGAATTCTAGCGGCCGCCACCATGGC<br>CTTGCTCATCCACCTCAAGACAGTCTCGGAGCTGCGG<br>GGCAGGGGCGACCGGATCGCCAAAGTGACTTTCCGA<br>GGGCAATCCTTCTACTCTCGGGTCCTGGAGAACTGTG<br>AGGATGTGGCTGACTTTGATGAGACATTTCGGTGGCC<br>GGTGGCCAGCAGCATCGACAGAAATGAGATGCTGGAG<br>ATTCAGGTTTTCAACTACAGCAAAGTCTTCAGCAACAA<br>GCTCATCGGGACCTTCCGCATGGTGCTGCAGAAGGTG |

TABLE 4-continued

Transfer plasmids for the production of dual hybrid vector systems

| SEQ ID NO. | Description | Plasmid Sequence |
|---|---|---|
| | | GTAGAGGAGAGCCATGTGGAGGTGACTGACACGCTGA |
| | | TTGATGACAACAATGCTATCATCAAGACCAGCCTGTGC |
| | | GTGGAGGTCCGGTATCAGGCCACTGACGGCACAGTG |
| | | GGCTCCTGGGACGATGGGGACTTCCTGGGAGATGAG |
| | | TCTCTTCAAGAGGAAGAGAAGGACAGCCAAGAGACGG |
| | | ATGGACTGCTCCCAGGCTCCCGGCCCAGCTCCCGGC |
| | | CCCCAGGAGAGAAGAGCTTCCGGAGAGCCGGGAGGA |
| | | GCGTGTTCTCCGCCATGAAGCTCGGCAAAAACCGGTC |
| | | TCACAAGGAGGAGCCCCAAAGACCAGATGAACCGGC |
| | | GGTGCTGGAGATGGAAGACCTTGACCATCTGGCCATT |
| | | CGGCTAGGAGATGGACTGGATCCCGACTCGGTGTCTC |
| | | TAGCCTCAGTCACAGCTCTCACCACTAATGTCTCCAAC |
| | | AAGCGATCTAAGCCAGACATTAAGATGGAGCCAAGTG |
| | | CTGGGCGGCCCATGGATTACCAGGTCAGCATCACGGT |
| | | GATCGAGGCCCGGCAGCTGGTGGGCTTGAACATGGA |
| | | CCCTGTGGTGTGCGTGGAGGTGGGTGACGACAAGAA |
| | | GTACACATCCATGAAGGAGTCCACTAACTGCCCCTATT |
| | | ACAACGAGTACTTCGTCTTCGACTTCCATGTCTCTCCG |
| | | GATGTCATGTTTGACAAGATCATCAAGATTTCGGTGAT |
| | | TCACTCCAAGAACCTGCTGCGCAGTGGCACCCTGGTG |
| | | GGCTCCTTCAAAATGGACGTGGGAACCGTGTACTCGC |
| | | AGCCAGAGCACCAGTTCCATCACAAGTGGGCCATCCT |
| | | GTCTGACCCCGATGACATCTCCTCGGGGCTGAAGGGC |
| | | TACGTGAAGTGTGACGTTGCCGTGGTGGGCAAAGGG |
| | | GACAACATCAAGACGCCCCACAAGGCCAATGAGACCG |
| | | ACGAAGATGACATTGAGGGGAACTTGCTGCTCCCCGA |
| | | GGGGGTGCCCCCCGAACGCCAGTGGGCCCGGTTCTA |
| | | TGTGAAAATTTACCGAGCAGAGGGGCTGCCCCGTATG |
| | | AACACAAGCCTCATGGCCAATGTAAAGAAGGCTTTCAT |
| | | CGGTGAAAACAAGGACCTCGTGGACCCCTACGTGCAA |
| | | GTCTTCTTTGCTGGCCAGAAGGGCAAGACTTCAGTGC |
| | | AGAAGAGCAGCTATGAGCCCCTGTGGAATGAGCAGGT |
| | | CGTCTTTACAGACCTCTTCCCCCCACTCTGCAAACGCA |
| | | TGAAGGTGCAGATCCGAGACTCGGACAAGGTCAACGA |
| | | CGTGGCCATCGGCACCCACTTCATTGACCTGCGCAAG |
| | | ATTTCTAATGACGGAGACAAAGGCTTCCTGCCCACACT |
| | | GGGCCCAGCCTGGGTGAACATGTACGGCTCCACACGT |
| | | AACTACACGCTGCTGGATGAGCATCAGGACCTGAACG |
| | | AGGGCCTGGGGGAGGGTGTGTCCTTCCGGGCCCGGC |
| | | TCCTGCTGGGGCCTGGCTGTGGAGATCGTAGACACCTC |
| | | CAACCCTGAGCTCACCAGCTCCACAGAGGTGCAGGTG |
| | | GAGCAGGCCACGCCCATCTCGGAGAGCTGTGCAGGT |
| | | AAAATGGAAGAATTCTTTCTCTTTGGAGCCTTCCTGGA |
| | | GGCCTCAATGATCGACCGGGAGAAACGGAGACAAGCCC |
| | | ATCACCTTTGAGGTCACCATAGGCAACTATGGGAACG |
| | | AAGTTGATGGCCTGTCCCGGCCCCAGCGGCCTCGGC |
| | | CCCGGAAGGAGCCGGGGGATGAGGAAGAAGTAGACC |
| | | TGATTCAGAACGCAAGTGATGACGAGGCCGGTGATGC |
| | | CGGGGACCTGGCCTCAGTCTCCTCCACTCCACCAATG |
| | | CGGCCCCAGGTCACCGACAGGAACTACTTCCATCTGC |
| | | CCTACCTGGAGCGAAAGCCCTGCATCTACATCAAGAG |
| | | CTGGTGGCCGGACCAGCGCCGCCGCCTCTACAATGC |
| | | CAACATCATGGACCACATTGCCGACAAGCTGGAAGAA |
| | | GGCCTGAACGACATACAGGAGATGATCAAAACGGAGA |
| | | AGTCCTACCCTGAGCGTCGCCTGCGGGGCGTCCTGG |
| | | AGGAGCTGAGCTGTGGCTGCTGCCGCTTCCTCTCCCT |
| | | CGCTGACAAGGACCAGGGCCACTCATCCCGCACCAG |
| | | GCTTGACCGGGAGCGCCTCAAGTCCTGCATGAGGGA |
| | | GCTGGTAAGTATCAAGGTTACAAGACAGGTTTAAGGA |
| | | GACCAATAGAAACTGGGCTTGTCGAGACAGAGAAGAC |
| | | TCTTGCGTTTCTGAGCTAGCCCCCGGGTGCGCGGCGT |
| | | CGGTGGTGCCGGCGGGGGGCGCCAGGTCGCAGGCG |
| | | GTGTAGGGCTCCAGGCAGGCGGCGAAGGCCATGACG |
| | | TGCGCTATGAAGGTCTGCTCCTGCACGCCGTGAACCA |
| | | GGTGCGCCTGCGGGCCGCGCGCGAACACCGCCACGT |
| | | CCTCGCCTGCGTGGGTCTCTTCGTCCAGGGGCACTGC |
| | | TGACTGCTGCCGATACTCGGGGCTCCCGCTCTCGCTC |
| | | TCGGTAACATCCGGCCGGGCGCCGTCCTTGAGCACAT |
| | | AGCCTGGACCGTTTCGTCGACCTCGAGTTAAGGGCGA |
| | | ATTCCCGATAAGGATCTTCCTAGAGCATGGCTACGTAG |
| | | ATAAGTAGCATGGCGGGTTAATCATTAACTACAAGGAA |
| | | CCCCTAGTGATGGAGTTGGCCACTCCCTCTCTGCGCG |
| | | CTCGCTCGCTCACTGAGGCCGGGCGACCAAAGGTCG |
| | | CCCGACGCCCGGGCTTTGCCCGGGCGGCCTCAGTGA |

TABLE 4-continued

Transfer plasmids for the production of dual hybrid vector systems

| SEQ ID NO. | Description | Plasmid Sequence |
|---|---|---|
| | | GCGAGCGAGCGCGCAGCCTTAATTAAATCCACATCTG |
| | | TATGTTTTTTATATTAATTTATTTTTTGCAGGGGGGCAT |
| | | TGTTTGGTAGGTGAGAGTTCTGAATTGCTATGTTTAGT |
| | | GAGTTGTATCTATTTATTTTTCAATAAATACAATTAGTTA |
| | | TGTGTTTTGGGGGCGATCGTGAGGCAAAGAAAACCCG |
| | | GCGCTGAGGCCGGGTTATTCTTGTTCTCTGGTCAAATT |
| | | ATATAGTTGGAAAACAAGGATGCATATATGAATGAACG |
| | | ATGCAGAGGCAATGCCGATGGCGATAGTGGGTATCAG |
| | | GTAGCCGCTTATGCTGGAAAGAAGCAATAACCCGCAG |
| | | AAAAACAAAGCTCCAAGCTCAACAAAACTAAGGGCATA |
| | | GACAATAACTACCTATGTCATATACCCATACTCTCTAAT |
| | | CTTGGCCAGTCGGCGCGTTCTGCTTCCGATTAGAAAC |
| | | GTCAAGGCAGCAATCAGGATTGCAATCTTGGTTCCTG |
| | | CATAGGATGACAATGTCGCCCCAAGACCATCTCTATGA |
| | | GCTGAAAAGAAACACAAGGAATGTAGTGGCGGAAAA |
| | | GGAGATAGCAAATGCTTACGATAACGTAAGGAATTATT |
| | | ACTATGTAAACACCAGGCAAGATTCTGTTCCGTATAAT |
| | | TACTCCTGATAATTAATCCTTAACTTTGCCCACCTGCCT |
| | | TTTAAAACATTCCAGTATATCACTTTTCATTCTTGCGTA |
| | | GCAATATGCCCTCTCTTCAGCTATCTCAGCATTGGTGA |
| | | CCTTGTTCAGAGGCGCTGAGAGATGGCCTTTTTCTGAT |
| | | AGATAATGTTCTGTTAAAATATCTCCGGCCTCATCTTTT |
| | | GCCCGCAGGCTAATGTCTGAAAATTGAGGTGACGGGT |
| | | TAAAAATAATATCCTTGGCAACCTTTTTTATATCCCTTTT |
| | | AAATTTTGGCTTAATGACTATATCCAATGAGTCAAAAAG |
| | | CTCCCCTTCAATATCTGTTGCCCCTAAGACCTTTAATAT |
| | | ATCGCCAAATACAGGTAGCTTGGCTTCTACCTTCACCG |
| | | TTGTTCTGCCGATGAAATGCTAATGCATAACATCGTCT |
| | | TTGGTGGTTCCCCTCATCAGTGGCTCTATCTGAACGC |
| | | GCTCTCCACTGCTTAATGACATTCCTTTCCCGATTAAA |
| | | AAATCTGTCAGATCGGATGTGGTCGGCCCGAAAACAG |
| | | TTCTGGCAAAACCAATGGTGTCGCCTTCAACAAACAAA |
| | | AAAGATGGGAATCCCAATGATTCGTCATCTGCGAGGC |
| | | TGTTCTTAATATCTTCAACTGTAGCTTTAGAGCGATTTA |
| | | TCTTCTGAACCAGACTCTTGTCATTTGTTTTGGTAAAGA |
| | | GAAAAGTTTTTCCATCGATTTTATGAATATACAAATAAT |
| | | TGGAGCCAACCTTCAGGTGATGATTATCAGCCAGCAG |
| | | AGAATTAAGGAAAACAGACAGGTTTATTGAGCACTTAT |
| | | CTTTCCCTTTATTTTTGCTGCGGTAAGTCGCATAAAAAC |
| | | CATTCTTCACAATTCAATCCATTTACTATGTTATGTTCT |
| | | GAGGGGAGTGAAAATTCCCCTAATTCGATGAAGATTCT |
| | | TGCTAAATTGTTATCAGCTATGCGCCGACCAGAACACC |
| | | TTGCCGATCAGCCAAACGTCTAATCAGGCCACTGACTA |
| | | GCGATAACTTTCCCCACAACGGAACAACTCTCATTGCA |
| | | TGGGATAATTGGGTACTGTGGGTTTAGTGGTTGTAAAA |
| | | ACACCTGACCGCTATCCCTGATCAGTTTCTTGAAGGTA |
| | | AACTCATCACCCCCAAGTCTGGCTATACAGAAATCACC |
| | | TGGCTCAACAGCCTGCTCAGGGTCAACGAGAATTTAC |
| | | ATTCCGTCAGGATAGCTTGGCTTGGAGCCTGTTGGTG |
| | | CGGTCACGGAATTACCTTCAACCTCAAGCCAGAATGC |
| | | AGAATCACTGGCTTTTTTGGTTGTGCTTACCCATCTCT |
| | | CCGCATCACCTTTGGTAAAGGTTCTAAGCTAAGGTGAG |
| | | AACATCCCTGCCTGAACATGAGAAAAAACAGGGTACTC |
| | | ATACTCACTTATTAGTGACGGCTATGAGCAAAAGGCCA |
| | | GCAAAAGGCCAGGAACCGTAAAAAGGCCGCGTTGCTG |
| | | GCGTTTTTCCATAGGCTCCGCCCCCCTGACGAGCATC |
| | | ACAAAAATCGACGCTCAAGTCAGAGGTGGCGAAACCC |
| | | GACAGGACTATAAAGATACCAGGCGTTTCCCCCTGGA |
| | | AGCTCCCTCGTGCGCTCTCCTGTTCCGACCCTGCCGC |
| | | TTACCGGATACCTGTCCGCCTTTCTCCCTTCGGGAAG |
| | | CGTGGCGCTTTCTCATAGCTCACGCTGTAGGTATCTCA |
| | | GTTCGGTGTAGGTCGTTCGCTCCAAGCTGGGCTGTGT |
| | | GCACGAACCCCCCGTTCAGCCCGACCGCTGCGCCTTA |
| | | TCCGGTAACTATCGTCTTGAGTCCAACCCGGTAAGACA |
| | | CGACTTATCGCCACTGGCAGCAGCCACTGGTAACAGG |
| | | ATTAGCAGAGCGAGGTATGTAGGCGGTGCTACAGAGT |
| | | TCTTGAAGTGGTGGCCTAACTACGGCTACACTAGAAG |
| | | AACAGTATTTGGTATCTGCGCTCTGCTGAAGCCAGTTA |
| | | CCTTCGGAAAAAGAGTTGGTAGCTCTTGATCCGGCAA |
| | | ACAAACCACCGCTGGTAGCGGTGGTTTTTTTGTTTGCA |
| | | AGCAGCAGATTACGCGCAGAAAAAAAGGATCTCAAGA |
| | | AGATCCTTTGATCTTTTCTACGGGGTCTGACGCTCAGT |
| | | GGAACGAAAACTCACGTTAAGGGATTTTGGTCATGAGA |
| | | TTATCAAAAAGGATCTTCACCTAGATCCTTTTAAATTAA |

TABLE 4-continued

Transfer plasmids for the production of dual hybrid vector systems

| SEQ ID NO. | Description | Plasmid Sequence |
|---|---|---|
| | | AAATGAAGTTTTAAATCAAGCCCAATCTGAATAATGTTA |
| | | CAACCAATTAACCAATTCTGATTAGAAAAACTCATCGA |
| | | GCATCAAATGAAACTGCAATTTATTCATATCAGGATTAT |
| | | CAATACCATATTTTTGAAAAAGCCGTTTCTGTAATGAAG |
| | | GAGAAAACTCACCGAGGCAGTTCCATAGGATGGCAAG |
| | | ATCCTGGTATCGGTCTGCGATTCCGACTCGTCCAACAT |
| | | CAATACAACCTATTAATTTCCCCTCGTCAAAAATAAGGT |
| | | TATCAAGTGAGAAATCACCATGAGTGACGACTGAATCC |
| | | GGTGAGAATGGCAAAAGTTTATGCATTTCTTTCCAGAC |
| | | TTGTTCAACAGGCCAGCCATTACGCTCGTCATCAAAAT |
| | | CACTCGCATCAACCAAACCGTTATTCATTCGTGATTGC |
| | | GCCTGAGCAAGACGAAATACGCGATCGCTGTTAAAAG |
| | | GACAATTACAAACAGGAATCGAATGCAACCGGCGCAG |
| | | GAACACTGCCAGCGCATCAACAATATTTTCACCTGAAT |
| | | CAGGATATTCTTCTAATACCTGGAATGCTGTTTTTCCG |
| | | GGGATCGCAGTGGTGAGTAACCATGCATCATCAGGAG |
| | | TACGGATAAAATGCTTGATGGTCGGAAGAGGCATAAAT |
| | | TCCGTCAGCCAGTTTAGTCTGACCATCTCATCTGTAAC |
| | | ATCATTGGCAACGCTACCTTTGCCATGTTTCAGAAACA |
| | | ACTCTGGCGCATCGGGCTTCCCATACAAGCGATAGAT |
| | | TGTCGCACCTGATTGCCCGACATTATCGCGAGCCCAT |
| | | TTATACCCATATAAATCAGCATCCATGTTGGAATTTAAT |
| | | CGCGGCCTCGACGTTTCCCGTTGAATATGGCTCATAA |
| | | CACCCCTTGTATTACTGTTTATGTAAGCAGACAGTTTTA |
| | | TTGTTCATGATGATATATTTTTATCTTGTGCAATGTAAC |
| | | ATCAGAGATTTTGAGACACGGGCCAGAGCTGCA |
| 65 | 5' transgene plasmid containing the following features: | GGGGGGGGGGGGGGGGGGTTGGCCACTCCCTCTCT |
| | ITR at positions 19-161 | GCGCGCTCGCTCGCTCACTGAGGCCGGGCGACCAAA |
| | CMV enhancer at positions | GGTCGCCCGACGCCCGGGCTTTGCCCGGGCGGCCTC |
| | 177-546 (part of smCBA | AGTGAGCGAGCGAGCGCGCAGAGAGGGAGTGGCCAA |
| | promoter) | CTCCATCACTAGGGGTTCCTCAGATCTGAATTCGGTAC |
| | Chicken β-actin promoter at | CTAGTTATTAATAGTAATCAATTACGGGGTCATTAGTTC |
| | positions 548-825 (part of | ATAGCCCATATATGGAGTTCCGCGTTACATAACTTACG |
| | smCBA promoter) | GTAAATGGCCCGCCTGGCTGACCGCCCAACGACCCC |
| | Exon1 at positions 826-918 | CGCCCATTGACGTCAATAATGACGTATGTTCCCATAGT |
| | (part of smCBA promoter) | AACGCCAATAGGGACTTTCCATTGACGTCAATGGGTG |
| | Chimeric intron at positions | GAGTATTTACGGTAAACTGCCCACTTGGCAGTACATCA |
| | 918-1119 (part of smCBA | AGTGTATCATATGCCAAGTACGCCCCCTATTGACGTCA |
| | promoter) | ATGACGGTAAATGGCCCGCCTGGCATTATGCCCAGTA |
| | N-terminal portion of human | CATGACCTTATGGGACTTTCCTACTTGGCAGTACATCT |
| | OTOF isoform 5 at positions | ACGTATTAGTCATCGCTATTACCATGGTCGAGGTGAGC |
| | 1142-3547 | CCCACGTTCTGCTTCACTCTCCCCATCTCCCCCCCCTC |
| | Splice donor sequence at | CCCACCCCCAATTTTGTATTTATTTATTTTTTAATTATTT |
| | positions 3548-3631 | TGTGCAGCGATGGGGGCGGGGGGGGGGGGGGGGCG |
| | AP head sequence at positions | CGCGCCAGGCGGGGCGGGGCGGGGCGAGGGGCGG |
| | 3638-3924 | GGCGGGGCGAGGCGGAGAGGTGCGGCGGCAGCCAA |
| | ITR at positions 3948-4090 | TCAGAGCGGCGCGCTCCGAAAGTTTCCTTTTATGGCG |
| | KanR at positions 4616-5410 | AGGCGGCGGCGGCGGCGGCCCTATAAAAAGCGAAGC |
| | pUC ori at positions 5796-6466 | GCGCGGCGGGCGGGAGTCGCTGCGCGCTGCCTTCGC |
| | Transgene to be transferred | CCCGTGCCCCGCTCCGCCGCCGCCTCGCGCCGCCCG |
| | into vector in dual vector | CCCCGGCTCTGACTGACCGCGTTACTCCCACAGGTGA |
| | system at positions 19-4090 | GCGGGCGGGACGGCCCTTCTCCTCCGGGCGTGAATTA |
| | | GCGCTTGGTTTAATGACGGCTTGTTTCTTTTCTGTGGC |
| | | TGCGTGAAAGCCTTGAGGGGCTCCGGGAGCTAGAGC |
| | | CTCTGCTAACCATGTTCATGCCTTCTTCTTTTTCCTACA |
| | | GCTCCTGGGCAACGTGCTGGTTATTGTGCTGTCTCAT |
| | | CATTTTGGCAAAGAATTCTAGCGGCCGCCACCATGGC |
| | | CTTGCTCATCCACCTCAAGACAGTCTCGGAGCTGCGG |
| | | GGCAGGGGCGACCGGATCGCCAAAGTGACTTTCCGA |
| | | GGGCAATCCTTCTACTCTCGGGTCCTGGAGAACTGTG |
| | | AGGATGTGGCTGACTTTGATGAGACATTTCGGTGGCC |
| | | GGTGGCCAGCAGCATCGACAGAAATGAGATGCTGGAG |
| | | ATTCAGGTTTTCAACTACAGCAAAGTCTTCAGCAACAA |
| | | GCTCATCGGGACCTTCCGCATGGTGCTGCAGAAGGTG |
| | | GTAGAGGAGAGCCATGTGGGAGGTGACTGACACGCTGA |
| | | TTGATGACAACAATGCTATCATCAAGACCAGCCTGTGC |
| | | GTGGAGGTCCGGTATCAGGCCACTGACGGCACAGTG |
| | | GGCTCCTGGGACGATGGGGACTTCCTGGGAGATGAG |
| | | TCTCTTCAAGAGGAAGAGAAGGACAGCCAAGAGACGG |
| | | ATGGACTGCTCCCAGGCTCCCGGCCCAGCTCCCGGC |
| | | CCCCAGGAGAGAAGAGCTTCCGGAGAGCCGGGAGGA |
| | | GCGTGTTCTCCGCCATGAAGCTCGGCAAAAACCGGTC |
| | | TCACAAGGAGGAGCCCCAAAGACCAGATGAACCGGC |

TABLE 4-continued

Transfer plasmids for the production of dual hybrid vector systems

| SEQ ID NO. | Description | Plasmid Sequence |
|---|---|---|
| | | GGTGCTGGAGATGGAAGACCTTGACCATCTGGCCATT |
| | | CGGCTAGGAGATGGACTGGATCCCGACTCGGTGTCTC |
| | | TAGCCTCAGTCACAGCTCTCACCACTAATGTCTCCAAC |
| | | AAGCGATCTAAGCCAGACATTAAGATGGAGCCAAGTG |
| | | CTGGGCGGCCCATGGATTACCAGGTCAGCATCACGGT |
| | | GATCGAGGCCCGGCAGCTGGTGGGCTTGAACATGGA |
| | | CCCTGTGGTGTGCGTGGAGGTGGGTGACGACAAGAA |
| | | GTACACATCCATGAAGGAGTCCACTAACTGCCCCTATT |
| | | ACAACGAGTACTTCGTCTTCGACTTCCATGTCTCTCCG |
| | | GATGTCATGTTTGACAAGATCATCAAGATTTCGGTGAT |
| | | TCACTCCAAGAACCTGCTGCGCAGTGGCACCCTGGTG |
| | | GGCTCCTTCAAAATGGACGTGGGAACCGTGTACTCGC |
| | | AGCCAGAGCACCAGTTCCATCACAAGTGGGCCATCCT |
| | | GTCTGACCCCGATGACATCTCCTCGGGGCTGAAGGGC |
| | | TACGTGAAGTGTGACGTTGCCGTGGTGGGCAAAGGG |
| | | GACAACATCAAGACGCCCCACAAGGCCAATGAGACCG |
| | | ACGAAGATGACATTGAGGGGAACTTGCTGCTCCCCGA |
| | | GGGGGTGCCCCCCGAACGCCAGTGGGCCCGGTTCTA |
| | | TGTGAAAATTTACCGAGCAGAGGGGCTGCCCCGTATG |
| | | AACACAAGCCTCATGGCCAATGTAAAGAAGGCTTTCAT |
| | | CGGTGAAAACAAGGACCTCGTGGACCCCTACGTGCAA |
| | | GTCTTCTTTGCTGGCCAGAAGGGCAAGACTTCAGTGC |
| | | AGAAGAGCAGCTATGAGCCCCTGTGGAATGAGCAGGT |
| | | CGTCTTTACAGACCTCTTCCCCCCACTCTGCAAACGCA |
| | | TGAAGGTGCAGATCCGAGACTCGGACAAGGTCAACGA |
| | | CGTGGCCATCGGCACCCACTTCATTGACCTGCGCAAG |
| | | ATTTCTAATGACGGAGACAAAGGCTTCCTGCCCACACT |
| | | GGGCCCAGCCTGGGTGAACATGTACGGCTCCACACGT |
| | | AACTACACGCTGCTGGATGAGCATCAGGACCTGAACG |
| | | AGGGCCTGGGGGAGGGTGTGTCCTTCCGGGCCCGGC |
| | | TCCTGCTGGGCCTGGCTGTGGAGATCGTAGACACCTC |
| | | CAACCCTGAGCTCACCAGCTCCACAGAGGTGCAGGTG |
| | | GAGCAGGCCACGCCCATCTCGGAGAGCTGTGCAGGT |
| | | AAAATGGAAGAATTCTTTCTCTTTGGAGCCTTCCTGGA |
| | | GGCCTCAATGATCGACCGGAGAAACGGAGACAAGCCC |
| | | ATCACCTTTGAGGTCACCATAGGCAACTATGGGAACG |
| | | AAGTTGATGGCCTGTCCCGGCCCCAGCGGCCTCGGC |
| | | CCCGGAAGGAGCCGGGGGATGAGGAAGAAGTAGACC |
| | | TGATTCAGAACGCAAGTGATGACGAGGCCGGTGATGC |
| | | CGGGGACCTGGCCTCAGTCTCCTCCACTCCACCAATG |
| | | CGGCCCCAGGTCACCGACAGGAACTACTTCCATCTGC |
| | | CCTACCTGGAGCGAAAGCCCTGCATCTACATCAAGAG |
| | | CTGGTGGCCGGACCAGCGCCGCCGCCTCTACAATGC |
| | | CAACATCATGGACCACATTGCCGACAAGCTGGAAGAA |
| | | GGCCTGAACGACATACAGGAGATGATCAAAACGGAGA |
| | | AGTCCTACCCTGAGCGTCGCCTGCCGGGGCGTCCTGG |
| | | AGGAGCTGAGCTGTGGCTGCTGCCGCTTCCTCTCCCT |
| | | CGCTGACAAGGACCAGGGCCACTCATCCCGCACCAG |
| | | GCTTGACCGGGAGCGCCTCAAGTCCTGCATGAGGGA |
| | | GCTGGTAAGTATCAAGGTTACAAGACAGGTTTAAGGA |
| | | GACCAATAGAAACTGGGCTTGTCGAGACAGAGAAGAC |
| | | TCTTGCGTTTCTGAGCTAGCCCCCGGGTGCGCGGCGT |
| | | CGGTGGTGCCGGCGGGGGGCGCCAGGTCGCAGGCG |
| | | GTGTAGGGCTCCAGGCAGGCGGCGAAGGCCATGACG |
| | | TGCGCTATGAAGGTCTGCTCCTGCACGCCGTGAACCA |
| | | GGTGCGCCTGCGGGCCGCGCGCGAACACCGCCACGT |
| | | CCTCGCCTGCGTGGGTCTCTTCGTCCAGGGGCACTGC |
| | | TGACTGCTGCCGATACTCGGGGCTCCCGCTCTCGCTC |
| | | TCGGTAACATCCGGCCGGGCGCCGTCCTTGAGCACAT |
| | | AGCCTGGACCGTTTCGTCGACTGGGGAGAGATCTGAG |
| | | GAACCCCTAGTGATGGAGTTGGCCACTCCCTCTCTGC |
| | | GCGCTCGCTCGCTCACTGAGGCCGCCCGGGCAAAGC |
| | | CCGGGCGTCGGGCGACCTTTGGTCGCCCGGCCTCAG |
| | | TGAGCGAGCGAGCGCGCAGAGAGGGAGTGGCCAACC |
| | | CCCCCCCCCCCCCCCTGCAGCCTGGCGTAATAGCG |
| | | AAGAGGCCCGCACCGATCGCCCTTCCCAACAGTTGCG |
| | | TAGCCTGAATGGCGAATGGCGCGACGCGCCCTGTAG |
| | | CGGCGCATTAAGCGCGGCGGGTGTGGTGGTTACGCG |
| | | CAGCGTGACCGCTACACTTGCCAGCGCCCTAGCGCCC |
| | | GCTCCTTTCGCTTTCTTCCCTTCCTTTCTCGCCACGTT |
| | | CGCCGGCTTTCCCCGTCAAGCTCTAAATCGGGGGCTC |
| | | CCTTTAGGGTTCCGATTTAGTGCTTTACGGCACCTCGA |
| | | CCCCAAAAAACTTGATTAGGGTGATGGTTCACGTAGTG |
| | | GGCCATCGCCCTGATAGACGGTTTTTCGCCCTTTGAC |

TABLE 4-continued

Transfer plasmids for the production of dual hybrid vector systems

| SEQ ID NO. | Description | Plasmid Sequence |
|---|---|---|
| | | GTTGGAGTCCACGTTCTTTAATAGTGGACTCTTGTTCC |
| | | AAACTGGAACAACACTCAACCCTATCGCGGTCTATTCT |
| | | TTTGATTTATAAGGGATGTTGCCGATTTCGGCCTATTG |
| | | GTTAAAAAATGAGCTGATTTAACAAAAATTTTAACAAAA |
| | | TTCAGAAGAACTCGTCAAGAAGGCGATAGAAGGCGAT |
| | | GCGCTGCGAATCGGGAGCGGCGATACCGTAAAGCAC |
| | | GAGGAAGCGGTCAGCCCATTCGCCGCCAAGCTCTTCA |
| | | GCAATATCACGGGTAGCCAACGCTATGTCCTGATAGC |
| | | GGTCCGCCACACCCAGCCGGCCACAGTCGATGAATCC |
| | | AGAAAAGCGGCCATTTTCCACCATGATATTCGGCAAGC |
| | | AGGCATCGCCATGGGTCACGACGAGATCCTCGCCGTC |
| | | GGGCATGCTCGCCTTGAGCCTGGCGAACAGTTCGGCT |
| | | GGCGCGAGCCCCTGATGCTCTTCGTCCAGATCATCCT |
| | | GATCGACAAGACCGGCTTCCATCCGAGTACGTGCTCG |
| | | CTCGATGCGATGTTTCGCTTGGTGGTCGAATGGGCAG |
| | | GTAGCCGGATCAAGCGTATGCAGCCGCCGCATTGCAT |
| | | CAGCCATGATGGATACTTTCTCGGCAGGAGCAAGGTG |
| | | AGATGACAGGAGATCCTGCCCCGGCACTTCGCCCAAT |
| | | AGCAGCCAGTCCCTTCCCGCTTCAGTGACAACGTCGA |
| | | GCACAGCTGCGCAAGGAACGCCCGTCGTGGCCAGCC |
| | | ACGATAGCCGCGCTGCCTCGTCTTGCAGTTCATTCAG |
| | | GGCACCGGACAGGTCGGTCTTGACAAAAAGAACCGG |
| | | GCGCCCCTGCGCTGACAGCCGGAACACGGCGGCATC |
| | | AGAGCAGCCGATTGTCTGTTGTGCCCAGTCATAGCCG |
| | | AATAGCCTCTCCACCCAAGCGGCCGGAGAACCTGCGT |
| | | GCAATCCATCTTGTTCAATCATGCGAAACGATCCTCAT |
| | | CCTGTCTCTTGATCAGATCTTGATCCCCTGCGCCATCA |
| | | GATCCTTGGCGGCGAGAAAGCCATCCAGTTTACTTTG |
| | | CAGGGCTTCCCAACCTTACCAGAGGGCGCCCCAGCTG |
| | | GCAATTCCGGTTCGCTTGCTGTCCATAAAACCGCCCA |
| | | GTCTAGCTATCGCCATGTAAGCCCACTGCAAGCTACCT |
| | | GCTTTCTCTTTGCGCTTGCGTTTTCCCTTGTCCAGATA |
| | | GCCCAGTAGCTGACATTCATCCGGGGTCAGCACCGTT |
| | | TCTGCGGACTGGCTTTCTACGTGAAAAGGATCTAGGT |
| | | GAAGATCCTTTTTGATAATCTCATGACCAAAATCCCTTA |
| | | ACGTGAGTTTTCGTTCCACTGAGCGTCAGACCCCGTA |
| | | GAAAAGATCAAAGGATCTTCTTGAGATCCTTTTTTTCTG |
| | | CGCGTAATCTGCTGCTTGCAAACAAAAAAACCACCGCT |
| | | ACCAGCGGTGGTTTGTTTGCCGGATCAAGAGCTACCA |
| | | ACTCTTTTTCCGAAGGTAACTGGCTTCAGCAGAGCGCA |
| | | GATACCAAATACTGTCCTTCTAGTGTAGCCGTAGTTAG |
| | | GCCACCACTTCAAGAACTCTGTAGCACCGCCTACATAC |
| | | CTCGCTCTGCTAATCCTGTTACCAGTGGCTGCTGCCA |
| | | GTGGCGATAAGTCGTGTCTTACCGGGTTGGACTCAAG |
| | | ACGATAGTTACCGGATAAGGCGCAGCGGTCGGGCTGA |
| | | ACGGGGGGTTCGTGCACACAGCCCAGCTTGGAGCGA |
| | | ACGACCTACACCGAACTGAGATACCTACAGCGTGAGC |
| | | TATGAGAAAGCGCCACGCTTCCCGAAGGGAGAAAGGC |
| | | GGACAGGTATCCGGTAAGCGGCAGGGTCGGAACAGG |
| | | AGAGCGCACGAGGGAGCTTCCAGGGGGAAACGCCTG |
| | | GTATCTTTATAGTCCTGTCGGGTTTCGCCACCTCTGAC |
| | | TTGAGCGTCGATTTTTGTGATGCTCGTCAGGGGGGCG |
| | | GAGCCTATGGAAAAACGCCAGCAACGCGGCCTTTTTA |
| | | CGGTTCCTGGGCTTTTGCTGGCCTTTTGCTCACATGTT |
| | | CTTTCCTGCGTTATCCCCTGATTCTGTGGATAACCGTA |
| | | TTACCGCCTTTGAGTGAGCTGATACCGCTCGCCGCAG |
| | | CCGAACGACCGAGCGCAGCGAGTCAGTGAGCGAGGA |
| | | AGCGGAAGAGCGCCCAATACGCAAACCGCCTCTCCCC |
| | | GCGCGTTGGCCGATTCATTAATGCAGGGCTGCA |
| 66 | 5' transgene plasmid containing the following features:<br>ITR at positions 12-141<br>Myo15 promoter at positions 235-1199<br>Kozak sequence at positions 1216-1225<br>N-terminal portion of human OTOF isoform 5 at positions 1222-3627<br>Splice donor sequence at positions 3628-3711<br>AP head sequence at positions 3718-4004 | CCTTAATTAGGCTGCGCGCTCGCTCGCTCACTGAGGC<br>CGCCCGGGCAAAGCCCGGGCGTCGGGCGACCTTTGG<br>TCGCCCGGCCTCAGTGAGCGAGCGAGCGCGCAGAGA<br>GGGAGTGGCCAACTCCATCACTAGGGGTTCCTTGTAG<br>TTAATGATTAACCCGCCATGCTACTTATCTACGTAGCC<br>ATGCTCTAGGAAGATCGGAATTCGCCCTTAAGCTAGC<br>GGCGCGCCCAATTCTGCAGCTCAGCCTACTACTTGCT<br>TTCCAGGCTGTTCCTAGTTCCCATGTCAGCTGCTTGTG<br>CTTTCCAGAGACAAAACAGGAATAATAGATGTCATTAA<br>ATATACATTGGGCCCCAGGCGGTCAATGTGGCAGCCT<br>GAGCCTCCTTTCCATCTCTGTGGAGGCAGACATAGGA<br>CCCCCAACAAACAGCATGCAGGTTGGGAGCCAGCCAC<br>AGGACCCAGGTAAGGGGCCCTGGGTCCTTAAGCTTCT<br>GCCACTGGCTCCGGCATTGCAGAGAGAAGAGAAGGG |

TABLE 4-continued

Transfer plasmids for the production of dual hybrid vector systems

| SEQ ID NO. | Description | Plasmid Sequence |
|---|---|---|
| | ITR at positions 4098-4227<br>M13 fwd at positions 4246-4262<br>f1 ori at positions 4404-4859<br>AmpR promoter at positions 4885-4989<br>KanR at positions 4990-5799<br>mutBsmBI at positions 5430-5430<br>ori at positions 5970-6558<br>CAP binding site at positions 6846-6867<br>lac promoter at positions 6882-6912<br>lac operator at positions 6920-6936<br>M13 rev at positions 6944-6960<br>Transgene to be transferred into vector in dual vector system at positions 12-4227 | GCGGCAGACTGGAGAGCTGGGCTCCATTTTTGTTCCT<br>TGGTGCCCTGCCCCTCCCCATGACCTGCAGAGACATT<br>CAGCCTGCCAGGCTTTATGAGGTGGGAGCTGGGCTCT<br>CCCTGATGTATTATTCAGCTCCCTGGAGTTGGCCAGCT<br>CCTGTTACACTGGCCACAGCCCTGGGCATCCGCTTCT<br>CACTTCTAGTTTCCCCTCCAAGGTAATGTGGTGGGTCA<br>TGATCATTCTATCCTGGCTTCAGGGACCTGACTCCACT<br>TTGGGGCCATTCGAGGGGTCTAGGGTAGATGATGTCC<br>CCCTGTGGGGATTAATGTCCTGCTCTGTAAAACTGAGC<br>TAGCTGAGATCCAGGAGGGCTTGGCCAGAGACAGCAA<br>GTTGTTGCCATGGTGACTTTAAAGCCAGGTTGCTGCC<br>CCAGCACAGGCCTCCCAGTCTACCCTCACTAGAAAAC<br>AACACCCAGGCACTTTCCACCACCTCTCAAAGGTGAAA<br>CCCAAGGCTGGTCTAGAGAATGAATTATGGATCCTCG<br>CTGTCCGTGCCACCCAGCTAGTCCCAGCGGCTCAGAC<br>ACTGAGGAGAGACTGTAGGTTCAGCTACAAGCAAAAA<br>GACCTAGCTGGTCTCCAAGCAGTGTCTCCAAGTCCCT<br>GAACCTGTGACACCTGCCCCAGGCATCATCAGGCACA<br>GAGGGCCACCAAGAATTCTAGCGGCCGCCCACCATGG<br>CCTTGCTCATCCACCTCAAGACAGTCTCGGAGCTGCG<br>GGGCAGGGGCGACCGGATCGCCAAAGTGACTTTCCG<br>AGGGCAATCCTTCTACTCTCGGGTCCTGGAGAACTGT<br>GAGGATGTGGCTGACTTTGATGAGACATTTCGGTGGC<br>CGGTGGCCAGCAGCATCGACAGAAATGAGATGCTGGA<br>GATTCAGGTTTTCAACTACAGCAAAGTCTTCAGCAACA<br>AGCTCATCGGGACCTTCCGCATGGTGCTGCAGAAGGT<br>GGTAGAGGAGAGCCATGTGGAGGTGACTGACACGCT<br>GATTGATGACAACAATGCTATCATCAAGACCAGCCTGT<br>GCGTGGAGGTCCGGTATCAGGCCACTGACGGCACAG<br>TGGGCTCCTGGGACGATGGGGACTTCCTGGGAGATG<br>AGTCTCTTCAAGAGGAAGAGAAGGACAGCCAAGAGAC<br>GGATGGACTGCTCCCAGGCTCCCGGCCCAGCTCCCG<br>GCCCCCAGGAGAGAAGAGCTTCCGGAGAGCCGGGAG<br>GAGCGTGTTCTCCGCCATGAAGCTCGGCAAAAACCGG<br>TCTCACAAGGAGGAGCCCCAAAGACCAGATGAACCGG<br>CGGTGCTGGAGATGGAAGACCTTGACCATCTGGCCAT<br>TCGGCTAGGAGATGGACTGGATCCCGACTCGGTGTCT<br>CTAGCCTCAGTCACAGCTCTCACCACTAATGTCTCCAA<br>CAAGCGATCTAAGCCAGACATTAAGATGGAGCCAAGT<br>GCTGGGCGGCCCATGGATTACCAGGTCAGCATCACG<br>GTGATCGAGGCCCGGCAGCTGGTGGGCTTGAACATG<br>GACCCTGTGGTGTGCGTGGAGGTGGGTGACGACAAG<br>AAGTACACATCCATGAAGGAGTCCACTAACTGCCCCTA<br>TTACAACGAGTACTTCGTCTTCGACTTCCATGTCTCTC<br>CGGATGTCATGTTTGACAAGATCATCAAGATTTCGGTG<br>ATTCACTCCAAGAACCTGCTGCGCAGTGGCACCCTGG<br>TGGGCTCCTTCAAAATGGACGTGGGAACCGTGTACTC<br>GCAGCCAGAGCACCAGTTCCATCACAAGTGGGCCATC<br>CTGTCTGACCCCGATGACATCTCCTCGGGGCTGAAGG<br>GCTACGTGAAGTGTGACGTTGCCGTGGTGGGCAAAGG<br>GGACAACATCAAGACGCCCCACAAGGCCAATGAGACC<br>GACGAAGATGACATTGAGGGGAACTTGCTGCTCCCCG<br>AGGGGGTGCCCCCCGAACGCCAGTGGGCCCGGTTCT<br>ATGTGAAAATTTACCGAGCAGAGGGGCTGCCCCGTAT<br>GAACACAAGCCTCATGGCCAATGTAAAGAAGGCTTTCA<br>TCGGTGAAAACAAGGACCTCGTGGACCCCTACGTGCA<br>AGTCTTCTTTGCTGGCCAGAAGGGCAAGACTTCAGTG<br>CAGAAGAGCAGCTATGAGCCCCTGTGGAATGAGCAGG<br>TCGTCTTTACAGACCTCTTCCCCCCCACTCTGCAAACGC<br>ATGAAGGTGCAGATCCGAGACTCGGACAAGGTCAACG<br>ACGTGGCCATCGGCACCCACTTCATTGACCTGCGCAA<br>GATTTCTAATGACGGAGACAAAGGCTTCCTGCCCCACA<br>CTGGGCCCAGCCTGGGTGAACATGTACGGCTCCACAC<br>GTAACTACACGCTGCTGGATGAGCATCAGGACCTGAA<br>CGAGGGCCTGGGGGAGGGTGTGTCCTTCCGGGCCCG<br>GCTCCTGCTGGGCCTGGCTGTGGAGATCGTAGACACC<br>TCCAACCCTGAGCTCACCAGCTCCACAGAGGTGCAGG<br>TGGAGCAGGCCACGCCCATCTCGGAGAGCTGTGCAG<br>GTAAAATGGAAGAATTCTTTCTCTTTGGAGCCTTCCTG<br>GAGGCCTCAATGATCGACCGGAGAAACGGAGACAAGC<br>CCATCACCTTTGAGGTCACCATAGGCAACTATGGGAA<br>CGAAGTTGATGGCCTGTCCCGGCCCCAGCGGCCTCG<br>GCCCCGGAAGGAGCCGGGGGATGAGGAAGAAGTAGA<br>CCTGATTCAGAACGCAAGTGATGACGAGGCCGGTGAT |

TABLE 4-continued

Transfer plasmids for the production of dual hybrid vector systems

| SEQ ID NO. Description | Plasmid Sequence |
|---|---|
| | GCCGGGGACCTGGCCTCAGTCTCCTCCACTCCACCAA |
| | TGCGGCCCCAGGTCACCGACAGGAACTACTTCCATCT |
| | GCCCTACCTGGAGCGAAAGCCCTGCATCTACATCAAG |
| | AGCTGGTGGCCGGACCAGCGCCGCCGCCTCTACAAT |
| | GCCAACATCATGGACCACATTGCCGACAAGCTGGAAG |
| | AAGGCCTGAACGACATACAGGAGATGATCAAAACGGA |
| | GAAGTCCTACCCTGAGCGTCGCCTGCGGGGCGTCCT |
| | GGAGGAGCTGAGCTGTGGCTGCTGCCGCTTCCTCTCC |
| | CTCGCTGACAAGGACCAGGGCCACTCATCCCGCACCA |
| | GGCTTGACCGGGAGCGCCTCAAGTCCTGCATGAGGG |
| | AGCTGGTAAGTATCAAGGTTACAAGACAGGTTTAAGGA |
| | GACCAATAGAAACTGGGCTTGTCGAGACAGAGAAGAC |
| | TCTTGCGTTTCTGAGCTAGCCCCCGGGTGCGCGGCGT |
| | CGGTGGTGCCGGCGGGGGGCGCCAGGTCGCAGGCG |
| | GTGTAGGGCTCCAGGCAGGCGGCGAAGGCCATGACG |
| | TGCGCTATGAAGGTCTGCTCCTGCACGCCGTGAACCA |
| | GGTGCGCCTGCGGGCCGCGCGCGAACACCGCCACGT |
| | CCTCGCCTGCGTGGGTCTCTTCGTCCAGGGGCACTGC |
| | TGACTGCTGCCGATACTCGGGGGCTCCCGCTCTCGCTC |
| | TCGGTAACATCCGGCCGGGCGCCGTCCTTGAGCACAT |
| | AGCCTGGACCGTTTCGTCGACCTCGAGTTAAGGGCGA |
| | ATTCCCGATAAGGATCTTCCTAGAGCATGGCTACGTAG |
| | ATAAGTAGCATGGCGGGTTAATCATTAACTACAAGGAA |
| | CCCCTAGTGATGGAGTTGGCCACTCCCTCTCTGCGCG |
| | CTCGCTCGCTCACTGAGGCCGGGCGACCAAAGGTCG |
| | CCCGACGCCCGGGCTTTGCCCGGGCGGCCTCAGTGA |
| | GCGAGCGAGCGCGCAGCCTTAATTAACCTAATTCACT |
| | GGCCGTCGTTTTACAACGTCGTGACTGGGAAAACCCT |
| | GGCGTTACCCAACTTAATCGCCTTGCAGCACATCCCC |
| | CTTTCGCCAGCTGGCGTAATAGCGAAGAGGCCCGCAC |
| | CGATCGCCCTTCCCAACAGTTGCGCAGCCTGAATGGC |
| | GAATGGGACGCGCCCTGTAGCGGCGCATTAAGCGCG |
| | GCGGGTGTGGTGGTTACGCGCAGCGTGACCGCTACA |
| | CTTGCCAGCGCCCTAGCGCCCGCTCCTTTCGCTTTCT |
| | TCCCTTCCTTTCTCGCCACGTTCGCCGGCTTTCCCCGT |
| | CAAGCTCTAAATCGGGGGCTCCCTTTAGGGTTCCGAT |
| | TTAGTGCTTTACGGCACCTCGACCCCAAAAAACTTGAT |
| | TAGGGTGATGGTTCACGTAGTGGGCCATCGCCCTGAT |
| | AGACGGTTTTTCGCCCTTTGACGTTGGAGTCCACGTTC |
| | TTTAATAGTGGACTCTTGTTCCAAACTGGAACAACACT |
| | CAACCCTATCTCGGTCTATTCTTTTGATTTATAAGGGAT |
| | TTTGCCGATTTCGGCCTATTGGTTAAAAAATGAGCTGA |
| | TTTAACAAAAATTTAACGCGAATTTTAACAAAATATTAA |
| | CGCTTACAATTTAGGTGGCACTTTTCGGGGAAATGTGC |
| | GCGGAACCCCTATTTGTTTATTTTTCTAAATACATTCAA |
| | ATATGTATCCGCTCATGAGACAATAACCCTGATAAATG |
| | CTTCAATAATATTGAAAAAGGAAGAGTATGAGCCATAT |
| | TCAACGGGAAACGTCGAGGCCGCGATTAAATTCCAAC |
| | ATGGATGCTGATTTATATGGGTATAAATGGGCTCGCGA |
| | TAATGTCGGGCAATCAGGTGCGACAATCTATCGCTTGT |
| | ATGGGAAGCCCGATGCGCCAGAGTTGTTTCTGAAACA |
| | TGGCAAAGGTAGCGTTGCCAATGATGTTACAGATGAG |
| | ATGGTCAGACTAAACTGGCTGACGGAATTTATGCCTCT |
| | TCCGACCATCAAGCATTTTATCCGTACTCCTGATGATG |
| | CATGGTTACTCACCACTGCGATCCCCGGAAAAACAGC |
| | ATTCCAGGTATTAGAAGAATATCCTGATTCAGGTGAAA |
| | ATATTGTTGATGCGCTGGCAGTGTTCCTGCGCCGGTT |
| | GCATTCGATTCCTGTTTGTAATTGTCCTTTTAACAGCGA |
| | TCGCGTATTTCGTCTTGCTCAGGCGCAATCACGAATGA |
| | ATAACGGTTTGGTTGATGCGAGTGATTTTGATGACGAG |
| | CGTAATGGCTGGCCTGTTGAACAAGTCTGGAAAGAAA |
| | TGCATAAACTTTTGCCATTCTCACCGGATTCAGTCGTC |
| | ACTCATGGTGATTTCTCACTTGATAACCTTATTTTTGAC |
| | GAGGGGAAATTAATAGGTTGTATTGATGTTGGACGAGT |
| | CGGAATCGCAGACCGATACCAGGATCTTGCCATCCTA |
| | TGGAACTGCCTCGGTGAGTTTTCTCCTTCATTACAGAA |
| | ACGGCTTTTTCAAAAATATGGTATTGATAATCCTGATAT |
| | GAATAAATTGCAGTTTCATTTGATGCTCGATGAGTTTTT |
| | CTAACTGTCAGACCAAGTTTACTCATATATACTTTAGAT |
| | TGATTTAAAACTTCATTTTTAATTTAAAAGGATCTAGGT |
| | GAAGATCCTTTTTGATAATCTCATGACCAAAATCCCTTA |
| | ACGTGAGTTTTCGTTCCACTGAGCGTCAGACCCCGTA |
| | GAAAAGATCAAAGGATCTTCTTGAGATCCTTTTTTTCTG |
| | CGCGTAATCTGCTGCTTGCAAACAAAAAAACCACCGCT |

TABLE 4-continued

Transfer plasmids for the production of dual hybrid vector systems

| SEQ ID NO. | Description | Plasmid Sequence |
|---|---|---|
| | | ACCAGCGGTGGTTTGTTTGCCGGATCAAGAGCTACCA ACTCTTTTTCCGAAGGTAACTGGCTTCAGCAGAGCGCA GATACCAAATACTGTTCTTCTAGTGTAGCCGTAGTTAG GCCACCACTTCAAGAACTCTGTAGCACCGCCTACATAC CTCGCTCTGCTAATCCTGTTACCAGTGGCTGCTGCCA GTGGCGATAAGTCGTGTCTTACCGGGTTGGACTCAAG ACGATAGTTACCGGATAAGGCGCAGCGGTCGGGCTGA ACGGGGGGTTCGTGCACACAGCCCAGCTTGGAGCGA ACGACCTACACCGAACTGAGATACCTACAGCGTGAGC TATGAGAAAGCGCCACGCTTCCCGAAGGGAGAAAGGC GGACAGGTATCCGGTAAGCGGCAGGGTCGGAACAGG AGAGCGCACGAGGGAGCTTCCAGGGGGAAACGCCTG GTATCTTTATAGTCCTGTCGGGTTTCGCCACCTCTGAC TTGAGCGTCGATTTTTGTGATGCTCGTCAGGGGGGCG GAGCCTATGGAAAAACGCCAGCAACGCGGCCTTTTTA CGGTTCCTGGCCTTTTGCTGGCCTTTTGCTCACATGTT CTTTCCTGCGTTATCCCCTGATTCTGTGGATAACCGTA TTACCGCCTTTGAGTGAGCTGATACCGCTCGCCGCAG CCGAACGACCGAGCGCAGCGAGTCAGTGAGCGAGGA AGCGGAAGAGCGCCCAATACGCAAACCGCCTCTCCCC GCGCGTTGGCCGATTCATTAATGCAGCTGGCACGACA GGTTTCCCGACTGGAAAGCGGGCAGTGAGCGCAACG CAATTAATGTGAGTTAGCTCACTCATTAGGCACCCCAG GCTTTACACTTTATGCTTCCGGCTCGTATGTTGTGTGG AATTGTGAGCGGATAACAATTTCACACAGGAAACAGCT ATGACCATGATTACGCCAGATTTAATTAAGG |
| 67 | 3' transgene plasmid containing the following features: ITR at positions 12-141 AP head sequence at positions 229-515 Splice acceptor sequence at positions 538-586 C-terminal portion of human OTOF isoform 5 at positions 587-4174 bGH poly(A) sequence at positions 4217-4438 ITR at positions 4526-4655 M13 fwd at positions 4674-4690 f1 ori at positions 4832-5287 AmpR promoter at positions 5313-5417 KanR at positions 5418-6227 mutBsmBI at positions 5858-5858 ori at positions 6398-6986 CAP binding site at positions 7274-7295 lac promoter at positions 7310-7340 lac operator at positions 7348-7364 M13 rev at positions 7372-7388 Transgene to be transferred into vector in dual vector system at positions 12-4655 | CCTTAATTAGGCTGCGCGCTCGCTCGCTCACTGAGGC CGCCCGGGCAAAGCCCGGGCGTCGGGCGACCTTTGG TCGCCCGGCCTCAGTGAGCGAGCGAGCGCGCAGAGA GGGGAGTGGCCAACTCCATCACTAGGGGTTCCTTGTAG TTAATGATTAACCCGCCATGCTACTTATCTACGTAGCC ATGCTCTAGGAAGATCGGAATTCGCCCTTAAGCTAGC GGCGCGCCCCCGGGTGCGCGGCGTCGGTGGTGCCG GCGGGGGGCGCCAGGTCGCAGGCGGTGTAGGGCTC CAGGCAGGCGGCGAAGGCCATGACGTGCGCTATGAA GGTCTGCTCCTGCACGCCGTGAACCAGGTGCGCCTG CGGGCCGCGCGCGAACACCGCCACGTCCTCGCCTGC GTGGGTCTCTTCGTCCAGGGGCACTGCTGACTGCTGC CGATACTCGGGGCTCCCGCTCTCGCTCTCGGTAACAT CCGGCCGGGCGCCGTCCTTGAGCACATAGCCTGGAC CGTTTCCTTAAGCGACGCATGCTCGCGATAGGCACCT ATTGGTCTTACTGACATCCACTTTGCCTTTCTCTCCACA GGAAAACATGGGCAGCAGGCCAGGATGCTGCGGGC CCAGGTGAAGCGGCACACGGTGCGGGACAAGCTGAG GCTGTGCCAGAACTTCCTGCAGAAGCTGCGCTTCCTG GCGGACGAGCCCCAGCACAGCATTCCCGACATCTTCA TCTGGATGATGAGCAACAACAAGCGTGTCGCCTATGC CCGTGTGCCCTCCAAGGACCTGCTCTTCTCCATCGTG GAGGAGGAGACTGGCAAGGACTGCGCCAAGGTCAAG ACGCTCTTCCTTAAGCTGCCAGGGAAGCGGGGCTTCG GCTCGGCAGGCTGGACAGTGCAGGCCAAGGTGGAGC TGTACCTGTGGCTGGGCCTCAGCAAACAGCGCAAGGA GTTCCTGTGCGGCCTGCCCTGTGGCTTCCAGGAGGTC AAGGCAGCCCAGGGCCTGGGCCTGCATGCCTTCCCA CCCGTCAGCCTGGTCTACACCAAGAAGCAGGCGTTCC AGCTCCGAGCGCACATGTACCAGGCCCGCAGCCTCTT TGCCGCCGACAGCAGCGGACTCTCAGACCCCCTTTGCC CGCGTCTTCTTCATCAATCAGAGTCAGTGCACAGAGGT GCTGAATGAGACCCTGTGTCCCACCTGGGACCAGATG CTGGTGTTCGACAACCTGGAGCTCTATGGTGAAGCTC ATGAGCTGAGGGACGATCCGCCCATCATTGTCATTGA AATCTATGACCAGGATTCCATGGGCAAAGCTGACTTCA TGGGCCGGACCTTCGCCAAACCCCTGGTGAAGATGGC AGACGAGGCGTACTGCCCACCCCGCTTCCCACCTCAG CTCGAGTACTACCAGATCTACCGTGGCAACGCCACAG CTGGAGACCTGCTGGCGGCCTTCGAGCTGCTGCAGAT TGGACCAGCAGGGAAGGCTGACCTGCCCCCCCATCAAT GGCCCGGTGGACGTGGACCGAGGTCCCATCATGCCC GTGCCCATGGGCATCCGGCCCGTGCTCAGCAAGTACC GAGTGGAGGTGCTGTTCTGGGGCCTACGGGACCTAAA GCGGGTGAACCTGGCCCAGGTGGACCGGCCACGGGT GGACATCGAGTGTGCAGGGAAGGGGGTGCAGTCGTC CCTGATCCACAATTATAAGAAGAACCCCAACTTCAACA |

TABLE 4-continued

Transfer plasmids for the production of dual hybrid vector systems

| SEQ ID NO. | Description | Plasmid Sequence |
|---|---|---|
| | | CCCTCGTCAAGTGGTTTGAAGTGGACCTCCCAGAGAA |
| | | CGAGCTGCTGCACCCGCCCTTGAACATCCGTGTGGTG |
| | | GACTGCCGGGCCTTCGGTCGCTACACACTGGTGGGCT |
| | | CCCATGCCGTCAGCTCCCTGCGACGCTTCATCTACCG |
| | | GCCCCCAGACCGCTCGGCCCCCAGCTGGAACACCAC |
| | | GGTCAGGCTTCTCCGGCGCTGCCGTGTGCTGTGCAAT |
| | | GGGGGCTCCTCCTCTCACTCCACAGGGGAGGTTGTG |
| | | GTGACTATGGAGCCAGAGGTACCCATCAAGAAACTGG |
| | | AGACCATGGTGAAGCTGGACGCGACTTCTGAAGCTGT |
| | | TGTCAAGGTGGATGTGGCTGAGGAGGAGAAGGAGAA |
| | | GAAGAAGAAGAAGAGGGCACTGCGGAGGAGCCAGA |
| | | GGAGGAGGAGCCAGACGAGAGCATGCTGGACTGGTG |
| | | GTCCAAGTACTTTGCCTCCATTGACACCATGAAGGAGC |
| | | AACTTCGACAACAAGAGCCCTCTGGAATTGACTTGGA |
| | | GGAGAAGGAGGAAGTGGACAATACCGAGGGCCTGAA |
| | | GGGGTCAATGAAGGGCAAGGAGAAGGCAAGGGCTGC |
| | | CAAAGAGGAGAAGAAGAAGAAACTCAGAGCTCTGGC |
| | | TCTGGCCAGGGGTCCGAGGCCCCCGAGAAGAAGAAA |
| | | CCCAAGATTGATGAGCTTAAGGTATACCCCAAAGAGCT |
| | | GGAGTCCGAGTTTGATAACTTTGAGGACTGGCTGCAC |
| | | ACTTTCAACTTGCTTCGGGGCAAGACCGGGGATGATG |
| | | AGGATGGCTCCACCGAGGAGGAGCGCATTGTGGGAC |
| | | GCTTCAAGGGCTCCCTCTGCGTGTACAAAGTGCCACT |
| | | CCCAGAGGACGTGTCCCGGGAAGCCGGCTACGACTC |
| | | CACCTACGGCATGTTCCAGGGCATCCCGAGCAATGAC |
| | | CCCATCAATGTGCTGGTCCGAGTCTATGTGGTCCGGG |
| | | CCACGGACCTGCACCCTGCTGACATCAACGGCAAAGC |
| | | TGACCCCTACATCGCCATCCGGCTAGGCAAGACTGAC |
| | | ATCCGCGACAAGGAGAACTACATCTCCAAGCAGCTCA |
| | | ACCCTGTCTTTGGGAAGTCCTTTGACATCGAGGCCTC |
| | | CTTCCCCATGGAATCCATGCTGACGGTGGCTGTGTAT |
| | | GACTGGGACCTGGTGGGCACTGATGACCTCATTGGGG |
| | | AAACCAAGATCGACCTGGAGAACCGCTTCTACAGCAA |
| | | GCACCGCGCCACCTGCGGCATCGCCCAGACCTACTC |
| | | CACACATGGCTACAATATCTGGCGGGACCCCATGAAG |
| | | CCCAGCCAGATCCTGACCCGCCTCTGCAAAGACGGCA |
| | | AAGTGGACGGCCCCCACTTTGGGCCCCCTGGGAGAG |
| | | TGAAGGTGGCCAACCGCGTCTTCACTGGGCCCTCTGA |
| | | GATTGAGGACGAGAACGGTCAGAGGAAGCCCACAGA |
| | | CGAGCATGTGGCGCTGTTGGCCCTGAGGCACTGGGA |
| | | GGACATCCCCCGCGCAGGCTGCCGCCTGGTGCCAGA |
| | | GCATGTGGAGACGAGGCCGCTGCTCAACCCCGACAA |
| | | GCCGGGCATCGAGCAGGGCCGCCTGGAGCTGTGGGT |
| | | GGACATGTTCCCCATGGACATGCCAGCCCCTGGGACG |
| | | CCTCTGGACATCTCACCTCGGAAGCCCAAGAAGTACG |
| | | AGCTGCGGGTCATCATCTGGAACACAGATGAGGTGGT |
| | | CTTGGAGGACGACGACTTCTTCACAGGGGAGAAGTCC |
| | | AGTGACATCTTCGTGAGGGGGTGGCTGAAGGGCCAG |
| | | CAGGAGGACAAGCAGGACACAGACGTCCACTACCACT |
| | | CCCTCACTGGCGAGGGCAACTTCAACTGGCGCTACCT |
| | | GTTCCCCTTCGACTACCTGGCGGCGGAGGAGAAGATC |
| | | GTCATCTCCAAGAAGGAGTCCATGTTCTCCTGGGACG |
| | | AGACCGAGTACAAGATCCCCGCGCGGCTCACCCTGCA |
| | | GATCTGGGATGCGGACCACTTCTCCGCTGACGACTTC |
| | | CTGGGGGCCATCGAGCTGGACCTGAACCGGTTCCCG |
| | | CGGGGCGCAAAGACAGCCAAGCAGTGCACCATGGAG |
| | | ATGGCCACCGGGGAGGTGGACGTGCCCCTCGTGTCC |
| | | ATCTTCAAGCAAAAGCGCGTCAAAGGCTGGTGGCCCC |
| | | TCCTGGCCCGCAATGAGAACGATGAGTTTGAGCTCAC |
| | | GGGCAAGGTGGAGGCTGAGCTGCATTTACTGACAGCA |
| | | GAGGAGGCAGAGAAGAACCCAGTGGGCCTGGCCCGC |
| | | AATGAACCTGACCCCCTAGAGAAACCCAACCGGCCCG |
| | | ACACGGCCTTCGTCTGGTTCCTCAACCCTCTCAAGTCC |
| | | ATCAAGTACCTCATCTGCACCCGGTACAAGTGGCTCAT |
| | | CATCAAGATCGTGCTGGCGCTGTTGGGGCTGCTCATG |
| | | TTGGGGCTCTTCCTCTACAGCCTCCCTGGCTACATGG |
| | | TCAAAAAGCTCCTTGGGGCATGAACGGCCGCTATGCT |
| | | AGCTTGGTACCAAGGGCGGATCCTGCATAGAGCTCGC |
| | | TGATCAGCCTCGACTGTGCCTTCTAGTTGCCAGCCATC |
| | | TGTTGTTTGCCCCTCCCCCGTGCCTTCCTTGACCCTG |
| | | GAAGGTGCCACTCCCACTGTCCTTTCCTAATAAAATGA |
| | | GGAAATTGCATCGCATTGTCTGAGTAGGTGTCATTCTA |
| | | TTCTGGGGGGTGGGGTGGGGCAGGACAGCAAGGGG |
| | | GAGGATTGGGAAGACAATAGCAGGCATCTCGAGTTAA |

TABLE 4-continued

Transfer plasmids for the production of dual hybrid vector systems

| SEQ ID NO. | Description | Plasmid Sequence |
|---|---|---|
| | | GGGCGAATTCCCGATAAGGATCTTCCTAGAGCATGGC |
| | | TACGTAGATAAGTAGCATGGCGGGTTAATCATTAACTA |
| | | CAAGGAACCCCTAGTGATGGAGTTGGCCACTCCCTCT |
| | | CTGCGCGCTCGCTCGCTCACTGAGGCCGGGCGACCA |
| | | AAGGTCGCCCGACGCCCGGGCTTTGCCCGGGCGGCC |
| | | TCAGTGAGCGAGCGAGCGCGCAGCCTTAATTAACCTA |
| | | ATTCACTGGCCGTCGTTTTACAACGTCGTGACTGGGAA |
| | | AACCCTGGCGTTACCCAACTTAATCGCCTTGCAGCACA |
| | | TCCCCCTTTCGCCAGCTGGCGTAATAGCGAAGAGGCC |
| | | CGCACCGATCGCCCTTCCCAACAGTTGCGCAGCCTGA |
| | | ATGGCGAATGGGACGCGCCCTGTAGCGGCGCATTAA |
| | | GCGCGGCGGGTGTGGTGGTTACGCGCAGCGTGACCG |
| | | CTACACTTGCCAGCGCCCTAGCGCCCGCTCCTTTCGC |
| | | TTTCTTCCCTTCCTTTCTCGCCACGTTCGCCGGCTTTC |
| | | CCCGTCAAGCTCTAAATCGGGGGCTCCCTTTAGGGTT |
| | | CCGATTTAGTGCTTTACGGCACCTCGACCCCAAAAAAC |
| | | TTGATTAGGGTGATGGTTCACGTAGTGGGCCATCGCC |
| | | CTGATAGACGGTTTTTCGCCCTTTGACGTTGGAGTCCA |
| | | CGTTCTTTAATAGTGGACTCTTGTTCCAAACTGGAACA |
| | | ACACTCAACCCTATCTCGGTCTATTCTTTTGATTTATAA |
| | | GGGATTTTGCCGATTTCGGCCTATTGGTTAAAAAATGA |
| | | GCTGATTTAACAAAAATTTAACGCGAATTTTAACAAAAT |
| | | ATTAACGCTTACAATTTAGGTGGCACTTTTCGGGGAAA |
| | | TGTGCGCGGAACCCCTATTTGTTTATTTTTCTAAATACA |
| | | TTCAAATATGTATCCGCTCATGAGACAATAACCCTGAT |
| | | AAATGCTTCAATAATATTGAAAAAGGAAGAGTATGAGC |
| | | CATATTCAACGGGAAACGTCGAGGCCGCGATTAAATT |
| | | CCAACATGGATGCTGATTTATATGGGTATAAATGGGCT |
| | | CGCGATAATGTCGGGCAATCAGGTGCGACAATCTATC |
| | | GCTTGTATGGGAAGCCCGATGCGCCAGAGTTGTTTCT |
| | | GAAACATGGCAAAGGTAGCGTTGCCAATGATGTTACA |
| | | GATGAGATGGTCAGACTAAACTGGCTGACGGAATTTAT |
| | | GCCTCTTCCGACCATCAAGCATTTTATCCGTACTCCTG |
| | | ATGATGCATGGTTACTCACCACTGCGATCCCCGGAAA |
| | | AACAGCATTCCAGGTATTAGAAGAATATCCTGATTCAG |
| | | GTGAAAATATTGTTGATGCGCTGGCAGTGTTCCTGCG |
| | | CCGGTTGCATTCGATTCCTGTTTGTAATTGTCCTTTTAA |
| | | CAGCGATCGCGTATTTCGTCTTGCTCAGGCGCAATCA |
| | | CGAATGAATAACGGTTTGGTTGATGCGAGTGATTTTGA |
| | | TGACGAGCGTAATGGCTGGCCTGTTGAACAAGTCTGG |
| | | AAAGAAATGCATAAACTTTTGCCATTCTCACCGGATTC |
| | | AGTCGTCACTCATGGTGATTTCTCACTTGATAACCTTAT |
| | | TTTTGACGAGGGGAAATTAATAGGTTGTATTGATGTTG |
| | | GACGAGTCGGAATCGCAGACCGATACCAGGATCTTGC |
| | | CATCCTATGGAACTGCCTCGGTGAGTTTTCTCCTTCAT |
| | | TACAGAAACGGCTTTTTCAAAAATATGGTATTGATAATC |
| | | CTGATATGAATAAATTGCAGTTTCATTTGATGCTCGATG |
| | | AGTTTTTCTAACTGTCAGACCAAGTTTACTCATATATAC |
| | | TTTAGATTGATTTAAAACTTCATTTTTAATTTAAAAGGAT |
| | | CTAGGTGAAGATCCTTTTTGATAATCTCATGACCAAAAT |
| | | CCCTTAACGTGAGTTTTCGTTCCACTGAGCGTCAGACC |
| | | CCGTAGAAAAGATCAAAGGATCTTCTTGAGATCCTTTT |
| | | TTTCTGCGCGTAATCTGCTGCTTGCAAACAAAAAAACC |
| | | ACCGCTACCAGCGGTGGTTTGTTTGCCGGATCAAGAG |
| | | CTACCAACTCTTTTTTCCGAAGGTAACTGGCTTCAGCAG |
| | | AGCGCAGATACCAAATACTGTTCTTCTAGTGTAGCCGT |
| | | AGTTAGGCCACCACTTCAAGAACTCTGTAGCACCGCC |
| | | TACATACCTCGCTCTGCTAATCCTGTTACCAGTGGCTG |
| | | CTGCCAGTGGCGATAAGTCGTGTCTTACCGGGTTGGA |
| | | CTCAAGACGATAGTTACCGGATAAGGCGCAGCGGTCG |
| | | GGCTGAACGGGGGGTTCGTGCACACAGCCCAGCTTG |
| | | GAGCGAACGACCTACACCGAACTGAGATACCTACAGC |
| | | GTGAGCTATGAGAAAGCGCCACGCTTCCCGAAGGGAG |
| | | AAAGGCGGACAGGTATCCGGTAAGCGGCAGGGTCGG |
| | | AACAGGAGAGCGCACGAGGGAGCTTCCAGGGGGAAA |
| | | CGCCTGGTATCTTTATAGTCCTGTCGGGTTTCGCCACC |
| | | TCTGACTTGAGCGTCGATTTTTGTGATGCTCGTCAGGG |
| | | GGGCGGAGCCTATGGAAAAACGCCAGCAACGCGGCC |
| | | TTTTTACGGTTCCTGGCCTTTTGCTGGCCTTTTGCTCA |
| | | CATGTTCTTTCCTGCGTTATCCCCTGATTCTGTGGATA |
| | | ACCGTATTACCGCCTTTGAGTGAGCTGATACCGCTCG |
| | | CCGCAGCCGAACGACCGAGCGCAGCGAGTCAGTGAG |
| | | CGAGGAAGCGGAAGAGCGCCCAATACGCAAACCGCC |
| | | TCTCCCCGCGCGTTGGCCGATTCATTAATGCAGCTGG |

TABLE 4-continued

Transfer plasmids for the production of dual hybrid vector systems

| SEQ ID NO. | Description | Plasmid Sequence |
|---|---|---|
| | | CACGACAGGTTTCCCGACTGGAAAGCGGGCAGTGAG |
| | | CGCAACGCAATTAATGTGAGTTAGCTCACTCATTAGGC |
| | | ACCCCAGGCTTTACACTTTATGCTTCCGGCTCGTATGT |
| | | TGTGTGGAATTGTGAGCGGATAACAATTTCACACAGGA |
| | | AACAGCTATGACCATGATTACGCCAGATTTAATTAAGG |
| 68 | 5' transgene plasmid containing the following features: | CCTTAATTAGGCTGCGCGCTCGCTCGCTCACTGAGGC |
| | ITR at positions 12-141 | CGCCCGGGCAAAGCCCGGGCGTCGGGCGACCTTTGG |
| | CMV i.e enhancer at positions 230-594 | TCGCCCGGCCTCAGTGAGCGAGCGAGCGCGCAGAGA |
| | | GGGAGTGGCCAACTCCATCACTAGGGGTTCCTTGTAG |
| | CMV enhancer at positions 296-599 | TTAATGATTAACCCGCCATGCTACTTATCTACGTAGCC |
| | | ATGCTCTAGGAAGATCGGAATTCGCCCTTAAGCTAGC |
| | Chicken β-actin promoter at positions 596-878 | GGCGCGCCGGTACCTAGTTATTAATAGTAATCAATTAC |
| | | GGGGTCATTAGTTCATAGCCCATATATGGAGTTCCGC |
| | Exon 1 at positions 879-971 | GTTACATAACTTACGGTAAATGGCCCGCCTGGCTGAC |
| | Chimeric intron at positions 971-1172 | CGCCCAACGACCCCCGCCCATTGACGTCAATAATGAC |
| | | GTATGTTCCCATAGTAACGCCAATAGGGACTTTCCATT |
| | Kozak sequence at positions 1189-1198 | GACGTCAATGGGTGGAGTATTTACGGTAAACTGCCCA |
| | | CTTGGCAGTACATCAAGTGTATCATATGCCAAGTACGC |
| | N-terminal portion of human OTOF isoform 5 at positions 1195-3600 | CCCCTATTGACGTCAATGACGGTAAATGGCCCGCCTG |
| | | GCATTATGCCCAGTACATGACCTTATGGGACTTTCCTA |
| | | CTTGGCAGTACATCTACGTATTAGTCATCGCTATTACC |
| | Splice donor sequence at positions 3601-3684 | ATGGTCGAGGTGAGCCCCACGTTCTGCTTCACTCTCC |
| | | CCATCTCCCCCCCCTCCCCACCCCCAATTTTGTATTTA |
| | AP head sequence at positions 3691-3977 | TTTATTTTTTAATTATTTTGTGCAGCGATGGGGGCGGG |
| | | GGGGGGGGGGGGGCGCGCGCCAGGCGGGGCGGGG |
| | ITR at positions 4071-4200 | CGGGGCGAGGGGCGGGGCGGGGCGAGGCGGAGAG |
| | M13 fwd at positions 4219-4235 | GTGCGGCGGCAGCCAATCAGAGCGGCGCGCTCCGAA |
| | f1 on at positions 4377-4832 | AGTTTCCTTTTATGGCGAGGCGGCGGCGGCGGCGGC |
| | AmpR promoter at positions 4858-4962 | CCTATAAAAAGCGAAGCGCGCGGCGGGCGGGAGTCG |
| | | CTGCGCGCTGCCTTCGCCCCGTGCCCCGCTCCGCCG |
| | KanR at positions 4963-5772 | CCGCCTCGCGCCGCCCGCCCCGGCTCTGACTGACCG |
| | mutBsmBI at positions 4963-5772 | CGTTACTCCCACAGGTGAGCGGGCGGGACGGCCCTT |
| | | CTCCTCCGGGCTGTAATTAGCGCTTGGTTTAATGACG |
| | ori at positions 5943-6531 | GCTTGTTTCTTTTCTGTGGCTGCGTGAAAGCCTTGAGG |
| | CAP binding site at positions 6819-6840 | GGCTCCGGGAGCTAGAGCCTCTGCTAACCATGTTCAT |
| | | GCCTTCTTCTTTTTCCTACAGCTCCTGGGCAACGTGCT |
| | lac promoter at positions 6855-6885 | GGTTATTGTGCTGTCTCATCATTTTGGCAAAGAATTCTA |
| | | GCGGCCGCCACCATGGCCTTGCTCATCCACCTCAAGA |
| | lac operator at positions 6835-6909 | CAGTCTCGGAGCTGCGGGGCAGGGGCGACCGGATCG |
| | | CCAAAGTGACTTTCCGAGGGCAATCCTTCTACTCTCGG |
| | M13 rev at positions 6917-6933 | GTCCTGGAGAACTGTGAGGATGTGGCTGACTTTGATG |
| | Transgene to be transferred into vector in dual vector system at positions 12-4200 | AGACATTTCGGTGGCCGGTGGCCAGCAGCATCGACAG |
| | | AAATGACAGCCTGTGCGGAGATTCAGGTTTTCAACTACAGCA |
| | | AAGTCTTCAGCAACAAGCTCATCGGGACCTTCCGCAT |
| | | GGTGCTGCAGAAGGTGGTAGAGGAGAGCCATGTGGA |
| | | GGTGACTGACACGCTGATTGATGACAACAATGCTATCA |
| | | TCAAGACCAGCCTGTGCGTGGAGGTCCGGTATCAGGC |
| | | CACTGACGGCACAGTGGGCTCCTGGGACGATGGGGA |
| | | CTTCCTGGGAGATGAGTCTCTTCAAGAGGAAGAGAAG |
| | | GACAGCCAAGAGACGGATGGACTGCTCCCAGGCTCC |
| | | CGGCCCAGCTCCCGGCCCCCAGGAGGAGAAGAGCTTC |
| | | CGGAGAGCCGGGAGGAGCGTGTTCTCCGCCATGAAG |
| | | CTCGGCAAAAACCGGTCTCACAAGGAGGAGCCCCAAA |
| | | GACCAGATGAACCGGCGGTGCTGGAGATGGAAGACC |
| | | TTGACCATCTGGCCATTCGGCTAGGAGATGGACTGGA |
| | | TCCCGACTCGGTGTCTCTAGCCTCAGTCACAGCTCTC |
| | | ACCACTAATGTCTCCAACAAGCGATCTAAGCCAGACAT |
| | | TAAGATGGAGCCAAGTGCTGGGCGGCCCATGGATTAC |
| | | CAGGTCAGCATCACGGTGATCGAGGCCCGGCAGCTG |
| | | GTGGGCTTGAACATGGACCCTGTGGTGTGCGTGGAG |
| | | GTGGGTGACGACAAGAAGTACACATCCATGAAGGAGT |
| | | CCACTAACTGCCCCTATTACAACGAGTACTTCGTCTTC |
| | | GACTTCCATGTCTCTCCGGATGTCATGTTTGACAAGAT |
| | | CATCAAGATTTCGGTGATTCACTCCAAGAACCTGCTGC |
| | | GCAGTGGCACCCTGGTGGGCTCCTTCAAAATGGACGT |
| | | GGGAACCGTGTACTCGCAGCCAGAGCACCAGTTCCAT |
| | | CACAAGTGGGCCATCCTGTCTGACCCCGATGACATCT |
| | | CCTCGGGGCTGAAGGGCTACGTGAAGTGTGACGTTGC |
| | | CGTGGTGGGCAAAGGGGACAACATCAAGACGCCCCA |
| | | CAAGGCCAATGAGACCGACGAAGATGACATTGAGGGG |
| | | AACTTGCTGCTCCCCGAGGGGGTGCCCCCCGAACGC |
| | | CAGTGGGCCCGGTTCTATGTGAAAATTTACCGAGCAG |
| | | AGGGGCTGCCCCGTATGAACACAAGCCTCATGGCCAA |

TABLE 4-continued

Transfer plasmids for the production of dual hybrid vector systems

| SEQ ID NO. | Description | Plasmid Sequence |
|---|---|---|
| | | TGTAAAGAAGGCTTTCATCGGTGAAAACAAGGACCTC |
| | | GTGGACCCCTACGTGCAAGTCTTCTTTGCTGGCCAGA |
| | | AGGGCAAGACTTCAGTGCAGAAGAGCAGCTATGAGCC |
| | | CCTGTGGAATGAGCAGGTCGTCTTTACAGACCTCTTCC |
| | | CCCCACTCTGCAAACGCATGAAGGTGCAGATCCGAGA |
| | | CTCGGACAAGGTCAACGACGTGGCCATCGGCACCCAC |
| | | TTCATTGACCTGCGCAAGATTTCTAATGACGGAGACAA |
| | | AGGCTTCCTGCCCACACTGGGCCCAGCCTGGGTGAAC |
| | | ATGTACGGCTCCACACGTAACTACACGCTGCTGGATG |
| | | AGCATCAGGACCTGAACGAGGGCCTGGGGGAGGGTG |
| | | TGTCCTTCCGGGCCCGGCTCCTGCTGGGCCTGGCTGT |
| | | GGAGATCGTAGACACCTCCAACCCTGAGCTCACCAGC |
| | | TCCACAGAGGTGCAGGTGGAGCAGGCCACGCCCATC |
| | | TCGGAGAGCTGTGCAGGTAAAATGGAAGAATTCTTTCT |
| | | CTTTGGAGCCTTCCTGGAGGCCTCAATGATCGACCGG |
| | | AGAAACGGAGACAAGCCCATCACCTTTGAGGTCACCA |
| | | TAGGCAACTATGGGAACGAAGTTGATGGCCTGTCCCG |
| | | GCCCCAGCGGCCTCGGCCCCGGAAGGAGCCGGGGG |
| | | ATGAGGAAGAAGTAGACCTGATTCAGAACGCAAGTGA |
| | | TGACGAGGCCGGTGATGCCGGGGACCTGGCCTCAGT |
| | | CTCCTCCACTCCACCAATGCGGCCCCAGGTCACCGAC |
| | | AGGAACTACTTCCATCTGCCCTACCTGGAGCGAAAGC |
| | | CCTGCATCTACATCAAGAGCTGGTGGCCGGACCAGCG |
| | | CCGCCGCCTCTACAATGCCAACATCATGGACCACATT |
| | | GCCGACAAGCTGGAAGAAGGCCTGAACGACATACAGG |
| | | AGATGATCAAAACGGAGAAGTCCTACCCTGAGCGTCG |
| | | CCTGCGGGGCGTCCTGGAGGAGCTGAGCTGTGGCTG |
| | | CTGCCGCTTCCTCTCCCTCGCTGACAAGGACCAGGGC |
| | | CACTCATCCCGCACCAGGCTTGACCGGGAGCGCCTCA |
| | | AGTCCTGCATGAGGGAGCTGGTAAGTATCAAGGTTAC |
| | | AAGACAGGTTTAAGGAGACCAATAGAAACTGGGCTTG |
| | | TCGAGACAGAGAAGACTCTTGCGTTTCTGAGCTAGCC |
| | | CCCGGGTGCGCGGCGTCGGTGGTGCCGGCGGGGGG |
| | | CGCCAGGTCGCAGGCGGTGTAGGGCTCCAGGCAGGC |
| | | GGCGAAGGCCATGACGTGCGCTATGAAGGTCTGCTCC |
| | | TGCACGCCGTGAACCAGGTGCGCCTGCGGGCCGCGC |
| | | GCGAACACCGCCACGTCCTCGCCTGCGTGGGTCTCTT |
| | | CGTCCAGGGGCACTGCTGACTGCTGCCGATACTCGG |
| | | GGCTCCCGCTCTCGCTCTCGGTAACATCCGGCCGGG |
| | | CGCCGTCCTTGAGCACATAGCCTGGACCGTTTCGTCG |
| | | ACCTCGAGTTAAGGGCGAATTCCCGATAAGGATCTTC |
| | | CTAGAGCATGGCTACGTAGATAAGTAGCATGGCGGGT |
| | | TAATCATTAACTACAAGGAACCCCTAGTGATGGAGTTG |
| | | GCCACTCCCTCTCTGCGCGCTCGCTCGCTCACTGAGG |
| | | CCGGGCGACCAAAGGTCGCCCGACGCCCGGGCTTTG |
| | | CCCGGGCGGCCTCAGTGAGCGAGCGAGCGCGCAGCC |
| | | TTAATTAACCTAATTCACTGGCCGTCGTTTTACAACGTC |
| | | GTGACTGGGAAAACCCTGGCGTTACCCAACTTAATCG |
| | | CCTTGCAGCACATCCCCCTTTCGCCAGCTGGCGTAAT |
| | | AGCGAAGAGGCCCGCACCGATCGCCCTTCCCAACAGT |
| | | TGCGCAGCCTGAATGGCGAATGGGACGCGCCCTGTA |
| | | GCGGCGCATTAAGCGCGGCGGGTGTGGTGGTTACGC |
| | | GCAGCGTGACCGCTACACTTGCCAGCGCCCTAGCGC |
| | | CCGCTCCTTTCGCTTTCTTCCCTTCCTTTCTCGCCACG |
| | | TTCGCCGGCTTTCCCCGTCAAGCTCTAAATCGGGGGC |
| | | TCCCTTTAGGGTTCCGATTTAGTGCTTTACGGCACCTC |
| | | GACCCCAAAAAACTTGATTAGGGTGATGGTTCACGTAG |
| | | TGGGCCATCGCCCTGATAGACGGTTTTTCGCCCTTTG |
| | | ACGTTGGAGTCCACGTTCTTTAATAGTGGACTCTTGTT |
| | | CCAAACTGGAACAACACTCAACCCTATCTCGGTCTATT |
| | | CTTTTGATTTATAAGGGATTTTGCCGATTTCGGCCTATT |
| | | GGTTAAAAAATGAGCTGATTTAACAAAAATTTAACGCG |
| | | AATTTTAACAAAATATTAACGCTTACAATTTAGGTGGCA |
| | | CTTTTCGGGGAAATGTGCGCGGAACCCCTATTTGTTTA |
| | | TTTTTCTAAATACATTCAAATATGTATCCGCTCATGAGA |
| | | CAATAACCCTGATAAATGCTTCAATAATATTGAAAAAGG |
| | | AAGAGTATGAGCCATATTCAACGGGAAACGTCGAGGC |
| | | CGCGATTAAATTCCAACATGGATGCTGATTTATATGGG |
| | | TATAAATGGGCTCGCGATAATGTCGGGCAATCAGGTG |
| | | CGACAATCTATCGCTTGTATGGGAAGCCCGATGCGCC |
| | | AGAGTTGTTTCTGAAACATGGCAAAGGTAGCGTTGCCA |
| | | ATGATGTTACAGATGAGATGGTCAGACTAAACTGGCTG |
| | | ACGGAATTTATGCCTCTTCCGACCATCAAGCATTTTAT |
| | | CCGTACTCCTGATGATGCATGGTTACTCACCACTGCGA |

TABLE 4-continued

Transfer plasmids for the production of dual hybrid vector systems

| SEQ ID NO. Description | Plasmid Sequence |
| --- | --- |
| | TCCCCGGAAAAACAGCATTCCAGGTATTAGAAGAATAT |
| | CCTGATTCAGGTGAAAATATTGTTGATGCGCTGGCAGT |
| | GTTCCTGCGCCGGTTGCATTCGATTCCTGTTTGTAATT |
| | GTCCTTTTAACAGCGATCGCGTATTCGTCTTGCTCAG |
| | GCGCAATCACGAATGAATAACGGTTTGGTTGATGCGA |
| | GTGATTTTGATGACGAGCGTAATGGCTGGCCTGTTGA |
| | ACAAGTCTGGAAAGAAATGCATAAACTTTTGCCATTCT |
| | CACCGGATTCAGTCGTCACTCATGGTGATTTCTCACTT |
| | GATAACCTTATTTTTGACGAGGGGAAATTAATAGGTTG |
| | TATTGATGTTGGACGAGTCGGAATCGCAGACCGATAC |
| | CAGGATCTTGCCATCCTATGGAACTGCCTCGGTGAGT |
| | TTTCTCCTTCATTACAGAAACGGCTTTTTCAAAAATATG |
| | GTATTGATAATCCTGATATGAATAAATTGCAGTTTCATT |
| | TGATGCTCGATGAGTTTTTCTAACTGTCAGACCAAGTT |
| | TACTCATATATACTTTAGATTGATTTAAAACTTCATTTTT |
| | AATTTAAAAGGATCTAGGTGAAGATCCTTTTTGATAATC |
| | TCATGACCAAAATCCCTTAACGTGAGTTTTCGTTCCAC |
| | TGAGCGTCAGACCCCGTAGAAAAGATCAAAGGATCTT |
| | CTTGAGATCCTTTTTTTCTGCGCGTAATCTGCTGCTTG |
| | CAAACAAAAAAACCACCGCTACCAGCGGTGGTTTGTTT |
| | GCCGGATCAAGAGCTACCAACTCTTTTTCCGAAGGTAA |
| | CTGGCTTCAGCAGAGCGCAGATACCAAATACTGTTCTT |
| | CTAGTGTAGCCGTAGTTAGGCCACCACTTCAAGAACTC |
| | TGTAGCACCGCCTACATACCTCGCTCTGCTAATCCTGT |
| | TACCAGTGGCTGCTGCCAGTGGCGATAAGTCGTGTCT |
| | TACCGGGTTGGACTCAAGACGATAGTTACCGGATAAG |
| | GCGCAGCGGTCGGGCTGAACGGGGGGTTCGTGCACA |
| | CAGCCCAGCTTGGAGCGAACGACCTACACCGAACTGA |
| | GATACCTACAGCGTGAGCTATGAGAAAGCGCCACGCT |
| | TCCCGAAGGGAGAAAGGCGGACAGGTATCCGGTAAG |
| | CGGCAGGGTCGGAACAGGAGAGCGCACGAGGGAGCT |
| | TCCAGGGGGAAACGCCTGGTATCTTTATAGTCCTGTC |
| | GGGTTTCGCCACCTCTGACTTGAGCGTCGATTTTTGTG |
| | ATGCTCGTCAGGGGGGCGGAGCCTATGGAAAAACGC |
| | CAGCAACGCGGCCTTTTTACGGTTCCTGGCCTTTTGCT |
| | GGCCTTTTGCTCACATGTTCTTTCCTGCGTTATCCCCT |
| | GATTCTGTGGATAACCGTATTACCGCCTTTGAGTGAGC |
| | TGATACCGCTCGCCGCAGCCGAACGACCGAGCGCAG |
| | CGAGTCAGTGAGCGAGGAAGCGGAAGAGCGCCCAAT |
| | ACGCAAACCGCCTCTCCCCGCGCGTTGGCCGATTCAT |
| | TAATGCAGCTGGCACGACAGGTTTCCCGACTGGAAAG |
| | CGGGCAGTGAGCGCAACGCAATTAATGTGAGTTAGCT |
| | CACTCATTAGGCACCCCAGGCTTTACACTTTATGCTTC |
| | CGGCTCGTATGTTGTGTGGAATTGTGAGCGGATAACA |
| | ATTTCACACAGGAAACAGCTATGACCATGATTACGCCA |
| | GATTTAATTAAGG |

Vectors for the Expression of OTOF

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a polynucleotide sequence that encodes a portion of OTOF, as well as, e.g., additional sequence elements used for the expression of these agents and/or the integration of these polynucleotide sequences into the genome of a mammalian cell. Certain vectors that can be used for the expression of OTOF include plasmids that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

AAV Vectors for Nucleic Acid Delivery

In some embodiments, nucleic acids of the compositions and methods described herein are incorporated into recombinant AAV (rAAV) vectors and/or virions in order to facilitate their introduction into a cell. rAAV vectors useful in the compositions and methods described herein are recombinant nucleic acid constructs that include (1) a heterologous sequence to be expressed (e.g., a polynucleotide encoding an N-terminal or C-terminal portion of an OTOF protein) and (2) viral sequences that facilitate stability and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. For use in the methods and compositions described herein, the ITRs can be AAV2 ITRs. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S. For targeting cochlear hair cells, AAV1, AAV2, AAV6, AAV9, Anc80, Anc80L65, DJ/9, 7m8, and PHP.B may be particularly useful. Serotypes evolved for transduction of the retina may also be used in the methods and compositions described herein. The first and second nucleic acid vectors (e.g., AAV vectors) in the compositions and methods described herein may have the same serotype or different serotypes. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

In some embodiments, the use of AAV vectors for delivering a functional OTOF isoform 5 protein requires the use of a dual vector system, in in which the first member of the dual vector system encodes an N-terminal portion of an OTOF isoform 5 protein and the second member encodes a C-terminal portion of an OTOF isoform 5 protein such that, upon administration of the dual vector system to a cell, the polynucleotide sequences contained within the two vectors can join to form a single sequence that results in the production of a full-length OTOF isoform 5 protein.

In some embodiments, the first member of the dual vector system will also include, in 5' to 3' order, a first inverted terminal repeat ("ITR"); a promoter (e.g., a Myo15 promoter); a Kozak sequence; an N-terminal portion of an OTOF isoform 5 coding sequence; a splice donor sequence; an AP gene fragment (e.g., an AP head sequence); and a second ITR; and the second member of the dual vector system will include, in 5' to 3' order, a first ITR; an AP gene fragment (e.g., an AP head sequence); a splice acceptor sequence; a C-terminal portion of an OTOF isoform 5 coding sequence; a polyA sequence; and a second ITR. In some embodiments, the N-terminal portion of the OTOF isoform 5 coding sequence and the C-terminal portion of the OTOF isoform 5 coding sequence do not overlap and are joined in a cell (e.g., by recombination at the overlapping region (the AP gene fragment), or by concatemerization of the ITRs) to produce the full-length OTOF isoform 5 amino sequence as set forth in SEQ ID NO:1. In particular embodiments, the N-terminal portion of the OTOF isoform 5 coding sequence encodes amino acids 1-802 of SEQ ID NO:1 (SEQ ID NO: 58) and the C-terminal portion of the OTOF isoform 5 coding sequence encodes amino acids 803-1997 of SEQ ID NO:1 (SEQ ID NO: 59).

In some embodiments, the first member of the dual vector system includes the Myo15 promoter of SEQ ID NO:21 (also represented by nucleotides 235-1199 of SEQ ID NO:66) operably linked to nucleotides that encode the N-terminal 802 amino acids of the OTOF isoform 5 protein (amino acids 1-802 of SEQ ID NO:1), which are encoded by exons 1-20 of the native polynucleotide sequence encoding that protein. In certain embodiments, the nucleotide sequence that encodes the N-terminal amino acids of the OTOF isoform 5 protein is nucleotides 1222-3627 of SEQ ID NO:66. In some embodiments, the nucleotide sequence that encodes the N-terminal amino acids of the OTOF isoform 5 protein is any nucleotide sequence that, by redundancy of the genetic code, encodes amino acids 1-802 of SEQ ID NO:1. The nucleotide sequences that encode the OTOF isoform 5 protein can be partially or fully codon-optimized for expression. In some embodiments, the first member of the dual vector system includes the Kozak sequence corresponding to nucleotides 1216-1225 of SEQ ID NO:66. In some embodiments, the first member of the dual vector system includes the splice donor sequence corresponding to nucleotides 3628-3711 of SEQ ID NO:66. In some embodiments, the first member of the dual vector system includes the AP head sequence corresponding to nucleotides 3718-4004 of SEQ ID NO:66. In particular embodiments, the first member of the dual vector system includes nucleotides 235-4004 of SEQ ID NO:66 flanked on each of the 5' and 3' sides by an inverted terminal repeat. In some embodiments, the flanking inverted terminal repeats are any variant of AAV2 inverted terminal repeats that can be encapsidated by a plasmid that carries the AAV2 Rep gene. In certain embodiments, the 5' flanking inverted terminal repeat has a sequence corresponding to nucleotides 12-141 of SEQ ID NO:66 or a sequence having at least 80% sequence identity (at least 80%, 81%, 82%, 83%, 84%, 85%, 86%, 87%, 88%, 89%, 90%, 91%, 92%, 93%, 94%, 95%, 96%, 97%, 98%, or 99% sequence identity) thereto; and the 3' flanking inverted terminal repeat has a sequence corresponding to nucleotides 4098-4227 of SEQ ID NO:66 or a sequence having at least 80% sequence identity (at least 80%, 81%, 82%, 83%, 84%, 85%, 86%, 87%, 88%, 89%, 90%, 91%, 92%, 93%, 94%, 95%, 96%, 97%, 98%, or 99% sequence identity) thereto. It will be understood by those of skill in the art that, for any given pair of inverted terminal repeat sequences in a transfer plasmid that is used to create the viral vector (typically by transfecting cells with that plasmid together with other plasmids carrying the necessary AAV genes for viral vector formation) (e.g., any of SEQ ID NOs: 60, 62, 64, 65, 66, or 68), that the corresponding sequence in the viral vector can be altered due to the ITRs adopting a "flip" or "flop" orientation during recombination. Thus, the sequence of the ITR in the transfer plasmid is not necessarily the same sequence that is found in the viral vector prepared therefrom. However, in some very specific embodiments, the first member of the dual vector system includes nucleotides 12-4227 of SEQ ID NO:66.

In some embodiments, the second member of the dual vector system includes nucleotides that encode the C-terminal 1195 amino acids of the OTOF isoform 5 protein (amino acids 803-1997 of SEQ ID NO:1) immediately followed by a stop codon. In certain embodiments, the nucleotide sequence that encodes the C-terminal amino acids of the OTOF isoform 5 protein is nucleotides 587-4174 of SEQ ID NO:67. In some embodiments, the nucleotide sequence that encodes the C-terminal amino acids of the OTOF isoform 5 protein is any nucleotide sequence that, by redundancy of the genetic code, encodes amino acids 803-1997 of SEQ ID NO:1. The nucleotide sequences that encode the OTOF isoform 5 protein can be partially or fully codon-optimized for expression. In some embodiments, the second member of the dual vector system includes the splice acceptor sequence corresponding to nucleotides 538-586 of SEQ ID NO:67. In some embodiments, the second member of the dual vector system includes the AP head sequence corresponding to nucleotides 229-515 of SEQ ID NO:67. In some embodiments, the second member of the dual vector system includes the poly(A) sequence corresponding to nucleotides 4217-4438 of SEQ ID NO:67. In particular embodiments, the second member of the dual vector system includes nucleotides 229-4438 of SEQ ID NO:67 flanked on each of the 5' and 3' sides by an inverted terminal repeat. In some embodiments, the flanking inverted terminal repeats are any variant of AAV2 inverted terminal repeats that can be encapsidated by a plasmid that carries the AAV2 Rep gene. In certain embodiments, the 5' flanking inverted terminal repeat has a sequence corresponding to nucleotides 12-141 of SEQ ID NO:67 or a sequence having at least 80% sequence identity (at least 80%, 81%, 82%, 83%, 84%, 85%, 86%, 87%, 88%, 89%, 90%, 91%, 92%, 93%, 94%, 95%, 96%, 97%, 98%, or 99% sequence identity) thereto; and the 3' flanking inverted terminal repeat has a sequence corresponding to nucleotides 4526-4655 of SEQ ID NO:67 or a sequence having at least 80% sequence identity (at least 80%, 81%, 82%, 83%, 84%, 85%, 86%, 87%, 88%, 89%, 90%, 91%, 92%, 93%, 94%, 95%, 96%, 97%, 98%, or 99% sequence identity) thereto. It will be understood by those of skill in the art that, for any given pair of inverted terminal repeat sequences in a transfer plasmid that is used to create the viral vector (typically by transfecting cells with that plasmid together with other plasmids carrying the necessary AAV genes for viral vector formation) (e.g., any of SEQ ID NOs: 61, 63, or 67), that the corresponding sequence in the viral vector can be altered due to the ITRs adopting a "flip" or "flop" orientation during recombination. Thus, the sequence of the ITR in the transfer plasmid is not necessarily the same sequence that is found in the viral vector prepared therefrom. However, in some very specific embodiments, the first member of the dual vector system includes nucleotides 12-4655 of SEQ ID NO:67.

In some embodiments, the dual vector system is an AAV1 dual vector system.

In some embodiments, the dual vector system is an AAV9 dual vector system.

Pharmaceutical Compositions

The nucleic acid vectors (e.g., AAV vectors) described herein may be incorporated into a vehicle for administration into a patient, such as a human patient suffering from sensorineural hearing loss or auditory neuropathy, as described herein. Pharmaceutical compositions containing vectors, such as viral vectors, that contain a polynucleotide encoding a portion of an OTOF isoform 5 protein can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions.

Mixtures of the nucleic acid vectors (e.g., AAV vectors) described herein may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466, 468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. For local administration to the inner ear, the composition may be formulated to contain a synthetic perilymph solution. An exemplary synthetic perilymph solution includes 20-200 mM NaCl, 1-5 mM KCl, 0.1-10 mM $CaCl_2$), 1-10 mM glucose, and 2-50 mM HEPEs, with a pH between about 6 and 9 and an osmolality of about 300 mOsm/kg. The person responsible for administration will, in any event, determine the appropriate dose for the individual subject. Moreover, for human administration, preparations may meet sterility, pyrogenicity, general safety, and purity standards as required by FDA Office of Biologics standards.

Methods of Treatment

The compositions described herein may be administered to a subject with sensorineural hearing loss or auditory neuropathy by a variety of routes, such as local administration to the inner ear (e.g., administration into the perilymph or endolymph, e.g., by injection or catheter insertion through the round window membrane, injection into a semicircular canal, by canalostomy, or by intratympanic or transtympanic injection, e.g., administration to a cochlear hair cell), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. If the compositions are administered by direct delivery to the inner ear, a second fenestration or vent hole may be added elsewhere in the inner ear. The most suitable route for administration in any given case will depend on the particular composition administered, the patient, pharmaceutical formulation methods, administration methods (e.g., administration time and administration route), the patients age, body weight, sex, severity of the disease being treated, the patient's diet, and the patient's excretion rate. Compositions may be administered once, or more than once (e.g., once annually, twice annually, three times annually, bi-monthly, monthly, or bi-weekly). In some embodiments, the first and second nucleic acid vectors (e.g., AAV vectors) are administered simultaneously (e.g., in one composition). In some embodiments, the first and second nucleic acid vectors (e.g., AAV vectors) are administered sequentially (e.g., the second nucleic acid vector is administered immediately after the first nucleic acid vector, or 5 minutes, 10 minutes, 15 minutes, 20 minutes, 25 minutes, 30 minutes, 45 minutes, 1 hour, 2 hours, 8 hours, 12 hours, 1 day, 2 days, 7 days, two weeks, 1 month or more after the first nucleic acid vector). The first and second nucleic acid vector can have the same serotype or different serotypes (e.g., AAV serotypes).

Subjects that may be treated as described herein are subjects having or at risk of developing sensorineural hearing loss or auditory neuropathy. The compositions and methods described herein can be used to treat subjects having a mutation in OTOF (e.g., a mutation that reduces OTOF function or expression, or an OTOF mutation associated with sensorineural hearing loss), subjects having a family history of autosomal recessive sensorineural hearing loss or deafness (e.g., a family history of OTOF-related hearing loss), or subjects whose OTOF mutational status and/or OTOF activity level is unknown. The methods described herein may include a step of screening a subject for a mutation in OTOF prior to treatment with or administration of the compositions described herein. A subject can be screened for an OTOF mutation using standard methods known to those of skill in the art (e.g., genetic testing). The methods described herein may also include a step of assessing hearing in a subject prior to treatment with or administration of the compositions described herein. Hearing can be assessed using standard tests, such as audiometry, ABR, electrocochleography (ECOG), and otoacoustic emissions. The compositions and methods described herein may also be administered as a preventative treatment to patients at risk of developing hearing loss or auditory neuropathy, e.g., patients who have a family history of inherited hearing loss or patients carrying an OTOF mutation who do not yet exhibit hearing loss or impairment.

Treatment may include administration of a composition containing the nucleic acid vectors (e.g., AAV vectors) described herein in various unit doses. Each unit dose will ordinarily contain a predetermined quantity of the therapeutic composition. The quantity to be administered, and the particular route of administration and formulation, are within the skill of those in the clinical arts. A unit dose need not be administered as a single injection but may include continuous infusion over a set period of time. Dosing may be performed using a syringe pump to control infusion rate in order to minimize damage to the cochlea. In cases in which the nucleic acid vectors are AAV vectors (e.g., AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, or PHP.S vectors), the AAV vectors may have a titer of, for example, from about $1\times10^9$ vector genomes (VG)/mL to about $1\times10^{16}$ VG/mL (e.g., $1\times10^9$ VG/mL, $2\times10^9$ VG/mL, $3\times10^9$ VG/mL, $4\times10^9$ VG/mL, $5\times10^9$ VG/mL, $6\times10^9$ VG/mL, $7\times10^9$ VG/mL, $8\times10^9$ VG/mL, $9\times10^9$ VG/mL, $1\times10^{10}$ VG/mL, $2\times10^{10}$ VG/mL, $3\times10^{10}$ VG/mL, $4\times10^{10}$ VG/mL, $5\times10^{10}$ VG/mL, $6\times10^{10}$ VG/mL, $7\times10^{10}$ VG/mL, $8\times10^{10}$ VG/mL, $9\times10^{10}$ VG/mL, $1\times10^{11}$ VG/mL, $2\times10^{11}$ VG/mL, $3\times10^{11}$ VG/mL, $4\times10^{11}$ VG/mL, $5\times10^{11}$ VG/mL, $6\times10^{11}$ VG/mL, $7\times10^{11}$ VG/mL, $8\times10^{11}$ VG/mL, $9\times10^{11}$ VG/mL, $1\times10^{12}$ VG/mL, $2\times10^{12}$ VG/mL, $3\times10^{12}$ VG/mL, $4\times10^{12}$ VG/mL, $5\times10^{12}$ VG/mL, $6\times10^{12}$ VG/mL, $7\times10^{12}$ VG/mL, $8\times10^{12}$ VG/mL, $9\times10^{12}$ VG/mL, $1\times10^{13}$ VG/mL, $2\times10^{13}$ VG/mL, $3\times10^{13}$ VG/mL, $4\times10^{13}$ VG/mL, $5\times10^{13}$ VG/mL, $6\times10^{13}$ VG/mL, $7\times10^{13}$VG/mL, $8\times10^{13}$ VG/mL, $9\times10^{13}$ VG/mL, $1\times10^{14}$ VG/mL, $2\times10^{14}$ VG/mL, $3\times10^{14}$ VG/mL, $4\times10^{14}$VG/mL, $5\times10^{14}$ VG/mL, $6\times10^{14}$ VG/mL, $7\times10^{14}$ VG/mL, $8\times10^{14}$VG/mL, $9\times10^{14}$ VG/mL, $1\times10^{16}$VG/mL, $2\times10^{16}$ VG/mL, $3\times10^{16}$ VG/mL, $4\times10^{16}$VG/mL, $5\times10^{16}$VG/mL, $6\times10^{16}$ VG/mL, $7\times10^{16}$VG/mL, $8\times10^{16}$ VG/mL, $9\times10^{16}$ VG/mL, or $1\times10^{16}$ VG/mL) in a volume of 1 µL to 200 µL (e.g., 1, 2, 3, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 µL). The AAV vectors may be administered to the subject at a dose of about $1\times10^7$ VG/ear to about $2\times10^{16}$VG/ear (e.g., $1\times10^7$VG/ear, $2\times10^7$ VG/ear, $3\times10^7$ VG/ear, $4\times10^7$ VG/ear, $5\times10^7$VG/ear, $6\times10^7$ VG/ear, $7\times10^7$ VG/ear, $8\times10^7$VG/ear, $9\times10^7$ VG/ear, $1\times10^8$ VG/ear, $2\times10^8$ VG/ear, $3\times10^8$ VG/ear, $4\times10^8$ VG/ear, $5\times10^8$VG/ear, $6\times10^8$ VG/ear, $7\times10^8$ VG/ear, $8\times10^8$ VG/ear, $9\times10^8$ VG/ear, $1\times10^9$ VG/ear, $2\times10^9$ VG/ear, $3\times10^9$VG/ear, $4\times10^9$ VG/ear, $5\times10^9$ VG/ear, $6\times10^9$ VG/ear, $7\times10^9$ VG/ear, $8\times10^9$ VG/ear, $9\times10^9$VG/ear, $1\times10^{10}$ VG/ear, $2\times10^{10}$ VG/ear, $3\times10^{10}$ VG/ear, $4\times10^{10}$ VG/ear, $5\times10^{10}$ VG/ear, $6\times10^{10}$ VG/ear, $7\times10^{10}$ VG/ear, $8\times10^{10}$ VG/ear, $9\times10^{10}$ VG/ear, $1\times10^{11}$ VG/ear, $2\times10^{11}$ VG/ear, $3\times10^{11}$ VG/ear, $4\times10^{11}$ VG/ear, $5\times10^{11}$ VG/ear, $6\times10^{11}$ VG/ear, $7\times10^{11}$ VG/ear, $8\times10^{11}$ VG/ear, $9\times10^{11}$ VG/ear, $1\times10^{12}$ VG/ear, $2\times10^{12}$ VG/ear, $3\times10^{12}$ VG/ear, $4\times10^{12}$ VG/ear, $5\times10^{12}$ VG/ear, $6\times10^{12}$ VG/ear, $7\times10^{12}$ VG/ear, $8\times10^{12}$ VG/ear, $9\times10^{12}$ VG/ear, $1\times10^{13}$ VG/ear, $2\times10^{13}$ VG/ear, $3\times10^{13}$ VG/ear, $4\times10^{13}$ VG/ear, $5\times10^{13}$ VG/ear, $6\times10^{13}$ VG/ear, $7\times10^{13}$ VG/ear, $8\times10^{13}$ VG/ear, $9\times10^{13}$ VG/ear, $1\times10^{14}$ VG/ear, $2\times10^{14}$ VG/ear, $3\times10^{14}$ VG/ear, $4\times10^{14}$ VG/ear, $5\times10^{14}$ VG/ear, $6\times10^{14}$ VG/ear, $7\times10^{14}$ VG/ear, $8\times10^{14}$ VG/ear, $9\times10^{14}$ VG/ear, $1\times10^{16}$ VG/ear, or $2\times10^{16}$ VG/ear).

The compositions described herein are administered in an amount sufficient to improve hearing, increase WT OTOF expression (e.g., expression of OTOF isoform 5 in a cochlear hair cell, e.g., an inner hair cell), or increase OTOF function. Hearing may be evaluated using standard hearing tests (e.g., audiometry, ABR, electrocochleography (ECOG), and otoacoustic emissions) and may be improved by 5% or more (e.g., 5%, 10%, 15%, 20%, 30%, 40%, 50%, 60%, 70%, 80%, 90%, 100% or more) compared to hearing measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss or auditory neuropathy (e.g., in subjects who carry a mutation in OTOF or have a family history of autosomal recessive hearing loss but do not exhibit hearing impairment, or in subjects exhibiting mild to moderate hearing loss). OTOF expression may be evaluated using immunohistochemistry, Western blot analysis, quantitative real-time PCR, or other methods known in the art for detection protein or mRNA, and may be increased by 5% or more (e.g., 5%, 10%, 15%, 20%, 30%, 40%, 50%, 60%, 70%, 80%, 90%, 100% or more) compared to OTOF expression prior to administration of the compositions described herein. OTOF function may be evaluated directly (e.g., using electrophysiological methods or imaging methods to assess exocytosis) or indirectly based on hearing tests, and may be increased by 5% or more (e.g., 5%, 10%, 15%, 20%, 30%, 40%, 50%, 60%, 70%, 80%, 90%, 100% or more) compared to OTOF function prior to administration of the compositions described herein. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Kits

The compositions described herein can be provided in a kit for use in treating sensorineural hearing loss or auditory neuropathy (e.g., hearing loss associated with a mutation in OTOF). Compositions may include nucleic acid vectors (e.g., AAV vectors) described herein (e.g., a first nucleic acid vector containing a polynucleotide that encodes and N-terminal portion of an OTOF isoform 5 protein and a second nucleic acid vector containing a polynucleotide that encodes a C-terminal portion of an OTOF isoform 5 protein), optionally packaged in an AAV virus capsid (e.g., an AAV1 capsid). The kit can further include a package insert that instructs a user of the kit, such as a physician, to perform the methods described herein. The kit may optionally include a syringe or other device for administering the composition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Human OTOF Isoform 5, but not Human OTOF Isoform 1, Rescued Function in OTOF$^{Q828X/Q828X}$ Mice There are multiple long and short isoforms of the Otoferlin (OTOF) gene. Studies of human genetic deafness have suggested that long isoforms are important for inner ear function. However, the role of these individual long isoforms and other protein variants in inner ear function is not understood. To develop effective gene transfer therapies for patients who experience deafness secondary to genetically driven OTOF deficiency, a cDNA sequence that encodes functional OTOF isoforms in the ear must be identified.

In human, seven OTOF isoforms have been identified in extra-aural tissues. Two of these isoforms (isoform 1 (V1) and isoform 5 (V5)) are long (both 1997 amino acids in length).

Figure 1A:
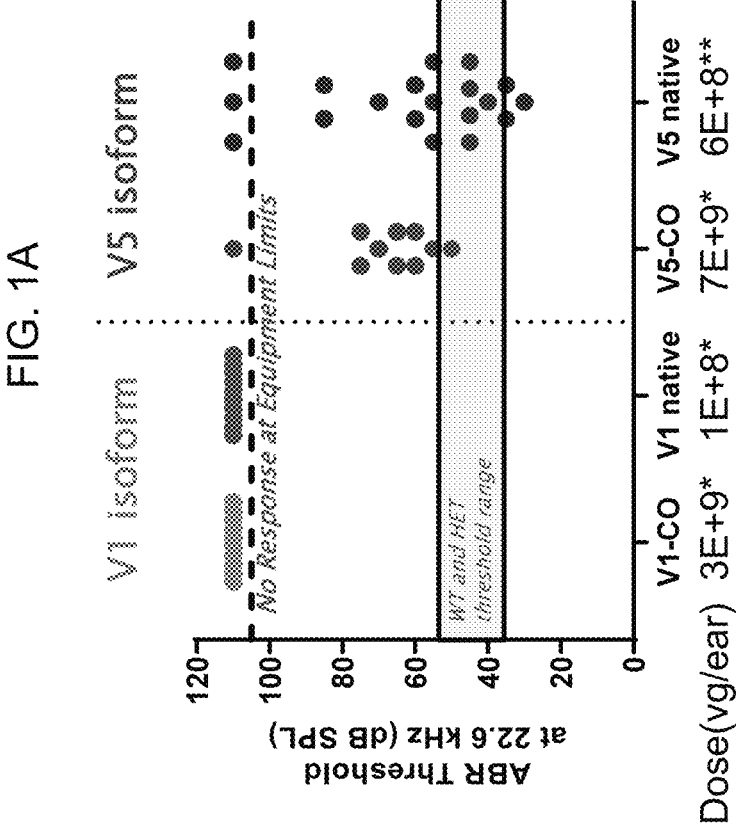
FIG. 1A is a graph showing the analysis of the auditory brainstem response (ABR) in OTOF homozygous mutant (OTOF$^{Q828X/Q828X}$) mice administered an OTOF dual vector system demonstrating that AAV-mediated gene transfer of human OTOF isoform 5 but not human OTOF isoform 1 improved auditory function. ABR thresholds to pure tone stimuli at 22.6 kHz were recorded from mice that received OTOF dual vector systems carrying either codon-optimized (CO) or native (native) sequences encoding human OTOF isoform 1 (V1) (SEQ ID NO: 4) or isoform 5 (V5) (SEQ ID NO: 1). The dose of virus, in vector genomes (vg), delivered to the ear is indicated below the description of the sequence administered to each treatment group. OTOF virus was injected through the round window membrane of four- to seven-week-old OTOF$^{Q828X/Q828X}$ mice (a mouse model of the human OTOF mutation p.Gln828Ter). ABR responses were measured approximately four weeks after injection of the viruses. ABR responses significantly improved in mice treated with human OTOF isoform 5, irrespective of codon-optimization. No ABR response was detected in mice treated with human OTOF isoform 1. The range of ABR thresholds observed in wild-type and heterozygous OTOF mutant mice (OTOF$^{Q828X/+}$) are indicated by a box.

We used dual hybrid AAV technology to locally deliver the human V1 and V5 isoforms to the inner ears of genetically engineered, congenitally deaf mice with Otoferlin deficiency. One month after delivery of the human V5 isoform in the congenitally deaf mice, we observed rescue of hearing (FIG. 1A). By contrast, we saw no hearing recovery in mice that were injected with the V1 human long isoform. These studies establish the OTOF V5 sequence as being capable for restoring hearing in the context of a gene transfer therapeutic.

The experiments performed to compare functional recovery and OTOF expression using dual hybrid vector systems encoding OTOF isoform 1 or OTOF isoform 5 are described in detail below.

AAV Delivery to Inner Ear

Vector (AAV2quad(Y-F)-smCBA-OTOF isoform 1 (native or codon-optimized) or AAV2quad(Y-F)-smCBA-OTOF isoform 5 (native or codon-optimized)) was delivered to P30-50 OTOF$^{Q828X/Q828X}$ mutant mice (a mouse model of human OTOF mutation p.Gln828Ter) by injection through the round window membrane. The polynucleotide encoding the N-terminal portion of the OTOF protein and the polynucleotide encoding the C-terminal portion of the OTOF protein were divided between the two vectors in the dual hybrid vector system using the exon 20/21 boundary and an AP gene fragment (SEQ ID NO: 51) was used as the recombinogenic region in both vectors of the dual hybrid vector system. Vector was delivered as follows. Animals were anesthetized with isoflurane. Ophthalmic ointment (Puralube Vet) was applied to both eyes, and Meloxicam (Putney)/Rimadyl was administered at 0.3-2.0 mg/kg, SC as an analgesic. The surgical site was shaved and disinfected by scrubbing with Betadine (Avrio Health L.P.) and 70% alcohol before post-auricular incision to expose the bulla. A small hole was created in the bulla using a sterile 26-30 G needle or diameter 0.004-0.008 mm drill bits (Performance Micro Tool) and expanded using sterile sharp forceps to visualize the round window niche. The round window was then punctured with the tip of a pulled glass micropipette or a 35 G polyimide tubing (WPI Instrument) and any leaking fluid was absorbed using sterile gauze. Two microliters of vector were then injected using a micropipette (approximately 0.5 mm depth) or a polyimide tubing. Injection lasted approximately 30 seconds. When delivery was complete, a small piece of the cleidomastoideus muscle was cut and pushed through the bulla to cover the round window. Fat tissue was moved back to its original area. The skin incision was then closed using three to four drops of GLUture (Zoetis Inc.), allowing 1-2 minutes for it to dry. Animals were then moved to a clean and warm recovery cage. Animals were checked post-operatively for five days for signs of pain, infection, or other signs of distress. Analgesic was given once daily for the first three days after surgery. Animals were also given saline, nutritional support, and additional analgesia as appropriate.

Auditory Brainstem Response

Mice were evaluated for peripheral auditory function by auditory brainstem response (ABR) at four weeks post-injection. Following administration of anesthesia (ketamine 100 mg/kg, i.p., xylazine 10 mg/kg, i.p.; supplemental ketamine as needed) and verifying appropriate anesthetic depth, subdermal needle electrodes were placed at vertex and ventral pinna (differential recording) and at base of tail (ground). A custom acoustic system (Eaton-Peabody Laboratories, MEE) containing two speakers and a probe-tube microphone was placed in the ear canal and in-ear calibration was performed before each test session. Probe-tube microphone calibration was performed using a reference ¼-in. microphone and preamplifier (PCB Piezotronics models 2530, 426B31; Larson-Davis model 2221); in-ear calibration was performed with the probe-tube microphone and custom microphone amplifier (Eaton-Peabody Laboratories, MEE). All ABR stimuli and responses were generated with and acquired by an RZ6 Multi-I/O signal processor and BioSigRZ software (Tucker-Davis Technologies). Responses from needle electrodes were amplified and digitized with a RA4PA Medusa preamp connected to a RA4L1 low-impedance headstage (Tucker-Davis Technologies). ABR stimuli were 5 ms tone pips (0.5 ms cost ramp) at 22.6 kHz, presented at a rate of 40/s with alternating polarity, from 5 to 105 dB SPL in 5 dB steps. For each sound level, a total of 1024 trials were averaged (after artifact rejection), digitally filtered (0.1-5 kHz), then additionally high-pass filtered offline (0.3 kHz). ABR threshold was determined by visual inspection of stacked waveforms ("waterfall plot") as the lowest sound level at which a reproducible peak or trough was detected. If no response was detected up to equipment limit (105 dB SPL), a ceiling value of 110 dB SPL was assigned. The results of ABR threshold at 22.6 kHz are shown in FIG. 1A.

Immunohistochemistry

Figure 1B:
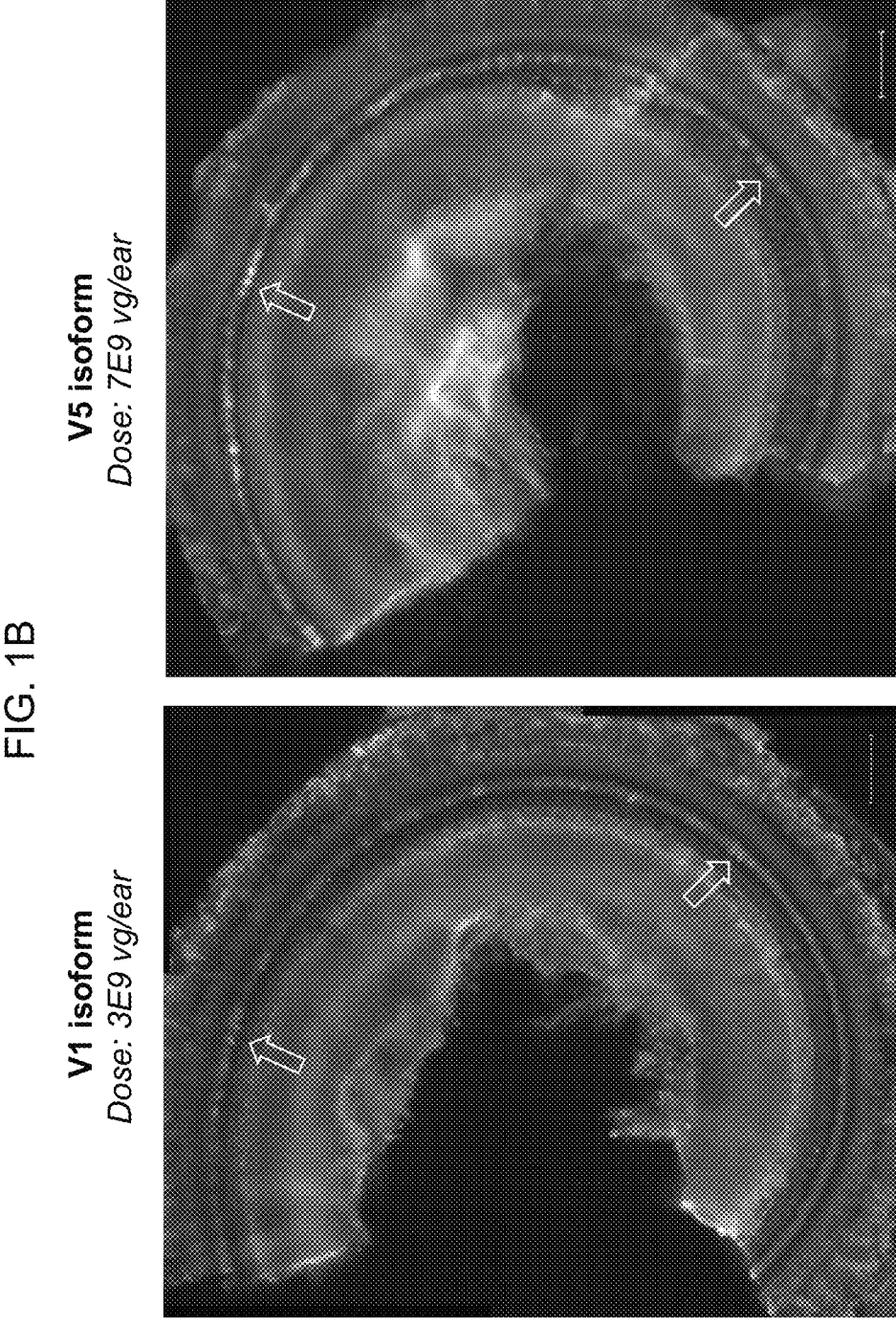
FIG. 1B is a series of fluorescent images of mouse *cochleae* transduced with OTOF dual vector systems carrying codon-optimized (CO) sequences encoding human OTOF isoform 1 (V1) or isoform 5 (V5). Mice were injected with OTOF dual vector systems carrying codon-optimized (CO) sequences of human OTOF isoform 1 (V1) (SEQ ID NO: 6) or isoform 5 (V5) (SEQ ID NO: 3). After physiology testing was completed, (see data in FIG. 1A), mice were euthanized and perfused with 10% neutral buffered formalin. The inner ear temporal bone was harvested and decalcified in 8% EDTA for 3 days. The cochlea was dissected from the de-calcified temporal bone, immunostained with OTOF antibody to detect expression of the OTOF transgene, and mounted on a slide for fluorescence imaging. *Cochleae* injected with dual vector systems encoding either human OTOF isoform 1 (V1) or isoform 5 (V5) showed comparable levels of OTOF expression (FIG. 1B). Since functional recovery was only observed for human OTOF isoform 5 (V5) but not isoform 1 (V1) (see FIG. 1A), these data indicate that human OTOF isoform 5 (V5) is the functionally relevant OTOF isoform in cochlear inner hair cells.

After physiology testing was completed, mice were euthanized via carbon dioxide inhalation overdose. Immediately after euthanasia, mice were perfused via the vascular system with 10% neutral buffered formalin (NBF). The inner ear temporal bone was collected and submerged in 10% NBF for 2-16 hours and then decalcified in 8% EDTA for 3 days. The cochlea was dissected from the de-calcified temporal bone and washed 3 times in PBS. After incubating with a blocking solution of 5% horse serum in PBST (0.5% triton X-100 in 1×PBS) at room temperature for one hour, the dissected cochlear pieces were incubated with a mouse anti-Otoferlin antibody (abcam ab53233, 1:200 diluted in PBST) at 4° C. for 12-16 hours, followed by 3 washes in PBS and incubation in Alexa 568 donkey anti-mouse secondary antibody (ThermoFisher Scientific A10037) at room temperature for 1-2 hours. After counter staining with DAPI and final washes with PBS, the cochlear pieces were mounted on a glass slide using Vectashield mounting medium (Vector Laboratories H-1000) and covered with a glass coverslip. The tissue was imaged using a Zeiss Axio Imager M2 microscope. Images are shown in FIG. 1B.

Figure 2:
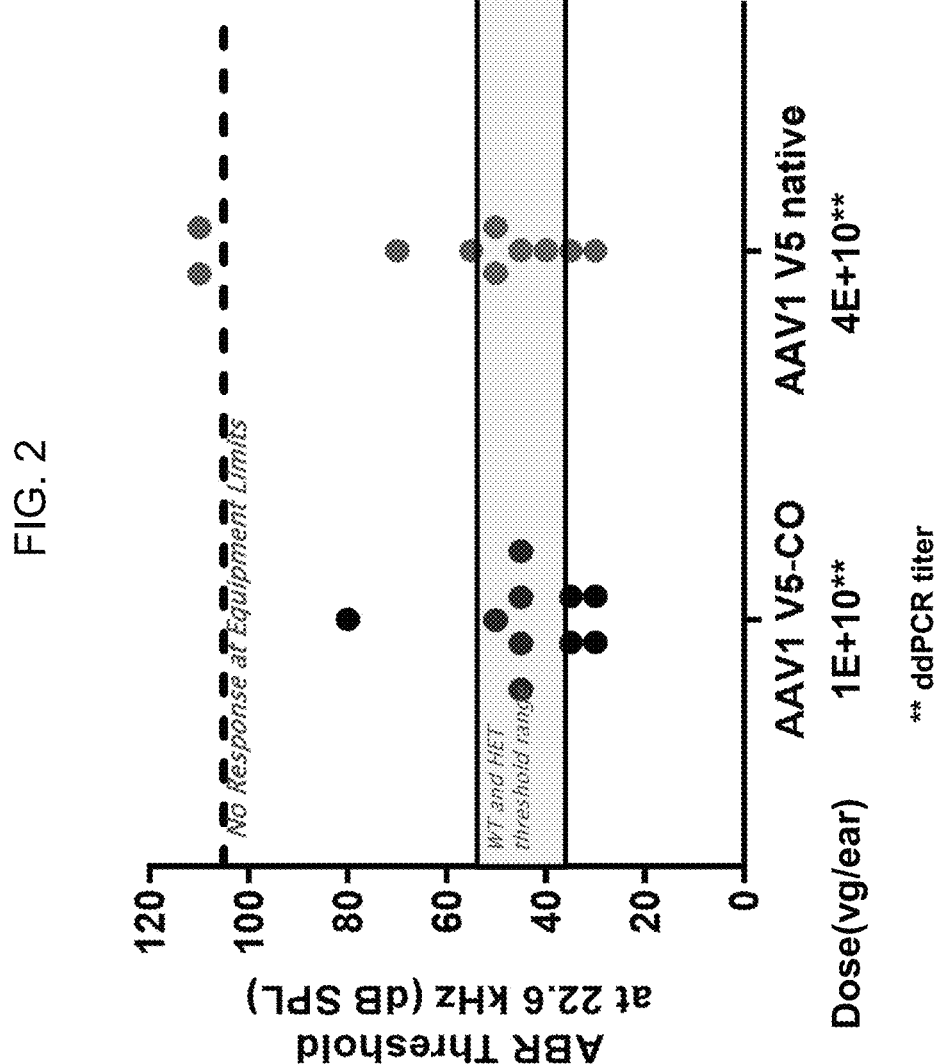
FIG. 2 is a graph showing the analysis of ABR in in OTOF homozygous mutant (OTOF$^{Q828X/Q828X}$) mice demonstrating that AAV-mediated gene transfer of human OTOF isoform 5 improves auditory function to wild-type levels when delivered at higher dose. ABR thresholds to pure tone stimuli at 22.6 kHz were recorded from mice that received OTOF dual vectors carrying either codon-optimized (CO) or native (native) sequences of human OTOF isoform 5 (V5) (SEQ ID NOs: 3 and 2, respectively). For each treatment group, the dose of virus, in vector genomes (vg), delivered to the ear is indicated below the description of the sequence administered to each treatment group. OTOF virus was injected through the round window membrane of four- to seven-week-old OTOF$^{Q828X/Q828X}$ mice. ABR responses were measured approximately four weeks after injection of the viruses. Relative to animals dosed with 7E9 or 6E9 vector genomes/ear (FIG. 1A), these animals showed even stronger ABR responses, irrespective of codon-optimization (FIG. 2). The range of ABR thresholds observed in wild-type and heterozygous OTOF mutant mice (OTOF$^{Q828X/+}$) are indicated by a box.

Example 2. Administration of Higher Doses of OTOF Isoform 5 Improves Functional Recovery in OTOF$^{Q828X/Q828X}$ Mice To evaluate the effect of administration of a higher dose of OTOF isoform 5 on functional recovery in OTOF$^{Q828X/}$ $_{Q828X}$ mutant mice, vector (AAV1-smCBA-OTOF isoform 5 (native or codon-optimized)) was injected through the round window membrane of 4-7-week-old OTOF$^{Q828X/Q828X}$ mice as described in Example 1, above. Similar to the vectors used in Example 1, the polynucleotide encoding the N-terminal portion of the OTOF protein and the polynucleotide encoding the C-terminal portion of the OTOF protein were divided between the two vectors in the dual hybrid vector system using the exon 20/21 boundary and an AP gene fragment (SEQ ID NO: 51) was used as the recombinogenic region in both vectors of the dual hybrid vector system. ABR responses were measured approximately four weeks after injection of the viruses, as described in Example 1, above. Relative to animals dosed with 7E9 or 6E9 vector genomes/ear (FIG. 1A), these animals showed even stronger ABR responses irrespective of codon-optimization (FIG. 2).

Example 3. Administration of a Composition Containing Dual Hybrid Vectors that Express OTOF to Mice Restores Electrophysiological Signatures of Hearing Function Homozygous (HOM) OTOF-Q828X mice (7 weeks old) were either left untreated or treated (by injection through the round window membrane) with 4E10 (4×10$^{10}$) vector genomes (vg)/ear of an AAV1-Myo15 (SEQ ID NO: 21)-hOTOF (isoform 5, SEQ ID NO: 1) dual hybrid vector system in which exons 1-20 of the polynucleotide encoding the N-terminal portion of the OTOF protein (SEQ ID NO: 56) and exons 21-45 and 47 of the polynucleotide encoding the C-terminal portion of the OTOF protein (SEQ ID NO: 57) were delivered in separate vectors (FIG. 3A). An AP recombinogenic region (SEQ ID NO: 51) was included in both vectors of the dual hybrid vector system. Auditory brainstem response (ABR) thresholds were used to assess hearing function. Untreated animals (untreated Otof HOM) showed no detectable recovery in hearing function, whereas treated animals exhibited a robust recovery, which was consistent from four weeks post-treatment (Otof HOM at 4 weeks after treatment) to eight weeks post-treatment (Otof HOM at 8-11 weeks after treatment). ABR thresholds in heterozygous animals (Otof HET) were also tested.

In a separate set of experiments, homozygous OTOF-Q828X mice were either left untreated or treated (by injection through the round window membrane) with 4E10 (4×10$^{10}$) vg/ear of an AAV1-truncated chimeric CMV-chicken β-actin (smCBA, SEQ ID NO: 44)-hOTOF (isoform 5, SEQ ID NO: 1) dual hybrid vector system as described above (FIG. 3B). The first vector contained exons 1-20 of the polynucleotide encoding the N-terminal portion of the OTOF protein (SEQ ID NO: 56) and exons 21-45 and 47 of the polynucleotide encoding the C-terminal portion of the OTOF protein (SEQ ID NO: 57) and both vectors contained an AP recombinogenic region (SEQ ID NO: 51). Untreated animals had no detectable recovery in hearing function, whereas treated animals exhibited a robust recovery at 4 weeks post-treatment (Otof HOM at 4 weeks after treatment). When these same animals were evaluated at 8 weeks post-treatment (Otof HOM at 8 weeks after treatment), ABR thresholds increased, suggesting less durable recovery with the smCBA promoter. ABR thresholds in heterozygous animals were also tested.

In yet another set of experiments, homozygous OTOF-Q828X mice were either left untreated or treated (by injection through the round window membrane) with an AAV1-smCBA (SEQ ID NO: 44)-hOTOF (isoform 5, SEQ ID NO: 1) dual hybrid vector, as described above, at either 8E9 ($8\times10^9$) vg/ear (low dose), 1.6E10 ($1.6\times10^{10}$) vg vg/ear (mid dose), or 6.4E10 ($6.4\times10^{10}$) vg/ear (high dose). The first vector contained exons 1-20 of the polynucleotide encoding the N-terminal portion of the OTOF protein (SEQ ID NO: 56) and exons 21-45 and 47 of the polynucleotide encoding the C-terminal portion of the OTOF protein (SEQ ID NO: 57) and both vectors contained an AP recombinogenic region (SEQ ID NO: 51). ABR thresholds were used to assess hearing function at four weeks and eight weeks post-treatment (FIG. 3C). A dose-dependent recovery in ABR was observed at both timepoints. When comparing the eight weeks versus the four weeks timepoint, recovery of hearing function was steady for the low and mid doses but decreased for the high dose animals. ABR thresholds in heterozygous animals were also tested.

Example 4. Administration of a Composition Containing Dual Hybrid Vectors that Express Murine OTOF to Mice Restores Electrophysiological Signatures of Hearing Function Homozygous OTOF-Q828X mice (6-7 weeks old) were treated with AAV2quad(Y-F)-Myo15 (SEQ ID NO: 21)-murine OTOF (mOTOF, transcript variant 1, RefSeq NM_001100395) and AAV2quad(Y-F)-Myo15 (SEQ ID NO: 31)-mOTOF (transcript variant 1, RefSeq NM_001100395) dual hybrid vector systems by injection through the round window membrane as described above (2 μL total volume injected, 1 μL of each vector) and ABR thresholds were used to assess hearing function. Exons 1-20 of the polynucleotide encoding the N-terminal portion of the mOTOF protein were included in the 5' vector and the remaining C-terminal portion of the mOTOF polynucleotide was included in the 3' vector. An AP recombinogenic region (SEQ ID NO: 51) was included in both vectors of the dual hybrid vector system. The titer of the 5' AAV2quad(Y-F)-Myo15 (SEQ ID NO: 21)-mOTOF vector was 1.49E12 vg/mL, the titer of the 5' AAV2quad(Y-F)-Myo15 (SEQ ID NO: 31)-mOTOF vector was 2.68E12 vg/mL, and the titer of the corresponding 3' vectors was 1.05E12 vg/mL and 1.58E12 vg/mL. Untreated animals showed no detectable recovery in hearing function, whereas treated animals exhibited robust recovery, which was consistent from four weeks post-treatment to seventeen weeks post-treatment (FIG. 4). FIG. 4 depicts mean hearing thresholds at 22.6 kHz+/− standard deviation.

Example 5. Dual Hybrid Vectors can be Used to Express Full Length, Functional GFP in Hair Cells of a Non-Human Primate A non-human primate of 2.6 years of age received a local injection to the round window of the inner ear at a flow rate of 6 μL/min with an AAV1-Myo15 (SEQ ID NO: 21)-GFP (viral titer of 3.18E13 vg/mL for the 5' vector and 3.42E13 vg/mL for the 3' vector) dual hybrid vector system (60 μL total volume injected, 30 μL of each vector). Four weeks post-injection, inner ears were removed, and a surface preparation of the basilar membranes was made. Dual hybrid vectors resulted in GFP expression in hair cells across the entire baso-apical axis of the cochlea. High magnification images at 4 kHz showed GFP expression was observed within inner hair cells (IHCs) (FIG. 5B). Immunohistochemistry for Myo7A was used to visualize hair cells (FIG. 5A) and nuclei were stained with DAPI (FIG. 5C).

Example 6. Construction of Dual Hybrid Vector Systems that Encode Human OTOF

HEK293T cells (obtained from ATCC, Manassas, VA) were seeded into cell culture-treated dishes until they reached 70-80% confluence in the vessel. Transfection was carried out using the AAV-1 Packaging System from Cell Biolabs, Inc. (San Diego, CA). Per 175 cm$^2$ of culture surface area, 16 μg pHelper, 8 μg pAAV-RC1, and 8 μg of transfer plasmid SEQ ID NO:66 were mixed with PEI (PEIpro, polyplus) at a 1:1 weight ratio. The DNA/PEI mixture was subsequently added into the cell culture medium. Three days after transfection, the cell culture medium and the cells were collected to extract and purify the AAV. AAV from the cell culture medium was concentrated through tangential flow filtration. AAV from the cells was released from cells through three cycles of freeze thaw. AAV from either fraction was finally purified through iodixanol density gradient purification and the buffer was exchanged by passing the purified AAV and sterile DPBS (Mg+, Ca+) with 0.01% pluronic F68 across a 100 kDa MWCO centrifugal filter to produce purified AAV, which is the first member of the dual vector system. A similar procedure was carried out using transfer plasmid SEQ ID NO:67 to create the second member of the dual vector system.

The same procedure was used to create a dual vector system that encodes OTOF in AAV9, except that pAAV-RC1 was replaced with a comparable plasmid that contained the AAV9 cap gene instead of the AAV1 cap gene during the transfection step.

Example 7. Dual Hybrid Vector Systems that Encode Human OTOF are Expressed in Non-Human Primates In non-human primates (NHP) native Otoferlin protein is expressed in the sensory cells of the inner ear. We used the BaseScope™ system to detect expression of virally transduced human Otoferlin in NHPs.

A first cohort of six naïve NHP (1.5-4 years old) were injected through the round window membrane with the Myo15-Otoferlin dual hybrid vectors packaged into the AAV1 serotype as described in Example 6. Each ear received a dose of $1.1\times10^{12}$ copies of each of the two vectors together in a total volume of 60 μl. The ears were vented at the lateral semicircular canals to allow an outflow of perilymph during viral delivery. A second cohort of naïve NHP (1.5-4 years old) was injected in the same manner and dosage as the first cohort with a Myo15-Otoferlin dual hybrid system packaged into the AAV9 serotype, also as described in Example 6.

All animals were sacrificed by cardiac perfusion of 10% neutral buffered formalin (NBF) four weeks after viral vector injections and their temporal bones were harvested. After decalcification for five days in Immunocal, the temporal bones were embedded in paraffin, sectioned in 5 μm intervals and stained for BaseScope™ (Advanced Cell Diagnostics, Newark, CA) using a probe specific to the spliced mRNA at the junction of the two vectors between Exons 20 and 21 of human Otoferlin. Thus, detection required that the dual vectors properly hybridized in vivo and expressed full-length human OTOF isoform 5.

The BaseScope™ assay was performed on the Leica Bond RX automatic staining platform. Briefly, paraffin sections were baked for 30 min at 60° C. and deparaffinized. A target retrieval step for 5 min at 95° C. was followed by a proteinase step for 10 min at 40° C. and finally a standard BaseScope™ protocol including 8 amplification steps was run on the E20/21-probe. The probe-signal was detected vectors were replaced with the first 393 nucleotides encoding a 5' portion of eGFP in the 5' vector and the last 908 nucleotides encoding a 3' portion of eGFP in the 3' vector, respectively. eGFP is easily detectable even in an otoferlin wildtype background.

All animals received injections of 60 μl the dual viral vectors through the round window membrane and their ears were vented at the lateral semicircular canal. The animals used in this study were 1.5-4 years old. Six NHP ears were injected with a surrogate vector expressing eGFP under the Myo15 promoter in the AAV1 serotype described above at a titer of $1.6 \times 10^{12}$ vector genomes per ear. Another six NHP ears were injected with a similar surrogate dual viral vector system expressing eGFP under the Myo15 promoter in the AAV9 serotype at a titer of $1.9 \times 10^{12}$ vector genomes per ear. The dose for the NHP study was scaled by correlating mouse expression data from prior mid and high dose experiments and comparing it to a smaller scale NHP mid dose experiment (Table 5, below). We estimated the potential outcome in NHP as a percentage of Inner hair cells (IHCs) expressing eGFP from a high dose dual vector approach (Table 5).

TABLE 5

| | Dose scaling from mouse to NHP in dual vector eGFP delivery | | | | | |
|---|---|---|---|---|---|---|
| | Predicted Minimum Efficacious Dose (MED) Range | | | Predicted Dose Range for Saturation of Efficacy | | |
| Species | Dose Concentration | Total Dose* | % IHC expression** | Dose Concentration | Total Dose* | % IHC expression** |
| Mouse | 3.9e10 vg/μL | 7.4e10 vg/ear | 57% | 6.2e10 vg/μL | 1.2e11 vg/ear | 82% |
| Cynomolgus | 3.1e10 vg/μL | 1.2e12 vg/ear | 40-60% | 5.2e10 vg/μL | 2e12 vg/ear | 75-100% | vg = viral genomes
*Toal Dose calculated as 5' + 3'
**% IHC expression of hOTOF in mouse averaged across 8, 11.3, 16, 22.6, and 32 kHz
% IHC expression of dualGFP in cynomolgus monkey averaged across 1, 2, 4, and 8 kHz using the Fast Red dye, which could be observed as a red staining in bright field microscopy. Initially, images where scanned and digitized at 40× magnification and screened for positivity. Afterward, the positive signal was confirmed using the fluorescent signal of the fast red dye using confocal imaging (63×, 1.4 NA, excitation: 568 nm at 1% laser power; emission BP 578-730 nm at 642V detector). FIG. 6** shows sections from representative NHPs treated with the Myo15-Otoferlin AAV1 dual vector system. In the AAV1-injected animals, clear positivity could be observed in sensory cells in all injected animals with a bias toward the apical turns of the cochlea and the utricle. In the AAV9-injected animals, three out of the six animals showed clear positivity with a similar trend toward cochlear apical turn and utricular expression (figure not shown). In each case, the OTOF transcript was localized to inner hair cells, outer hair cells and hair cells in the vestibular organs.

Example 8. Quantification and Localization of Surrogate Myo15 Promoter Dual Hybrid Vector Systems Encoding eGFP in NHP To ascertain the specificity of the hair cell-specific Myo15 promoter and transduction efficiency in NHPs, dual vector systems having the same recombinatory regions and promoter as described in Example 6 were used, except that the 5' and 3' portions of human otoferlin in the two respective We confirmed expression in NHPs throughout the organ of Corti using whole mount confocal imaging (40×, 0.95 NA, excitation: 488 nm at 14% laser power; emission BP 495-543 nm at 600V detector gain) using native eGFP signal as a readout (FIG. 7A). The quantification of the number of inner hair cells showing expression correlated well to the prediction from dose scaling (FIG. 7B) for the AAV1 serotype, while the AAV9 serotype showed a lower expression percentage.

Example 9. Administration of a Composition Containing Dual Hybrid Vectors that Express OTOF Isoform 5 to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1) containing a Myo15 promoter (e.g., SEQ ID NO: 19, 21, 22, 31, or 32) operably linked to exons 1-20 of a polynucleotide encoding an OTOF isoform 5 protein (e.g., human OTOF isoform 5, e.g., SEQ ID NO: 1, e.g., a polynucleotide having the sequence of SEQ ID NO: 56), a splice donor sequence 3' of the polynucleotide sequence, and an AP recombinogenic region (e.g., an AP gene fragment, any one of SEQ ID NOs: 48-53, e.g., SEQ ID NO: 51) 3' of the splice donor sequence, and a second AAV vector (e.g., AAV1) containing an AP recombinogenic region (an AP gene fragment, any one of SEQ ID NOs: 48-53, e.g., SEQ ID NO: 51), a splice acceptor sequence 3' of the recombinogenic region, a polynucleotide 3' of the splice acceptor sequence that contains exons 21-45 and 47 of a polynucleotide encoding an OTOF isoform 5 protein (e.g., human OTOF isoform 5, e.g., SEQ ID NO: 1, e.g., a polynucleotide having the sequence of SEQ ID NO: 57), and a bGH poly(A) sequence. The composition containing the dual hybrid AAV vectors may be administered to the patient, for example, by local administration to the inner ear (e.g., injection through the round window membrane, injection into a semicircular canal, or by canalostomy), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrocochleography (ECOG), and measuring otoacoustic emissions following administration of the composition. A finding that the patient exhibits improved hearing (e.g., improved ABR) in one or more of the tests following administration of the composition compared to hearing test results prior to administration of the composition indicates that the patient is responding favorably to the treatment. Subsequent doses can be determined and administered as needed.

Exemplary embodiments of the invention are described in the enumerated paragraphs below.

E1. A dual vector system comprising:
    a first adeno-associated virus (AAV) vector comprising a Myo15 promoter operably linked to a first coding polynucleotide that encodes an N-terminal portion of an Otoferlin (OTOF) isoform 5 protein, a splice donor signal sequence positioned 3' of the first coding polynucleotide, and a first recombinogenic region positioned 3' of the splice donor signal sequence; and
    a second AAV vector comprising a second recombinogenic region, a splice acceptor signal sequence positioned 3' of the second recombinogenic region, a second coding polynucleotide that encodes a C-terminal portion of the OTOF isoform 5 protein positioned 3' of the splice acceptor signal sequence, and a poly(A) sequence positioned 3' of the second coding polynucleotide;
    wherein the first coding polynucleotide and the second coding polynucleotide that encode the OTOF isoform 5 protein do not overlap, and wherein neither the first nor second AAV vector encodes the full-length OTOF isoform 5 protein.
E2. The dual vector system of E1, wherein the first AAV vector and the second AAV vector comprise an AAV1 capsid.
E3. The dual vector system of E1 or E2, wherein the Myo15 promoter comprises a first region having at least 85% sequence identity to SEQ ID NO: 7 or a functional portion or derivative thereof comprising the sequence of SEQ ID NO: 9 and/or SEQ ID NO: 10 operably linked to a second region having at least 85% sequence identity to SEQ ID NO: 8 or a functional portion or derivative thereof comprising the sequence of SEQ ID NO: 14 and/or SEQ ID NO: 15, optionally comprising a linker comprising one to one hundred nucleotides between the first region and the second region.
E4. The dual vector system of E3, wherein the first region comprises or consists of the sequence of SEQ ID NO: 7.
E5. The dual vector system of E3, wherein the functional portion of SEQ ID NO: 7 comprises the sequence of SEQ ID NO: 9.
E6. The dual vector system of E3, wherein the functional portion of SEQ ID NO: 7 comprises the sequence of SEQ ID NO: 10.
E7. The dual vector system of E3, wherein the functional portion of SEQ ID NO: 7 comprises the sequence of SEQ ID NO: 9 and the sequence of SEQ ID NO: 10.
E8. The dual vector system of E7, wherein the functional portion of SEQ ID NO: 7 comprises the sequence of SEQ ID NO: 11.
E9. The dual vector system of E7, wherein the functional portion of SEQ ID NO: 7 comprises the sequence of SEQ ID NO: 12.
E10. The dual vector system of E7, wherein the functional portion of SEQ ID NO: 7 comprises the sequence of SEQ ID NO: 13.
E11. The dual vector system of E7, wherein the functional portion of SEQ ID NO: 7 comprises the sequence of SEQ ID NO: 33.
E12. The dual vector system of any one of E3-E11, wherein the second region comprises or consists of the sequence of SEQ ID NO: 8.
E13. The dual vector system of any one of E3-E11, wherein the functional portion of SEQ ID NO: 8 comprises the sequence of SEQ ID NO: 14.
E14. The dual vector system of any one of E3-E11, wherein the functional portion of SEQ ID NO: 8 comprises the sequence of SEQ ID NO: 15.
E15. The dual vector system of any one of E3-E11, wherein the functional portion of SEQ ID NO: 8 comprises the sequence of SEQ ID NO: 14 and the sequence of SEQ ID NO: 15.
E16. The dual vector system of E15, wherein the functional portion of SEQ ID NO: 8 comprises the sequence of SEQ ID NO: 16.
E17. The dual vector system of E15, wherein the functional portion of SEQ ID NO: 8 comprises the sequence of SEQ ID NO: 17.
E18. The dual vector system of E15, wherein the functional portion of SEQ ID NO: 8 comprises the sequence of SEQ ID NO: 18.
E19. The dual vector system of any one of E3-E11, wherein the functional portion of SEQ ID NO: 8 comprises the sequence of SEQ ID NO: 34.
E20. The dual vector system of any one of E3-E11, wherein the functional portion of SEQ ID NO: 8 comprises the sequence of SEQ ID NO: 35.
E21. The dual vector system of any one of E3-E11, wherein the functional portion of SEQ ID NO: 8 comprises the sequence of SEQ ID NO: 34 and the sequence of SEQ ID NO: 35.
E22. The dual vector system of E21, wherein the functional portion of SEQ ID NO: 8 comprises the sequence of SEQ ID NO: 38.
E23. The dual vector system of E3, wherein the Myo15 promoter comprises or consists of the sequence of SEQ ID NO: 19.

E24. The dual vector system of E3, wherein the Myo15 promoter comprises or consists of the sequence of SEQ ID NO: 21.

E25. The dual vector system of E3, wherein the Myo15 promoter comprises or consists of the sequence of SEQ ID NO: 22.

E26. The dual vector system of E3, wherein the Myo15 promoter comprises or consists of the sequence of SEQ ID NO: 42.

E27. The dual vector system of E3, wherein the Myo15 promoter comprises or consists of the sequence of SEQ ID NO: 43.

E28. The dual vector system of E1 or E2, wherein the Myo15 promoter comprises a first region having at least 85% sequence identity to SEQ ID NO: 23 or a functional portion or derivative thereof comprising the sequence of SEQ ID NO: 25 operably linked to a second region having at least 85% sequence identity to SEQ ID NO: 24 or a functional portion or derivative thereof comprising the sequence of SEQ ID NO: 26 and/or SEQ ID NO: 27, optionally comprising a linker comprising one to four hundred nucleotides between the first region and the second region.

E29. The dual vector system of E28, wherein the first region comprises or consists of the sequence of SEQ ID NO: 23.

E30. The dual vector system of E28, wherein the functional portion of SEQ ID NO: 23 comprises the sequence of SEQ ID NO: 25.

E31. The dual vector system of any one of E28-E30, wherein the second region comprises or consists of the sequence of SEQ ID NO: 24.

E32. The dual vector system of any one of E28-E30, wherein the functional portion of SEQ ID NO: 24 comprises the sequence of SEQ ID NO: 26.

E33. The dual vector system of any one of E28-E30, wherein the functional portion of SEQ ID NO: 24 comprises the sequence of SEQ ID NO: 27.

E34. The dual vector system of any one of E28-E30, wherein the functional portion of SEQ ID NO: 24 comprises the sequence of SEQ ID NO: 26 and the sequence of SEQ ID NO: 27.

E35. The dual vector system of E34, wherein the functional portion of SEQ ID NO: 24 comprises the sequence of SEQ ID NO: 28.

E36. The dual vector system of E34, wherein the functional portion of SEQ ID NO: 24 comprises the sequence of SEQ ID NO: 29.

E37. The dual vector system of E34, wherein the functional portion of SEQ ID NO: 24 comprises the sequence of SEQ ID NO: 30.

E38. The dual vector system of E28, wherein the Myo15 promoter comprises or consists of the sequence of SEQ ID NO: 31.

E39. The dual vector system of E28, wherein the Myo15 promoter comprises or consists of the sequence of SEQ ID NO: 32.

E40. The dual vector system of E1 or E2, wherein the Myo15 promoter comprises a sequence having at least 85% sequence identity to SEQ ID NO: 34.

E41. The dual vector system of E1 or E2, wherein the Myo15 promoter comprises a sequence having at least 85% sequence identity to SEQ ID NO: 38.

E42. The dual vector system of E1 or E2, wherein the Myo15 promoter comprises a sequence having at least 85% sequence identity to SEQ ID NO: 39.

E43. The dual vector system of E1 or E2, wherein the Myo15 promoter comprises a sequence having at least 85% sequence identity to SEQ ID NO: 40.

E44. A dual vector system comprising:
   a first AAV1 vector comprising a ubiquitous promoter operably linked to a first coding polynucleotide that encodes an N-terminal portion of an OTOF isoform 5 protein, a splice donor signal sequence positioned 3' of the first coding polynucleotide, and a first recombinogenic region positioned 3' of the splice donor signal sequence; and
   a second AAV1 vector comprising a second recombinogenic region, a splice acceptor signal sequence positioned 3' of the second recombinogenic region, a second coding polynucleotide that encodes a C-terminal portion of the OTOF isoform 5 protein positioned 3' of the splice acceptor signal sequence, and a poly(A) sequence positioned 3' of the second coding polynucleotide;
   wherein the first coding polynucleotide and the second coding polynucleotide do not overlap, and
   wherein neither the first nor second AAV1 vector encodes the full-length OTOF isoform 5 protein.

E45. The dual vector system of E44, wherein the ubiquitous promoter is selected from the group consisting of a CAG promoter, a cytomegalovirus (CMV) promoter, and a truncated CMV-chicken β-actin promoter (smCBA promoter).

E46. The dual vector system of E45, wherein the ubiquitous promoter is the smCBA promoter.

E47. The dual vector system of E46, wherein the smCBA promoter comprises or consists of the sequence of SEQ ID NO: 44.

E48. The dual vector system of any one of E1-E47, wherein the first and second recombinogenic regions are the same.

E49. The dual vector system of any one of E1-E48, wherein the first recombinogenic region and/or the second recombinogenic region is an AK recombinogenic region.

E50. The dual vector system of E49, wherein the AK recombinogenic region comprises or consists of the sequence of SEQ ID NO: 47.

E51. The dual vector system of any one of E1-E48, wherein the first recombinogenic region and/or the second recombinogenic region is an AP gene fragment.

E52. The dual vector system of E51, wherein the AP gene fragment comprises or consists of the sequence of any one of SEQ ID NOs: 48-53.

E53. The dual vector system of E52, wherein the AP gene fragment comprises or consists of the sequence of SEQ ID NO: 51.

E54. The dual vector system of any one of E1-E53, wherein each of the first and second coding polynucleotides encode about half of the OTOF isoform 5 protein sequence.

E55. The dual vector system of any one of E1-E54, wherein the first and second coding polynucleotides are divided at an OTOF exon boundary.

E56. The dual vector system of E55, wherein the first and second coding polynucleotides are divided at the OTOF exon 20/exon 21 boundary.

E57. The dual vector system of any one of E1-E55, wherein the first coding polynucleotide consists of exons 1-20 of a polynucleotide encoding the OTOF isoform 5 protein and the second coding polynucleotide consists of exons 21-45 and 47 of a polynucleotide encoding the OTOF isoform 5 protein.

E58. The dual vector system of any one of E1-E57, wherein the first and second coding polynucleotides that encode the OTOF isoform 5 protein do not comprise introns.

E59. The dual vector system of any one of E1-E58, wherein the OTOF isoform 5 protein is a human OTOF isoform 5 protein.

E60. The dual vector system of any one of E1-E59, wherein the OTOF isoform 5 protein comprises the sequence of SEQ ID NO: 1 or a variant thereof having one or more conservative amino acid substitutions.

E61. The dual vector system of E60, wherein no more than 10% of the amino acids in the OTOF isoform 5 protein variant are conservative amino acid substitutions.

E62. The dual vector system of E60, wherein the OTOF isoform 5 protein consists of the sequence of SEQ ID NO: 1.

E63. The dual vector system of any one of E1-E60 and E62, wherein the OTOF isoform 5 protein is encoded by the sequence of SEQ ID NO: 2.

E64. The dual vector system of any one of E1-E60 and E62, wherein the OTOF isoform 5 protein is encoded by the sequence of SEQ ID NO: 3.

E65. The dual vector system of any one of E1-E64, wherein the first coding polynucleotide encodes amino acids 1-802 of SEQ ID NO: 1 and the second coding polynucleotide encodes amino acids 803-1997 of SEQ ID NO: 1.

E66. The dual vector system of any one of E1-E65, wherein the N-terminal portion of the OTOF isoform 5 protein consists of the sequence of SEQ ID NO: 58 or a variant thereof having one or more conservative amino acid substitutions.

E67. The dual vector system of E66, wherein no more than 10% (e.g., 10%, 9%, 8%, 7%, 6%, 5%, 4%, 3%, 2%, 1% or fewer) of the amino acids in the N-terminal portion of the OTOF isoform 5 protein variant are conservative amino acid substitutions.

E68. The dual vector system of E66, wherein the N-terminal portion of the OTOF isoform 5 protein consists of the sequence of SEQ ID NO: 58.

E69. The dual vector system of any one of E1-E66 and E68, wherein the N-terminal portion of the OTOF isoform 5 protein is encoded by the sequence of SEQ ID NO: 56.

E70. The dual vector system of any one of E1-E69, wherein the C-terminal portion of the OTOF isoform 5 protein consists of the sequence of SEQ ID NO: 59 or a variant thereof having one or more conservative amino acid substitutions.

E71. The dual vector system of E70, wherein no more than 10% (e.g., 10%, 9%, 8%, 7%, 6%, 5%, 4%, 3%, 2%, 1% or fewer) of the amino acids in the C-terminal portion of the OTOF isoform 5 protein variant are conservative amino acid substitutions.

E72. The dual vector system of E70, wherein the C-terminal portion of the OTOF isoform 5 protein consists of the sequence of SEQ ID NO: 59.

E73. The dual vector system of any one of E1-E70 and E72, wherein the C-terminal portion of the OTOF isoform 5 protein is encoded by the sequence of SEQ ID NO: 57.

E74. The dual vector system of any one of E1-E73, wherein the first vector comprises a first inverted terminal repeat (ITR) sequence 5' of the promoter and a second ITR sequence 3' of the recombinogenic region, and the second vector comprises a first ITR sequence 5' of the recombinogenic region and a second ITR sequence 3' of the poly(A) sequence.

E75. The dual vector system of E74, wherein the ITRs in the first vector and second vector are AAV2 ITRs or have at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to AAV2 ITRs.

E76. The dual vector system of any one of E1-E75, wherein the poly(A) sequence is a bovine growth hormone (bGH) poly(A) signal sequence.

E77. The dual vector system of any one of E1-E76, wherein the splice donor sequence in the first vector comprises or consists of the sequence of SEQ ID NO: 54.

E78. The dual vector system of any one of E1-E77, wherein the splice acceptor sequence in the second vector comprises or consists of the sequence of SEQ ID NO: 55.

E79. The dual vector system of any one of E1-E78, wherein the first AAV vector comprises a Kozak sequence 3' of the promoter and 5' of the first coding polynucleotide that encodes the N-terminal portion of the OTOF isoform 5 protein.

E80. The dual vector system of E1, wherein the first AAV vector comprises a polynucleotide sequence comprising the sequence of nucleotides 2272 to 6041 of SEQ ID NO: 60.

E81. The dual vector system of E1 or E80, wherein the first AAV vector comprises a polynucleotide sequence comprising or consisting of the sequence of nucleotides 2049 to 6264 of SEQ ID NO: 60.

E82. The dual vector system of E1, wherein the first AAV vector comprises a polynucleotide sequence comprising the sequence of nucleotides 182 to 3949 of SEQ ID NO: 62.

E83. The dual vector system of E1 or E82, wherein the first AAV vector comprises a polynucleotide sequence comprising or consisting of the sequence of nucleotides 19 to 4115 of SEQ ID NO: 62.

E84. The dual vector system of E44, wherein the first AAV vector comprises a polynucleotide sequence comprising the sequence of positions 2267 to 6014 of SEQ ID NO: 64.

E85. The dual vector system of E44 or E84, wherein the first AAV vector comprises a polynucleotide sequence comprising or consisting of the sequence of positions 2049 to 6237 of SEQ ID NO: 64.

E86. The dual vector system of E44, wherein the first AAV vector comprises a polynucleotide sequence comprising the sequence of positions 177 to 3924 of SEQ ID NO: 65.

E87. The dual vector system of E44 or E86, wherein the first AAV vector comprises a polynucleotide sequence comprising or consisting of the sequence of positions 19 to 4090 of SEQ ID NO: 65.

E88. The dual vector system of any one of E1, E44, E80, E81, E84, and E85, wherein the second AAV vector comprises a polynucleotide sequence comprising the sequence of nucleotides 2267 to 6476 of SEQ ID NO: 61.

E89. The dual vector system of any one of E1, E44, E80, E81, E84, E85, and E88, wherein the second AAV vector comprises a polynucleotide sequence comprising or consisting of the sequence of nucleotides 2049 to 6693 of SEQ ID NO: 61.

E90. The dual vector system of any one of E1, E44, E82, E83, E86, and E87, wherein the second AAV vector comprises a polynucleotide sequence comprising the sequence of nucleotides 187 to 4396 of SEQ ID NO: 63.

E91. The dual vector system of any one of E1, E44, E82, E83, E86, E87, and E90, wherein the second AAV vector comprises a polynucleotide sequence comprising or consisting of the sequence of nucleotides 19 to 4589 of SEQ ID NO: 63.

E92. The dual vector system of E1, wherein the first AAV vector comprises a polynucleotide sequence comprising the sequence of nucleotides 235 to 4004 of SEQ ID NO: 66.

E93. The dual vector system of E1 or E92, wherein the first AAV vector comprises a polynucleotide sequence comprising or consisting of the sequence of nucleotides 12 to 4227 of SEQ ID NO: 66.

E94. The dual vector system of E44, wherein the first AAV vector comprises a polynucleotide sequence comprising the sequence of nucleotides 230 to 3977 of SEQ ID NO: 68.

E95. The dual vector system of E44 or E94, wherein the first AAV vector comprises a polynucleotide sequence comprising or consisting of the sequence of nucleotides 12 to 4200 of SEQ ID NO: 68.

E96. The dual vector system of any one of E1, E44, and E92-E95, wherein the second AAV vector comprises a polynucleotide sequence comprising the sequence of nucleotides 229 to 4438 of SEQ ID NO: 67.

E97. The dual vector system of any one of E1, E44, and E92-E96, wherein the second AAV vector comprises a polynucleotide sequence comprising or consisting of the sequence of nucleotides 12 to 4655 of SEQ ID NO: 67.

E98. A method of increasing OTOF expression in a subject in need thereof, the method comprising administering to the subject a therapeutically effective amount of the dual vector system of any one of E1-E97.

E99. A method of treating a subject having or at risk of developing sensorineural hearing loss, the method comprising administering to the subject a therapeutically effective amount of the dual vector system of any one of E1-E97.

E100. A method of treating a subject having or at risk of developing auditory neuropathy, the method comprising administering to the subject a therapeutically effective amount of the dual vector system of any one of E1-E97.

E101. The method of any one of E98-E100, wherein the subject has a mutation in OTOF.

E102. The method of any one of E98-E100, wherein the subject has been identified as having a mutation in OTOF.

E103. The method of any one of E98-E100, wherein the method further comprises identifying the subject as having a mutation in OTOF prior to administering the dual vector system.

E104. The method of any one of E98-E103, wherein the subject has or is identified as having Deafness, Autosomal Recessive 9 (DFNB9).

E105. The method of any one of E98-E104, wherein the method further comprises evaluating the hearing of the subject prior to administering the dual vector system.

E106. The method of any one of E98-E105, wherein the dual vector system is administered locally to the middle or inner ear.

E107. The method of E106, wherein the dual vector system is administered by injection through the round window membrane, injection into a semicircular canal, canalostomy, insertion of a catheter through the round window membrane, transtympanic injection, or intratympanic injection.

E108. The method of any one of E98-107, wherein the method increases OTOF expression in a cochlear hair cell.

E109. The method of E108, wherein the cochlear hair cell is an inner hair cell.

E110. The method of any one of E98-E109, wherein the subject is a mammal.

E111. The method of E110, wherein the subject is a human.

E112. The method of any one of E98-E111, wherein the method further comprises evaluating the hearing of the subject after administering the dual vector system.

E113. The method of any one of E98-E112, wherein the dual vector system prevents or reduces hearing loss, delays the development of hearing loss, slows the progression of hearing loss, improves hearing, improves speech discrimination, or improves hair cell function.

E114. The method of any one of E98-E113, wherein the dual vector system is administered in an amount sufficient to increase OTOF expression in a cochlear hair cell, prevent or reduce hearing loss, delay the development of hearing loss, slow the progression of hearing loss, improve hearing, improve speech discrimination, or improve hair cell function.

E115. A method of increasing OTOF expression in a cell, the method comprising introducing the dual vector system of any one of E1-E97 into the cell.

E116. The method of E115, wherein the cell is a cochlear hair cell.

E117. The method of E116, wherein the cell is an inner hair cell.

E118. The method of any one of E115-117, wherein the cell is a mammalian cell.

E119. The method of E118, wherein the cell is a human cell.

E120. The method of any one of E98-E119, wherein the first vector and the second vector are administered concurrently.

E121. The method of any one of E98-E120, wherein the first vector and the second vector are administered sequentially.

E122. The method of any one of E98-E121, wherein the first vector and the second vector are administered at a concentration of about $1 \times 10^7$ vector genomes (VG)/ear to about $2 \times 10^{15}$ VG/ear.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

The invention claimed is:

1. A dual vector system comprising:
a first adeno-associated virus (AAV) vector comprising a Myo15 promoter operably linked to a first coding polynucleotide that encodes an N-terminal portion of an Otoferlin (OTOF) isoform 5 protein, a splice donor signal sequence positioned 3' of the first coding polynucleotide, and a first recombinogenic region positioned 3' of the splice donor signal sequence; and
a second AAV vector comprising a second recombinogenic region, a splice acceptor signal sequence positioned 3' of the second recombinogenic region, a second coding polynucleotide that encodes a C-terminal portion of the OTOF isoform 5 protein positioned 3' of the splice acceptor signal sequence, and a poly(A) sequence positioned 3' of the second coding polynucleotide,
wherein the first coding polynucleotide and the second coding polynucleotide that encode the OTOF isoform 5 protein do not overlap,
wherein neither the first nor second AAV vector encodes the full-length OTOF isoform 5 protein,
and wherein the first AAV vector comprises a polynucleotide sequence comprising the sequence of nucleotides 235 to 4004 of SEQ ID NO: 66 and the second AAV vector comprises a polynucleotide sequence comprising the sequence of nucleotides 229 to 4438 of SEQ ID NO: 67.

2. A dual vector system comprising:
a first AAV vector comprising a Myo15 promoter operably linked to a first coding polynucleotide that encodes an N-terminal portion of an OTOF isoform 5 protein, a splice donor signal sequence positioned 3' of the first coding polynucleotide, and a first recombinogenic region positioned 3' of the splice donor signal sequence; and
a second AAV vector comprising a second recombinogenic region, a splice acceptor signal sequence positioned 3' of the second recombinogenic region, a second coding polynucleotide that encodes a C-terminal portion of the OTOF isoform 5 protein positioned 3' of the splice acceptor signal sequence, and a poly(A) sequence positioned 3' of the second coding polynucleotide,
wherein the first coding polynucleotide and the second coding polynucleotide that encode the OTOF isoform 5 protein do not overlap,
wherein neither the first nor second AAV vector encodes the full-length OTOF isoform 5 protein,
and wherein the first AAV vector comprises a polynucleotide sequence comprising the sequence of nucleotides 182 to 3949 of SEQ ID NO: 62 and the second AAV vector comprises a polynucleotide sequence comprising the sequence of nucleotides 187 to 4396 of SEQ ID NO: 63.

3. The dual vector system of claim 1, wherein the first AAV vector and the second AAV vector comprise an AAV1 capsid.

4. The dual vector system of claim 2, wherein the first AAV vector and the second AAV vector comprise an AAV1 capsid.

* * * * *

SEQUENCE LISTING

<160> NUMBER OF SEQ ID NOS: 68

<210> SEQ ID NO 1
<211> LENGTH: 1997
<212> TYPE: PRT
<213> ORGANISM: Homo sapiens

<400> SEQUENCE: 1

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
            115                 120                 125

Asp Asp Gly Asp Phe Leu Gly Asp Glu Ser Leu Gln Glu Glu Glu Lys
        130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
            195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270

Pro Val Val Cys Val Glu Val Gly Asp Asp Lys Lys Tyr Thr Ser Met
            275                 280                 285

Lys Glu Ser Thr Asn Cys Pro Tyr Tyr Asn Glu Tyr Phe Val Phe Asp
        290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
        355                 360                 365

-continued

```
Leu Lys Gly Tyr Val Lys Cys Asp Val Ala Val Val Gly Lys Gly Asp
    370             375                 380

Asn Ile Lys Thr Pro His Lys Ala Asn Glu Thr Asp Glu Asp Ile
385                 390                 395                 400

Glu Gly Asn Leu Leu Leu Pro Glu Gly Val Pro Pro Glu Arg Gln Trp
                405             410                 415

Ala Arg Phe Tyr Val Lys Ile Tyr Arg Ala Glu Gly Leu Pro Arg Met
            420             425                 430

Asn Thr Ser Leu Met Ala Asn Val Lys Lys Ala Phe Ile Gly Glu Asn
        435             440                 445

Lys Asp Leu Val Asp Pro Tyr Val Gln Val Phe Phe Ala Gly Gln Lys
    450             455                 460

Gly Lys Thr Ser Val Gln Lys Ser Ser Tyr Glu Pro Leu Trp Asn Glu
465             470                 475                 480

Gln Val Val Phe Thr Asp Leu Phe Pro Pro Leu Cys Lys Arg Met Lys
                485             490                 495

Val Gln Ile Arg Asp Ser Asp Lys Val Asn Asp Val Ala Ile Gly Thr
            500             505                 510

His Phe Ile Asp Leu Arg Lys Ile Ser Asn Asp Gly Asp Lys Gly Phe
        515             520                 525

Leu Pro Thr Leu Gly Pro Ala Trp Val Asn Met Tyr Gly Ser Thr Arg
    530             535                 540

Asn Tyr Thr Leu Leu Asp Glu His Gln Asp Leu Asn Glu Gly Leu Gly
545             550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
            580             585                 590

Val Glu Gln Ala Thr Pro Ile Ser Glu Ser Cys Ala Gly Lys Met Glu
            595             600                 605

Glu Phe Phe Leu Phe Gly Ala Phe Leu Glu Ala Ser Met Ile Asp Arg
    610             615                 620

Arg Asn Gly Asp Lys Pro Ile Thr Phe Glu Val Thr Ile Gly Asn Tyr
625             630                 635                 640

Gly Asn Glu Val Asp Gly Leu Ser Arg Pro Gln Arg Pro Arg Pro Arg
            645             650                 655

Lys Glu Pro Gly Asp Glu Glu Glu Val Asp Leu Ile Gln Asn Ala Ser
            660             665                 670

Asp Asp Glu Ala Gly Asp Ala Gly Asp Leu Ala Ser Val Ser Ser Thr
            675             680                 685

Pro Pro Met Arg Pro Gln Val Thr Asp Arg Asn Tyr Phe His Leu Pro
    690             695                 700

Tyr Leu Glu Arg Lys Pro Cys Ile Tyr Ile Lys Ser Trp Trp Pro Asp
705             710                 715                 720

Gln Arg Arg Arg Leu Tyr Asn Ala Asn Ile Met Asp His Ile Ala Asp
            725             730                 735

Lys Leu Glu Glu Gly Leu Asn Asp Ile Gln Glu Met Ile Lys Thr Glu
            740             745                 750

Lys Ser Tyr Pro Glu Arg Arg Leu Arg Gly Val Leu Glu Glu Leu Ser
        755             760                 765

Cys Gly Cys Cys Arg Phe Leu Ser Leu Ala Asp Lys Asp Gln Gly His
    770             775                 780

Ser Ser Arg Thr Arg Leu Asp Arg Glu Arg Leu Lys Ser Cys Met Arg
```

-continued

```
785              790              795              800

Glu Leu Glu Asn Met Gly Gln Gln Ala Arg Met Leu Arg Ala Gln Val
            805              810              815

Lys Arg His Thr Val Arg Asp Lys Leu Arg Leu Cys Gln Asn Phe Leu
            820              825              830

Gln Lys Leu Arg Phe Leu Ala Asp Glu Pro Gln His Ser Ile Pro Asp
            835              840              845

Ile Phe Ile Trp Met Met Ser Asn Asn Lys Arg Val Ala Tyr Ala Arg
    850              855              860

Val Pro Ser Lys Asp Leu Leu Phe Ser Ile Val Glu Glu Glu Thr Gly
865              870              875              880

Lys Asp Cys Ala Lys Val Lys Thr Leu Phe Leu Lys Leu Pro Gly Lys
            885              890              895

Arg Gly Phe Gly Ser Ala Gly Trp Thr Val Gln Ala Lys Val Glu Leu
            900              905              910

Tyr Leu Trp Leu Gly Leu Ser Lys Gln Arg Lys Glu Phe Leu Cys Gly
            915              920              925

Leu Pro Cys Gly Phe Gln Glu Val Lys Ala Ala Gln Gly Leu Gly Leu
    930              935              940

His Ala Phe Pro Pro Val Ser Leu Val Tyr Thr Lys Lys Gln Ala Phe
945              950              955              960

Gln Leu Arg Ala His Met Tyr Gln Ala Arg Ser Leu Phe Ala Ala Asp
            965              970              975

Ser Ser Gly Leu Ser Asp Pro Phe Ala Arg Val Phe Phe Ile Asn Gln
            980              985              990

Ser Gln Cys Thr Glu Val Leu Asn  Glu Thr Leu Cys Pro  Thr Trp Asp
        995              1000             1005

Gln Met  Leu Val Phe Asp Asn  Leu Glu Leu Tyr Gly  Glu Ala His
    1010             1015             1020

Glu Leu  Arg Asp Asp Pro Pro  Ile Ile Val Ile Glu  Ile Tyr Asp
    1025             1030             1035

Gln Asp  Ser Met Gly Lys Ala  Asp Phe Met Gly Arg  Thr Phe Ala
    1040             1045             1050

Lys Pro  Leu Val Lys Met Ala  Asp Glu Ala Tyr Cys  Pro Pro Arg
    1055             1060             1065

Phe Pro  Pro Gln Leu Glu Tyr  Tyr Gln Ile Tyr Arg  Gly Asn Ala
    1070             1075             1080

Thr Ala  Gly Asp Leu Leu Ala  Ala Phe Glu Leu Leu  Gln Ile Gly
    1085             1090             1095

Pro Ala  Gly Lys Ala Asp Leu  Pro Pro Ile Asn Gly  Pro Val Asp
    1100             1105             1110

Val Asp  Arg Gly Pro Ile Met  Pro Val Pro Met Gly  Ile Arg Pro
    1115             1120             1125

Val Leu  Ser Lys Tyr Arg Val  Glu Val Leu Phe Trp  Gly Leu Arg
    1130             1135             1140

Asp Leu  Lys Arg Val Asn Leu  Ala Gln Val Asp Arg  Pro Arg Val
    1145             1150             1155

Asp Ile  Glu Cys Ala Gly Lys  Gly Val Gln Ser Ser  Leu Ile His
    1160             1165             1170

Asn Tyr  Lys Lys Asn Pro Asn  Phe Asn Thr Leu Val  Lys Trp Phe
    1175             1180             1185

Glu Val  Asp Leu Pro Glu Asn  Glu Leu Leu His Pro  Pro Leu Asn
    1190             1195             1200
```

-continued

```
Ile Arg  Val Val Asp Cys Arg  Ala Phe Gly Arg Tyr  Thr Leu Val
    1205             1210              1215

Gly Ser  His Ala Val Ser Ser  Leu Arg Arg Phe Ile  Tyr Arg Pro
    1220             1225              1230

Pro Asp  Arg Ser Ala Pro Ser  Trp Asn Thr Thr Val  Arg Leu Leu
    1235             1240              1245

Arg Arg  Cys Arg Val Leu Cys  Asn Gly Gly Ser Ser  Ser His Ser
    1250             1255              1260

Thr Gly  Glu Val Val Val Thr  Met Glu Pro Glu Val  Pro Ile Lys
    1265             1270              1275

Lys Leu  Glu Thr Met Val Lys  Leu Asp Ala Thr Ser  Glu Ala Val
    1280             1285              1290

Val Lys  Val Asp Val Ala Glu  Glu Glu Lys Glu Lys  Lys Lys Lys
    1295             1300              1305

Lys Lys  Gly Thr Ala Glu Glu  Pro Glu Glu Glu Glu  Pro Asp Glu
    1310             1315              1320

Ser Met  Leu Asp Trp Trp Ser  Lys Tyr Phe Ala Ser  Ile Asp Thr
    1325             1330              1335

Met Lys  Glu Gln Leu Arg Gln  Gln Glu Pro Ser Gly  Ile Asp Leu
    1340             1345              1350

Glu Glu  Lys Glu Glu Val Asp  Asn Thr Glu Gly Leu  Lys Gly Ser
    1355             1360              1365

Met Lys  Gly Lys Glu Lys Ala  Arg Ala Ala Lys Glu  Glu Lys Lys
    1370             1375              1380

Lys Lys  Thr Gln Ser Ser Gly  Ser Gly Gln Gly Ser  Glu Ala Pro
    1385             1390              1395

Glu Lys  Lys Lys Pro Lys Ile  Asp Glu Leu Lys Val  Tyr Pro Lys
    1400             1405              1410

Glu Leu  Glu Ser Glu Phe Asp  Asn Phe Glu Asp Trp  Leu His Thr
    1415             1420              1425

Phe Asn  Leu Leu Arg Gly Lys  Thr Gly Asp Asp Glu  Asp Gly Ser
    1430             1435              1440

Thr Glu  Glu Glu Arg Ile Val  Gly Arg Phe Lys Gly  Ser Leu Cys
    1445             1450              1455

Val Tyr  Lys Val Pro Leu Pro  Glu Asp Val Ser Arg  Glu Ala Gly
    1460             1465              1470

Tyr Asp  Ser Thr Tyr Gly Met  Phe Gln Gly Ile Pro  Ser Asn Asp
    1475             1480              1485

Pro Ile  Asn Val Leu Val Arg  Val Tyr Val Val Arg  Ala Thr Asp
    1490             1495              1500

Leu His  Pro Ala Asp Ile Asn  Gly Lys Ala Asp Pro  Tyr Ile Ala
    1505             1510              1515

Ile Arg  Leu Gly Lys Thr Asp  Ile Arg Asp Lys Glu  Asn Tyr Ile
    1520             1525              1530

Ser Lys  Gln Leu Asn Pro Val  Phe Gly Lys Ser Phe  Asp Ile Glu
    1535             1540              1545

Ala Ser  Phe Pro Met Glu Ser  Met Leu Thr Val Ala  Val Tyr Asp
    1550             1555              1560

Trp Asp  Leu Val Gly Thr Asp  Asp Leu Ile Gly Glu  Thr Lys Ile
    1565             1570              1575

Asp Leu  Glu Asn Arg Phe Tyr  Ser Lys His Arg Ala  Thr Cys Gly
    1580             1585              1590
```

```
Ile Ala Gln Thr Tyr Ser Thr  His Gly Tyr Asn Ile  Trp Arg Asp
    1595            1600            1605

Pro Met Lys Pro Ser Gln Ile  Leu Thr Arg Leu Cys  Lys Asp Gly
    1610            1615            1620

Lys Val Asp Gly Pro His Phe  Gly Pro Pro Gly Arg  Val Lys Val
    1625            1630            1635

Ala Asn Arg Val Phe Thr Gly  Pro Ser Glu Ile Glu  Asp Glu Asn
    1640            1645            1650

Gly Gln Arg Lys Pro Thr Asp  Glu His Val Ala Leu  Leu Ala Leu
    1655            1660            1665

Arg His Trp Glu Asp Ile Pro  Arg Ala Gly Cys Arg  Leu Val Pro
    1670            1675            1680

Glu His Val Glu Thr Arg Pro  Leu Leu Asn Pro Asp  Lys Pro Gly
    1685            1690            1695

Ile Glu Gln Gly Arg Leu Glu  Leu Trp Val Asp Met  Phe Pro Met
    1700            1705            1710

Asp Met Pro Ala Pro Gly Thr  Pro Leu Asp Ile Ser  Pro Arg Lys
    1715            1720            1725

Pro Lys Lys Tyr Glu Leu Arg  Val Ile Ile Trp Asn  Thr Asp Glu
    1730            1735            1740

Val Val Leu Glu Asp Asp Asp  Phe Phe Thr Gly Glu  Lys Ser Ser
    1745            1750            1755

Asp Ile Phe Val Arg Gly Trp  Leu Lys Gly Gln Gln  Glu Asp Lys
    1760            1765            1770

Gln Asp Thr Asp Val His Tyr  His Ser Leu Thr Gly  Glu Gly Asn
    1775            1780            1785

Phe Asn Trp Arg Tyr Leu Phe  Pro Phe Asp Tyr Leu  Ala Ala Glu
    1790            1795            1800

Glu Lys Ile Val Ile Ser Lys  Lys Glu Ser Met Phe  Ser Trp Asp
    1805            1810            1815

Glu Thr Glu Tyr Lys Ile Pro  Ala Arg Leu Thr Leu  Gln Ile Trp
    1820            1825            1830

Asp Ala Asp His Phe Ser Ala  Asp Asp Phe Leu Gly  Ala Ile Glu
    1835            1840            1845

Leu Asp Leu Asn Arg Phe Pro  Arg Gly Ala Lys Thr  Ala Lys Gln
    1850            1855            1860

Cys Thr Met Glu Met Ala Thr  Gly Glu Val Asp Val  Pro Leu Val
    1865            1870            1875

Ser Ile Phe Lys Gln Lys Arg  Val Lys Gly Trp Trp  Pro Leu Leu
    1880            1885            1890

Ala Arg Asn Glu Asn Asp Glu  Phe Glu Leu Thr Gly  Lys Val Glu
    1895            1900            1905

Ala Glu Leu His Leu Leu Thr  Ala Glu Glu Ala Glu  Lys Asn Pro
    1910            1915            1920

Val Gly Leu Ala Arg Asn Glu  Pro Asp Pro Leu Glu  Lys Pro Asn
    1925            1930            1935

Arg Pro Asp Thr Ala Phe Val  Trp Phe Leu Asn Pro  Leu Lys Ser
    1940            1945            1950

Ile Lys Tyr Leu Ile Cys Thr  Arg Tyr Lys Trp Leu  Ile Ile Lys
    1955            1960            1965

Ile Val Leu Ala Leu Leu Gly  Leu Leu Met Leu Gly  Leu Phe Leu
    1970            1975            1980

Tyr Ser Leu Pro Gly Tyr Met  Val Lys Lys Leu Leu  Gly Ala
```

-continued

```
         1985              1990              1995
```

<210> SEQ ID NO 2
<211> LENGTH: 5994
<212> TYPE: DNA
<213> ORGANISM: Homo sapiens

<400> SEQUENCE: 2

```
atggccttgc tcatccacct caagacagtc tcggagctgc ggggcagggg cgaccggatc      60
gccaaagtga ctttccgagg gcaatccttc tactctcggg tcctggagaa ctgtgaggat     120
gtggctgact ttgatgagac atttcggtgg ccggtggcca gcagcatcga cagaaatgag     180
atgctggaga ttcaggtttt caactacagc aaagtcttca gcaacaagct catcgggacc     240
ttccgcatgg tgctgcagaa ggtggtagag gagagccatg tggaggtgac tgacacgctg     300
attgatgaca caaatgctat catcaagacc agcctgtgcg tggaggtccg gtatcaggcc     360
actgacggca cagtgggctc ctgggacgat ggggacttcc tgggagatga gtctcttcaa     420
gaggaagaga aggacagcca agagacggat ggactgctcc caggctcccg gcccagctcc     480
cggcccccag agagaagag cttccggaga gccgggagga gcgtgttctc cgccatgaag     540
ctcggcaaaa accggtctca caggaggag ccccaaagac cagatgaacc ggcggtgctg     600
gagatggaag accttgacca tctggccatt cggctaggag atggactgga tcccgactcg     660
gtgtctctag cctcagtcac agctctcacc actaatgtct ccaacaagcg atctaagcca     720
gacattaaga tggagccaag tgctgggcgg cccatggatt accaggtcag catcacggtg     780
atcgaggccc ggcagctggt gggcttgaac atggaccctg tggtgtgcgt ggaggtgggt     840
gacgacaaga gtacacatc catgaaggag tccactaact gcccctatta caacgagtac     900
ttcgtcttcg acttccatgt ctctccggat gtcatgtttg acaagatcat caagatttcg     960
gtgattcact ccaagaacct gctgcgcagt ggcaccctgg tgggctcctt caaaatggac    1020
gtgggaaccg tgtactcgca gccagagcac cagttccatc acaagtgggc catcctgtct    1080
gaccccgatg acatctcctc ggggctgaag ggctacgtga agtgtgacgt tgccgtggtg    1140
ggcaaagggg acaacatcaa gacgccccac aaggccaatg agaccgacga agatgacatt    1200
gaggggaact tgctgctccc cgagggggtg ccccccgaac gccagtgggc ccggttctat    1260
gtgaaaattt accgagcaga ggggctgccc cgtatgaaca caagcctcat ggccaatgta    1320
aagaaggctt tcatcggtga aaacaaggac ctcgtggacc cctacgtgca agtcttcttt    1380
gctggccaga gggcaagac ttcagtgcag aagagcagct atgagcccct gtggaatgag    1440
caggtcgtct ttacagacct cttccccca ctctgcaaac gcatgaaggt gcagatccga    1500
gactcggaca aggtcaacga cgtggccatc ggcacccact tcattgacct cgcgcaagatt    1560 tctaatgacg agacaaagg cttcctgccc acactgggcc cagcctgggt gaacatgtac    1620
ggctccacac gtaactacac gctgctggat gagcatcagg acctgaacga gggcctgggg    1680
gagggtgtgt ccttccgggc ccggctcctg ctggcctgg ctgtggagat cgtagacacc    1740
tccaaccctg agctcaccag ctccacagag gtgcaggtgg agcaggccac gcccatctcg    1800
gagagctgtg caggtaaaat ggaagaattc tttctctttg gagccttcct ggaggcctca    1860
atgatcgacc ggagaaacgg agacaagccc atcacctttg aggtcaccat aggcaactat    1920
gggaacgaag ttgatggcct gtcccggccc cagcggcctc ggccccgaa ggagccgggg    1980 gatgaggaag aagtagacct gattcagaac gcaagtgatg acgaggccgg tgatgccggg    2040
gacctggcct cagtctcctc cactccacca atgcggcccc aggtcaccga caggaactac    2100
```

-continued

```
ttccatctgc cctacctgga gcgaaagccc tgcatctaca tcaagagctg gtggccggac     2160
cagcgccgcc gcctctacaa tgccaacatc atggaccaca ttgccgacaa gctggaagaa     2220
ggcctgaacg acatacagga gatgatcaaa acggagaagt cctaccctga gcgtcgcctg     2280
cggggcgtcc tggaggagct gagctgtggc tgctgccgct tcctctccct cgctgacaag     2340
gaccagggcc actcatcccg caccaggctt gaccgggagc gcctcaagtc ctgcatgagg     2400
gagctggaaa acatggggca gcaggccagg atgctgcggg cccaggtgaa gcggcacacg     2460
gtgcgggaca agctgaggct gtgccagaac ttcctgcaga agctgcgctt cctggcggac     2520
gagccccagc acagcattcc cgacatcttc atctggatga tgagcaacaa caagcgtgtc     2580
gcctatgccc gtgtgccctc caaggacctg ctcttctcca tcgtggagga ggagactggc     2640
aaggactgcg ccaaggtcaa gacgctcttc cttaagctgc cagggaagcg gggcttcggc     2700
tcggcaggct ggacagtgca ggccaaggtg gagctgtacc tgtggctggg cctcagcaaa     2760
cagcgcaagg agttcctgtg cggcctgccc tgtggcttcc aggaggtcaa ggcagcccag     2820
ggcctgggcc tgcatgcctt cccacccgtc agcctggtct acaccaagaa gcaggcgttc     2880
cagctccgag cgcacatgta ccaggcccgc agcctctttg ccgccgacag cagcggactc     2940
tcagacccct ttgcccgcgt cttcttcatc aatcagagtc agtgcacaga ggtgctgaat     3000
gagaccctgt gtcccacctg ggaccagatg ctggtgttcg acaacctgga gctctatggt     3060
gaagctcatg agctgaggga cgatccgccc atcattgtca ttgaaatcta tgaccaggat     3120
tccatgggca aagctgactt catgggccgg accttcgcca aaccctggt gaagatggca     3180 gacgaggcgt actgcccacc ccgcttccca cctcagctcg agtactacca gatctaccgt     3240
ggcaacgcca cagctggaga cctgctggcg gccttcgagc tgctgcagat tggaccagca     3300
gggaaggctg acctgccccc catcaatggc ccggtggacg tggaccgagg tcccatcatg     3360
cccgtgccca tgggcatccg gcccgtgctc agcaagtacc gagtggaggt gctgttctgg     3420
ggcctacggg acctaaagcg ggtgaacctg gcccaggtgg accggccacg ggtggacatc     3480
gagtgtgcag ggaagggggt gcagtcgtcc ctgatccaca attataagaa gaaccccaac     3540
ttcaacaccc tcgtcaagtg gtttgaagtg gacctcccag agaacgagct gctgcacccg     3600
cccttgaaca tccgtgtggt ggactgccgg gccttcggtc gctacacact ggtgggctcc     3660
catgccgtca gctccctgcg acgcttcatc taccggcccc cagaccgctc ggcccccagc     3720
tggaacacca cggtcaggct tctccggcgc tgccgtgtgc tgtgcaatgg gggctcctcc     3780
tctcactcca caggggaggt tgtggtgact atggagccag aggtacccat caagaaactg     3840
gagaccatgg tgaagctgga cgcgacttct gaagctgttg tcaaggtgga tgtggctgag     3900 gaggagaag agaagaagaa gaagaagaag ggcactgcgg aggagccaga ggaggaggag     3960
ccagacgaga gcatgctgga ctggtggtcc aagtactttg cctccattga caccatgaag     4020
gagcaacttc gacaacaaga gccctctgga attgacttgg aggagaagga ggaagtggac     4080
aataccgagg gcctgaaggg gtcaatgaag ggcaaggaga aggcaagggc tgccaaagag     4140
gagaagaaga gaaaactca gagctctggc tctggccagg ggtccgaggc ccccgagaag     4200
aagaaaccca agattgatga gcttaaggta taccccaaag agctggagtc cgagtttgat     4260
aactttgagg actggctgca cactttcaac ttgcttcggg gcaagaccgg ggatgatgag     4320
gatggctcca ccgaggagga gcgcattgtg ggacgcttca agggctccct ctgcgtgtac     4380
aaagtgccac tcccagagga cgtgtcccgg gaagccggct acgactccac ctacggcatg     4440
```

```
ttccagggca tcccgagcaa tgaccccatc aatgtgctgg tccgagtcta tgtggtccgg    4500
gccacggacc tgcaccctgc tgacatcaac ggcaaagctg accctacat cgccatccgg     4560 ctaggcaaga ctgacatccg cgacaaggag aactacatct ccaagcagct caaccctgtc    4620
tttgggaagt cctttgacat cgaggcctcc ttccccatgg aatccatgct gacggtggct    4680
gtgtatgact gggacctggt gggcactgat gacctcattg gggaaaccaa gatcgacctg    4740
gagaaccgct tctacagcaa gcaccgcgcc acctgcggca tcgcccagac ctactccaca    4800
catggctaca atatctggcg ggaccccatg aagcccagcc agatcctgac ccgcctctgc    4860
aaagacggca aagtggacgg cccccacttt gggccccctg ggagagtgaa ggtggccaac    4920
cgcgtcttca ctgggccctc tgagattgag gacgagaacg gtcagaggaa gcccacagac    4980
gagcatgtgg cgctgttggc cctgaggcac tgggaggaca tcccccgcgc aggctgccgc    5040
ctggtgccag agcatgtgga gacgaggccg ctgctcaacc ccgacaagcc gggcatcgag    5100
cagggccgcc tggagctgtg ggtggacatg ttccccatgg acatgccagc ccctgggacg    5160
cctctggaca tctcacctcg gaagcccaag aagtacgagc tgcgggtcat catctggaac    5220
acagatgagg tggtcttgga ggacgacgac ttcttcacag gggagaagtc cagtgacatc    5280
ttcgtgaggg ggtggctgaa gggccagcag gaggacaagc aggacacaga cgtccactac    5340
cactccctca ctggcgaggg caacttcaac tggcgctacc tgttcccctt cgactacctg    5400
gcggcggagg agaagatcgt catctccaag aaggagtcca tgttctcctg ggacgagacc    5460
gagtacaaga tccccgcgcg gctcacccctg cagatctggg atgcggacca cttctccgct    5520
gacgacttcc tggggggccat cgagctggac ctgaaccggt tccgcgcggg cgcaaagaca    5580
gccaagcagt gcaccatgga gatggccacc ggggaggtgg acgtgcccct cgtgtccatc    5640
ttcaagcaaa agcgcgtcaa aggctggtgg cccctcctgg cccgcaatga gaacgatgag    5700
tttgagctca cgggcaaggt ggaggctgag ctgcatttac tgacagcaga ggaggcagag    5760
aagaacccag tgggcctggc ccgcaatgaa cctgacccccc tagagaaacc caaccggccc    5820
gacacggcct tcgtctggtt cctcaacccct ctcaagtcca tcaagtacct catctgcacc    5880
cggtacaagt ggctcatcat caagatcgtg ctggcgctgt tggggctgct catgttgggg    5940
ctcttcctct acagcctccc tggctacatg gtcaaaaagc tccttggggc atga         5994
```

<210> SEQ ID NO 3
<211> LENGTH: 5994
<212> TYPE: DNA
<213> ORGANISM: Artificial Sequence
<220> FEATURE:
<223> OTHER INFORMATION: Synthetic Construct
<400> SEQUENCE: 3

```
atggcactgc tgatccacct gaaaaccgtc tccgaactga gaggcagagg ggacagaatc      60
gctaaagtca ccttccgggg acagagcttt tacagcaggg tgctggagaa ctgcgaggac     120
gtggccgact ttgacgagac attcaggtgg cccgtggcca gctccatcga tcgcaatgag     180
atgctggaga tccaggtgtt taactatagc aaggtgttct ccaataagct gatcggcacc     240
ttccggatgg tgctgcagaa ggtggtggag agtcccacg tggaggtgac cgacacactg     300
atcgacgata acaatgccat catcaagaca tccctgtgcg tggaggtgcg ctaccaggcc     360
accgatggca cagtgggctc ttgggacgat ggcgacttcc tgggcgatga gtccctgcag    420
gaggaggaga aggactctca ggagacagat ggcctgctgc ctggctcccg gccatctagc     480
cgcccccctg gcgagaagtc tttttaggaga gccggcaggt ccgtgttctc tgccatgaag    540
```

-continued

```
ctgggcaaga acaggagcca caaggaggag cctcagaggc ccgacgagcc agccgtgctg      600
gagatggagg acctggatca cctggccatc agactgggcg atggcctgga ccctgatagc      660
gtgtccctgg cctccgtgac cgccctgacc acaaacgtgt ctaataagcg gagcaagcca      720
gacatcaaga tggagccatc tgccggcagg cccatggatt accaggtgag catcacagtg      780
atcgaggcca gacagctggt gggcctgaac atggaccccg tggtgtgcgt ggaagtgggc      840
gacgataaga agtacacctc catgaaggag tctacaaact gtccatacta caacgagtac      900
ttcgtgtttg atttccacgt gagccccgac gtgatgttcg ataagatcat caagatcagc      960
gtgatccact ccaagaatct gctgcggtct ggcaccctgg tgggaagctt taagatggac     1020
gtgggcacag tgtactctca gcctgagcac cagttccacc acaagtgggc catcctgagc     1080
gatccagacg atatctcctc tggcctgaag ggctatgtga agtgcgacgt ggcagtggtg     1140
ggcaagggcg ataacatcaa gacccccacac aaggccaatg agacagacga ggacgatatc     1200
gagggaaacc tgctgctgcc agagggagtg ccacccgaga ggcagtgggc caggttctac     1260
gtgaagatct ataggggcaga gggcctgcct aggatgaaca ccagcctgat ggccaatgtg     1320
aagaaggcct tcatcggcga gaacaaggac ctggtggatc cctacgtgca ggtgttcttt     1380
gccggccaga agggcaagac ctccgtgcag aagagctcct atgagcctct gtggaatgag     1440
caggtggtgt ttacagacct gttccctcca ctgtgcaaga ggatgaaggt gcagatcaga     1500
gactctgata aggtgaacga cgtggccatc ggcacccact ttatcgatct gaggaagatc     1560
agcaatgacg gcgataaggg cttcctgccc accctgggcc ccgcctgggt gaacatgtac     1620
ggcagcacca gaaattatac actgctggac gagcaccagg atctgaacga gggcctgggc     1680
gagggcgtga gctttagagc caggctgctg ctgggcctgg ccgtggagat cgtggacacc     1740
tccaatcccg agctgaccctc tagcacagag gtgcaggtgg agcaggccac acctatctct     1800
gagagctgtg ccggcaagat ggaggagttc tttctgtttg gcgccttcct ggaggcctcc     1860
atgatcgacc ggcgcaacgg cgataagcct atcaccttcg aggtgacaat cggcaactac     1920
ggcaatgagg tggacggcct gtctcggccc cagcgcccaa ggcccagaaa ggagcctggc     1980
gacgaggagg aggtggatct gatccagaac gccagcgacg atgaggcagg cgacgcaggc     2040
gatctggcct ccgtgtcctc tacccccccct atgcggccac aggtgacaga ccgcaattac     2100
tttcacctgc cttatctgga gcgcaagcca tgcatctaca tcaagtcttg gtggcccgat     2160
cagaggagac ggctgtataa cgccaatatc atggaccaca tcgccgataa gctggaggag     2220
ggcctgaatg acatccagga gatgatcaag accgagaagt cctatccaga gcgcaggctg     2280
aggggcgtgc tggaggagct gagctgtggc tgctgtagat cctgtccct ggccgacaag     2340 gatcaggggc actcatcacg gacacggctg gaccgggagc ggctgaaatc atgtatgcgg     2400
gagctggaaa atatgggaca gcaggcaagg atgctgcgcg cccaggtgaa gaggcacacc     2460
gtgagagaca agctgcggct gtgccagaac ttcctgcaga agctgcgctt tctggccgat     2520
gagccacagc acagcatccc cgacatcttc atctggatga tgtccaacaa taagagagtg     2580
gcctacgccc gggtgccctc taaggatctg ctgtttagca tcgtggagga ggagacaggc     2640
aaggactgtg ccaaggtgaa gacccttgttc ctgaagctgc ctggcaagag aggctttggc     2700
agcgccggat ggaccgtgca ggcaaaggtg gagctgtatc tgtggctggg cctgtctaag     2760
cagcggaagg agttcctgtg cggcctgccc tgtggctttc aggaggtgaa ggcagcacag     2820
ggactgggac tgcacgccct ccccccccgtg agcctggtgt acaccaagaa gcaggccttt     2880
```

-continued

```
cagctgaggg cccatatgta ccaggccagg tctctgttcg ccgccgatag ctccggactg    2940
agcgacccct ttgccagggt gttctttatc aatcagagcc agtgcacaga ggtgctgaac    3000
gagaccctgt gcccaacatg ggatcagatg ctggtgttcg acaacctgga gctgtacgga    3060
gaggcacacg agctgaggga cgatccaccc atcatcgtga tcgagatcta tgatcaggac    3120
tccatgggca aggccgattt catgggcagg acctttgcca agccctggt gaagatggcc    3180 gacgaggcct actgccctcc aagattcccc cctcagctcg agtactatca gatctatagg    3240
ggaaatgcaa ccgccggaga cctgctggcc gcctttgagc tgctgcagat cggccccgcc    3300
ggaaaggcag acctgccacc catcaacggc ccagtggatg tggacagagg ccccatcatg    3360
cctgtgccaa tgggcatcag accagtgctg tccaagtaca gggtggaggt gctgttctgg    3420
ggactgcgcg acctgaagag ggtgaatctg gcccaggtgg ataggcccag agtggacatc    3480
gagtgcgccg aaagggcgt gcagtctagc ctgatccaca actataagaa gaacccaaat    3540
ttcaacaccc tggtgaagtg gtttgaggtg atctgcccg agaatgagct gctgcaccct    3600
ccactgaaca tccgggtggt ggactgtaga gccttcggca ggtacaccct ggtgggcagc    3660
cacgccgtga gcagcctgag gaggttcatc tacaggcccc ctgacaggtc cgcccttct    3720 tggaatacca cagtgagact gctgcggcgc tgcagggtgc tgtgcaacgg aggcagctcc    3780
tctcactcta ccggcgaggt ggtggtgaca atggagcctg aggtacccat caagaagctg    3840
gagaccatgg tgaagctgga tgccacaagc gaggcagtgg tgaaggtgga cgtggcagag    3900
gaggagaagg agaagaagaa gaagaagaag ggaaccgccg aggagcctga ggaagaggag    3960
ccagatgaga gcatgctgga ctggtggtcc aagtacttcg cctctatcga cacaatgaag    4020
gagcagctga cacagcagga gcctagcggc atcgatctgg aggagaagga ggaggtggac    4080
aataccgagg gcctgaaggg ctccatgaag ggcaaggaga aggcaagggc agcaaaggaa    4140
gagaagaaga agaagaccca gagcagcggc tctggacagg gcagcgaggc accagagaag    4200
aagaagccta agatcgatga gctgaaggtg tacccaaagg agctggagtc cgagttcgat    4260 aatttttgagg actggctgca caccttcaac ctgctgcgcg gcaagacagg cgacgatgag    4320
gacggcagca ccgaggagga gagaatcgtg ggccggttta agggctccct gtgcgtgtac    4380
aaggtgccac tgcctgagga cgtgagcagg gaggccggat acgactctac ctatggcatg    4440
ttccagggca tcccctctaa tgatcctatc aacgtgctgg tgcgcgtgta tgtggtgagg    4500
gccacagatc tgcaccccgc cgacatcaac ggcaaggccg acccttacat cgccatccgc    4560
ctgggcaaga ccgatatcag ggacaaggag aattatatct ccaagcagct gaaccccgtg    4620
ttcggcaagt ctttttgacat cgaggccagc ttccctatgg agtccatgct gaccgtggcc    4680
gtgtacgatt gggaccctggt gggcaccgac gatctgatcg gcgagacaaa gatcgatctg    4740
gagaatcgct tttattctaa gcacagggca acctgcggaa tcgcacagac ctacagcaca    4800
cacggctata acatctggcg cgaccccatg aagcctagcc agatcctgac aaggctgtgc    4860
aaggatggca aggtggacgg accacacttc ggaccaccc gcagagtgaa ggtggccaat    4920
cgggtgttta caggcccttc cgagatcgag gatgagaacg gccagcgcaa gccaaccgac    4980
gagcacgtgg ccctgctggc cctgaggcac tgggaggata tcccaagggc cggatgtagg    5040
ctggtgcctg agcacgtgga gaccagacca ctgctgaatc cagacaagcc aggaatcgag    5100
cagggcaggc tggagctgtg ggtggatatg ttcccaatgg acatgccagc cccaggaaca    5160
cccctggata tctcccctag aaagccaaag aagtacgagc tgagagtgat catctggaac    5220
acagacgagg tggtgctgga ggacgatgac ttctttaccg gcgagaagtc tagcgatatc    5280
```

```
tttgtgcgcg gatggctgaa gggacagcag gaggacaagc aggatacaga cgtgcactac      5340
cactccctga ccggcgaggg caatttcaac tggagatacc tgttcccttt tgattatctg      5400
gccgccgagg agaagatcgt gatctctaag aaggagagca tgttttcctg ggacgagaca      5460
gagtataaga tcccagccag actgaccctg cagatctggg atgccgacca cttcagcgcc      5520
gatgactttc tgggcgccat cgagctggac ctgaaccggt cccaagagg cgccaagacc      5580 gccaagcagt gcacaatgga gatggcaacc ggagaggtgg acgtgcctct ggtgtctatc      5640
ttcaagcaga agcgggtgaa gggatggtgg ccactgctgg ccaggaacga gaatgatgag      5700
tttgagctga caggcaaggt ggaggcagag ctgcacctgc tgaccgccga ggaggcagag      5760
aagaacccag tgggcctggc caggaatgag cccgaccctc tggagaagcc aaacaggccc      5820
gatacagcct cgtgtggtt tctgaatcct ctgaagagca tcaagtacct gatctgtacc      5880
aggtataagt ggctgatcat caagatcgtg ctggccctgc tgggactgct gatgctgggc      5940
ctgtttctgt actccctgcc cggctatatg gtgaagaagc tgctgggcgc ctga          5994
```

<210> SEQ ID NO 4
<211> LENGTH: 1997
<212> TYPE: PRT
<213> ORGANISM: Homo sapiens

<400> SEQUENCE: 4

```
Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
```

-continued

```
              245              250              255
Ser Ile Thr Val Ile Glu Ala Arg Gln Leu Val Gly Leu Asn Met Asp
              260              265              270

Pro Val Val Cys Val Glu Val Gly Asp Asp Lys Lys Tyr Thr Ser Met
              275              280              285

Lys Glu Ser Thr Asn Cys Pro Tyr Tyr Asn Glu Tyr Phe Val Phe Asp
              290              295              300

Phe His Val Ser Pro Asp Val Met Phe Asp Lys Ile Ile Lys Ile Ser
          305              310              315              320

Val Ile His Ser Lys Asn Leu Leu Arg Ser Gly Thr Leu Val Gly Ser
              325              330              335

Phe Lys Met Asp Val Gly Thr Val Tyr Ser Gln Pro Glu His Gln Phe
              340              345              350

His His Lys Trp Ala Ile Leu Ser Asp Pro Asp Asp Ile Ser Ser Gly
              355              360              365

Leu Lys Gly Tyr Val Lys Cys Asp Val Ala Val Val Gly Lys Gly Asp
              370              375              380

Asn Ile Lys Thr Pro His Lys Ala Asn Glu Thr Asp Glu Asp Asp Ile
          385              390              395              400

Glu Gly Asn Leu Leu Leu Pro Glu Gly Val Pro Pro Glu Arg Gln Trp
                  405              410              415

Ala Arg Phe Tyr Val Lys Ile Tyr Arg Ala Glu Gly Leu Pro Arg Met
              420              425              430

Asn Thr Ser Leu Met Ala Asn Val Lys Lys Ala Phe Ile Gly Glu Asn
              435              440              445

Lys Asp Leu Val Asp Pro Tyr Val Gln Val Phe Phe Ala Gly Gln Lys
          450              455              460

Gly Lys Thr Ser Val Gln Lys Ser Ser Tyr Glu Pro Leu Trp Asn Glu
      465              470              475              480

Gln Val Val Phe Thr Asp Leu Phe Pro Pro Leu Cys Lys Arg Met Lys
              485              490              495

Val Gln Ile Arg Asp Ser Asp Lys Val Asn Asp Val Ala Ile Gly Thr
              500              505              510

His Phe Ile Asp Leu Arg Lys Ile Ser Asn Asp Gly Asp Lys Gly Phe
              515              520              525

Leu Pro Thr Leu Gly Pro Ala Trp Val Asn Met Tyr Gly Ser Thr Arg
              530              535              540

Asn Tyr Thr Leu Leu Asp Glu His Gln Asp Leu Asn Glu Gly Leu Gly
          545              550              555              560

Glu Gly Val Ser Phe Arg Ala Arg Leu Leu Leu Gly Leu Ala Val Glu
                  565              570              575

Ile Val Asp Thr Ser Asn Pro Glu Leu Thr Ser Ser Thr Glu Val Gln
              580              585              590

Val Glu Gln Ala Thr Pro Ile Ser Glu Ser Cys Ala Gly Lys Met Glu
              595              600              605

Glu Phe Phe Leu Phe Gly Ala Phe Leu Glu Ala Ser Met Ile Asp Arg
              610              615              620

Arg Asn Gly Asp Lys Pro Ile Thr Phe Glu Val Thr Ile Gly Asn Tyr
          625              630              635              640

Gly Asn Glu Val Asp Gly Leu Ser Arg Pro Gln Arg Pro Arg Pro Arg
                  645              650              655

Lys Glu Pro Gly Asp Glu Glu Glu Val Asp Leu Ile Gln Asn Ala Ser
              660              665              670
```

-continued

```
Asp Asp Glu Ala Gly Asp Ala Gly Asp Leu Ala Ser Val Ser Ser Thr
    675             680             685

Pro Pro Met Arg Pro Gln Val Thr Asp Arg Asn Tyr Phe His Leu Pro
    690             695             700

Tyr Leu Glu Arg Lys Pro Cys Ile Tyr Ile Lys Ser Trp Trp Pro Asp
705             710             715             720

Gln Arg Arg Arg Leu Tyr Asn Ala Asn Ile Met Asp His Ile Ala Asp
            725             730             735

Lys Leu Glu Glu Gly Leu Asn Asp Ile Gln Glu Met Ile Lys Thr Glu
            740             745             750

Lys Ser Tyr Pro Glu Arg Arg Leu Arg Gly Val Leu Glu Glu Leu Ser
            755             760             765

Cys Gly Cys Cys Arg Phe Leu Ser Leu Ala Asp Lys Asp Gln Gly His
    770             775             780

Ser Ser Arg Thr Arg Leu Asp Arg Glu Arg Leu Lys Ser Cys Met Arg
785             790             795             800

Glu Leu Glu Asn Met Gly Gln Gln Ala Arg Met Leu Arg Ala Gln Val
            805             810             815

Lys Arg His Thr Val Arg Asp Lys Leu Arg Leu Cys Gln Asn Phe Leu
            820             825             830

Gln Lys Leu Arg Phe Leu Ala Asp Glu Pro Gln His Ser Ile Pro Asp
            835             840             845

Ile Phe Ile Trp Met Met Ser Asn Asn Lys Arg Val Ala Tyr Ala Arg
    850             855             860

Val Pro Ser Lys Asp Leu Leu Phe Ser Ile Val Glu Glu Glu Thr Gly
865             870             875             880

Lys Asp Cys Ala Lys Val Lys Thr Leu Phe Leu Lys Leu Pro Gly Lys
            885             890             895

Arg Gly Phe Gly Ser Ala Gly Trp Thr Val Gln Ala Lys Val Glu Leu
            900             905             910

Tyr Leu Trp Leu Gly Leu Ser Lys Gln Arg Lys Glu Phe Leu Cys Gly
            915             920             925

Leu Pro Cys Gly Phe Gln Glu Val Lys Ala Ala Gln Gly Leu Gly Leu
    930             935             940

His Ala Phe Pro Pro Val Ser Leu Val Tyr Thr Lys Lys Gln Ala Phe
945             950             955             960

Gln Leu Arg Ala His Met Tyr Gln Ala Arg Ser Leu Phe Ala Ala Asp
            965             970             975

Ser Ser Gly Leu Ser Asp Pro Phe Ala Arg Val Phe Phe Ile Asn Gln
            980             985             990

Ser Gln Cys Thr Glu Val Leu Asn Glu Thr Leu Cys Pro Thr Trp Asp
            995             1000            1005

Gln Met Leu Val Phe Asp Asn Leu Glu Leu Tyr Gly Glu Ala His
    1010            1015            1020

Glu Leu Arg Asp Asp Pro Pro Ile Ile Val Ile Glu Ile Tyr Asp
    1025            1030            1035

Gln Asp Ser Met Gly Lys Ala Asp Phe Met Gly Arg Thr Phe Ala
    1040            1045            1050

Lys Pro Leu Val Lys Met Ala Asp Glu Ala Tyr Cys Pro Pro Arg
    1055            1060            1065

Phe Pro Pro Gln Leu Glu Tyr Tyr Gln Ile Tyr Arg Gly Asn Ala
    1070            1075            1080
```

```
Thr Ala Gly Asp Leu Leu Ala Ala Phe Glu Leu Leu Gln Ile Gly
    1085              1090              1095

Pro Ala Gly Lys Ala Asp Leu Pro Pro Ile Asn Gly Pro Val Asp
    1100              1105              1110

Val Asp Arg Gly Pro Ile Met Pro Val Pro Met Gly Ile Arg Pro
    1115              1120              1125

Val Leu Ser Lys Tyr Arg Val Glu Val Leu Phe Trp Gly Leu Arg
    1130              1135              1140

Asp Leu Lys Arg Val Asn Leu Ala Gln Val Asp Arg Pro Arg Val
    1145              1150              1155

Asp Ile Glu Cys Ala Gly Lys Gly Val Gln Ser Ser Leu Ile His
    1160              1165              1170

Asn Tyr Lys Lys Asn Pro Asn Phe Asn Thr Leu Val Lys Trp Phe
    1175              1180              1185

Glu Val Asp Leu Pro Glu Asn Glu Leu Leu His Pro Pro Leu Asn
    1190              1195              1200

Ile Arg Val Val Asp Cys Arg Ala Phe Gly Arg Tyr Thr Leu Val
    1205              1210              1215

Gly Ser His Ala Val Ser Ser Leu Arg Arg Phe Ile Tyr Arg Pro
    1220              1225              1230

Pro Asp Arg Ser Ala Pro Ser Trp Asn Thr Thr Val Arg Leu Leu
    1235              1240              1245

Arg Arg Cys Arg Val Leu Cys Asn Gly Gly Ser Ser Ser His Ser
    1250              1255              1260

Thr Gly Glu Val Val Val Thr Met Glu Pro Glu Val Pro Ile Lys
    1265              1270              1275

Lys Leu Glu Thr Met Val Lys Leu Asp Ala Thr Ser Glu Ala Val
    1280              1285              1290

Val Lys Val Asp Val Ala Glu Glu Glu Lys Glu Lys Lys Lys Lys
    1295              1300              1305

Lys Lys Gly Thr Ala Glu Glu Pro Glu Glu Glu Glu Pro Asp Glu
    1310              1315              1320

Ser Met Leu Asp Trp Trp Ser Lys Tyr Phe Ala Ser Ile Asp Thr
    1325              1330              1335

Met Lys Glu Gln Leu Arg Gln Gln Glu Pro Ser Gly Ile Asp Leu
    1340              1345              1350

Glu Glu Lys Glu Glu Val Asp Asn Thr Glu Gly Leu Lys Gly Ser
    1355              1360              1365

Met Lys Gly Lys Glu Lys Ala Arg Ala Ala Lys Glu Glu Lys Lys
    1370              1375              1380

Lys Lys Thr Gln Ser Ser Gly Ser Gly Gln Gly Ser Glu Ala Pro
    1385              1390              1395

Glu Lys Lys Lys Pro Lys Ile Asp Glu Leu Lys Val Tyr Pro Lys
    1400              1405              1410

Glu Leu Glu Ser Glu Phe Asp Asn Phe Glu Asp Trp Leu His Thr
    1415              1420              1425

Phe Asn Leu Leu Arg Gly Lys Thr Gly Asp Asp Glu Asp Gly Ser
    1430              1435              1440

Thr Glu Glu Glu Arg Ile Val Gly Arg Phe Lys Gly Ser Leu Cys
    1445              1450              1455

Val Tyr Lys Val Pro Leu Pro Glu Asp Val Ser Arg Glu Ala Gly
    1460              1465              1470

Tyr Asp Ser Thr Tyr Gly Met Phe Gln Gly Ile Pro Ser Asn Asp
```

```
          1475              1480              1485

Pro Ile Asn Val Leu Val Arg  Val Tyr Val Val Arg  Ala Thr Asp
    1490              1495              1500

Leu His Pro Ala Asp Ile Asn  Gly Lys Ala Asp Pro  Tyr Ile Ala
    1505              1510              1515

Ile Arg Leu Gly Lys Thr Asp  Ile Arg Asp Lys Glu  Asn Tyr Ile
    1520              1525              1530

Ser Lys Gln Leu Asn Pro Val  Phe Gly Lys Ser Phe  Asp Ile Glu
    1535              1540              1545

Ala Ser Phe Pro Met Glu Ser  Met Leu Thr Val Ala  Val Tyr Asp
    1550              1555              1560

Trp Asp Leu Val Gly Thr Asp  Asp Leu Ile Gly Glu  Thr Lys Ile
    1565              1570              1575

Asp Leu Glu Asn Arg Phe Tyr  Ser Lys His Arg Ala  Thr Cys Gly
    1580              1585              1590

Ile Ala Gln Thr Tyr Ser Thr  His Gly Tyr Asn Ile  Trp Arg Asp
    1595              1600              1605

Pro Met Lys Pro Ser Gln Ile  Leu Thr Arg Leu Cys  Lys Asp Gly
    1610              1615              1620

Lys Val Asp Gly Pro His Phe  Gly Pro Pro Gly Arg  Val Lys Val
    1625              1630              1635

Ala Asn Arg Val Phe Thr Gly  Pro Ser Glu Ile Glu  Asp Glu Asn
    1640              1645              1650

Gly Gln Arg Lys Pro Thr Asp  Glu His Val Ala Leu  Leu Ala Leu
    1655              1660              1665

Arg His Trp Glu Asp Ile Pro  Arg Ala Gly Cys Arg  Leu Val Pro
    1670              1675              1680

Glu His Val Glu Thr Arg Pro  Leu Leu Asn Pro Asp  Lys Pro Gly
    1685              1690              1695

Ile Glu Gln Gly Arg Leu Glu  Leu Trp Val Asp Met  Phe Pro Met
    1700              1705              1710

Asp Met Pro Ala Pro Gly Thr  Pro Leu Asp Ile Ser  Pro Arg Lys
    1715              1720              1725

Pro Lys Lys Tyr Glu Leu Arg  Val Ile Ile Trp Asn  Thr Asp Glu
    1730              1735              1740

Val Val Leu Glu Asp Asp Asp  Phe Phe Thr Gly Glu  Lys Ser Ser
    1745              1750              1755

Asp Ile Phe Val Arg Gly Trp  Leu Lys Gly Gln Gln  Glu Asp Lys
    1760              1765              1770

Gln Asp Thr Asp Val His Tyr  His Ser Leu Thr Gly  Glu Gly Asn
    1775              1780              1785

Phe Asn Trp Arg Tyr Leu Phe  Pro Phe Asp Tyr Leu  Ala Ala Glu
    1790              1795              1800

Glu Lys Ile Val Ile Ser Lys  Lys Glu Ser Met Phe  Ser Trp Asp
    1805              1810              1815

Glu Thr Glu Tyr Lys Ile Pro  Ala Arg Leu Thr Leu  Gln Ile Trp
    1820              1825              1830

Asp Ala Asp His Phe Ser Ala  Asp Asp Phe Leu Gly  Ala Ile Glu
    1835              1840              1845

Leu Asp Leu Asn Arg Phe Pro  Arg Gly Ala Lys Thr  Ala Lys Gln
    1850              1855              1860

Cys Thr Met Glu Met Ala Thr  Gly Glu Val Asp Val  Pro Leu Val
    1865              1870              1875
```

-continued

```
Ser Ile Phe Lys Gln Lys Arg  Val Lys Gly Trp Trp  Pro Leu Leu
    1880                1885               1890

Ala Arg  Asn Glu Asn Asp Glu  Phe Glu Leu Thr Gly  Lys Val Glu
    1895                1900               1905

Ala Glu  Leu His Leu Leu Thr  Ala Glu Glu Ala Glu  Lys Asn Pro
    1910                1915               1920

Val Gly  Leu Ala Arg Asn Glu  Pro Asp Pro Leu Glu  Lys Pro Asn
    1925                1930               1935

Arg Pro  Asp Thr Ser Phe Ile  Trp Phe Leu Asn Pro  Leu Lys Ser
    1940                1945               1950

Ala Arg  Tyr Phe Leu Trp His  Thr Tyr Arg Trp Leu  Leu Leu Lys
    1955                1960               1965

Leu Leu  Leu Leu Leu Leu Leu  Leu Leu Leu Leu Ala  Leu Phe Leu
    1970                1975               1980

Tyr Ser  Val Pro Gly Tyr Leu  Val Lys Lys Ile Leu  Gly Ala
    1985                1990               1995

<210> SEQ ID NO 5
<211> LENGTH: 5979
<212> TYPE: DNA
<213> ORGANISM: Homo sapiens

<400> SEQUENCE: 5
atggccctga ttgttcacct caagactgtc tcagagctcc gaggcaaagg tgaccggatt        60
gccaaagtca ctttccgagg gcagtctttc tactcccggg tcctggagaa ctgcgagggt       120
gtggctgact ttgatgagac gttccggtgg ccagtggcca gcagcatcga ccggaatgaa       180
gtgttggaga ttcagatttt caactacagc aaagtcttca gcaacaagct gatagggacc       240
ttctgcatgg tgctgcagaa agtggtggag gagaatcggg tagaggtgac cgacacgctg       300
atggatgaca gcaatgctat catcaagacc agcctgagca tggaggtccg gtatcaggcc       360
acagatggca ctgtgggccc ctgggatgat ggagacttcc tgggagatga atccctccag       420
gaggagaagg acagccagga gacagatggg ctgctacctg gttcccgacc cagcacccgg       480
atatctggcg agaagagctt tcgcagcaaa ggcagagaga agaccaaggg aggcagagat       540
ggcgagcaca agcgggaag gagtgtgttc tcggccatga aactcggcaa aactcggtcc       600
cacaaagagg agcccaaag acaagatgag ccagcagtgc tggagatgga ggacctggac       660
cacctagcca ttcagctggg ggatgggctg gatcctgact ccgtgtctct agcctcggtc       720
accgctctca ccagcaatgt ctccaacaaa cggtctaagc cagatattaa gatggagccc       780
agtgctggaa ggcccatgga ttaccaggtc agcatcacag tgattgaggc tcggcagctg       840
gtgggcttga acatggaccc tgtggtgtgt gtggaggtgg gtgatgacaa gaaatacacg       900
tcaatgaagg agtccacaaa ctgcccttac tacaacgagt actttgtctt cgacttccat       960
gtctctcctg atgtcatgtt tgacaagatc atcaagatct cggttatcca ttctaagaac      1020
ctgcttcgga gcggcaccct ggtgggttcc ttcaaaatgg atgtggggac tgtgtattcc      1080
cagcctgaac accagttcca tcacaaatgg gccatcctgt cagacccga tgacatctct       1140 gctgggttga agggttatgt aaagtgtgat gtcgctgtgg tgggcaaggg agacaacatc      1200
aagacacccc acaaggccaa cgagacggat gaggacgaca ttgaagggaa cttgctgctc      1260
cccgagggcg tgcccccga acggcagtgg gcacggttct atgtgaaaat ttaccgagca       1320
gagggactgc cccggatgaa cacaagcctc atggccaacg tgaagaaggc gttcatcggt      1380
```

-continued

```
gagaacaagg acctcgtcga cccctatgtg caagtcttct ttgctggaca aaagggcaaa    1440
acatcagtgc agaagagcag ctatgagccg ctatggaatg agcaggtcgt cttcacagac    1500
ttgttccccc cactctgcaa acgcatgaag gtgcagatcc gggactctga caaggtcaat    1560
gatgtggcca tcggcaccca cttcatcgac ctgcgcaaga tttccaacga tggagacaaa    1620
ggcttcctgc ctaccctcgg tccagcctgg gtgaacatgt acggctccac gcgcaactac    1680
acactgctgg acgagcacca ggacttgaat gaaggcctgg gggagggtgt gtccttccgg    1740
gcccgcctca tgttgggact agctgtggag atcctggaca cctccaaccc agagctcacc    1800
agctccacgg aggtgcaggt ggagcaggcc acgcctgtct cggagagctg cacagggaga    1860
atggaagaat tttttctatt tggagccttc ttggaagcct caatgattga ccggaaaaat    1920
ggggacaagc caattacctt tgaggtgacc ataggaaact acggcaatga agtcgatggt    1980
atgtcccggc ccctgaggcc tcggccccgg aaagagcctg gggatgaaga agaggtagac    2040
ctgattcaga actccagtga cgatgaaggt gacgaagccg gggacctggc ctcggtgtcc    2100
tccaccccac ctatgcggcc ccagatcacg gacaggaact atttccacct gccctacctg    2160
gagcgcaagc cctgcatcta tatcaagagc tggtggcctg accagaggcg gcgcctctac    2220
aatgccaaca tcatggatca cattgctgac aagctggaag aaggcctgaa tgatgtacag    2280
gagatgatca aaacggagaa gtcctacccg gagcgccgcc tgcggggtgt gctagaggaa    2340
ctcagctgtg gctgccaccg cttcctctcc ctctcggaca aggaccaggg ccgctcgtcc    2400
cgcaccaggc tggatcgaga gcgtcttaag tcctgtatga gggagttgga gagcatggga    2460
cagcaggcca agagcctgag ggctcaggtg aagcggcaca ctgttcggga caagctgagg    2520
tcatgccaga actttctgca gaagctacgc ttcctggcgg atgagcccca gcacagcatt    2580
cctgatgtgt tcatttggat gatgagcaac aacaaacgta tcgcctatgc ccgcgtgcct    2640
tccaaagacc tgctcttctc catcgtggag gaggaactgg gcaaggactg cgccaaagtc    2700
aagaccctct tcctgaagct gccagggaag aggggcttcg gctcggcagg ctggacagta    2760
caggccaagc tggagctcta cctgtggctg ggcctcagca agcagcgaaa ggacttcctg    2820
tgtggtctgc cctgtggctt cgaggaggtc aaggcagccc aaggcctggg cctgcattcc    2880
tttccgccca tcagcctagt ctacaccaag aagcaagcct tccagctccg agcacacatg    2940
tatcaggccc gaagcctctt tgctgctgac agcagtgggc tctctgatcc ctttgcccgt    3000
gtcttcttca tcaaccagag ccaatgcact gaggttctaa acgagacact gtgtcccacc    3060
tgggaccaga tgctggtatt tgacaacctg gagctgtacg gtgaagctca cgagttacga    3120
gatgatcccc ccatcattgt cattgaaatc tacgaccagg acagcatggg caaagccgac    3180
ttcatgggcc ggaccttcgc caagcccctg gtgaagatgg cagatgaagc atactgccca    3240
cctcgcttcc cgccgcagct tgagtactac cagatctacc gaggcagtgc cactgccgga    3300
gacctactgg ctgccttcga gctgctgcag attgggccat cagggaaggc tgacctgcca    3360
cccatcaatg gcccagtgga catggacaga gggcccatca tgcctgtgcc cgtgggaatc    3420
cggccagtgc tcagcaagta ccgagtggag gtgctgttct ggggcctgag ggacctaaag    3480
agggtgaacc tggcccaggt ggaccgacca cgggtggaca tcgagtgtgc aggaaagggg    3540
gtacaatcct ccctgattca caattataag aagaacccca acttcaacac gctggtcaag    3600
tggtttgaag tggacctccc ggagaatgag ctcctgcacc caccccttgaa catccgagtg    3660 gtagattgcc gggcctttgg acgatacacc ctggtgggtt cccacgcagt cagctcactg    3720
aggcgcttca tctaccgacc tccagaccgc tcagccccca actggaacac cacaggggag    3780
```

-continued

```
gttgtagtaa gcatggagcc tgaggagcca gttaagaagc tggagaccat ggtgaaactg    3840
gatgcgactt ctgatgctgt ggtcaaggtg gatgtggctg aagatgagaa ggaaaggaag    3900
aagaagaaaa agaaaggccc gtcagaggag ccagaggagg aagagcccga tgagagcatg    3960
ctggattggt ggtccaagta cttcgcctcc atcgacacaa tgaaggagca acttcgacaa    4020
catgagacct ctggaactga cttggaagag aaggaagaga tggaaagcgc tgagggcctg    4080
aagggaccaa tgaagagcaa ggagaagtcc agagctgcaa aggaggagaa aaagaagaaa    4140
aaccagagcc ctggccctgg ccagggatcg gaggctcctg agaagaagaa agccaagatc    4200
gatgagctta aggtgtaccc caaggagctg gaatcggagt ttgacagctt tgaggactgg    4260
ctgcacacct tcaacctgtt gaggggcaag acgggagatg atgaggatgg ctccacagag    4320
gaggagcgca tagtaggccg attcaagggc tccctctgtg tgtacaaagt gccactccca    4380
gaagatgtat ctcgagaagc tggctatgat cccacctatg gaatgttcca gggcatccca    4440
agcaatgacc ccatcaatgt gctggtccga atctatgtgg tccgggccac agacctgcac    4500
ccggccgaca tcaatggcaa agctgacccc tatattgcca tcaagttagg caagaccgac    4560
atccgagaca aggagaacta catctccaag cagctcaacc ctgtgtttgg gaagtccttt    4620
gacattgagg cctccttccc catggagtcc atgttgacag tggccgtgta cgactgggat    4680
ctggtgggca ctgatgacct catcggagaa accaagattg acctggaaaa ccgcttctac    4740
agcaagcatc gcgccacctg cggcatcgca cagacctatt ccatacatgg ctacaatatc    4800
tggagggacc ccatgaagcc cagccagatc ctgacacgcc tctgtaaaga gggcaaagtg    4860
gacggccccc actttggtcc ccatgggaga gtgagggttg ccaaccgtgt cttcacgggg    4920
ccttcagaaa tagaggatga gaatggtcag aggaagccca cagatgagca cgtggcactg    4980
tctgctctga gacactggga ggacatcccc cgggtgggct gccgccttgt gccggaacac    5040
gtggagacca ggccgctgct caaccctgac aagccaggca ttgagcaggg ccgcctggag    5100
ctgtgggtgg acatgttccc catggacatg ccagcccctg ggacacctct ggatatatcc    5160
cccaggaaac ccaagaagta cgagctgcgg gtcatcgtgt ggaacacaga cgaggtggtc    5220
ctggaagacg atgatttctt cacgggagag aagtccagtg acattttttgt gagggggtgg    5280 ctgaagggcc agcaggagga caaacaggac acagatgtcc actatcactc cctcacgggg    5340
gagggcaact tcaactggag ataccttctc cccttcgact acctagcggc cgaagagaag    5400
atcgttatgt ccaaaaagga gtctatgttc tcctgggatg agacggagta caagatccct    5460
gcgcggctca ccctgcagat ctgggacgct gaccacttct cggctgacga cttcctgggg    5520
gctatcgagc tggacctgaa ccggttcccg aggggcgcta agacagccaa gcagtgcacc    5580
atggagatgg ccaccgggga ggtggacgta cccctggttt ccatctttaa acagaaacgt    5640
gtcaaaggct ggtggcccct cctggcccgc aatgagaatg atgagtttga gctcacaggc    5700
aaagtggagg cggagctaca cctactcacg gcagaggagg cagagaagaa ccctgtgggc    5760
ctggctcgca atgaacctga tcccctagaa aaacccaacc ggcctgacac ggcattcgtc    5820
tggttcctga acccactcaa atctatcaag tacctcatct gcacccggta caagtggctg    5880
atcatcaaga tcgtgctggc gctgctgggg ctgctcatgc tggccctctt cctttacagc    5940
ctcccaggct acatggtcaa gaagctccta ggggcctga                          5979
```

<210> SEQ ID NO 6
<211> LENGTH: 5994
<212> TYPE: DNA

-continued

```
<213> ORGANISM: Artificial Sequence
<220> FEATURE:
<223> OTHER INFORMATION: Synthetic Construct

<400> SEQUENCE: 6
atggcactgc tgatccacct gaaaaccgtc tccgaactga gaggcagagg ggacagaatc      60
gctaaagtca ccttccgggg acagagcttt tacagcaggg tgctggagaa ctgcgaggac     120
gtggccgact ttgacgagac attcaggtgg cccgtggcca gctccatcga tcgcaatgag     180
atgctggaga tccaggtgtt taactatagc aaggtgttct ccaataagct gatcggcacc     240
ttccggatgg tgctgcagaa ggtggtggag gagtcccacg tggaggtgac cgacacactg     300
atcgacgata acaatgccat catcaagaca tccctgtgcg tggaggtgcg ctaccaggcc     360
accgatggca cagtgggctc ttgggacgat ggcgacttcc tgggcgatga gtccctgcag     420
gaggaggaga aggactctca ggagacagat ggcctgctgc ctggctcccg gccatctagc     480
cgcccccctg gcgagaagtc ttttaggaga gccggcaggt ccgtgttctc tgccatgaag     540
ctgggcaaga acaggagcca caaggaggag cctcagaggc ccgacgagcc agccgtgctg     600
gagatggagg acctggatca cctggccatc agactgggcg atggcctgga ccctgatagc     660
gtgtccctgg cctccgtgac cgccctgacc acaaacgtgt ctaataagcg gagcaagcca     720
gacatcaaga tggagccatc tgccggcagg cccatggatt accaggtgag catcacagtg     780
atcgaggcca gacagctggt gggcctgaac atggacccccg tggtgtgcgt ggaagtgggc     840
gacgataaga agtacacctc catgaaggag tctacaaact gtccatacta caacgagtac     900
ttcgtgtttg atttccacgt gagccccgac gtgatgttcg ataagatcat caagatcagc     960
gtgatccact ccaagaatct gctgcggtct ggcaccctgg tgggaagctt taagatggac    1020
gtgggcacag tgtactctca gcctgagcac cagttccacc acaagtgggc catcctgagc    1080
gatccagacg atatctcctc tggcctgaag ggctatgtga agtgcgacgt ggcagtggtg    1140
ggcaagggcg ataacatcaa gacccccacac aaggccaatg agacagacga ggacgatatc    1200
gagggaaacc tgctgctgcc agagggagtg ccacccgaga ggcagtgggc caggttctac    1260
gtgaagatct atagggcaga gggcctgcct aggatgaaca ccagcctgat ggccaatgtg    1320
aagaaggcct tcatcggcga gaacaaggac ctggtggatc cctacgtgca ggtgttcttt    1380
gccggccaga agggcaagac ctccgtgcag aagagctcct atgagcctct gtggaatgag    1440
caggtggtgt ttacagacct gttccctcca ctgtgcaaga ggatgaaggt gcagatcaga    1500
gactctgata aggtgaacga cgtggccatc ggcacccact ttatcgatct gaggaagatc    1560
agcaatgacg gcgataaggg cttcctgccc accctgggcc ccgcctgggt gaacatgtac    1620
ggcagcacca gaattatac actgctggac gagcaccagg atctgaacga gggcctgggc    1680
gagggcgtga gctttagagc caggctgctg ctgggcctgg ccgtggagat cgtggacacc    1740
tccaatcccg agctgacctc tagcacagag gtgcaggtgg agcaggccac acctatctct    1800
gagagctgtg ccggcaagat ggaggagttc tttctgtttg gcgccttcct ggaggcctcc    1860
atgatcgacc ggcgcaacgg cgataagcct atcaccttcg aggtgacaat cggcaactac    1920
ggcaatgagg tggacggcct gtctcggccc cagcgcccaa ggcccagaaa ggagcctggc    1980
gacgaggagg aggtggatct gatccagaac gccagcgacg atgaggcagg cgacgcaggc    2040
gatctggcct ccgtgtcctc tacccccccct atgcggccac aggtgacaga ccgcaattac    2100
tttcacctgc cttatctgga gcgcaagcca tgcatctaca tcaagtcttg gtggcccgat    2160
cagaggagac ggctgtataa cgccaatatc atggaccaca tcgccgataa gctggaggag    2220
```

-continued

```
ggcctgaatg acatccagga gatgatcaag accgagaagt cctatccaga gcgcaggctg      2280
aggggcgtgc tggaggagct gagctgtggc tgctgtagat tcctgtccct ggccgacaag      2340
gatcaggggc actcatcacg gacacggctg gaccgggagc ggctgaaatc atgtatgcgg      2400
gagctggaaa atatgggaca gcaggcaagg atgctgcgcg cccaggtgaa gaggcacacc      2460
gtgagagaca agctgcggct gtgccagaac ttcctgcaga agctgcgctt tctggccgat      2520
gagccacagc acagcatccc cgacatcttc atctggatga tgtccaacaa taagagagtg      2580
gcctacgccc gggtgccctc taaggatctg ctgtttagca tcgtggagga ggagacaggc      2640
aaggactgtg ccaaggtgaa gaccctgttc ctgaagctgc ctggcaagag aggctttggc      2700
agcgccggat ggaccgtgca ggcaaaggtg gagctgtatc tgtggctggg cctgtctaag      2760
cagcggaagg agttcctgtg cggcctgccc tgtggctttc aggaggtgaa ggcagcacag      2820
ggactgggac tgcacgcctt cccccccgtg agcctggtgt acaccaagaa gcaggccttt      2880
cagctgaggg cccatatgta ccaggccagg tctctgttcg ccgccgatag ctccggactg      2940
agcgacccct ttgccagggt gttctttatc aatcagagcc agtgcacaga ggtgctgaac      3000
gagaccctgt gcccaacatg ggatcagatg ctggtgttcg acaacctgga gctgtacgga      3060
gaggcacacg agctgaggga cgatccaccc atcatcgtga tcgagatcta tgatcaggac      3120
tccatgggca aggccgattt catgggcagg acctttgcca agccctggt gaagatggcc       3180 gacgaggcct actgccctcc aagattcccc cctcagctcg agtactatca gatctatagg      3240
ggaaatgcaa ccgccggaga cctgctggcc gcctttgagc tgctgcagat cggccccgcc      3300
ggaaaggcag acctgccacc catcaacggc ccagtggatg tggacagagg ccccatcatg      3360
cctgtgccaa tgggcatcag accagtgctg tccaagtaca gggtggaggt gctgttctgg      3420
ggactgcgcg acctgaagag ggtgaatctg gcccaggtgg ataggcccag agtggacatc      3480
gagtgcgccg gaaagggcgt gcagtctagc ctgatccaca actataagaa gaacccaaat      3540
ttcaacaccc tggtgaagtg gtttgaggtg gatctgcccg agaatgagct gctgcaccct      3600
ccactgaaca tccgggtggt ggactgtaga gccttcggca ggtacaccct ggtgggcagc      3660
cacgccgtga gcagcctgag gaggttcatc tacaggcccc ctgacaggtc cgccccttct      3720
tggaatacca cagtgagact gctgcggcgc tgcagggtgc tgtgcaacgg aggcagctcc      3780
tctcactcta ccggcgaggt ggtggtgaca atggagcctg aggtacccat caagaagctg      3840
gagaccatgg tgaagctgga tgccacaagc gaggcagtgg tgaaggtgga cgtggcagag      3900
gaggagaagg agaagaagaa gaagaagaag ggaaccgccg aggagcctga ggaagaggag      3960
ccagatgaga gcatgctgga ctggtggtcc aagtacttcg cctctatcga cacaatgaag      4020
gagcagctga cacagcagga gcctagcggc atcgatctgg aggagaagga ggaggtggac      4080
aataccgagg gcctgaaggg ctccatgaag ggcaaggaga aggcaagggc agcaaaggaa      4140
gagaagaaga agaagaccca gagcagcggc tctggacagg gcagcgaggc accagagaag      4200
aagaagccta agatcgatga gctgaaggtg tacccaaagg agctggagtc cgagttcgat      4260
aattttgagg actggctgca caccttcaac ctgctgcgcg gcaagacagg cgacgatgag      4320
gacggcagca ccgaggagga gagaatcgtg gccggtttta agggctccct gtgcgtgtac      4380
aaggtgccac tgcctgagga cgtgagcagg gaggccggat acgactctac ctatggcatg      4440
ttccagggca tcccctctaa tgatcctatc aacgtgctgg tgcgcgtgta tgtggtgagg      4500
gccacagatc tgcaccccgc cgacatcaac ggcaaggccg acccttacat cgccatccgc      4560
```

```
ctgggcaaga ccgatatcag ggacaaggag aattatatct ccaagcagct gaaccccgtg        4620
ttcggcaagt cttttgacat cgaggccagc ttccctatgg agtccatgct gaccgtggcc        4680
gtgtacgatt gggacctggt gggcaccgac gatctgatcg gcgagacaaa gatcgatctg        4740
gagaatcgct tttattctaa gcacagggca acctgcggaa tcgcacagac ctacagcaca        4800
cacggctata acatctggcg cgaccccatg aagcctagcc agatcctgac aaggctgtgc        4860
aaggatggca aggtggacgg accacacttc ggaccacccg gcagagtgaa ggtggccaat        4920
cgggtgttta caggcccttc cgagatcgag gatgagaacg gccagcgcaa gccaaccgac        4980
gagcacgtgg ccctgctggc cctgaggcac tgggaggata tcccaagggc cggatgtagg        5040
ctggtgcctg agcacgtgga gaccagacca ctgctgaatc cagacaagcc aggaatcgag        5100
cagggcaggc tggagctgtg ggtggatatg ttcccaatgg acatgccagc cccaggaaca        5160
cccctggata tctcccctag aaagccaaag aagtacgagc tgagagtgat catctggaac        5220
acagacgagg tggtgctgga ggacgatgac ttctttaccg gcgagaagtc tagcgatatc        5280
tttgtgcgcg gatggctgaa gggacagcag gaggacaagc aggatacaga cgtgcactac        5340
cactccctga ccggcgaggg caatttcaac tggagatacc tgttcccttt tgattatctg        5400
gccgccgagg agaagatcgt gatctctaag aaggagagca tgttttcctg ggacgagaca        5460
gagtataaga tcccagccag actgaccctg cagatctggg atgccgacca cttcagcgcc        5520
gatgactttc tgggcgccat cgagctggac ctgaaccggt tcccaagagg cgccaagacc        5580
gccaagcagt gcacaatgga gatggcaacc ggagaggtgg acgtgcctct ggtgtctatc        5640
ttcaagcaga agagggtgaa gggctggtgg ccactgctgg ccagaaacga gaatgatgag        5700
tttgagctga caggcaaggt ggaggcagag ctgcacctgc tgaccgccga ggaggcagag        5760
aagaacccag tgggcctggc caggaatgag cccgaccctc tggagaagcc aaacaggccc        5820
gacaccagct tcatctggtt tctgaatcct ctgaagtccg cccggtactt cctgtggcac        5880
acctatcgct ggctgctgct gaagctgtta ttactgttat tactgctgct gctgctggcc        5940
ctgtttctgt acagcgtgcc cggctatctg gtgaagaaga tcctgggcgc ctga             5994
```

```
<210> SEQ ID NO 7
<211> LENGTH: 454
<212> TYPE: DNA
<213> ORGANISM: Mus musculus

<400> SEQUENCE: 7
ctgcagctca gcctactact tgctttccag gctgttccta gttccatgt cagctgcttg          60 tgctttccag agacaaaaca ggaataatag atgtcattaa atatacattg ggccccaggc        120
ggtcaatgtg gcagcctgag cctcctttcc atctctgtgg aggcagacat aggaccccca        180
acaaacagca tgcaggttgg gagccagcca caggacccag gtaaggggcc ctgggtcctt        240
aagcttctgc cactggctcc ggcattgcag agagaagaga aggggcggca gagctgaacc        300
ttagccttgc cttcctgggt accttctga gcctcactgt cttctgtgag atgggcaaag        360
tgcgggtgtg actccttggc aacggtgtta caccagggca ggtaaagttg tagttatttg        420
tggggtacac caggactgtt aaaggtgtaa ctat                                    454
```

```
<210> SEQ ID NO 8
<211> LENGTH: 1157
<212> TYPE: DNA
<213> ORGANISM: Mus musculus

<400> SEQUENCE: 8
```

-continued

```
ggtctcaccc agcattttca cttctaataa gttcaaatgt gatacggcac ctttctaaaa        60
attagttttc agggaaatag ggttcaaaac tggtagtggg agggtccatt ctcacgaccc       120
ccaggcctgc taaccctgac caagctacct attacttacc ctcctctttc tcctcctcct       180
ctttctcctt ctcctgcttc ccctcttcct tctccctccc ttcctctccc tcctcccct        240 ccttggctgt gatcagatcc agagcctgaa tgagcctcct gaccccacac ccccactagc       300
atgggcctgc aagtgcccag aagtccctcc tgcctcctaa actgcccagc cgatccatta       360
gctcttcctt cttcccagtg aaagaagcag gcacagcctg tccctcccgt tctacagaaa       420
ggaagctaca gcacagggag ggccaaaggc cttcctggga ctagacagtt gatcaacagc       480
aggactggag agctgggctc catttttgtt ccttggtgcc ctgcccctcc ccatgacctg       540
cagagacatt cagcctgcca ggctttatga ggtgggagct gggctctccc tgatgtatta       600
ttcagctccc tggagttggc cagctcctgt tacactggcc acagccctgg gcatccgctt       660
ctcacttcta gtttcccctc caaggtaatg tggtgggtca tgatcattct atcctggctt       720
cagggacctg actccacttt ggggccattc gaggggtcta gggtagatga tgtccccctg       780
tggggattaa tgtcctgctc tgtaaaactg agctagctga gatccaggag ggcttggcca       840
gagacagcaa gttgttgcca tggtgacttt aaagccaggt tgctgcccca gcacaggcct       900
cccagtctac cctcactaga aaacaacacc caggcacttt ccaccacctc tcaaaggtga       960
aacccaaggc tggtctagag aatgaattat ggatcctcgc tgtccgtgcc acccagctag      1020
tcccagcggc tcagacactg aggagagact gtaggttcag ctacaagcaa aaagacctag      1080
ctggtctcca agcagtgtct ccaagtccct gaacctgtga cacctgcccc aggcatcatc      1140
aggcacagag ggccacc                                                      1157
```

```
<210> SEQ ID NO 9
<211> LENGTH: 76
<212> TYPE: DNA
<213> ORGANISM: Mus musculus

<400> SEQUENCE: 9
cccatgtcag ctgcttgtgc tttccagaga caaaacagga ataatagatg tcattaaata        60
tacattgggc cccagg                                                        76
```

```
<210> SEQ ID NO 10
<211> LENGTH: 95
<212> TYPE: DNA
<213> ORGANISM: Mus musculus

<400> SEQUENCE: 10
agcctgagcc tcctttccat ctctgtggag gcagacatag dacccccaac aaacagcatg        60
caggttggga gccagccaca ggacccaggt aaggg                                   95
```

```
<210> SEQ ID NO 11
<211> LENGTH: 171
<212> TYPE: DNA
<213> ORGANISM: Artificial Sequence
<220> FEATURE:
<223> OTHER INFORMATION: Synthetic Construct

<400> SEQUENCE: 11
cccatgtcag ctgcttgtgc tttccagaga caaaacagga ataatagatg tcattaaata        60
tacattgggc cccaggagcc tgagcctcct ttccatctct gtggaggcag acataggacc       120
```

-continued

```
cccaacaaac agcatgcagg ttgggagcca gccacaggac ccaggtaagg g              171
```

```
<210> SEQ ID NO 12
<211> LENGTH: 171
<212> TYPE: DNA
<213> ORGANISM: Artificial Sequence
<220> FEATURE:
<223> OTHER INFORMATION: Synthetic Construct

<400> SEQUENCE: 12
agcctgagcc tcctttccat ctctgtggag gcagacatag gaccccaac aaacagcatg      60 caggttggga gccagccaca ggacccaggt aagggcccat gtcagctgct tgtgctttcc     120
agagacaaaa caggaataat agatgtcatt aaatatacat tgggccccag g              171
```

```
<210> SEQ ID NO 13
<211> LENGTH: 184
<212> TYPE: DNA
<213> ORGANISM: Mus musculus

<400> SEQUENCE: 13
cccatgtcag ctgcttgtgc tttccagaga caaaacagga ataatagatg tcattaaata      60
tacattgggc cccaggcggt caatgtggca gcctgagcct cctttccatc tctgtggagg     120
cagacatagg acccccaaca aacagcatgc aggttgggag ccagccacag gacccaggta     180
aggg                                                                  184
```

```
<210> SEQ ID NO 14
<211> LENGTH: 82
<212> TYPE: DNA
<213> ORGANISM: Mus musculus

<400> SEQUENCE: 14
tgaggtggga gctgggctct ccctgatgta ttattcagct ccctggagtt ggccagctcc      60
tgttacactg gccacagccc tg                                               82
```

```
<210> SEQ ID NO 15
<211> LENGTH: 106
<212> TYPE: DNA
<213> ORGANISM: Mus musculus

<400> SEQUENCE: 15
cacaggcctc ccagtctacc ctcactagaa aacaacaccc aggcactttc caccacctct      60
caaaggtgaa acccaaggct ggtctagaga atgaattatg gatcct                    106
```

```
<210> SEQ ID NO 16
<211> LENGTH: 188
<212> TYPE: DNA
<213> ORGANISM: Artificial Sequence
<220> FEATURE:
<223> OTHER INFORMATION: Synthetic Construct

<400> SEQUENCE: 16
tgaggtggga gctgggctct ccctgatgta ttattcagct ccctggagtt ggccagctcc      60
tgttacactg gccacagccc tgcacaggcc tcccagtcta ccctcactag aaaacaacac     120
ccaggcactt tccaccacct ctcaaaggtg aaacccaagg ctggtctaga gaatgaatta     180
tggatcct                                                              188
```

```
<210> SEQ ID NO 17
<211> LENGTH: 188
```

```
<212> TYPE: DNA
<213> ORGANISM: Artificial Sequence
<220> FEATURE:
<223> OTHER INFORMATION: Synthetic Construct

<400> SEQUENCE: 17
cacaggcctc ccagtctacc ctcactagaa aacaacaccc aggcactttc caccacctct        60
caaaggtgaa acccaaggct ggtctagaga atgaattatg gatccttgag gtgggagctg       120
ggctctccct gatgtattat tcagctccct ggagttggcc agctcctgtt acactggcca       180
cagccctg                                                               188

<210> SEQ ID NO 18
<211> LENGTH: 430
<212> TYPE: DNA
<213> ORGANISM: Mus musculus

<400> SEQUENCE: 18
tgaggtggga gctgggctct ccctgatgta ttattcagct ccctggagtt ggccagctcc        60
tgttacactg gccacagccc tgggcatccg cttctcactt ctagtttccc ctccaaggta       120
atgtggtggg tcatgatcat tctatcctgg cttcagggac ctgactccac tttggggcca       180
ttcgaggggt ctagggtaga tgatgtcccc ctgtggggat taatgtcctg ctctgtaaaa       240
ctgagctagc tgagatccag gagggcttgg ccagagacag caagtgttg ccatggtgac       300 tttaaagcca ggttgctgcc ccagcacagg cctcccagtc taccctcact agaaaacaac       360
acccaggcac tttccaccac ctctcaaagg tgaaacccaa ggctggtcta gagaatgaat       420
tatggatcct                                                             430

<210> SEQ ID NO 19
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 19
ctgcagctca gcctactact tgctttccag gctgttccta gttcccatgt cagctgcttg        60
tgctttccag agacaaaaca ggaataaatg atgtcattaa atatacattg ggccccaggc       120
ggtcaatgtg gcagcctgag cctcctttcc atctctgtgg aggcagacat aggacccca        180 acaaacagca tgcaggttgg gagccagcca caggacccag gtaaggggcc ctgggtcctt       240
aagcttctgc cactggctcc ggcattgcag agagaagaga aggggcggca gagctgaacc       300
ttagccttgc cttcctgggt acccttctga gcctcactgt cttctgtgag atgggcaaag       360
tgcgggtgtg actccttggc aacggtgtta caccagggca ggtaaagttg tagttatttg       420
tggggtacac caggactgtt aaaggtgtaa ctatggtctc acccagcatt ttcacttcta       480
ataagttcaa atgtgatacg gcacctttct aaaaattagt tttcagggaa ataggttca        540 aaactggtag tggtagggtc cattctcacg accccaggc ctgctaaccc tgaccaagct       600
acctattact accctcctc tttctcctcc tcctctttct ccttctcctg cttcccctct       660
tccttctccc tcccttcctc tccctcctcc ccctccttgg ctgtgatcag atccagagcc       720
tgaatgagcc tcctgacccc acaccccac tagcatgggc ctgcaagtgc ccagaagtcc       780
ctcctgcctc ctaaactgcc cagccgatcc attagctctt ccttcttccc agtgaaagaa       840
gcaggcacag cctgtccctc ccgttctaca gaaaggaagc tacagcacag ggagggccaa       900
```

```
aggccttcct gggactagac agttgatcaa cagcaggact ggagagctgg gctccatttt      960
tgttccttgg tgccctgccc ctccccatga cctgcagaga cattcagcct gccaggcttt     1020
atgaggtggg agctgggctc tccctgatgt attattcagc tccctggagt tggccagctc     1080
ctgttacact ggccacagcc ctgggcatcc gcttctcact tctagtttcc cctccaaggt     1140
aatgtggtgg gtcatgatca ttctatcctg gcttcaggga cctgactcca ctttggggcc     1200
attcgagggg tctagggtag atgatgtccc cctgtgggga ttaatgtcct gctctgtaaa     1260
actgagctag ctgagatcca ggagggcttg gccagagaca gcaagttgtt gccatggtga     1320
ctttaaagcc aggttgctgc cccagcacag gcctcccagt ctaccctcac tagaaaacaa     1380
cacccaggca ctttccacca cctctcaaag gtgaaaccca aggctggtct agagaatgaa     1440
ttatggatcc tcgctgtccg tgccacccag ctagtcccag cggctcagac actgaggaga     1500
gactgtaggt tcagctacaa gcaaaaagac ctagctggtc tccaagcagt gtctccaagt     1560
ccctgaacct gtgacacctg ccccaggcat catcaggcac agagggccac c               1611

<210> SEQ ID NO 20
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 20
ggtctcaccc agcattttca cttctaataa gttcaaatgt gatacggcac ctttctaaaa       60
attagttttc agggaaatag ggttcaaaac tggtagtggt agggtccatt ctcacgaccc      120
ccaggcctgc taaccctgac caagctacct attacttacc ctcctctttc tcctcctcct      180
ctttctcctt ctcctgcttc ccctcttcct tctccctccc ttcctctccc tcctcccct      240 ccttggctgt gatcagatcc agagcctgaa tgagcctcct gaccccacac ccccactagc      300
atgggcctgc aagtgcccag aagtccctcc tgcctcctaa actgcccagc cgatccatta      360
gctcttcctt cttcccagtg aaagaagcag gcacagcctg tccctcccgt tctacagaaa      420
ggaagctaca gcacagggag ggccaaaggc cttcctggga ctagacagtt gatcaacagc      480
aggactggag agctgggctc cattttttgtt ccttggtgcc ctgcccctcc ccatgacctg      540
cagagacatt cagcctgcca ggctttatga ggtgggagct gggctctccc tgatgtatta      600
ttcagctccc tggagttggc agctcctgt tacactggcc acagccctgg gcatccgctt      660
ctcacttcta gttccccctc caaggtaatg tggtgggtca tgatcattct atcctggctt      720
cagggacctg actccacttt ggggccattc gaggggtcta gggtagatga tgtccccctg      780 tgggattaa tgtcctgctc tgtaaaactg agctagctga gatccaggag ggcttggcca      840
gagacagcaa gttgttgcca tggtgacttt aaagccaggt tgctgcccca gcacaggcct      900
cccagtctac cctcactaga aaacaacacc caggcacttt ccaccacctc tcaaaggtga      960
aacccaaggc tggtctagag aatgaattat ggatcctcgc tgtccgtgcc acccagctag     1020
tcccagcggc tcagacactg aggagagact gtaggttcag ctacaagcaa aaagacctag     1080
ctggtctcca agcagtgtct ccaagtccct gaacctgtga cacctgcccc aggcatcatc     1140
aggcacagag ggccaccctg cagctcagcc tactacttgc tttccaggct gttcctagtt     1200
cccatgtcag ctgcttgtgc tttccagaga caaaacagga ataatagatg tcattaaata     1260
tacattgggc cccaggcggt caatgtggca gcctgagcct cctttccatc tctgtggagg     1320
cagacatagg accccaaca aacagcatgc aggttgggag ccagccacag gacccaggta     1380
```

-continued

```
aggggccctg ggtccttaag cttctgccac tggctccggc attgcagaga gaagagaagg    1440
ggcggcagag ctgaacctta gccttgcctt cctgggtacc cttctgagcc tcactgtctt    1500
ctgtgagatg ggcaaagtgc gggtgtgact ccttggcaac ggtgttacac cagggcaggt    1560
aaagttgtag ttatttgtgg ggtacaccag gactgttaaa ggtgtaacta t             1611

<210> SEQ ID NO 21
<211> LENGTH: 965
<212> TYPE: DNA
<213> ORGANISM: Artificial Sequence
<220> FEATURE:
<223> OTHER INFORMATION: Synthetic Construct

<400> SEQUENCE: 21
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctcctttcc atctctgtgg aggcagacat aggaccccca     180
acaaacagca tgcaggttgg agccagcca caggacccag gtaaggggcc ctgggtcctt      240
aagcttctgc cactggctcc ggcattgcag agagaagaga aggggcggca gactggagag     300
ctgggctcca ttttttgttcc ttggtgccct gcccctcccc atgacctgca gagacattca    360
gcctgccagg ctttatgagg tgggagctgg gctctccctg atgtattatt cagctccctg     420
gagttggcca gctcctgtta cactggccac agccctgggc atccgcttct cacttctagt     480
ttcccctcca aggtaatgtg gtgggtcatg atcattctat cctggcttca gggacctgac     540
tccactttgg ggccattcga ggggtctagg gtagatgatg tccccctgtg gggattaatg     600
tcctgctctg taaaactgag ctagctgaga tccaggaggg cttggccaga gacagcaagt     660
tgttgccatg gtgactttaa agccaggttg ctgccccagc acaggcctcc cagtctaccc     720
tcactagaaa acaacaccca ggcactttcc accacctctc aaaggtgaaa cccaaggctg     780
gtctagagaa tgaattatgg atcctcgctg tccgtgccac ccagctagtc ccagcggctc     840
agacactgag gagagactgt aggttcagct acaagcaaaa agacctagct ggtctccaag     900
cagtgtctcc aagtccctga acctgtgaca cctgccccag gcatcatcag gcacagaggg     960
ccacc                                                                965

<210> SEQ ID NO 22
<211> LENGTH: 520
<212> TYPE: DNA
<213> ORGANISM: Artificial Sequence
<220> FEATURE:
<223> OTHER INFORMATION: Synthetic Construct

<400> SEQUENCE: 22
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctcctttcc atctctgtgg aggcagacat aggaccccca     180
acaaacagca tgcaggttgg agccagcca caggacccag gtaaggggcc ctgggtcctt      240
tttatgaggt gggagctggg ctctccctga tgtattattc agctccctgg agttggccag     300
ctcctgttac actggccaca gccctgggca tccgctgcca tggtgacttt aaagccaggt     360
tgctgcccca gcacaggcct cccagtctac cctcactaga aacaacacc caggcacttt      420 ccaccacctc tcaaaggtga aacccaaggc tggtctagag aatgaattat ggatcctcgc     480
```

```
tgtccgtgcc acccagctag tcccagcggc tcagacactg                        520

<210> SEQ ID NO 23
<211> LENGTH: 235
<212> TYPE: DNA
<213> ORGANISM: Homo sapiens

<400> SEQUENCE: 23
gtatgccttt tgagatggat gcagcaggtt ctgtgaggct gccaggaggg gtagagttcc    60 cggggggcctc gggccccgct ggagtgtgga gcaggcccat gctcagctct ccaggctgtt   120
cgtggctccc ctgtcagctg ctcactcctt tccagagaca aaacaggaat aatagacatc   180
attaaatata catagggccc caggcggtcg gcgtggtggg ctgggcctcc cttcc         235

<210> SEQ ID NO 24
<211> LENGTH: 688
<212> TYPE: DNA
<213> ORGANISM: Homo sapiens

<400> SEQUENCE: 24
tgccctgcct tctgagccgg cagcctggct ccccaccccca tgtattattc agctcctgag    60
agccagccag ctcctgttac actgaccgca gcccagcacc tgctctgccc attcccctcc    120
tcccttgcct aggacctaga gggttcaaag ttctcctcca agatgacttg gtgggctttg    180
gccatcccac cctaggcccc acttctggcc cagtgcaggt gtgctggtga tttagggcag    240
gtggcattcc atctctgtgg ctcaatgtct tcctctgtga agccgaagtg acccaagggc    300
tcccttcatg gggttgagcc agctgtggcc cagggagggc ctaaccagga tgagcactga    360
tgttgccatg acgactccga ggccagaatg tctcccccag cacaggcctc ataggcaggc    420
ttccccatcc tggtaaacaa cacccacaca ctttctacta ctgctctagg gtgaaaccca    480
aggcgctcta gaggagatga attatggatc cgccctcccg gaatcctggc tcggccctcc    540
ccacgccacc cagggccagt cgggtctgct cacagcccga ggaggccgcg tgtccagccg    600
cgggcaagag acagagcagg tccctgtgtc tccaagtccc tgagcccgtg acaccggccc    660
caggccctgt agagagcagg cagccacc                                       688

<210> SEQ ID NO 25
<211> LENGTH: 77
<212> TYPE: DNA
<213> ORGANISM: Homo sapiens

<400> SEQUENCE: 25
cccctgtcag ctgctcactc ctttccagag acaaaacagg aataatagac atcattaaat    60
atacataggg ccccagg                                                   77

<210> SEQ ID NO 26
<211> LENGTH: 82
<212> TYPE: DNA
<213> ORGANISM: Homo sapiens

<400> SEQUENCE: 26
tgagccggca gcctggctcc ccaccccatg tattattcag ctcctgagag ccagccagct    60
cctgttacac tgaccgcagc cc                                             82

<210> SEQ ID NO 27
<211> LENGTH: 111
<212> TYPE: DNA
<213> ORGANISM: Homo sapiens
```

-continued

<400> SEQUENCE: 27
cacaggcctc ataggcaggc ttccccatcc tggtaaacaa cacccacaca ctttctacta     60
ctgctctagg gtgaaaccca aggcgctcta gaggagatga attatggatc c     111

<210> SEQ ID NO 28
<211> LENGTH: 193
<212> TYPE: DNA
<213> ORGANISM: Artificial Sequence
<220> FEATURE:
<223> OTHER INFORMATION: Synthetic Construct

<400> SEQUENCE: 28
tgagccggca gcctggctcc caccccatg tattattcag ctcctgagag ccagccagct     60
cctgttacac tgaccgcagc cccacaggcc tcataggcag gcttccccat cctggtaaac     120
aacacccaca cactttctac tactgctcta gggtgaaacc caaggcgctc tagaggagat     180
gaattatgga tcc     193

<210> SEQ ID NO 29
<211> LENGTH: 193
<212> TYPE: DNA
<213> ORGANISM: Artificial Sequence
<220> FEATURE:
<223> OTHER INFORMATION: Synthetic Construct

<400> SEQUENCE: 29
cacaggcctc ataggcaggc ttccccatcc tggtaaacaa cacccacaca ctttctacta     60
ctgctctagg gtgaaaccca aggcgctcta gaggagatga attatggatc ctgagccggc     120
agcctggctc cccaccccat gtattattca gctcctgaga gccagccagc tcctgttaca     180
ctgaccgcag ccc     193

<210> SEQ ID NO 30
<211> LENGTH: 499
<212> TYPE: DNA
<213> ORGANISM: Homo sapiens

<400> SEQUENCE: 30
tgagccggca gcctggctcc caccccatg tattattcag ctcctgagag ccagccagct     60
cctgttacac tgaccgcagc ccagcacctg ctctgcccat tccctcctc ccttgcctag     120 gacctagagg gttcaaagtt ctcctccaag atgacttggt gggctttggc catcccaccc     180
taggccccac ttctggccca gtgcaggtgt gctggtgatt tagggcaggt ggcattccat     240
ctctgtggct caatgtcttc ctctgtgaag ccgaagtgac ccaagggctc ccttcatggg     300
gttgagccag ctgtggccca gggagggcct aaccaggatg agcactgatg ttgccatgac     360
gactccgagg ccagaatgtc tccccagca caggcctcat aggcaggctt ccccatcctg     420
gtaaacaaca cccacacact ttctactact gctctagggt gaaacccaag gcgctctaga     480
ggagatgaat tatggatcc     499

<210> SEQ ID NO 31
<211> LENGTH: 1262
<212> TYPE: DNA
<213> ORGANISM: Artificial Sequence
<220> FEATURE:
<223> OTHER INFORMATION: Synthetic Construct

<400> SEQUENCE: 31

-continued

```
gtatgccttt tgagatggat gcagcaggtt ctgtgaggct gccaggaggg gtagagttcc      60 cggggggcctc gggccccgct ggagtgtgga gcaggcccat gctcagctct ccaggctgtt     120
cgtggctccc ctgtcagctg ctcactcctt tccagagaca aaacaggaat aatagacatc     180
attaaatata catagggccc caggcggtcg gcgtggtggg ctgggcctcc cttccccata     240
acactgagct gctctgctgg gccaaccgtg ctcctgggcc agccagagga cccccatgag     300
gcggcatgca ggcggggagc aggccacaga acgcaggtaa ggagacctta gcctagagtc     360
cttggggtct gtcactggcc accctcgcat cccaggctgc aggaaactga ggcccagaga     420
ggacaaggac tttcctggac ccacacagcc agtcagtgac agagcctagg gtctgagcca     480
ggcctgaccc aacctccatt tctgcctctc tacccctgcc cccgccccaa cacacacaca     540
cacacaagtg gagttccact gaaacgcccc tccttgccct gccttctgag ccggcagcct     600
ggctccccac cccatgtatt attcagctcc tgagagccag ccagctcctg ttacactgac     660
cgcagcccag cacctgctct gcccattccc ctcctccctt gcctaggacc tagagggttc     720
aaagttctcc tccaagatga cttggtgggc tttggccatc ccaccctagg ccccacttct     780
ggcccagtgc aggtgtgctg gtgatttagg gcaggtggca ttccatctct gtggctcaat     840
gtcttcctct gtgaagccga agtgacccaa gggctccctt catggggttg agccagctgt     900
ggcccaggga gggcctaacc aggatgagca ctgatgttgc catgacgact ccgaggccag     960
aatgtctccc ccagcacagg cctcataggc aggcttcccc atcctggtaa acaacaccca    1020
cacactttct actactgctc tagggtgaaa cccaaggcgc tctagaggag atgaattatg    1080
gatccgccct cccggaatcc tggctcggcc ctccccacgc cacccagggc cagtcgggtc    1140
tgctcacagc ccgaggaggc cgcgtgtcca gccgcgggca agagacagag caggtccctg    1200
tgtctccaag tccctgagcc cgtgacaccg gccccaggcc ctgtagagag caggcagcca    1260
cc                                                                   1262
```

<210> SEQ ID NO 32
<211> LENGTH: 649
<212> TYPE: DNA
<213> ORGANISM: Artificial Sequence
<220> FEATURE:
<223> OTHER INFORMATION: Synthetic Construct

<400> SEQUENCE: 32

```
gcaggcccat gctcagctct ccaggctgtt cgtggctccc ctgtcagctg ctcactcctt      60
tccagagaca aaacaggaat aatagacatc attaaatata catagggccc caggcggtcg     120
gcgtggtggg ctgggcctcc cttccccata acactgagct gctctgctgg gccaaccgtg     180
ctcctgggcc agccagagga cccccatgag gcggcatgca ggcggggagc aggccacaga     240
acgcaggtaa ggagaccttg ccttctgagc cggcagcctg ctcccacc ccatgtatta     300 ttcagctcct gagagccagc cagctcctgt tacactgacc gcagcccagc acctgctctg     360
cccattcccc tcctcccttg cctaggacct agagggttca aagttctcct ccaagatgac     420
ttggtgggct ttggccatcg ggcctaacca ggatgagcac tgatgttgcc atgacgactc     480
cgaggccaga atgtctcccc cagcacaggc tcataggca ggcttcccca tcctggtaaa     540
caacacccac acactttcta ctactgctct agggtgaaac ccaaggcgct ctagaggaga     600
tgaattatgg atccgccctc ccggaatcct ggctcggccc tccccacgc                649
```

<210> SEQ ID NO 33
<211> LENGTH: 240

-continued

```
<212> TYPE: DNA
<213> ORGANISM: Mus musculus

<400> SEQUENCE: 33
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctccttttcc atctctgtgg aggcagacat aggacccccca   180 acaaacagca tgcaggttgg gagccagcca caggacccag gtaaggggcc ctgggtcctt     240

<210> SEQ ID NO 34
<211> LENGTH: 95
<212> TYPE: DNA
<213> ORGANISM: Mus musculus

<400> SEQUENCE: 34
tttatgaggt gggagctggg ctctccctga tgtattattc agctccctgg agttggccag      60
ctcctgttac actggccaca gccctgggca tccgc                                95

<210> SEQ ID NO 35
<211> LENGTH: 185
<212> TYPE: DNA
<213> ORGANISM: Mus musculus

<400> SEQUENCE: 35
tgccatggtg actttaaagc caggttgctg ccccagcaca ggcctccag tctaccctca        60 ctagaaaaca acacccaggc actttccacc acctctcaaa ggtgaaaccc aaggctggtc     120
tagagaatga attatggatc ctcgctgtcc gtgccaccca gctagtccca gcggctcaga     180
cactg                                                                 185

<210> SEQ ID NO 36
<211> LENGTH: 335
<212> TYPE: DNA
<213> ORGANISM: Artificial Sequence
<220> FEATURE:
<223> OTHER INFORMATION: Synthetic Construct

<400> SEQUENCE: 36
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctccttttcc atctctgtgg aggcagacat aggacccccca   180 acaaacagca tgcaggttgg gagccagcca caggacccag gtaaggggcc ctgggtcctt     240
tttatgaggt gggagctggg ctctccctga tgtattattc agctccctgg agttggccag     300
ctcctgttac actggccaca gccctgggca tccgc                                335

<210> SEQ ID NO 37
<211> LENGTH: 425
<212> TYPE: DNA
<213> ORGANISM: Artificial Sequence
<220> FEATURE:
<223> OTHER INFORMATION: Synthetic Construct

<400> SEQUENCE: 37
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctccttttcc atctctgtgg aggcagacat aggacccccca   180
```

-continued

```
acaaacagca tgcaggttgg gagccagcca caggacccag gtaaggggcc ctgggtcctt        240
tgccatggtg actttaaagc caggttgctg ccccagcaca ggcctcccag tctaccctca        300
ctagaaaaca acacccaggc actttccacc acctctcaaa ggtgaaaccc aaggctggtc        360
tagagaatga attatggatc ctcgctgtcc gtgccaccca gctagtccca gcggctcaga        420
cactg                                                                   425

<210> SEQ ID NO 38
<211> LENGTH: 280
<212> TYPE: DNA
<213> ORGANISM: Artificial Sequence
<220> FEATURE:
<223> OTHER INFORMATION: Synthetic Construct

<400> SEQUENCE: 38
tttatgaggt gggagctggg ctctccctga tgtattattc agctccctgg agttggccag         60
ctcctgttac actggccaca gccctgggca tccgctgcca tggtgacttt aaagccaggt        120
tgctgcccca gcacaggcct cccagtctac cctcactaga aaacaacacc caggcacttt        180
ccaccacctc tcaaaggtga aacccaaggc tggtctagag aatgaattat ggatcctcgc        240
tgtccgtgcc acccagctag tcccagcggc tcagacactg                              280

<210> SEQ ID NO 39
<211> LENGTH: 520
<212> TYPE: DNA
<213> ORGANISM: Artificial Sequence
<220> FEATURE:
<223> OTHER INFORMATION: Synthetic Construct

<400> SEQUENCE: 39
tttatgaggt gggagctggg ctctccctga tgtattattc agctccctgg agttggccag         60
ctcctgttac actggccaca gccctgggca tccgcctgca gctcagccta ctacttgctt        120
tccaggctgt tcctagttcc catgtcagct gcttgtgctt ccagagacaa aaacaggaat        180
aatagatgtc attaaatata cattgggccc caggcggtca atgtggcagc ctgagcctcc        240
tttccatctc tgtggaggca gacataggac ccccaacaaa cagcatgcag gttgggagcc        300
agccacagga cccaggtaag gggccctggg tcctttgcca tggtgacttt aaagccaggt        360
tgctgcccca gcacaggcct cccagtctac cctcactaga aaacaacacc caggcacttt        420
ccaccacctc tcaaaggtga aacccaaggc tggtctagag aatgaattat ggatcctcgc        480
tgtccgtgcc acccagctag tcccagcggc tcagacactg                              520

<210> SEQ ID NO 40
<211> LENGTH: 520
<212> TYPE: DNA
<213> ORGANISM: Artificial Sequence
<220> FEATURE:
<223> OTHER INFORMATION: Synthetic Construct

<400> SEQUENCE: 40
tgccatggtg actttaaagc caggttgctg ccccagcaca ggcctcccag tctaccctca         60
ctagaaaaca acacccaggc actttccacc acctctcaaa ggtgaaaccc aaggctggtc        120
tagagaatga attatggatc ctcgctgtcc gtgccaccca gctagtccca gcggctcaga        180
cactgctgca gctcagccta ctacttgctt tccaggctgt tcctagttcc catgtcagct        240
gcttgtgctt ccagagacaa aaacaggaat aatagatgtc attaaatata cattgggccc        300
caggcggtca atgtggcagc ctgagcctcc tttccatctc tgtggaggca gacataggac        360
```

-continued

```
ccccaacaaa cagcatgcag gttgggagcc agccacagga cccaggtaag gggccctggg        420
tcctttttat gaggtgggag ctgggctctc cctgatgtat tattcagctc cctggagttg        480
gccagctcct gttacactgg ccacagccct gggcatccgc                               520

<210> SEQ ID NO 41
<211> LENGTH: 520
<212> TYPE: DNA
<213> ORGANISM: Artificial Sequence
<220> FEATURE:
<223> OTHER INFORMATION: Synthetic Construct

<400> SEQUENCE: 41
tttatgaggt gggagctggg ctctccctga tgtattattc agctccctgg agttggccag        60
ctcctgttac actggccaca gccctgggca tccgctgcca tggtgacttt aaagccaggt       120
tgctgcccca gcacaggcct cccagtctac cctcactaga aaacaacacc caggcacttt       180
ccaccacctc tcaaaggtga aacccaaggc tggtctagag aatgaattat ggatcctcgc       240
tgtccgtgcc acccagctag tcccagcggc tcagacactg ctgcagctca gcctactact       300
tgctttccag gctgttccta gttcccatgt cagctgcttg tgctttccag agacaaaaca       360
ggaataatag atgtcattaa atatacattg ggccccaggc ggtcaatgtg gcagcctgag       420
cctcctttcc atctctgtgg aggcagacat aggaccccca acaaacagca tgcaggttgg       480
gagccagcca caggacccag gtaaggggcc ctgggtcctt                               520

<210> SEQ ID NO 42
<211> LENGTH: 964
<212> TYPE: DNA
<213> ORGANISM: Artificial Sequence
<220> FEATURE:
<223> OTHER INFORMATION: Synthetic Construct

<400> SEQUENCE: 42
tgcagctcag cctactactt gctttccagg ctgttcctag ttcccatgtc agctgcttgt        60
gctttccaga gacaaaacag gaataataga tgtcattaaa tatacattgg gccccaggcg       120
gtcaatgtgg cagcctgagc ctcctttcca tctctgtgga ggcagacata ggacccccaa       180
caaacagcat gcaggttggg agccagccac aggacccagg taaggggccc tgggtcctta       240
agcttctgcc actggctccg gcattgcaga gagaagagaa ggggcggcag actggagagc       300
tgggctccat ttttgttcct tggtgccctg cccctcccca tgacctgcag agacattcag       360
cctgccaggc tttatgaggt gggagctggg ctctccctga tgtattattc agctccctgg       420
agttggccag ctcctgttac actggccaca gccctgggca tccgcttctc acttctagtt       480
tcccctccaa ggtaatgtgg tgggtcatga tcattctatc ctggcttcag ggacctgact       540
ccactttggg gccattcgag gggtctaggg tagatgatgt cccctgtgg ggattaatgt        600 cctgctctgt aaaactgagc tagctgagat ccaggagggc ttggcagag acagcaagtt       660 gttgccatgg tgactttaaa gccaggttgc tgccccagca caggcctccc agtctaccct       720
cactagaaaa caacacccag gcactttcca ccacctctca aaggtgaaac ccaaggctgg       780
tctagagaat gaattatgga tcctcgctgt ccgtgccacc cagctagtcc cagcggctca       840
gacactgagg agagactgta ggttcagcta caagcaaaaa gacctagctg gtctccaagc       900
agtgtctcca agtccctgaa cctgtgacac ctgccccagg catcatcagg cacagagggc       960
cacc                                                                     964
```

<210> SEQ ID NO 43
<211> LENGTH: 519
<212> TYPE: DNA
<213> ORGANISM: Artificial Sequence
<220> FEATURE:
<223> OTHER INFORMATION: Synthetic Construct

<400> SEQUENCE: 43
tgcagctcag cctactactt gctttccagg ctgttcctag ttcccatgtc agctgcttgt      60
gctttccaga gacaaaacag gaataataga tgtcattaaa tatacattgg gccccaggcg     120
gtcaatgtgg cagcctgagc ctcctttcca tctctgtgga ggcagacata ggacccccaa     180
caaacagcat gcaggttggg agccagccac aggacccagg taaggggccc tgggtccttt     240
ttatgaggtg ggagctgggc tctccctgat gtattattca gctccctgga gttggccagc     300
tcctgttaca ctggccacag ccctgggcat ccgctgccat ggtgacttta aagccaggtt     360
gctgccccag cacaggcctc ccagtctacc ctcactagaa aacaacaccc aggcactttc     420
caccacctct caaaggtgaa acccaaggct ggtctagaga atgaattatg gatcctcgct     480
gtccgtgcca cccagctagt cccagcggct cagacactg                            519

<210> SEQ ID NO 44
<211> LENGTH: 943
<212> TYPE: DNA
<213> ORGANISM: Artificial Sequence
<220> FEATURE:
<223> OTHER INFORMATION: Synthetic Construct

<400> SEQUENCE: 44
ggtacctagt tattaatagt aatcaattac ggggtcatta gttcatagcc catatatgga      60
gttccgcgtt acataactta cggtaaatgg cccgcctggc tgaccgccca acgacccccg     120
cccattgacg tcaataatga cgtatgttcc catagtaacg ccaatagGga ctttccattg     180
acgtcaatgg gtggagtatt tacggtaaac tgcccacttg gcagtacatc aagtgtatca     240
tatgccaagt acgccccctta ttgacgtcaa tgacggtaaa tggcccgcct ggcattatgc     300
ccagtacatg accttatggg actttcctac ttggcagtac atctacgtat tagtcatcgc     360
tattaccatg gtcgaggtga gccccacgtt ctgcttcact ctccccatct ccccccctc      420 cccaccccca attttgtatt tatttatttt ttaattattt tgtgcagcga tgggggcggg     480 ggggggggg gggcgcgcgc caggcggggc ggggcggggc gaggggcggg gcggggcgag     540
gcggagaggt gcggcggcag ccaatcagag cggcgcgctc cgaaagtttc cttttatggc     600
gaggcggcgg cggcggcggc cctataaaaa gcgaagcgcg cggcgggcgg gagtcgctgc     660
gcgctgcctt cgccccgtgc cccgctccgc cgccgcctcg cgccgcccgc cccggctctg     720
actgaccgcg ttactcccac aggtgagcgg gcgggacggc ccttctcctc cgggctgtaa     780
ttagcgcttg gtttaatgac ggcttgtttc ttttctgtgg ctgcgtgaaa gccttgaggg     840
gctccgggag ctagagcctc tgctaaccat gttcatgcct tcttctttt cctacagctc      900 ctgggcaacg tgctggttat tgtgctgtct catcattttg gca                       943

<210> SEQ ID NO 45
<211> LENGTH: 548
<212> TYPE: DNA
<213> ORGANISM: Artificial Sequence
<220> FEATURE:
<223> OTHER INFORMATION: Synthetic Construct

<400> SEQUENCE: 45

-continued

```
gatccaatca acctctggat tacaaaattt gtgaaagatt gactggtatt cttaactatg      60
ttgctccttt tacgctatgt ggatacgctg ctttaatgcc tttgtatcat gctattgctt     120
cccgtatggc tttcattttc tcctccttgt ataaatcctg gttgctgtct ctttatgagg     180
agttgtggcc cgttgtcagg caacgtggcg tggtgtgcac tgtgtttgct gacgcaaccc     240
ccactggttg gggcattgcc accacctgtc agctcctttc cgggactttc gctttccccc     300
tccctattgc cacggcggaa ctcatcgccg cctgccttgc ccgctgctgg acaggggctc     360
ggctgttggg cactgacaat tccgtggtgt tgtcggggaa atcatcgtcc tttccttggc     420
tgctcgcctg tgttgccacc tggattctgc gcgggacgtc cttctgctac gtcccttcgg     480
ccctcaatcc agcggacctt ccttcccgcg gcctgctgcc ggctctgcgg cctcttccgc     540
gtcttcga                                                               548
```

<210> SEQ ID NO 46
<211> LENGTH: 425
<212> TYPE: DNA
<213> ORGANISM: Artificial Sequence
<220> FEATURE:
<223> OTHER INFORMATION: Synthetic Construct

<400> SEQUENCE: 46

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttag ttcttgccac ggcggaactc     180
atcgccgcct gccttgcccg ctgctggaca ggggctcggc tgttgggcac tgacaattcc     240
gtggtgttta tttgtgaaat ttgtgatgct attgctttat ttgtaaccat ctagctttat     300
ttgtgaaatt tgtgatgcta ttgctttatt tgtaaccatt ataagctgca ataaacaagt     360
taacaacaac aattgcattc attttatgtt tcaggttcag ggggagatgt gggaggtttt     420
ttaaa                                                                  425
```

<210> SEQ ID NO 47
<211> LENGTH: 77
<212> TYPE: DNA
<213> ORGANISM: Artificial Sequence
<220> FEATURE:
<223> OTHER INFORMATION: Synthetic Construct

<400> SEQUENCE: 47

```
gggattttgc cgatttcggc ctattggtta aaaaatgagc tgatttaaca aaaatttaac      60
gcgaatttta acaaaat                                                      77
```

<210> SEQ ID NO 48
<211> LENGTH: 865
<212> TYPE: DNA
<213> ORGANISM: Homo sapiens

<400> SEQUENCE: 48

```
ccccgggtgc gcggcgtcgg tggtgccggc gggggcgcc aggtcgcagg cggtgtaggg      60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
```

```
cgtgtaggcc ttcctgtccc gggccttgcc agcggccagc ccgatgaagg agctccctcg     360 caggggtag  cctccgaagg agaagacgtg ggagtggtcg gcagtgacga ggctcagcgt     420
gtcctcctcg ctggtgagct ggcccgccct ctcaatggcg tcgtcgaaca tgatcgtctc     480
agtcagtgcc cggtaagccc tgctttcatg atgaccatgg tcgatgcgac caccctccac     540
gaagaggaag aagccgcggg ggtgtctgct cagcaggcgc agggcagcct ctgtcatctc     600
catcagggag gggtccagtg tggagtctcg gtggatctcg tatttcatgt ctccaggctc     660
aaagagaccc atgagatggg tcacagacgg gtccagggaa gcctgcatga gctcagtgcg     720
gttccacacg taccgggcac cctggcgttc gccgagccat tcctgcacca gattcttccc     780
gtccagcctg gtcccacctt ggctgtagtc atctgggtac tcagggtctg gggttcccat     840
gcgaaacatg tactttcggc ctcca                                          865
```

```
<210> SEQ ID NO 49
<211> LENGTH: 437
<212> TYPE: DNA
<213> ORGANISM: Homo sapiens

<400> SEQUENCE: 49
ccccgggtgc gcggcgtcgg tggtgccggc ggggggcgcc aggtcgcagg cggtgtaggg      60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
cgtgtaggcc ttcctgtccc gggccttgcc agcggccagc ccgatgaagg agctccctcg     360 caggggtag  cctccgaagg agaagacgtg ggagtggtcg gcagtgacga ggctcagcgt     420
gtcctcctcg ctggtga                                                   437
```

```
<210> SEQ ID NO 50
<211> LENGTH: 428
<212> TYPE: DNA
<213> ORGANISM: Homo sapiens

<400> SEQUENCE: 50
gctggcccgc cctctcaatg gcgtcgtcga acatgatcgt ctcagtcagt gcccggtaag      60
ccctgctttc atgatgacca tggtcgatgc gaccaccctc cacgaagagg aagaagccgc     120
gggggtgtct gctcagcagg cgcagggcag cctctgtcat ctccatcagg gaggggtcca     180
gtgtggagtc tcggtggatc tcgtatttca tgtctccagg ctcaaagaga cccatgagat     240
gggtcacaga cgggtccagg gaagcctgca tgagctcagt gcggttccac acgtaccggg     300
caccctggcg ttcgccgagc cattcctgca ccagattctt cccgtccagc ctggtcccac     360
cttggctgta gtcatctggg tactcagggt ctggggttcc catgcgaaac atgtactttc     420
ggcctcca                                                             428
```

```
<210> SEQ ID NO 51
<211> LENGTH: 287
<212> TYPE: DNA
<213> ORGANISM: Homo sapiens

<400> SEQUENCE: 51
ccccgggtgc gcggcgtcgg tggtgccggc ggggggcgcc aggtcgcagg cggtgtaggg      60
ctccaggcag gcggcgaagg ccatgacgtg cgctatgaag gtctgctcct gcacgccgtg     120
```

```
aaccaggtgc gcctgcgggc cgcgcgcgaa caccgccacg tcctcgcctg cgtgggtctc      180
ttcgtccagg ggcactgctg actgctgccg atactcgggg ctcccgctct cgctctcggt      240
aacatccggc cgggcgccgt ccttgagcac atagcctgga ccgtttc                    287
```

```
<210> SEQ ID NO 52
<211> LENGTH: 290
<212> TYPE: DNA
<213> ORGANISM: Homo sapiens

<400> SEQUENCE: 52
cgtataggag gaccgtgtag gccttcctgt cccgggcctt gccagcggcc agcccgatga       60
aggagctccc tcgcaggggg tagcctccga aggagaagac gtgggagtgg tcggcagtga      120
cgaggctcag cgtgtcctcc tcgctggtga gctggcccgc cctctcaatg cgtcgtcga      180 acatgatcgt ctcagtcagt gcccggtaag ccctgctttc atgatgacca tggtcgatgc      240
gaccaccctc cacgaagagg aagaagccgc gggggtgtct gctcagcagg                 290
```

```
<210> SEQ ID NO 53
<211> LENGTH: 288
<212> TYPE: DNA
<213> ORGANISM: Homo sapiens

<400> SEQUENCE: 53
cgcagggcag cctctgtcat ctccatcagg gaggggtcca gtgtggagtc tcggtggatc       60
tcgtatttca tgtctccagg ctcaaagaga cccatgagat gggtcacaga cgggtccagg      120
gaagcctgca tgagctcagt gcggttccac acgtaccggg caccctggcg ttcgccgagc      180
cattcctgca ccagattctt cccgtccagc ctggtcccac cttggctgta gtcatctggg      240
tactcagggt ctggggttcc catgcgaaac atgtactttc ggcctcca                   288
```

```
<210> SEQ ID NO 54
<211> LENGTH: 84
<212> TYPE: DNA
<213> ORGANISM: Artificial Sequence
<220> FEATURE:
<223> OTHER INFORMATION: Synthetic Construct

<400> SEQUENCE: 54
gtaagtatca aggttacaag acaggtttaa ggagaccaat agaaactggg cttgtcgaga       60
cagagaagac tcttgcgttt ctga                                             84
```

```
<210> SEQ ID NO 55
<211> LENGTH: 49
<212> TYPE: DNA
<213> ORGANISM: Artificial Sequence
<220> FEATURE:
<223> OTHER INFORMATION: Synthetic Construct

<400> SEQUENCE: 55
taggcaccta ttggtcttac tgacatccac tttgcctttc tctccacag                  49
```

```
<210> SEQ ID NO 56
<211> LENGTH: 2406
<212> TYPE: DNA
<213> ORGANISM: Homo sapiens

<400> SEQUENCE: 56
atggccttgc tcatccacct caagacagtc tcggagctgc ggggcagggg cgaccggatc       60
```

-continued

```
gccaaagtga ctttccgagg gcaatccttc tactctcggg tcctggagaa ctgtgaggat      120
gtggctgact ttgatgagac atttcggtgg ccggtggcca gcagcatcga cagaaatgag      180
atgctggaga ttcaggtttt caactacagc aaagtcttca gcaacaagct catcgggacc      240
ttccgcatgg tgctgcagaa ggtggtagag gagagccatg tggaggtgac tgacacgctg      300
attgatgaca acaatgctat catcaagacc agcctgtgcg tggaggtccg gtatcaggcc      360
actgacggca cagtgggctc ctgggacgat ggggacttcc tgggagatga gtctcttcaa      420
gaggaagaga aggacagcca agagacggat ggactgctcc caggctcccg gcccagctcc      480
cggcccccag gagagaagag cttccggaga gccgggagga gcgtgttctc cgccatgaag      540
ctcggcaaaa accggtctca caaggaggag ccccaaagac cagatgaacc ggcggtgctg      600
gagatggaag accttgacca tctggccatt cggctaggag atggactgga tcccgactcg      660
gtgtctctag cctcagtcac agctctcacc actaatgtct ccaacaagcg atctaagcca      720
gacattaaga tggagccaag tgctgggcgg cccatggatt accaggtcag catcacggtg      780
atcgaggccc ggcagctggt gggcttgaac atggaccctg tggtgtgcgt ggaggtgggt      840
gacgacaaga agtacacatc catgaaggag tccactaact gccctatta caacgagtac      900 ttcgtcttcg acttccatgt ctctccggat gtcatgtttg acaagatcat caagatttcg      960
gtgattcact ccaagaacct gctgcgcagt ggcaccctgg tgggctcctt caaaatggac     1020
gtgggaaccg tgtactcgca gccagagcac cagttccatc acaagtgggc catcctgtct     1080
gaccccgatg acatctcctc ggggctgaag ggctacgtga agtgtgacgt tgccgtggtg     1140
ggcaaagggg acaacatcaa gacgccccac aaggccaatg agaccgacga agatgacatt     1200
gaggggaact tgctgctccc cgaggggggtg cccccgaac gccagtgggc ccggttctat     1260
gtgaaaattt accgagcaga ggggctgccc cgtatgaaca caagcctcat ggccaatgta     1320
aagaaggctt tcatcggtga aaacaaggac ctcgtggacc cctacgtgca agtcttcttt     1380
gctggccaga agggcaagac ttcagtgcag aagagcagct atgagcccct gtggaatgag     1440
caggtcgtct ttacagacct cttcccccca ctctgcaaac gcatgaaggt gcagatccga     1500
gactcggaca aggtcaacga cgtggccatc ggcacccact tcattgacct gcgcaagatt     1560
tctaatgacg gagacaaagg cttcctgccc acactgggcc cagcctgggt gaacatgtac     1620
ggctccacac gtaactacac gctgctggat gagcatcagg acctgaacga gggcctgggg     1680
gagggtgtgt ccttccgggc ccggctcctg ctgggcctgg ctgtggagat cgtagacacc     1740
tccaaccctg agctcaccag ctccacagag gtgcaggtgg agcaggccac gcccatctcg     1800
gagagctgtg caggtaaaat ggaagaattc tttctctttg gagccttcct ggaggcctca     1860
atgatcgacc ggagaaacgg agacaagccc atcacctttg aggtcaccat aggcaactat     1920
gggaacgaag ttgatggcct gtcccggccc cagcggcctc ggccccggaa ggagccgggg     1980
gatgaggaag aagtagacct gattcagaac gcaagtgatg acgaggccgg tgatgccggg     2040
gacctggcct cagtctcctc cactccacca atgcggcccc aggtcaccga caggaactac     2100
ttccatctgc cctacctgga gcgaaagccc tgcatctaca tcaagagctg gtggccggac     2160
cagcgccgcc gcctctacaa tgccaacatc atggaccaca ttgccgacaa gctggaagaa     2220
ggcctgaacg acatacagga gatgatcaaa acggagaagt cctaccctga gcgtcgcctg     2280
cggggcgtcc tggaggagct gagctgtggc tgctgccgct tcctctccct cgctgacaag     2340
gaccagggcc actcatcccg caccaggctt gaccgggagc gcctcaagtc ctgcatgagg     2400
gagctg                                                                2406
```

-continued

```
<210> SEQ ID NO 57
<211> LENGTH: 3588
<212> TYPE: DNA
<213> ORGANISM: Homo sapiens

<400> SEQUENCE: 57
gaaaacatgg ggcagcaggc caggatgctg cgggcccagg tgaagcggca cacggtgcgg      60
gacaagctga ggctgtgcca gaacttcctg cagaagctgc gcttcctggc ggacgagccc     120
cagcacagca ttcccgacat cttcatctgg atgatgagca caacaagcg tgtcgcctat      180 gcccgtgtgc cctccaagga cctgctcttc tccatcgtgg aggaggagac tggcaaggac     240
tgcgccaagg tcaagacgct cttccttaag ctgccaggga agcggggctt cggctcggca     300
ggctggacag tgcaggccaa ggtggagctg tacctgtggc tgggcctcag caaacagcgc     360
aaggagttcc tgtgcggcct gccctgtggc ttccaggagg tcaaggcagc ccagggcctg     420
ggcctgcatg ccttcccacc cgtcagcctg gtctacacca agaagcaggc gttccagctc     480
cgagcgcaca tgtaccaggc ccgcagcctc tttgccgccg acagcagcgg actctcagac     540
ccctttgccc gcgtcttctt catcaatcag agtcagtgca cagaggtgct gaatgagacc     600
ctgtgtccca cctgggacca gatgctggtg ttcgacaacc tggagctcta tggtgaagct     660
catgagctga gggacgatcc gcccatcatt gtcattgaaa tctatgacca ggattccatg     720
ggcaaagctg acttcatggg ccggaccttc gccaaacccc tggtgaagat ggcagacgag     780
gcgtactgcc cacccgcctt cccacctcag ctcgagtact accagatcta ccgtggcaac     840
gccacagctg agacctgct ggcggccttc gagctgctgc agattggacc agcagggaag     900
gctgacctgc cccccatcaa tggcccggtg gacgtggacc gaggtcccat catgcccgtg     960
cccatgggca tccggcccgt gctcagcaag taccgagtgg aggtgctgtt ctggggccta    1020
cgggacctaa agcgggtgaa cctgcccag gtggaccggc cacgggtgga catcgagtgt    1080
gcagggaagg gggtgcagtc gtccctgatc cacaattata agaagaaccc caacttcaac    1140
accctcgtca agtggtttga agtggacctc ccagagaacg agctgctgca cccgcccttg    1200
aacatccgtg tggtggactg ccgggccttc ggtcgctaca cactggtggg ctcccatgcc    1260
gtcagctccc tgcgacgctt catctaccgg cccccagacc gctcggcccc cagctggaac    1320
accacggtca ggcttctccg gcgctgccgt gtgctgtgca atggggggctc ctcctctcac    1380 tccacagggg aggttgtggt gactatggag ccagaggtac ccatcaagaa actggagacc    1440
atggtgaagc tggacgcgac ttctgaagct gttgtcaagg tggatgtggc tgaggaggag    1500
aaggagaaga agaagaagaa gaagggcact gcggaggagc cagaggagga ggagccagac    1560
gagagcatgc tggactggtg gtccaagtac tttgcctcca ttgacaccat gaaggagcaa    1620
cttcgacaac aagagccctc tggaattgac ttggaggaga aggaggaagt ggacaatacc    1680
gagggcctga aggggtcaat gaagggcaag gagaaggcaa gggctgccaa agaggagaag    1740
aagaagaaaa ctcagagctc tggctctggc caggggtccg aggcccccga gaagaagaaa    1800
cccaagattg atgagcttaa ggtataccc aaagagctgg agtccgagtt tgataactt     1860 gaggactggc tgcacacttt caacttgctt cggggcaaga ccggggatga tgaggatggc    1920
tccaccgagg aggagcgcat tgtgggacgc ttcaagggct ccctctgcgt gtacaaagtg    1980
ccactcccag aggacgtgtc ccgggaagcc ggctacgact ccacctacgg catgttccag    2040
ggcatcccga gcaatgaccc catcaatgtg ctggtccgag tctatgtggt ccgggccacg    2100
```

```
gacctgcacc ctgctgacat caacggcaaa gctgacccct acatcgccat ccggctaggc    2160
aagactgaca tccgcgacaa ggagaactac atctccaagc agctcaaccc tgtctttggg    2220
aagtcctttg acatcgaggc ctccttcccc atggaatcca tgctgacggt ggctgtgtat    2280
gactgggacc tggtgggcac tgatgacctc attggggaaa ccaagatcga cctggagaac    2340
cgcttctaca gcaagcaccg cgccacctgc ggcatcgccc agacctactc cacacatggc    2400
tacaatatct ggcgggaccc catgaagccc agccagatcc tgacccgcct ctgcaaagac    2460
ggcaaagtgg acggccccca ctttgggccc cctgggagag tgaaggtggc caaccgcgtc    2520
ttcactgggc cctctgagat tgaggacgag aacggtcaga ggaagcccac agacgagcat    2580
gtggcgctgt tggccctgag gcactgggag gacatccccc gcgcaggctg ccgcctggtg    2640
ccagagcatg tggagacgag gccgctgctc aaccccgaca agccgggcat cgagcagggc    2700
cgcctggagc tgtgggtgga catgttcccc atggacatgc cagcccctgg gacgcctctg    2760
gacatctcac ctcggaagcc caagaagtac gagctgcggg tcatcatctg gaacacagat    2820
gaggtggtct tggaggacga cgacttcttc acaggggaga agtccagtga catcttcgtg    2880 aggggggtggc tgaagggcca gcaggaggac aagcaggaca cagacgtcca ctaccactcc    2940
ctcactggcg agggcaactt caactggcgc tacctgttcc ccttcgacta cctggcggcg    3000
gaggagaaga tcgtcatctc caagaaggag tccatgttct cctgggacga gaccgagtac    3060
aagatccccg cgcggctcac cctgcagatc tgggatgcgg accacttctc cgctgacgac    3120
ttcctggggg ccatcgagct ggacctgaac cggttcccgc ggggcgcaaa gacagccaag    3180
cagtgcacca tggagatggc caccggggag gtggacgtgc ccctcgtgtc catcttcaag    3240
caaaagcgcg tcaaaggctg gtggcccctc ctggcccgca tgagaacga tgagtttgag    3300 ctcacgggca aggtggaggc tgagctgcat ttactgacag cagaggaggc agagaagaac    3360
ccagtgggcc tggcccgcaa tgaacctgac cccctagaga aacccaaccg gcccgacacg    3420
gccttcgtct ggttcctcaa ccctctcaag tccatcaagt acctcatctg caccggtac    3480 aagtggctca tcatcaagat cgtgctggcg ctgttggggc tgctcatgtt ggggctcttc    3540
ctctacagcc tccctggcta catggtcaaa aagctccttg gggcatga             3588

<210> SEQ ID NO 58
<211> LENGTH: 802
<212> TYPE: PRT
<213> ORGANISM: Homo sapiens

<400> SEQUENCE: 58

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110
```

-continued

```
Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
        130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
            195                 200                 205

Ala Ile Arg Leu Gly Asp Gly Leu Asp Pro Asp Ser Val Ser Leu Ala
        210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
                260                 265                 270

Pro Val Val Cys Val Glu Val Gly Asp Asp Lys Lys Tyr Thr Ser Met
            275                 280                 285

Lys Glu Ser Thr Asn Cys Pro Tyr Tyr Asn Glu Tyr Phe Val Phe Asp
        290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
            355                 360                 365

Leu Lys Gly Tyr Val Lys Cys Asp Val Ala Val Val Gly Lys Gly Asp
        370                 375                 380

Asn Ile Lys Thr Pro His Lys Ala Asn Glu Thr Asp Glu Asp Asp Ile
385                 390                 395                 400

Glu Gly Asn Leu Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
        450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
            515                 520                 525

Leu Pro Thr Leu Gly Pro Ala Trp Val Asn Met Tyr Gly Ser Thr Arg
```

-continued

```
            530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
                580                 585                 590

Val Glu Gln Ala Thr Pro Ile Ser Glu Ser Cys Ala Gly Lys Met Glu
            595                 600                 605

Glu Phe Phe Leu Phe Gly Ala Phe Leu Glu Ala Ser Met Ile Asp Arg
            610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Glu Val Asp Leu Ile Gln Asn Ala Ser
                660                 665                 670

Asp Asp Glu Ala Gly Asp Ala Gly Asp Leu Ala Ser Val Ser Ser Thr
            675                 680                 685

Pro Pro Met Arg Pro Gln Val Thr Asp Arg Asn Tyr Phe His Leu Pro
            690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
                740                 745                 750

Lys Ser Tyr Pro Glu Arg Arg Leu Arg Gly Val Leu Glu Glu Leu Ser
                755                 760                 765

Cys Gly Cys Cys Arg Phe Leu Ser Leu Ala Asp Lys Asp Gln Gly His
            770                 775                 780

Ser Ser Arg Thr Arg Leu Asp Arg Glu Arg Leu Lys Ser Cys Met Arg
785                 790                 795                 800

Glu Leu
```

<210> SEQ ID NO 59
<211> LENGTH: 1195
<212> TYPE: PRT
<213> ORGANISM: Homo sapiens

<400> SEQUENCE: 59

```
Glu Asn Met Gly Gln Gln Ala Arg Met Leu Arg Ala Gln Val Lys Arg
1               5                   10                  15

His Thr Val Arg Asp Lys Leu Arg Leu Cys Gln Asn Phe Leu Gln Lys
                20                  25                  30

Leu Arg Phe Leu Ala Asp Glu Pro Gln His Ser Ile Pro Asp Ile Phe
            35                  40                  45

Ile Trp Met Met Ser Asn Asn Lys Arg Val Ala Tyr Ala Arg Val Pro
            50                  55                  60

Ser Lys Asp Leu Leu Phe Ser Ile Val Glu Glu Thr Gly Lys Asp
65                  70                  75                  80

Cys Ala Lys Val Lys Thr Leu Phe Leu Lys Leu Pro Gly Lys Arg Gly
                85                  90                  95

Phe Gly Ser Ala Gly Trp Thr Val Gln Ala Lys Val Glu Leu Tyr Leu
```

-continued

```
                  100                105                110

Trp Leu Gly Leu Ser Lys Gln Arg Lys Glu Phe Leu Cys Gly Leu Pro
            115                120                125

Cys Gly Phe Gln Glu Val Lys Ala Ala Gln Gly Leu Gly Leu His Ala
        130                135                140

Phe Pro Pro Val Ser Leu Val Tyr Thr Lys Lys Gln Ala Phe Gln Leu
145                150                155                160

Arg Ala His Met Tyr Gln Ala Arg Ser Leu Phe Ala Ala Asp Ser Ser
                165                170                175

Gly Leu Ser Asp Pro Phe Ala Arg Val Phe Phe Ile Asn Gln Ser Gln
            180                185                190

Cys Thr Glu Val Leu Asn Glu Thr Leu Cys Pro Thr Trp Asp Gln Met
            195                200                205

Leu Val Phe Asp Asn Leu Glu Leu Tyr Gly Glu Ala His Glu Leu Arg
        210                215                220

Asp Asp Pro Pro Ile Ile Val Ile Glu Ile Tyr Asp Gln Asp Ser Met
225                230                235                240

Gly Lys Ala Asp Phe Met Gly Arg Thr Phe Ala Lys Pro Leu Val Lys
                245                250                255

Met Ala Asp Glu Ala Tyr Cys Pro Pro Arg Phe Pro Pro Gln Leu Glu
                260                265                270

Tyr Tyr Gln Ile Tyr Arg Gly Asn Ala Thr Ala Gly Asp Leu Leu Ala
                275                280                285

Ala Phe Glu Leu Leu Gln Ile Gly Pro Ala Gly Lys Ala Asp Leu Pro
        290                295                300

Pro Ile Asn Gly Pro Val Asp Val Asp Arg Gly Pro Ile Met Pro Val
305                310                315                320

Pro Met Gly Ile Arg Pro Val Leu Ser Lys Tyr Arg Val Glu Val Leu
                325                330                335

Phe Trp Gly Leu Arg Asp Leu Lys Arg Val Asn Leu Ala Gln Val Asp
            340                345                350

Arg Pro Arg Val Asp Ile Glu Cys Ala Gly Lys Gly Val Gln Ser Ser
            355                360                365

Leu Ile His Asn Tyr Lys Lys Asn Pro Asn Phe Asn Thr Leu Val Lys
        370                375                380

Trp Phe Glu Val Asp Leu Pro Glu Asn Glu Leu Leu His Pro Pro Leu
385                390                395                400

Asn Ile Arg Val Val Asp Cys Arg Ala Phe Gly Arg Tyr Thr Leu Val
                405                410                415

Gly Ser His Ala Val Ser Ser Leu Arg Arg Phe Ile Tyr Arg Pro Pro
                420                425                430

Asp Arg Ser Ala Pro Ser Trp Asn Thr Thr Val Arg Leu Leu Arg Arg
            435                440                445

Cys Arg Val Leu Cys Asn Gly Gly Ser Ser Ser His Ser Thr Gly Glu
        450                455                460

Val Val Val Thr Met Glu Pro Glu Val Pro Ile Lys Lys Leu Glu Thr
465                470                475                480

Met Val Lys Leu Asp Ala Thr Ser Glu Ala Val Val Lys Val Asp Val
                485                490                495

Ala Glu Glu Glu Lys Glu Lys Lys Lys Lys Lys Gly Thr Ala Glu
            500                505                510

Glu Pro Glu Glu Glu Glu Pro Asp Glu Ser Met Leu Asp Trp Trp Ser
            515                520                525
```

-continued

```
Lys Tyr Phe Ala Ser Ile Asp Thr Met Lys Glu Gln Leu Arg Gln Gln
    530                 535                 540

Glu Pro Ser Gly Ile Asp Leu Glu Glu Lys Glu Glu Val Asp Asn Thr
545                 550                 555                 560

Glu Gly Leu Lys Gly Ser Met Lys Gly Lys Glu Lys Ala Arg Ala Ala
                565                 570                 575

Lys Glu Glu Lys Lys Lys Lys Thr Gln Ser Ser Gly Ser Gly Gln Gly
                580                 585                 590

Ser Glu Ala Pro Glu Lys Lys Pro Lys Ile Asp Glu Leu Lys Val
                595                 600                 605

Tyr Pro Lys Glu Leu Glu Ser Glu Phe Asp Asn Phe Glu Asp Trp Leu
    610                 615                 620

His Thr Phe Asn Leu Leu Arg Gly Lys Thr Gly Asp Asp Glu Asp Gly
625                 630                 635                 640

Ser Thr Glu Glu Glu Arg Ile Val Gly Arg Phe Lys Gly Ser Leu Cys
                645                 650                 655

Val Tyr Lys Val Pro Leu Pro Glu Asp Val Ser Arg Glu Ala Gly Tyr
                660                 665                 670

Asp Ser Thr Tyr Gly Met Phe Gln Gly Ile Pro Ser Asn Asp Pro Ile
                675                 680                 685

Asn Val Leu Val Arg Val Tyr Val Val Arg Ala Thr Asp Leu His Pro
    690                 695                 700

Ala Asp Ile Asn Gly Lys Ala Asp Pro Tyr Ile Ala Ile Arg Leu Gly
705                 710                 715                 720

Lys Thr Asp Ile Arg Asp Lys Glu Asn Tyr Ile Ser Lys Gln Leu Asn
                725                 730                 735

Pro Val Phe Gly Lys Ser Phe Asp Ile Glu Ala Ser Phe Pro Met Glu
                740                 745                 750

Ser Met Leu Thr Val Ala Val Tyr Asp Trp Asp Leu Val Gly Thr Asp
                755                 760                 765

Asp Leu Ile Gly Glu Thr Lys Ile Asp Leu Glu Asn Arg Phe Tyr Ser
    770                 775                 780

Lys His Arg Ala Thr Cys Gly Ile Ala Gln Thr Tyr Ser Thr His Gly
785                 790                 795                 800

Tyr Asn Ile Trp Arg Asp Pro Met Lys Pro Ser Gln Ile Leu Thr Arg
                805                 810                 815

Leu Cys Lys Asp Gly Lys Val Asp Gly Pro His Phe Gly Pro Pro Gly
                820                 825                 830

Arg Val Lys Val Ala Asn Arg Val Phe Thr Gly Pro Ser Glu Ile Glu
                835                 840                 845

Asp Glu Asn Gly Gln Arg Lys Pro Thr Asp Glu His Val Ala Leu Leu
    850                 855                 860

Ala Leu Arg His Trp Glu Asp Ile Pro Arg Ala Gly Cys Arg Leu Val
865                 870                 875                 880

Pro Glu His Val Glu Thr Arg Pro Leu Leu Asn Pro Asp Lys Pro Gly
                885                 890                 895

Ile Glu Gln Gly Arg Leu Glu Leu Trp Val Asp Met Phe Pro Met Asp
                900                 905                 910

Met Pro Ala Pro Gly Thr Pro Leu Asp Ile Ser Pro Arg Lys Pro Lys
                915                 920                 925

Lys Tyr Glu Leu Arg Val Ile Ile Trp Asn Thr Asp Glu Val Val Leu
    930                 935                 940
```

```
Glu Asp Asp Asp Phe Phe Thr Gly Glu Lys Ser Ser Asp Ile Phe Val
945                 950                 955                 960

Arg Gly Trp Leu Lys Gly Gln Gln Glu Asp Lys Gln Asp Thr Asp Val
                965                 970                 975

His Tyr His Ser Leu Thr Gly Glu Gly Asn Phe Asn Trp Arg Tyr Leu
                980                 985                 990

Phe Pro Phe Asp Tyr Leu Ala Ala  Glu Glu Lys Ile Val  Ile Ser Lys
        995                 1000                 1005

Lys Glu Ser Met Phe Ser Trp  Asp Glu Thr Glu Tyr  Lys Ile Pro
    1010                 1015                 1020

Ala Arg Leu Thr Leu Gln Ile  Trp Asp Ala Asp His  Phe Ser Ala
    1025                 1030                 1035

Asp Asp Phe Leu Gly Ala Ile  Glu Leu Asp Leu Asn  Arg Phe Pro
    1040                 1045                 1050

Arg Gly Ala Lys Thr Ala Lys  Gln Cys Thr Met Glu  Met Ala Thr
    1055                 1060                 1065

Gly Glu Val Asp Val Pro Leu  Val Ser Ile Phe Lys  Gln Lys Arg
    1070                 1075                 1080

Val Lys Gly Trp Trp Pro Leu  Leu Ala Arg Asn Glu  Asn Asp Glu
    1085                 1090                 1095

Phe Glu Leu Thr Gly Lys Val  Glu Ala Glu Leu His  Leu Leu Thr
    1100                 1105                 1110

Ala Glu Glu Ala Glu Lys Asn  Pro Val Gly Leu Ala  Arg Asn Glu
    1115                 1120                 1125

Pro Asp Pro Leu Glu Lys Pro  Asn Arg Pro Asp Thr  Ala Phe Val
    1130                 1135                 1140

Trp Phe Leu Asn Pro Leu Lys  Ser Ile Lys Tyr Leu  Ile Cys Thr
    1145                 1150                 1155

Arg Tyr Lys Trp Leu Ile Ile  Lys Ile Val Leu Ala  Leu Leu Gly
    1160                 1165                 1170

Leu Leu Met Leu Gly Leu Phe  Leu Tyr Ser Leu Pro  Gly Tyr Met
    1175                 1180                 1185

Val Lys Lys Leu Leu Gly Ala
    1190                 1195
```

```
<210> SEQ ID NO 60
<211> LENGTH: 10032
<212> TYPE: DNA
<213> ORGANISM: Artificial Sequence
<220> FEATURE:
<223> OTHER INFORMATION: Synthetic Construct

<400> SEQUENCE: 60
tcgcgcgttt cggtgatgac ggtgaaaacc tctgacacat gcagctcccg gatagaggtc      60
atccttcctg accatttcca tcattccagt cgaactcaca cacaacacca aatgcattta     120
agtcgcttga aattgctata agcagagcat gttgcgccag catgattaat acagcattta     180
atacagagcc gtgtttattg agtcggtatt cagagtctga ccagaaatta ttaatctggt     240
gaagttattc ctctgtcatt acgtcatggt cgatttcaat ttctattgat gctttccagt     300
cgtaatcaat gatgtatttt ttgatgtttg acctctgttc atatcctcac agataaaaaa     360
tcgccctcac actggagggc aaagaagatt tccaataatc agaacaagtc ggctcctgtt     420
tagttacgag cgacattgct ccgtgtattc actcgttgga atgaatacac agtgcagtgt     480
ttattctgtt atttatgcca aaaattaagg ccactatcag gcagctttgt tgttctgttt     540
```

-continued

```
accaagttct ctggcaatca ttgccgtcgt tcgtattgcc catttatcga catatttccc       600
atcttcctat acaggaaaca tttcttcagg cttaaccatg cattccgatt gcagcttgca       660
tccattgcat cgcttgaatt gtccacacca ttgattttta tcaatagtcg tagtttaacg       720
gatagtcctg gtattgttcc atcacatcct gaggatgccc ttcgaactct tcaaattctt       780
cttcctaata tcaccttaaa tagtggattg cggtagtaaa gattgtgcct gtcttttaac       840
cacatcaggc tcggtggttc tcgtgtaccc ctacagcgag aaatcggata aactattaca       900
acccctacag tttgtagagt atagaaaatg atccactcgt tattctcgga cgagtgttca       960
gtaatgaacc tctggagaga accatctata tgatcgttat ctgggtttga cttctgcttt      1020
taagcccaga taacttgcct gaatatgtta atgagagaat cggtattcct catgtgtggc      1080
atgttttcgt ctttgctctt gcattttcac tagcaattaa tgtgcatcga ttatcagcta      1140
ttgccagcgc cagatataag cgatttaagc taagaaaacg cattaaggtg caaaacgata      1200
aagtgcgatc agtaattcaa aaccttacag gagagcaatc tatggttttg tgctcagccc      1260
ttaatgaagg caggtagtat gtggttacat caaaacaatt cccatacatt agtgagttga      1320
ttgagcttgg tgtgttgaac aaaacttttt cccgatggaa tggaaagcat atattattcc      1380
ctattgagga tatttactgg actgaattag ttgccagcta tgatccatat aatattgaga      1440
taaagccaag gccaatatct aagtaactag ataagaggaa tcgatttttcc cttaattttc      1500 tggcgtccac tgcatgttat gccgcgttcg ccaggcttgc tgtaccatgt gcgctgattc      1560
ttgcgctcaa tacgttgcag gttgctttca atctgtttgt ggtattcagc cagcactgta      1620
aggtctatcg gatttagtgc gctttctact cgtgatttcg gtttgcgatt cagcgagaga      1680
atagggcggt taactggttt tgcgcttacc ccaaccaaca ggggatttgc tgctttccat      1740
tgagcctgtt actctgcgcg acgttcgcgg cggcgtgttt gtgcatccat ctggattctc      1800
ctgtcagtta gctttggtgg tgtgtggcag ttgtagtcct gaacgaaaac cccccgcgat      1860
tggcacgttg gcagctaatc cggaatcgca cttacggcca atgcttcgtt tcgtatcaca      1920
caccccaaag ccttctgctt tgaatgctgc ccttcttcag ggcttaattt ttaagagcgt      1980
caccttcatg gtggtcagtg cgtcctgctg atgtgctcag gcacgattta attaaggcct      2040
taattaggct gcgcgctcgc tcgctcactg aggccgcccg ggcaaagccc gggcgtcggg      2100
cgacctttgg tcgcccggcc tcagtgagcg agcgagcgcg cagagaggga gtggccaact      2160
ccatcactag gggttccttg tagttaatga ttaacccgcc atgctactta tctacgtagc      2220
catgctctag gaagatcgga attcgcccct aagctagcgg cgcgcccaat tctgcagctc      2280
agcctactac ttgctttcca ggctgttcct agttcccatg tcagctgctt gtgctttcca      2340
gagacaaaac aggaataata gatgtcatta aatatacatt gggccccagg cggtcaatgt      2400
ggcagcctga gcctcctttc catctctgtg gaggcagaca taggaccccc aacaaacagc      2460
atgcaggttg ggagccagcc acaggaccca ggtaaggggc cctgggtcct taagcttctg      2520
ccactggctc cggcattgca gagagaagag aaggggcggc agactggaga gctgggctcc      2580 attttttgttc cttggtgccc tgcccctccc catgacctgc agagacattc agcctgccag      2640
gctttatgag gtgggagctg ggctctccct gatgtattat tcagctccct ggagttggcc      2700
agctcctgtt acactggcca cagccctggg catccgcttc tcacttctag tttcccctcc      2760
aaggtaatgt ggtgggtcat gatcattcta tcctggcttc agggacctga ctccactttg      2820
gggccattcg aggggtctag ggtagatgat gtcccctgt ggggattaat gtcctgctct      2880
gtaaaactga gctagctgag atccaggagg gcttggccag agacagcaag ttgttgccat      2940
```

-continued

```
ggtgacttta aagccaggtt gctgccccag cacaggcctc ccagtctacc ctcactagaa      3000
aacaacaccc aggcactttc caccacctct caaaggtgaa acccaaggct ggtctagaga      3060
atgaattatg gatcctcgct gtccgtgcca cccagctagt cccagcggct cagacactga      3120
ggagagactg taggttcagc tacaagcaaa aagacctagc tggtctccaa gcagtgtctc      3180
caagtccctg aacctgtgac acctgcccca ggcatcatca ggcacagagg gccaccaaga      3240
attctagcgg ccgccaccat ggccttgctc atccacctca agacagtctc ggagctgcgg      3300
ggcaggggcg accggatcgc caaagtgact ttccgagggc aatccttcta ctctcgggtc      3360
ctggagaact gtgaggatgt ggctgacttt gatgagacat ttcggtggcc ggtggccagc      3420
agcatcgaca gaaatgagat gctggagatt caggttttca actacagcaa agtcttcagc      3480
aacaagctca tcgggacctt ccgcatggtg ctgcagaagg tggtagagga gagccatgtg      3540
gaggtgactg acacgctgat tgatgacaac aatgctatca tcaagaccag cctgtgcgtg      3600
gaggtccggt atcaggccac tgacggcaca gtgggctcct gggacgatgg ggacttcctg      3660
ggagatgagt ctcttcaaga ggaagagaag gacagccaag agacggatgg actgctccca      3720
ggctcccggc ccagctcccg gcccccagga gagaagagct ccggagagc cgggaggagc      3780 gtgttctccg ccatgaagct cggcaaaaac cggtctcaca aggaggagcc ccaaagacca      3840
gatgaaccgg cggtgctgga gatggaagac cttgaccatc tggccattcg gctaggagat      3900
ggactggatc ccgactcggt gtctctagcc tcagtcacag ctctcaccac taatgtctcc      3960
aacaagcgat ctaagccaga cattaagatg gagccaagtg ctgggcggcc catggattac      4020
caggtcagca tcacggtgat cgaggcccgg cagctggtgg gcttgaacat ggaccctgtg      4080
gtgtgcgtgg aggtgggtga cgacaagaag tacacatcca tgaaggagtc cactaactgc      4140
ccctattaca acgagtactt cgtcttcgac ttccatgtct ctccggatgt catgtttgac      4200
aagatcatca gatttcggt gattcactcc aagaacctgc tgcgcagtgg caccctggtg      4260
ggctccttca aaatggacgt gggaaccgtg tactcgcagc cagagcacca gttccatcac      4320
aagtgggcca tcctgtctga ccccgatgac atctcctcgg ggctgaaggg ctacgtgaag      4380
tgtgacgttg ccgtggtggg caaagggga aacatcaaga cgccccacaa ggccaatgag      4440
accgacgaag atgacattga ggggaacttg ctgctccccg aggggtgcc ccccgaacgc      4500 cagtgggccc ggttctatgt gaaaatttac cgagcagagg ggctgccccg tatgaacaca      4560
agcctcatgg ccaatgtaaa gaaggctttc atcggtgaaa acaaggacct cgtggacccc      4620
tacgtgcaag tcttctttgc tggccagaag ggcaagactt cagtgcagaa gagcagctat      4680
gagcccctgt ggaatgagca ggtcgtctt acagacctct ccccccact ctgcaaacgc      4740 atgaaggtgc agatccgaga ctcggacaag gtcaacgacg tggccatcgg cacccacttc      4800
attgacctgc gcaagatttc taatgacgga gacaaaggct cctgcccac actgggccca      4860 gcctgggtga acatgtacgg ctccacacgt aactacgc tgctggatga gcatcaggac      4920
ctgaacgagg gcctggggga gggtgtgtcc ttccgggccc ggctcctgct gggcctggct      4980
gtggagatcg tagacacctc caaccctgag ctcaccagct ccacagaggt gcaggtggag      5040
caggccacgc ccatctcgga gagctgtgca ggtaaaatgg aagaattctt tctctttgga      5100
gccttcctgg aggcctcaat gatcgaccgg agaaacggag acaagcccat caccctttgag      5160 gtcaccatag gcaactatgg gaacgaagtt gatggcctgt cccggccccca gcggcctcgg      5220 cccccggaagg agccggggga tgaggaagaa gtagacctga ttcagaacgc aagtgatgac      5280
```

-continued

```
gaggccggtg atgccgggga cctggcctca gtctcctcca ctccaccaat gcggccccag    5340
gtcaccgaca ggaactactt ccatctgccc tacctggagc gaaagccctg catctacatc    5400
aagagctggt ggccggacca gcgccgccgc ctctacaatg ccaacatcat ggaccacatt    5460
gccgacaagc tggaagaagg cctgaacgac atacaggaga tgatcaaaac ggagaagtcc    5520
taccctgagc gtcgcctgcg gggcgtcctg gaggagctga gctgtggctg ctgccgcttc    5580
ctctccctcg ctgacaagga ccagggccac tcatcccgca ccaggcttga ccgggagcgc    5640
ctcaagtcct gcatgaggga gctggtaagt atcaaggtta caagacaggt ttaaggagac    5700
caatagaaac tgggcttgtc gagacagaga agactcttgc gtttctgagc tagcccccgg    5760
gtgcgcggcg tcggtggtgc cggcgggggg cgccaggtcg caggcggtgt agggctccag    5820
gcaggcggcg aaggccatga cgtgcgctat gaaggtctgc tcctgcacgc cgtgaaccag    5880
gtgcgcctgc gggccgcgcg cgaacaccgc cacgtcctcg cctgcgtggg tctcttcgtc    5940
caggggcact gctgactgct gccgatactc ggggctcccg ctctcgctct cggtaacatc    6000
cggccgggcg ccgtccttga gcacatagcc tggaccgttt cgtcgacctc gagttaaggg    6060
cgaattcccg ataaggatct tcctagagca tggctacgta gataagtagc atggcgggtt    6120
aatcattaac tacaaggaac ccctagtgat ggagttggcc actccctctc tgcgcgctcg    6180
ctcgctcact gaggccgggc gaccaaaggt cgcccgacgc ccgggctttg cccgggcggc    6240
ctcagtgagc gagcgagcgc gcagccttaa ttaaatccac atctgtatgt tttttatatt    6300
aatttatttt ttgcaggggg gcattgtttg gtaggtgaga gttctgaatt gctatgttta    6360
gtgagttgta tctatttatt tttcaataaa tacaattagt tatgtgtttt gggggcgatc    6420
gtgaggcaaa gaaaacccgg cgctgaggcc gggttattct tgttctctgg tcaaattata    6480
tagttggaaa acaaggatgc atatatgaat gaacgatgca gaggcaatgc cgatggcgat    6540
agtgggtatc aggtagccgc ttatgctgga aagaagcaat aacccgcaga aaaacaaagc    6600
tccaagctca acaaaactaa gggcatagac aataactacc tatgtcatat acccatactc    6660
tctaatcttg gccagtcggc gcgttctgct tccgattaga aacgtcaagg cagcaatcag    6720
gattgcaatc ttggttcctg cataggatga caatgtcgcc ccaagaccat ctctatgagc    6780
tgaaaaagaa acacaaggaa tgtagtggcg gaaaaggaga tagcaaatgc ttacgataac    6840
gtaaggaatt attactatgt aaacaccagg caagattctg ttccgtataa ttactcctga    6900
taattaatcc ttaactttgc ccacctgcct tttaaaacat tccagtatat cacttttcat    6960
tcttgcgtag caatatgccc tctcttcagc tatctcagca ttggtgacct tgttcagagg    7020
cgctgagaga tggccttttt ctgatagata atgttctgtt aaaatatctc cggcctcatc    7080
ttttgcccgc aggctaatgt ctgaaaattg aggtgacggg ttaaaaataa tatccttggc    7140
aacctttttt atatcccttt taaattttgg cttaatgact atatccaatg agtcaaaaag    7200
ctccccttca atatctgttg cccctaagac ctttaatata tcgccaaata caggtagctt    7260
ggcttctacc ttcaccgttg ttctgccgat gaaatgctaa tgcataacat cgtctttggt    7320
ggttcccctc atcagtggct ctatctgaac gcgctctcca ctgcttaatg acattccttt    7380
cccgattaaa aaatctgtca gatcggatgt ggtcggcccg aaaacagttc tggcaaaacc    7440
aatggtgtcg ccttcaacaa acaaaaaaga tgggaatccc aatgattcgt catctgcgag    7500
gctgttctta atatcttcaa ctgtagcttt agagcgattt atcttctgaa ccagactctt    7560
gtcatttgtt ttggtaaaga gaaagttttt tccatcgatt ttatgaatat acaaataatt    7620
ggagccaacc ttcaggtgat gattatcagc cagcagagaa ttaaggaaaa cagacaggtt    7680
```

-continued

```
tattgagcac ttatctttcc ctttattttt gctgcggtaa gtcgcataaa aaccattctt    7740
cacaattcaa tccatttact atgttatgtt ctgaggggag tgaaaattcc cctaattcga    7800
tgaagattct tgctaaattg ttatcagcta tgcgccgacc agaacacctt gccgatcagc    7860
caaacgtcta atcaggccac tgactagcga taactttccc cacaacgaaa caactctcat    7920
tgcatgggat aattgggtac tgtgggttta gtggttgtaa aaacacctga ccgctatccc    7980
tgatcagttt cttgaaggta aactcatcac ccccaagtct ggctatacag aaatcacctg    8040
gctcaacagc ctgctcaggg tcaacgagaa tttacattcc gtcaggatag cttggcttgg    8100
agcctgttgg tgcggtcacg gaattacctt caacctcaag ccagaatgca gaatcactgg    8160
cttttttggt tgtgcttacc catctctccg catcaccttt ggtaaaggtt ctaagctaag    8220
gtgagaacat ccctgcctga acatgagaaa aaacagggta ctcatactca cttattagtg    8280
acggctatga gcaaaaggcc agcaaaaggc caggaaccgt aaaaaggccg cgttgctggc    8340 gttttttccat aggctccgcc cccctgacga gcatcacaaa aatcgacgct caagtcagag    8400
gtggcgaaac ccgacaggac tataaagata ccaggcgttt cccctggaa gctccctcgt    8460 gcgctctcct gttccgaccc tgccgcttac cggatacctg tccgccttc tcccttcggg    8520 aagcgtggcg ctttctcata gctcacgctg taggtatctc agttcggtgt aggtcgttcg    8580
ctccaagctg ggctgtgtgc acgaacccc cgttcagccc gaccgctgcg ccttatccgg    8640
taactatcgt cttgagtcca acccggtaag acacgactta tcgccactgg cagcagccac    8700
tggtaacagg attagcagag cgaggtatgt aggcggtgct acagagttct tgaagtggtg    8760
gcctaactac ggctacacta gaagaacagt atttggtatc tgcgctctgc tgaagccagt    8820
taccttcgga aaaagagttg gtagctcttg atccggcaaa caaaccaccg ctggtagcgg    8880 tggtttttttt gtttgcaagc agcagattac gcgcagaaaa aaaggatctc aagaagatcc    8940
tttgatcttt tctacggggt ctgacgctca gtggaacgaa aactcacgtt aagggatttt    9000
ggtcatgaga ttatcaaaaa ggatcttcac ctagatcctt ttaaattaaa aatgaagttt    9060
taaatcaagc ccaatctgaa taatgttaca accaattaac caattctgat tagaaaaact    9120
catcgagcat caaatgaaac tgcaatttat tcatatcagg attatcaata ccatattttt    9180
gaaaaagccg tttctgtaat gaaggagaaa actcaccgag gcagttccat aggatggcaa    9240
gatcctggta tcggtctgcg attccgactc gtccaacatc aatacaacct attaatttcc    9300
cctcgtcaaa aataaggtta tcaagtgaga atcaccatg agtgacgact gaatccggtg    9360
agaatggcaa aagtttatgc atttctttcc agacttgttc aacaggccag ccattacgct    9420
cgtcatcaaa atcactcgca tcaaccaaac cgttattcat tcgtgattgc gcctgagcaa    9480
gacgaaatac gcgatcgctg ttaaaaggac aattacaaac aggaatcgaa tgcaaccggc    9540
gcaggaacac tgccagcgca tcaacaatat tttcacctga atcaggatat tcttctaata    9600
cctggaatgc tgtttttccg gggatcgcag tggtgagtaa ccatgcatca tcaggagtac    9660
ggataaaatg cttgatggtc ggaagaggca taaattccgt cagccagttt agtctgacca    9720
tctcatctgt aacatcattg gcaacgctac ctttgccatg tttcagaaac aactctggcg    9780
catcgggctt cccatacaag cgatagattg tcgcacctga ttgcccgaca ttatcgcgag    9840
cccatttata cccatataaa tcagcatcca tgttggaatt taatcgcggc ctcgacgttt    9900
cccgttgaat atggctcata acaccccttg tattactgtt tatgtaagca gacagtttta    9960
ttgttcatga tgatatattt ttatcttgtg caatgtaaca tcagagattt tgagacacgg    10020
```

-continued gccagagctg ca                                                                10032

```
<210> SEQ ID NO 61
<211> LENGTH: 10461
<212> TYPE: DNA
<213> ORGANISM: Artificial Sequence
<220> FEATURE:
<223> OTHER INFORMATION: Synthetic Construct

<400> SEQUENCE: 61
tcgcgcgttt cggtgatgac ggtgaaaacc tctgacacat gcagctcccg gatagaggtc        60
atccttcctg accatttcca tcattccagt cgaactcaca cacaacacca aatgcattta       120
agtcgcttga aattgctata agcagagcat gttgcgccag catgattaat acagcattta       180
atacagagcc gtgtttattg agtcggtatt cagagtctga ccagaaatta ttaatctggt       240
gaagttattc ctctgtcatt acgtcatggt cgatttcaat ttctattgat gctttccagt       300
cgtaatcaat gatgtatttt ttgatgtttg acctctgttc atatcctcac agataaaaaa       360
tcgccctcac actggagggc aaagaagatt tccaataatc agaacaagtc ggctcctgtt       420
tagttacgag cgacattgct ccgtgtattc actcgttgga atgaatacac agtgcagtgt       480
ttattctgtt atttatgcca aaaattaagg ccactatcag gcagctttgt tgttctgttt       540
accaagttct ctggcaatca ttgccgtcgt tcgtattgcc catttatcga catatttccc       600
atcttcctat acaggaaaca tttcttcagg cttaaccatg cattccgatt gcagcttgca       660
tccattgcat cgcttgaatt gtccacacca ttgattttta tcaatagtcg tagtttaacg       720
gatagtcctg gtattgttcc atcacatcct gaggatgccc ttcgaactct tcaaattctt       780
cttcctaata tcaccttaaa tagtggattg cggtagtaaa gattgtgcct gtcttttaac       840
cacatcaggc tcggtggttc tcgtgtaccc ctacagcgag aaatcggata aactattaca       900 accccctacag tttgtagagt atagaaaatg atccactcgt tattctcgga cgagtgttca       960
gtaatgaacc tctggagaga accatctata tgatcgttat ctgggtttga cttctgcttt      1020
taagcccaga taacttgcct gaatatgtta atgagagaat cggtattcct catgtgtggc      1080
atgttttcgt ctttgctctt gcattttcac tagcaattaa tgtgcatcga ttatcagcta      1140
ttgccagcgc cagatataag cgatttaagc taagaaaacg cattaaggtg caaaacgata      1200
aagtgcgatc agtaattcaa aaccttacag gagagcaatc tatggttttg tgctcagccc      1260
ttaatgaagg caggtagtat gtggttacat caaaacaatt cccatacatt agtgagttga      1320
ttgagcttgg tgtgttgaac aaaacttttt cccgatggaa tggaaagcat atattattcc      1380
ctattgagga tatttactgg actgaattag ttgccagcta tgatccatat aatattgaga      1440
taaagccaag gccaatatct aagtaactag ataagaggaa tcgattttcc cttaattttc      1500
tggcgtccac tgcatgttat gccgcgttcg ccaggcttgc tgtaccatgt gcgctgattc      1560
ttgcgctcaa tacgttgcag gttgctttca atctgtttgt ggtattcagc cagcactgta      1620
aggtctatcg gatttagtgc gctttctact cgtgatttcg gtttgcgatt cagcgagaga      1680
ataggtcggt taactggttt tgcgcttacc ccaaccaaca ggggatttgc tgctttccat      1740
tgagcctgtt actctgcgcg acgttcgcgg cggcgtgttt gtgcatccat ctggattctc      1800
ctgtcagtta gctttggtgg tgtgtggcag ttgtagtcct gaacgaaaac cccccgcgat      1860
tggcacgttg gcagctaatc cggaatcgca cttacggcca atgcttcgtt tcgtatcaca      1920
caccccaaag ccttctgctt tgaatgctgc ccttcttcag ggcttaattt ttaagagcgt      1980
caccttcatg gtggtcagtg cgtcctgctg atgtgctcag gcacgattta attaaggcct      2040
```

-continued

```
taattaggct gcgcgctcgc tcgctcactg aggccgcccg ggcaaagccc gggcgtcggg   2100
cgacctttgg tcgcccggcc tcagtgagcg agcgagcgcg cagagaggga gtggccaact   2160
ccatcactag gggttccttg tagttaatga ttaacccgcc atgctactta tctacgtagc   2220
catgctctag gaagatcgga attcgccctt aagctagcgg cgcgccccc gggtgcgcgg    2280 cgtcggtggt gccggcgggg ggcgccaggt cgcaggcggt gtagggctcc aggcaggcgg   2340
cgaaggccat gacgtgcgct atgaaggtct gctcctgcac gccgtgaacc aggtgcgcct   2400
gcgggccgcg cgcgaacacc gccacgtcct cgcctgcgtg ggtctcttcg tccaggggca   2460
ctgctgactg ctgccgatac tcggggctcc cgctctcgct ctcggtaaca tccggccggg   2520
cgccgtcctt gagcacatag cctggaccgt ttccttaagc gacgcatgct cgcgataggc   2580
acctattggt cttactgaca tccactttgc ctttctctcc acaggaaaac atggggcagc   2640
aggccaggat gctgcgggcc caggtgaagc ggcacacggt gcgggacaag ctgaggctgt   2700
gccagaactt cctgcagaag ctgcgcttcc tggcggacga gccccagcac agcattcccg   2760
acatcttcat ctggatgatg agcaacaaca agcgtgtcgc ctatgcccgt gtgccctcca   2820
aggacctgct cttctccatc gtggaggagg agactggcaa ggactgcgcc aaggtcaaga   2880
cgctcttcct taagctgcca gggaagcggg gcttcggctc ggcaggctgg acagtgcagg   2940
ccaaggtgga gctgtacctg tggctgggcc tcagcaaaca gcgcaaggag ttcctgtgcg   3000
gcctgccctg tggcttccag gaggtcaagg cagcccaggg cctgggcctg catgccttcc   3060
cacccgtcag cctggtctac accaagaagc aggcgttcca gctccgagcg cacatgtacc   3120
aggcccgcag cctctttgcc gccgacagca gcggactctc agaccccttt gcccgcgtct   3180
tcttcatcaa tcagagtcag tgcacagagg tgctgaatga gaccctgtgt cccacctggg   3240
accagatgct ggtgttcgac aacctggagc tctatggtga agctcatgag ctgagggacg   3300
atccgcccat cattgtcatt gaaatctatg accaggattc catgggcaaa gctgacttca   3360
tgggccggac cttcgccaaa cccctggtga agatggcaga cgaggcgtac tgcccacccc   3420 gcttccacc tcagctcgag tactaccaga tctaccgtgg caacgccaca gctggagacc    3480
tgctggcggc cttcgagctg ctgcagattg gaccagcagg gaaggctgac ctgccccca    3540 tcaatggccc ggtggacgtg gaccgaggtc ccatcatgcc cgtgcccatg ggcatccggc   3600
ccgtgctcag caagtaccga gtggaggtgc tgttctgggg cctacgggac ctaaagcggg   3660
tgaacctggc ccaggtggac cggccacggg tggacatcga gtgtgcaggg aagggggtgc   3720
agtcgtccct gatccacaat tataagaaga accccaactt caacaccctc gtcaagtggt   3780
ttgaagtgga cctcccagag aacgagctgc tgcacccgcc cttgaacatc cgtgtggtgg   3840
actgccgggc cttcggtcgc tacacactgg tgggctcca tgccgtcagc tccctgcgac    3900
gcttcatcta ccggccccca gaccgctcgg cccccagctg gaacaccacg gtcaggcttc   3960
tccggcgctg ccgtgtgctg tgcaatgggg gctcctcctc tcactccaca ggggaggttg   4020
tggtgactat ggagccagag gtacccatca agaaactgga gaccatggtg aagctggacg   4080
cgacttctga agctgttgtc aaggtggatg tggctgagga ggagaaggag aagaagaaga   4140
agaagaaggg cactgcggag gagccagagg aggaggagcc agacgagagc atgctggact   4200
ggtggtccaa gtactttgcc tccattgaca ccatgaagga gcaacttcga caacaagagc   4260
cctctggaat tgacttggag gagaaggagg aagtggacaa taccgagggc ctgaaggggt   4320
caatgaaggg caaggagaag gcaagggctg ccaaagagga gaagaagaag aaaactcaga   4380
```

-continued

```
gctctggctc tggccagggg tccgaggccc ccgagaagaa gaaacccaag attgatgagc    4440
ttaaggtata cccccaaagag ctggagtccg agtttgataa cttttgaggac tggctgcaca    4500 cttttcaactt gcttcggggc aagaccgggg atgatgagga tggctccacc gaggaggagc    4560
gcattgtggg acgcttcaag ggctccctct gcgtgtacaa agtgccactc ccagaggacg    4620
tgtcccggga agccggctac gactccacct acggcatgtt ccagggcatc ccgagcaatg    4680
accccatcaa tgtgctggtc cgagtctatg tggtccgggc cacggacctg caccctgctg    4740
acatcaacgg caaagctgac ccctacatcg ccatccggct aggcaagact gacatccgcg    4800
acaaggagaa ctacatctcc aagcagctca accctgtctt tgggaagtcc tttgacatcg    4860
aggcctcctt ccccatggaa tccatgctga cggtggctgt gtatgactgg gacctggtgg    4920
gcactgatga cctcattggg gaaaccaaga tcgacctgga gaaccgcttc tacagcaagc    4980
accgcgccac ctgcggcatc gcccagacct actccacaca tggctacaat atctggcggg    5040
accccatgaa gcccagccag atcctgaccc gcctctgcaa agacggcaaa gtggacggcc    5100
cccactttgg gcccctggg agagtgaagg tggccaaccg cgtcttcact gggccctctg    5160
agattgagga cgagaacggt cagaggaagc ccacagacga gcatgtggcg ctgttggccc    5220
tgaggcactg ggaggacatc ccccgcgcag gctgccgcct ggtgccagag catgtggaga    5280
cgaggccgct gctcaacccc gacaagccgg gcatcgagca gggccgcctg gagctgtggg    5340
tggacatgtt ccccatggac atgccagccc ctggacgcc tctggacatc tcacctcgga    5400
agcccaagaa gtacgagctg cgggtcatca tctggaacac agatgaggtg gtcttggagg    5460
acgacgactt cttcacaggg gagaagtcca gtgacatctt cgtgagggggg tggctgaagg    5520 gccagcagga ggacaagcag gacacagacg tccactacca ctccctcact ggcgagggca    5580
acttcaactg gcgctacctg ttccccttcg actacctggc ggcggaggag aagatcgtca    5640
tctccaagaa ggagtccatg ttctcctggg acgagaccga gtacaagatc cccgcgcggc    5700
tcaccctgca gatctgggat gcggaccact ctccgctga cgacttcctg gggggccatcg    5760 agctggacct gaaccggttc ccgcgggggcg caaagacagc caagcagtgc accatggaga    5820
tggccaccgg ggaggtggac gtgccccctcg tgtccatctt caagcaaaag cgcgtcaaag    5880
gctggtggcc cctcctggcc cgcaatgaga acgatgagtt tgagctcacg ggcaaggtgg    5940
aggctgagct gcatttactg acagcagagg aggcagagaa gaacccagtg ggcctggccc    6000
gcaatgaacc tgacccccta gagaaaccca accggcccga cacggccttc gtctggttcc    6060
tcaaccctct caagtccatc aagtacctca tctgcacccg gtacaagtgg ctcatcatca    6120
agatcgtgct ggcgctgttg gggctgctca tgttggggct cttcctctac agcctccctg    6180
gctacatggt caaaaagctc cttgggggcat gaacggccgc tatgctagct tggtaccaag    6240
ggcggatcct gcatagagct cgctgatcag cctcgactgt gccttctagt tgccagccat    6300
ctgttgtttg cccctcccccc gtgccttcct tgacccctgga aggtgccact cccactgtcc    6360
tttcctaata aaatgaggaa attgcatcgc attgtctgag taggtgtcat tctattctgg    6420
ggggtggggt ggggcaggac agcaagggggg aggattggga agacaatagc aggcatctcg    6480
agttaagggc gaattcccga taaggatctt cctagagcat ggctacgtag ataagtagca    6540
tggcgggtta atcattaact acaaggaacc cctagtgatg gagttggcca ctccctctct    6600
gcgcgctcgc tcgctcactg aggccgggcg accaaaggtc gcccgacgcc cgggctttgc    6660
ccgggcggcc tcagtgagcg agcgagcgcg cagccttaat taaatccaca tctgtatgtt    6720
ttttatatta atttatttttt tgcagggggg cattgtttgg taggtgagag ttctgaattg    6780
```

```
ctatgtttag tgagttgtat ctatttattt ttcaataaat acaattagtt atgtgttttg   6840
ggggcgatcg tgaggcaaag aaaacccggc gctgaggccg ggttattctt gttctctggt   6900
caaattatat agttggaaaa caaggatgca tatatgaatg aacgatgcag aggcaatgcc   6960
gatggcgata gtgggtatca ggtagccgct tatgctggaa agaagcaata acccgcagaa   7020
aaacaaagct ccaagctcaa caaaactaag ggcatagaca ataactacct atgtcatata   7080
cccatactct ctaatcttgg ccagtcggcg cgttctgctt ccgattagaa acgtcaaggc   7140
agcaatcagg attgcaatct tggttcctgc ataggatgac aatgtcgccc caagaccatc   7200
tctatgagct gaaaaagaaa cacaaggaat gtagtggcgg aaaaggagat agcaaatgct   7260
tacgataacg taaggaatta ttactatgta aacaccaggc aagattctgt tccgtataat   7320
tactcctgat aattaatcct taactttgcc cacctgcctt ttaaaacatt ccagtatatc   7380
acttttcatt cttgcgtagc aatatgccct ctcttcagct atctcagcat tggtgacctt   7440
gttcagaggc gctgagagat ggcctttttc tgatagataa tgttctgtta aaatatctcc   7500
ggcctcatct tttgcccgca ggctaatgtc tgaaaattga ggtgacgggt taaaaataat   7560
atccttggca accttttttta tatccctttt aaatttggc ttaatgacta tatccaatga   7620
gtcaaaaagc tccccttcaa tatctgttgc ccctaagacc tttaatatat cgccaaatac   7680
aggtagcttg gcttctacct tcaccgttgt tctgccgatg aaatgctaat gcataacatc   7740
gtctttggtg gttcccctca tcagtggctc tatctgaacg cgctctccac tgcttaatga   7800
cattcctttc ccgattaaaa aatctgtcag atcggatgtg gtcggcccga aaacagttct   7860
ggcaaaacca atggtgtcgc cttcaacaaa caaaaaagat gggaatccca atgattcgtc   7920
atctgcgagg ctgttcttaa tatcttcaac tgtagcttta gagcgattta tcttctgaac   7980
cagactcttg tcatttgttt tggtaaagag aaaagttttt ccatcgattt tatgaatata   8040
caaataattg gagccaacct tcaggtgatg attatcagcc agcagagaat taaggaaaac   8100
agacaggttt attgagcact tatctttccc tttatttttg ctgcggtaag tcgcataaaa   8160
accattcttc acaattcaat ccatttacta tgttatgttc tgaggggagt gaaaattccc   8220
ctaattcgat gaagattctt gctaaattgt tatcagctat gcgccgacca gaacaccttg   8280
ccgatcagcc aaacgtctaa tcaggccact gactagcgat aactttcccc acaacggaac   8340
aactctcatt gcatgggata attgggtact gtgggtttag tggttgtaaa aacacctgac   8400
cgctatccct gatcagtttc ttgaaggtaa actcatcacc cccaagtctg gctatacaga   8460
aatcacctgg ctcaacagcc tgctcagggt caacgagaat ttacattccg tcaggatagc   8520
ttggcttgga gcctgttggt gcggtcacgg aattaccttc aacctcaagc cagaatgcag   8580
aatcactggc ttttttggtt gtgcttaccc atctctccgc atcacctttg gtaaaggttc   8640
taagctaagg tgagaacatc cctgcctgaa catgagaaaa aacagggtac tcatactcac   8700
ttattagtga cggctatgag caaaaggcca gcaaaaggcc aggaaccgta aaaaggccgc   8760
gttgctggcg ttttttccata ggctccgccc ccctgacgag catcacaaaa atcgacgctc   8820
aagtcagagg tggcgaaacc cgacaggact ataaagatac caggcgtttc ccctggaag   8880 ctccctcgtg cgctctcctg ttccgaccct gccgcttacc ggatacctgt ccgcctttct   8940
cccttcggga agcgtggcgc tttctcatag ctcacgctgt aggtatctca gttcggtgta   9000
ggtcgttcgc tccaagctgg gctgtgtgca cgaacccccc gttcagcccg accgctgcgc   9060
cttatccggt aactatcgtc ttgagtccaa cccggtaaga cacgacttat cgccactggc   9120
```

```
agcagccact ggtaacagga ttagcagagc gaggtatgta ggcggtgcta cagagttctt      9180
gaagtggtgg cctaactacg gctacactag aagaacagta tttggtatct gcgctctgct      9240
gaagccagtt accttcggaa aaagagttgg tagctcttga tccggcaaac aaaccaccgc      9300
tggtagcggt ggtttttttg tttgcaagca gcagattacg cgcagaaaaa aaggatctca      9360
agaagatcct ttgatctttt ctacggggtc tgacgctcag tggaacgaaa actcacgtta      9420
agggattttg gtcatgagat tatcaaaaag gatcttcacc tagatccttt taaattaaaa      9480
atgaagtttt aaatcaagcc caatctgaat aatgttacaa ccaattaacc aattctgatt      9540
agaaaaactc atcgagcatc aaatgaaact gcaatttatt catatcagga ttatcaatac      9600
catatttttg aaaaagccgt ttctgtaatg aaggagaaaa ctcaccgagg cagttccata      9660
ggatggcaag atcctggtat cggtctgcga ttccgactcg tccaacatca atacaaccta      9720
ttaatttccc ctcgtcaaaa ataaggttat caagtgagaa atcaccatga gtgacgactg      9780
aatccggtga gaatggcaaa agtttatgca tttctttcca gacttgttca acaggccagc      9840
cattacgctc gtcatcaaaa tcactcgcat caaccaaacc gttattcatt cgtgattgcg      9900
cctgagcaag acgaaatacg cgatcgctgt taaaaggaca attacaaaca ggaatcgaat      9960
gcaaccggcg caggaacact gccagcgcat caacaatatt ttcacctgaa tcaggatatt     10020
cttctaatac ctggaatgct gttttccgg ggatcgcagt ggtgagtaac catgcatcat     10080
caggagtacg gataaaatgc ttgatggtcg gaagaggcat aaattccgtc agccagttta     10140
gtctgaccat ctcatctgta acatcattgg caacgctacc tttgccatgt ttcagaaaca     10200
actctggcgc atcgggcttc ccatacaagc gatagattgt cgcacctgat tgcccgacat     10260
tatcgcgagc ccatttatac ccatataaat cagcatccat gttggaattt aatcgcggcc     10320
tcgacgtttc ccgttgaata tggctcataa caccccttgt attactgttt atgtaagcag     10380
acagttttat tgttcatgat gatatatttt tatcttgtgc aatgtaacat cagagatttt     10440
gagacacggg ccagagctgc a                                                10461
```

```
<210> SEQ ID NO 62
<211> LENGTH: 6678
<212> TYPE: DNA
<213> ORGANISM: Artificial Sequence
<220> FEATURE:
<223> OTHER INFORMATION: Synthetic Construct

<400> SEQUENCE: 62
gggggggggg gggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actaggggtt cctcagatct gaattcggta       180
cctgcagctc agcctactac ttgctttcca ggctgttcct agttcccatg tcagctgctt       240
gtgctttcca gagacaaaac aggaataata gatgtcatta aatatacatt gggccccagg       300
cggtcaatgt ggcagcctga gcctcctttc catctctgtg gaggcagaca taggaccccc       360
aacaaacagc atgcaggttg ggagccagcc acaggaccca ggtaagggc cctgggtcct       420 taagcttctg ccactggctc cggcattgca gagagaagag aagggcggc agactggaga       480 gctgggctcc attttttgttc cttggtgccc tgcccctccc catgacctgc agagacattc       540
agcctgccag gctttatgag gtgggagctg ggctctccct gatgtattat tcagctccct       600
ggagttggcc agctcctgtt acactggcca cagccctggg catccgcttc tcacttctag       660
tttcccctcc aaggtaatgt ggtgggtcat gatcattcta tcctggcttc agggacctga       720
```

-continued

```
ctccactttg gggccattcg aggggtctag ggtagatgat gtccccctgt ggggattaat       780
gtcctgctct gtaaaactga gctagctgag atccaggagg gcttggccag agacagcaag       840
ttgttgccat ggtgacttta aagccaggtt gctgccccag cacaggcctc ccagtctacc       900
ctcactagaa aacaacaccc aggcactttc caccacctct caaaggtgaa acccaaggct       960
ggtctagaga atgaattatg gatcctcgct gtccgtgcca cccagctagt cccagcggct      1020
cagacactga ggagagactg taggttcagc tacaagcaaa aagacctagc tggtctccaa      1080
gcagtgtctc caagtccctg aacctgtgac acctgcccca ggcatcatca ggcacagagg      1140
gccaccgaat tctagcggcc gccaccatgg ccttgctcat ccacctcaag acagtctcgg      1200
agctgcgggg cagggggcgac cggatcgcca aagtgacttt ccgagggcaa tccttctact      1260
ctcgggtcct ggagaactgt gaggatgtgg ctgactttga tgagacattt cggtggccgg      1320
tggccagcag catcgacaga aatgagatgc tggagattca ggttttcaac tacagcaaag      1380
tcttcagcaa caagctcatc gggaccttcc gcatggtgct gcagaaggtg gtagaggaga      1440
gccatgtgga ggtgactgac acgctgattg atgacaacaa tgctatcatc aagaccagcc      1500
tgtgcgtgga ggtccggtat caggccactg acggcacagt gggctcctgg gacgatgggg      1560
acttcctggg agatgagtct cttcaagagg aagagaagga cagccaagag acggatggac      1620
tgctcccagg ctcccggccc agctcccggc ccccaggaga gaagagcttc cggagagccg      1680
ggaggagcgt gttctccgcc atgaagctcg gcaaaaaccg gtctcacaag gaggagcccc      1740
aaagaccaga tgaaccggcg gtgctggaga tggaagacct tgaccatctg gccattcggc      1800
taggagatgg actggatccc gactcggtgt ctctagcctc agtcacagct ctcaccacta      1860
atgtctccaa caagcgatct aagccagaca ttaagatgga gccaagtgct gggcggccca      1920
tggattacca ggtcagcatc acggtgatcg aggcccggca gctggtgggc ttgaacatgg      1980
accctgtggt gtgcgtggag gtgggtgacg acaagaagta cacatccatg aaggagtcca      2040
ctaactgccc ctattacaac gagtacttcg tcttcgactt ccatgtctct ccggatgtca      2100
tgtttgacaa gatcatcaag atttcggtga ttcactccaa gaacctgctg cgcagtggca      2160
ccctggtggg ctccttcaaa atggacgtgg gaaccgtgta ctcgcagcca gagcaccagt      2220
tccatcacaa gtgggccatc ctgtctgacc ccgatgacat ctcctcgggg ctgaagggct      2280
acgtgaagtg tgacgttgcc gtggtgggca aggggacaa catcaagacg ccccacaagg      2340
ccaatgagac cgacgaagat gacattgagg ggaacttgct gctccccgag ggggtgcccc      2400
ccgaacgcca gtgggcccgg ttctatgtga aaatttaccg agcagagggg ctgccccgta      2460
tgaacacaag cctcatggcc aatgtaaaga aggctttcat cggtgaaaac aaggacctcg      2520 tggacccccta cgtgcaagtc ttctttgctg gccagaaggg caagacttca gtgcagaaga      2580
gcagctatga gcccctgtgg aatgagcagg tcgtctttac agacctcttc cccccactct      2640
gcaaacgcat gaaggtgcag atccgagact cggacaaggt caacgacgtg gccatcggca      2700
cccacttcat tgacctgcgc aagatttcta atgacggaga caaaggcttc ctgcccacac      2760
tgggcccagc ctgggtgaac atgtacggct ccacacgtaa ctacgctg ctggatgagc      2820 atcaggacct gaacgagggc ctggggggagg gtgtgtcctt ccgggcccgg ctcctgctgg      2880
gcctggctgt ggagatcgta gacacctcca accctgagct caccagctcc acagaggtgc      2940
aggtggagca ggccacgccc atctcggaga gctgtgcagg taaaatggaa gaattctttc      3000
tctttggagc cttcctggag gcctcaatga tcgaccggag aaacggagac aagcccatca      3060
```

-continued

```
cctttgaggt caccataggc aactatggga acgaagttga tggcctgtcc cggccccagc    3120
ggcctcggcc ccggaaggag ccgggggatg aggaagaagt agacctgatt cagaacgcaa    3180
gtgatgacga ggccggtgat gccggggacc tggcctcagt ctcctccact ccaccaatgc    3240
ggccccaggt caccgacagg aactacttcc atctgcccta cctggagcga aagccctgca    3300
tctacatcaa gagctggtgg ccggaccagc gccgccgcct ctacaatgcc aacatcatgg    3360
accacattgc cgacaagctg gaagaaggcc tgaacgacat acaggagatg atcaaaacgg    3420
agaagtccta ccctgagcgt cgcctgcggg gcgtcctgga ggagctgagc tgtggctgct    3480
gccgcttcct ctccctcgct gacaaggacc agggccactc atcccgcacc aggcttgacc    3540
gggagcgcct caagtcctgc atgagggagc tggtaagtat caaggttaca agacaggttt    3600
aaggagacca atagaaactg ggcttgtcga gacagagaag actcttgcgt ttctgagcta    3660
gcccccgggt gcgcggcgtc ggtggtgccg gcgggggggcg ccaggtcgca ggcggtgtag    3720
ggctccaggc aggcggcgaa ggccatgacg tgcgctatga aggtctgctc ctgcacgccg    3780
tgaaccaggt gcgcctgcgg gccgcgcgcg aacaccgcca cgtcctcgcc tgcgtgggtc    3840
tcttcgtcca ggggcactgc tgactgctgc cgatactcgg ggctcccgct ctcgctctcg    3900
gtaacatccg gccgggcgcc gtccttgagc acatagcctg gaccgtttcg tcgactgggg    3960
agagatctga ggaacccta gtgatggagt tggccactcc ctctctgcgc gctcgctcgc    4020
tcactgaggc cgcccgggca aagcccgggc gtcgggcgac ctttggtcgc ccggcctcag    4080
tgagcgagcg agcgcgcaga gagggagtgg ccaacccccc cccccccccc cctgcagcct    4140
ggcgtaatag cgaagaggcc cgcaccgatc gcccttccca acagttgcgt agcctgaatg    4200
gcgaatggcg cgacgcgccc tgtagcggcg cattaagcgc ggcgggtgtg gtggttacgc    4260
gcagcgtgac cgctacactt gccagcgccc tagcgcccgc tcctttcgct ttcttccctt    4320
cctttctcgc cacgttcgcc ggctttcccc gtcaagctct aaatcggggg ctcccttag    4380 ggttccgatt tagtgcttta cggcacctcg accccaaaaa acttgattag ggtgatggtt    4440
cacgtagtgg gccatcgccc tgatagacgg tttttcgccc tttgacgttg gagtccacgt    4500
tctttaatag tggactcttg ttccaaactg gaacaacact caaccctatc gcggtctatt    4560
cttttgattt ataagggatg ttgccgattt cggcctattg gttaaaaaat gagctgattt    4620
aacaaaaatt ttaacaaaat tcagaagaac tcgtcaagaa ggcgatagaa ggcgatgcgc    4680
tgcgaatcgg gagcggcgat accgtaaagc acgaggaagc ggtcagccca ttcgccgcca    4740
agctcttcag caatatcacg ggtagccaac gctatgtcct gatagcggtc cgccacaccc    4800
agccggccac agtcgatgaa tccagaaaag cggccatttt ccaccatgat attcggcaag    4860
caggcatcgc catgggtcac gacgagatcc tcgccgtcgg gcatgctcgc cttgagcctg    4920
gcgaacagtt cggctggcgc gagcccctga tgctcttcgt ccagatcatc ctgatcgaca    4980
agaccggctt ccatccgagt acgtgctcgc tcgatgcgat gtttcgcttg gtggtcgaat    5040
gggcaggtag ccggatcaag cgtatgcagc cgccgcattg catcagccat gatggatact    5100
ttctcggcag gagcaaggtg agatgacagg agatcctgcc ccggcacttc gcccaatagc    5160
agccagtccc ttcccgcttc agtgacaacg tcgagcacag ctgcgcaagg aacgcccgtc    5220
gtggccagcc acgatagccg cgctgcctcg tcttgcagtt cattcagggc accggacagg    5280
tcggtcttga caaaaagaac cgggcgcccc tgcgctgaca gccggaacac ggcggcatca    5340
gagcagccga ttgtctgttg tgcccagtca tagccgaata gcctctccac ccaagcggcc    5400
ggagaacctg cgtgcaatcc atcttgttca atcatgcgaa acgatcctca tcctgtctct    5460
```

-continued

```
tgatcagatc ttgatcccct gcgccatcag atccttggcg gcgagaaagc catccagttt      5520
actttgcagg gcttcccaac cttaccagag ggcgccccag ctggcaattc cggttcgctt      5580
gctgtccata aaaccgccca gtctagctat cgccatgtaa gcccactgca agctacctgc      5640
tttctctttg cgcttgcgtt ttcccttgtc cagatagccc agtagctgac attcatccgg      5700
ggtcagcacc gtttctgcgg actggctttc tacgtgaaaa ggatctaggt gaagatcctt      5760
tttgataatc tcatgaccaa aatcccttaa cgtgagtttt cgttccactg agcgtcagac      5820
cccgtagaaa agatcaaagg atcttcttga gatcctttt ttctgcgcgt aatctgctgc       5880
ttgcaaacaa aaaaccacc gctaccagcg gtggtttgtt tgccggatca agagctacca       5940 actcttttc cgaaggtaac tggcttcagc agagcgcaga taccaaatac tgtccttcta       6000
gtgtagccgt agttaggcca ccacttcaag aactctgtag caccgcctac atacctcgct      6060
ctgctaatcc tgttaccagt ggctgctgcc agtggcgata agtcgtgtct taccgggttg      6120
gactcaagac gatagttacc ggataaggcg cagcggtcgg gctgaacggg gggttcgtgc      6180
acacagccca gcttggagcg aacgacctac accgaactga gatacctaca gcgtgagcta      6240
tgagaaagcg ccacgcttcc cgaagggaga aaggcggaca ggtatccggt aagcggcagg      6300
gtcggaacag gagagcgcac gagggagctt ccaggggaa acgcctggta tctttatagt       6360
cctgtcgggt ttcgccacct ctgacttgag cgtcgatttt tgtgatgctc gtcaggggg       6420 cggagcctat ggaaaaacgc cagcaacgcg gcctttttac ggttcctggg cttttgctgg      6480
ccttttgctc acatgttctt tcctgcgtta tcccctgatt ctgtggataa ccgtattacc      6540
gcctttgagt gagctgatac cgctcgccgc agccgaacga ccgagcgcag cgagtcagtg      6600
agcgaggaag cggaagagcg cccaatacgc aaaccgcctc tccccgcgcg ttggccgatt      6660
cattaatgca gggctgca                                                    6678
```

```
<210> SEQ ID NO 63
<211> LENGTH: 7152
<212> TYPE: DNA
<213> ORGANISM: Artificial Sequence
<220> FEATURE:
<223> OTHER INFORMATION: Synthetic Construct

<400> SEQUENCE: 63
gggggggggg gggggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actagggggtt cctcagatct gaattctagc      180
ggccgccccc gggtgcgcgg cgtcggtggt gccggcgggg ggcgccaggt cgcaggcggt       240
gtagggctcc aggcaggcgg cgaaggccat gacgtgcgct atgaaggtct gctcctgcac       300
gccgtgaacc aggtgcgcct gcgggccgcg cgcgaacacc gccacgtcct cgcctgcgtg       360
ggtctcttcg tccaggggca ctgctgactg ctgccgatac tcgggctcc cgctctcgct        420 ctcggtaaca tccggccggg cgccgtcctt gagcacatag cctggaccgt ttccttaagc      480
gacgcatgct cgcgataggc acctattggt cttactgaca tccactttgc ctttctctcc      540
acaggaaaac atggggcagc aggccaggat gctgcgggcc caggtgaagc ggcacacggt       600
gcgggacaag ctgaggctgt gccagaactt cctgcagaag ctgcgcttcc tggcggacga      660
gccccagcac agcattcccg acatcttcat ctggatgatg agcaacaaca agcgtgtcgc       720
ctatgcccgt gtgccctcca aggacctgct cttctccatc gtggaggagg agactggcaa      780
```

-continued

```
ggactgcgcc aaggtcaaga cgctcttcct taagctgcca gggaagcggg gcttcggctc      840
ggcaggctgg acagtgcagg ccaaggtgga gctgtacctg tggctgggcc tcagcaaaca      900
gcgcaaggag ttcctgtgcg gcctgccctg tggcttccag gaggtcaagg cagcccaggg      960
cctgggcctg catgccttcc cacccgtcag cctggtctac accaagaagc aggcgttcca     1020
gctccgagcg cacatgtacc aggcccgcag cctctttgcc gccgacagca gcggactctc     1080 agacccettt gcccgcgtct tcttcatcaa tcagagtcag tgcacagagg tgctgaatga     1140
gaccctgtgt cccacctggg accagatgct ggtgttcgac aacctggagc tctatggtga     1200
agctcatgag ctgagggacg atccgcccat cattgtcatt gaaatctatg accaggattc     1260
catgggcaaa gctgacttca tgggccggac cttcgccaaa cccctggtga agatggcaga     1320
cgaggcgtac tgcccacccc gcttcccacc tcagctcgag tactaccaga tctaccgtgg     1380
caacgccaca gctggagacc tgctggcggc cttcgagctg ctgcagattg gaccagcagg     1440
gaaggctgac ctgcccccca tcaatggccc ggtggacgtg gaccgaggtc ccatcatgcc     1500
cgtgcccatg ggcatccggc ccgtgctcag caagtaccga gtggaggtgc tgttctgggg     1560
cctacgggac ctaaagcggg tgaacctggc ccaggtggac cggccacggg tggacatcga     1620
gtgtgcaggg aaggggtgc agtcgtccct gatccacaat tataagaaga accccaactt      1680
caacaccctc gtcaagtggt ttgaagtgga cctcccagag aacgagctgc tgcacccgcc     1740
cttgaacatc cgtgtggtgg actgccgggc cttcggtcgc tacacactgg tgggctccca     1800
tgccgtcagc tccctgcgac gcttcatcta ccggccccca gaccgctcgg ccccagctg      1860 gaacaccacg gtcaggcttc tccggcgctg ccgtgtgctg tgcaatgggg gctcctcctc     1920
tcactccaca ggggaggttg tggtgactat ggagccagag gtacccatca agaaactgga     1980
gaccatggtg aagctggacg cgacttctga agctgttgtc aaggtggatg tggctgagga     2040
ggagaaggag aagaagaaga agaagaaggg cactgcggag gagccagagg aggaggagcc     2100
agacgagagc atgctggact ggtggtccaa gtactttgcc tccattgaca ccatgaagga     2160
gcaacttcga caacaagagc cctctggaat tgacttggag gagaaggagg aagtggacaa     2220
taccgagggc ctgaagggg tcaatgaggg caaggagaag gcaagggctg ccaaagagga     2280
gaagaagaag aaaactcaga gctctggctc tggccagggg tccgaggccc ccgagaagaa     2340
gaaacccaag attgatgagc ttaaggtata ccccaaagag ctggagtccg agtttgataa     2400
ctttgaggac tggctgcaca ctttcaactt gcttcggggc aagaccgggg atgatgagga     2460
tggctccacc gaggaggagc gcattgtggg acgcttcaag ggctccctct gcgtgtacaa     2520
agtgccactc ccagaggacg tgtcccggga agccggctac gactccacct acggcatgtt     2580
ccagggcatc ccgagcaatg accccatcaa tgtgctggtc cgagtctatg tggtccgggc     2640
cacggacctg caccctgctg acatcaacgg caaagctgac ccctacatcg ccatccggct     2700
aggcaagact gacatccgcg acaaggagaa ctacatctcc aagcagctca accctgtctt     2760
tgggaagtcc tttgacatcg aggcctcctt ccccatggaa tccatgctga cggtggctgt     2820
gtatgactgg gacctggtgg gcactgatga cctcattggg gaaaccaaga tcgacctgga     2880
gaaccgcttc tacagcaagc accgcgccac ctgcggcatc gcccagacct actccacaca     2940
tggctacaat atctggcggg accccatgaa gcccagccag atcctgaccc gcctctgcaa     3000
agacggcaaa gtggacggcc cccactttgg gccccctggg agagtgaagg tggccaaccg     3060
cgtcttcact gggccctctg agattgagga cgagaacggt cagaggaagc ccacagacga     3120
gcatgtggcg ctgttggccc tgaggcactg ggaggacatc ccccgcgcag gctgccgcct     3180
```

-continued

```
ggtgccagag catgtggaga cgaggccgct gctcaacccc gacaagccgg gcatcgagca    3240
gggccgcctg gagctgtggg tggacatgtt ccccatggac atgccagccc ctgggacgcc    3300
tctggacatc tcacctcgga agcccaagaa gtacgagctg cgggtcatca tctggaacac    3360
agatgaggtg gtcttggagg acgacgactt cttcacaggg gagaagtcca gtgacatctt    3420
cgtgaggggg tggctgaagg gccagcagga ggacaagcag gacacagacg tccactacca    3480
ctccctcact ggcgagggca acttcaactg gcgctacctg ttccccttcg actacctggc    3540
ggcggaggag aagatcgtca tctccaagaa ggagtccatg ttctcctggg acgagaccga    3600
gtacaagatc cccgcgcggc tcaccctgca gatctgggat gcggaccact tctccgctga    3660
cgacttcctg ggggccatcg agctggacct gaaccggttc ccgcggggcg caaagacagc    3720
caagcagtgc accatggaga tggccaccgg ggaggtggac gtgcccctcg tgtccatctt    3780
caagcaaaag cgcgtcaaag ctggtggcc cctcctggcc cgcaatgaga acgatgagtt    3840
tgagctcacg ggcaaggtgg aggctgagct gcatttactg acagcagagg aggcagagaa    3900
gaacccagtg ggcctggccc gcaatgaacc tgaccccta gagaaaccca accggcccga    3960
cacggccttc gtctggttcc tcaaccctct caagtccatc aagtacctca tctgcacccg    4020
gtacaagtgg ctcatcatca agatcgtgct ggcgctgttg gggctgctca tgttggggct    4080
cttcctctac agcctccctg gctacatggt caaaaagctc cttggggcat gaacggccgc    4140
tatgctagct tggtaccaag ggcggatcct gcatagagct cgctgatcag cctcgactgt    4200
gccttctagt tgccagccat ctgttgtttg cccctcccc gtgccttcct tgaccctgga    4260
aggtgccact cccactgtcc tttcctaata aaatgaggaa attgcatcgc attgtctgag    4320
taggtgtcat tctattctgg ggggtggggt ggggcaggac agcaagggg aggattggga    4380 agacaatagc aggcatgctg gggagagatc tgaggactag tccgtcgact ggggagagat    4440
ctgaggaacc cctagtgatg gagttggcca ctccctctct gcgcgctcgc tcgctcactg    4500
aggccgcccg ggcaaagccc gggcgtcggg cgacctttgg tcgcccggcc tcagtgagcg    4560
agcgagcgcg cagagaggga gtggccaacc cccccccccc cccccctgca gcctggcgta    4620
atagcgaaga ggcccgcacc gatcgccctt cccaacagtt gcgtagcctg aatggcgaat    4680
ggcgcgacgc gccctgtagc ggcgcattaa gcgcggcggg tgtggtggtt acgcgcagcg    4740
tgaccgctac acttgccagc gccctagcgc ccgctccttt cgctttcttc ccttcctttc    4800
tcgccacgtt cgccggcttt ccccgtcaag ctctaaatcg ggggctccct ttagggttcc    4860
gatttagtgc tttacggcac ctcgacccca aaaaacttga ttagggtgat ggttcacgta    4920
gtgggccatc gccctgatag acggtttttc gccctttgac gttggagtcc acgttcttta    4980
atagtggact cttgttccaa actggaacaa cactcaaccc tatcgcggtc tattcttttg    5040
atttataagg gatgttgccg atttcggcct attggttaaa aaatgagctg atttaacaaa    5100 aatttttaaca aaattcagaa gaactcgtca agaaggcgat agaaggcgat gcgctgcgaa    5160
tcgggagcgg cgataccgta aagcacgagg aagcggtcag cccattcgcc gccaagctct    5220
tcagcaatat cacgggtagc caacgctatg tcctgatagc ggtccgccac acccagccgg    5280
ccacagtcga tgaatccaga aaagcggcca ttttccacca tgatattcgg caagcaggca    5340
tcgccatggg tcacgacgag atcctcgccg tcgggcatgc tcgccttgag cctggcgaac    5400
agttcggctg cgcgcgagccc ctgatgctct tcgtccagat catcctgatc gacaagaccg    5460
gcttccatcc gagtacgtgc tcgctcgatg cgatgtttcg cttggtggtc gaatgggcag    5520
```

-continued

```
gtagccggat caagcgtatg cagccgccgc attgcatcag ccatgatgga tactttctcg    5580
gcaggagcaa ggtgagatga caggagatcc tgccccggca cttcgcccaa tagcagccag    5640
tcccttcccg cttcagtgac aacgtcgagc acagctgcgc aaggaacgcc cgtcgtggcc    5700
agccacgata gccgcgctgc ctcgtcttgc agttcattca gggcaccgga caggtcggtc    5760
ttgacaaaaa gaaccgggcg cccctgcgct gacagccgga acacggcggc atcagagcag    5820
ccgattgtct gttgtgccca gtcatagccg aatagcctct ccacccaagc ggccggagaa    5880
cctgcgtgca atccatcttg ttcaatcatg cgaaacgatc ctcatcctgt ctcttgatca    5940
gatcttgatc ccctgcgcca tcagatcctt ggcggcgaga aagccatcca gtttactttg    6000
cagggcttcc caaccttacc agagggcgcc ccagctggca attccggttc gcttgctgtc    6060
cataaaaccg cccagtctag ctatcgccat gtaagcccac tgcaagctac ctgctttctc    6120
tttgcgcttg cgttttccct tgtccagata gcccagtagc tgacattcat ccggggtcag    6180
caccgtttct gcggactggc tttctacgtg aaaaggatct aggtgaagat cctttttgat    6240
aatctcatga ccaaaatccc ttaacgtgag ttttcgttcc actgagcgtc agaccccgta    6300
gaaaagatca aaggatcttc ttgagatcct ttttttctgc gcgtaatctg ctgcttgcaa    6360
acaaaaaaac caccgctacc agcggtggtt tgtttgccgg atcaagagct accaactctt    6420
tttccgaagg taactggctt cagcagagcg cagataccaa atactgtcct tctagtgtag    6480
ccgtagttag gccaccactt caagaactct gtagcaccgc ctacatacct cgctctgcta    6540
atcctgttac cagtggctgc tgccagtggc gataagtcgt gtcttaccgg gttggactca    6600
agacgatagt taccggataa ggcgcagcgg tcgggctgaa cggggggttc gtgcacacag    6660
cccagcttgg agcgaacgac ctacaccgaa ctgagatacc tacagcgtga gctatgagaa    6720
agcgccacgc ttcccgaagg gagaaaggcg gacaggtatc cggtaagcgg cagggtcgga    6780
acaggagagc gcacgaggga gcttccaggg ggaaacgcct ggtatcttta gtgtcctgtc    6840
gggtttcgcc acctctgact tgagcgtcga ttttgtgat gctcgtcagg ggggcggagc    6900
ctatggaaaa acgccagcaa cgcggccttt ttacggttcc tgggcttttg ctggcctttt    6960
gctcacatgt tctttcctgc gttatcccct gattctgtgg ataaccgtat taccgccttt    7020
gagtgagctg ataccgctcg ccgcagccga acgaccgagc gcagcgagtc agtgagcgag    7080
gaagcggaag agcgcccaat acgcaaaccg cctctccccg cgcgttggcc gattcattaa    7140
tgcagggctg ca                                                       7152

<210> SEQ ID NO 64
<211> LENGTH: 10005
<212> TYPE: DNA
<213> ORGANISM: Artificial Sequence
<220> FEATURE:
<223> OTHER INFORMATION: Synthetic Construct

<400> SEQUENCE: 64
tcgcgcgttt cggtgatgac ggtgaaaacc tctgacacat gcagctcccg gatagaggtc      60
atccttcctg accatttcca tcattccagt cgaactcaca cacaacacca aatgcattta     120
agtcgcttga aattgctata agcagagcat gttgcgccag catgattaat acagcattta     180
atacagagcc gtgtttattg agtcggtatt cagagtctga ccagaaatta ttaatctggt     240
gaagttattc ctctgtcatt acgtcatggt cgatttcaat ttctattgat gctttccagt     300
cgtaatcaat gatgtatttt ttgatgtttg acctctgttc atatcctcac agataaaaaa     360
tcgccctcac actggagggc aaagaagatt ccaataatc agaacaagtc ggctcctgtt     420
```

```
tagttacgag cgacattgct ccgtgtattc actcgttgga atgaatacac agtgcagtgt      480
ttattctgtt atttatgcca aaaattaagg ccactatcag gcagctttgt tgttctgttt      540
accaagttct ctggcaatca ttgccgtcgt tcgtattgcc catttatcga catatttccc      600
atcttcctat acaggaaaca tttcttcagg cttaaccatg cattccgatt gcagcttgca      660
tccattgcat cgcttgaatt gtccacacca ttgattttta tcaatagtcg tagtttaacg      720
gatagtcctg gtattgttcc atcacatcct gaggatgccc ttcgaactct tcaaattctt      780
cttcctaata tcaccttaaa tagtggattg cggtagtaaa gattgtgcct gtcttttaac      840
cacatcaggc tcggtggttc tcgtgtaccc ctacagcgag aaatcggata aactattaca      900
acccctacag tttgtagagt atagaaaatg atccactcgt tattctcgga cgagtgttca      960
gtaatgaacc tctggagaga accatctata tgatcgttat ctgggtttga cttctgcttt     1020
taagcccaga taacttgcct gaatatgtta atgagagaat cggtattcct catgtgtggc     1080
atgttttcgt ctttgctctt gcattttcac tagcaattaa tgtgcatcga ttatcagcta     1140
ttgccagcgc cagatataag cgatttaagc taagaaaacg cattaaggtg caaaacgata     1200
aagtgcgatc agtaattcaa aaccttacag gagagcaatc tatggttttg tgctcagccc     1260
ttaatgaagg caggtagtat gtggttacat caaaacaatt cccatacatt agtgagttga     1320
ttgagcttgg tgtgttgaac aaaacttttt cccgatggaa tggaaagcat atattattcc     1380
ctattgagga tatttactgg actgaattag ttgccagcta tgatccatat aatattgaga     1440
taaagccaag gccaatatct aagtaactag ataagaggaa tcgattttcc cttaattttc     1500
tggcgtccac tgcatgttat gccgcgttcg ccaggcttgc tgtaccatgt gcgctgattc     1560
ttgcgctcaa tacgttgcag gttgctttca atctgtttgt ggtattcagc cagcactgta     1620
aggtctatcg gatttagtgc gctttctact cgtgatttcg gtttgcgatt cagcgagaga     1680
atagggcggt taactggttt tgcgcttacc ccaaccaaca ggggatttgc tgctttccat     1740
tgagcctgtt actctgcgcg acgttcgcgg cggcgtgttt gtgcatccat ctggattctc     1800
ctgtcagtta gctttggtgg tgtgtggcag ttgtagtcct gaacgaaaac ccccgcgat     1860 tggcacgttg gcagctaatc cggaatcgca cttacggcca atgcttcgtt tcgtatcaca     1920
caccccaaag ccttctgctt tgaatgctgc ccttcttcag ggcttaattt ttaagagcgt     1980
caccttcatg gtggtcagtg cgtcctgctg atgtgctcag gcacgattta attaaggcct     2040
taattaggct gcgcgctcgc tcgctcactg aggccgcccg ggcaaagccc gggcgtcggg     2100
cgacctttgg tcgcccggcc tcagtgagcg agcgagcgcg cagagaggga gtggccaact     2160
ccatcactag gggttccttg tagttaatga ttaacccgcc atgctactta tctacgtagc     2220
catgctctag gaagatcgga attcgcccct aagctagcgg cgcgccggta cctagttatt     2280
aatagtaatc aattacgggg tcattagttc atagcccata tatggagttc cgcgttacat     2340
aacttacggt aaatggcccg cctggctgac cgcccaacga cccccgccca ttgacgtcaa     2400
taatgacgta tgttcccata gtaacgccaa tagggacttt ccattgacgt caatgggtgg     2460
agtatttacg gtaaactgcc cacttggcag tacatcaagt gtatcatatg ccaagtacgc     2520
cccctattga cgtcaatgac ggtaaatggc ccgcctggca ttatgcccag tacatgacct     2580
tatgggactt tcctacttgg cagtacatct acgtattagt catcgctatt accatggtcg     2640
aggtgagccc cacgttctgc ttcactctcc ccatctcccc ccctccccca ccccaatttt     2700
tgtatttatt tattttttaa ttattttgtg cagcgatggg ggcggggggg gggggggggc     2760
```

-continued

```
gcgcgccagg cggggcgggg cggggcgagg ggcggggcgg ggcgaggcgg agaggtgcgg      2820
cggcagccaa tcagagcggc gcgctccgaa agtttccttt tatggcgagg cggcggcggc      2880 ggcggccta taaaaagcga agcgcgcggc gggcgggagt cgctgcgcgc tgccttcgcc       2940
ccgtgccccg ctccgccgcc gcctcgcgcc gcccgccccg gctctgactg accgcgttac      3000
tcccacaggt gagcgggcgg gacggccctt ctcctccggg ctgtaattag cgcttggttt      3060
aatgacggct tgtttctttt ctgtggctgc gtgaaagcct tgaggggctc cgggagctag      3120
agcctctgct aaccatgttc atgccttctt cttttttccta cagctcctgg gcaacgtgct      3180
ggttattgtg ctgtctcatc attttggcaa agaattctag cggccgccac catggccttg       3240
ctcatccacc tcaagacagt ctcggagctg cggggcaggg gcgaccggat cgccaaagtg        3300
actttccgag ggcaatcctt ctactctcgg gtcctggaga actgtgagga tgtggctgac        3360
tttgatgaga catttcggtg gccggtggcc agcagcatcg acagaaatga gatgctggag       3420
attcaggttt tcaactacag caaagtcttc agcaacaagc tcatcgggac cttccgcatg        3480
gtgctgcaga aggtggtaga ggagagccat gtggaggtga ctgacacgct gattgatgac       3540
aacaatgcta tcatcaagac cagcctgtgc gtggaggtcc ggtatcaggc cactgacggc        3600
acagtgggct cctgggacga tggggacttc ctgggagatg agtctcttca agaggaagag       3660
aaggacagcc aagagacgga tggactgctc ccaggctccc ggcccagctc ccggccccca       3720
ggagagaaga gcttccggag agccgggagg agcgtgttct ccgccatgaa gctcggcaaa        3780
aaccggtctc acaaggagga gccccaaaga ccagatgaac cggcggtgct ggagatggaa        3840
gaccttgacc atctggccat tcggctagga gatggactgg atcccgactc ggtgtctcta        3900
gcctcagtca cagctctcac cactaatgtc tccaacaagc gatctaagcc agacattaag       3960
atggagccaa gtgctgggcg gcccatggat taccaggtca gcatcacggt gatcgaggcc       4020
cggcagctgg tgggcttgaa catggaccct gtggtgtgcg tggaggtggg tgacgacaag       4080
aagtacacat ccatgaagga gtccactaac tgcccctatt acaacgagta cttcgtcttc       4140
gacttccatg tctctccgga tgtcatgttt gacaagatca tcaagatttc ggtgattcac       4200
tccaagaacc tgctgcgcag tggcaccctg gtgggctcct tcaaaatgga cgtgggaacc       4260
gtgtactcgc agccagagca ccagttccat cacaagtggg ccatcctgtc tgaccccgat       4320
gacatctcct cggggctgaa gggctacgtg aagtgtgacg ttgccgtggt gggcaaaggg       4380
gacaacatca agacgccca caaggccaat gagaccgacg aagatgacat tgaggggaac        4440
ttgctgctcc ccgagggggt gcccccgaa cgccagtggg cccggttcta tgtgaaaatt        4500
taccgagcag aggggctgcc ccgtatgaac acaagcctca tggccaatgt aaagaaggct       4560
ttcatcggtg aaaacaagga cctcgtggac ccctacgtgc aagtcttctt tgctggccag       4620
aagggcaaga cttcagtgca gaagagcagc tatgagcccc tgtggaatga gcaggtcgtc       4680
tttacagacc tcttcccccc actctgcaaa cgcatgaagg tgcagatccg agactcggac        4740
aaggtcaacg acgtggccat cggcacccac ttcattgacc tgcgcaagat ttctaatgac       4800
ggagacaaag gcttcctgcc cacactgggc ccagcctggg tgaacatgta cggctccaca       4860
cgtaactaca cgctgctgga tgagcatcag gacctgaacg agggcctggg ggagggtgtg       4920
tccttccggg cccggctcct gctgggcctg gctgtggaga tcgtagacac ctccaaccct      4980
gagctcacca gctccacaga ggtgcaggtg gagcaggcca cgcccatctc ggagagctgt      5040
gcaggtaaaa tggaagaatt ctttctctttt ggagccttcc tggaggcctc aatgatcgac      5100
cggagaaacg gagacaagcc catcaccttt gaggtcacca taggcaacta tgggaacgaa       5160
```

-continued

```
gttgatggcc tgtcccggcc ccagcggcct cggccccgga aggagccggg ggatgaggaa     5220
gaagtagacc tgattcagaa cgcaagtgat gacgaggccg gtgatgccgg ggacctggcc     5280
tcagtctcct ccactccacc aatgcggccc caggtcaccg acaggaacta cttccatctg     5340
ccctacctgg agcgaaagcc ctgcatctac atcaagagct ggtggccgga ccagcgccgc     5400
cgcctctaca atgccaacat catggaccac attgccgaca agctggaaga aggcctgaac     5460
gacatacagg agatgatcaa aacggagaag tcctaccctg agcgtcgcct gcggggcgtc     5520
ctggaggagc tgagctgtgg ctgctgccgc ttcctctccc tcgctgacaa ggaccagggc     5580
cactcatccc gcaccaggct tgaccgggag cgcctcaagt cctgcatgag ggagctggta     5640
agtatcaagg ttacaagaca ggtttaagga gaccaataga aactgggctt gtcgagacag     5700
agaagactct tgcgtttctg agctagcccc cgggtgcgcg cgtcggtgg tgccggcggg      5760 gggcgccagg tcgcaggcgg tgtagggctc caggcaggcg gcgaaggcca tgacgtgcgc     5820
tatgaaggtc tgctcctgca cgccgtgaac caggtgcgcc tgcgggccgc gcgcgaacac     5880
cgccacgtcc tcgcctgcgt gggtctcttc gtccaggggc actgctgact gctgccgata     5940
ctcggggctc ccgctctcgc tctcggtaac atccggccgg gcgccgtcct tgagcacata     6000
gcctggaccg tttcgtcgac ctcgagttaa gggcgaattc ccgataagga tcttcctaga     6060
gcatggctac gtagataagt agcatggcgg gttaatcatt aactacaagg aacccctagt     6120
gatggagttg gccactccct ctctgcgcgc tcgctcgctc actgaggccg ggcgaccaaa     6180
ggtcgcccga cgcccgggct ttgcccgggc ggcctcagtg agcgagcgag cgcgcagcct     6240
taattaaatc cacatctgta tgtttttttat attaatttat tttttgcagg ggggcattgt     6300
ttggtaggtg agagttctga attgctatgt ttagtgagtt gtatctattt atttttcaat     6360
aaatacaatt agttatgtgt tttgggggcg atcgtgaggc aaagaaaacc cggcgctgag     6420
gccgggttat tcttgttctc tggtcaaatt atatagttgg aaaacaagga tgcatatatg     6480
aatgaacgat gcagaggcaa tgccgatggc gatagtgggt atcaggtagc cgcttatgct     6540
ggaaagaagc aataacccgc agaaaaacaa agctccaagc tcaacaaaac taagggcata     6600
gacaataact acctatgtca tatacccata ctctctaatc ttggccagtc ggcgcgttct     6660
gcttccgatt agaaacgtca aggcagcaat caggattgca atcttggttc ctgcatagga     6720
tgacaatgtc gccccaagac catctctatg agctgaaaaa gaaacacaag gaatgtagtg     6780
gcggaaaagg agatagcaaa tgcttacgat aacgtaagga attattacta tgtaaacacc     6840
aggcaagatt ctgttccgta taattactcc tgataattaa tccttaactt tgcccacctg     6900
ccttttaaaa cattccagta tatcactttt cattcttgcg tagcaatatg ccctctcttc     6960
agctatctca gcattggtga ccttgttcag aggcgctgag agatggcctt tttctgatag     7020
ataatgttct gttaaaatat ctccggcctc atcttttgcc cgcaggctaa tgtctgaaaa     7080
ttgaggtgac gggttaaaaa taatatcctt ggcaaccttt tttatatccc ttttaaattt     7140
tggcttaatg actatatcca atgagtcaaa aagctcccct tcaatatctg ttgcccctaa     7200
gacctttaat atatcgccaa atacaggtag cttggcttct accttcaccg ttgttctgcc     7260
gatgaaatgc taatgcataa catcgtcttt ggtggttccc ctcatcagtg gctctatctg     7320
aacgcgctct ccactgctta atgacattcc tttcccgatt aaaaaatctg tcagatcgga     7380
tgtggtcggc ccgaaaacag ttctggcaaa accaatggtg tcgccttcaa caaacaaaaa     7440
agatgggaat cccaatgatt cgtcatctgc gaggctgttc ttaatatctt caactgtagc     7500
```

-continued

```
tttagagcga tttatcttct gaaccagact cttgtcattt gttttggtaa agagaaaagt   7560
ttttccatcg attttatgaa tatacaaata attggagcca accttcaggt gatgattatc   7620
agccagcaga gaattaagga aaacagacag gtttattgag cacttatctt tccctttatt   7680
tttgctgcgg taagtcgcat aaaaaccatt cttcacaatt caatccattt actatgttat   7740
gttctgaggg gagtgaaaat tcccctaatt cgatgaagat tcttgctaaa ttgttatcag   7800
ctatgcgccg accagaacac cttgccgatc agccaaacgt ctaatcaggc cactgactag   7860
cgataacttt ccccacaacg gaacaactct cattgcatgg gataattggg tactgtgggt   7920
ttagtggttg taaaaacacc tgaccgctat ccctgatcag tttcttgaag gtaaactcat   7980
cacccccaag tctggctata cagaaatcac ctggctcaac agcctgctca gggtcaacga   8040
gaatttacat tccgtcagga tagcttggct tggagcctgt tggtgcggtc acggaattac   8100
cttcaacctc aagccagaat gcagaatcac tggctttttt ggttgtgctt acccatctct   8160
ccgcatcacc tttggtaaag gttctaagct aaggtgagaa catccctgcc tgaacatgag   8220
aaaaaacagg gtactcatac tcacttatta gtgacggcta tgagcaaaag gccagcaaaa   8280
ggccaggaac cgtaaaaagg ccgcgttgct ggcgtttttc cataggctcc gcccccctga   8340
cgagcatcac aaaaatcgac gctcaagtca gaggtggcga aacccgacag gactataaag   8400
ataccaggcg tttcccccctg gaagctccct cgtgcgctct cctgttccga cccctgccgct   8460 taccggatac ctgtccgcct ttctcccttc gggaagcgtg gcgctttctc atagctcacg   8520
ctgtaggtat ctcagttcgg tgtaggtcgt tcgctccaag ctgggctgtg tgcacgaacc   8580
ccccgttcag cccgaccgct gcgccttatc cggtaactat cgtcttgagt ccaacccggt   8640
aagacacgac ttatcgccac tggcagcagc cactggtaac aggattagca gagcgaggta   8700
tgtaggcggt gctacagagt tcttgaagtg gtggcctaac tacggctaca ctagaagaac   8760
agtatttggt atctgcgctc tgctgaagcc agttaccttc ggaaaaagag ttggtagctc   8820
ttgatccggc aaacaaacca ccgctggtag cggtggtttt tttgtttgca agcagcagat   8880
tacgcgcaga aaaaaaggat ctcaagaaga tcctttgatc ttttctacgg ggtctgacgc   8940
tcagtggaac gaaaactcac gttaagggat tttggtcatg agattatcaa aaaggatctt   9000
cacctagatc cttttaaatt aaaaatgaag ttttaaatca gcccaatct gaataatgtt   9060 acaaccaatt aaccaattct gattagaaaa actcatcgag catcaaatga aactgcaatt   9120
tattcatatc aggattatca ataccatatt tttgaaaaag ccgtttctgt aatgaaggag   9180
aaaactcacc gaggcagttc cataggatgg caagatcctg gtatcggtct gcgattccga   9240
ctcgtccaac atcaatacaa cctattaatt tcccctcgtc aaaaataagg ttatcaagtg   9300
agaaatcacc atgagtgacg actgaatccg gtgagaatgg caaaagttta tgcatttctt   9360
tccagacttg ttcaacaggc cagccattac gctcgtcatc aaaatcactc gcatcaacca   9420
aaccgttatt cattcgtgat tgcgcctgag caagacgaaa tacgcgatcg ctgttaaaag   9480
gacaattaca aacaggaatc gaatgcaacc ggcgcaggaa cactgccagc gcatcaacaa   9540
tattttcacc tgaatcagga tattcttcta atacctggaa tgctgttttt ccggggatcg   9600
cagtggtgag taaccatgca tcatcaggag tacgataaa atgcttgatg gtcggaagag   9660
gcataaattc cgtcagccag tttagtctga ccatctcatc tgtaacatca ttggcaacgc   9720
tacctttgcc atgtttcaga aacaactctg cgcatcgggg cttcccatac aagcgataga   9780
ttgtcgcacc tgattgcccg acattatcgc gagcccattt atacccatat aaatcagcat   9840
ccatgttgga atttaatcgc ggcctcgacg tttcccgttg aatatggctc ataacacccc   9900
```

-continued

```
ttgtattact gtttatgtaa gcagacagtt ttattgttca tgatgatata ttttttatctt      9960 gtgcaatgta acatcagaga ttttgagaca cgggccagag ctgca                        10005
```

```
<210> SEQ ID NO 65
<211> LENGTH: 6653
<212> TYPE: DNA
<213> ORGANISM: Artificial Sequence
<220> FEATURE:
<223> OTHER INFORMATION: Synthetic Construct

<400> SEQUENCE: 65
gggggggggg gggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actaggggtt cctcagatct gaattcggta       180
cctagttatt aatagtaatc aattacgggg tcattagttc atagcccata tatggagttc       240
cgcgttacat aacttacggt aaatggcccg cctggctgac cgcccaacga cccccgccca       300
ttgacgtcaa taatgacgta tgttcccata gtaacgccaa tagggacttt ccattgacgt       360
caatgggtgg agtatttacg gtaaactgcc cacttggcag tacatcaagt gtatcatatg       420
ccaagtacgc cccctattga cgtcaatgac ggtaaatggc ccgcctggca ttatgcccag       480
tacatgacct tatgggactt tcctacttgg cagtacatct acgtattagt catcgctatt       540
accatggtcg aggtgagccc cacgttctgc ttcactctcc ccatctcccc ccctccccca       600 ccccaattt tgtatttatt tatttttaa ttattttgtg cagcgatggg ggcggggggg       660
gggggggggc gcgcgccagg cggggcgggg cggggcgagg ggcggggcgg ggcgaggcgg       720
agaggtgcgg cggcagccaa tcagagcggc gcgctccgaa agtttccttt tatggcgagg       780
cggcggcggc ggcggcccta taaaaagcga agcgcgcggc gggcgggagt cgctgcgcgc       840
tgccttcgcc ccgtgccccg ctccgccgcc gcctcgcgcc gcccgccccg gctctgactg       900
accgcgttac tcccacaggt gagcgggcgg gacggccctt ctcctccggg ctgtaattag       960
cgcttggttt aatgacggct tgtttctttt ctgtggctgc gtgaaagcct tgagggggctc      1020 cgggagctag agcctctgct aaccatgttc atgccttctt cttttttccta cagctcctgg     1080 gcaacgtgct ggttattgtg ctgtctcatc attttggcaa agaattctag cggccgccac      1140
catggccttg ctcatccacc tcaagacagt ctcggagctg cggggcaggg gcgaccggat      1200
cgccaaagtg actttccgag ggcaatcctt ctactctcgg gtcctggaga actgtgagga      1260
tgtggctgac tttgatgaga catttcggtg gccggtggcc agcagcatcg acagaaatga      1320
gatgctggag attcaggttt tcaactacag caaagtcttc agcaacaagc tcatcgggac      1380
cttccgcatg gtgctgcaga aggtggtaga ggagagccat gtggaggtga ctgacacgct      1440
gattgatgac aacaatgcta tcatcaagac cagcctgtgc gtggaggtcc ggtatcaggc      1500
cactgacggc acagtgggct cctgggacga tgggggactc ctgggagatg agtctcttca      1560
agaggaagag aaggacagcc aagagacgga tggactgctc ccaggctccc ggcccagctc      1620 ccggcccca ggagagaaga gcttccggag agccgggagg agcgtgttct ccgccatgaa      1680
gctcggcaaa aaccggtctc acaaggagga gccccaaaga ccagatgaac cggcggtgct      1740
ggagatggaa gaccttgacc atctggccat tcggctagga gatggactgg atcccgactc      1800
ggtgtctcta gcctcagtca cagctctcac cactaatgtc tccaacaagc gatctaagcc      1860
agacattaag atggagccaa gtgctgggcg gcccatggat taccaggtca gcatcacggt      1920
```

-continued

```
gatcgaggcc cggcagctgg tgggcttgaa catggaccct gtggtgtgcg tggaggtggg   1980
tgacgacaag aagtacacat ccatgaagga gtccactaac tgcccctatt acaacgagta   2040
cttcgtcttc gacttccatg tctctccgga tgtcatgttt gacaagatca tcaagatttc   2100
ggtgattcac tccaagaacc tgctgcgcag tggcaccctg gtgggctcct tcaaaatgga   2160
cgtgggaacc gtgtactcgc agccagagca ccagttccat cacaagtggg ccatcctgtc   2220
tgaccccgat gacatctcct cggggctgaa gggctacgtg aagtgtgacg ttgccgtggt   2280
gggcaaaggg gacaacatca agacgcccca caaggccaat gagaccgacg aagatgacat   2340
tgaggggaac ttgctgctcc ccgaggggggt gccccccgaa cgccagtggg cccggttcta   2400
tgtgaaaatt taccgagcag aggggctgcc ccgtatgaac acaagcctca tggccaatgt   2460
aaagaaggct ttcatcggtg aaaacaagga cctcgtggac ccctacgtgc aagtcttctt   2520
tgctggccag aagggcaaga cttcagtgca gaagagcagc tatgagcccc tgtggaatga   2580
gcaggtcgtc tttacagacc tcttcccccc actctgcaaa cgcatgaagg tgcagatccg   2640
agactcggac aaggtcaacg acgtggccat cggcacccac ttcattgacc tgcgcaagat   2700
ttctaatgac ggagacaaag gcttcctgcc cacactgggc ccagcctggg tgaacatgta   2760
cggctccaca cgtaactaca cgctgctgga tgagcatcag gacctgaacg agggcctggg   2820
ggagggtgtg tccttccggg cccggctcct gctgggcctg gctgtggaga tcgtagacac   2880
ctccaaccct gagctcacca gctccacaga ggtgcaggtg gagcaggcca cgcccatctc   2940
ggagagctgt gcaggtaaaa tggaagaatt ctttctcttt ggagccttcc tggaggcctc   3000
aatgatcgac cggagaaacg gagacaagcc catcaccttt gaggtcacca taggcaacta   3060
tgggaacgaa gttgatggcc tgtcccggcc ccagcggcct cggccccgga aggagccggg   3120
ggatgaggaa gaagtagacc tgattcagaa cgcaagtgat gacgaggccg gtgatgccgg   3180
ggacctggcc tcagtctcct ccactccacc aatgcggccc caggtcaccg acaggaacta   3240
cttccatctg ccctacctgg agcgaaagcc ctgcatctac atcaagagct ggtgcgccgga   3300 ccagcgccgc cgcctctaca atgccaacat catggaccac attgccgaca agctggaaga   3360
aggcctgaac gacatacagg agatgatcaa aacggagaag tcctaccctg agcgtcgcct   3420
gcggggcgtc ctggaggagc tgagctgtgg ctgctgccgc ttcctctccc tcgctgacaa   3480
ggaccagggc cactcatccc gcaccaggct tgaccgggag cgcctcaagt cctgcatgag   3540
ggagctggta agtatcaagg ttacaagaca ggtttaagga gaccaataga aactgggctt   3600
gtcgagacag agaagactct tgcgtttctg agctagcccc cgggtgcgcg gcgtcggtgg   3660
tgccggcggg gggcgccagg tcgcaggcgg tgtagggctc caggcaggcg gcgaaggcca   3720
tgacgtgcgc tatgaaggtc tgctcctgca cgccgtgaac caggtgcgcc tgcgggccgc   3780
gcgcgaacac cgccacgtcc tcgcctgcgt gggtctcttc gtccaggggc actgctgact   3840
gctgccgata ctcggggctc ccgctctcgc tctcggtaac atccggccgg cgccgtcct   3900 tgagcacata gcctggaccg tttcgtcgac tggggagaga tctgaggaac ccctagtgat   3960
ggagttggcc actccctctc tgcgcgctcg ctcgctcact gaggccgccc gggcaaagcc   4020 cggggcgtcgg gcgacctttg gtcgcccggc ctcagtgagc gagcgagcgc gcagagaggg   4080
agtggccaac cccccccccc cccccctgc agcctggcgt aatagcgaag aggcccgcac   4140
cgatcgccct tcccaacagt tgcgtagcct gaatggcgaa tggcgcgacg cgccctgtag   4200
cggcgcatta gcgcggcggg gtgtggtggt tacgcgcagc gtgaccgcta cacttgccag   4260
cgccctagcg cccgctcctt tcgctttctt cccttccttt ctcgccacgt tcgccggctt   4320
```

-continued

```
tccccgtcaa gctctaaatc gggggctccc tttagggttc cgatttagtg ctttacggca      4380
cctcgacccc aaaaaacttg attagggtga tggttcacgt agtgggccat cgccctgata      4440
gacggttttt cgccctttga cgttggagtc cacgttcttt aatagtggac tcttgttcca      4500
aactggaaca acactcaacc ctatcgcggt ctattctttt gatttataag ggatgttgcc      4560
gatttcggcc tattggttaa aaaatgagct gatttaacaa aaattttaac aaaaattcaga     4620 agaactcgtc aagaaggcga tagaaggcga tgcgctgcga atcgggagcg gcgataccgt      4680
aaagcacgag gaagcggtca gcccattcgc cgccaagctc ttcagcaata tcacgggtag      4740
ccaacgctat gtcctgatag cggtccgcca cacccagccg gccacagtcg atgaatccag      4800
aaaagcggcc attttccacc atgatattcg gcaagcaggc atcgccatgg gtcacgacga      4860
gatcctcgcc gtcgggcatg ctcgccttga gcctggcgaa cagttcggct ggcgcgagcc      4920
cctgatgctc ttcgtccaga tcatcctgat cgacaagacc ggcttccatc cgagtacgtg      4980
ctcgctcgat gcgatgtttc gcttggtggt cgaatgggca ggtagccgga tcaagcgtat      5040
gcagccgccg cattgcatca gccatgatgg atactttctc ggcaggagca aggtgagatg      5100
acaggagatc ctgccccggc acttcgccca atagcagcca gtcccttccc gcttcagtga      5160
caacgtcgag cacagctgcg caaggaacgc ccgtcgtggc cagccacgat agccgcgctg      5220
cctcgtcttg cagttcattc agggcaccgg acaggtcggt cttgacaaaa agaaccgggc      5280
gcccctgcgc tgacagccgg aacacggcgg catcagagca gccgattgtc tgttgtgccc      5340
agtcatagcc gaatagcctc tccacccaag cggccggaga acctgcgtgc aatccatctt      5400
gttcaatcat gcgaaacgat cctcatcctg tctcttgatc agatcttgat cccctgcgcc      5460
atcagatcct tggcggcgag aaagccatcc agtttacttt gcagggcttc ccaaccttac      5520
cagagggcgc cccagctggc aattccggtt cgcttgctgt ccataaaacc gcccagtcta      5580
gctatcgcca tgtaagccca ctgcaagcta cctgctttct cttgtcgctt gcgtttttcc     5640
ttgtccagat agcccagtag ctgacattca tccgggtca gcaccgtttc tgcggactgg       5700
ctttctacgt gaaaaggatc taggtgaaga tcctttttga taatctcatg accaaaatcc      5760
cttaacgtga gttttcgttc cactgagcgt cagaccccgt agaaaagatc aaaggatctt      5820
cttgagatcc ttttttttctg cgcgtaatct gctgcttgca aacaaaaaaa ccaccgctac      5880
cagcggtggt ttgtttgccg gatcaagagc taccaactct ttttccgaag gtaactggct      5940
tcagcagagc gcagatacca aatactgtcc ttctagtgta gccgtagtta ggccaccact      6000
tcaagaactc tgtagcaccg cctacatacc tcgctctgct aatcctgtta ccagtggctg      6060
ctgccagtgg cgataagtcg tgtcttaccg ggttggactc aagacgatag ttaccggata      6120
aggcgcagcg gtcgggctga acggggggtt cgtgcacaca gcccagcttg gagcgaacga      6180
cctacaccga actgagatac ctacagcgtg agctatgaga aagcgccacg cttcccgaag      6240
ggagaaaggc ggacaggtat ccggtaagcg gcagggtcgg aacaggagag cgcacgaggg      6300
agcttccagg gggaaacgcc tggtatcttt atagtcctgt cgggtttcgc cacctctgac      6360
ttgagcgtcg atttttgtga tgctcgtcag ggggcggag cctatggaaa aacgccagca       6420
acgcggcctt tttacggttc ctgggctttt gctggccttt tgctcacatg ttctttcctg      6480
cgttatcccc tgattctgtg ataaccgta ttaccgcctt tgagtgagct gataccgctc       6540
gccgcagccg aacgaccgag cgcagcgagt cagtgagcga ggaagcggaa gagcgcccaa      6600
tacgcaaacc gcctctcccc gcgcgttggc cgattcatta atgcagggct gca             6653
```

```
<210> SEQ ID NO 66
<211> LENGTH: 6986
<212> TYPE: DNA
<213> ORGANISM: Artificial Sequence
<220> FEATURE:
<223> OTHER INFORMATION: Synthetic Construct

<400> SEQUENCE: 66
ccttaattag gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc ttgtagttaa tgattaaccc gccatgctac ttatctacgt     180
agccatgctc taggaagatc ggaattcgcc cttaagctag cggcgcgccc aattctgcag     240
ctcagcctac tacttgcttt ccaggctgtt cctagttccc atgtcagctg cttgtgcttt     300
ccagagacaa aacaggaata atagatgtca ttaaatatac attgggcccc aggcggtcaa     360
tgtggcagcc tgagcctcct ttccatctct gtggaggcag acataggacc cccaacaaac     420
agcatgcagg ttgggagcca gccacaggac ccaggtaagg ggccctgggt ccttaagctt     480
ctgccactgg ctccggcatt gcagagagaa gagaaggggc ggcagactgg agagctgggc     540 tccattttg ttccttggtg ccctgccct ccccatgacc tgcagagaca ttcagcctgc     600
caggctttat gaggtgggag ctgggctctc cctgatgtat tattcagctc cctggagttg     660
gccagctcct gttacactgg ccacagccct gggcatccgc ttctcacttc tagtttcccc     720
tccaaggtaa tgtggtgggt catgatcatt ctatcctggc ttcagggacc tgactccact     780
ttggggccat tcgaggggtc tagggtagat gatgtccccc tgtggggatt aatgtcctgc     840
tctgtaaaac tgagctagct gagatccagg agggcttggc cagagacagc aagttgttgc     900
catggtgact ttaaagccag gttgctgccc cagcacaggc ctcccagtct accctcacta     960
gaaaacaaca cccaggcact ttccaccacc tctcaaaggt gaaacccaag gctggtctag    1020
agaatgaatt atggatcctc gctgtccgtg ccacccagct agtcccagcg gctcagacac    1080
tgaggagaga ctgtaggttc agctacaagc aaaaagacct agctggtctc caagcagtgt    1140
ctccaagtcc ctgaacctgt gacacctgcc ccaggcatca tcaggcacag agggccacca    1200
agaattctag cggccgccac catggccttg ctcatccacc tcaagacagt ctcggagctg    1260
cggggcaggg gcgaccggat cgccaaagtg actttccgag ggcaatcctt ctactctcgg    1320
gtcctggaga actgtgagga tgtggctgac tttgatgaga catttcggtg gccggtggcc    1380
agcagcatcg acagaaatga gatgctggag attcaggttt tcaactacag caaagtcttc    1440
agcaacaagc tcatcgggac cttccgcatg gtgctgcaga aggtggtaga ggagagccat    1500
gtggaggtga ctgacacgct gattgatgac aacaatgcta tcatcaagac agcctgtgc    1560 gtggaggtcc ggtatcaggc cactgacggc acagtgggct cctgggacga tgggggacttc    1620 ctgggagatg agtctcttca agaggaagag aaggacagcc aagagacgga tggactgctc    1680
ccaggctccc ggcccagctc ccggccccca ggagagaaga gcttccggag agccgggagg    1740
agcgtgttct ccgccatgaa gctcggcaaa aaccggtctc acaaggagga gccccaaaga    1800
ccagatgaac cggcggtgct ggagatggaa gaccttgacc atctggccat tcggctagga    1860
gatggactgg atcccgactc ggtgtctcta gcctcagtca cagctctcac cactaatgtc    1920
tccaacaagc gatctaagcc agacattaag atggagccaa gtgctgggcg gcccatggat    1980
taccaggtca gcatcacggt gatcgaggcc cggcagctgg tgggcttgaa catggaccct    2040
gtggtgtgcg tggaggtggg tgacgacaag aagtacacat ccatgaagga gtccactaac    2100
```

-continued

```
tgcccctatt acaacgagta cttcgtcttc gacttccatg tctctccgga tgtcatgttt   2160
gacaagatca tcaagatttc ggtgattcac tccaagaacc tgctgcgcag tggcaccctg   2220
gtgggctcct tcaaaatgga cgtgggaacc gtgtactcgc agccagagca ccagttccat   2280
cacaagtggg ccatcctgtc tgaccccgat gacatctcct cggggctgaa gggctacgtg   2340
aagtgtgacg ttgccgtggt gggcaaaggg gacaacatca agacgcccca caaggccaat   2400
gagaccgacg aagatgacat tgaggggaac ttgctgctcc ccgaggggt gcccccgaa    2460 cgccagtggg cccggttcta tgtgaaaatt taccgagcag aggggctgcc ccgtatgaac   2520
acaagcctca tggccaatgt aaagaaggct ttcatcggtg aaaacaagga cctcgtggac   2580
ccctacgtgc aagtcttctt tgctggccag aagggcaaga cttcagtgca gaagagcagc   2640
tatgagcccc tgtggaatga gcaggtcgtc tttacagacc tcttccccc actctgcaaa    2700 cgcatgaagg tgcagatccg agactcggac aaggtcaacg acgtggccat cggcacccac   2760
ttcattgacc tgcgcaagat ttctaatgac ggagacaaag gcttcctgcc cacactgggc   2820
ccagcctggg tgaacatgta cggctccaca cgtaactaca cgctgctgga tgagcatcag   2880
gacctgaacg agggcctggg ggagggtgtg tccttccggg cccggctcct gctgggcctg   2940
gctgtggaga tcgtagacac ctccaaccct gagctcacca gctccacaga ggtgcaggtg   3000
gagcaggcca cgcccatctc ggagagctgt gcaggtaaaa tggaagaatt ctttctcttt   3060
ggagccttcc tggaggcctc aatgatcgac cggagaaacg gagacaagcc catcaccttt   3120
gaggtcacca taggcaacta tgggaacgaa gttgatggcc tgtcccggcc ccagcggcct   3180 cggcccgga aggagccggg ggatgaggaa gaagtagacc tgattcagaa cgcaagtgat    3240
gacgaggccg tgatgccgg ggacctggcc tcagtctcct ccactccacc aatgcggccc    3300
caggtcaccg acaggaacta cttccatctg ccctacctgg agcgaaagcc ctgcatctac   3360
atcaagagct ggtggccgga ccagcgccgc cgcctctaca tgccaacat catggaccac    3420 attgccgaca agctggaaga aggcctgaac gacatacagg agatgatcaa aacggagaag   3480
tcctaccctg agcgtcgcct gcggggcgtc ctggaggagc tgagctgtgg ctgctgccgc   3540
ttcctctccc tcgctgacaa ggaccagggc cactcatccc gcaccaggct tgaccgggag   3600
cgcctcaagt cctgcatgag ggagctggta agtatcaagg ttacaagaca ggtttaagga   3660
gaccaataga aactgggctt gtcgagacag agaagactct tgcgtttctg agctagcccc   3720
cgggtgcgcg cgtcggtgg tgccggcggg gggcgccagg tcgcaggcgg tgtagggctc    3780
caggcaggcg cgaaggcca tgacgtgcgc tatgaaggtc tgctcctgca cgccgtgaac   3840
caggtgcgcc tgcgggccgc gcgcgaacac cgccacgtcc tcgcctgcgt gggtctcttc   3900
gtccaggggc actgctgact gctgccgata ctcgggggctc ccgctctcgc tctcggtaac   3960
atccggccgg gcgccgtcct tgagcacata gcctggaccg tttcgtcgac ctcgagttaa   4020
gggcgaattc ccgataagga tcttcctaga gcatggctac gtagataagt agcatggcgg   4080
gttaatcatt aactacaagg aacccctagt gatggagttg gccactccct ctctgcgcgc   4140
tcgctcgctc actgaggccg ggcgaccaaa ggtcgcccga cgcccgggct ttgcccgggc   4200
ggcctcagtg agcgagcgag cgcgcagcct taattaacct aattcactgg ccgtcgtttt   4260
acaacgtcgt gactgggaaa accctggcgt tacccaactt aatcgccttg cagcacatcc   4320
ccctttcgcc agctggcgta atagcgaaga ggcccgcacc gatcgccctt cccaacagtt   4380
gcgcagcctg aatggcgaat gggacgcgcc ctgtagcggc gcattaagcg cggcgggtgt   4440
```

-continued

```
ggtggttacg cgcagcgtga ccgctacact tgccagcgcc ctagcgcccg ctcctttcgc    4500
tttcttccct tcctttctcg ccacgttcgc cggctttccc cgtcaagctc taaatcgggg    4560
gctcccttta gggttccgat ttagtgcttt acggcacctc gaccccaaaa aacttgatta    4620
gggtgatggt tcacgtagtg ggccatcgcc ctgatagacg gtttttcgcc ctttgacgtt    4680
ggagtccacg ttctttaata gtggactctt gttccaaact ggaacaacac tcaaccctat    4740
ctcggtctat tcttttgatt tataagggat tttgccgatt tcggcctatt ggttaaaaaa    4800
tgagctgatt taacaaaaat ttaacgcgaa ttttaacaaa atattaacgc ttacaattta    4860
ggtggcactt ttcggggaaa tgtgcgcgga acccctattt gtttattttt ctaaatacat    4920
tcaaatatgt atccgctcat gagacaataa ccctgataaa tgcttcaata atattgaaaa    4980
aggaagagta tgagccatat tcaacgggaa acgtcgaggc cgcgattaaa ttccaacatg    5040
gatgctgatt tatatgggta taaatgggct cgcgataatg tcgggcaatc aggtgcgaca    5100
atctatcgct tgtatgggaa gcccgatgcg ccagagttgt ttctgaaaca tggcaaaggt    5160
agcgttgcca atgatgttac agatgagatg gtcagactaa actggctgac ggaatttatg    5220
cctcttccga ccatcaagca tttttatccgt actcctgatg atgcatggtt actcaccact    5280
gcgatccccg gaaaaacagc attccaggta ttagaagaat atcctgattc aggtgaaaat    5340
attgttgatg cgctggcagt gttcctgcgc cggttgcatt cgattcctgt ttgtaattgt    5400
ccttttaaca gcgatcgcgt atttcgtctt gctcaggcgc aatcacgaat gaataacggt    5460
ttggttgatg cgagtgattt tgatgacgag cgtaatggct ggcctgttga acaagtctgg    5520
aaagaaatgc ataaacttttt gccattctca ccggattcag tcgtcactca tggtgatttc    5580
tcacttgata accttatttt tgacgagggg aaattaatag gttgtattga tgttggacga    5640
gtcggaatcg cagaccgata ccaggatctt gccatcctat ggaactgcct cggtgagttt    5700
tctccttcat tacagaaacg gctttttcaa aaatatggta ttgataatcc tgatatgaat    5760
aaattgcagt ttcatttgat gctcgatgag ttttttctaac tgtcagacca agtttactca    5820
tatatacttt agattgattt aaaacttcat ttttaattta aaaggatcta ggtgaagatc    5880
ctttttgata atctcatgac caaaatccct taacgtgagt tttcgttcca ctgagcgtca    5940
gaccccgtag aaaagatcaa aggatcttct tgagatcctt tttttctgcg cgtaatctgc    6000
tgcttgcaaa caaaaaaacc accgctacca gcggtggttt gtttgccgga tcaagagcta    6060
ccaactcttt ttccgaaggt aactggcttc agcagagcgc agataccaaa tactgttctt    6120
ctagtgtagc cgtagttagg ccaccacttc aagaactctg tagcaccgcc tacatacctc    6180
gctctgctaa tcctgttacc agtggctgct gccagtggcg ataagtcgtg tcttaccggg    6240
ttggactcaa gacgatagtt accggataag gcgcagcggt cgggctgaac ggggggttcg    6300
tgcacacagc ccagcttgga gcgaacgacc tacaccgaac tgagatacct acagcgtgag    6360
ctatgagaaa gcgccacgct tcccgaaggg agaaaggcgg acaggtatcc ggtaagcggc    6420
agggtcggaa caggagagcg cacgagggag cttccagggg gaaacgcctg gtatctttat    6480
agtcctgtcg ggtttcgcca cctctgactt gagcgtcgat ttttgtgatg ctcgtcaggg    6540
gggcggagcc tatggaaaaa cgccagcaac gcggcctttt tacggttcct ggccttttgc    6600
tggccttttg ctcacatgtt ctttcctgcg ttatcccctg attctgtgga taaccgtatt    6660
accgcctttg agtgagctga taccgctcgc cgcagccgaa cgaccgagcg cagcgagtca    6720
gtgagcgagg aagcggaaga gcgcccaata cgcaaaccgc ctctccccgc gcgttggccg    6780
attcattaat gcagctggca cgacaggttt cccgactgga aagcgggcag tgagcgcaac    6840
```

-continued

```
gcaattaatg tgagttagct cactcattag gcaccccagg ctttacactt tatgcttccg    6900
gctcgtatgt tgtgtggaat tgtgagcgga taacaatttc acacaggaaa cagctatgac    6960
catgattacg ccagatttaa ttaagg                                          6986
```

```
<210> SEQ ID NO 67
<211> LENGTH: 7414
<212> TYPE: DNA
<213> ORGANISM: Artificial Sequence
<220> FEATURE:
<223> OTHER INFORMATION: Synthetic Construct

<400> SEQUENCE: 67
ccttaattag gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc ttgtagttaa tgattaaccc gccatgctac ttatctacgt     180
agccatgctc taggaagatc ggaattcgcc cttaagctag cggcgcgccc ccgggtcgcc     240
ggcgtcggtg gtgccggcgg ggggcgccag gtcgcaggcg gtgtagggct ccaggcaggc     300
ggcgaaggcc atgacgtgcg ctatgaaggt ctgctcctgc acgccgtgaa ccaggtcgcg     360
ctgcgggccg cgcgcgaaca ccgccacgtc ctcgcctgcg tgggtctctt cgtccagggg     420
cactgctgac tgctgccgat actcggggct cccgctctcg ctctcggtaa catccggccg     480
ggcgccgtcc ttgagcacat agcctggacc gtttccttaa gcgacgcatg ctcgcgatag     540
gcacctattg gtcttactga catccacttt gcctttctct ccacaggaaa acatggggca     600
gcaggccagg atgctgcggg cccaggtgaa gcggcacacg gtgcgggaca agctgaggct     660
gtgccagaac ttcctgcaga agctgcgctt cctggcggac gagccccagc acagcattcc     720
cgacatcttc atctggatga tgagcaacaa caagcgtgtc gcctatgccc gtgtgccctc     780
caaggacctg ctcttctcca tcgtggagga ggagactggc aaggactgcg ccaaggtcaa     840
gacgctcttc cttaagctgc cagggaagcg gggcttcggc tcggcaggct ggacagtgca     900
ggccaaggtg gagctgtacc tgtggctggg cctcagcaaa cagcgcaagg agttcctgtg     960
cggcctgccc tgtggcttcc aggaggtcaa ggcagcccag ggcctgggcc tgcatgcctt    1020
cccacccgtc agcctggtct acaccaagaa gcaggcgttc cagctccgag cgcacatgta    1080
ccaggcccgc agcctctttg ccgccgacag cagcggactc tcagacccct ttgcccgcgt    1140
cttcttcatc aatcagagtc agtgcacaga ggtgctgaat gagaccctgt gtcccacctg    1200
ggaccagatg ctggtgttcg acaacctgga gctctatggt gaagctcatg agctgaggga    1260
cgatccgccc atcattgtca ttgaaatcta tgaccaggat tccatgggca aagctgactt    1320
catgggccgg accttcgcca aacccctggt gaagatggca gacgaggcgt actgcccacc    1380
ccgcttccca cctcagctcg agtactacca gatctaccgt ggcaacgcca cagctggaga    1440
cctgctggcg gccttcgagc tgctgcagat tggaccagca gggaaggctg acctgccccc    1500
catcaatggc ccggtggacg tggaccgagg tcccatcatg cccgtgccca tgggcatccg    1560
gcccgtgctc agcaagtacc gagtggaggt gctgttctgg ggcctacggg acctaaagcg    1620
ggtgaacctg gccaggtgg accggccacg ggtggacatc gagtgtgcag ggaagggggt    1680
gcagtcgtcc ctgatccaca attataagaa gaaccccaac ttcaacaccc tcgtcaagtg    1740
gtttgaagtg gacctcccag agaacgagct gctgcacccg cccttgaaca tccgtgtggt    1800
ggactgccgg gccttcggtc gctacacact ggtgggctcc catgccgtca gctccctgcg    1860
```

```
acgcttcatc taccggcccc cagaccgctc ggcccccagc tggaacacca cggtcaggct    1920
tctccggcgc tgccgtgtgc tgtgcaatgg gggctcctcc tctcactcca caggggaggt    1980
tgtggtgact atggagccag aggtacccat caagaaactg gagaccatgg tgaagctgga    2040
cgcgacttct gaagctgttg tcaaggtgga tgtggctgag gaggagaagg agaagaagaa    2100
gaagaagaag ggcactgcgg aggagccaga ggaggaggag ccagacgaga gcatgctgga    2160
ctggtggtcc aagtactttg cctccattga caccatgaag gagcaacttc gacaacaaga    2220
gccctctgga attgacttgg aggagaagga ggaagtggac aataccgagg gcctgaaggg    2280
gtcaatgaag ggcaaggaga aggcaagggc tgccaaagag gagaagaaga agaaaactca    2340
gagctctggc tctggccagg ggtccgaggc ccccgagaag aagaaaccca agattgatga    2400
gcttaaggta taccccaaag agctggagtc cgagtttgat aactttgagg actggctgca    2460
cactttcaac ttgcttcggg gcaagaccgg ggatgatgag gatggctcca ccgaggagga    2520
gcgcattgtg ggacgcttca agggctccct ctgcgtgtac aaagtgccac tcccagagga    2580
cgtgtcccgg gaagccggct acgactccac ctacggcatg ttccagggca tcccgagcaa    2640
tgaccccatc aatgtgctgg tccgagtcta tgtggtccgg gccacggacc tgcaccctgc    2700
tgacatcaac ggcaaagctg accccctacat cgccatccgg ctaggcaaga ctgacatccg    2760
cgacaaggag aactacatct ccaagcagct caaccctgtc tttgggaagt cctttgacat    2820
cgaggcctcc ttccccatgg aatccatgct gacggtggct gtgtatgact gggacctggt    2880
gggcactgat gacctcattg gggaaaccaa gatcgacctg gagaaccgct tctacagcaa    2940
gcaccgcgcc acctgcggca tcgcccagac ctactccaca catggctaca atatctggcg    3000
ggaccccatg aagcccagcc agatcctgac ccgcctctgc aaagacggca agtggacggg    3060
cccccacttt gggcccccctg ggagagtgaa ggtggccaac cgcgtcttca ctgggccctc    3120
tgagattgag gacgagaacg gtcagaggaa gcccacagac gagcatgtgg cgctgttggc    3180
cctgaggcac tgggaggaca tccccgcgcg aggctgccgc ctggtgccag agcatgtgga    3240
gacgaggccg ctgctcaacc ccgacaagcc gggcatcgag cagggccgcc tggagctgtg    3300
ggtggacatg ttccccatgg acatgccagc ccctgggacg cctctggaca tctcacctcg    3360
gaagcccaag aagtacgagc tgcgggtcat catctggaac acagatgagg tggtcttgga    3420
ggacgacgac ttcttcacag gggagaagtc cagtgacatc ttcgtgaggg ggtggctgaa    3480
gggccagcag gaggacaagc aggacacaga cgtccactac cactccctca ctggcgaggg    3540
caacttcaac tggcgctacc tgttcccctt cgactacctg gcggcggagg agaagatcgt    3600
catctccaag aaggagtcca tgttctcctg ggacgagacc gagtacaaga tccccgcgcg    3660 gctcacccctg cagatctggg atgcggacca cttctccgct gacgacttcc tggggggccat    3720 cgagctggac ctgaaccggt tcccgcgggg cgcaaagaca gccaagcagt gcaccatgga    3780
gatggccacc gggggaggtgg acgtgcccct cgtgtccatc ttcaagcaaa agcgcgtcaa    3840
aggctggtgg cccctcctgg cccgcaatga gaacgatgag tttgagctca cggcaaggt     3900 ggaggctgag ctgcatttac tgacagcaga ggaggcagag aagaacccag tgggcctggc    3960
ccgcaatgaa cctgaccccc tagagaaacc caaccggccc gacacggcct cgtctggtt     4020 cctcaacccct ctcaagtcca tcaagtacct catctgcacc cggtacaagt ggctcatcat    4080
caagatcgtg ctggcgctgt tggggctgct catgttgggg ctcttcctct acagcctccc    4140
tggctacatg gtcaaaaagc tccttggggc atgaacggcc gctatgctag cttggtacca    4200
agggcggatc ctgcatagag ctcgctgatc agcctcgact gtgccttcta gttgccagcc    4260
```

-continued

```
atctgttgtt tgccctccc ccgtgccttc cttgaccctg gaaggtgcca ctcccactgt    4320
cctttcctaa taaaatgagg aaattgcatc gcattgtctg agtaggtgtc attctattct    4380
gggggtgggg gtggggcagg acagcaaggg ggaggattgg gaagacaata gcaggcatct    4440
cgagttaagg gcgaattccc gataaggatc ttcctagagc atggctacgt agataagtag    4500
catggcgggt taatcattaa ctacaaggaa cccctagtga tggagttggc cactccctct    4560
ctgcgcgctc gctcgctcac tgaggccggg cgaccaaagg tcgcccgacg cccgggcttt    4620
gcccgggcgg cctcagtgag cgagcgagcg cgcagcctta attaacctaa ttcactggcc    4680
gtcgttttac aacgtcgtga ctgggaaaac cctggcgtta cccaacttaa tcgccttgca    4740
gcacatcccc ctttcgccag ctggcgtaat agcgaagagg cccgcaccga tcgcccttcc    4800
caacagttgc gcagcctgaa tggcgaatgg gacgcgccct gtagcggcgc attaagcgcg    4860
gcgggtgtgg tggttacgcg cagcgtgacc gctacacttg ccagcgccct agcgcccgct    4920
cctttcgctt tcttcccttc ctttctcgcc acgttcgccg gctttccccg tcaagctcta    4980
aatcgggggc tccctttagg gttccgattt agtgctttac ggcacctcga ccccaaaaaa    5040
cttgattagg gtgatggttc acgtagtggg ccatcgccct gatagacggt ttttcgccct    5100
ttgacgttgg agtccacgtt ctttaatagt ggactcttgt tccaaactgg aacaacactc    5160
aaccctatct cggtctattc ttttgattta taagggattt tgccgatttc ggcctattgg    5220
ttaaaaaatg agctgattta acaaaaattt aacgcgaatt ttaacaaaat attaacgctt    5280
acaatttagg tggcacttttt cggggaaatg tgcgcggaac ccctatttgt ttatttttct    5340
aaatacattc aaatatgtat ccgctcatga caataaccc ctgataaatg cttcaataat    5400
attgaaaaag gaagagtatg agccatattc aacgggaaac gtcgaggccg cgattaaatt    5460
ccaacatgga tgctgattta tatgggtata aatgggctcg cgataatgtc gggcaatcag    5520
gtgcgacaat ctatcgcttg tatgggaagc ccgatcgcc agagttgttt ctgaaacatg    5580
gcaaaggtag cgttgccaat gatgttacag atgagatggt cagactaaac tggctgacgg    5640
aatttatgcc tcttccgacc atcaagcatt ttatccgtac tcctgatgat gcatggttac    5700
tcaccactgc gatccccgga aaaacagcat tccaggtatt agaagaatat cctgattcag    5760
gtgaaaatat tgttgatgcg ctggcagtgt tcctgcgccg gttgcattcg attcctgttt    5820
gtaattgtcc ttttaacagc gatcgcgtat ttcgtcttgc tcaggcgcaa tcacgaatga    5880
ataacggttt ggttgatgcg agtgattttg atgacgagcg taatggctgg cctgttgaac    5940
aagtctggaa agaaatgcat aaacttttgc cattctcacc ggattcagtc gtcactcatg    6000
gtgatttctc acttgataac cttattttg acgaggggaa attaataggt tgtattgatg    6060
ttggacgagt cggaatcgca gaccgatacc aggatcttgc catcctatgg aactgcctcg    6120 gtgagtttc tccttcatta cagaaacggc tttttcaaaa atatggtatt gataatcctg    6180
atatgaataa attgcagttt catttgatgc tcgatgagtt tttctaactg tcagaccaag    6240
tttactcata tatactttag attgatttaa aacttcattt ttaatttaaa aggatctagg    6300
tgaagatcct ttttgataat ctcatgacca aaatccctta acgtgagttt tcgttccact    6360
gagcgtcaga ccccgtagaa aagatcaaag gatcttcttg agatcctttt tttctgcgcg    6420
taatctgctg cttgcaaaca aaaaaaccac cgctaccagc ggtggtttgt ttgccggatc    6480
aagagctacc aactcttttt ccgaaggtaa ctggcttcag cagagcgcag ataccaaata    6540
ctgttcttct agtgtagccg tagttaggcc accacttcaa gaactctgta gcaccgccta    6600
```

-continued

```
catacctcgc tctgctaatc ctgttaccag tggctgctgc cagtggcgat aagtcgtgtc    6660
ttaccgggtt ggactcaaga cgatagttac cggataaggc gcagcggtcg ggctgaacgg    6720
ggggttcgtg cacacagccc agcttggagc gaacgaccta caccgaactg agatacctac    6780
agcgtgagct atgagaaagc gccacgcttc ccgaagggag aaaggcggac aggtatccgg    6840
taagcggcag ggtcggaaca ggagagcgca cgagggagct tccagggggga aacgcctggt    6900 atctttatag tcctgtcggg tttcgccacc tctgacttga gcgtcgattt ttgtgatgct    6960 cgtcagggggg gcggagccta tggaaaaacg ccagcaacgc ggcctttttta cggttcctgg    7020 cctttttgctg gcctttttgct cacatgttct ttcctgcgtt atccctgat tctgtggata    7080 accgtattac cgcctttgag tgagctgata ccgctcgccg cagccgaacg accgagcgca    7140
gcgagtcagt gagcgaggaa gcggaagagc gcccaatacg caaaccgcct ctccccgcgc    7200
gttggccgat tcattaatgc agctggcacg acaggtttcc cgactggaaa gcgggcagtg    7260
agcgcaacgc aattaatgtg agttagctca ctcattaggc accccaggct ttacacttta    7320
tgcttccggc tcgtatgttg tgtggaattg tgagcggata acaatttcac acaggaaaca    7380
gctatgacca tgattacgcc agatttaatt aagg    7414
```

```
<210> SEQ ID NO 68
<211> LENGTH: 6959
<212> TYPE: DNA
<213> ORGANISM: Artificial Sequence
<220> FEATURE:
<223> OTHER INFORMATION: Synthetic Construct

<400> SEQUENCE: 68
```

```
ccttaattag gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac taggggttcc ttgtagttaa tgattaaccc gccatgctac ttatctacgt    180
agccatgctc taggaagatc ggaattcgcc cttaagctag cggcgcgccg gtacctagtt    240
attaatagta atcaattacg gggtcattag ttcatagccc atatatggag ttccgcgtta    300
cataacttac ggtaaatggc ccgcctggct gaccgcccaa cgacccccgc ccattgacgt    360
caataatgac gtatgttccc atagtaacgc caatagggac tttccattga cgtcaatggg    420
tggagtattt acggtaaact gcccacttgg cagtacatca agtgtatcat atgccaagta    480 cgcccctat tgacgtcaat gacggtaaat ggcccgcctg gcattatgcc cagtacatga    540 ccttatgggga ctttcctact tggcagtaca tctacgtatt agtcatcgct attaccatgg    600
tcgaggtgag ccccacgttc tgcttcactc tccccatctc cccccctcc ccaccccaa    660 ttttgtattt attatttttt aattattttt gtgcagcgat gggggcgggg ggggggggggg    720 ggcgcgcgcc aggcggggcg gggcggggcg aggggcgggg cggggcgagg cggagaggtg    780
cggcggcagc caatcagagc ggcgcgctcc gaaagtttcc ttttatggcg aggcggcggc    840
ggcggcggcc ctataaaaag cgaagcgcgc ggcgggcggg agtcgctgcg cgctgccttc    900
gccccgtgcc ccgctccgcc gccgcctcgc gccgcccgcc ccggctctga ctgaccgcgt    960
tactcccaca ggtgagcggg cgggacggcc cttctcctcc gggctgtaat tagcgcttgg    1020
tttaatgacg gcttgtttct tttctgtggc tgcgtgaaag ccttgagggg ctccgggagc    1080
tagagcctct gctaaccatg ttcatgcctt cttctttttc ctacagctcc tgggcaacgt    1140
gctggttatt gtgctgtctc atcatttttgg caaagaattc tagcggccgc caccatggcc    1200
ttgctcatcc acctcaagac agtctcggag ctgcggggca ggggcgaccg gatcgccaaa    1260
```

-continued

```
gtgactttcc gagggcaatc cttctactct cgggtcctgg agaactgtga ggatgtggct    1320
gactttgatg agacatttcg gtggccggtg gccagcagca tcgacagaaa tgagatgctg    1380
gagattcagg ttttcaacta cagcaaagtc ttcagcaaca agctcatcgg gaccttccgc    1440
atggtgctgc agaaggtggt agaggagagc catgtggagg tgactgacac gctgattgat    1500
gacaacaatg ctatcatcaa gaccagcctg tgcgtggagg tccggtatca ggccactgac    1560
ggcacagtgg gctcctggga cgatggggac ttcctgggag atgagtctct tcaagaggaa    1620
gagaaggaca gccaagagac ggatggactg ctcccaggct cccggcccag ctcccggccc    1680
ccaggagaga agagcttccg gagagccggg aggagcgtgt tctccgccat gaagctcggc    1740
aaaaaccggt ctcacaagga ggagccccaa agaccagatg aaccggcggt gctggagatg    1800
gaagaccttg accatctggc cattcggcta ggagatggac tggatcccga ctcggtgtct    1860
ctagcctcag tcacagctct caccactaat gtctccaaca agcgatctaa gccagacatt    1920
aagatggagc caagtgctgg gcggcccatg gattaccagg tcagcatcac ggtgatcgag    1980 gccccggcagc tggtgggctt gaacatggac cctgtggtgt gcgtggaggt gggtgacgac    2040
aagaagtaca catccatgaa ggagtccact aactgcccct attacaacga gtacttcgtc    2100
ttcgacttcc atgtctctcc ggatgtcatg tttgacaaga tcatcaagat ttcggtgatt    2160
cactccaaga acctgctgcg cagtggcacc ctggtgggct ccttcaaaat ggacgtggga    2220
accgtgtact cgcagccaga gcaccagttc catcacaagt gggccatcct gtctgacccc    2280
gatgacatct cctcggggct gaagggctac gtgaagtgtg acgttgccgt ggtgggcaaa    2340
ggggacaaca tcaagacgcc ccacaaggcc aatgagaccg acgaagatga cattgagggg    2400
aacttgctgc tccccgaggg ggtgccccccc gaacgccagt gggcccggtt ctatgtgaaa    2460
atttaccgag cagaggggct gccccgtatg aacacaagcc tcatggccaa tgtaaagaag    2520
gctttcatcg gtgaaaacaa ggacctcgtg gaccccotacg tgcaagtctt ctttgctggc    2580
cagaagggca agacttcagt gcagaagagc agctatgagc ccctgtggaa tgagcaggtc    2640
gtctttacag acctcttccc cccactctgc aaacgcatga aggtgcagat ccgagactcg    2700
gacaaggtca acgacgtggc catcggcacc cacttcattg acctgcgcaa gatttctaat    2760
gacggagaca aaggcttcct gcccacactg ggcccagcct gggtgaacat gtacggctcc    2820
acacgtaact acacgctgct ggatgagcat caggacctga acgagggcct gggggagggt    2880
gtgtccttcc gggcccggct cctgctgggc ctggctgtgg agatcgtaga cacctccaac    2940
cctgagctca ccagctccac agaggtgcag gtggagcagg ccacgcccat ctcggagagc    3000
tgtgcaggta aaatggaaga attctttctc tttggagcct tcctggaggc ctcaatgatc    3060
gaccggagaa acgagacaa gcccatcacc tttgaggtca ccataggcaa ctatgggaac    3120
gaagttgatg gcctgtcccg gccccagcgg cctcggcccc ggaaggagcc gggggatgag    3180
gaagaagtag acctgattca gaacgcaagt gatgacgagg ccggtgatgc cggggacctg    3240
gcctcagtct cctccactcc accaatgcgg ccccaggtca ccgacaggaa ctacttccat    3300 ctgcccctacc tggagcgaaa gccctgcatc tacatcaaga gctggtggcc ggaccagcgc    3360
cgccgcctct acaatgccaa catcatggac acattgccg acaagctgga agaaggcctg    3420
aacgacatac aggagatgat caaaacggag aagtcctacc ctgagcgtcg cctgcggggc    3480
gtcctggagg agctgagctg tggctgctgc cgcttcctct ccctcgctga caaggaccag    3540
ggccactcat cccgcaccag gcttgaccgg gagcgcctca agtcctgcat gagggagctg    3600
```

-continued

```
gtaagtatca aggttacaag acaggtttaa ggagaccaat agaaactggg cttgtcgaga   3660
cagagaagac tcttgcgttt ctgagctagc ccccgggtgc gcggcgtcgg tggtgccggc   3720
ggggggcgcc aggtcgcagg cggtgtaggg ctccaggcag gcggcgaagg ccatgacgtg   3780
cgctatgaag gtctgctcct gcacgccgtg aaccaggtgc gcctgcgggc cgcgcgcgaa   3840
caccgccacg tcctcgcctg cgtgggtctc ttcgtccagg ggcactgctg actgctgccg   3900
atactcgggg ctcccgctct cgctctcggt aacatccggc cgggcgccgt ccttgagcac   3960
atagcctgga ccgtttcgtc gacctcgagt taagggcgaa ttcccgataa ggatcttcct   4020
agagcatggc tacgtagata agtagcatgg cgggttaatc attaactaca aggaacccct   4080
agtgatggag ttggccactc cctctctgcg cgctcgctcg ctcactgagg ccgggcgacc   4140
aaaggtcgcc cgacgcccgg gctttgcccg ggcggcctca gtgagcgagc gagcgcgcag   4200
ccttaattaa cctaattcac tggccgtcgt tttacaacgt cgtgactggg aaaaccctgg   4260
cgttacccaa cttaatcgcc ttgcagcaca tccccctttc gccagctggc gtaatagcga   4320
agaggcccgc accgatcgcc cttcccaaca gttgcgcagc ctgaatggcg aatgggacgc   4380
gccctgtagc ggcgcattaa gcgcggcggg tgtggtggtt acgcgcagcg tgaccgctac   4440
acttgccagc gccctagcgc ccgctccttt cgctttcttc ccttcctttc tcgccacgtt   4500
cgccggcttt ccccgtcaag ctctaaatcg ggggctccct ttagggttcc gatttagtgc   4560
tttacggcac ctcgacccca aaaaacttga ttagggtgat ggttcacgta gtgggccatc   4620
gccctgatag acggtttttc gccctttgac gttggagtcc acgttcttta atagtggact   4680
cttgttccaa actggaacaa cactcaaccc tatctcggtc tattcttttg atttataagg   4740
gattttgccg atttcggcct attggttaaa aaatgagctg atttaacaaa aatttaacgc   4800
gaattttaac aaaatattaa cgcttacaat ttaggtggca cttttcgggg aaatgtgcgc   4860 ggaacccta tttgtttatt tttctaaata cattcaaata tgtatccgct catgagacaa   4920
taaccctgat aaatgcttca ataatattga aaaaggaaga gtatgagcca tattcaacgg   4980
gaaacgtcga ggccgcgatt aaattccaac atggatgctg atttatatgg gtataaatgg   5040
gctcgcgata atgtcgggca atcaggtgcg acaatctatc gcttgtatgg gaagcccgat   5100
gcgccagagt tgtttctgaa acatggcaaa ggtagcgttg ccaatgatgt tacagatgag   5160
atggtcagac taaactggct gacggaattt atgcctcttc cgaccatcaa gcattttatc   5220
cgtactcctg atgatgcatg gttactcacc actgcgatcc ccggaaaaac agcattccag   5280
gtattagaag aatatcctga ttcaggtgaa aatattgttg atgcgctggc agtgttcctg   5340
cgccggttgc attcgattcc tgtttgtaat tgtcctttta acagcgatcg cgtatttcgt   5400
cttgctcagg cgcaatcacg aatgaataac ggtttggttg atgcgagtga ttttgatgac   5460
gagcgtaatg gctggcctgt tgaacaagtc tggaaagaaa tgcataaact tttgccattc   5520
tcaccggatt cagtcgtcac tcatggtgat ttctcacttg ataaccttat ttttgacgag   5580
gggaaattaa taggttgtat tgatgttgga cgagtcggaa tcgcagaccg ataccaggat   5640
cttgccatcc tatggaactg cctcggtgag ttttctcctt cattacagaa acggcttttt   5700
caaaaatatg gtattgataa tcctgatatg aataaattgc agtttcattt gatgctcgat   5760
gagtttttct aactgtcaga ccaagtttac tcatatatac tttagattga tttaaaactt   5820 cattttaat ttaaaaggat ctaggtgaag atccttttg ataatctcat gaccaaaatc   5880
ccttaacgtg agttttcgtt ccactgagcg tcagaccccg tagaaaagat caaaggatct   5940
tcttgagatc ctttttttct gcgcgtaatc tgctgcttgc aaacaaaaaa accaccgcta   6000
```

-continued

```
ccagcggtgg tttgtttgcc ggatcaagag ctaccaactc tttttccgaa ggtaactggc    6060
ttcagcagag cgcagatacc aaatactgtt cttctagtgt agccgtagtt aggccaccac    6120
ttcaagaact ctgtagcacc gcctacatac ctcgctctgc taatcctgtt accagtggct    6180
gctgccagtg gcgataagtc gtgtcttacc gggttggact caagacgata gttaccggat    6240
aaggcgcagc ggtcgggctg aacgggggt tcgtgcacac agcccagctt ggagcgaacg     6300
acctacaccg aactgagata cctacagcgt gagctatgag aaagcgccac gcttcccgaa    6360
gggagaaagg cggacaggta tccggtaagc ggcagggtcg gaacaggaga gcgcacgagg    6420
gagcttccag ggggaaacgc ctggtatctt tatagtcctg tcgggtttcg ccacctctga    6480
cttgagcgtc gatttttgtg atgctcgtca ggggggcgga gcctatggaa aaacgccagc    6540
aacgcggcct ttttacggtt cctggccttt tgctggcctt ttgctcacat gttctttcct    6600
gcgttatccc ctgattctgt ggataaccgt attaccgcct ttgagtgagc tgataccgct    6660
cgccgcagcc gaacgaccga gcgcagcgag tcagtgagcg aggaagcgga agagcgccca    6720
atacgcaaac cgcctctccc cgcgcgttgg ccgattcatt aatgcagctg gcacgacagg    6780
tttcccgact ggaaagcggg cagtgagcgc aacgcaatta atgtgagtta gctcactcat    6840
taggcacccc aggctttaca ctttatgctt ccggctcgta tgttgtgtgg aattgtgagc    6900
ggataacaat ttcacacagg aaacagctat gaccatgatt acgccagatt taattaagg     6959
```